(12) United States Patent
Bekkali et al.

(10) Patent No.: US 8,741,897 B2
(45) Date of Patent: *Jun. 3, 2014

(54) GLUCOCORTICOID MIMETICS, METHODS OF MAKING THEM, PHARMACEUTICAL COMPOSITIONS AND USES THEREOF

(75) Inventors: Younes Bekkali, Danbury, CT (US); Rajashekhar Betageri, Bethel, CT (US); Michel J. Emmanuel, Danbury, CT (US); Abdelhakim Hammach, Danbury, CT (US); Christian Hanke Justus Joachim Harcken, New Milford, CT (US); Thomas Martin Kirrane, Jr., Southbury, CT (US); Daniel Kuzmich, Danbury, CT (US); Thomas Wai-Ho Lee, Danbury, CT (US); Pingrong Liu, Southbury, CT (US); Usha R. Patel, Brookfield, CT (US); John Robert Proudfoot, Danbury, CT (US); Hossein Razavi, Danbury, CT (US); Doris Riether, New York, NY (US); Hidenori Takahashi, LaGrangeville, NY (US); David S. Thomson, Ridgefield, CT (US); Ji Wang, Danbury, CT (US); Renee Zindell, Danbury, CT (US)

(73) Assignee: Boehringer Ingelheim Pharmaceuticals Inc., Ridgefield, CT (US)

(*) Notice: Subject to any disclaimer, the term of this patent is extended or adjusted under 35 U.S.C. 154(b) by 2036 days.

This patent is subject to a terminal disclaimer.

(21) Appl. No.: 10/947,420

(22) Filed: Sep. 22, 2004

(65) Prior Publication Data

US 2005/0176706 A1    Aug. 11, 2005

Related U.S. Application Data

(60) Provisional application No. 60/505,456, filed on Sep. 24, 2003, provisional application No. 60/507,079, filed on Sep. 29, 2003.

(51) Int. Cl.
| | | |
|---|---|---|
| *C07D 487/04* | (2006.01) |
| *A61K 31/519* | (2006.01) |
| *A61K 31/5377* | (2006.01) |
| *A61K 31/4355* | (2006.01) |
| *A61K 31/5025* | (2006.01) |
| *A61P 25/28* | (2006.01) |
| *A61P 9/00* | (2006.01) |
| *A61P 35/00* | (2006.01) |
| *A61K 31/4402* | (2006.01) |
| *A61K 31/4409* | (2006.01) |
| *A61K 31/4418* | (2006.01) |
| *A61K 31/4406* | (2006.01) |
| *A61K 31/497* | (2006.01) |
| *A61K 31/506* | (2006.01) |
| *A61K 31/4184* | (2006.01) |
| *A61K 31/404* | (2006.01) |
| *A61K 31/416* | (2006.01) |
| *A61K 31/47* | (2006.01) |

(52) U.S. Cl.
USPC ............ 514/234.5; 514/265.1; 514/300; 514/248; 546/113; 546/181; 546/277.4; 544/280; 544/128; 544/236; 544/333; 544/405; 548/315.41; 548/323.5; 548/516; 548/360.1

(58) Field of Classification Search
USPC ........ 544/280, 128, 236; 546/113; 514/265.1, 514/234.5, 248, 300
See application file for complete search history.

(56) References Cited

U.S. PATENT DOCUMENTS

| | | | |
|---|---|---|---|
| 3,772,273 | A | 11/1973 | Gilbert |
| 4,551,534 | A | 11/1985 | Sulkowski et al. |

(Continued)

FOREIGN PATENT DOCUMENTS

| | | |
|---|---|---|
| BE | 900594 | 3/1985 |
| CA | 2305458 A1 | 12/1998 |

(Continued)

OTHER PUBLICATIONS

Hamann, Lawrence, et al ; Discovery of a potent, Orally active, Nonsteroidal Androgen Receptor Agonist: 4-Ethyl-1,2,3,4-tetrahydro-6-(trifluoromethyl)-8-pyridono[5,6-gl-quinoline(LG12107I), J. Med. Chem, 1999, 42, 210-212.

(Continued)

*Primary Examiner* — Susanna Moore
(74) *Attorney, Agent, or Firm* — Michael P. Morris; Timothy X. Witkowski; Usha R. Patel

(57) ABSTRACT

Compounds of Formula (IA), (IB), (IC), and (ID)

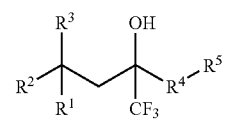

(IA)

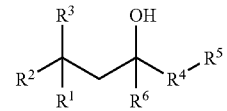

(IB)

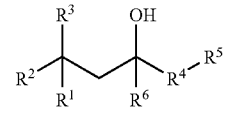

(IC)

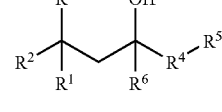

(ID)

wherein $R^1$, $R^2$, $R^3$, $R^4$, $R^5$, and $R^6$ are as respectively defined herein for Formula (IA), (IB), (IC), and (ID), or a tautomer, prodrug, solvate, or salt thereof; pharmaceutical compositions containing such compounds, and methods of modulating the glucocorticoid receptor function and methods of treating disease-states or conditions mediated by the glucocorticoid receptor function or characterized by inflammatory, allergic, or proliferative processes in a patient using these compounds.

3 Claims, No Drawings

(56) References Cited

U.S. PATENT DOCUMENTS

| | | | |
|---|---|---|---|
| 4,774,240 A | 9/1988 | Boshagen et al. | |
| 4,880,839 A | 11/1989 | Tucker | |
| 5,039,691 A | 8/1991 | Spagnuolo et al. | |
| 5,206,377 A | 4/1993 | McAfee | |
| 5,688,810 A | 11/1997 | Jones et al. | |
| 5,948,820 A | 9/1999 | Fujita et al. | |
| 6,169,106 B1 | 1/2001 | Heckel et al. | |
| 6,187,918 B1 | 2/2001 | Nugent | |
| 6,323,199 B1 | 11/2001 | Lehmann et al. | |
| 6,329,534 B1 | 12/2001 | Kym et al. | |
| 6,362,344 B1 | 3/2002 | Nugent | |
| 6,380,223 B1 | 4/2002 | Dow et al. | |
| 6,436,986 B1 | 8/2002 | Kym et al. | |
| 6,506,766 B1 | 1/2003 | Coghlan et al. | |
| 6,583,180 B2 | 6/2003 | Link et al. | |
| 6,589,947 B1 | 7/2003 | Hamanaka et al. | |
| 6,699,893 B2 | 3/2004 | Dow et al. | |
| 6,777,404 B2 | 8/2004 | Hamanaka et al. | |
| 6,858,627 B2 | 2/2005 | Bekkali et al. | |
| 6,903,215 B2 * | 6/2005 | Betageri et al. | 546/113 |
| 6,960,581 B2 | 11/2005 | Betageri et al. | |
| 7,074,806 B2 | 7/2006 | Kirrane, Jr. et al. | |
| 7,125,996 B2 | 10/2006 | Prokopowicz, III et al. | |
| 7,166,593 B2 | 1/2007 | Dow et al. | |
| 7,179,919 B2 | 2/2007 | Song et al. | |
| 7,186,864 B2 | 3/2007 | Kirrane, Jr. et al. | |
| 7,189,758 B2 | 3/2007 | Betageri et al. | |
| 7,256,300 B2 | 8/2007 | Lee et al. | |
| 7,268,152 B2 | 9/2007 | Bekkali et al. | |
| 7,425,629 B2 | 9/2008 | Song et al. | |
| 7,507,843 B2 | 3/2009 | Song et al. | |
| 7,553,966 B2 | 6/2009 | Betageri et al. | |
| 7,579,469 B2 | 8/2009 | Kuzmich et al. | |
| 7,622,594 B2 | 11/2009 | Mugge et al. | |
| 7,635,711 B2 | 12/2009 | Kuzmich et al. | |
| 7,713,989 B2 | 5/2010 | Dow et al. | |
| 7,741,361 B2 | 6/2010 | Kuzmich et al. | |
| 7,888,381 B2 | 2/2011 | Duan et al. | |
| 7,932,392 B2 | 4/2011 | Betageri et al. | |
| 2001/0014754 A1 | 8/2001 | Suzuki et al. | |
| 2002/0077356 A1 | 6/2002 | Jaroch et al. | |
| 2002/0156311 A1 | 10/2002 | Link et al. | |
| 2003/0105099 A1 | 6/2003 | Graupe et al. | |
| 2003/0108910 A1 | 6/2003 | Toland et al. | |
| 2003/0171359 A1 | 9/2003 | Dahmann et al. | |
| 2003/0232823 A1 | 12/2003 | Betageri et al. | |
| 2004/0010020 A1 | 1/2004 | Kirrane, Jr. et al. | |
| 2004/0010148 A1 | 1/2004 | Kirrane, Jr. et al. | |
| 2004/0023999 A1 | 2/2004 | Bekkali et al. | |
| 2004/0029932 A1 | 2/2004 | Bekkali et al. | |
| 2004/0058978 A1 | 3/2004 | Walter et al. | |
| 2004/0075864 A1 | 4/2004 | Kato et al. | |
| 2004/0097574 A1 | 5/2004 | Marshall | |
| 2004/0116455 A1 | 6/2004 | Bekkali et al. | |
| 2004/0116694 A1 | 6/2004 | Jaroch et al. | |
| 2004/0162321 A1 | 8/2004 | Kuzmich et al. | |
| 2004/0209875 A1 | 10/2004 | Schmees et al. | |
| 2004/0224992 A1 | 11/2004 | Cywin et al. | |
| 2004/0242613 A1 | 12/2004 | Cardozo et al. | |
| 2004/0254249 A1 | 12/2004 | Jaroch et al. | |
| 2005/0043301 A1 | 2/2005 | Liu et al. | |
| 2005/0059714 A1 | 3/2005 | Betageri et al. | |
| 2005/0124640 A1 | 6/2005 | Cardozo et al. | |
| 2005/0131241 A1 | 6/2005 | Song et al. | |
| 2005/0203128 A1 | 9/2005 | Kirrane et al. | |
| 2005/0209488 A1 | 9/2005 | Song et al. | |
| 2005/0234091 A1 | 10/2005 | Regan et al. | |
| 2005/0234250 A1 | 10/2005 | Lee et al. | |
| 2005/0282881 A1 | 12/2005 | Bekkali et al. | |
| 2006/0014787 A1 | 1/2006 | Kirrane et al. | |
| 2006/0030561 A1 | 2/2006 | Betageri et al. | |
| 2006/0030608 A1 | 2/2006 | Nelson et al. | |
| 2006/0122189 A1 | 6/2006 | Feenstra et al. | |
| 2006/0154925 A1 | 7/2006 | Kuzmich et al. | |
| 2006/0189646 A1 | 8/2006 | Kuzmich et al. | |
| 2006/0189647 A1 | 8/2006 | Bekkali et al. | |
| 2006/0205712 A1 | 9/2006 | Calvani et al. | |
| 2007/0060633 A1 | 3/2007 | Mugge et al. | |
| 2007/0100142 A1 | 5/2007 | Song et al. | |
| 2009/0176807 A1 | 7/2009 | Regan et al. | |
| 2009/0325988 A1 | 12/2009 | Harcken et al. | |

FOREIGN PATENT DOCUMENTS

| | | |
|---|---|---|
| CA | 2323111 A1 | 10/1999 |
| CA | 2342622 A1 | 4/2000 |
| CA | 2411165 A1 | 12/2002 |
| CA | 2463989 A1 | 4/2003 |
| DE | 1017612 B | 10/1957 |
| EP | 0 154 528 A2 | 3/1985 |
| EP | 0311447 | 12/1989 |
| EP | 0 253 500 | 2/1991 |
| EP | 0 253 503 | 12/1991 |
| GB | 2 146 987 A | 9/1984 |
| JP | 5194404 A | 8/1993 |
| JP | 11080131 A | 3/1999 |
| WO | 9315047 A1 | 8/1993 |
| WO | WO 96/19458 | 6/1996 |
| WO | WO 97/27852 | 8/1997 |
| WO | WO 98/54159 | 12/1998 |
| WO | WO 99/41256 | 2/1999 |
| WO | 9933786 A1 | 7/1999 |
| WO | 9952869 A1 | 10/1999 |
| WO | 9963976 A2 | 12/1999 |
| WO | 0018734 A1 | 4/2000 |
| WO | WO 00/32584 | 6/2000 |
| WO | WO 00/66522 | 11/2000 |
| WO | 0105784 A1 | 1/2001 |
| WO | 0183471 A1 | 11/2001 |
| WO | 189445 A1 | 11/2001 |
| WO | WO 02/02565 | 1/2002 |
| WO | 0209702 A2 | 2/2002 |
| WO | WO 02/10143 | 2/2002 |
| WO | 02051983 A2 | 7/2002 |
| WO | WO 02064550 | 8/2002 |
| WO | 03031606 A2 | 4/2003 |
| WO | 03032997 A1 | 4/2003 |
| WO | WO 03/059899 A1 | 7/2003 |
| WO | 03082827 A1 | 10/2003 |
| WO | WO 03/082280 A1 | 10/2003 |
| WO | WO 03/082787 A1 | 10/2003 |
| WO | 03104195 A1 | 12/2003 |
| WO | 2004005278 A1 | 1/2004 |
| WO | 2004018429 A2 | 3/2004 |
| WO | 2004019935 A1 | 3/2004 |
| WO | WO 2004/063163 A1 | 7/2004 |
| WO | 2004071389 A2 | 8/2004 |
| WO | 2004075864 A2 | 9/2004 |
| WO | 2004089415 A2 | 10/2004 |
| WO | 2005019202 A1 | 3/2005 |
| WO | 2005030213 A1 | 4/2005 |
| WO | 2005090343 A1 | 9/2005 |
| WO | 2006046916 A1 | 5/2006 |
| WO | 2006071609 A2 | 7/2006 |
| WO | 2006135826 A1 | 12/2006 |
| WO | 2007040959 A1 | 4/2007 |

OTHER PUBLICATIONS

Pooley, Charlotte, et al; Discovery and Preliminary SAR Studies of a Novel Nonsteroidal Progesterone Receptor Antagonist Pharmacophore, J. Med. Chem 1998, 41, 3461-3466.

Edwards, James, P. et al; 5-Aryl-1,2-dihydro-5H-chromeno[3,4-f]quinolines as Potent, Orally Active, Nonsteroidal Progestgerone Receptor Agonists; The Effect of D-Ring Substituents, J. Med. Chem 1998, 41, 303-310.

Zhi, Lin, et al; 5-Aryl-1,2-dihydro-5H-chromeno[3,4-f]quinolines: A Novel Class of Nonsteroidal Human Progesterone Receptor Agonists, J. Med. Chem 1998, 41, 291-302.

Zhi, Lin; et al 5-Aryl-1,2,3,4-tetrahydrochromeno[3,4-f]quinolin-3-ones as a Novel Class of Nonsteroidal Progrestrone Receptor Agonists: Effect of A-Ring Modification, J. Med. Chem 1999, 42, 1466-1472.

(56) References Cited

OTHER PUBLICATIONS

Tegley, Christopher, et al; 5-Benzylidene 1,2-Dihydrochromeno[3,4-f]quinolines, A Novel Class of Nonsteroidal Human Progesterone Receptor Agonists; J. Med. Chem 1998, 41, 4354-4359.
Edwards, James, P. et al; Preparation, Resolution and Biological Evaluation of 5-Aryl-1,2-dihydro-5H-chromeno[3,4-f]quinolines as Potent, Orally Active, Nonsteroidal Progestgerone Receptor Agonists; J. Med. Chem. 1998,41, 2779-2785.
Hamann, Lawrence, et al; Synthesis and Biological Activity of a Novel Series of Nonsteroidal, Peripherally Selective androgen Receptor Antagonists Derived from 1,2-Dihydropyridono[5,6-g]quinolines J. Med. Chem. 1998, 41, 623-639.
English Translation of WO/02/10143, Feb. 7, 2002.
Bekkali, Y., et al; Appkication entitled Glucocorticoid Mimetics, Methods of Making Them, Pharmaceutical Compositions and Uses Thereof, accorded U.S. Appl. No. 10/639,131, filed Jun. 17, 2004.
Cywin, C., , et al; Application entitled Glocorticoid Mimetics, Methods of Making Them, Pharmaceutical Compositions and Uses Thereof, accorded U.S. Appl. No. 10/785,222, filed Nov. 11, 2004.
Kuzmich, D., et al; Application entitled Glucocorticoid Mimetics, Methods of Making Them, Pharmaceutical Compositions and Uses Thereof, accorded U.S. Appl. No. 10/739,208, filed Aug. 19, 2004.
Krishnamurti, et al; Journal of Organic Chemistry 1991, 56, 984-989.
Kutney, J.P., et al; Total synthesis of Dregamine and Epidregamine, A General Routge to 2 Acylindole Alkaloids, J. Am., Chem. Soc. vol. 100 No. 3, 1978 p. 938-943.
Lagidze et al., CA 102:184944, 1985.
Lagidze, D.R., et al: Synthesis of Some new analogs of melatonin and beta carboline from 4 phenylpentanoic acid; p. 637, 1981.
Marshall, Daniel R; et al; Poster entitled: a-Methyltryptamine sulfonamide derivatives as novel glucocorticoid receptor ligands, presented at the 227th American Chemical Society National Meeting, Anaheim CA, Apr. 28-May 1, 2004.
Marshall, Daniel; et al; a-Methyltryptamine sulfonamide derivatives as novel glucocorticoid receptor ligands, Bioorganic and Medicinal Chemistry Letters 17, (2007) p. 315-319.
Nenajdenko, Valetine G., et al; A new convenient approach to chiral -aryl(heteroaryl)alkylamines, Tetrahedron: Asymmetry 12(18) 2517-2527, Oct. 15, 2001.
Oakley, R.N., et al; The glucocorticoid receptor; expression, function and regulation of glucocorticoid responsiveness; Glucocorticoids, 2001, pp. 55-80.
Onistschenko et al., CA 112:55520, 1990.
Outinen et al., European Journal of Pharmaceutical Sciences (1998), 6(3), pp. 197-205.
Palmisano, G., et al; Synthetic Studies on Indole Alkaloids. A Stereocontrolled Entry to the Cuanzine Structural Unit, Tetrahedron, Elsevier Sccience Publisher, Amsterdam, NL. vol. 45, No. 11, 1989, pp. 3583-3595.
Parente, L,; The development of synthetic glucocorticoids,; Glucocorticoids, 2001, pp. 35-54.
Pargellis et al. Inhibition of P38 Map Kinase by Utilizing a Novel Allosteric Binding Site; Nature Structural Biology, vol. 9, No. 4 (2002) pp. 268-272.
Peeters, B.W.M.M, et al; Glucocorticoid Receptor Antagonistis: New Tools to Investigate Disorders Characterized by Cortisol Hypersecretion; Stress, vol. 7(4), pp. 233-241, 2004.
Pelicano et al. Study of the Substrate-Binding Properties of Bovine Liver Adenosine Kinase and Inhibition by Fluorescent Nucleoside Analogues; European Journal of Biochemistry, vol. 248 (1997) pp. 930-937.
Plihal W., et al, Psychoneuroendocrinology 1996 vol. 21 No. 6, p. 515-523.
Prakash, et al; "Asymmetric Synthesis of Trifluoromethylated Allylic Amines Using alpha,beta-Unsaturated N-tert-Butanesulfinimines", Organic Letters, 2001, vol. 3, No. 18, pp. 2847-2850.
Ramaiah, et al; "Direct Trifluoromethylation of alpha-Keto Esters to beta,beta,beta-Trifluorolactic Acid Derivatives Using Trifluoromethyltrimethylsilane"; Synlett, 1991, vol. 9, pp. 643-644.
Regan, John, et al; Advances Toward Dissociated Non-Steroidal Glucocorticoid Receptors Agonists, Annual reports in Medicinal Chemistry, vol. 43, pp. 141-151, 2008.
Reichartd, H.M., et al; DNA Binding of the Glucocorticoid Receptor is not Essential for Survival, Cell, 1998, 93, pp. 531-541.
Schisla et al; "Quaternary-Substituted Hydrocarbons. A General Method of Synthesis of Hydrocarbons Interspersed with Four gem-Dimethyl Unites" Journal of Organic Chemistry, vol. 35, No. 10, 1970, p. 3224-3230.
Shono, Tatsuya, et al: Electroorganic Chimistry 81, Anodic Oxidation of Sulfonamides and Amidophosphates, J. Org. Chem; 1984, 49, 3711-3716.
Song et al. Journal of Organic Chemistry, 2007, 72, 292-294.
Souillac, et al., Characterization of Delivery Systems, Differential Scanning Calorimetry in Encyclopedia of Controlled Drug Delivery, 1999, John Wiley & Sons, pp. 212-227.
Toogood, J.H.; Glucocorticoids and Asthma; Glucocorticoids, 2001, pp. 161-174.
Tronche, F., et al; Genetic dissection of glucocorticoid receptor function in mice; Curr. Opin in Genetics and Dev., 1998, 8, pp. 532-538.
Vainshtein et al. A High-Throughput, Nonisotopic, Competitive Binding Assay for Kinases Using Nonselective Inhibitor Probes (ED-NSIP); Journal of Biomolecular Screening, vol. 7, No. 6 (2003) pp. 507-514.
Vankayalapati, H. et al. "Targeting Aurora2 Kinase in Oncogenesis: A Structural Bioinformatics Approach to Target Validation and Rational Drug Design" Molecular Cancer Therapeutics 2003, 2, p. 283-294.
Vas et al. Antagonistic Binding of Substrates to 3-Phosphoglycerate Kinase Monitored by the Fluorescent Analogue 2'(3')-O-(2,4,6-Trinitrophenyl)Adenosine 5'-Triphosphate; Biochemical Journal, vol. 301 (1994) pp. 885-891.
Vippagunta, et al; "Crystalline solids" Advanced Drug Delivery Reviews, 48, 2001, p. 3-26.
Wolff, Manfred E., Ed. Burger's Medicinal Chemistry and Drug Discovery—Fifth Edition, New York: John Wiley & Sons, 1996 vol. 1, pp. 975-976.
Hu,Hong, et al: "Synthesis and protein kinase C inhibitory activities of indane analogs of balanol" Bioorganic & Medicinal Chemistry Letters, Oxford, GB vol. 6, No. 8, Apr. 23, 1996, pp. 973-978.
Abstract JP37004545, inventors Yoshida and Fukuda, assignee Nippon Shinyaku Co., Ltd, Jun. 14, 1962.
Bravo, P., et al; Synthesis of (-)-(1S,5R) and (+)-1R,5S)-trifluoroanalogues of frontalin; Tetrahedron Letters 40 (1999)—6317-6320.
Arnone et al: "Highly Diastereoselective Methylene Transfer from Diazomethane to the Carbonyl of b-Keto Sulfoxides. A General approach to Synthetically Versatile Fluorine-Containing Chiral Building Blocks." Tetrahedron 54 (1998) pp. 11841-11860.
Ambrosi et al: "Stereoselective Ssynthesis of Trifluoro- and Monofluro-Analogues of Frontaliln and Evaluation of Their Biological Activity." J. Org. Chem. 2001, 66, p. 8336-8343.
Wu and Farrley, Toxicology 236: 1-6 2007.
Osipov, Serge J.N. et al: a-Fluoromethyl Tryptophans via Imino Ene Reaction Synlett 2001, No. 8, 1287-1289, Letter.
Zembower, D.E. et al: "Enantiospecific Syntheses of Alpha-Fluoromethyl) Tryptophan Analogues: Interatctions with Tryptophan Hydroxylase and Aromatic L-Amino Acid Decarboxylase", Journal of Medicinal Chemistry, American Chemical Society, Washing, US vol. 36, No. 3 Feb. 5, 1993 p. 305-313.
Patani, et al; Bioisosterism: A Rational Approach in Drug Design, 1996, Chem Rev, vol. 96, p. 3147-3150.
Bundgaard, Design of Prodrugs, 1985, Elsevier, p. 1-3.
Prodrug [online], [retrieved on Mar. 26, 2007], Retrieved from the Internet, URL: http://en.wikipedia.org/wiki/Prodrug>.
Takami et al.: synthesis of 4,4,4-trifluoro-3-indolylisocrotonamides: Medicinal Chemistry Research, vol. 9, No. 4, 1999, pp. 239-248.
Maligres, P et al: "Nosylaziridines: Activated Aziridine Electrophiles" Tetrhedron Letters, Elsevier, Amsterdam, vol. 38, No. 30, Jul. 28, 1997, p. 5253-5256.
International Search Report PCT/US07/85831 mailed Jul. 4, 2008.

(56) References Cited

OTHER PUBLICATIONS

Amat-M-et-al-Preparations-and-reactions-of-4-5-and-6-methoxy-substituted-3-lithioindoles-and-3-indolylzinc-derivatives-Synthesis-2001-pp. 267-275.
Berry-M-B-et-al-A-convenient-method-for-preparation-of-enantiomerically-pure-2-substituted-N-tosylaziridines-Synlett-1992-pp. 41-44.
Tochilkin-A-I-et-al-8-methoxy-5-quinolinesulfonyl-chloride-A-new-fluorogenic-reagent-for-the-detection-of-amines-and-amino-acids-Bioorganicheskaya-Khimiya-1990-vol. 16-pp. 956-962.
Abstract of DE 1017612 cited herein under foreign documents—1959-121889 caplus 53:121889;53:21820H-i21821a-c; Tertiary Amines and Derivatives Thereof, Thomae GmbH DE 1017612.
Abstract—JP 59 053479A Mar. 28, 1984.
Abstract Mikhailitsyn, F.S, et al Search for New Antiparasitic Agents 10, Synthesis, Toxicity and Antimalarial Effect of Some Nitrogen Containing Heterocycles iwth 4-(4-alkylpiperazin-1yl)phenylamino-substituents-CAPLUS accession No. 1888, AN-1992:651317.
Abstract of JP 11080131A cited herein under Foreign documents—New ethynyl-pyrimidine derivatives have excellent tyrosine kinase inhibiting and cancer cell growth inhibiting activity Sep. 1, 1997 Mitsubishi Chemical Corporation.
Abstract of Japan vol. 010 No. 004(C322) Jan. 9, 1986 & JP 60 163814A, (Wataru Mori), Aug. 26, 1985 Abstract.
Bailey et al., CA 80:3337,1974.
Bailey, A. Sydney, et al: Further Examination of the reactions of Simple Indoles with Arenosulphonyl Azides, PD 1973, pp. 1602-1606.
Bamberger, C.M, et al; Molecular mechanisms of dissociative glucocorticoid activity; Eur. J. Clin. Invest. 2000, 30, Suppl 3, pp. 6-9.
Barnes N.J. Allergy Clin. Immunol. Apr. 1998; 101 (4 Pt 2), S460-464 Abstract.
Barnes, P.J., Anti-inflammatory actions of glucocorticoids; molecular mechanisms; Clinical Science 1998 vol. 94, pp. 557-572.
Barnes, P.J., Anti-inflammatory actions of steroids; molecular mechanisms; Trends Pharm. Sci. 1993, 14, pp. 436-441.
Beilstein No. 7067440—J. Chem. Soc. Dalton, Trans. , vol. 22, 1994, pp. 3202-3210.
Bledsoe, K.R., Cell, 2002, vol. II0, p. 93-105.
CA Registry No. 288843-68-5—entry date into Registry file on STN is Sep. 13, 2000.
CA Registry No. 311781-49-4—entry date into Registry file on STN is Dec. 28, 2000.
CA Registry No. 442531-80-8—entry date into Registry file on STN is Aug. 5, 2002.
CA Registry No. 442531-85-3—entry date into Registry file on STN is Aug. 5, 2002.
CA Registry No. 442630-99-1—entry date into Registry file on STN is Aug. 6, 2002.
CA Registry No. 442632-92-0—entry date into Registry file on STN is Aug. 6, 2002.
CA Registry No. 442632-93-1—entry date into Registry file on STN is Aug. 6, 2002.
CA Registry No. 442633-42-3—entry date into Registry file on STN is Aug. 6, 2002.
CA Registry No. 442657-75-2—entry date into Registry file on STN is Aug. 6, 2006.
CA Registry No. 442657-79-6—entry date into Registry file on STN is Aug. 6, 2006.
CA Registry No. 442657-92-3—entry date into Registry file on STN is Aug. 6, 2006.
CA Registry No. 442658-57-3—entry date into Registry file on STN is Aug. 6, 2006.
CA Registry No. 442658-66-4—entry date into Registry file on STN is Aug. 6, 2006.
CA Registry No. 442658-95-9—entry date into Registry file on STN is Aug. 6, 2006.
CA Registry No. 442666-01-5—entry date into Registry file on STN is Aug. 6, 2006.
CA Registry No. 442666-02-6—entry date into Registry file on STN is Aug. 6, 2006.
Casella, Luigi, et al. "Cytochrome c Oxidase Models; Synthesis and Reactivity of Iron (III)-Copper (II) Complexes of Deuterohaemin-Polybenzimidazole Dinucleating Ligands" J. Chem. Soc. Dalton Trans, 1994, vol. 22, pp. 3202-3210.
Coghlan M.J. et al J. Med Chem. 2001, 44, 2879,-2885 (pp. 2880).
Beilstein Registry No. 318403 and 341608; Beilstein Institut zur Foerderung ger Chemischen Wissenschaffen, Frankfurt Am Main, DE, Entry date Jun. 27, 1998 update date May 13, 1992.
Davis, CA 92:40803, 1980.
Doerwald, F.Z.: "Side Reactions in Organic Synthesis: A Guide o Successful Synthesis Design" 2005 Wiley & Co KGaA Weinheim.
Epps et al. An Experimental Method for the Determination of Ensyme-Competitive Inhibitor Dissociation Constants from Displacement Curves: Application to Human Renin Using Fluorescence Energy Transfer to a Synthetic Dansylated Inhibitor Peptide; Analytical Biochemistry, vol. 181 (1989) pp. 172-181.
Evans, R.M., The Steroid and Thyroid Hormone Receptor Superfamily; Science 1988, 240, pp. 889-895.
Friedman, J.E., et al; Phosphoenolpyruvate Carboxykinase (GTP) Gene Transcription and Hyperglycemia Are Regulated by Glucocorticoids in Genetically Obese db/db Transgenic Mice; J. Biol. Chem. 1997, 272, pp. 31475-31481.
Hagiwara, et al; "Lewis Base Catalyzed Trifluoromethylation of Carbonyl Compounds with Trialkyl(trifluoromethyl) silanes," Main Group Chem. 1997, vol. 2, p. 13.
Hall et al., Tetrahedron, 23, (1967), pp. 4131-4141.
Heck, S., et al "A distinct modulating domain in glucocorticoid receptor monomers in the repression of activity of the transcription factor AP-1" EMBO. J. 1994, 17, pp. 4087-4095.
Ho et al., Journal of Pharmaceutical Sciences (1971), 60(4), pp. 636-637.
Ho, B.T., et al; Central Nervous system Depressive Activity of some Amides of Tryptamine, J. Med. Chem., vol. 14, No. 6, 1971 pp. 553-554.
International Search Report PCT/US2004/031009 mailed Mar. 2, 2005.
Iseki, K. et al; "Asymmetric Trifluoromethylation of Aldehydes and Ketones with Trifluoromethyltrimethylsilane Catalysed by Chiral Quarternary Ammonium Fluorides"; Tetrahedron Letters, vol. 35, No. 19, 1994, pp. 3137-3138.
Janoshazi, A. et al. "Rapid Vitro Conformational Changes of the Catalytic Site of PKCalpha Assessed by FIM-1 Fluorescence" Biochemistry 1999,38, p. 13316-13327.
Jordan V.C., Nature Reviews: Drug Discovery, 2, 2003, p. 205.
Misztal-S-et-al-New-synthesis-of-5-nitro-and-5-benzyloxytryptamine-and-theirN-acyl-derivatives—Polish-Journal-of-Pharmacology-and-Pharmacy-1984-vol. 36-pp. 345-349.
Abstract—Chemical Encylopaedic Dictionary, Moscow Soviet Encyclopeadia (1983) pp. 130-131.
Abstract—Mashkovsky M.D. Drugs, Moscow, Medicine (1993) vol. 1, p. 8.
Abstract Karavan V.S., et al "Method of producing benzyl trifluorornethyl ketones by Grignard reaction" CAPLUS accession No.: AN-1992:128371 (1992).
Abstract, Mikhailitsyn, F.S. et al, New Synthesis of Derivatives of 6,6' diquinoline from 4,4'-diaminodiphenykl-3,3'dicarboxylic acid;—XP002266777 (1974).
Bailey et al.; New asymmetric route to bridged indole alkaloids: formal enantiospecific syntheses of (-)-suaveoline, (-)-raumacline and (-)-Nb-methylraumacline; Journal of the Chemical Society; 1997; Perkin Trans. pp. 1209-1214.
Banker G.S. et al.; editor "Modern Pharmaceutics, 3rd edition" Marcel Dekker, Inc. 1996, pp. 451 and 596.
Beilstein Registry No. 7178110 and 7178430, Online, Beilstein Institut zur Foerderung ger Chemischen Wissenschaffen, Frankfurt Am Main, DE, (1989).
Betageri, R.; U.S. Appl. No. 11/185,349, Office Action dated Jul. 14, 2009.
Biggadike, Keith et al. "Nonsteroidal Glucocorticoid Agonists: Tetrahydronaphthalens with Alternative Steroidal A-Ring Mimetics

(56) References Cited

OTHER PUBLICATIONS

Possessing Dissociated (Transrepression/Transactivation) Efficacy Selectivity" J. Med. Chem. (2007) vol. 50, pp. 6519-6534.

Elliott et al.; Studies in the Indole Series. Part IV. Sulphonamides derived from Indole; Journal of Chemical Society; 1944; pp. 632-633.

Fahrenholtz, Kenneth E. et al. "3-Phenyl-5-[2,2,2-trifluoro-1-hydroxy-1-(trifluoromethyl)ethyl]indole-2-carbonitrile, a Potent Inhibitor of Prostaglandin Synthetase and of Platelet Aggregation" (1979) Journal of Medicinal Chemistry vol. 22, No. 8, pp. 948-953.

Fleming et al.; CA 64:9697 f-g; 1966.

Hawley's Condensed Chemical Dictionary 14th Edition (2001).

Hoffmann, Reinhard W. et al. "Towards an Understanding of Cram/anti-Cram Selectivity on Addition of Crotylboronates to a-Methylbutyraldehyde" Chem. Ber. (1990) vol. 123, pp. 2387-2394.

Lee, Thomas W. et al. "A concise asymmetric route for the synthesis of a novel class of glucocorticoid mimetics containing a trifluoromethyl-substituted alcohol" (2006) Bioorganic & Medicinal Chemistry Letters pp. 654-657.

McGill et al.; Telmisartan Plus Hydrochlorothiazide Versus Telmisartan or Hydrochlorothiazide Monotherapy in Patients with Mild to Moderate Hypertension: A Multicenter, Randomized, Double-Blind, Placebo-Controlled, Parallel-Group Trial; Clinical Therapeutics; 2001; vol. 23; No. 6; pp. 833-850.

Otsuki et al.; Reaction of N-Haloamide. XXII. Reaction of N,N-dibromobenzenesulfonamide with safrole; Chemical Pharmaceutical Bulletin; 1975; vol. 23; No. 3; pp. 482-486.

Response filed Sep. 18, 2009 to Office Action dated Jul. 14, 2009, U.S. Appl. No. 11/185,349.

Takami, Hitoshi et al. "Synthetic Studies on Trifluoroacetylindoles" Heterocycles (1999) vol. 51, No. 5 pp. 1119-1124.

Troschuetz et al.; Sensitive and Specific Determination of Serotonin in the Presence of Tryptamine and 5-Methoxytryptamine by High-Pressure Liquid-Chromatography; Fresenious Zeitschrift fuer Analytische Chemi; 1978; No. 289; pp. 202-205.

West, Anthony R. "Solid state chemistry and its applications" Wiley & Sons, 1988 pp. 358 and 365.

WO02051983 (Part 1 of 2) International Publication Date: Jul. 4, 2002. Patentee: Celera, an Applera Corporation Business. Inventor: Frank Halley. Title: Novel Compounds and Compositions of Cathespin Inhibitors. Total pp. 724. Part 1 of 2. This foreign patent is too large for EFS submission via the Foreign patent section, therefore filing in two parts in the NPL section. pp. 1-350.

WO02051983 (Part 2 of 2) International Publication Date: Jul. 4, 2002. Patentee: Celera, an Applera Corporation Business. Inventor: Frank Halley. Title: Novel Compounds and Compositions of Cathespin Inhibitors. Total pp. 724. Part 2 of 2. This foreign patent is too large for EFS submission via the Foreign patent section, therefore filing in two parts in the NPL section. pp. 351-724.

* cited by examiner

GLUCOCORTICOID MIMETICS, METHODS OF MAKING THEM, PHARMACEUTICAL COMPOSITIONS AND USES THEREOF

RELATED APPLICATIONS

This application claims benefit of U.S. Ser. No. 60/505,456, filed Sep. 24, 2003, and U.S. Ser. No. 60/507,079, filed Sep. 29, 2003, each of which is hereby incorporated by reference in its entirety.

FIELD OF THE INVENTION

The present invention relates to glucocorticoid mimetics or ligands, methods of making such compounds, their use in pharmaceutical compositions, and their use in modulating the glucocorticoid receptor function, treating disease-states or conditions mediated by the glucocorticoid receptor function in a patient in need of such treatment, and other uses.

BACKGROUND OF THE INVENTION

Glucocorticoids, a class of corticosteroids, are endogenous hormones with profound effects on the immune system and multiple organ systems. They suppress a variety of immune and inflammatory functions by inhibition of inflammatory cytokines such as IL-1, IL-2, IL-6, and TNF, inhibition of arachidonic acid metabolites including prostaglandins and leukotrienes, depletion of T-lymphocytes, and reduction of the expression of adhesion molecules on endothelial cells (P. J. Barnes, Clin. Sci., 1998, 94, pp. 557-572; P. J. Barnes et al., Trends Pharmacol. Sci., 1993, 14, pp. 436-441). In addition to these effects, glucocorticoids stimulate glucose production in the liver and catabolism of proteins, play a role in electrolyte and water balance, reduce calcium absorption, and inhibit osteoblast function.

The anti-inflammatory and immune suppressive activities of endogenous glucocorticoids have stimulated the development of synthetic glucocorticoid derivatives including dexamethasone, prednisone, and prednisolone (L. Parente, Glucocorticoids, N. J. Goulding and R. J. Flowers (eds.), Boston: Birkhauser, 2001, pp. 35-54). These have found wide use in the treatment of inflammatory, immune, and allergic disorders including rheumatic diseases such as rheumatoid arthritis, juvenile arthritis, and ankylosing spondylitis, dermatological diseases including psoriasis and pemphigus, allergic disorders including allergic rhinitis, atopic dermatitis, and contact dermatitis, pulmonary conditions including asthma and chronic obstructive pulmonary disease (COPD), and other immune and inflammatory diseases including Crohn disease, ulcerative colitis, systemic lupus erythematosus, autoimmune chronic active hepatitis, osteoarthritis, tendonitis, and bursitis (J. Toogood, Glucocorticoids, N. J. Goulding and R. J. Flowers (eds.), Boston: Birkhauser, 2001, pp. 161-174). They have also been used to help prevent rejection in organ transplantation.

Unfortunately, in addition to the desired therapeutic effects of glucocorticoids, their use is associated with a number of adverse side effects, some of which can be severe and life-threatening. These include alterations in fluid and electrolyte balance, edema, weight gain, hypertension, muscle weakness, development or aggravation of diabetes mellitus, and osteoporosis. Therefore, a compound that exhibited a reduced side effect profile while maintaining the potent anti-inflammatory effects would be particularly desirable especially when treating a chronic disease.

The effects of glucocorticoids are mediated at the cellular level by the glucocorticoid receptor (R. H. Oakley and J. Cidlowski, Glucocorticoids, N. J. Goulding and R. J. Flowers (eds.), Boston: Birkhauser, 2001, pp. 55-80). The glucocorticoid receptor is a member of a class of structurally related intracellular receptors that when coupled with a ligand can function as a transcription factor that affects gene expression (R. M. Evans, Science, 1988, 240, pp. 889-895). Other members of the family of steroid receptors include the mineralocorticoid, progesterone, estrogen, and androgen receptors. In addition to the effects mentioned above for glucocorticoids, hormones that act on this receptor family have a profound influence on body homeostasis, mineral metabolism, the stress response, and development of sexual characteristics. Glucocorticoids, N. J. Goulding and R. J. Flowers (eds.), Boston: Birkhauser, 2001, is hereby incorporated by reference in its entirety to better describe the state of the art.

A molecular mechanism which accounts for the beneficial anti-inflammatory effects and the undesired side effects has been proposed (e.g., S. Heck et al., EMBO J. 1994, 17, pp. 4087-4095; H. M. Reichardt et al., Cell, 1998, 93, pp. 531-541; F. Tronche et al., Curr. Opin. in Genetics and Dev., 1998, 8, pp. 532-538). Many of the metabolic and cardiovascular side effects are thought to be the result of a process called transactivation. In transactivation, the translocation of the ligand-bound glucocorticoid receptor to the nucleus is followed by binding to glucocorticoid response elements (GREs) in the promoter region of side effect-associated genes, for example, phosphoenolpyruvate carboxy kinase (PEPCK), in the case of increased glucose production. The result is an increased transcription rate of these genes which is believed to result, ultimately, in the observed side effects. The anti-inflammatory effects are thought to be due to a process called transrepression. In general, transrepression is a process independent of DNA binding that results from inhibition of NF-kB and AP-1-mediated pathways, leading to down regulation of many inflammatory and immune mediators. Additionally, it is believed that a number of the observed side effects may be due to the cross-reactivity of the currently available glucocorticoids with other steroid receptors, particularly the mineralocorticoid and progesterone receptors.

Thus, it may be possible to discover ligands for the glucocorticoid receptor that are highly selective and, upon binding, can dissociate the transactivation and transrepression pathways, providing therapeutic agents with a reduced side effect profile. Assay systems to determine effects on transactivation and transrepression have been described (e.g., C. M. Bamberger and H. M. Schulte, Eur. J. Clin. Invest., 2000, 30 (suppl. 3), pp. 6-9). Selectivity for the glucocorticoid receptor may be determined by comparing the binding affinity for this receptor with that of other steroid family receptors including those mentioned above.

Glucocorticoids also stimulate the production of glucose in the liver by a process called gluconeogenesis and it is believed that this process is mediated by transactivation events. Increased glucose production can exacerbate type II diabetes, therefore a compound that selectivity inhibited glucocorticoid mediated glucose production may have therapeutic utility in this indication (J. E. Freidman et al., J. Biol. Chem., 1997, 272, pp. 31475-31481).

Novel ligands for the glucocorticoid receptor have been described in the scientific and patent literature. For example, PCT International Publication No. WO 99/33786 discloses triphenylpropanamide compounds with potential use in treating inflammatory diseases. PCT International Publication No. WO 00/66522 describes non-steroidal compounds as selective modulators of the glucocorticoid receptor potentially useful in treating metabolic and inflammatory diseases. PCT International Publication No. WO 99/41256 describes tetracyclic modulators of the glucocorticoid receptor potentially useful in treating immune, autoimmune, and inflammatory diseases. U.S. Pat. No. 5,688,810 describes various non-steroidal compounds as modulators of glucocorticoid and other steroid receptors. PCT International Publication No. WO 99/63976 describes a non-steroidal, liver-selective glucocorticoid antagonist potentially useful in the treatment of diabetes. PCT International Publication No. WO 00/32584 discloses non-steroidal compounds having anti-inflammatory activity with dissociation between anti-inflammatory and metabolic effects. PCT International Publication No. WO 98/54159 describes non-steroidal cyclically substituted acylanilides with mixed gestagen and androgen activity. U.S. Pat. No. 4,880,839 describes acylanilides having progestational activity and EP 253503 discloses acylanilides with antiandrogenic properties. PCT International Publication No. WO 97/27852 describes amides that are inhibitors of farnesyl-protein transferase.

A compound that is found to interact with the glucocorticoid receptor in a binding assay could be an agonist or an antagonist. The agonist properties of the compound could be evaluated in the transactivation or transrepression assays described above. Given the efficacy demonstrated by available glucocorticoid drugs in inflammatory and immune diseases and their adverse side effects, there remains a need for novel glucocorticoid receptor agonists with selectivity over other members of the steroid receptor family and a dissociation of the transactivation and transrepression activities. Alternatively, the compound may be found to have antagonist activity. As mentioned above, glucocorticoids stimulate glucose production in the liver. Increased glucose production induced by glucocorticoid excess can exacerbate existing diabetes, or trigger latent diabetes. Thus a ligand for the glucocorticoid receptor that is found to be an antagonist may be useful, inter alia, for treating or preventing diabetes.

Prior applications U.S. Ser. No. 60/367,798, filed Mar. 26, 2002, U.S. Ser. No. 60/431,817, filed Dec. 12, 2002, U.S. Ser. No. 60/442,404, filed Jan. 24, 2003, and U.S. patent application Pub. No. 2004/0023999, are each incorporated by reference in their entireties.

SUMMARY OF THE INVENTION

The instant invention is directed to compounds of Formula (IA)

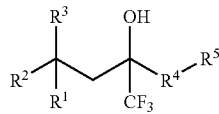

(IA)

wherein:
$R^1$ is an aryl or heteroaryl group, each optionally independently substituted with one to three substituent groups,
wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, $C_1$-$C_5$ alkanoyl, aroyl, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, nitro, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
wherein each substituent group of $R^1$ is optionally independently substituted with one to three substituent groups selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl;
$R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring;
$R^4$ is $C_1$-$C_5$ alkyl, $C_2$-$C_5$ alkenyl, or $C_2$-$C_5$ alkynyl, each optionally independently substituted with one to three substituent groups,
wherein each substituent group of $R^4$ is independently $C_1$-$C_3$ alkyl, hydroxy, halogen, amino, or oxo; and
$R^5$ is a heteroaryl group optionally independently substituted with one to three substituent groups,
wherein each substituent group of $R^5$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, heterocyclylcarbonyl, aroyl, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
wherein each substituent group of $R^5$ is optionally independently substituted with one to three substituent groups selected from $C_1$-$C_3$ alkyl, $C_1$-$C_3$ alkoxy, acyl, $C_1$-$C_3$ silanyloxy, $C_1$-$C_5$ alkoxycarbonyl, carboxy, halogen, hydroxy, oxo, cyano, aryl, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or trifluoromethyl,
or a tautomer, prodrug, solvate, or salt thereof.

Another aspect of the invention includes compounds of Formula (IA), wherein:
$R^1$ is thienyl, phenyl, naphthyl, dihydrobenzofuranyl, benzofuranyl, chromanyl, dihydroindolyl, indolyl, dihydrobenzothienyl, benzothienyl, benzodioxolanyl, dihydrobenzoxazolyl, benzoxazolyl, benzisoxazolyl, benzpyrazolyl, benzimidazolyl, thienyl, quinolinyl, pyridinyl, pyrimidinyl, or pyrazinyl, each optionally independently substituted with one to three substituent groups,
    wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, heterocyclyl, trifluoromethyl, trifluoromethoxy, nitro, amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or $C_1$-$C_3$ alkylthio wherein the sulfur atom is optionally oxidized to a sulfoxide or sulfone,
        wherein each substituent group of $R^1$ is optionally independently substituted with a substituent group selected from methyl, methoxy, halogen, hydroxy, oxo, cyano, or amino;

$R^2$ and $R^3$ are each independently hydrogen or $C_1$-$C_3$ alkyl, or $R^2$ and $R^3$ together with the carbon atom they are commonly attached to form a $C_3$-$C_6$ spiro cycloalkyl ring;

$R^4$ is $CH_2$; and $R^5$ is an imidazolyl, pyridyl, indolyl, indazolyl, azaindolyl, diazaindolyl, benzofuranyl, furanopyridinyl, furanopyrimidinyl, imidazolopyrimidinyl, imidazolopyridazinyl, imidazolopyrazinyl, benzothienyl, thienopyridinyl, thienopyrimidinyl, thienopyridazinyl, benzoxazolyl, oxazolopyridinyl, benzothiazolyl, thiazolopyridinyl, benzimidazolyl, imidazolopyridinyl, quinolinyl, or isoquinolinyl group, each optionally independently substituted with one to three substituent groups,
    wherein each substituent group of $R^5$ is independently $C_1$-$C_3$ alkyl, $C_2$-$C_3$ alkenyl, phenyl, $C_1$-$C_3$ alkoxy, methoxycarbonyl, aminocarbonyl, $C_1$-$C_3$ alkylaminocarbonyl, $C_1$-$C_3$ dialkylaminocarbonyl, heterocyclylcarbonyl, hydroxy, oxo, fluoro, chloro, bromo, cyano, trifluoromethyl, amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or $C_1$-$C_3$ alkylthio wherein the sulfur atom is optionally oxidized to a sulfoxide or sulfone,
        wherein each substituent group of $R^5$ is optionally independently substituted with a substituent group selected from methyl, methoxy, fluoro, chloro, bromo, oxo, or trifluoromethyl, hydroxy, cyano, or amino wherein the nitrogen atom is optionally independently mono- or di-substituted by $C_1$-$C_5$ alkyl or aryl, or a tautomer, prodrug, solvate, or salt thereof.

Yet another aspect of the invention includes compounds of Formula (IA), wherein:

$R^1$ is thienyl, phenyl, naphthyl, pyridyl, chromanyl, dihydrobenzofuranyl, or benzofuranyl, each optionally independently substituted with one or two substituent groups,
    wherein each substituent group of $R^1$ is independently methyl, ethyl, methoxy, ethoxy, fluoro, chloro, bromo, hydroxy, trifluoromethyl, trifluoromethoxy, cyano, or $C_1$-$C_3$ alkylthio wherein the sulfur atom is optionally oxidized to a sulfoxide or sulfone;

$R^2$ and $R^3$ are each independently methyl or ethyl, or $R^2$ and $R^3$ together with the carbon atom they are commonly attached to form a spiro cyclopropyl ring;

$R^4$ is $CH_2$; and $R^5$ is a pyridyl, indolyl, azaindolyl, diazaindolyl, benzofuranyl, furanopyridinyl, thienopyridinyl, benzoxazolyl, benzimidazolyl, quinolinyl, or isoquinolinyl group, each optionally independently substituted with one to three substituent groups,
    wherein each substituent group of $R^5$ is independently methyl, phenyl, methoxy, ethoxy, isopropoxy, methoxycarbonyl, aminocarbonyl, methylaminocarbonyl, dimethylaminocarbonyl, morpholinylcarbonyl, morpholinyl, piperidinyl, trifluoromethyl, fluoro, chloro, bromo, hydroxy, cyano, or amino wherein the nitrogen atom is optionally independently mono- or di-substituted by $C_1$-$C_5$ alkyl or aryl or trifluoromethyl, or a tautomer, prodrug, solvate, or salt thereof.

Yet another aspect of the invention includes compounds of Formula (IA), wherein:

$R^1$ is phenyl, dihydrobenzofuranyl, or benzofuranyl, each optionally independently substituted with one to three substituent groups,
    wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, or $C_1$-$C_3$ alkylthio wherein the sulfur atom is optionally oxidized to a sulfoxide or sulfone; and $R^2$ and $R^3$ are each independently hydrogen or $C_1$-$C_3$ alkyl, or a tautomer, prodrug, solvate, or salt thereof.

Yet another aspect of the invention includes compounds of Formula (IA), wherein:

$R^5$ is a pyridyl, indolyl, azaindolyl, diazaindolyl, benzofuranyl, furanopyridinyl, thienopyridinyl, benzoxazolyl, benzimidazolyl, quinolinyl, or isoquinolinyl group, each optionally independently substituted with one to three substituent groups, or a tautomer, prodrug, solvate, or salt thereof.

Another aspect of the invention includes compounds of Formula (IA), wherein:

$R^1$ is thienyl, phenyl, naphthyl, dihydrobenzofuranyl, benzofuranyl, chromanyl, dihydroindolyl, indolyl, dihydrobenzothienyl, benzothienyl, benzodioxolyl, dihydrobenzoxazolyl, benzoxazolyl, benzisoxazolyl, benzpyrazolyl, benzimidazolyl, thienyl, quinolinyl, pyridinyl, pyrimidinyl, or pyrazinyl, each optionally independently substituted with one to three substituent groups,
    wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, aryl, heteroaryl, halogen, hydroxy, carboxy, cyano, heterocyclyl, trifluoromethyl, trifluoromethoxy, nitro, aminosulfonyl, dialkylaminosulfonyl, amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or $C_1$-$C_3$ alkylthio wherein the sulfur atom is optionally oxidized to a sulfoxide or sulfone,
        wherein each substituent group of $R^1$ is optionally independently substituted with one or two substituent groups selected from methyl, methoxy, halogen, hydroxy, oxo, cyano, morpholinyl, or amino wherein the nitrogen atom is optionally independently mono- or di-substituted by $C_1$-$C_5$ alkyl;

$R^2$ and $R^3$ are each independently hydrogen or $C_1$-$C_3$ alkyl, or $R^2$ and $R^3$ together with the carbon atom they are commonly attached to form a $C_3$-$C_6$ spiro cycloalkyl ring;

$R^4$ is $CH_2$; and $R^5$ is an imidazolyl, pyridyl, indolyl, indazolyl, azaindolyl, diazaindolyl, benzofuranyl, furanopyridinyl, furanopyrimidinyl, imidazolopyrimidinyl, imidazolopyridazinyl, imidazolopyrazinyl, benzothienyl, thienopyridinyl, thienopyrimidinyl, thienopyridazinyl, benzoxazolyl, oxazolopyridinyl, benzothiazolyl, thiazolopyridinyl, benzimidazolyl, imidazolopyridinyl, quinolinyl, or isoquinolinyl group, each optionally independently substituted with one to three substituent groups, wherein each substituent group of $R^5$ is independently $C_1$-$C_3$ alkyl, $C_2$-$C_3$ alkenyl, phenyl, heteroaryl, heterocyclyl, acyl, dialkylaminosulfonyl, $C_1$-$C_3$ alkoxy, methoxycarbonyl, aminocarbonyl, $C_1$-$C_3$ alkylaminocarbonyl, $C_1$-$C_3$ dialkylaminocarbonyl, heterocyclylcarbonyl, hydroxy, oxo, fluoro, chloro, bromo, cyano, trifluoromethyl, amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl; or $C_1$-$C_3$ alkylthio wherein the sulfur atom is optionally oxidized to a sulfoxide or sulfone, wherein each substituent group of $R^5$ is optionally independently substituted with one or two substituent groups selected from methyl, methoxy, fluoro, chloro, bromo, oxo, trifluoromethyl, hydroxy, cyano, morpholinyl, pyrrolidinyl, or amino wherein the nitrogen atom is optionally independently mono- or di-substituted by $C_1$-$C_5$ alkyl or aryl, or a tautomer, prodrug, solvate, or salt thereof.

Yet another aspect of the invention includes compounds of Formula (IA), wherein:

$R^1$ is thienyl, phenyl, naphthyl, pyridyl, chromanyl, benzodioxolyl, dihydrobenzofuranyl, or benzofuranyl, each optionally independently substituted with one or two substituent groups, wherein each substituent group of $R^1$ is independently methyl, ethyl, methoxy, ethoxy, fluoro, chloro, bromo, hydroxy, trifluoromethyl, trifluoromethoxy, morpholinylmethyl, dimethylaminomethyl, aminosulfonyl, dimethylaminosulfonyl, phenyl, pyrimidinyl, pyridinyl, thienyl, naphthalenyl, morpholinyl, piperidinyl, cyano, or $C_1$-$C_3$ alkylthio wherein the sulfur atom is optionally oxidized to a sulfoxide or sulfone, wherein each substituent group of $R^1$ is optionally independently substituted with one or two groups selected from cyano, chloro, bromo, or fluoro;

$R^2$ and $R^3$ are each independently methyl or ethyl, or $R^2$ and $R^3$ together with the carbon atom they are commonly attached to form a spiro cyclopropyl ring;

$R^4$ is $CH_2$; and $R^5$ is a pyridyl, indolyl, azaindolyl, diazaindolyl, benzofuranyl, thienopyridazinyl, furanopyridinyl, thienopyridinyl, benzoxazolyl, benzimidazolyl, quinolinyl, or isoquinolinyl group, each optionally independently substituted with one to three substituent groups, wherein each substituent group of $R^5$ is independently methyl, phenyl, methoxy, ethoxy, isopropoxy, methoxycarbonyl, aminocarbonyl, methylaminocarbonyl, dimethylaminocarbonyl, morpholinylcarbonyl, morpholinyl, piperidinyl, phenoxy, pyrrolidinyl, acetyl, pivaloyl, ethylcarbonyl, isopropylcarbonyl, pyridinyl, pyrimidinyl, trifluoromethyl, fluoro, chloro, bromo, hydroxy, cyano, or amino wherein the nitrogen atom is optionally independently mono- or di-substituted by $C_1$-$C_5$ alkyl or aryl or trifluoromethyl, wherein each substituent group of $R^5$ is optionally independently substituted with one or two substituent groups selected from cyano, halogen, methyl, dimethylamino, morpholinyl, pyrrolidinyl, or piperidinyl, or a tautomer, prodrug, solvate, or salt thereof.

Yet another aspect of the invention includes compounds of Formula (IA), wherein:

$R^1$ is phenyl, dihydrobenzofuranyl, or benzofuranyl, each optionally independently substituted with one to three substituent groups, wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, aryl, heteroaryl, heterocyclyl, or $C_1$-$C_3$ alkylthio wherein the sulfur atom is optionally oxidized to a sulfoxide or sulfone; and $R^2$ and $R^3$ are each independently hydrogen or $C_1$-$C_3$ alkyl, or a tautomer, prodrug, solvate, or salt thereof.

Yet another aspect of the invention includes compounds of Formula (IA), wherein:

$R^5$ is a pyridyl, indolyl, azaindolyl, diazaindolyl, benzofuranyl, thienopyridazinyl furanopyridinyl, thienopyridinyl, benzoxazolyl, benzimidazolyl, quinolinyl, or isoquinolinyl group, each optionally independently substituted with one to three substituent groups, or a tautomer, prodrug, solvate, or salt thereof.

Representative compounds of Formula (IA) according to the invention are appended hereto as Table IA, where column A is the compound name according to standard nomenclature and column B is the corresponding chemical structure.

Preferred compounds of Formula (IA) include the following:

4-Cyclohexyl-1,1,1-trifluoro-4-methyl-2-quinolin-4-ylm-ethylpentan-2-ol;

4-Pyrimidin-5-yl-2-[4,4,4-trifluoro-3-hydroxy-1,1-dimethyl-3-(1H-pyrrolo[2,3-c]pyridin-2-ylmethyl)butyl]phenol;

1,1,1-Trifluoro-4-(5-fluoro-2-methoxyphenyl)-4-methyl-2-(3-methyl-1H-pyrrolo[3,2-c]pyridin-2-ylmethyl)pentan-2-ol;

1,1,1-Trifluoro-4-(5-fluoro-2,3-dihydrobenzofuran-7-yl)-4-methyl-2-(1H-pyrrolo[3,2-c]pyridin-2-ylmethyl)pentan-2-ol;

1,1,1-Trifluoro-4-(5-fluoro-2-methylphenyl)-4-methyl-2-(3-methyl-1H-pyrrolo[2,3-c]pyridin-2-ylmethyl)pentan-2-ol;

2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol;

2-(5,7-Dimethyl-1H-pyrrolo[2,3-c]pyridin-2-ylmethyl)-1,1,1-trifluoro-4-(5-fluoro-2-methoxyphenyl)-4-methylpentan-2-ol;

2-[4-(5-Fluoro-2-methoxyphenyl)-2-hydroxy-4-methyl-2-trifluoromethylpentyl]-1H-pyrrolo[3,2-b]pyridine-5-carbonitrile;

1,1,1-Trifluoro-4-(5-fluoro-2-methoxyphenyl)-4-methyl-2-(6-methyl-1H-pyrrolo[3,2-c]pyridin-2-ylmethyl)pentan-2-ol;

1,1,1-Trifluoro-4-(5-fluoro-2-methoxyphenyl)-4-methyl-2-(4-methyl-1H-pyrrolo[3,2-c]pyridin-2-ylmethyl)pentan-2-ol;

2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile;

2-[4-(5-Fluoro-2-methoxyphenyl)-2-hydroxy-4-methyl-2-trifluoromethylpentyl]-1H-pyrrolo[2,3-c]pyridine-5-carbonitrile;

2-[4-(5-Fluoro-2-methoxyphenyl)-2-hydroxy-4-methyl-2-trifluoromethylpentyl]-1H-pyrrolo[3,2-c]pyridine-4-carbonitrile;

1,1,1-Trifluoro-4-(5-fluoro-2-methoxyphenyl)-4-methyl-2-(5H-pyrrolo[3,2-d]pyrimidin-6-ylmethyl)pentan-2-ol;

1,1,1-Trifluoro-4-(5-fluoro-2-methoxyphenyl)-4-methyl-2-thieno[2,3-d]pyridazin-2-ylmethylpentan-2-ol;

1,1,1-Trifluoro-4-(5-fluoro-2-methoxyphenyl)-4-methyl-2-(5H-pyrrolo[3,2-c]pyridazin-6-ylmethyl)pentan-2-ol;

1,1,1-Trifluoro-4-(5-fluoro-2-methoxyphenyl)-4-methyl-2-(2-methyl-5H-pyrrolo[3,2-d]pyrimidin-6-ylmethyl)pentan-2-ol;

1,1,1-Trifluoro-4-(5-fluoro-2-methylphenyl)-4-methyl-2-(1H-pyrrolo[2,3-d]pyridazin-2-ylmethyl)pentan-2-ol;

2-(4,6-Dimethyl-1H-pyrrolo[3,2-c]pyridin-2-ylmethyl)-1,1,1-trifluoro-4-(5-fluoro-2-methylphenyl)-4-methylpentan-2-ol;

4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol;

2-[4-(5-Fluoro-2-methylphenyl)-2-hydroxy-4-methyl-2-trifluoromethylpentyl]-1H-pyrrolo[3,2-b]pyridine-5-carbonitrile;

4-(5-Chloro-2,3-dihydrobenzofuran-7-yl)-1,1,1-trifluoro-4-methyl-2-(3-methyl-1H-pyrrolo[2,3-c]pyridin-2-ylmethyl)pentan-2-ol;

1,1,1-Trifluoro-4-(5-fluoro-2-methylphenyl)-4-methyl-2-(5H-pyrrolo[3,2-c]pyridazin-6-ylmethyl)pentan-2-ol;

4-(5-Chloro-2,3-dihydrobenzofuran-7-yl)-1,1,1-trifluoro-4-methyl-2-(5H-pyrrolo[3,2-c]pyridazin-6-ylmethyl)pentan-2-ol;

4-(5-Chloro-2,3-dihydrobenzofuran-7-yl)-1,1,1-trifluoro-4-methyl-2-(1H-pyrrolo[2,3-d]pyridazin-2-ylmethyl)pentan-2-ol;

1,1,1-Trifluoro-4-(5-fluoro-2-methoxyphenyl)-2-(7-fluoro-1H-pyrrolo[2,3-c]pyridin-2-ylmethyl)-4-methylpentan-2-ol;

1,1,1-Trifluoro-4-(5-fluoro-2-methoxyphenyl)-4-methyl-2-(4-methyl-1H-pyrrolo[2,3-c]pyridin-2-ylmethyl)pentan-2-ol;

2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-(5-trifluoromethyl-1H-pyrrolo[2,3-c]pyridin-2-ylmethyl)pentan-2-ol;

1,1,1-Trifluoro-4-(5-fluoro-2-methoxyphenyl)-2-(5-methoxy-1H-pyrrolo[2,3-c]pyridin-2-ylmethyl)-4-methylpentan-2-ol;

1,1,1-Trifluoro-4-(5-fluoro-2-methylphenyl)-4-methyl-2-(4-methyl-1H-pyrrolo[2,3-c]pyridin-2-ylmethyl)pentan-2-ol;

1,1,1-Trifluoro-4-(5-fluoro-2-methylphenyl)-2-(5-isopropoxy-1H-pyrrolo[2,3-c]pyridin-2-ylmethyl)-4-methylpentan-2-ol;

1,1,1-Trifluoro-4-(5-fluoro-2-methylphenyl)-2-(5-methoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol;

1,1,1-Trifluoro-4-(5-fluoro-2-methylphenyl)-2-(7-fluoro-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(5-trifluoromethyl-1H-pyrrolo[2,3-c]pyridin-2-ylmethyl)pentan-2-ol;

1,1,1-Trifluoro-4-(5-fluoro-2-methylphenyl)-4-methyl-2-(5-trifluoromethyl-1H-pyrrolo[2,3-c]pyridin-2-ylmethyl)pentan-2-ol;

4-(5-Chloro-2,3-dihydrobenzofuran-7-yl)-1,1,1-trifluoro-2-(5-isopropoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-2-(7-fluoro-1H-pyrrolo[2,3-c]pyridin-2-ylmethyl)-4-methylpentan-2-ol;

4-(5-Chloro-2,3-dihydrobenzofuran-7-yl)-2-(5-dimethylamino-1H-pyrrolo[2,3-c]pyridin-2-ylmethyl)-1,1,1-trifluoro-4-methylpentan-2-ol;

4-(5-Chloro-2,3-dihydrobenzofuran-7-yl)-1,1,1-trifluoro-4-methyl-2-(5-piperidin-1-yl-1H-pyrrolo[2,3-c]pyridin-2-ylmethyl)pentan-2-ol;

4-(5-Chloro-2,3-dihydrobenzofuran-7-yl)-1,1,1-trifluoro-4-methyl-2-(5-morpholin-4-yl-1H-pyrrolo[2,3-c]pyridin-2-ylmethyl)pentan-2-ol;

1,1,1-Trifluoro-4-(5-fluoro-2-methylphenyl)-4-methyl-2-(5-piperidin-1-yl-1H-pyrrolo[2,3-c]pyridin-2-ylmethyl)pentan-2-ol;

4-(5-Chloro-2,3-dihydrobenzofuran-7-yl)-2-(5-ethoxy-1H-pyrrolo[2,3-c]pyridin-2-ylmethyl)-1,1,1-trifluoro-4-methylpentan-2-ol;

2-(5-Benzyloxy-1H-pyrrolo[2,3-c]pyridin-2-ylmethyl)-1,1,1-trifluoro-4-(5-fluoro-2-methylphenyl)-4-methylpentan-2-ol;

2-(5-Benzyloxy-1H-pyrrolo[2,3-c]pyridin-2-ylmethyl)-4-(5-chloro-2,3-dihydrobenzofuran-7-yl)-1,1,1-trifluoro-4-methylpentan-2-ol;

1,1,1-Trifluoro-4-(5-fluoro-2-methoxyphenyl)-2-(5-chloro-1H-pyrrolo[2,3-c]pyridin-2-ylmethyl)-4-methylpentan-2-ol;

1,1,1-Trifluoro-4-(5-fluoro-2-methoxyphenyl)-4-methyl-2-[5-(methylamino)-1H-pyrrolo[2,3-c]pyridin-2-ylmethyl]pentan-2-ol;

1,1,1-Trifluoro-4-(5-fluoro-2-methoxyphenyl)-4-methyl-2-(5-amino-1H-pyrrolo[2,3-c]pyridin-2-ylmethyl)pentan-2-ol;

1,1,1-Trifluoro-4-(5-fluoro-2-methylphenyl)-4-methyl-2-(6-amino-1H-pyrrolo[2,3-c]pyridin-2-ylmethyl)pentan-2-ol;

4-(5-Chloro-2,3-dihydrobenzofuran-7-yl)-1,1,1-trifluoro-2-(5-amino-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(5-methylamino-1H-pyrrolo[2,3-c]pyridin-2-ylmethyl)pentan-2-ol;

7-[4-(5-Fluoro-2-methoxyphenyl)-2-hydroxy-4-methyl-2-trifluoromethylpentyl]-1H-pyrrolo[2,3-b]pyridin-7-ium chloride;

6-[4-(5-Fluoro-2-methoxyphenyl)-2-hydroxy-4-methyl-2-trifluoromethylpentyl]-2-methyl-1H-pyrrolo[2,3-c]pyridin-6-ium chloride;

4-(5-Bromo-2,3-dihydrobenzofuran-7-yl)-1,1,1-trifluoro-4-methyl-2-(1H-pyrrolo[2,3-c]pyridin-2-ylmethyl)pentan-2-ol;
1,1,1-Trifluoro-4-methyl-4-(5-methyl-2,3-dihydrobenzofuran-7-yl)-2-(1H-pyrrolo[2,3-c]pyridin-2-ylmethyl)pentan-2-ol;
4-(5-Chloro-2,3-dihydrobenzofuran-7-yl)-1,1,1-trifluoro-4-methyl-2-(1H-pyrrolo[2,3-c]pyridin-2-ylmethyl)pentan-2-ol;
1,1,1-Trifluoro-4-(5-fluoro-2-methoxyphenyl)-4-methyl-2-pyrrolo[2,3-b]pyridin-1-ylmethylpentan-2-ol;
1,1,1-Trifluoro-4-(5-fluoro-2-methoxyphenyl)-4-methyl-2-(6-oxy-1H-pyrrolo[2,3-c]pyridin-2-ylmethyl)pentan-2-ol;
1,1,1-Trifluoro-4-(5-fluoro-2-methoxyphenyl)-4-methyl-2-pyrrolo[2,3-c]pyridin-1-ylmethylpentan-2-ol;
2-Benzo[b]thiophen-2-ylmethyl-1,1,1-trifluoro-4-(5-fluoro-2-methoxyphenyl)-4-methylpentan-2-ol;
1,1,1-Trifluoro-4-(5-fluoro-2-methoxyphenyl)-4-methyl-2-thieno[2,3-c]pyridin-2-ylmethylpentan-2-ol;
1,1,1-Trifluoro-4-(5-fluoro-2-methoxyphenyl)-2-indazol-1-ylmethyl-4-methylpentan-2-ol;
1,1,1-Trifluoro-4-(5-fluoro-2-methoxyphenyl)-4-methyl-2-[4-((Z)propenyl)-3-vinylpyrazol-1-ylmethyl]pentan-2-ol;
1,1,1-Trifluoro-4-(5-fluoro-2-methoxyphenyl)-4-methyl-2-pyrazolo[1,5-a]pyridin-2-ylmethylpentan-2-ol;
4-(5-Chloro-2,3-dihydrobenzofuran-7-yl)-2,4-dimethyl-1-thieno[2,3-c]pyridin-2-ylpentan-2-ol;
4-(5-Fluoro-2-methylphenyl)-2,4-dimethyl-1-thieno[2,3-c]pyridin-2-ylpentan-2-ol;
1,1,1-Trifluoro-4-(5-fluoro-2-methoxyphenyl)-2-furo[2,3-c]pyridin-2-ylmethyl-4-methylpentan-2-ol;
4-(5-Chloro-2,3-dihydrobenzofuran-7-yl)-1-furo[2,3-c]pyridin-2-yl-2,4-dimethylpentan-2-ol;
4-(5-Fluoro-2-methylphenyl)-1-furo[2,3-c]pyridin-2-yl-2,4-dimethylpentan-2-ol;
1,1,1-Trifluoro-4-(5-fluoro-2-methylphenyl)-4-methyl-2-(1H-pyrrolo[3,2-c]pyridin-2-ylmethyl)pentan-2-ol;
1,1,1-Trifluoro-4-methyl-4-(5-methyl-2,3-dihydrobenzofuran-7-yl)-2-(1H-pyrrolo[3,2-c]pyridin-2-ylmethyl)pentan-2-ol;
4-(5-Chloro-2,3-dihydrobenzofuran-7-yl)-1,1,1-trifluoro-4-methyl-2-(1H-pyrrolo[3,2-c]pyridin-2-ylmethyl)pentan-2-ol;
4-(5-Bromo-2,3-dihydrobenzofuran-7-yl)-1,1,1-trifluoro-4-methyl-2-(1H-pyrrolo[3,2-c]pyridin-2-ylmethyl)pentan-2-ol;
2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol;
1,1,1-Trifluoro-4-(5-fluoro-2-methoxyphenyl)-4-methyl-2-pyrrolo[3,2-c]pyridin-1-ylmethylpentan-2-ol;
1,1,1-Trifluoro-4-(5-fluoro-2-methoxyphenyl)-4-methyl-2-pyrrolo[3,2-b]pyridin-1-ylmethylpentan-2-ol;
1,1,1-Trifluoro-4-(5-fluoro-2-methoxyphenyl)-2-furo[3,2-c]pyridin-2-ylmethyl-4-methylpentan-2-ol;
4-(5-Chloro-2,3-dihydrobenzofuran-7-yl)-1,1,1-trifluoro-4-methyl-2-pyrrolo[3,2-b]pyridin-1-ylmethylpentan-2-ol;
1,1-Difluoro-4-(5-fluoro-2-methoxyphenyl)-4-methyl-2-(1H-pyrrolo[3,2-c]pyridin-2-ylmethyl)pentan-2-ol;
1,1,1-Trifluoro-4-(5-fluoro-2-methoxyphenyl)-4-methyl-2-thieno[3,2-c]pyridin-2-ylmethylpentan-2-ol;
4-(5-Chloro-2,3-dihydrobenzofuran-7-yl)-1,1,1-trifluoro-4-methyl-2-thieno[3,2-c]pyridin-2-ylmethylpentan-2-ol;
1,1,1-Trifluoro-4-(5-fluoro-2-methylphenyl)-4-methyl-2-pyrrolo[3,2-b]pyridin-1-ylmethylpentan-2-ol;
1,1,1-Trifluoro-4-(5-fluoro-2-methoxyphenyl)-4-methyl-2-thieno[3,2-c]pyridin-2-ylmethylpentan-2-ol;
4-Fluoro-2-(4,4,4-trifluoro-3-hydroxy-1,1-dimethyl-3-thieno[3,2-c]pyridin-2-ylmethylbutyl)phenol;
4-Fluoro-2-(4,4,4-trifluoro-3-furo[3,2-c]pyridin-2-ylmethyl-3-hydroxy-1,1-dimethylbutyl)phenol;
4-Fluoro-2-(4,4,4-trifluoro-3-hydroxy-1,1-dimethyl-3-pyrrolo[3,2-b]pyridin-1-ylmethylbutyl)phenol;
2-[4-(5-Fluoro-2-hydroxyphenyl)-2-hydroxy-4-methyl-2-trifluoromethylpentyl]-1H-indole-6-carboxylic acid;
2-[4-(5-Fluoro-2-hydroxyphenyl)-2-hydroxy-4-methyl-2-trifluoromethylpentyl]-1H-indole-6-carboxylic acid dimethylamide;
{2-[4-(5-Fluoro-2-hydroxyphenyl)-2-hydroxy-4-methyl-2-trifluoromethylpentyl]-1H-indol-6-yl}morpholin-4-yl-methanone;
2-[4-(5-Fluoro-2-methoxyphenyl)-2-hydroxy-4-methyl-2-trifluoromethylpentyl]-1H-indole-6-carboxylic acid dimethylamide;
2-[4-(5-Fluoro-2-methoxyphenyl)-2-hydroxy-4-methyl-2-trifluoromethylpentyl]-1H-indole-6-carboxylic acid dimethylamide;
{2-[4-(5-Fluoro-2-methoxyphenyl)-2-hydroxy-4-methyl-2-trifluoromethylpentyl]-1H-indol-6-yl}morpholin-4-yl-methanone;
2-[4-(2,3-Dihydrobenzofuran-7-yl)-2-hydroxy-4-methyl-2-trifluoromethylpentyl]-4-methyl-1H-indole-6-carbonitrile;
2-[4-(5-Fluoro-2-hydroxyphenyl)-2-hydroxy-4-methyl-2-trifluoromethylpentyl]-1H-indole-6-carboxylic acid amide;
2-[4-(5-Fluoro-2-methoxyphenyl)-2-hydroxy-4-methyl-2-trifluoromethylpentyl]-1H-indole-6-carboxylic acid amide;
4-Fluoro-2-[4,4,4-trifluoro-3-hydroxy-1,1-dimethyl-3-(5-nitro-1H-indol-2-ylmethyl)butyl]phenol;
2-[4-(5-Fluoro-2-methoxyphenyl)-2-hydroxy-4-methyl-2-trifluoromethylpentyl]-1H-indole-6-carbonitrile;
2-[4-(5-Fluoro-2-hydroxyphenyl)-2-hydroxy-4-methyl-2-trifluoromethylpentyl]-1H-indole-6-carbonitrile;
N-{2-[4-(5-Fluoro-2-methoxyphenyl)-2-hydroxy-4-methyl-2-trifluoromethylpentyl]-1H-indol-5-yl}acetamide;
1,1,1-Trifluoro-4-(4-fluoro-2-methoxyphenyl)-2-(7-fluoro-4-methyl-1H-indol-2-ylmethyl)-4-methylpentan-2-ol;
5-Fluoro-2-[4,4,4-trifluoro-3-(7-fluoro-4-methyl-1H-indol-2-ylmethyl)-3-hydroxy-1,1-dimethylbutyl]phenol;
2-[4-(3-[1,3]Dioxolan-2-ylphenyl)-2-hydroxy-4-methyl-2-trifluoromethylpentyl]-1H-indole-5-carbonitrile;
2-[4-(5-Fluoro-2-methoxyphenyl)-2-hydroxy-4-methyl-2-trifluoromethylpentyl]-1H-indole-5-carboxylic acid-2-trimethylsilanylethyl ester;
2-[4-(5-Fluoro-2-methoxyphenyl)-2-hydroxy-4-methyl-2-trifluoromethylpentyl]-1H-indole-5-carboxylic acid;
2-[4-(4-Fluoro-2-hydroxyphenyl)-2-hydroxy-4-methyl-2-trifluoromethylpentyl]-4-methyl-1H-indole-6-carbonitrile;
{2-[4-(5-Fluoro-2-methoxyphenyl)-2-hydroxy-4-methyl-2-trifluoromethylpentyl]-1H-indol-5-yl}piperidin-1-yl-methanone;
2-[4-(5-Fluoro-2-methoxyphenyl)-2-hydroxy-4-methyl-2-trifluoromethylpentyl]-1H-indole-5-carboxylic acid methylamide;
{2-[4-(5-Fluoro-2-methoxyphenyl)-2-hydroxy-4-methyl-2-trifluoromethylpentyl]-1H-indol-5-yl}pyrrolidin-1-yl-methanone;
1-{2-[4-(5-Fluoro-2-methoxyphenyl)-2-hydroxy-4-methyl-2-trifluoromethylpentyl]-1H-indole-5-carbonyl}piperidin-4-one;

2-[4-(5-Fluoro-2-methoxyphenyl)-2-hydroxy-4-methyl-2-trifluoromethylpentyl]-1H-indole-5-carboxylic acid (2-hydroxyethyl)amide;

{2-[4-(5-Fluoro-2-methoxyphenyl)-2-hydroxy-4-methyl-2-trifluoromethylpentyl]-1H-indol-5-yl}(4-hydroxypiperidin-1-yl)methanone;

{2-[4-(5-Fluoro-2-methoxyphenyl)-2-hydroxy-4-methyl-2-trifluoromethylpentyl]-1H-indol-5-yl}(3-hydroxypyrrolidin-1-yl)methanone;

2-[4-(5-Fluoro-2-methoxyphenyl)-2-hydroxy-4-methyl-2-trifluoromethylpentyl]-1H-indole-5-carboxylic acid cyanomethylamide;

2-[4-(5-Fluoro-2-methoxyphenyl)-2-hydroxy-4-methyl-2-trifluoromethylpentyl]-1H-indole-5-carboxylic acid (2-dimethylaminoethyl)amide;

{2-[4-(5-Fluoro-2-methoxyphenyl)-2-hydroxy-4-methyl-2-trifluoromethylpentyl]-1H-indol-5-yl}(4-methylpiperazin-1-yl)methanone;

({2-[4-(5-Fluoro-2-methoxyphenyl)-2-hydroxy-4-methyl-2-trifluoromethylpentyl]-1H-indole-5-carbonyl}amino)acetic acid methyl ester;

2-[4-(5-Fluoro-2-methoxyphenyl)-2-hydroxy-4-methyl-2-trifluoromethylpentyl]-1H-indole-5-carboxylic acid carbamoylmethylamide;

4-({2-[4-(5-Fluoro-2-methoxyphenyl)-2-hydroxy-4-methyl-2-trifluoromethylpentyl]-1H-indole-5-carbonyl}amino)butyric acid methyl ester;

({2-[4-(5-Fluoro-2-methoxyphenyl)-2-hydroxy-4-methyl-2-trifluoromethylpentyl]-1H-indole-5-carbonyl}amino)acetic acid;

4-({2-[4-(5-Fluoro-2-methoxyphenyl)-2-hydroxy-4-methyl-2-trifluoromethylpentyl]-1H-indole-5-carbonyl}amino)butyric acid;

2-[4-(3-Dimethylaminomethylphenyl)-2-hydroxy-4-methyl-2-trifluoromethylpentyl]1H-indole-5-carbonitrile;

4-Fluoro-2-[4,4,4-trifluoro-3-hydroxy-1,1-dimethyl-3-(5-trifluoromethyl-1H-indol-2-ylmethyl)butyl]phenol;

2-[4-(5-Bromo-2,3-dihydrobenzofuran-7-yl)-2-hydroxy-4-methyl-2-trifluoromethylpentyl]-4-methyl-1H-indole-6-carbonitrile;

2-[2-Hydroxy-4-(5-methanesulfonyl-2,3-dihydrobenzofuran-7-yl)-4-methyl-2-trifluoromethylpentyl]-4-methyl-1H-indole-6-carbonitrile;

2-[4-(5-Bromo-2,3-dihydrobenzofuran-7-yl)-2-hydroxy-4-methyl-2-trifluoromethylpentyl]-1H-indole-5-carboxylic acid;

2-[4-(5-Bromo-2,3-dihydrobenzofuran-7-yl)-2-hydroxy-4-methyl-2-trifluoromethylpentyl]-1H-indole-5-carboxylic acid amide;

2-[4-(5-Bromo-2,3-dihydrobenzofuran-7-yl)-2-hydroxy-4-methyl-2-trifluoromethylpentyl]-1H-indole-5-carboxylic acid dimethylamide;

2-[4-(5-Bromo-2,3-dihydrobenzofuran-7-yl)-2-hydroxy-4-methyl-2-trifluoromethylpentyl]-1H-indole-5-carboxylic acid cyanomethylamide;

{2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone;

{2-[4-(5-Bromo-2,3-dihydrobenzofuran-7-yl)-2-hydroxy-4-methyl-2-trifluoromethylpentyl]-1H-indol-5-yl}morpholin-4-ylmethanone;

2-[4-(5-Fluoro-2-methoxyphenyl)-2-hydroxy-4-methyl-2-trifluoromethylpentyl]-1H-indole-5-carboxylic acid amide;

{2-[4-(5-Fluoro-2-methoxyphenyl)-2-hydroxy-4-methyl-2-trifluoromethylpentyl]-1H-indol-5-yl}morpholin-4-ylmethanone;

2-(4-Benzo[1,3]dioxol-4-yl-2-hydroxy-4-methyl-2-trifluoromethylpentyl)-4-methyl-1H-indole-6-carbonitrile;

1,1,1-Trifluoro-4-methyl-4-phenyl-2-quinolin-4-ylmethylhexan-2-ol;

2-[2-Hydroxy-4-methyl-4-(5-methylsulfanyl-2,3-dihydrobenzofuran-7-yl)-2-trifluoromethylpentyl]-1H-indole-3-carbonitrile;

7-(4,4,4-Trifluoro-3-hydroxy-1,1-dimethyl-3-quinolin-4-ylmethylbutyl)-2,3-dihydrobenzofuran-5-carbonitrile;

2-[2-Hydroxy-4-(5-methanesulfonyl-2,3-dihydrobenzofuran-7-yl)-4-methyl-2-trifluoromethylpentyl]-1H-indole-3-carbonitrile;

2-[2-Hydroxy-4-(2-hydroxy-5-methylphenyl)-4-methyl-2-trifluoromethylpentyl]-4-methyl-1H-indole-6-carbonitrile;

1,1,1-Trifluoro-4-(5-fluoro-2,3-dihydrobenzofuran-7-yl)-4-methyl-2-(5-methylsulfanyl-1H-indol-2-ylmethyl)pentan-2-ol;

2-[2-Hydroxy-4-(2-methoxy-5-methylsulfanylphenyl)-4-methyl-2-trifluoromethylpentyl]-1H-indole-3-carbonitrile;

2-[2-Hydroxy-4-(5-methanesulfonyl-2-methoxyphenyl)-4-methyl-2-trifluoromethylpentyl]-1H-indole-3-carbonitrile;

2-[4-(5-Fluoro-2,3-dihydrobenzofuran-7-yl)-2-hydroxy-4-methyl-2-trifluoromethylpentyl]-1H-indole-5-sulfonic acid dimethylamide;

1,1,1-Trifluoro-4-(5-fluoro-2,3-dihydrobenzofuran-7-yl)-4-methyl-2-(5-phenyl-1H-indol-2-ylmethyl)pentan-2-ol;

2-[4-(5-tert-Butyl-2-hydroxyphenyl)-2-hydroxy-4-methyl-2-trifluoromethylpentyl]-1H-indole-3-carbonitrile;

2-[2-Hydroxy-4-(2-hydroxy-5-isopropylphenyl)-4-methyl-2-trifluoromethylpentyl]-1H-indole-3-carbonitrile;

2-[2-Hydroxy-4-(2-hydroxy-3,5-dimethylphenyl)-4-methyl-2-trifluoromethylpentyl]-1H-indole-3-carbonitrile;

2-[2-Hydroxy-4-(5-hydroxy-2,4-dimethylphenyl)-4-methyl-2-trifluoromethylpentyl]-1H-indole-3-carbonitrile;

2-[4-(5-tert-Butyl-2-methoxyphenyl)-2-hydroxy-4-methyl-2-trifluoromethylpentyl]-1H-indole-3-carbonitrile;

2-[4-(5-tert-Butyl-2-methoxyphenyl)-2-hydroxy-4-methyl-2-trifluoromethylpentyl]-1-methyl-1H-indole-3-carbonitrile;

2-[2-Hydroxy-4-(5-isopropyl-2-methoxyphenyl)-4-methyl-2-trifluoromethylpentyl]-1H-indole-3-carbonitrile;

2-[2-Hydroxy-4-(5-isopropyl-2-methoxyphenyl)-4-methyl-2-trifluoromethylpentyl]-1-methyl-1H-indole-3-carbonitrile;

2-[2-Hydroxy-4-(2-hydroxy-5-methanesulfonylphenyl)-4-methyl-2-trifluoromethylpentyl]-1H-indole-3-carbonitrile;

2-[2-Hydroxy-4-(2-methoxy-5-methylphenyl)-4-methyl-2-trifluoromethylpentyl]-4-methyl-1H-indole-6-carbonitrile;

1,1,1-Trifluoro-4-methyl-2-quinolin-4-ylmethyl-4-o-tolyl-pentan-2-ol;

1,1,1-Trifluoro-4-methyl-2-quinolin-4-ylmethyl-4-m-tolyl-pentan-2-ol;

1,1,1-Trifluoro-4-(2-fluorophenyl)-2-(1H-indol-2-ylmethyl)-4-methylpentan-2-ol;

1,1,1-Trifluoro-4-(2-fluorophenyl)-4-methyl-2-quinolin-4-ylmethylpentan-2-ol;

1,1,1-Trifluoro-4-(3-fluorophenyl)-2-(1H-indol-2-ylmethyl)-4-methylpentan-2-ol;

1,1,1-Trifluoro-4-(3-fluorophenyl)-4-methyl-2-quinolin-4-ylmethylpentan-2-ol;

1,1,1-Trifluoro-4-(4-fluorophenyl)-2-(1H-indol-2-ylmethyl)-4-methylpentan-2-ol;

1,1,1-Trifluoro-4-(4-fluorophenyl)-4-methyl-2-quinolin-4-ylmethylpentan-2-ol;
3-(4,4,4-Trifluoro-3-hydroxy-1,1-dimethyl-3-quinolin-4-ylmethylbutyl)phenol;
1,1,1-Trifluoro-4-methyl-2-quinolin-4-ylmethyl-4-(2-trifluoromethylphenyl)pentan-2-ol;
1,1,1-Trifluoro-2-(1H-indol-2-ylmethyl)-4-methyl-4-(4-trifluoromethylphenyl)pentan-2-ol;
1,1,1-Trifluoro-4-methyl-2-quinolin-4-ylmethyl-4-(4-trifluoromethylphenyl)pentan-2-ol;
4-(3-Chlorophenyl)-1,1,1-trifluoro-2-(1H-indol-2-ylmethyl)-4-methylpentan-2-ol;
4-(3-Chlorophenyl)-1,1,1-trifluoro-4-methyl-2-quinolin-4-ylmethylpentan-2-ol;
4-(4-Dimethylaminophenyl)-1,1,1-trifluoro-2-(1H-indol-2-ylmethyl)-4-methylpentan-2-ol;
4-Biphenyl-3-yl-1,1,1-trifluoro-4-methyl-2-quinolin-4-ylmethylpentan-2-ol;
4-(3-Bromophenyl)-1,1,1-trifluoro-2-(1H-indol-2-ylmethyl)-4-methylpentan-2-ol;
4-(2-Difluoromethoxy-5-fluorophenyl)-1,1,1-trifluoro-2-(1H-indol-2-ylmethyl)-4-methylpentan-2-ol;
4-Biphenyl-3-yl-1,1,1-trifluoro-2-(1H-indol-2-ylmethyl)-4-methylpentan-2-ol;
4-(4-Dimethylaminophenyl)-1,1,1-trifluoro-4-methyl-2-quinolin-4-ylmethylpentan-2-ol;
2-[4-(5-Fluoro-2-methylphenyl)-2-hydroxy-4-methyl-2-trifluoromethylpentyl]-1,6-dihydropyrrolo[2,3-c]pyridin-5-one;
2-[4-(5-Fluoro-2-methylphenyl)-2-hydroxy-4-methyl-2-trifluoromethylpentyl]-6-methyl-1,6-dihydropyrrolo[2,3-c]pyridin-5-one;
2-[4-(5-Fluoro-2-methylphenyl)-2-hydroxy-4-methyl-2-trifluoromethylpentyl]-4-methyl-1,4-dihydropyrrolo[3,2-b]pyridin-5-one;
1,1,1-Trifluoro-4-(5-fluoro-2-methylphenyl)-2-(6-methoxy-1H-pyrrolo[3,2-c]pyridin-2-ylmethyl)-4-methylpentan-2-ol;
2-[4-(5-Fluoro-2-methylphenyl)-2-hydroxy-4-methyl-2-trifluoromethylpentyl]-5-methyl-1,5-dihydropyrrolo[3,2-c]pyridin-6-one;
2-[4-(5-Fluoro-2-methylphenyl)-2-hydroxy-4-methyl-2-trifluoromethylpentyl]-1,3a-dihydropyrrolo[3,2-c]pyridin-6-one;
2-[4-(5-Fluoro-2-methylphenyl)-2-hydroxy-4-methyl-2-trifluoromethylpentyl]-1,7-dihydropyrrolo[3,2-c]pyridine-4,6-dione;
6-[4-(5-Fluoro-2-methylphenyl)-2-hydroxy-4-methyl-2-trifluoromethylpentyl]-1,7-dihydropyrrolo[2,3-d]pyrimidine-2,4-dione;
2-[4-(5-Chloro-2,3-dihydrobenzofuran-7-yl)-2-hydroxy-4-methyl-2-trifluoromethylpentyl]-1,6-dihydropyrrolo[2,3-c]pyridin-5-one;
2-[4-(5-Chloro-2,3-dihydrobenzofuran-7-yl)-2-hydroxy-4-methyl-2-trifluoromethylpentyl]-6-methyl-1,6-dihydropyrrolo[2,3-c]pyridin-5-one;
2-[4-(5-Chloro-2,3-dihydrobenzofuran-7-yl)-2-hydroxy-4-methyl-2-trifluoromethylpentyl]-1,4-dihydropyrrolo[3,2-b]pyridin-5-one;
2-[4-(5-Chloro-2,3-dihydrobenzofuran-7-yl)-2-hydroxy-4-methyl-2-trifluoromethylpentyl]-4-methyl-1,4-dihydropyrrolo[3,2-b]pyridin-5-one;
2-[4-(5-Chloro-2,3-dihydrobenzofuran-7-yl)-2-hydroxy-4-methyl-2-trifluoromethylpentyl]-1,5-dihydropyrrolo[3,2-c]pyridin-6-one;
2-[4-(5-Chloro-2,3-dihydrobenzofuran-7-yl)-2-hydroxy-4-methyl-2-trifluoromethylpentyl]-5-methyl-1,5-dihydropyrrolo[3,2-c]pyridin-6-one;
4-(5-Chloro-2,3-dihydrobenzofuran-7-yl)-1,1,1-trifluoro-2-(6-methoxy-5,6-dihydro-1H-pyrrolo[3,2-c]pyridin-2-ylmethyl)-4-methylpentan-2-ol;
2-[4-(5-Chloro-2,3-dihydrobenzofuran-7-yl)-2-hydroxy-4-methyl-2-trifluoromethylpentyl]-1,7-dihydropyrrolo[3,2-c]pyridine-4,6-dione;
6-[4-(5-Chloro-2,3-dihydrobenzofuran-7-yl)-2-hydroxy-4-methyl-2-trifluoromethylpentyl]-3-methyl-1,7-dihydropyrrolo[2,3-d]pyrimidine-2,4-dione;
2-[4-(3-Dimethylaminomethylphenyl)-2-hydroxy-4-methyl-2-trifluoromethylpentyl]-1H-indole-5-carbonitrile;
1,1,1-Trifluoro-2-(1H-indol-2-ylmethyl)-4-methyl-4-(3-morpholin-4-ylmethylphenyl)pentan-2-ol;
1,1,1-Trifluoro-4-methyl-4-(3-morpholin-4-ylmethylphenyl)-2-(1H-pyrrolo[2,3-d]pyridazin-2-ylmethyl)pentan-2-ol;
1,1,1-Trifluoro-4-(5-fluoro-2-methylphenyl)-4-methyl-2-(5-morpholin-4-ylmethyl-1H-indol-2-ylmethyl)pentan-2-ol;
1,1,1-Trifluoro-4-(5-fluoro-2-methylphenyl)-4-methyl-2-(5-morpholin-4-ylmethyl-1H-pyrrolo[2,3-c]pyridin-2-ylmethyl)pentan-2-ol;
{2-[4-(5-Fluoro-2-methylphenyl)-2-hydroxy-4-methyl-2-trifluoromethylpentyl]-1H-indol-5-yl}phenylmethanone;
{2-[4-(5-Fluoro-2-methylphenyl)-2-hydroxy-4-methyl-2-trifluoromethylpentyl]-1H-pyrrolo[2,3-c]pyridin-5-yl}phenylmethanone;
{2-[4-(5-Fluoro-2-methylphenyl)-2-hydroxy-4-methyl-2-trifluoromethylpentyl]-1H-indol-5-yl}furan-2-ylmethanone;
{2-[4-(5-Fluoro-2-methylphenyl)-2-hydroxy-4-methyl-2-trifluoromethylpentyl]-1H-pyrrolo[2,3-c]pyridin-5-yl}furan-2-ylmethanone;
1,1,1-Trifluoro-2-(1H-indol-2-ylmethyl)-4-methyl-4-pyridin-2-ylpentan-2-ol;
4-(3-Chloro-2-fluoro-5-trifluoromethylbenzyl)-5,5,5-trifluoro-4-hydroxy-2-methyl-2-phenylpentanenitrile;
1,1,1-Trifluoro-4-methyl-4-pyridin-4-yl-2-quinolin-4-ylmethylpentan-2-ol;
2-(2,6-Dimethylpyridin-4-ylmethyl)-1,1,1-trifluoro-4-(5-fluoro-2-methoxyphenyl)-4-methylpentan-2-ol;
2-[3-(2,6-Dimethylpyridin-4-ylmethyl)-4,4,4-trifluoro-3-hydroxy-1,1-dimethylbutyl]-4-fluorophenol;
1,1,1-Trifluoro-4,4-dimethyl-5-phenyl-2-quinolin-4-ylmethylpentan-2-ol;
1,1,1-Trifluoro-4-(5-fluoro-2-methoxyphenyl)-4-methyl-2-pyridin-4-ylmethylpentan-2-ol;
4-Fluoro-2-[4,4,4-trifluoro-3-(2-fluoropyridin-4-ylmethyl)-3-hydroxy-1,1-dimethylbutyl]phenol;
2-[3-(2-Bromopyridin-4-ylmethyl)-4,4,4-trifluoro-3-hydroxy-1,1-dimethylbutyl]-4-fluorophenol;
2-(6,8-Dimethylquinolin-4-ylmethyl)-1,1,1-trifluoro-4-(5-fluoro-2-methoxyphenyl)-4-methylpentan-2-ol;
4-[4-(5-Fluoro-2-methoxyphenyl)-2-hydroxy-4-methyl-2-trifluoromethylpentyl]pyridine-2-carbonitrile;
2,6-Dichloro-4-[4-(5-fluoro-2-methoxyphenyl)-2-hydroxy-4-methyl-2-trifluoromethylpentyl]nicotinonitrile; 4-[4-(5-Fluoro-2-methoxyphenyl)-2-hydroxy-4-methyl-2-trifluoromethylpentyl]quinolin-2-ol;
2,6-Dichloro-4-[4-(5-fluoro-2-hydroxyphenyl)-2-hydroxy-4-methyl-2-trifluoromethylpentyl]nicotinonitrile;
2-(2-Chloro-8-methylquinolin-4-ylmethyl)-1,1,1-trifluoro-4-(5-fluoro-2-methoxyphenyl)-4-methylpentan-2-ol;
2-(2,6-Dichloroquinolin-4-ylmethyl)-1,1,1-trifluoro-4-(5-fluoro-2-methoxyphenyl)-4-methylpentan-2-ol;

2-[3-(2-Chloro-8-methylquinolin-4-ylmethyl)-4,4,4-trifluoro-3-hydroxy-1,1-dimethylbutyl]-4-fluorophenol;
2-[3-(2,6-Dichloroquinolin-4-ylmethyl)-4,4,4-trifluoro-3-hydroxy-1,1-dimethylbutyl]-4-fluorophenol;
4-(2,3-Dihydrobenzofuran-7-yl)-2-(2,6-dimethylpyridin-4-ylmethyl)-1,1,1-trifluoro-4-methylpentan-2-ol;
2-(2,6-Dimethylpyridin-4-ylmethyl)-1,1,1-trifluoro-4-(3-fluorophenyl)-4-methylpentan-2-ol;
2-(2,6-Dimethylpyridin-4-ylmethyl)-1,1,1-trifluoro-4-(4-fluorophenyl)-4-methylpentan-2-ol;
1,1,1-Trifluoro-4-(5-fluoro-2-methylphenyl)-4-methyl-2-quinolin-4-ylmethylpentan-2-ol;
2-(2,6-Dimethylpyridin-4-ylmethyl)-1,1,1-trifluoro-4-(5-fluoro-2-methylphenyl)-4-methylpentan-2-ol;
2-(2,6-Dimethylpyridin-4-ylmethyl)-1,1,1-trifluoro-4-methyl-4-m-tolylpentan-2-ol;
1,1,1-Trifluoro-4-(5-fluoro-2-methoxyphenyl)-4-methyl-2-(2-methylquinolin-4-ylmethyl)pentan-2-ol;
4-Fluoro-2-(4,4,4-trifluoro-3-hydroxy-1,1-dimethyl-3-quinolin-4-ylmethylbutyl)phenol;
4-Fluoro-2-[4,4,4-trifluoro-3-hydroxy-1,1-dimethyl-3-(2-methylquinolin-4-ylmethyl)butyl]phenol;
2-(2,6-Dimethylpyridin-4-ylmethyl)-1,1,1-trifluoro-4-(4-fluoro-2-methoxyphenyl)-4-methylpentan-2-ol;
1,1,1-Trifluoro-4-(5-fluoro-2-methoxyphenyl)-4-methyl-2-(7-methylquinolin-4-ylmethyl)pentan-2-ol;
2-[3-(2,6-Dimethylpyridin-4-ylmethyl)-4,4,4-trifluoro-3-hydroxy-1,1-dimethylbutyl]-5-fluorophenol;
2-(5,7-Dimethylquinolin-4-ylmethyl)-1,1,1-trifluoro-4-(5-fluoro-2-methoxyphenyl)-4-methylpentan-2-ol;
1,1,1-Trifluoro-4-(4-fluorophenyl)-4-methyl-2-(2-methylquinolin-4-ylmethyl)pentan-2-ol;
1,1,1-Trifluoro-4-(3-fluorophenyl)-4-methyl-2-(3-methyl-1H-indol-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-2-(7-fluoro-4-methylquinolin-8-yl)-4-methylpentan-2-ol;
4-(2,6-Dimethylphenyl)-1,1,1-trifluoro-2-(1H-indol-2-ylmethyl)-4-methylpentan-2-ol;
2-(3-Bromo-1H-indol-2-ylmethyl)-1,1,1-trifluoro-4-(3-fluorophenyl)-4-methylpentan-2-ol;
4-(3,4-Dimethylphenyl)-1,1,1-trifluoro-2-(1H-indol-2-ylmethyl)-4-methylpentan-2-ol;
1,1,1-Trifluoro-4-(3-fluoro-4-methylphenyl)-2-(1H-indol-2-ylmethyl)-4-methylpentan-2-ol;
1,1,1-Trifluoro-4-(4-fluoro-3-methylphenyl)-2-(1H-indol-2-ylmethyl)-4-methylpentan-2-ol;
1,1,1-Trifluoro-4-(3-fluoro-4-methylphenyl)-4-methyl-2-quinolin-4-ylmethylpentan-2-ol;
1,1,1-Trifluoro-4-(4-fluoro-2-methylphenyl)-4-methyl-2-quinolin-4-ylmethylpentan-2-ol;
4-(3,4-Dimethylphenyl)-1,1,1-trifluoro-4-methyl-2-quinolin-4-ylmethylpentan-2-ol;
4-(2,5-Dimethylphenyl)-1,1,1-trifluoro-2-(1H-indol-2-ylmethyl)-4-methylpentan-2-ol;
1,1,1-Trifluoro-2-(1H-indol-2-ylmethyl)-4-(2-methoxy-5-methylphenyl)-4-methylpentan-2-ol;
4-Methyl-2-[4,4,4-trifluoro-3-hydroxy-3-(1H-indol-2-ylmethyl)-1,1-dimethylbutyl]phenol;
4-(2,5-Dimethylphenyl)-1,1,1-trifluoro-4-methyl-2-quinolin-4-ylmethylpentan-2-ol;
1,1,1-Trifluoro-4-(2-methoxy-5-methylphenyl)-4-methyl-2-quinolin-4-ylmethylpentan-2-ol;
4-(2,5-Dimethoxyphenyl)-1,1,1-trifluoro-4-methyl-2-(1H-pyrrolo[2,3-c]pyridin-2-ylmethyl)pentan-2-ol;
1,1,1-Trifluoro-4-(5-fluoro-2-methoxyphenyl)-4-methyl-2-(7H-pyrrolo[2,3-d]pyrimidin-6-ylmethyl)pentan-2-ol;
1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol;
2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol;
2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol;
2-(2,4-Dimethyl-7H-pyrrolo[2,3-d]pyrimidin-6-ylmethyl)-1,1,1-trifluoro-4-(5-fluoro-2-methylphenyl)-4-methylpentan-2-ol;
2-(5-Chloro-1H-pyrrolo[2,3-c]pyridin-2-ylmethyl)-1,1,1-trifluoro-4-(5-fluoro-2-methylphenyl)-4-methylpentan-2-ol;
4-(5-Bromo-2-methoxyphenyl)-1,1,1-trifluoro-4-methyl-2-(5-piperidin-1-yl-1H-pyrrolo[2,3-c]pyridin-2-ylmethyl)pentan-2-ol;
1,1,1-Trifluoro-4-(5-fluoro-2-methoxyphenyl)-4-methyl-2-(5-morpholin-4-yl-1H-pyrrolo[2,3-c]pyridin-2-ylmethyl)pentan-2-ol;
4-(5-Bromo-2-methoxyphenyl)-1,1,1-trifluoro-4-methyl-2-(5-morpholin-4-yl-1H-pyrrolo[2,3-c]pyridin-2-ylmethyl)pentan-2-ol;
1,1,1-Trifluoro-4-(5-fluoro-2-methylphenyl)-4-methyl-2-(5-morpholin-4-yl-1H-pyrrolo[2,3-c]pyridin-2-ylmethyl)pentan-2-ol;
2-(5-Dimethylamino-1H-pyrrolo[2,3-c]pyridin-2-ylmethyl)-1,1,1-trifluoro-4-(5-methanesulfonyl-2,3-dihydrobenzofuran-7-yl)-4-methylpentan-2-ol;
1,1,1-Trifluoro-4-(5-methanesulfonyl-2,3-dihydrobenzofuran-7-yl)-4-methyl-2-(5-piperidin-1-yl-1H-pyrrolo[2,3-c]pyridin-2-ylmethyl)pentan-2-ol;
2-(5-Dimethylamino-1H-pyrrolo[2,3-c]pyridin-2-ylmethyl)-1,1,1-trifluoro-4-(5-fluoro-2-methylphenyl)-4-methylpentan-2-ol;
2-[5-(Ethylmethylamino)-1H-pyrrolo[2,3-c]pyridin-2-ylmethyl]-1,1,1-trifluoro-4-(5-fluoro-2-methylphenyl)-4-methylpentan-2-ol;
4-(5-Chloro-2,3-dihydrobenzofuran-7-yl)-2-[5-(ethylmethylamino)-1H-pyrrolo[2,3-c]pyridin-2-ylmethyl]-1,1,1-trifluoro-4-methylpentan-2-ol;
2-[5-(Ethylmethylamino)-1H-pyrrolo[2,3-c]pyridin-2-ylmethyl]-1,1,1-trifluoro-4-(5-fluoro-2-methoxyphenyl)-4-methylpentan-2-ol;
1,1,1-Trifluoro-4-methyl-2-(5-morpholin-4-yl-1H-pyrrolo[2,3-c]pyridin-2-ylmethyl)-4-phenylpentan-2-ol;
1,1,1-Trifluoro-4-(3-fluorophenyl)-4-methyl-2-(5-morpholin-4-yl-1H-pyrrolo[2,3-c]pyridin-2-ylmethyl)pentan-2-ol;
1,1,1-Trifluoro-4-(5-fluoro-2-methylphenyl)-4-methyl-2-(5-pyrrolidin-1-yl-1H-pyrrolo[2,3-c]pyridin-2-ylmethyl)pentan-2-ol;
1,1,1-Trifluoro-4-methyl-4-phenyl-2-(5-pyrrolidin-1-yl-1H-pyrrolo[2,3-c]pyridin-2-ylmethyl)pentan-2-ol;
4'-Methoxy-3'-[4,4,4-trifluoro-3-hydroxy-1,1-dimethyl-3-(5-morpholin-4-yl-1H-pyrrolo[2,3-c]pyridin-2-ylmethyl)butyl]biphenyl-2-carbonitrile;
2-(5-Diethylamino-1H-pyrrolo[2,3-c]pyridin-2-ylmethyl)-1,1,1-trifluoro-4-(5-fluoro-2-methylphenyl)-4-methylpentan-2-ol;
1,1,1-Trifluoro-4-(5-fluoro-2-methylphenyl)-2-[5-(isopropylmethylamino)-1H-pyrrolo[2,3-c]pyridin-2-ylmethyl]-4-methylpentan-2-ol;

1,1,1-Trifluoro-2-[5-(isopropylmethylamino)-1H-pyrrolo[2,3-c]pyridin-2-ylmethyl]-4-methyl-4-phenylpentan-2-ol;
2-(5-Diethylamino-1H-pyrrolo[2,3-c]pyridin-2-ylmethyl)-1,1,1-trifluoro-4-methyl-4-phenylpentan-2-ol;
4-(3-Bromophenyl)-1,1,1-trifluoro-4-methyl-2-(5-morpholin-4-yl-1H-pyrrolo[2,3-c]pyridin-2-ylmethyl)pentan-2-ol;
1,1,1-Trifluoro-4-(4-fluorophenyl)-4-methyl-2-(5-morpholin-4-yl-1H-pyrrolo[2,3-c]pyridin-2-ylmethyl)pentan-2-ol;
1,1,1-Trifluoro-4-(4-fluorophenyl)-4-methyl-2-(5-pyrrolidin-1-yl-1H-pyrrolo[2,3-c]pyridin-2-ylmethyl)pentan-2-ol;
1,1,1-Trifluoro-4-methyl-2-(5-morpholin-4-yl-1H-pyrrolo[2,3-c]pyridin-2-ylmethyl)-4-(3-pyrimidin-5-ylphenyl)pentan-2-ol;
2-[5-(2,6-Dimethylmorpholin-4-yl)-1H-pyrrolo[2,3-c]pyridin-2-ylmethyl]-1,1,1-trifluoro-4-(5-fluoro-2-methylphenyl)-4-methylpentan-2-ol;
2-[5-(Ethylmethylamino)-1H-pyrrolo[2,3-c]pyridin-2-ylmethyl]-1,1,1-trifluoro-4-methyl-4-phenylpentan-2-ol;
2-[5-(Ethylmethylamino)-1H-pyrrolo[2,3-c]pyridin-2-ylmethyl]-1,1,1-trifluoro-4-(3-fluorophenyl)-4-methylpentan-2-ol;
1,1,1-Trifluoro-4-(3-fluorophenyl)-4-methyl-2-(5-pyrrolidin-1-yl-1H-pyrrolo[2,3-c]pyridin-2-ylmethyl)pentan-2-ol;
2-(5-Diethylamino-1H-pyrrolo[2,3-c]pyridin-2-ylmethyl)-1,1,1-trifluoro-4-(3-fluorophenyl)-4-methylpentan-2-ol;
1,1,1-Trifluoro-4-(3-fluorophenyl)-2-[5-(isopropylmethylamino)-1H-pyrrolo[2,3-c]pyridin-2-ylmethyl]-4-methylpentan-2-ol;
3'-{3-[5-(Ethylmethylamino)-1H-pyrrolo[2,3-c]pyridin-2-ylmethyl]-4,4,4-trifluoro-3-hydroxy-1,1-dimethylbutyl}-4'-methoxybiphenyl-2-carbonitrile;
2-[5-(Ethylmethylamino)-1H-pyrrolo[2,3-c]pyridin-2-ylmethyl]-1,1,1-trifluoro-4-(2-methoxy-5-pyrimidin-5-ylphenyl)-4-methylpentan-2-ol;
3'-{3-[5-(Ethylmethylamino)-1H-pyrrolo[2,3-c]pyridin-2-ylmethyl]-4,4,4-trifluoro-3-hydroxy-1,1-dimethylbutyl}-4'-hydroxybiphenyl-2-carbonitrile;
4'-Hydroxy-3'-[4,4,4-trifluoro-3-hydroxy-1,1-dimethyl-3-(5-morpholin-4-yl-1H-pyrrolo[2,3-c]pyridin-2-ylmethyl)butyl]biphenyl-2-carbonitrile;
1,1,1-Trifluoro-4-(5-fluoro-2-methylphenyl)-4-methyl-2-(5-morpholin-4-ylmethyl-1H-pyrrolo[3,2-b]pyridin-2-ylmethyl)pentan-2-ol;
2-(5-Dimethylaminomethyl-1H-pyrrolo[3,2-b]pyridin-2-ylmethyl)-1,1,1-trifluoro-4-(5-fluoro-2-methylphenyl)-4-methylpentan-2-ol;
1,1,1-Trifluoro-4-(5-fluoro-2-methylphenyl)-4-methyl-2-[5-(4-methylpiperazin-1-ylmethyl)-1H-pyrrolo[3,2-b]pyridin-2-ylmethyl]pentan-2-ol;
4-(5-Chloro-2,3-dihydrobenzofuran-7-yl)-2-(5-dimethylaminomethyl-1H-pyrrolo[3,2-b]pyridin-2-ylmethyl)-1,1,1-trifluoro-4-methylpentan-2-ol;
4-(5-Chloro-2,3-dihydrobenzofuran-7-yl)-1,1,1-trifluoro-4-methyl-2-(5-morpholin-4-ylmethyl-1H-pyrrolo[3,2-b]pyridin-2-ylmethyl)pentan-2-ol;
4-Chloro-2-[4,4,4-trifluoro-3-hydroxy-1,1-dimethyl-3-(5-morpholin-4-ylmethyl-1H-pyrrolo[3,2-b]pyridin-2-ylmethyl)butyl]phenol;
1,1,1-Trifluoro-4-(5-fluoro-2-methylphenyl)-4-methyl-2-(4-methyl-1H-pyrrolo[3,2-c]pyridin-2-ylmethyl)pentan-2-ol;
4-(5-Chloro-2,3-dihydrobenzofuran-7-yl)-1,1,1-trifluoro-4-methyl-2-(4-methyl-1H-pyrrolo[3,2-c]pyridin-2-ylmethyl)pentan-2-ol;
1,1,1-Trifluoro-4-(5-fluoro-2-methylphenyl)-4-methyl-2-(5-methyl-1H-pyrrolo[2,3-c]pyridin-2-ylmethyl)pentan-2-ol;
4-(5-Chloro-2,3-dihydrobenzofuran-7-yl)-1,1,1-trifluoro-4-methyl-2-(5-methyl-1H-pyrrolo[2,3-c]pyridin-2-ylmethyl)pentan-2-ol;
2-[2-Hydroxy-4-(5-methanesulfonyl-2,3-dihydrobenzofuran-7-yl)-4-methyl-2-trifluoromethylpentyl]-4-methyl-1H-pyrrolo[3,2-c]pyridine-6-carbonitrile;
2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile;
1,1,1-Trifluoro-4-(5-fluoro-2-methylphenyl)-4-methyl-2-(5H-pyrrolo[3,2-d]pyrimidin-6-ylmethyl)pentan-2-ol;
2-[4-(5-Chloro-2,3-dihydrobenzofuran-7-yl)-2-hydroxy-4-methyl-2-trifluoromethylpentyl]-1H-pyrrolo[2,3-c]pyridine-5-carbonitrile;
2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid methyl ester;
1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}ethanone;
4-(5-Chloro-2,3-dihydrobenzofuran-7-yl)-1,1,1-trifluoro-4-methyl-2-(6H-pyrrolo[2,3-g]quinoxalin-7-ylmethyl)pentan-2-ol;
2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid amide;
2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid;
{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}morpholin-4-ylmethanone;
4-(5-Chloro-2,3-dihydrobenzofuran-7-yl)-1,1,1-trifluoro-2-(5-hydroxymethyl-1H-pyrrolo[3,2-b]pyridin-2-ylmethyl)-4-methylpentan-2-ol;
2-(5-Aminomethyl-1H-pyrrolo[3,2-b]pyridin-2-ylmethyl)-4-(5-chloro-2,3-dihydrobenzofuran-7-yl)-1,1,1-trifluoro-4-methylpentan-2-ol;
1,1,1-Trifluoro-4-(5-fluoro-2-methylphenyl)-4-methyl-2-(5H-pyrrolo[3,2-c]pyridazin-6-ylmethyl)pentan-2-ol;
4-Fluoro-2-[4,4,4-trifluoro-3-hydroxy-1,1-dimethyl-3-(5H-pyrrolo[3,2-c]pyridazin-6-ylmethyl)butyl]phenol;
4-Fluoro-2-[4,4,4-trifluoro-3-hydroxy-1,1-dimethyl-3-(5H-pyrrolo[3,2-d]pyrimidin-6-ylmethyl)butyl]phenol;
2-(6-Chloro-1H-pyrrolo[3,2-b]pyridin-2-ylmethyl)-1,1,1-trifluoro-4-(5-fluoro-2-methylphenyl)-4-methylpentan-2-ol;
4-(5-Chloro-2,3-dihydrobenzofuran-7-yl)-2-(6-chloro-1H-pyrrolo[3,2-b]pyridin-2-ylmethyl)-1,1,1-trifluoro-4-methylpentan-2-ol;
1,1,1-Trifluoro-4-(4-fluoro-2-methoxyphenyl)-4-methyl-2-(3-methyl-1H-pyrrolo[2,3-c]pyridin-2-ylmethyl)pentan-2-ol;
1,1,1-Trifluoro-4-(3-fluorophenyl)-4-methyl-2-(3-methyl-1H-pyrrolo[2,3-c]pyridin-2-ylmethyl)pentan-2-ol;
5-Fluoro-2-[4,4,4-trifluoro-3-hydroxy-1,1-dimethyl-3-(3-methyl-1H-pyrrolo[2,3-c]pyridin-2-ylmethyl)butyl]phenol;
4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(3-phenyl-7H-pyrrolo[2,3-c]pyridazin-6-ylmethyl)pentan-2-ol;

1,1,1-Trifluoro-4-(5-fluoro-2-methylphenyl)-4-methyl-2-(3-phenyl-7H-pyrrolo[2,3-c]pyridazin-6-ylmethyl)pentan-2-ol;

1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2,2-dimethylpropan-1-one;

2-[5-(1-tert-Butyl-1-hydroxy-2,2-dimethylpropyl)-1H-pyrrolo[3,2-b]pyridin-2-ylmethyl]-4-(5-chloro-2,3-dihydrobenzofuran-7-yl)-1,1,1-trifluoro-4-methylpentan-2-ol;

1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}propan-1-one;

1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2-methylpropan-1-one;

1,1,1-Trifluoro-4-(4-fluoro-2-methoxyphenyl)-4-methyl-2-(4-methyl-1H-pyrrolo[3,2-c]pyridin-2-ylmethyl)pentan-2-ol;

1,1,1-Trifluoro-4-(2-methoxy-5-thiophen-3-ylphenyl)-4-methyl-2-(4-methyl-1H-pyrrolo[3,2-c]pyridin-2-ylmethyl)pentan-2-ol;

1,1,1-Trifluoro-4-(4-methoxybiphenyl-3-yl)-4-methyl-2-(4-methyl-1H-pyrrolo[3,2-c]pyridin-2-ylmethyl)pentan-2-ol;

5-Fluoro-2-[4,4,4-trifluoro-3-hydroxy-1,1-dimethyl-3-(4-methyl-1H-pyrrolo[3,2-c]pyridin-2-ylmethyl)butyl]phenol;

4-Thiophen-3-yl-2-[4,4,4-trifluoro-3-hydroxy-1,1-dimethyl-3-(4-methyl-1H-pyrrolo[3,2-c]pyridin-2-ylmethyl)butyl]phenol;

3-[4,4,4-Trifluoro-3-hydroxy-1,1-dimethyl-3-(4-methyl-1H-pyrrolo[3,2-c]pyridin-2-ylmethyl)butyl]biphenyl-4-ol;

1,1,1-Trifluoro-4-methyl-2-(3-methyl-1H-pyrrolo[2,3-c]pyridin-2-ylmethyl)-4-(5-pyrimidin-5-yl-2,3-dihydrobenzofuran-7-yl)pentan-2-ol;

1,1,1-Trifluoro-4-(2-methoxy-5-pyridin-3-ylphenyl)-4-methyl-2-(3-methyl-1H-pyrrolo[2,3-c]pyridin-2-ylmethyl)pentan-2-ol;

4-Pyridin-3-yl-2-[4,4,4-trifluoro-3-hydroxy-1,1-dimethyl-3-(3-methyl-1H-pyrrolo[2,3-c]pyridin-2-ylmethyl)butyl]phenol;

1,1,1-Trifluoro-4-(5-fluoro-2,3-dihydrobenzofuran-7-yl)-4-methyl-2-(5H-pyrrolo[3,2-d]pyrimidin-6-ylmethyl)pentan-2-ol;

1,1,1-Trifluoro-4-(2-methoxy-5-pyridin-3-ylphenyl)-4-methyl-2-(5-phenoxy-1H-pyrrolo[2,3-c]pyridin-2-ylmethyl)pentan-2-ol;

1,1,1-Trifluoro-4-methyl-4-phenyl-2-(3-phenyl-7H-pyrrolo[2,3-c]pyridazin-6-ylmethyl)pentan-2-ol;

1,1,1-Trifluoro-4-(3-fluorophenyl)-4-methyl-2-(3-phenyl-7H-pyrrolo[2,3-c]pyridazin-6-ylmethyl)pentan-2-ol;

1,1,1-Trifluoro-4-(5-fluoro-2,3-dihydrobenzofuran-7-yl)-4-methyl-2-(5H-pyrrolo[3,2-d]pyrimidin-6-ylmethyl)pentan-2-ol;

1,1,1-Trifluoro-4-(2-methoxy-5-pyridin-3-ylphenyl)-4-methyl-2-(5-phenoxy-1H-pyrrolo[2,3-c]pyridin-2-ylmethyl)pentan-2-ol;

1,1,1-Trifluoro-4-methyl-4-phenyl-2-(3-phenyl-7H-pyrrolo[2,3-c]pyridazin-6-ylmethyl)pentan-2-ol;

1,1,1-Trifluoro-4-(3-fluorophenyl)-4-methyl-2-(3-phenyl-7H-pyrrolo[2,3-c]pyridazin-6-ylmethyl)pentan-2-ol;

1,1,1-Trifluoro-4-methyl-4-(3-morpholin-4-ylmethylphenyl)-2-(5-phenyl-1H-pyrrolo[2,3-c]pyridin-2-ylmethyl)pentan-2-ol;

1,1,1-Trifluoro-4-(3-fluorophenyl)-2-[5-(4-fluorophenyl)-1H-pyrrolo[2,3-c]pyridin-2-ylmethyl]-4-methylpentan-2-ol;

2-(5-Dimethylamino-1H-pyrrolo[2,3-c]pyridin-2-ylmethyl)-1,1,1-trifluoro-4-(5-fluoro-2-methoxyphenyl)-4-methylpentan-2-ol;

2-(5-Dimethylamino-1H-pyrrolo[2,3-c]pyridin-2-ylmethyl)-1,1,1-trifluoro-4-(4-fluoro-2-methoxyphenyl)-4-methylpentan-2-ol;

1,1,1-Trifluoro-4-(3-fluorophenyl)-4-methyl-2-(4-methyl-1H-pyrrolo[2,3-c]pyridin-2-ylmethyl)pentan-2-ol;

1,1,1-Trifluoro-4-(4-fluoro-2-methoxyphenyl)-4-methyl-2-(4-methyl-1H-pyrrolo[2,3-c]pyridin-2-ylmethyl)pentan-2-ol;

2-[3-(5-Dimethylamino-1H-pyrrolo[2,3-c]pyridin-2-ylmethyl)-4,4,4-trifluoro-3-hydroxy-1,1-dimethylbutyl]-4-fluorophenol;

2-[3-(5-Dimethylamino-1H-pyrrolo[2,3-c]pyridin-2-ylmethyl)-4,4,4-trifluoro-3-hydroxy-1,1-dimethylbutyl]-5-fluorophenol;

5-Fluoro-2-[4,4,4-trifluoro-3-hydroxy-1,1-dimethyl-3-(4-methyl-1H-pyrrolo[2,3-c]pyridin-2-ylmethyl)butyl]phenol;

4-(5-Bromo-2-methoxyphenyl)-1,1,1-trifluoro-4-methyl-2-(1H-pyrrolo[2,3-c]pyridin-2-ylmethyl)pentan-2-ol;

4-Bromo-2-[4,4,4-trifluoro-3-hydroxy-1,1-dimethyl-3-(1H-pyrrolo[2,3-c]pyridin-2-ylmethyl)butyl]phenol;

1,1,1-Trifluoro-4-(2-methoxy-5-pyrimidin-5-ylphenyl)-4-methyl-2-(1H-pyrrolo[2,3-c]pyridin-2-ylmethyl)pentan-2-ol;

4-(3-[1,3]Dioxan-2-ylphenyl)-1,1,1-trifluoro-4-methyl-2-(1H-pyrrolo[2,3-c]pyridin-2-ylmethyl)pentan-2-ol;

1,1,1-Trifluoro-4-(4-methoxybiphenyl-3-yl)-4-methyl-2-(1H-pyrrolo[2,3-c]pyridin-2-ylmethyl)pentan-2-ol;

1,1,1-Trifluoro-4-(2-methoxy-5-pyridin-3-ylphenyl)-4-methyl-2-(1H-pyrrolo[2,3-c]pyridin-2-ylmethyl)pentan-2-ol;

1,1,1-Trifluoro-4-(2-methoxy-5-thiophen-3-ylphenyl)-4-methyl-2-(1H-pyrrolo[2,3-c]pyridine-2-ylmethyl)pentan-2-ol;

1,1,1-Trifluoro-4-methyl-4-(3-morpholin-4-ylmethylphenyl)-2-(1H-pyrrolo[2,3-c]pyridin-2-ylmethyl)pentan-2-ol;

3-[4,4,4-Trifluoro-3-hydroxy-1,1-dimethyl-3-(1H-pyrrolo[2,3-c]pyridin-2-ylmethyl)butyl]biphenyl-4-ol;

4-Thiophen-3-yl-2-[4,4,4-trifluoro-3-hydroxy-1,1-dimethyl-3-(1H-pyrrolo[2,3-c]pyridin-2-ylmethyl)butyl]phenol;

4-Thiophen-3-yl-2-[4,4,4-trifluoro-3-hydroxy-1,1-dimethyl-3-(1H-pyrrolo[2,3-c]pyridin-2-ylmethyl)butyl]phenol;

4-Thiophen-3-yl-2-[4,4,4-trifluoro-3-hydroxy-1,1-dimethyl-3-(1H-pyrrolo[2,3-c]pyridin-2-ylmethyl)butyl]phenol;

4'-Methoxy-3'-[4,4,4-trifluoro-3-hydroxy-1,1-dimethyl-3-(4-methyl-1H-pyrrolo[2,3-c]pyridin-2-ylmethyl)butyl]biphenyl-2-carbonitrile;

4'-Methoxy-3'-[4,4,4-trifluoro-3-hydroxy-1,1-dimethyl-3-(1H-pyrrolo[2,3-c]pyridin-2-ylmethyl)butyl]biphenyl-3-carbonitrile;

1,1,1-Trifluoro-4-(2-methoxy-5-pyridin-3-ylphenyl)-4-methyl-2-(4-methyl-1H-pyrrolo[2,3-c]pyridin-2-ylmethyl)pentan-2-ol;

4-(3-Chlorophenyl)-1,1,1-trifluoro-4-methyl-2-(1H-pyrrolo[3,2-c]pyridin-2-ylmethyl)pentan-2-ol;

1,1,1-Trifluoro-4-(2-methoxy-5-pyrimidin-5-ylphenyl)-4-methyl-2-(1H-pyrrolo[3,2-c]pyridin-2-ylmethyl)pentan-2-ol;

4-Pyridin-3-yl-2-[4,4,4-trifluoro-3-hydroxy-1,1-dimethyl-3-(1H-pyrrolo[3,2-c]pyridin-2-ylmethyl)butyl]phenol;

1,1,1-Trifluoro-4-methyl-4-(3-morpholin-4-ylmethylphenyl)-2-(1H-pyrrolo[3,2-c]pyridin-2-ylmethyl)pentan-2-ol;

1,1,1-Trifluoro-4-(2-methoxy-5-pyridin-3-ylphenyl)-4-methyl-2-(1H-pyrrolo[3,2-c]pyridin-2-ylmethyl)pentan-2-ol;

1,1,1-Trifluoro-4-methyl-4-(3-pyridin-3-ylphenyl)-2-(1H-pyrrolo[3,2-c]pyridin-2-ylmethyl)pentan-2-ol;

1,1,1-Trifluoro-4-methyl-4-(3-pyrimidin-5-ylphenyl)-2-(1H-pyrrolo[3,2-c]pyridin-2-ylmethyl)pentan-2-ol;

1,1,1-Trifluoro-4-methyl-4-(3-pyridin-3-ylphenyl)-2-(1H-pyrrolo[2,3-c]pyridin-2-ylmethyl)pentan-2-ol;

1,1,1-Trifluoro-4-methyl-4-(3-pyrimidin-5-ylphenyl)-2-(1H-pyrrolo[2,3-c]pyridin-2-ylmethyl)pentan-2-ol;

4-(5-Chloro-2,3-dihydrobenzofuran-7-yl)-1,1,1-trifluoro-4-methyl-2-(5-pyridin-2-yl-1H-indol-2-ylmethyl)pentan-2-ol;

2-(5-Bromo-1H-indol-2-ylmethyl)-4-(5-chloro-2,3-dihydrobenzofuran-7-yl)-1,1,1-trifluoro-4-methylpentan-2-ol;

1,1,1-Trifluoro-4-(5-fluoro-2,3-dihydrobenzofuran-7-yl)-2-(5-methanesulfinyl-1H-indol-2-ylmethyl)-4-methylpentan-2-ol;

7-[3-(5-Bromo-1H-indol-2-ylmethyl)-4,4,4-trifluoro-3-hydroxy-1,1-dimethylbutyl]-2,3-dihydrobenzofuran-5-sulfonic acid amide;

7-[3-(5-Bromo-1H-indol-2-ylmethyl)-4,4,4-trifluoro-3-hydroxy-1,1-dimethylbutyl]-2,3-dihydrobenzofuran-5-sulfonic acid dimethylamide;

2-(1-Benzenesulfonyl-5-pyridin-3-yl-1H-indol-2-ylmethyl)-1,1,1-trifluoro-4-(5-fluoro-2,3-dihydrobenzofuran-7-yl)-4-methylpentan-2-ol;

3-{2-[4-(5-Fluoro-2,3-dihydrobenzofuran-7-yl)-2-hydroxy-4-methyl-2-trifluoromethylpentyl]-1H-indol-5-yl}benzonitrile;

1,1,1-Trifluoro-4-(5-fluoro-2,3-dihydrobenzofuran-7-yl)-4-methyl-2-(5-pyridin-4-yl-1H-indol-2-ylmethyl)pentan-2-ol;

1,1,1-Trifluoro-4-(5-fluoro-2,3-dihydrobenzofuran-7-yl)-4-methyl-2-(5-pyridin-3-yl-1H-indol-2-ylmethyl)pentan-2-ol;

1,1,1-Trifluoro-4-(5-fluoro-2,3-dihydrobenzofuran-7-yl)-4-methyl-2-(5-pyrimidin-5-yl-indol-2-ylmethyl)pentan-2-ol;

2-{2-[4-(5-Fluoro-2,3-dihydrobenzofuran-7-yl)-2-hydroxy-4-methyl-2-trifluoromethylpentyl]-1H-indol-5-yl}benzamide;

2-[5-(4-Dimethylaminophenyl)-1H-indol-2-ylmethyl]-1,1,1-trifluoro-4-(5-fluoro-2,3-dihydrobenzofuran-7-yl)-4-methylpentan-2-ol;

1,1,1-Trifluoro-2-(7-fluoro-4-methyl-1H-indol-2-ylmethyl)-4-(5-methanesulfonyl-2,3-dihydrobenzofuran-7-yl)-4-methylpentan-2-ol;

2-[2-Hydroxy-4-(5-methanesulfonyl-2,3-dihydrobenzofuran-7-yl)-4-methyl-2-trifluoromethylpentyl]-1H-indole-5-carbonitrile;

2-[2-Hydroxy-4-(5-methanesulfonyl-2,3-dihydrobenzofuran-7-yl)-4-methyl-2-trifluoromethylpentyl]-1H-indole-6-carbonitrile;

1,1,1-Trifluoro-2-(7-fluoro-1H-indol-2-ylmethyl)-4-(5-methanesulfonyl-2,3-dihydrobenzofuran-7-yl)-4-methylpentan-2-ol;

1,1,1-Trifluoro-4-(5-methanesulfonyl-2,3-dihydrobenzofuran-7-yl)-4-methyl-2-(4-methyl-1H-indol-2-ylmethyl)pentan-2-ol;

4-Methanesulfonyl-2-[4,4,4-trifluoro-3-hydroxy-1,1-dimethyl-3-(5-trifluoromethyl-1H-indol-2-ylmethyl)butyl]phenol;

1,1,1-Trifluoro-2-(7-fluoro-5-methyl-1H-indol-2-ylmethyl)-4-(5-methanesulfonyl-2,3-dihydrobenzofuran-7-yl)-4-methylpentan-2-ol;

7-Fluoro-2-[2-hydroxy-4-(5-methanesulfonyl-2,3-dihydrobenzofuran-7-yl)-4-methyl-2-trifluoromethylpentyl]-1H-indole-5-carbonitrile;

2-[4-(5-Fluoro-2-methoxyphenyl)-2-hydroxy-4-methyl-2-trifluoromethylpentyl]-1H-indole-4-carboxylic acid methyl ester;

2-[4-(5-Fluoro-2-hydroxyphenyl)-2-hydroxy-4-methyl-2-trifluoromethylpentyl]-1H-indole-4-carboxylic acid methyl ester;

2-[4-(5-Fluoro-2-methoxyphenyl)-2-hydroxy-4-methyl-2-trifluoromethylpentyl]-1H-indole-4-carboxylic acid;

2-[4-(5-Fluoro-2-methoxyphenyl)-2-hydroxy-4-methyl-2-trifluoromethylpentyl]-1H-indole-4-carboxylic acid amide;

2-[4-(5-Fluoro-2-hydroxyphenyl)-2-hydroxy-4-methyl-2-trifluoromethylpentyl]-1H-indole-4-carboxylic acid amide;

2-[4-(5-Fluoro-2-methoxyphenyl)-2-hydroxy-4-methyl-2-trifluoromethylpentyl]-1H-indole-4-carbonitrile;

2-[4-(5-Fluoro-2-hydroxyphenyl)-2-hydroxy-4-methyl-2-trifluoromethylpentyl]-1H-indole-4-carbonitrile;

2-(4-Ethyl-1H-indol-2-ylmethyl)-1,1,1-trifluoro-4-(5-fluoro-2-methoxyphenyl)-4-methylpentan-2-ol;

2-[3-(4-Ethyl-1H-indol-2-ylmethyl)-4,4,4-trifluoro-3-hydroxy-1,1-dimethylbutyl]-4-fluorophenol;

4-(5-Chloro-2,3-dihydrobenzofuran-7-yl)-1,1,1-trifluoro-2-(2-isopropyl-5H-pyrrolo[3,2-d]pyrimidin-6-ylmethyl)-4-methylpentan-2-ol;

1,1,1-Trifluoro-4-(5-fluoro-2-methylphenyl)-2-(2-isopropyl-5H-pyrrolo[3,2-d]pyrimidin-6-ylmethyl)-4-methylpentan-2-ol;

1,1,1-Trifluoro-4-(5-fluoro-2-methoxyphenyl)-2-(2-isopropyl-5H-pyrrolo[3,2-d]pyrimidin-6-ylmethyl)-4-methylpentan-2-ol;

4-Fluoro-2-[4,4,4-trifluoro-3-hydroxy-3-(2-isopropyl-5H-pyrrolo[3,2-d]pyrimidin-6-1,1-dimethylbutyl]phenol;

4-(5-Chloro-2,3-dihydrobenzofuran-7-yl)-1,1,1-trifluoro-4-methyl-2-(2-pyrrolidin-1-yl-5H-pyrrolo[3,2-d]pyrimidin-6-ylmethyl)pentan-2-ol;

1,1,1-Trifluoro-4-(5-fluoro-2-methylphenyl)-4-methyl-2-(2-pyrrolidin-1-yl-5H-pyrrolo[3,2-d]pyrimidin-6-ylmethyl)pentan-2-ol;

1,1,1-Trifluoro-4-(5-fluoro-2-methoxyphenyl)-4-methyl-2-(2-pyrrolidin-1-yl-5H-pyrrolo[3,2-d]pyrimidin-6-ylmethyl)pentan-2-ol;

4-Fluoro-2-[4,4,4-trifluoro-3-hydroxy-1,1-dimethyl-3-(2-pyrrolidin-1-yl-5H-pyrrolo[3,2-d]pyrimidin-6-ylmethyl)butyl]phenol;

4-(5-Chloro-2,3-dihydrobenzofuran-7-yl)-1,1,1-trifluoro-4-methyl-2-(2-phenyl-5H-pyrrolo[3,2-d]pyrimidin-6-ylmethyl)pentan-2-ol;

1,1,1-Trifluoro-4-(5-fluoro-2-methylphenyl)-4-methyl-2-(2-phenyl-5H-pyrrolo[3,2-d]pyrimidin-6-ylmethyl)pentan-2-ol;

1,1,1-Trifluoro-4-(5-fluoro-2-methoxyphenyl)-4-methyl-2-(2-phenyl-5H-pyrrolo[3,2-d]pyrimidin-6-ylmethyl)pentan-2-ol;

4-Fluoro-2-[4,4,4-trifluoro-3-hydroxy-1,1-dimethyl-3-(2-phenyl-5H-pyrrolo[3,2-d]pyrimidin-6-ylmethyl)butyl]phenol;

4-(5-Chloro-2,3-dihydrobenzofuran-7-yl)-2-(2-chloro-5H-pyrrolo[3,2-d]pyrimidin-6-ylmethyl)-1,1,1-trifluoro-4-methylpentan-2-ol;

1,1,1-Trifluoro-4-methyl-4-phenyl-2-(2-phenyl-5H-pyrrolo[3,2-d]pyrimidin-6-ylmethyl)pentan-2-ol;

1,1,1-Trifluoro-4-(3-fluorophenyl)-4-methyl-2-(2-phenyl-5H-pyrrolo[3,2-d]pyrimidin-6-ylmethyl)pentan-2-ol;

4-[4,4,4-Trifluoro-3-hydroxy-1,1-dimethyl-3-(2-phenyl-5H-pyrrolo[3,2-d]pyrimidin-6-ylmethyl)butyl]benzonitrile;

1,1,1-Trifluoro-4-(2-methoxy-5-methylphenyl)-4-methyl-2-(2-pyrrolidin-1-yl-5H-pyrrolo[3,2-d]pyrimidin-6-ylmethyl)pentan-2-ol;

1,1,1-Trifluoro-4-(2-methoxy-5-methylphenyl)-4-methyl-2-(2-pyrrolidin-1-yl-5H-pyrrolo[3,2-d]pyrimidin-6-ylmethyl)pentan-2-ol;

1,1,1-Trifluoro-4-(4-fluoro-2-methoxyphenyl)-4-methyl-2-(2-pyrrolidin-1-yl-5H-pyrrolo[3,2-d]pyrimidin-6-ylmethyl)pentan-2-ol;

5-Fluoro-2-[4,4,4-trifluoro-3-hydroxy-1,1-dimethyl-3-(2-pyrrolidin-1-yl-5H-pyrrolo[3,2-d]pyrimidin-6-ylmethyl)butyl]phenol;

2-(5-Ethoxy-1H-pyrrolo[2,3-c]pyridin-2-ylmethyl)-1,1,1-trifluoro-4-(5-fluoro-2-methylphenyl)-4-methylpentan-2-ol;

1,1,1-Trifluoro-4-(5-fluoro-2-methoxyphenyl)-4-methyl-2-(5-phenyl-1H-pyrrolo[2,3-c]pyridin-2-ylmethyl)pentan-2-ol;

1,1,1-Trifluoro-4-(5-fluoro-2-methylphenyl)-4-methyl-2-(6-methyl-1H-pyrrolo[3,2c]pyridin-2-ylmethyl)pentan-2-ol;

1,1,1-Trifluoro-4-(5-fluoro-2-methylphenyl)-4-methyl-2-(4-methyl-1H-pyrrolo[3,2-c]pyridin-2-ylmethyl)pentan-2-ol;

4-(5-Bromo-2-methoxyphenyl)-2-(5-dimethylamino-1H-pyrrolo[2,3-c]pyridin-2-ylmethyl)-1,1,1-trifluoro-4-methylpentan-2-ol;

4-(5-Bromo-2-methoxyphenyl)-1,1,1-trifluoro-2-(5-isopropoxy-1H-pyrrolo[2,3-c]pyridin-2-ylmethyl)-4-methylpentan-2-ol;

1,1,1-Trifluoro-4-(5-fluoro-2-trifluoromethylphenyl)-2-(5-isopropoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol;

1,1,1-Trifluoro-2-(5-isopropoxy-1H-pyrrolo[2,3-c]pyridin-2-ylmethyl)-4-(2-methoxy-5-pyrimidin-5-ylphenyl)-4-methylpentan-2-ol;

1,1,1-Trifluoro-2-(5-isopropoxy-1H-pyrrolo[2,3-c]pyridin-2-ylmethyl)-4-(4-methoxybiphenyl-3-yl)-4-methylpentan-2-ol;

1,1,1-Trifluoro-2-(5-isopropoxy-1H-pyrrolo[2,3-c]pyridin-2-ylmethyl)-4-(2-methoxy-5-thiophen-3-ylphenyl)-4-methylpentan-2-ol;

2-(5-Dimethylamino-1H-pyrrolo[2,3-c]pyridin-2-ylmethyl)-1,1,1-trifluoro-4-methyl-4-phenylpentan-2-ol;

1,1,1-Trifluoro-4-(2-methoxy-5-pyrimidin-5-ylphenyl)-4-methyl-2-(5-piperidin-1-yl-1H-pyrrolo[2,3-c]pyridin-2-ylmethyl)pentan-2-ol;

1,1,1-Trifluoro-4-(4-methoxybiphenyl-3-yl)-4-methyl-2-(5-piperidin-1-yl-1H-pyrrolo[2,3-c]pyridin-2-ylmethyl)pentan-2-ol;

1,1,1-Trifluoro-4-(2-methoxy-5-pyridin-3-ylphenyl)-4-methyl-2-(5-piperidin-1-yl-1H-pyrrolo[2,3-c]pyridin-2-ylmethyl)pentan-2-ol;

2-(5-Dimethylamino-1H-pyrrolo[2,3-c]pyridin-2-ylmethyl)-1,1,1-trifluoro-4-(2-methoxy-5-pyrimidin-5-ylphenyl)-4-methylpentan-2-ol;

4-Bromo-2-[3-(5-chloro-1H-pyrrolo[2,3-c]pyridin-2-ylmethyl)-4,4,4-trifluoro-3-hydroxy-1,1-dimethylbutyl]phenol;

2-[3-(5-Chloro-1H-pyrrolo[2,3-c]pyridin-2-ylmethyl)-4,4,4-trifluoro-3-hydroxy-1,1-dimethylbutyl]-4-fluorophenol;

2-[2-Hydroxy-4-(4-hydroxybiphenyl-3-yl)-4-methyl-2-trifluoromethylpentyl]-1H-pyrrolo[2,3-c]pyridin-5-ol;

1,1,1-Trifluoro-2-(5-isopropoxy-1H-pyrrolo[2,3-c]pyridin-2-ylmethyl)-4-methyl-4-(5-phenyl-2,3-dihydrobenzofuran-7-yl)pentan-2-ol;

2-[2-Hydroxy-4-(2-methoxy-5-pyrimidin-5-ylphenyl)-4-methyl-2-trifluoromethylpentyl]-1H-pyrrolo[2,3-c]pyridin-5-ol;

Trifluoromethanesulfonic acid 2-[4-(5-fluoro-2-methylphenyl)-2-hydroxy-4-methyl-2-trifluoromethylpentyl]-1H-pyrrolo[2,3-c]pyridin-5-yl ester;

2-[5-(2,6-Dimethylmorpholin-4-yl)-1H-pyrrolo[2,3-c]pyridin-2-ylmethyl]-1,1,1-trifluoro-4-methyl-4-phenylpentan-2-ol;

1,1,1-Trifluoro-4-(3-fluorophenyl)-4-methyl-2-(5-piperidin-1-yl-1H-pyrrolo[2,3-c]pyridin-2-ylmethyl)pentan-2-ol;

1,1,1-Trifluoro-4-methyl-4-phenyl-2-(5-piperidin-1-yl-1H-pyrrolo[2,3-c]pyridin-2-ylmethyl)pentan-2-ol;

1,1,1-Trifluoro-4-(3-fluorophenyl)-2-(5-isopropoxy-1H-pyrrolo[2,3-c]pyridin-2-ylmethyl)-4-methylpentan-2-ol;

1,1,1-Trifluoro-2-(5-isopropoxy-1H-pyrrolo[2,3-c]pyridin-2-ylmethyl)-4-methyl-4-phenylpentan-2-ol;

1,1,1-Trifluoro-4-methyl-4-(3-morpholin-4-ylmethylphenyl)-2-(5-piperidin-1-yl-1H-pyrrolo[2,3-c]pyridin-2-ylmethyl)pentan-2-ol;

1,1,1-Trifluoro-4-methyl-4-(3-morpholin-4-ylmethylphenyl)-2-(5-morpholin-4-yl-1H-pyrrolo[2,3-c]pyridin-2-ylmethyl)pentan-2-ol;

2-(5-Diethylamino-1H-pyrrolo[2,3-c]pyridin-2-ylmethyl)-1,1,1-trifluoro-4-(2-methoxy-5-pyrimidin-5-ylphenyl)-4-methylpentan-2-ol;

4-(5-Chloro-2,3-dihydrobenzofuran-7-yl)-1,1,1-trifluoro-2-(5-methoxy-1H-pyrrolo[3,2-b]pyridin-2-ylmethyl)-4-methylpentan-2-ol;

1,1,1-Trifluoro-4-(5-fluoro-2-methylphenyl)-2-(5-methoxy-1H-pyrrolo[3,2-b]pyridin-2-ylmethyl)-4-methylpentan-2-ol;

4-(5-Chloro-2,3-dihydrobenzofuran-7-yl)-2-(5-chloro-1H-pyrrolo[2,3-c]pyridin-2-ylmethyl)-1,1,1-trifluoro-4-methylpentan-2-ol;

1,1,1-Trifluoro-4-(5-fluoro-2-methylphenyl)-2-(4-methoxy-1H-pyrrolo[3,2-c]pyridin-2-ylmethyl)-4-methylpentan-2-ol;

2-[4-(5-Fluoro-2-methylphenyl)-2-hydroxy-4-methyl-2-trifluoromethylpentyl]-1,5-dihydropyrrolo[3,2-c]pyridin-4-one;

2-[4-(5-Fluoro-2-methylphenyl)-2-hydroxy-4-methyl-2-trifluoromethylpentyl]-1,4-dihydropyrrolo[3,2-b]pyridin-5-one;

2-[4-(5-Fluoro-2-methylphenyl)-2-hydroxy-4-methyl-2-trifluoromethylpentyl]-5-hydroxy-1,6-dihydropyrrolo[2,3-c]pyridin-7-one;

2-(5-Chloro-1H-pyrrolo[2,3-c]pyridin-2-ylmethyl)-1,1,1-trifluoro-4-(5-methanesulfonyl-2,3-dihydrobenzofuran-7-yl)-4-methylpentan-2-ol;

2-(5-Chloro-1H-pyrrolo[2,3-c]pyridin-2-ylmethyl)-1,1,1-trifluoro-4-(2-methoxy-5-thiophen-3-ylphenyl)-4-methylpentan-2-ol;

2-[2-Hydroxy-4-(5-methanesulfonyl-2,3-dihydrobenzofuran-7-yl)-4-methyl-2-trifluoromethylpentyl]-1H-pyrrolo[3,2-b]pyridine-5-carbonitrile;

2-(5-Chloro-1H-pyrrolo[2,3-c]pyridin-2-ylmethyl)-1,1,1-trifluoro-4-methyl-4-(5-methylsulfanyl-2,3-dihydrobenzofuran-7-yl)pentan-2-ol;

4-(5-Bromo-2-methoxyphenyl)-2-(5-chloro-1H-pyrrolo[2,3-c]pyridin-2-ylmethyl)-1,1,1-trifluoro-4-methylpentan-2-ol;

1,1,1-Trifluoro-4-(5-fluoro-2-methoxyphenyl)-4-methyl-2-(7H-pyrrolo[2,3-d]pyrimidin-6-ylmethyl)pentan-2-ol;

1,1,1-Trifluoro-4-(2-methoxy-5-naphthalen-1-ylphenyl)-4-methyl-2-(5-morpholin-4-yl-1H-pyrrolo[2,3-c]pyridin-2-ylmethyl)pentan-2-ol;

4-(2'-Chloro-4-methoxybiphenyl-3-yl)-1,1,1-trifluoro-4-methyl-2-(5-morpholin-4-yl-1H-pyrrolo[2,3-c]pyridin-2-ylmethyl)pentan-2-ol;

2-(5-Chloro-1H-pyrrolo[2,3-c]pyridin-2-ylmethyl)-1,1,1-trifluoro-4-(2-methoxy-5-ylphenyl)-4-methylpentan-2-ol;

4'-Methoxy-3'-[4,4,4-trifluoro-3-hydroxy-1,1-dimethyl-3-(5-piperidin-1-yl-1H-pyrrolo[2,3-c]pyridin-2-ylmethyl)butyl]biphenyl-2-carbonitrile;

4-(2'-Chloro-4-methoxybiphenyl-3-yl)-1,1,1-trifluoro-4-methyl-2-(5-piperidin-1-yl-1H-pyrrolo[2,3-c]pyridin-2-ylmethyl)pentan-2-ol;

2-[3-(3-Dimethylaminomethyl-1H-pyrrolo[3,2-c]pyridin-2-ylmethyl)-4,4,4-trifluoro-3-hydroxy-1,1-dimethylbutyl]-4-fluorophenol;

1,1,1-Trifluoro-4-(5-methanesulfonyl-2,3-dihydrobenzofuran-7-yl)-4-methyl-2-(1H-pyrrolo[3,2-c]pyridin-2-ylmethyl)pentan-2-ol;

2-(3-Chloro-1H-pyrrolo[3,2-c]pyridin-2-ylmethyl)-1,1,1-trifluoro-4-(5-fluoro-2-methoxyphenyl)-4-methylpentan-2-ol;

1,1,1-Trifluoro-4-methyl-4-(5-methylsulfanyl-2,3-dihydrobenzofuran-7-yl)-2-pyrrolo[3,2-b]pyridin-1-ylmethylpentan-2-ol;

1,1,1-Trifluoro-4-(5-methanesulfonyl-2,3-dihydrobenzofuran-7-yl)-4-methyl-2-pyrrolo[3,2-b]pyridin-1-ylmethylpentan-2-ol;

4-(5-Chloro-2,3-dihydrobenzofuran-7-yl)-1,1,1-trifluoro-4-methyl-2-(5-phenyl-1H-pyrrolo[2,3-c]pyridin-2-ylmethyl)pentan-2-ol; and 1,1,1-Trifluoro-4-(5-fluoro-2-methylphenyl)-4-methyl-2-(5-phenyl-1H-pyrrolo[2,3-c]pyridin-2-ylmethyl)pentan-2-ol, or a tautomer, prodrug, solvate, or salt thereof.

More preferred compounds of Formula (IA) include:

1,1,1-Trifluoro-4-(5-fluoro-2-methoxyphenyl)-4-methyl-2-(3-methyl-1H-pyrrolo[3,2-c]pyridin-2-ylmethyl)pentan-2-ol;

1,1,1-Trifluoro-4-(5-fluoro-2,3-dihydrobenzofuran-7-yl)-4-methyl-2-(1H-pyrrolo[3,2-c]pyridin-2-ylmethyl)pentan-2-ol;

1,1,1-Trifluoro-4-(5-fluoro-2-methylphenyl)-4-methyl-2-(3-methyl-1H-pyrrolo[2,3-c]pyridin-2-ylmethyl)pentan-2-ol;

2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol;

2-[4-(5-Fluoro-2-methoxyphenyl)-2-hydroxy-4-methyl-2-trifluoromethylpentyl]-1H-pyrrolo[3,2-b]pyridine-5-carbonitrile;

1,1,1-Trifluoro-4-(5-fluoro-2-methoxyphenyl)-4-methyl-2-(6-methyl-1H-pyrrolo[3,2-c]pyridin-2-ylmethyl)pentan-2-ol;

1,1,1-Trifluoro-4-(5-fluoro-2-methoxyphenyl)-4-methyl-2-(4-methyl-1H-pyrrolo[3,2-c]pyridin-2-ylmethyl)pentan-2-ol;

2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile;

2-[4-(5-Fluoro-2-methoxyphenyl)-2-hydroxy-4-methyl-2-trifluoromethylpentyl]-1H-pyrrolo[2,3-c]pyridine-5-carbonitrile;

2-[4-(5-Fluoro-2-methoxyphenyl)-2-hydroxy-4-methyl-2-trifluoromethylpentyl]-1H-pyrrolo[3,2-c]pyridine-4-carbonitrile;

1,1,1-Trifluoro-4-(5-fluoro-2-methoxyphenyl)-4-methyl-2-(5H-pyrrolo[3,2-d]pyrimidin-6-ylmethyl)pentan-2-ol;

1,1,1-Trifluoro-4-(5-fluoro-2-methoxyphenyl)-4-methyl-2-thieno[2,3-d]pyridazin-2-ylmethylpentan-2-ol;

1,1,1-Trifluoro-4-(5-fluoro-2-methoxyphenyl)-4-methyl-2-(5H-pyrrolo[3,2-c]pyridazin-6-ylmethyl)pentan-2-ol;

1,1,1-Trifluoro-4-(5-fluoro-2-methoxyphenyl)-4-methyl-2-(2-methyl-5H-pyrrolo[3,2-d]pyrimidin-6-ylmethyl)pentan-2-ol;

1,1,1-Trifluoro-4-(5-fluoro-2-methylphenyl)-4-methyl-2-(1H-pyrrolo[2,3-d]pyridazin-2-ylmethyl)pentan-2-ol;

2-(4,6-Dimethyl-1H-pyrrolo[3,2-c]pyridin-2-ylmethyl)-1,1,1-trifluoro-4-(5-fluoro-2-methylphenyl)-4-methylpentan-2-ol;

4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol;

4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol;

1,1,1-Trifluoro-4-(5-fluoro-2-methylphenyl)-4-methyl-2-(6-methyl-1H-pyrrolo[3,2-c]pyridin-2-ylmethyl)pentan-2-ol;

2-[4-(5-Fluoro-2-methylphenyl)-2-hydroxy-4-methyl-2-trifluoromethylpentyl]-1H-pyrrolo[3,2-b]pyridine-5-carbonitrile;

2-[4-(5-Chloro-2,3-dihydrobenzofuran-7-yl)-2-hydroxy-4-methyl-2-trifluoromethylpentyl]-1H-pyrrolo[3,2-]pyridine-5-carbonitrile;

1,1,1-Trifluoro-4-(5-fluoro-2-methylphenyl)-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(3-methyl-1H-pyrrolo[2,3-c]pyridin-2-ylmethyl)pentan-2-ol;

1,1,1-Trifluoro-4-(5-fluoro-2-methylphenyl)-4-methyl-2-(5H-pyrrolo[3,2-c]pyridazin-6-ylmethyl)pentan-2-ol;

1,1,1-Trifluoro-4-(5-fluoro-2-methoxyphenyl)-2-(7-fluoro-1H-pyrrolo[2,3-c]pyridin-2-ylmethyl)-4-methylpentan-2-ol;

1,1,1-Trifluoro-4-(5-fluoro-2-methoxyphenyl)-4-methyl-2-(4-methyl-1H-pyrrolo[2,3-c]pyridin-2-ylmethyl)pentan-2-ol;

2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-(5-trifluoromethyl-1H-pyrrolo[2,3-c]pyridin-2-ylmethyl)pentan-2-ol;

1,1,1-Trifluoro-4-(5-fluoro-2-methoxyphenyl)-2-(5-methoxy-1H-pyrrolo[2,3-c]pyridin-2-ylmethyl)-4-methylpentan-2-ol;

1,1,1-Trifluoro-4-(5-fluoro-2-methylphenyl)-4-methyl-2-(4-methyl-1H-pyrrolo[2,3-c]pyridin-2-ylmethyl)pentan-2-ol;

1,1,1-Trifluoro-4-(5-fluoro-2-methylphenyl)-2-(5-isopropoxy-1H-pyrrolo[2,3-c]pyridin-2-ylmethyl)-4-methylpentan-2-ol;

1,1,1-Trifluoro-4-(5-fluoro-2-methylphenyl)-2-(5-methoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol;

1,1,1-Trifluoro-4-(5-fluoro-2-methylphenyl)-2-(7-fluoro-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(5-trifluoromethyl-1H-pyrrolo[2,3-c]pyridin-2-ylmethyl)pentan-2-ol;

2-(5-Dimethylamino-1H-pyrrolo[2,3-c]pyridin-2-ylmethyl)-1,1,1-trifluoro-4-(5-fluoro-2-methylphenyl)-4-methylpentan-2-ol;

1,1,1-Trifluoro-4-(5-fluoro-2-methoxyphenyl)-2-(5-chloro-1H-pyrrolo[2,3-c]pyridin-2-ylmethyl)-4-methylpentan-2-ol;

4-(5-Bromo-2,3-dihydrobenzofuran-7-yl)-1,1,1-trifluoro-4-methyl-2-(1H-pyrrolo[2,3-c]pyridin-2-ylmethyl)pentan-2-ol;

1,1,1-Trifluoro-4-methyl-4-(5-methyl-2,3-dihydrobenzofuran-7-yl)-2-(1H-pyrrolo[2,3-c]pyridin-2-ylmethyl)pentan-2-ol;

4-(5-Chloro-2,3-dihydrobenzofuran-7-yl)-1,1,1-trifluoro-4-methyl-2-(1H-pyrrolo[2,3-c]pyridin-2-ylmethyl)pentan-2-ol;

1,1,1-Trifluoro-4-(5-fluoro-2-methoxyphenyl)-4-methyl-2-pyrrolo[2,3-b]pyridin-1-ylmethylpentan-2-ol;

2-Benzo[b]thiophen-2-ylmethyl-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-thieno[2,3-c]pyridin-2-ylmethylpentan-2-ol;

1,1,1-Trifluoro-4-(5-fluoro-2-methoxyphenyl)-4-methyl-2-[4-((Z)propenyl)-3-vinylpyrazol-1-ylmethyl]pentan-2-ol;

4-(5-Chloro-2,3-dihydrobenzofuran-7-yl)-2,4-dimethyl-1-thieno[2,3-c]pyridin-2-ylpentan-2-ol;

4-(5-Fluoro-2-methylphenyl)-2,4-dimethyl-1-thieno[2,3-c]pyridin-2-ylpentan-2-ol;

1,1,1-Trifluoro-4-(5-fluoro-2-methylphenyl)-4-methyl-2-(1H-pyrrolo[3,2-c]pyridin-2-ylmethyl)pentan-2-ol;

1,1,1-Trifluoro-4-methyl-4-(5-methyl-2,3-dihydrobenzofuran-7-yl)-2-(1H-pyrrolo[3,2-c]pyridin-2-ylmethyl)pentan-2-ol;

4-(5-Chloro-2,3-dihydrobenzofuran-7-yl)-1,1,1-trifluoro-4-methyl-2-(1H-pyrrolo[3,2-c]pyridin-2-ylmethyl)pentan-2-ol;

4-(5-Bromo-2,3-dihydrobenzofuran-7-yl)-1,1,1-trifluoro-4-methyl-2-(1H-pyrrolo[3,2-c]pyridin-2-ylmethyl)pentan-2-ol;

2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-pyrrolo[3,2-c]pyridin-1-ylmethylpentan-2-ol;

1,1,1-Trifluoro-4-(5-fluoro-2-methoxyphenyl)-4-methyl-2-pyrrolo[3,2-b]pyridin-1-ylmethylpentan-2-ol;

1,1,1-Trifluoro-4-(5-fluoro-2-methoxyphenyl)-2-furo[3,2-c]pyridin-2-ylmethyl-4-methylpentan-2-ol;

4-(5-Chloro-2,3-dihydrobenzofuran-7-yl)-1,1,1-trifluoro-4-methyl-2-pyrrolo[3,2-b]pyridin-1-ylmethylpentan-2-ol;

1,1-Difluoro-4-(5-fluoro-2-methoxyphenyl)-4-methyl-2-(1H-pyrrolo[3,2-c]pyridin-2-ylmethyl)pentan-2-ol;

1,1,1-Trifluoro-4-(5-fluoro-2-methoxyphenyl)-4-methyl-2-thieno[3,2-c]pyridin-2-ylmethylpentan-2-ol;

4-(5-Chloro-2,3-dihydrobenzofuran-7-yl)-1,1,1-trifluoro-4-methyl-2-thieno[3,2-c]pyridin-2-ylmethylpentan-2-ol;

1,1,1-Trifluoro-4-(5-fluoro-2-methylphenyl)-4-methyl-2-pyrrolo[3,2-b]pyridin-1-ylmethylpentan-2-ol;

1,1,1-Trifluoro-4-(5-fluoro-2-methylphenyl)-4-methyl-2-thieno[3,2-c]pyridin-2-ylmethylpentan-2-ol;

2-[4-(5-Fluoro-2-hydroxyphenyl)-2-hydroxy-4-methyl-2-trifluoromethylpentyl]-1H-indole-6-carboxylic acid dimethylamide;

{2-[4-(5-Fluoro-2-hydroxyphenyl)-2-hydroxy-4-methyl-2-trifluoromethylpentyl]-1H-indol-6-yl}morpholin-4-ylmethanone;

2-[4-(5-Fluoro-2-methoxyphenyl)-2-hydroxy-4-methyl-2-trifluoromethylpentyl]-1H-indole-6-carboxylic acid dimethylamide;

2-[4-(5-Fluoro-2-methoxyphenyl)-2-hydroxy-4-methyl-2-trifluoromethylpentyl]-1H-indole-6-carboxylic acid dimethylamide;

{2-[4-(5-Fluoro-2-methoxyphenyl)-2-hydroxy-4-methyl-2-trifluoromethylpentyl]-1H-indol-6-yl}morpholin-4-ylmethanone;

2-[4-(2,3-Dihydrobenzofuran-7-yl)-2-hydroxy-4-methyl-2-trifluoromethylpentyl]-4-methyl-1H-indole-6-carbonitrile;

2-[4-(5-Fluoro-2-hydroxyphenyl)-2-hydroxy-4-methyl-2-trifluoromethylpentyl]-1H-indole-6-carboxylic acid amide;

2-[4-(5-Fluoro-2-methoxyphenyl)-2-hydroxy-4-methyl-2-trifluoromethylpentyl]-1H-indole-6-carboxylic acid amide;

4-Fluoro-2-[4,4,4-trifluoro-3-hydroxy-1,1-dimethyl-3-(5-nitro-1H-indol-2-ylmethyl)butyl]phenol;

2-[4-(5-Fluoro-2-methoxyphenyl)-2-hydroxy-4-methyl-2-trifluoromethylpentyl]-1H-indole-6-carbonitrile;

2-[4-(5-Fluoro-2-hydroxyphenyl)-2-hydroxy-4-methyl-2-trifluoromethylpentyl]-1H-indole-6-carbonitrile;

N-{2-[4-(5-Fluoro-2-methoxyphenyl)-2-hydroxy-4-methyl-2-trifluoromethylpentyl]-1H-indol-5-yl}acetamide;

1,1,1-Trifluoro-4-(4-fluoro-2-methoxyphenyl)-2-(7-fluoro-4-methyl-1H-indol-2-ylmethyl)-4-methylpentan-2-ol;

5-Fluoro-2-[4,4,4-trifluoro-3-(7-fluoro-4-methyl-1H-indol-2-ylmethyl)-3-hydroxy-1,1-dimethylbutyl]phenol;

2-[4-(3-[1,3]Dioxolan-2-ylphenyl)-2-hydroxy4-methyl-2-trifluoromethylpentyl]-1H-indole-5-carbonitrile;

2-[4-(5-Fluoro-2-methoxyphenyl)-2-hydroxy-4-methyl-2-trifluoromethylpentyl]-1H-indole-5-carboxylic acid-2-trimethylsilanylethyl ester;

2-[4-(4-Fluoro-2-hydroxyphenyl)-2-hydroxy-4-methyl-2-trifluoromethylpentyl]-4-methyl-1H-indole-6-carbonitrile;

{2-[4-(5-Fluoro-2-methoxyphenyl)-2-hydroxy-4-methyl-2-trifluoromethylpentyl]-1H-indol-5-yl}piperidin-1-ylmethanone;

2-[4-(5-Fluoro-2-methoxyphenyl)-2-hydroxy-4-methyl-2-trifluoromethylpentyl]-1H-indole-5-carboxylic acid methylamide;

{2-[4-(5-Fluoro-2-methoxyphenyl)-2-hydroxy-4-methyl-2-trifluoromethylpentyl]-1H-indol-5-yl}pyrrolidin-1-ylmethanone;

1-{2-[4-(5-Fluoro-2-methoxyphenyl)-2-hydroxy-4-methyl-2-trifluoromethylpentyl]-1H-indole-5-carbonyl}piperidin-4-one;

2-[4-(5-Fluoro-2-methoxyphenyl)-2-hydroxy-4-methyl-2-trifluoromethylpentyl]-1H-indole-5-carboxylic acid (2-hydroxyethyl)amide;

{2-[4-(5-Fluoro-2-methoxyphenyl)-2-hydroxy-4-methyl-2-trifluoromethylpentyl]-1H-indole-5-yl}(4-hydroxypiperidin-1-yl)methanone;

{2-[4-(5-Fluoro-2-methoxyphenyl)-2-hydroxy-4-methyl-2-trifluoromethylpentyl]-1H-indol-5-yl}(3-hydroxypyrrolidin-1-yl)methanone;

2-[4-(5-Fluoro-2-methoxyphenyl)-2-hydroxy-4-methyl-2-trifluoromethylpentyl]-1H-indole-5-carboxylic acid cyanomethylamide;

({2-[4-(5-Fluoro-2-methoxyphenyl)-2-hydroxy-4-methyl-2-trifluoromethylpentyl]-1H-indole-5-carbonyl}amino)acetic acid methyl ester;

2-[4-(5-Fluoro-2-methoxyphenyl)-2-hydroxy-4-methyl-2-trifluoromethylpentyl]-1H-indole-5-carboxylic acid carbamoylmethylamide;

4-({2-[4-(5-Fluoro-2-methoxyphenyl)-2-hydroxy-4-methyl-2-trifluoromethylpentyl]-1H-indole-5-carbonyl}amino)butyric acid methyl ester;

({2-[4-(5-Fluoro-2-methoxyphenyl)-2-hydroxy-4-methyl-2-trifluoromethylpentyl]-1H-indole-5-carbonyl}amino)acetic acid;

4-({2-[4-(5-Fluoro-2-methoxyphenyl)-2-hydroxy-4-methyl-2-trifluoromethylpentyl]-1H-indole-5-carbonyl}amino)butyric acid;

2-[4-(3-Dimethylaminomethylphenyl)-2-hydroxy-4-methyl-2-trifluoromethylpentyl]-1H-indole-5-carbonitrile;

4-Fluoro-2-[4,4,4-trifluoro-3-hydroxy-1,1-dimethyl-3-(5-trifluoromethyl-1H-indol-2-ylmethyl)butyl]phenol;

2-[4-(5-Bromo-2,3-dihydrobenzofuran-7-yl)-2-hydroxy-4-methyl-2-trifluoromethylpentyl]-4-methyl-1H-indole-6-carbonitrile;

2-[2-Hydroxy-4-(5-methanesulfonyl-2,3-dihydrobenzofuran-7-yl)-4-methyl-2-trifluoromethylpentyl]-4-methyl-1H-indole-6-carbonitrile;

2-[4-(5-Bromo-2,3-dihydrobenzofuran-7-yl)-2-hydroxy-4-methyl-2-trifluoromethylpentyl]-1H-indole-5-carboxylic acid;

2-[4-(5-Bromo-2,3-dihydrobenzofuran-7-yl)-2-hydroxy-4-methyl-2-trifluoromethylpentyl]-1H-indole-5-carboxylic acid amide;

2-[4-(5-Bromo-2,3-dihydrobenzofuran-7-yl)-2-hydroxy-4-methyl-2-trifluoromethylpentyl]-1H-indole-5-carboxylic acid dimethylamide;

2-[4-(5-Bromo-2,3-dihydrobenzofuran-7-yl)-2-hydroxy-4-methyl-2-trifluoromethylpentyl]-1H-indole-5-carboxylic acid cyanomethylamide;

{2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone;

{2-[4-(5-Bromo-2,3-dihydrobenzofuran-7-yl)-2-hydroxy-4-methyl-2-trifluoromethylpentyl]-1H-indol-5-yl}morpholin-4-ylmethanone;

2-[4-(5-Fluoro-2-methoxyphenyl)-2-hydroxy-4-methyl-2-trifluoromethylpentyl]-1H-indole-5-carboxylic acid amide;

{2-[4-(5-Fluoro-2-methoxyphenyl)-2-hydroxy-4-methyl-2-trifluoromethylpentyl]-1H-indol-5-yl}morpholin-4-ylmethanone;

2-(4-Benzo[1,3]dioxol-4-yl-2-hydroxy-4-methyl-2-trifluoromethylpentyl)-4-methyl-1H-indole-6-carbonitrile;

1,1,1-Trifluoro-4-methyl-4-phenyl-2-quinolin-4-ylmethylhexan-2-ol;

2-[2-Hydroxy-4-methyl-4-(5-methylsulfanyl-2,3-dihydrobenzofuran-7-yl)-2-trifluoromethylpentyl]-1H-indole-3-carbonitrile;

7-(4,4,4-Trifluoro-3-hydroxy-1,1-dimethyl-3-quinolin-4-ylmethylbutyl)-2,3-dihydrobenzofuran-5-carbonitrile;

2-[2-Hydroxy-4-(2-hydroxy-5-methylphenyl)-4-methyl-2-trifluoromethylpentyl]-4-methyl-1H-indole-6-carbonitrile;

1,1,1-Trifluoro-4-(5-fluoro-2,3-dihydrobenzofuran-7-yl)-4-methyl-2-(5-methylsulfanyl-1H-indol-2-ylmethyl)pentan-2-ol;

2-[2-Hydroxy-4-(5-methanesulfonyl-2-methoxyphenyl)-4-methyl-2-trifluoromethylpentyl]-1H-indole-3-carbonitrile;

1,1,1-Trifluoro-4-(5-fluoro-2,3-dihydrobenzofuran-7-yl)-4-methyl-2-(5-phenyl-1H-indol-2-ylmethyl)pentan-2-ol;

2-[4-(5-tert-Butyl-2-hydroxyphenyl)-2-hydroxy-4-methyl-2-trifluoromethylpentyl]-1H-indole-3-carbonitrile;

2-[2-Hydroxy-4-(2-hydroxy-5-isopropylphenyl)-4-methyl-2-trifluoromethylpentyl]-1H-indole-3-carbonitrile;

2-[2-Hydroxy-4-(2-hydroxy-3,5-dimethylphenyl)-4-methyl-2-trifluoromethylpentyl]-1H-indole-3-carbonitrile;

2-[2-Hydroxy-4-(5-hydroxy-2,4-dimethylphenyl)-4-methyl-2-trifluoromethylpentyl]-1H-indole-3-carbonitrile;

2-[4-(5-tert-Butyl-2-methoxyphenyl)-2-hydroxy-4-methyl-2-trifluoromethylpentyl]-1H-indole-3-carbonitrile;

2-[2-Hydroxy-4-(5-isopropyl-2-methoxyphenyl)-4-methyl-2-trifluoromethylpentyl]-1H-indole-3-carbonitrile;

2-[2-Hydroxy-4-(2-methoxy-5-methylphenyl)-4-methyl-2-trifluoromethylpentyl]-4-methyl-1H-indole-6-carbonitrile;

1,1,1-Trifluoro-4-methyl-2-quinolin-4-ylmethyl-4-o-tolylpentan-2-ol;

1,1,1-Trifluoro-4-methyl-2-quinolin-4-ylmethyl-4-m-tolylpentan-2-ol;

1,1,1-Trifluoro-4-(2-fluorophenyl)-2-(1H-indol-2-ylmethyl)-4-methylpentan-2-ol;

1,1,1-Trifluoro-4-(2-fluorophenyl)-4-methyl-2-quinolin-4-ylmethylpentan-2-ol;

1,1,1-Trifluoro-4-(3-fluorophenyl)-2-(1H-indol-2-ylmethyl)-4-methylpentan-2-ol;

1,1,1-Trifluoro-4-(3-fluorophenyl)-4-methyl-2-quinolin-4-ylmethylpentan-2-ol;

1,1,1-Trifluoro-4-(4-fluorophenyl)-2-(1H-indol-2-ylmethyl)-4-methylpentan-2-ol;

1,1,1-Trifluoro-4-(4-fluorophenyl)-4-methyl-2-quinolin-4-ylmethylpentan-2-ol;

3-(4,4,4-Trifluoro-3-hydroxy-1,1-dimethyl-3-quinolin-4-ylmethylbutyl)phenol;

1,1,1-Trifluoro-4-methyl-2-quinolin-4-ylmethyl-4-(2-trifluoromethylphenyl)pentan-2-ol;

1,1,1-Trifluoro-2-(1H-indol-2-ylmethyl)-4-methyl-4-(4-trifluoromethylphenyl)pentan-2-ol;

1,1,1-Trifluoro-4-methyl-2-quinolin-4-ylmethyl-4-(4-trifluoromethylphenyl)pentan-2-ol;

4-(3-Chlorophenyl)-1,1,1-trifluoro-2-(1H-indol-2-ylmethyl)-4-methylpentan-2-ol;

4-(3-Chlorophenyl)-1,1,1-trifluoro-4-methyl-2-quinolin-4-ylmethylpentan-2-ol;

4-(4-Dimethylaminophenyl)-1,1,1-trifluoro-2-(1H-indol-2-ylmethyl)-4-methylpentan-2-ol;

4-Biphenyl-3-yl-1,1,1-trifluoro-4-methyl-2-quinolin-4-ylmethylpentan-2-ol;

4-(3-Bromophenyl)-1,1,1-trifluoro-2-(1H-indol-2-ylmethyl)-4-methylpentan-2-ol;
4-(2-Difluoromethoxy-5-fluorophenyl)-1,1,1-trifluoro-2-(1H-indol-2-ylmethyl)-4-methylpentan-2-ol;
4-Biphenyl-3-yl-1,1,1-trifluoro-2-(1H-indol-2-ylmethyl)-4-methylpentan-2-ol;
4-(4-Dimethylaminophenyl)-1,1,1-trifluoro-4-methyl-2-quinolin-4-ylmethylpentan-2-ol;
2-[4-(5-Fluoro-2-methylphenyl)-2-hydroxy-4-methyl-2-trifluoromethylpentyl]-1,6-dihydropyrrolo[2,3-c]pyridin-5-one;
2-[4-(5-Fluoro-2-methylphenyl)-2-hydroxy-4-methyl-2-trifluoromethylpentyl]-6-methyl-1,6-dihydropyrrolo[2,3-c]pyridin-5-one;
1,1,1-Trifluoro-4-(5-fluoro-2-methylphenyl)-2-(5-methoxy-1H-pyrrolo[3,2-b]pyridin-2-ylmethyl)-4-methylpentan-2-ol;
2-[4-(3-Dimethylaminomethylphenyl)-2-hydroxy-4-methyl-2-trifluoromethylpentyl]-1H-indole-5-carbonitrile;
1,1,1-Trifluoro-2-(1H-indol-2-ylmethyl)-4-methyl-4-pyridin-2-ylpentan-2-ol;
1,1,1-Trifluoro-4-methyl-4-pyridin-4-yl-2-quinolin-4-ylmethylpentan-2-ol;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
1,1,1-Trifluoro-4-(5-fluoro-2-methoxyphenyl)-4-methyl-2-pyridin-4-ylmethylpentan-2-ol;
4-Fluoro-2-[4,4,4-trifluoro-3-(2-fluoropyridin-4-ylmethyl)-3-hydroxy-1,1-dimethylbutyl]phenol;
2-[3-(2-Bromopyridin-4-ylmethyl)-4,4,4-trifluoro-3-hydroxy-1,1-dimethylbutyl]-4-fluorophenol;
2-(6,8-Dimethylquinolin-4-ylmethyl)-1,1,1-trifluoro-4-(5-fluoro-2-methoxyphenyl)-4-methylpentan-2-ol;
4-[4-(5-Fluoro-2-methoxyphenyl)-2-hydroxy-4-methyl-2-trifluoromethylpentyl]pyridine-2-carbonitrile;
2,6-Dichloro-4-[4-(5-fluoro-2-methoxyphenyl)-2-hydroxy-4-methyl-2-trifluoromethylpentyl]nicotinonitrile;
2,6-Dichloro-4-[4-(5-fluoro-2-hydroxyphenyl)-2-hydroxy-4-methyl-2-trifluoromethylpentyl]nicotinonitrile;
2-(2,6-Dichloroquinolin-4-ylmethyl)-1,1,1-trifluoro-4-(5-fluoro-2-methoxyphenyl)-4-methylpentan-2-ol;
2-[3-(2-Chloro-8-methylquinolin-4-ylmethyl)-4,4,4-trifluoro-3-hydroxy-1,1-dimethylbutyl]-4-fluorophenol;
2-[3-(2,6-Dichloroquinolin-4-ylmethyl)-4,4,4-trifluoro-3-hydroxy-1,1-dimethylbutyl]-4-fluorophenol;
4-(2,3-Dihydrobenzofuran-7-yl)-2-(2,6-dimethylpyridin-4-ylmethyl)-1,1,1-trifluoro-4-methylpentan-2-ol;
2-(2,6-Dimethylpyridin-4-ylmethyl)-1,1,1-trifluoro-4-(3-fluorophenyl)-4-methylpentan-2-ol;
2-(2,6-Dimethylpyridin-4-ylmethyl)-1,1,1-trifluoro-4-(4-fluorophenyl)-4-methylpentan-2-ol;
1,1,1-Trifluoro-4-(5-fluoro-2-methylphenyl)-4-methyl-2-quinolin-4-ylmethylpentan-2-ol;
2-(2,6-Dimethylpyridin-4-ylmethyl)-1,1,1-trifluoro-4-(5-fluoro-2-methylphenyl)-4-methylpentan-2-ol;
2-(2,6-Dimethylpyridin-4-ylmethyl)-1,1,1-trifluoro-4-methyl-4-m-tolylpentan-2-ol;
1,1,1-Trifluoro-4-(5-fluoro-2-methoxyphenyl)-4-methyl-2-(2-methylquinolin-4-ylmethyl)pentan-2-ol;
4-Fluoro-2-(4,4,4-trifluoro-3-hydroxy-1,1-dimethyl-3-quinolin-4-ylmethylbutyl)phenol;
4-Fluoro-2-[4,4,4-trifluoro-3-hydroxy-1,1-dimethyl-3-(2-methylquinolin-4-ylmethyl)butyl]phenol;
2-(2,6-Dimethylpyridin-4-ylmethyl)-1,1,1-trifluoro-4-(4-fluoro-2-methoxyphenyl)-4-methylpentan-2-ol;
1,1,1-Trifluoro-4-(5-fluoro-2-methoxyphenyl)-4-methyl-2-(7-methylquinolin-4-ylmethyl)pentan-2-ol;
2-[3-(2,6-Dimethylpyridin-4-ylmethyl)-4,4,4-trifluoro-3-hydroxy-1,1-dimethylbutyl]-5-fluorophenol;
1,1,1-Trifluoro-4-(4-fluorophenyl)-4-methyl-2-(2-methylquinolin-4-ylmethyl)pentan-2-ol;
1,1,1-Trifluoro-4-(3-fluorophenyl)-4-methyl-2-(3-methyl-1H-indol-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-2-(7-fluoro-4-methylquinolin-8-yl)-4-methylpentan-2-ol;
4-(2,6-Dimethylphenyl)-1,1,1-trifluoro-2-(1H-indol-2-ylmethyl)-4-methylpentan-2-ol;
2-(3-Bromo-1H-indol-2-ylmethyl)-1,1,1-trifluoro-4-(3-fluorophenyl)-4-methylpentan-2-ol;
4-(3,4-Dimethylphenyl)-1,1,1-trifluoro-2-(1H-indol-2-ylmethyl)-4-methylpentan-2-ol;
1,1,1-Trifluoro-4-(3-fluoro-4-methylphenyl)-2-(1H-indol-2-ylmethyl)-4-methylpentan-2-ol;
1,1,1-Trifluoro-4-(4-fluoro-3-methylphenyl)-2-(1H-indol-2-ylmethyl)-4-methylpentan-2-ol;
1,1,1-Trifluoro-4-(3-fluoro-4-methylphenyl)-4-methyl-2-quinolin-4-ylmethylpentan-2-ol;
1,1,1-Trifluoro-4-(4-fluoro-2-methoxyphenyl)-4-methyl-2-quinolin-4-ylmethylpentan-2-ol;
4-(3,4-Dimethylphenyl)-1,1,1-trifluoro-4-methyl-2-quinolin-4-ylmethylpentan-2-ol;
4-(2,5-Dimethylphenyl)-1,1,1-trifluoro-2-(1H-indol-2-ylmethyl)-4-methylpentan-2-ol;
1,1,1-Trifluoro-2-(1H-indol-2-ylmethyl)-4-(2-methoxy-5-methylphenyl)-4-methylpentan-2-ol;
4-Methyl-2-[4,4,4-trifluoro-3-hydroxy-3-(1H-indol-2-ylmethyl)-1,1-dimethylbutyl]phenol;
4-(2,5-Dimethylphenyl)-1,1,1-trifluoro-4-methyl-2-quinolin-4-ylmethylpentan-2-ol;
1,1,1-Trifluoro-4-(2-methoxy-5-methylphenyl)-4-methyl-2-quinolin-4-ylmethylpentan-2-ol;
4-(2,5-Dimethoxyphenyl)-1,1,1-trifluoro-4-methyl-2-(1H-pyrrolo[2,3-c]pyridin-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-4-methyl-2-(7H-pyrrolo[2,3-d]pyrimidin-6-ylmethyl)pentan-2-ol;
1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol;
2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol;
2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol; and
2-(5-Chloro-1H-pyrrolo[2,3-c]pyridin-2-ylmethyl)-1,1,1-trifluoro-4-(5-fluoro-2-methylphenyl)-4-methylpentan-2-ol,
or a tautomer, prodrug, solvate, or salt thereof.

Most preferred compounds of Formula (IA) include:
1,1,1-Trifluoro-4-(5-fluoro-2-methoxyphenyl)-4-methyl-2-(3-methyl-1H-pyrrolo[3,2-c]pyridin-2-ylmethyl)pentan-2-ol;
1,1,1-Trifluoro-4-(5-fluoro-2,3-dihydrobenzofuran-7-yl)-4-methyl-2-(1H-pyrrolo[3,2-c]pyridin-2-ylmethyl)pentan-2-ol;
1,1,1-Trifluoro-4-(5-fluoro-2-methylphenyl)-4-methyl-2-(3-methyl-1H-pyrrolo[2,3-c]pyridin-2-ylmethyl)pentan-2-ol;

2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol;

2-[4-(5-Fluoro-2-methoxyphenyl)-2-hydroxy-4-methyl-2-trifluoromethylpentyl]-1H-pyrrolo[3,2-b]pyridine-5-carbonitrile;

1,1,1-Trifluoro-4-(5-fluoro-2-methoxyphenyl)-4-methyl-2-(6-methyl-1H-pyrrolo[3,2-c]pyridin-2-ylmethyl)pentan-2-ol;

1,1,1-Trifluoro-4-(5-fluoro-2-methoxyphenyl)-4-methyl-2-(4-methyl-1H-pyrrolo[3,2-c]pyridin-2-ylmethyl)pentan-2-ol;

2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile;

2-[4-(5-Fluoro-2-methoxyphenyl)-2-hydroxy-4-methyl-2-trifluoromethylpentyl]-1H-pyrrolo[2,3-c]pyridine-5-carbonitrile;

2-[4-(5-Fluoro-2-methoxyphenyl)-2-hydroxy-4-methyl-2-trifluoromethylpentyl]-1H-pyrrolo[3,2-c]pyridine-4-carbonitrile;

1,1,1-Trifluoro-4-(5-fluoro-2-methoxyphenyl)-4-methyl-2-(5H-pyrrolo[3,2-d]pyrimidin-6-ylmethyl)pentan-2-ol;

1,1,1-Trifluoro-4-(5-fluoro-2-methoxyphenyl)-4-methyl-2-thieno[2,3-d]pyridazin-2-ylmethylpentan-2-ol;

1,1,1-Trifluoro-4-(5-fluoro-2-methoxyphenyl)-4-methyl-2-(5H-pyrrolo[3,2-c]pyridazin-6-ylmethyl)pentan-2-ol;

1,1,1-Trifluoro-4-(5-fluoro-2-methylphenyl)-4-methyl-2-(1H-pyrrolo[2,3-d]pyridazin-2-ylmethyl)pentan-2-ol;

2-(4,6-Dimethyl-1H-pyrrolo[3,2-c]pyridin-2-ylmethyl)-1,1,1-trifluoro-4-(5-fluoro-2-methylphenyl)-4-methylpentan-2-ol;

4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol;

4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol;

1,1,1-Trifluoro-4-(5-fluoro-2-methylphenyl)-4-methyl-2-(6-methyl-1H-pyrrolo[3,2-c]pyridin-2-ylmethyl)pentan-2-ol;

2-[4-(5-Fluoro-2-methylphenyl)-2-hydroxy-4-methyl-2-trifluoromethylpentyl]-1H-pyrrolo[3,2-b]pyridine-5-carbonitrile;

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile;

1,1,1-Trifluoro-4-(5-fluoro-2-methylphenyl)-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(3-methyl-1H-pyrrolo[2,3-c]pyridin-2-ylmethyl)pentan-2-ol;

1,1,1-Trifluoro-4-(5-fluoro-2-methylphenyl)-4-methyl-2-(5H-pyrrolo[3,2-c]pyridazin-6-ylmethyl)pentan-2-ol;

1,1,1-Trifluoro-4-(5-fluoro-2-methoxyphenyl)-2-(7-fluoro-1H-pyrrolo[2,3-c]pyridin-2-ylmethyl)-4-methylpentan-2-ol;

1,1,1-Trifluoro-4-(5-fluoro-2-methoxyphenyl)-4-methyl-2-(4-methyl-1H-pyrrolo[2,3-c]pyridin-2-ylmethyl)pentan-2-ol;

2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-(5-trifluoromethyl-1H-pyrrolo[2,3-c]pyridin-2-ylmethyl)pentan-2-ol;

1,1,1-Trifluoro-4-(5-fluoro-2-methoxyphenyl)-2-(5-methoxy-1H-pyrrolo[2,3-c]pyridin-2-ylmethyl)-4-methylpentan-2-ol;

1,1,1-Trifluoro-4-(5-fluoro-2-methylphenyl)-4-methyl-2-(4-methyl-1H-pyrrolo[2,3-c]pyridin-2-ylmethyl)pentan-2-ol;

1,1,1-Trifluoro-4-(5-fluoro-2-methylphenyl)-2-(5-isopropoxy-1H-pyrrolo[2,3-c]pyridin-2-ylmethyl)-4-methylpentan-2-ol;

1,1,1-Trifluoro-4-(5-fluoro-2-methylphenyl)-2-(5-methoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol;

1,1,1-Trifluoro4-(5-fluoro-2-methylphenyl)-2-(7-fluoro-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(5-trifluoromethyl-1H-pyrrolo[2,3-c]pyridin-2-ylmethyl)pentan-2-ol;

2-(5-Dimethylamino-1H-pyrrolo[2,3-c]pyridin-2-ylmethyl)-1,1,1-trifluoro-4-(5-fluoro-2-methylphenyl)-4-methylpentan-2-ol;

1,1,1-Trifluoro-4-(5-fluoro-2-methoxyphenyl)-2-(5-chloro-1H-pyrrolo[2,3-c]pyridin-2-ylmethyl)-4-methylpentan-2-ol;

4-(5-Bromo-2,3-dihydrobenzofuran-7-yl)-1,1,1-trifluoro-4-methyl-2-(1H-pyrrolo[2,3-c]pyridin-2-ylmethyl)pentan-2-ol;

1,1,1-Trifluoro-4-methyl-4-(5-methyl-2,3-dihydrobenzofuran-7-yl)-2-(1H-pyrrolo[2,3-c]pyridin-2-ylmethyl)pentan-2-ol;

4-(5-Chloro-2,3-dihydrobenzofuran-7-yl)-1,1,1-trifluoro-4-methyl-2-(1H-pyrrolo[2,3-c]pyridin-2-ylmethyl)pentan-2-ol;

1,1,1-Trifluoro-4-(5-fluoro-2-methoxyphenyl)-4-methyl-2-thieno[2,3-c]pyridin-2-ylmethylpentan-2-ol;

4-(5-Chloro-2,3-dihydrobenzofuran-7-yl)-2,4-dimethyl-1-thieno[2,3-c]pyridin-2-ylpentan-2-ol;

4-(5-Fluoro-2-methylphenyl)-2,4-dimethyl-1-thieno[2,3-c]pyridin-2-ylpentan-2-ol;

1,1,1-Trifluoro-4-(5-fluoro-2-methylphenyl)-4-methyl-2-(1H-pyrrolo[3,2-c]pyridin-2-ylmethyl)pentan-2-ol;

1,1,1-Trifluoro-4-methyl-4-(5-methyl-2,3-dihydrobenzofuran-7-yl)-2-(1H-pyrrolo[3,2-c]pyridin-2-ylmethyl)pentan-2-ol;

4-(5-Chloro-2,3-dihydrobenzofuran-7-yl)-1,1,1-trifluoro-4-methyl-2-(1H-pyrrolo[3,2-c]pyridin-2-ylmethyl)pentan-2-ol;

4-(5-Bromo-2,3-dihydrobenzofuran-7-yl)-1,1,1-trifluoro-4-methyl-2-(1H-pyrrolo[3,2-c]pyridin-2-ylmethyl)pentan-2-ol;

2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-pyrrolo[3,2-b]pyridin-1-ylmethylpentan-2-ol;

1,1,1-Trifluoro-4-(5-fluoro-2-methoxyphenyl)-2-furo[3,2-c]pyridin-2-ylmethyl-4-methylpentan-2-ol;

4-(5-Chloro-2,3-dihydrobenzofuran-7-yl)-1,1,1-trifluoro-4-methyl-2-pyrrolo[3,2-b]pyridin-1-ylmethylpentan-2-ol;

1,1-Difluoro-4-(5-fluoro-2-methoxyphenyl)-4-methyl-2-(1H-pyrrolo[3,2-c]pyridin-2-ylmethyl)pentan-2-ol;

1,1,1-Trifluoro-4-(5-fluoro-2-methoxyphenyl)-4-methyl-2-thieno[3,2-c]pyridin-2-ylmethylpentan-2-ol;
4-(5-Chloro-2,3-dihydrobenzofuran-7-yl)-1,1,1-trifluoro-4-methyl-2-thieno[3,2-c]pyridin-2-ylmethylpentan-2-ol;
1,1,1-Trifluoro-4-(5-fluoro-2-methylphenyl)-4-methyl-2-pyrrolo[3,2-b]pyridin-1-ylmethylpentan-2-ol;
1,1,1-Trifluoro-4-(5-fluoro-2-methylphenyl)-4-methyl-2-thieno[3,2-c]pyridin-2-ylmethylpentan-2-ol;
2-[4-(2,3-Dihydrobenzofuran-7-yl)-2-hydroxy-4-methyl-2-trifluoromethylpentyl]-4-methyl-1H-indole-6-carbonitrile;
4-Fluoro-2-[4,4,4-trifluoro-3-hydroxy-1,1-dimethyl-3-(5-nitro-1H-indol-2-ylmethyl)butyl]phenol;
2-[4-(5-Fluoro-2-methoxyphenyl)-2-hydroxy-4-methyl-2-trifluoromethylpentyl]-1H-indole-6-carbonitrile;
2-[4-(5-Fluoro-2-hydroxyphenyl)-2-hydroxy-4-methyl-2-trifluoromethylpentyl]-1H-indol-6-carbonitrile;
N-{2-[4-(5-Fluoro-2-methoxyphenyl)-2-hydroxy-4-methyl-2-trifluoromethylpentyl]-1H-indol-5-yl}acetamide;
1,1,1-Trifluoro4-(4-fluoro-2-methoxyphenyl)-2-(7-fluoro-4-methyl-1H-indol-2-ylmethyl)-4-methylpentan-2-ol;
5-Fluoro-2-[4,4,4-trifluoro-3-(7-fluoro-4-methyl-1H-indol-2-ylmethyl)-3-hydroxy-1,1-dimethylbutyl]phenol;
2-[4-(3-[1,3]Dioxolan-2-ylphenyl)-2-hydroxy-4-methyl-2-trifluoromethylpentyl]-1H-indole-5-carbonitrile;
2-[4-(4-Fluoro-2-hydroxyphenyl)-2-hydroxy-4-methyl-2-trifluoromethylpentyl]-4-methyl-1H-indole-6-carbonitrile;
{2-[4-(5-Fluoro-2-methoxyphenyl)-2-hydroxy-4-methyl-2-trifluoromethylpentyl]-1H-indol-5-yl}piperidin-1-ylmethanone;
2-[4-(5-Fluoro-2-methoxyphenyl)-2-hydroxy-4-methyl-2-trifluoromethylpentyl]-1H-indole-5-carboxylic acid methylamide;
{2-[4-(5-Fluoro-2-methoxyphenyl)-2-hydroxy-4-methyl-2-trifluoromethylpentyl]-1H-indol-5-yl}pyrrolidin-1-ylmethanone;
2-[4-(5-Fluoro-2-methoxyphenyl)-2-hydroxy-4-methyl-2-trifluoromethylpentyl]-1H-indole-5-carboxylic acid (2-hydroxyethyl)amide;
{2-[4-(5-Fluoro-2-methoxyphenyl)-2-hydroxy-4-methyl-2-trifluoromethylpentyl]-1H-indol-5-yl}(3-hydroxypyrrolidin-1-yl)methanone;
2-[4-(5-Fluoro-2-methoxyphenyl)-2-hydroxy-4-methyl-2-trifluoromethylpentyl]-1H-indole-5-carboxylic acid cyanomethylamide;
({2-[4-(5-Fluoro-2-methoxyphenyl)-2-hydroxy-4-methyl-2-trifluoromethylpentyl]-1H-indole-5-carbonyl}amino)acetic acid methyl ester;
2-[4-(5-Fluoro-2-methoxyphenyl)-2-hydroxy-4-methyl-2-trifluoromethylpentyl]-1H-indole-5-carboxylic acid carbamoylmethylamide;
4-({2-[4-(5-Fluoro-2-methoxyphenyl)-2-hydroxy-4-methyl-2-trifluoromethylpentyl]-1H-indole-5-carbonyl}amino)butyric acid methyl ester;
4-Fluoro-2-[4,4,4-trifluoro-3-hydroxy-1,1-dimethyl-3-(5-trifluoromethyl-1H-indol-2-ylmethyl)butyl]phenol;
2-[4-(5-Bromo-2,3-dihydrobenzofuran-7-yl)-2-hydroxy-4-methyl-2-trifluoromethylpentyl]-4-methyl-1H-indole-6-carbonitrile;
2-[2-Hydroxy-4-(5-methanesulfonyl-2,3-dihydrobenzofuran-7-yl)-4-methyl-2-trifluoromethylpentyl]-4-methyl-1H-indole-6-carbonitrile;
2-[4-(5-Bromo-2,3-dihydrobenzofuran-7-yl)-2-hydroxy-4-methyl-2-trifluoromethylpentyl]-1H-indole-5-carboxylic acid amide;
2-[4-(5-Bromo-2,3-dihydrobenzofuran-7-yl)-2-hydroxy-4-methyl-2-trifluoromethylpentyl]-1H-indole-5-carboxylic acid dimethylamide;
2-[4-(5-Bromo-2,3-dihydrobenzofuran-7-yl)-2-hydroxy-4-methyl-2-trifluoromethylpentyl]-1H-indole-5-carboxylic acid cyanomethylamide;
{2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone;
{2-[4-(5-Bromo-2,3-dihydrobenzofuran-7-yl)-2-hydroxy-4-methyl-2-trifluoromethylpentyl]-1H-indol-5-yl}morpholin-4-ylmethanone;
2-[4-(5-Fluoro-2-methoxyphenyl)-2-hydroxy-4-methyl-2-trifluoromethylpentyl]-1H-indole-5-carboxylic acid amide;
{2-[4-(5-Fluoro-2-methoxyphenyl)-2-hydroxy-4-methyl-2-trifluoromethylpentyl]-1H-indol-5-yl}morpholin-4-ylmethanone;
2-(4-Benzo[1,3]dioxol-4-yl-2-hydroxy-4-methyl-2-trifluoromethylpentyl)-4-methyl-1H-indole-6-carbonitrile;
1,1,1-Trifluoro-4-methyl-4-phenyl-2-quinolin-4-ylmethylhexan-2-ol;
2-[2-Hydroxy-4-methyl-4-(5-methylsulfanyl-2,3-dihydrobenzofuran-7-yl)-2-trifluoromethylpentyl]-1H-indole-3-carbonitrile;
7-(4,4,4-Trifluoro-3-hydroxy-1,1-dimethyl-3-quinolin-4-ylmethylbutyl)-2,3-dihydrobenzofuran-5-carbonitrile;
2-[2-Hydroxy-4-(2-hydroxy-5-methylphenyl)-4-methyl-2-trifluoromethylpentyl]-4-methyl-1H-indole-6-carbonitrile;
1,1,1-Trifluoro-4-(5-fluoro-2,3-dihydrobenzofuran-7-yl)-4-methyl-2-(5-methylsulfanyl-1H-indol-2-ylmethyl)pentan-2-ol;
2-[2-Hydroxy-4-(5-methanesulfonyl-2-methoxyphenyl)-4-methyl-2-trifluoromethylpentyl]-1H-indole-3-carbonitrile;
2-[4-(5-tert-Butyl-2-hydroxyphenyl)-2-hydroxy-4-methyl-2-trifluoromethylpentyl]-1H-indole-3-carbonitrile;
2-[2-Hydroxy-4-(2-hydroxy-5-isopropylphenyl)-4-methyl-2-trifluoromethylpentyl]-1H-indole-3-carbonitrile;
2-[2-Hydroxy-4-(2-hydroxy-3,5-dimethylphenyl)-4-methyl-2-trifluoromethylpentyl]-1H-indole-3-carbonitrile;
2-[2-Hydroxy-4-(5-hydroxy-2,4-dimethylphenyl)-4-methyl-2-trifluoromethylpentyl]-1H-indole-3-carbonitrile;
2-[4-(5-tert-Butyl-2-methoxyphenyl)-2-hydroxy-4-methyl-2-trifluoromethylpentyl]-1H-indole-3-carbonitrile;
2-[2-Hydroxy-4-(5-isopropyl-2-methoxyphenyl)-4-methyl-2-trifluoromethylpentyl]-1H-indole-3-carbonitrile;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
1,1,1-Trifluoro-4-(2-fluorophenyl)-2-(1H-indol-2-ylmethyl)-4-methylpentan-2-ol;
1,1,1-Trifluoro-4-(2-fluorophenyl)-4-methyl-2-quinolin-4-ylmethylpentan-2-ol;
1,1,1-Trifluoro-4-(3-fluorophenyl)-2-(1H-indol-2-ylmethyl)-4-methylpentan-2-ol;
1,1,1-Trifluoro-4-(3-fluorophenyl)-4-methyl-2-quinolin-4-ylmethylpentan-2-ol;
1,1,1-Trifluoro-4-(4-fluorophenyl)-2-(1H-indol-2-ylmethyl)-4-methylpentan-2-ol;
1,1,1-Trifluoro-4-(4-fluorophenyl)-4-methyl-2-quinolin-4-ylmethylpentan-2-ol;
3-(4,4,4-Trifluoro-3-hydroxy-1,1-dimethyl-3-quinolin-4-ylmethylbutyl)phenol;

1,1,1-Trifluoro-4-methyl-2-quinolin-4-ylmethyl-4-(2-trifluoromethylphenyl)pentan-2-ol;
1,1,1-Trifluoro-4-methyl-2-quinolin-4-ylmethyl-4-(4-trifluoromethylphenyl)pentan-2-ol;
4-(3-Chlorophenyl)-1,1,1-trifluoro-2-(1H-indol-2-ylmethyl)-4-methylpentan-2-ol;
4-(3-Chlorophenyl)-1,1,1-trifluoro-4-methyl-2-quinolin-4-ylmethylpentan-2-ol;
4-Biphenyl-3-yl-1,1,1-trifluoro-4-methyl-2-quinolin-4-ylmethylpentan-2-ol;
4-(3-Bromophenyl)-1,1,1-trifluoro-2-(1H-indol-2-ylmethyl)-4-methylpentan-2-ol;
4-(2-Difluoromethoxy-5-fluorophenyl)-1,1,1-trifluoro-2-(1H-indol-2-ylmethyl)-4-methylpentan-2-ol;
4-(4-Dimethylaminophenyl)-1,1,1-trifluoro-4-methyl-2-quinolin-4-ylmethylpentan-2-ol;
2-[4-(5-Fluoro-2-methylphenyl)-2-hydroxy-4-methyl-2-trifluoromethylpentyl]-6-methyl-1,6-dihydropyrrolo[2,3-c]pyridin-5-one;
1,1,1-Trifluoro-4-(5-fluoro-2-methylphenyl)-2-(5-methoxy-1H-pyrrolo[3,2-b]pyridin-2-ylmethyl)-4-methylpentan-2-ol;
2-[4-(3-Dimethylaminomethylphenyl)-2-hydroxy-4-methyl-2-trifluoromethylpentyl]-1H-indole-5-carbonitrile;
1,1,1-Trifluoro-2-(1H-indol-2-ylmethyl)-4-methyl-4-pyridin-2-ylpentan-2-ol;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
4-Fluoro-2-[4,4,4-trifluoro-3-(2-fluoropyridin-4-ylmethyl)-3-hydroxy-1,1-dimethylbutyl]phenol;
2-[3-(2-Bromopyridin-4-ylmethyl)-4,4,4-trifluoro-3-hydroxy-1,1-dimethylbutyl]-4-fluorophenol;
2-(6,8-Dimethylquinolin-4-ylmethyl)-1,1,1-trifluoro-4-(5-fluoro-2-methoxyphenyl)-4-methylpentan-2-ol;
4-[4-(5-Fluoro-2-methoxyphenyl)-2-hydroxy-4-methyl-2-trifluoromethylpentyl]pyridine-2-carbonitrile;
2,6-Dichloro-4-[4-(5-fluoro-2-methoxyphenyl)-2-hydroxy-4-methyl-2-trifluoromethylpentyl]nicotinonitrile;
2,6-Dichloro-4-[4-(5-fluoro-2-hydroxyphenyl)-2-hydroxy-4-methyl-2-trifluoromethylpentyl]nicotinonitrile;
2-[3-(2,6-Dichloroquinolin-4-ylmethyl)-4,4,4-trifluoro-3-hydroxy-1,1-dimethylbutyl]-4-fluorophenol;
4-(2,3-Dihydrobenzofuran-7-yl)-2-(2,6-dimethylpyridin4-ylmethyl)-1,1,1-trifluoro-4-methylpentan-2-ol;
2-(2,6-Dimethylpyridin-4-ylmethyl)-1,1,1-trifluoro-4-(3-fluorophenyl)-4-methylpentan-2-ol;
2-(2,6-Dimethylpyridin-4-ylmethyl)-1,1,1-trifluoro-4-(4-fluorophenyl)-4-methylpentan-2-ol;
1,1,1-Trifluoro-4-(5-fluoro-2-methylphenyl)-4-methyl-2-quinolin-4-ylmethylpentan-2-ol;
2-(2,6-Dimethylpyridin-4-ylmethyl)-1,1,1-trifluoro-4-(5-fluoro-2-methylphenyl)-4-methylpentan-2-ol;
2-(2,6-Dimethylpyridin-4-ylmethyl)-1,1,1-trifluoro-4-methyl-4-m-tolylpentan-2-ol;
1,1,1-Trifluoro-4-(5-fluoro-2-methoxyphenyl)-4-methyl-2-(2-methylquinolin-4-ylmethyl)pentan-2-ol;
4-Fluoro-2-(4,4,4-trifluoro-3-hydroxy-1,1-dimethyl-3-quinolin-4-ylmethylbutyl)phenol;
4-Fluoro-2-[4,4,4-trifluoro-3-hydroxy-1,1-dimethyl-3-(2-methylquinolin-4-ylmethyl)butyl]phenol;
2-(2,6-Dimethylpyridin-4-ylmethyl)-1,1,1-trifluoro-4-(4-fluoro-2-methoxyphenyl)-4-methylpentan-2-ol;
1,1,1-Trifluoro-4-(5-fluoro-2-methoxyphenyl)-4-methyl-2-(7-methylquinolin-4-ylmethyl)pentan-2-ol;
2-[3-(2,6-Dimethylpyridin-4-ylmethyl)-4,4,4-trifluoro-3-hydroxy-1,1-dimethylbutyl]-5-fluorophenol;
1,1,1-Trifluoro-4-(4-fluorophenyl)-4-methyl-2-(2-methylquinolin-4-ylmethyl)pentan-2-ol;
1,1,1-Trifluoro-4-(3-fluorophenyl)-4-methyl-2-(3-methyl-1H-indol-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-2-(7-fluoro-4-methylquinolin-8-yl)-4-methylpentan-2-ol;
4-(2,6-Dimethylphenyl)-1,1,1-trifluoro-2-(1H-indol-2-ylmethyl)-4-methylpentan-2-ol;
2-(3-Bromo-1H-indol-2-ylmethyl)-1,1,1-trifluoro-4-(3-fluorophenyl)-4-methylpentan-2-ol;
4-(3,4-Dimethylphenyl)-1,1,1-trifluoro-2-(1H-indol-2-ylmethyl)-4-methylpentan-2-ol;
1,1,1-Trifluoro-4-(3-fluoro-4-methylphenyl)-2-(1H-indol-2-ylmethyl)-4-methylpentan-2-ol;
1,1,1-Trifluoro-4-(4-fluoro-3-methylphenyl)-2-(1H-indol-2-ylmethyl)-4-methylpentan-2-ol;
1,1,1-Trifluoro-4-(3-fluoro-4-methylphenyl)-4-methyl-2-quinolin-4-ylmethylpentan-2-ol;
1,1,1-Trifluoro-4-(4-fluoro-2-methylphenyl)-4-methyl-2-quinolin-4-ylmethylpentan-2-ol;
4-(3,4-Dimethylphenyl)-1,1,1-trifluoro-4-methyl-2-quinolin-4-ylmethylpentan-2-ol;
4-(2,5-Dimethylphenyl)-1,1,1-trifluoro-2-(1H-indol-2-ylmethyl)-4-methylpentan-2-ol;
1,1,1-Trifluoro-2-(1H-indol-2-ylmethyl)-4-(2-methoxy-5-methylphenyl)-4-methylpentan-2-ol;
4-Methyl-2-[4,4,4-trifluoro-3-hydroxy-3-(1H-indol-2-ylmethyl)-1,1-dimethylbutyl]phenol;
4-(2,5-Dimethylphenyl)-1,1,1-trifluoro-4-methyl-2-quinolin-4-ylmethylpentan-2-ol;
1,1,1-Trifluoro4-(2-methoxy-5-methylphenyl)-4-methyl-2-quinolin-4-ylmethylpentan-2-ol;
4-(2,5-Dimethoxyphenyl)-1,1,1-trifluoro-4-methyl-2-(1H-pyrrolo[2,3-c]pyridin-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-4-methyl-2-(7H-pyrrolo[2,3-d]pyrimidin-6-ylmethyl)pentan-2-ol;
1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol;
2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol;
2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol; and
2-(5-Chloro-1H-pyrrolo[2,3-c]pyridin-2-ylmethyl)-1,1,1-trifluoro-4-(5-fluoro-2-methylphenyl)-4-methylpentan-2-ol,
or a tautomer, prodrug, solvate, or salt thereof.

The invention also provides a method of making a compound of Formula (IA)

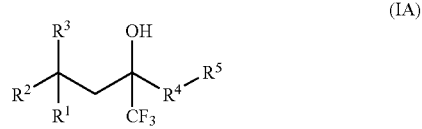

(IA)

where $R^1$, $R^2$, $R^3$, $R^4$, and $R^5$ are as defined above, the method comprising:

(a) reacting an ester of Formula (II) with a suitable reducing agent in a suitable solvent to form a diol of Formula (III)

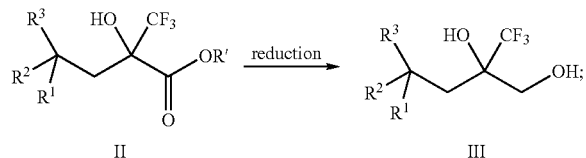

(b) reacting the diol of Formula (III) under suitable oxidative cleavage conditions to form a ketone of Formula (IV)

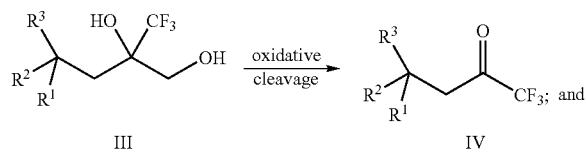

(c) reacting the ketone of Formula (IV) with a suitable organometallic reagent $R^5R^4M$ where M is Li or MgX and X is Cl, Br, or I, in a suitable solvent to form the compound of Formula (IA)

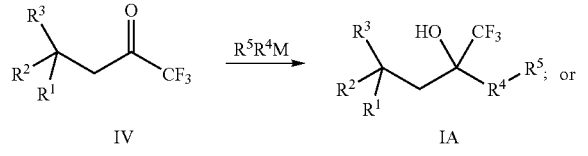

(a') reacting the trifluoroacetamide of Formula (X) with a vinyl magnesium bromide bearing $R^2$ and $R^3$ in a suitable solvent to provide the trifluoromethylenone of Formula (XI)

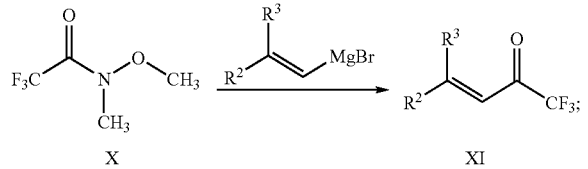

(b') reacting the trifluoromethylenone of Formula (XI) with a suitable organocopper reagent generated from an organometallic reagent $R^5R^4M$ where M is Li or MgX and a copper salt CuX, where X is Cl, Br, or I, in a suitable solvent to form the ketone of Formula (IV)

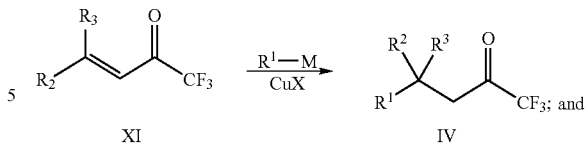

performing step (c) as set forth above.

The instant invention is also directed to compounds of Formula (IB)

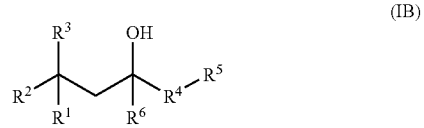

wherein:
  $R^1$ is an aryl or heteroaryl group, each optionally independently substituted with one to three substituent groups,
    wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, $C_1$-$C_5$ alkanoyl, aroyl, aminocarbonyl, $C_1$-$C_5$ alkylaminocarbonyl, $C_1$-$C_5$ dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, nitro, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
    wherein each substituent group of $R^1$ is optionally independently substituted with one to three substituent groups selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl;
  $R^2$ and $R^3$ are each independently $C_1$-$C_5$ alkyl;
  $R^4$ is $C_1$-$C_5$ alkyl, $C_2$-$C_5$ alkenyl, or $C_2$-$C_5$ alkynyl, each optionally independently substituted with one to three substituent groups,
    wherein each substituent group of $R^4$ is independently $C_1$-$C_3$ alkyl, hydroxy, halogen, or oxo;
  $R^5$ is a heteroaryl group optionally independently substituted with one to three substituent groups,
    wherein each substituent group of $R^5$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, $C_1$-$C_5$ alkylaminosulfonyl, $C_1$-$C_5$ dialkylaminosulfonyl, halogen, hydroxy, carboxy, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
  wherein each substituent group of $R^5$ is optionally independently substituted with one to three substituent groups selected from $C_1$-$C_3$ alkyl, $C_1$-$C_3$ alkoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or trifluoromethyl; and $R^6$ is hydrogen, $C_1$-$C_8$ alkyl, $C_2$-$C_8$ alkenyl, $C_2$-$C_8$ alkynyl, carbocycle, heterocyclyl, aryl, heteroaryl, carbocycle-$C_1$-$C_8$ alkyl, carboxy, alkoxycarbonyl, aryl-$C_1$-$C_8$ alkyl, aryl-$C_1$-$C_8$ haloalkyl, heterocyclyl-$C_1$-$C_8$ alkyl, heteroaryl-$C_1$-$C_8$ alkyl, carbocycle-$C_2$-$C_8$ alkenyl, aryl-$C_2$-$C_8$ alkenyl, heterocyclyl-$C_2$-$C_8$ alkenyl, or heteroaryl-$C_2$-$C_8$ alkenyl, each optionally independently substituted with one to three substituent groups,
  wherein each substituent group of $R^6$ is independently $C_1$-$C_5$ alkyl, $C_2$-$C_5$ alkenyl, $C_2$-$C_5$ alkynyl, $C_3$-$C_8$ cycloalkyl, phenyl, $C_1$-$C_5$ alkoxy, phenoxy, $C_1$-$C_5$ alkanoyl, aroyl, $C_1$-$C_5$ alkoxycarbonyl, $C_1$-$C_5$ alkanoyloxy, aminocarbonyloxy, $C_1$-$C_5$ alkylaminocarbonyloxy, $C_1$-$C_5$ dialkylaminocarbonyloxy, aminocarbonyl, $C_1$-$C_5$ alkylaminocarbonyl, $C_1$-$C_5$ dialkylaminocarbonyl, $C_1$-$C_5$ alkanoylamino, $C_1$-$C_5$ alkoxycarbonylamino, $C_1$-$C_5$ alkylsulfonylamino, $C_1$-$C_5$ alkylaminosulfonyl, $C_1$-$C_5$ dialkylaminosulfonyl, halogen, hydroxy, carboxy, cyano, oxo, trifluoromethyl, nitro, amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
wherein $R^6$ cannot be trifluoromethyl,
or a tautomer, prodrug, solvate, or salt thereof.

Another aspect of the invention includes compounds of Formula (IB), wherein:

$R^1$ is thienyl, phenyl, naphthyl, dihydrobenzofuranyl, benzofuranyl, chromanyl, dihydroindolyl, indolyl, dihydrobenzothienyl, benzothienyl, benzodioxolanyl, benzoxazolyl, benzisoxazolyl, benzpyrazolyl, benzimidazolyl, thienyl, quinolinyl, pyridinyl, pyrimidinyl, or pyrazinyl, each optionally independently substituted with one to three substituent groups,
  wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, or $C_1$-$C_3$ alkylthio wherein the sulfur atom is optionally oxidized to a sulfoxide or sulfone,
    wherein each substituent group of $R^1$ is optionally independently substituted with a substituent group selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl;

$R^2$ and $R^3$ are each independently $C_1$-$C_3$ alkyl;
$R^4$ is $CH_2$;
$R^5$ is an imidazolyl, pyridyl, indolyl, azaindolyl, diazaindolyl, benzofuranyl, furanopyridinyl, furanopyrimidinyl, benzothienyl, thienopyridinyl, thienopyrimidinyl, benzoxazolyl, oxazolopyridinyl, benzothiazolyl, thiazolopyridinyl, benzimidazolyl, imidazolopyridinyl, imidazolopyrimidinyl, imidazolopyridazinyl, imidazolopyrazinyl, quinolinyl, or isoquinolinyl group, each optionally independently substituted with one to three substituent groups,
  wherein each substituent group of $R^5$ is independently $C_1$-$C_3$ alkyl, $C_2$-$C_3$ alkenyl, phenyl, $C_1$-$C_3$ alkoxy, methoxycarbonyl, aminocarbonyl, $C_1$-$C_3$ alkylaminocarbonyl, $C_1$-$C_3$ dialkylaminocarbonyl, heterocyclylcarbonyl, hydroxy, fluoro, chloro, bromo, cyano, trifluoromethyl, or $C_1$-$C_3$ alkylthio wherein the sulfur atom is optionally oxidized to a sulfoxide or sulfone,
    wherein each substituent group of $R^5$ is optionally independently substituted with a substituent group selected from methyl, methoxy, fluoro, chloro, bromo, trifluoromethyl, heteroaryl, heterocyclyl, or amino wherein the nitrogen atom is optionally independently mono- or di-substituted by $C_1$-$C_5$ alkyl or aryl; and $R^6$ is $C_1$-$C_5$ alkyl, $C_2$-$C_5$ alkenyl, $C_3$-$C_6$ cycloalkyl, phenyl, $C_3$-$C_6$ cycloalkyl-$C_1$-$C_3$ alkyl, phenyl-$C_1$-$C_3$ alkyl, phenyl-$C_1$-$C_3$ haloalkyl, $C_3$-$C_6$ cycloalkyl-$C_2$-$C_3$ alkenyl, phenyl-$C_2$-$C_3$ alkenyl, each optionally independently substituted with one to three substituent groups,
  wherein each substituent group of $R^6$ is independently $C_1$-$C_3$ alkyl, $C_2$-$C_3$ alkenyl, $C_2$-$C_3$ alkynyl, $C_1$-$C_3$ alkoxy, aminocarbonyl, $C_1$-$C_3$ alkylaminocarbonyl, $C_1$-$C_3$ dialkylaminocarbonyl, halogen, hydroxy, oxo, carboxy, cyano, trifluoromethyl, nitro, or $C_1$-$C_3$ alkylthio wherein the sulfur atom is optionally oxidized to a sulfoxide or sulfone, or a tautomer, prodrug, solvate, or salt thereof.

Yet another aspect of the invention includes compounds of Formula (IB), wherein:

$R^1$ is thienyl, phenyl, naphthyl, pyridyl, chromanyl, dihydrobenzofuranyl, or benzofuranyl, each optionally independently substituted with one or two substituent groups,
  wherein each substituent group of $R^1$ is independently methyl, ethyl, methoxy, ethoxy, fluoro, chloro, bromo, hydroxy, trifluoromethyl, cyano, or $C_1$-$C_5$ alkylthio wherein the sulfur atom is optionally oxidized to a sulfoxide or sulfone;

$R^2$ and $R^3$ are each methyl;
$R^4$ is $CH_2$;
$R^5$ is a pyridyl, indolyl, azaindolyl, diazaindolyl, benzofuranyl, furanopyridinyl, thienopyridinyl, benzoxazolyl, benzimidazolyl, quinolinyl, or isoquinolinyl group, each optionally independently substituted with one to three substituent groups,
  wherein each substituent group of $R^5$ is independently methyl, phenyl, methoxycarbonyl, aminocarbonyl, methylaminocarbonyl, dimethylaminoaminocarbonyl, morpholinylcarbonyl, hydroxy, fluoro, chloro, bromo, cyano, or trifluoromethyl; and $R^6$ is $C_1$-$C_5$ alkyl, $C_3$-$C_6$ cycloalkyl, $C_3$-$C_6$ cycloalkylmethyl-, or benzyl, each optionally independently substituted with one to three substituent groups, wherein each substituent group of $R^6$ is independently methyl, methoxy, fluoro, chloro, bromo, cyano, trifluoromethyl, or hydroxy,
or a tautomer, prodrug, solvate, or salt thereof.

Yet another aspect of the invention includes compounds of Formula (IB), wherein:
$R^1$ is phenyl, dihydrobenzofuranyl, or benzofuranyl, each optionally independently substituted with one to three substituent groups,
wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1C_3$ alkanoyloxy, halogen, hydroxy, carboxy, cyano, trifluoromethyl, nitro, or $C_1$-$C_3$ alkylthio wherein the sulfur atom is optionally oxidized to a sulfoxide or sulfone; and
$R^2$ and $R^3$ are each independently $C_1$-$C_3$ alkyl,
or a tautomer, prodrug, solvate, or salt thereof.

Yet another aspect of the invention includes compounds of Formula (IB), wherein:
$R^1$ is thienyl, phenyl, naphthyl, pyridyl, chromanyl, dihydrobenzofuranyl, or benzofuranyl, each optionally independently substituted with one or two substituent groups,
wherein each substituent group of $R^1$ is independently methyl, ethyl, methoxy, ethoxy, fluoro, chloro, bromo, hydroxy, trifluoromethyl, cyano, or $C_1$-$C_5$ alkylthio wherein the sulfur atom is optionally oxidized to a sulfoxide or sulfone;
$R^2$ and $R^3$ are each methyl;
$R^4$ is $CH_2$;
$R^5$ is a pyridyl, indolyl, azaindolyl, diazaindolyl, benzofuranyl, furanopyridinyl, thienopyridinyl, benzoxazolyl, benzimidazolyl, quinolinyl, or isoquinolinyl group, each optionally independently substituted with one to three substituent groups,
wherein each substituent group of $R^5$ is independently methyl, phenyl, methoxycarbonyl, aminocarbonyl, methylaminocarbonyl, dimethylaminoaminocarbonyl, morpholinylcarbonyl, pyridinyl, hydroxy, fluoro, chloro, bromo, cyano, or trifluoromethyl; and
$R^6$ is $C_1$-$C_5$ alkyl, $C_3$-$C_6$ cycloalkyl, $C_3$-$C_6$ cycloalkylmethyl-, or benzyl, each optionally independently substituted with one to three substituent groups,
wherein each substituent group of $R^6$ is independently methyl, methoxy, fluoro, chloro, bromo, cyano, trifluoromethyl, or hydroxy,
or a tautomer, prodrug, solvate, or salt thereof.

In the above aspects of the invention of the compounds of Formula (IB), it is preferred that $R^6$ is not hydrogen.

Representative compounds of Formula (IB) according to the invention are appended hereto as Table IB, where column A is the compound name according to standard nomenclature and column B is the corresponding chemical structure.

Preferred compounds of Formula (IB) include the following:
2-Cyclopropyl-4-(5-fluoro-2-methoxyphenyl)-4-methyl-1-(1H-pyrrolo[3,2-c]pyridin-2-yl)pentan-2-ol;
2-Cyclopropyl-4-(5-fluoro-2-methylphenyl)-4-methyl-1-(1H-pyrrolo[2,3-c]pyridin-2-yl)pentan-2-ol;
4-(5-Chloro-2,3-dihydrobenzofuran-7-yl)-2-cyclopropyl-4-methyl-1-(1H-pyrrolo[2,3-c]pyridin-2-yl)pentan-2-ol;
2-Cyclopropyl-4-(5-fluoro-2-methylphenyl)-4-methyl-1-(1H-pyrrolo[3,2-c]pyridin-2-yl)pentan-2-ol;
4-(5-Chloro-2,3-dihydrobenzofuran-7-yl)-2-cyclopropyl-4-methyl-1-(1H-pyrrolo[3,2-c]pyridin-2-yl)pentan-2-ol;
4-(5-Fluoro-2-methoxyphenyl)-2,4-dimethyl-1-(1H-pyrrolo[2,3-c]pyridin-2-yl)pentan-2-ol;
5-(5-Fluoro-2-methoxyphenyl)-2,5-dimethyl-3-(1H-pyrrolo[2,3-c]pyridin-2-ylmethyl)hexan-3-ol;
5-(5-Fluoro-2-methoxyphenyl)-2,2,5-trimethyl-3-(1H-pyrrolo[2,3-c]pyridin-2-ylmethyl)hexan-3-ol;
2-Cyclohexyl-4-(5-fluoro-2-methoxyphenyl)-4-methyl-1-(1H-pyrrolo[2,3-c]pyridin-2-yl)pentan-2-ol;
2-Cyclopentyl-4-(5-fluoro-2-methoxyphenyl)-4-methyl-1-(1H-pyrrolo[2,3-c]pyridin-2-yl)pentan-2-ol;
5-(5-Fluoro-2-methoxyphenyl)-5-methyl-3-(1H-pyrrolo[2,3-c]pyridin-2-ylmethyl)hexan-3-ol;
2-(5-Fluoro-2-methoxyphenyl)-2,6-dimethyl-4-(1H-pyrrolo[2,3-c]pyridin-2-ylmethyl)heptan-4-ol;
2-(5-Fluoro-2-methoxyphenyl)-2,5,5-trimethyl-4-(1H-pyrrolo[2,3-c]pyridin-2-ylmethyl)heptan-4-ol;
1,1-Difluoro-4-(5-fluoro-2-methoxyphenyl)-4-methyl-2-(1H-pyrrolo[2,3-c]pyridin-2-ylmethyl)pentan-2-ol;
1-Cyclohexyl-4-(5-fluoro-2-methoxyphenyl)-4-methyl-2-(1H-pyrrolo[2,3-c]pyridin-2-ylmethyl)pentan-2-ol;
5-(5-Fluoro-2-methylphenyl)-2,5-dimethyl-3-(1H-pyrrolo[2,3-c]pyridin-2-ylmethyl)hexan-3-ol;
5-(5-Fluoro-2-methylphenyl)-2,2,5-trimethyl-3-(1H-pyrrolo[2,3-c]pyridin-2-ylmethyl)hexan-3-ol;
5-(5-Chloro-2,3-dihydrobenzofuran-7-yl)-2,5-dimethyl-3-(1H-pyrrolo[2,3-c]pyridin-2-ylmethyl)hexan-3-ol;
2-Cyclobutyl-4-(5-fluoro-2-methoxyphenyl)-4-methyl-1-(1H-pyrrolo[2,3-c]pyridin-2-yl)pentan-2-ol;
2-(5-Fluoro-2-methoxyphenyl)-2,6,6-trimethyl-4-(1H-pyrrolo[2,3-c]pyridin-2-ylmethyl)heptan-4-ol;
5-(5-Fluoro-2-methoxyphenyl)-5-methyl-3-(1H-pyrrolo[2,3-c]pyridin-2-ylmethyl)hex-1-en-3-ol;
5-(5-Fluoro-2-methoxyphenyl)-5-methyl-3-(1H-pyrrolo[2,3-c]pyridin-2-ylmethyl)hex-1-yn-3-ol;
1-Fluoro-4-(5-fluoro-2-methoxyphenyl)-4-methyl-2-(1H-pyrrolo[2,3-c]pyridin-2-ylmethyl)pentan-2-ol;
2,2-Difluoro-5-(5-fluoro-2-methoxyphenyl)-5-methyl-3-(1H-pyrrolo[2,3-c]pyridin-2-ylmethyl)hexan-3-ol;
2-Fluoro-5-(5-fluoro-2-methoxyphenyl)-2,5-dimethyl-3-(1H-pyrrolo[2,3-c]pyridin-2-ylmethyl)hexan-3-ol;
2-Fluoro-5-(5-fluoro-2-methoxyphenyl)-5-methyl-3-(1H-pyrrolo[2,3-c]pyridin-2-ylmethyl)hexan-3-ol;
5-(5-Fluoro-2-methoxyphenyl)-2,5-dimethyl-3-(1H-pyrrolo[2,3-c]pyridin-2-ylmethyl)hex-3-ol;
1,1,1-Trifluoro-5-(5-fluoro-2-methoxyphenyl)-5-methyl-3-(1H-pyrrolo[2,3-c]pyridin-2-ylmethyl)hexan-3-ol;
4-(5-Fluoro-2-methoxyphenyl)-4-methyl-2-phenyl-1-(1H-pyrrolo[2,3-c]pyridin-2-yl)pentan-2-ol;
5-(5-Chloro-2,3-dihydrobenzofuran-7-yl)-2,2,5-trimethyl-3-(1H-pyrrolo[2,3-c]pyridin-2-ylmethyl)hexan-3-ol;
5-(5-Fluoro-2-methylphenyl)-2,2,5-trimethyl-3-thieno[2,3-c]pyridin-2-ylmethylhexan-3-ol;
1,1-Difluoro-4-(5-fluoro-2-methoxyphenyl)-4-methyl-2-(1H-pyrrolo[3,2-c]pyridin-2-ylmethyl)pentan-2-ol;
5-(5-Fluoro-2-methoxyphenyl)-2,5-dimethyl-3-(1H-pyrrolo[3,2-c]pyridin-2-ylmethyl)hexan-3-ol;
5-(5-Fluoro-2-methoxyphenyl)-2,2,5-trimethyl-3-(1H-pyrrolo[3,2-c]pyridin-2-ylmethyl)hexan-3-ol;
2-(1-Fluorocyclopropyl)-4-(5-fluoro-2-methoxyphenyl)-4-methyl-1-(1H-pyrrolo[2,3-c]pyridin-2-yl)pentan-2-ol;
2-(1-Fluorocyclopropyl)-4-(4-fluorophenyl)-4-methyl-1-quinolin-4-ylpentan-2-ol;
2-[4,4-Difluoro-3-hydroxy-1,1-dimethyl-3-(1H-pyrrolo[3,2-c]pyridin-2-ylmethyl)butyl]-4-fluorophenol;
5-(5-Chloro-2,3-dihydrobenzofuran-7-yl)-2,5-dimethyl-3-(1H-pyrrolo[3,2-c]pyridin-2-ylmethyl)hexan-3-ol;

5-(5-Fluoro-2-methylphenyl)-2,5-dimethyl-3-(1H-pyrrolo[3,2-c]pyridin-2-ylmethyl)hexan-3-ol;
5-(5-Fluoro-2-methylphenyl)-2,2,5-trimethyl-3-(1H-pyrrolo[3,2-c]pyridin-2-ylmethyl)hexan-3-ol;
4-(5-Chloro-2,3-dihydrobenzofuran-7-yl)-1,1-difluoro-4-methyl-2-(1H-pyrrolo[3,2-c]pyridin-2-ylmethyl)pentan-2-ol;
4-(5-Chloro-2,3-dihydrobenzofuran-7-yl)-1,1-difluoro-4-methyl-2-pyrrolo[3,2-b]pyridin-1-ylmethylpentan-2-ol;
5-(5-Chloro-2,3-dihydrobenzofuran-7-yl)-2,2,5-trimethyl-3-(1H-pyrrolo[3,2-c]pyridin-2-ylmethyl)hexan-3-ol;
5-(5-Fluoro-2-methylphenyl)-2,2,5-trimethyl-3-(3-methyl-1H-pyrrolo[2,3-c]pyridin-2-ylmethyl)hexan-3-ol;
5-(5-Chloro-2,3-dihydrobenzofuran-7-yl)-2,5-dimethyl-3-(3-methyl-1H-pyrrolo[2,3-c]pyridin-2-ylmethyl)hexan-3-ol;
5-(5-Chloro-2,3-dihydrobenzofuran-7-yl)-2,5-dimethyl-3-(5-phenyl-1H-pyrrolo[2,3-c]pyridin-2-ylmethyl)hexan-3-ol;
5-(5-Fluoro-2-methylphenyl)-2,2,5-trimethyl-3-(5-phenyl-1H-pyrrolo[2,3-c]pyridin-2-ylmethyl)hexan-3-ol;
5-(5-Fluoro-2-methylphenyl)-2,5-dimethyl-3-(5-phenyl-1H-pyrrolo[2,3-c]pyridin-2-ylmethyl)hexan-3-ol;
4-(5-Chloro-2,3-dihydrobenzofuran-7-yl)-1,1-difluoro-4-methyl-2-(6-methyl-1H-pyrrolo[3,2-c]pyridin-2-ylmethyl)pentan-2-ol;
1,1-Difluoro-4-(5-methanesulfonyl-2,3-dihydrobenzofuran-7-yl)-4-methyl-2-(1H-pyrrolo[2,3-c]pyridin-2-ylmethyl)pentan-2-ol;
2-(5-Bromo-1H-indol-2-ylmethyl)-1,1-difluoro-4-(5-methanesulfonyl-2,3-dihydrobenzofuran-7-yl)-4-methylpentan-2-ol; and
2-[2-Difluoromethyl-2-hydroxy-4-(5-methanesulfonyl-2,3-dihydrobenzofuran-7-yl)-4-methylpentyl]-4-methyl-1H-indole-6-carbonitrile,
or a tautomer, prodrug, solvate, or salt thereof.
More preferred compounds of Formula (IB) include:
2-Cyclopropyl-4-(5-fluoro-2-methoxyphenyl)-4-methyl-1-(1H-pyrrolo[3,2-c]pyridin-2-yl)pentan-2-ol;
2-Cyclopropyl-4-(5-fluoro-2-methylphenyl)-4-methyl-1-(1H-pyrrolo[2,3-c]pyridin-2-yl)pentan-2-ol;
4-(5-Chloro-2,3-dihydrobenzofuran-7-yl)-2-cyclopropyl-4-methyl-1-(1H-pyrrolo[2,3-c]pyridin-2-yl)pentan-2-ol;
2-Cyclopropyl-4-(5-fluoro-2-methylphenyl)-4-methyl-1-(1H-pyrrolo[3,2-c]pyridin-2-yl)pentan-2-ol;
4-(5-Chloro-2,3-dihydrobenzofuran-7-yl)-2-cyclopropyl-4-methyl-1-(1H-pyrrolo[3,2-c]pyridin-2-yl)pentan-2-ol;
4-(5-Fluoro-2-methoxyphenyl)-2,4-dimethyl-1-(1H-pyrrolo[2,3-c]pyridin-2-yl)pentan-2-ol;
5-(5-Fluoro-2-methoxyphenyl)-2,5-dimethyl-3-(1H-pyrrolo[2,3-c]pyridin-2-ylmethyl)hexan-3-ol;
5-(5-Fluoro-2-methoxyphenyl)-2,2,5-trimethyl-3-(1H-pyrrolo[2,3-c]pyridin-2-ylmethyl)hexan-3-ol;
2-Cyclopentyl-4-(5-fluoro-2-methoxyphenyl)-4-methyl-1-(1H-pyrrolo[2,3-c]pyridin-2-yl)pentan-2-ol;
5-(5-Fluoro-2-methoxyphenyl)-5-methyl-3-(1H-pyrrolo[2,3-c]pyridin-2-ylmethyl)hexan-3-ol;
2-(5-Fluoro-2-methoxyphenyl)-2,6-dimethyl-4-(1H-pyrrolo[2,3-c]pyridin-2-ylmethyl)heptan-4-ol;
2-(5-Fluoro-2-methoxyphenyl)-2,5,5-trimethyl-4-(1H-pyrrolo[2,3-c]pyridin-2-ylmethyl)heptan-4-ol;
1,1-Difluoro-4-(5-fluoro-2-methoxyphenyl)-4-methyl-2-(1H-pyrrolo[2,3-c]pyridin-2-ylmethyl)pentan-2-ol;
1-Cyclohexyl-4-(5-fluoro-2-methoxyphenyl)-4-methyl-2-(1H-pyrrolo[2,3-c]pyridin-2-ylmethyl)pentan-2-ol;
5-(5-Fluoro-2-methylphenyl)-2,5-dimethyl-3-(1H-pyrrolo[2,3-c]pyridin-2-ylmethyl)hexan-3-ol;
5-(5-Fluoro-2-methylphenyl)-2,2,5-trimethyl-3-(1H-pyrrolo[2,3-c]pyridin-2-ylmethyl)hexan-3-ol;
5-(5-Chloro-2,3-dihydrobenzofuran-7-yl)-2,5-dimethyl-3-(1H-pyrrolo[2,3-c]pyridin-2-ylmethyl)hexan-3-ol;
1,1-Difluoro-4-(5-fluoro-2-methoxyphenyl)-4-methyl-2-(1H-pyrrolo[3,2-c]pyridin-2-ylmethyl)pentan-2-ol;
5-(5-Fluoro-2-methoxyphenyl)-2,5-dimethyl-3-(1H-pyrrolo[3,2-c]pyridin-2-ylmethyl)hexan-3-ol;
5-(5-Fluoro-2-methoxyphenyl)-2,2,5-trimethyl-3-(1H-pyrrolo[3,2-c]pyridin-2-ylmethyl)hexan-3-ol;
2-(1-Fluorocyclopropyl)-4-(5-fluoro-2-methoxyphenyl)-4-methyl-1-(1H-pyrrolo[2,3-c]pyridin-2-yl)pentan-2-ol;
2-(1-Fluorocyclopropyl)-4-(4-fluorophenyl)-4-methyl-1-quinolin-4-ylpentan-2-ol;
2-[4,4-Difluoro-3-hydroxy-1,1-dimethyl-3-(1H-pyrrolo[3,2-c]pyridin-2-ylmethyl)butyl]-4-fluorophenol;
5-(5-Chloro-2,3-dihydrobenzofuran-7-yl)-2,5-dimethyl-3-(1H-pyrrolo[3,2-c]pyridin-2-ylmethyl)hexan-3-ol;
5-(5-Fluoro-2-methylphenyl)-2,5-dimethyl-3-(1H-pyrrolo[3,2-c]pyridin-2-ylmethyl)hexan-3-ol;
5-(5-Fluoro-2-methylphenyl)-2,2,5-trimethyl-3-(1H-pyrrolo[3,2-c]pyridin-2-ylmethyl)hexan-3-ol;
4-(5-Chloro-2,3-dihydrobenzofuran-7-yl)-1,1-difluoro-4-methyl-2-(1H-pyrrolo[3,2-c]pyridin-2-ylmethyl)pentan-2-ol;
4-(5-Chloro-2,3-dihydrobenzofuran-7-yl)-1,1-difluoro-4-methyl-2-pyrrolo[3,2-b]pyridin-1-ylmethylpentan-2-ol;
5-(5-Chloro-2,3-dihydrobenzofuran-7-yl)-2,2,5-trimethyl-3-(1H-pyrrolo[3,2-c]pyridin-2-ylmethyl)hexan-3-ol;
5-(5-Fluoro-2-methylphenyl)-2,2,5-trimethyl-3-(3-methyl-1H-pyrrolo[2,3-c]pyridin-2-ylmethyl)hexan-3-ol;
5-(5-Chloro-2,3-dihydrobenzofuran-7-yl)-2,5-dimethyl-3-(3-methyl-1H-pyrrolo[2,3-c]pyridin-2-ylmethyl)hexan-3-ol;
5-(5-Chloro-2,3-dihydrobenzofuran-7-yl)-2,5-dimethyl-3-(5-phenyl-1H-pyrrolo[2,3-c]pyridin-2-ylmethyl)hexan-3-ol;
5-(5-Fluoro-2-methylphenyl)-2,2,5-trimethyl-3-(5-phenyl-1H-pyrrolo[2,3-c]pyridin-2-ylmethyl)hexan-3-ol;
5-(5-Fluoro-2-methylphenyl)-2,5-dimethyl-3-(5-phenyl-1H-pyrrolo[2,3-c]pyridin-2-ylmethyl)hexan-3-ol;
4-(5-Chloro-2,3-dihydrobenzofuran-7-yl)-1,1-difluoro-4-methyl-2-(6-methyl-1H-pyrrolo[3,2-c]pyridin-2-ylmethyl)pentan-2-ol;
1,1-Difluoro-4-(5-methanesulfonyl-2,3-dihydrobenzofuran-7-yl)-4-methyl-2-(1H-pyrrolo[2,3-c]pyridin-2-ylmethyl)pentan-2-ol;
2-(5-Bromo-1H-indol-2-ylmethyl)-1,1-difluoro-4-(5-methanesulfonyl-2,3-dihydrobenzofuran-7-yl)-4-methylpentan-2-ol; and
2-[2-Difluoromethyl-2-hydroxy-4-(5-methanesulfonyl-2,3-dihydrobenzofuran-7-yl)-4-methylpentyl]-4-methyl-1H-indole-6-carbonitrile,
or a tautomer, prodrug, solvate, or salt thereof.
Most preferred compounds of Formula (IB) include:
2-Cyclopropyl-4-(5-fluoro-2-methoxyphenyl)-4-methyl-1-(1H-pyrrolo[3,2-c]pyridin-2-yl)pentan-2-ol;
2-Cyclopropyl-4-(5-fluoro-2-methylphenyl)-4-methyl-1-(1H-pyrrolo[2,3-c]pyridin-2-yl)pentan-2-ol;
4-(5-Chloro-2,3-dihydrobenzofuran-7-yl)-2-cyclopropyl-4-methyl-1-(1H-pyrrolo[2,3-c]pyridin-2-yl)pentan-2-ol;
2-Cyclopropyl-4-(5-fluoro-2-methylphenyl)-4-methyl-1-(1H-pyrrolo[3,2-c]pyridin-2-yl)pentan-2-ol;
4-(5-Chloro-2,3-dihydrobenzofuran-7-yl)-2-cyclopropyl-4-methyl-1-(1H-pyrrolo[3,2-c]pyridin-2-yl)pentan-2-ol;
5-(5-Fluoro-2-methoxyphenyl)-2,5-dimethyl-3-(1H-pyrrolo[2,3-c]pyridin-2-ylmethyl)hexan-3-ol;

5-(5-Fluoro-2-methoxyphenyl)-2,2,5-trimethyl-3-(1H-pyrrolo[2,3-c]pyridin-2-ylmethyl)hexan-3-ol;

2-Cyclopentyl-4-(5-fluoro-2-methoxyphenyl)-4-methyl-1-(1H-pyrrolo[2,3-c]pyridin-2-yl)pentan-2-ol;

2-(5-Fluoro-2-methoxyphenyl)-2,5,5-trimethyl-4-(1H-pyrrolo[2,3-c]pyridin-2-ylmethyl)heptan-4-ol;

1,1-Difluoro-4-(5-fluoro-2-methoxyphenyl)-4-methyl-2-(1H-pyrrolo[2,3-c]pyridin-2-ylmethyl)pentan-2-ol;

5-(5-Fluoro-2-methylphenyl)-2,5-dimethyl-3-(1H-pyrrolo[2,3-c]pyridin-2-ylmethyl)hexan-3-ol;

5-(5-Fluoro-2-methylphenyl)-2,2,5-trimethyl-3-(1H-pyrrolo[2,3-c]pyridin-2-ylmethyl)hexan-3-ol;

5-(5-Chloro-2,3-dihydrobenzofuran-7-yl)-2,5-dimethyl-3-(1H-pyrrolo[2,3-c]pyridin-2-ylmethyl)hexan-3-ol;

1,1-Difluoro-4-(5-fluoro-2-methoxyphenyl)-4-methyl-2-(1H-pyrrolo[3,2-c]pyridin-2-ylmethyl)pentan-2-ol;

5-(5-Fluoro-2-methoxyphenyl)-2,5-dimethyl-3-(1H-pyrrolo[3,2-c]pyridin-2-ylmethyl)hexan-3-ol;

5-(5-Fluoro-2-methoxyphenyl)-2,2,5-trimethyl-3-(1H-pyrrolo[3,2-c]pyridin-2-ylmethyl)hexan-3-ol;

2-(1-Fluorocyclopropyl)-4-(5-fluoro-2-methoxyphenyl)-4-methyl-1-(1H-pyrrolo[2,3-c]pyridin-2-yl)pentan-2-ol;

2-(1-Fluorocyclopropyl)-4-(4-fluorophenyl)-4-methyl-1-quinolin-4-ylpentan-2-ol;

2-[4,4-Difluoro-3-hydroxy-1,1-dimethyl-3-(1H-pyrrolo[3,2-c]pyridin-2-ylmethyl)butyl]-4-fluorophenol;

5-(5-Chloro-2,3-dihydrobenzofuran-7-yl)-2,5-dimethyl-3-(1H-pyrrolo[3,2-c]pyridin-2-ylmethyl)hexan-3-ol;

5-(5-Fluoro-2-methylphenyl)-2,5-dimethyl-3-(1H-pyrrolo[3,2-c]pyridin-2-ylmethyl)hexan-3-ol;

5-(5-Fluoro-2-methylphenyl)-2,2,5-trimethyl-3-(1H-pyrrolo[3,2-c]pyridin-2-ylmethyl)hexan-3-ol;

4-(5-Chloro-2,3-dihydrobenzofuran-7-yl)-1,1-difluoro-4-methyl-2-(1H-pyrrolo[3,2-c]pyridin-2-ylmethyl)pentan-2-ol;

4-(5-Chloro-2,3-dihydrobenzofuran-7-yl)-1,1-difluoro-4-methyl-2-pyrrolo[3,2-b]pyridin-1-ylmethylpentan-2-ol;

5-(5-Chloro-2,3-dihydrobenzofuran-7-yl)-2,2,5-trimethyl-3-(1H-pyrrolo[3,2-c]pyridin-2-ylmethyl)hexan-3-ol;

5-(5-Fluoro-2-methylphenyl)-2,2,5-trimethyl-3-(3-methyl-1H-pyrrolo[2,3-c]pyridin-2-ylmethyl)hexan-3-ol;

5-(5-Chloro-2,3-dihydrobenzofuran-7-yl)-2,5-dimethyl-3-(3-methyl-1H-pyrrolo[2,3-c]pyridin-2-ylmethyl)hexan-3-ol;

5-(5-Chloro-2,3-dihydrobenzofuran-7-yl)-2,5-dimethyl-3-(5-phenyl-1H-pyrrolo[2,3-c]pyridin-2-ylmethyl)hexan-3-ol;

4-(5-Chloro-2,3-dihydrobenzofuran-7-yl)-1,1-difluoro-4-methyl-2-(6-methyl-1H-pyrrolo[3,2-c]pyridin-2-ylmethyl)pentan-2-ol;

2-(5-Bromo-1H-indol-2-ylmethyl)-1,1-difluoro-4-(5-methanesulfonyl-2,3-dihydrobenzofuran-7-yl)-4-methylpentan-2-ol; and 2-[2-Difluoromethyl-2-hydroxy-4-(5-methanesulfonyl-2,3-dihydrobenzofuran-7-yl)-4-methylpentyl]-4-methyl-1H-indole-6-carbonitrile, or a tautomer, prodrug, solvate, or salt thereof.

The invention further provides methods of making a compound of Formula (IB). One method of making a compound of Formula (IB)

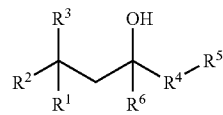

where $R^1$ is an optionally substituted 2-methoxyphenyl group and $R^2$, $R^3$, $R^4$, $R^5$, and $R^6$ are as defined above, the method comprising:

(a) reacting an optionally substituted phenol of Formula (XXII) with an acryloyl chloride of Formula (XIII) in the presence of a suitable base, followed by cyclization of the intermediate ester by treatment with a suitable Lewis acid to form a lactone of Formula (XIV)

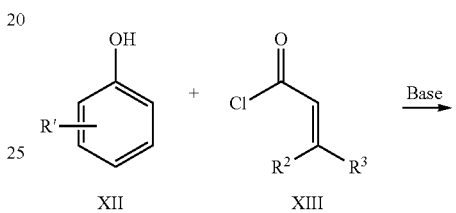

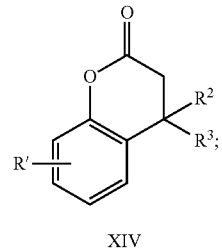

(b) reacting the lactone of Formula (XIV) with a suitable amine HNR'R", followed by treatment of the intermediate phenol with methyl iodide in the presence of a suitable base to form an amide of Formula (XV)

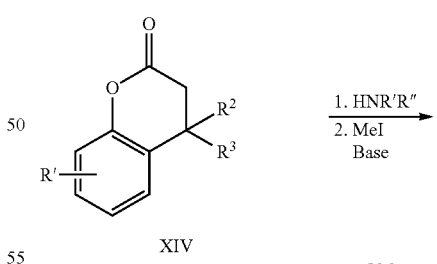

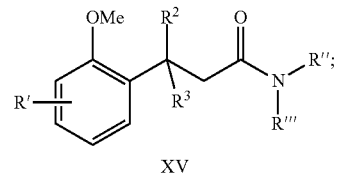

(c) reacting the amide of Formula (XV) with a suitable organometallic reagent $R^6M$, where M is Li or MgX and X is Cl, Br, or I, in a suitable solvent to form a ketone of Formula (XVI)

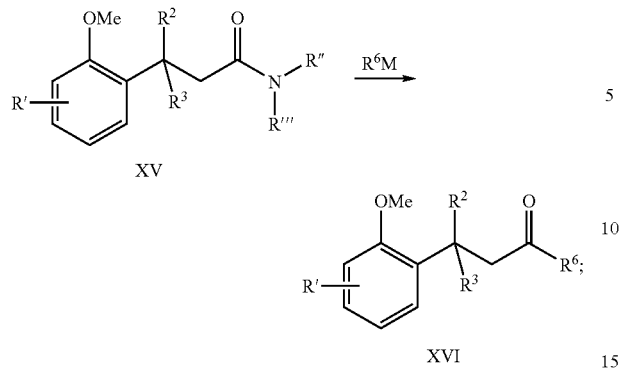

XV

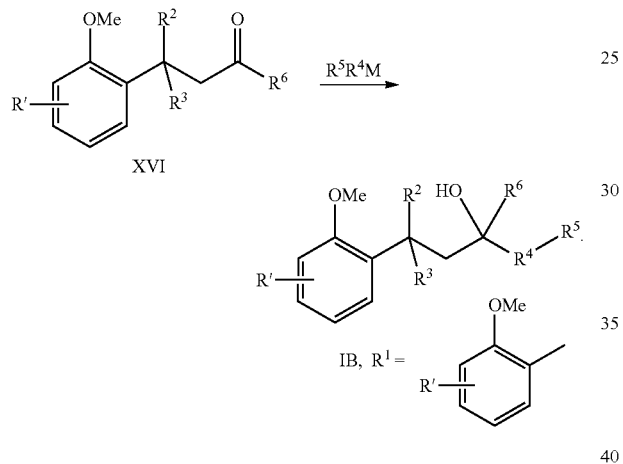

XVI (d) reacting the ketone of Formula (XVI) with a suitable organometallic reagent $R^5R^4M$ where M is Li or MgX and X is Cl, Br, or I, in a suitable solvent to form the compound of Formula (IB)

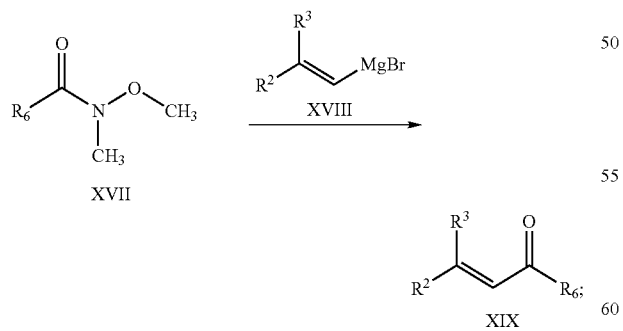

A second method for making a compound of Formula (IB) comprises:

(a') reacting an amide of Formula (XVII) with a vinyl magnesium bromide bearing $R^2$ and $R^3$ of Formula (XVIII) in a suitable solvent to provide an enone of Formula (XIX)

(b') reacting the enone of Formula (XIX) with a suitable organocopper reagent generated from an organometallic reagent $R^1M$, where M is Li or MgX, and a copper salt CuX, where X is Cl, Br, or I, in a suitable solvent to form a ketone of Formula (XX)

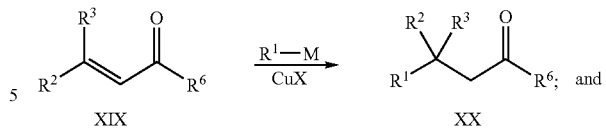

(c') reacting the ketone of Formula (XX) with a suitable organometallic reagent $R^5R^4M$, where M is Li or MgX, and X is Cl, Br, or I, in a suitable solvent to form the compound of Formula (IB)

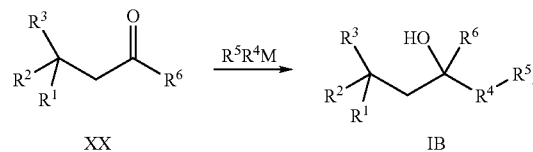

The instant invention is directed to compounds of Formula (IC)

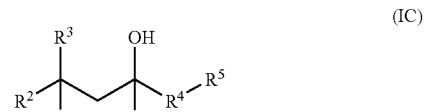

wherein:
R$^1$ is an aryl or heteroaryl group, each optionally independently substituted with one to three substituent groups, wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, $C_1$-$C_5$ alkanoyl, aroyl, aminocarbonyl, $C_1$-$C_5$ alkylaminocarbonyl, $C_1$-$C_5$ dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, nitro, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
wherein each substituent group of $R^1$ is optionally independently substituted with one to three substituent groups selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl;
$R^2$ and $R^3$ are each independently $C_1$-$C_5$ alkyl;
$R^4$ is $C_1$-$C_5$ alkyl, $C_2$-$C_5$ alkenyl, or $C_2$-$C_5$ alkynyl, each optionally independently substituted with one to three substituent groups, wherein each substituent group of $R^4$ is independently $C_1$-$C_3$ alkyl, hydroxy, halogen, or oxo;

$R^5$ is a heteroaryl group fused with a saturated or partially saturated carbocyclic ring optionally independently substituted with one to three substituent groups, wherein each substituent group of $R^5$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, $C_1$-$C_5$ alkylaminosulfonyl, $C_1$-$C_5$ dialkylaminosulfonyl, halogen, hydroxy, oxo, carboxy, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone, wherein each substituent group of $R^5$ is optionally independently substituted with one to three substituent groups selected from $C_1$-$C_3$ alkyl, $C_1$-$C_3$ alkoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or trifluoromethyl, and $R^6$ is hydrogen, $C_1$-$C_8$ alkyl, $C_2$-$C_8$ alkenyl, $C_2$-$C_8$ alkynyl, carbocycle, heterocyclyl, aryl, heteroaryl, carbocycle-$C_1$-$C_8$ alkyl, carboxy, trifluoromethyl, alkoxycarbonyl, aryl-$C_1$-$C_8$ alkyl, aryl-$C_1$-$C_8$ haloalkyl, heterocyclyl-$C_1$-$C_8$ alkyl, heteroaryl-$C_1$-$C_8$ alkyl, carbocycle-$C_2$-$C_8$ alkenyl, aryl-$C_2$-$C_8$ alkenyl, heterocyclyl-$C_2$-$C_8$ alkenyl, or heteroaryl-$C_2$-$C_8$ alkenyl, each optionally independently substituted with one to three substituent groups, wherein each substituent group of $R^6$ is independently $C_1$-$C_5$ alkyl, $C_2$-$C_5$ alkenyl, $C_2$-$C_5$ alkynyl, $C_3$-$C_8$ cycloalkyl, phenyl, $C_1$-$C_5$ alkoxy, phenoxy, $C_1$-$C_5$ alkanoyl, aroyl, $C_1$-$C_5$ alkoxycarbonyl, $C_1$-$C_5$ alkanoyloxy, aminocarbonyloxy, $C_1$-$C_5$ alkylaminocarbonyloxy, $C_1$-$C_5$ dialkylaminocarbonyloxy, aminocarbonyl, $C_1$-$C_5$ alkylaminocarbonyl, $C_1$-$C_5$ dialkylaminocarbonyl, $C_1$-$C_5$ alkanoylamino, $C_1$-$C_5$ alkoxycarbonylamino, $C_1$-$C_5$ alkylsulfonylamino, $C_1$-$C_5$ alkylaminosulfonyl, $C_1$-$C_5$ dialkylaminosulfonyl, halogen, hydroxy, carboxy, cyano, oxo, trifluoromethyl, nitro, amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (IC), wherein:

$R^1$ is thienyl, phenyl, naphthyl, dihydrobenzofuranyl, benzofuranyl, chromanyl, dihydroindolyl, indolyl, dihydrobenzothienyl, benzothienyl, benzodioxolanyl, benzoxazolyl, benzisoxazolyl, benzpyrazolyl, benzimidazolyl, thienyl, quinolinyl, pyridinyl, pyrimidinyl, or pyrazinyl, each optionally independently substituted with one to three substituent groups, wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, or $C_1$-$C_3$ alkylthio wherein the sulfur atom is optionally oxidized to a sulfoxide or sulfone, wherein each substituent group of $R^1$ is optionally independently substituted with a substituent group selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl;

$R^2$ and $R^3$ are each independently $C_1$-$C_3$ alkyl;

$R^4$ is $CH_2$;

$R^5$ is a N-linked heteroaryl with a fused 5-7 membered saturated carbocyclic ring optionally and independently substituted with one to three substituent groups, wherein each substituent group of $R^5$ is independently $C_1$-$C_3$ alkyl, $C_2$-$C_3$ alkenyl, phenyl, $C_1$-$C_3$ alkoxy, methoxycarbonyl, aminocarbonyl, $C_1$-$C_3$ alkylaminocarbonyl, $C_1$-$C_3$ dialkylaminocarbonyl, heterocyclylcarbonyl, fluoro, chloro, bromo, cyano, trifluoromethyl, hydroxyl, oxo, or $C_1$-$C_3$ alkylthio wherein the sulfur atom is optionally oxidized to a sulfoxide or sulfone, wherein each substituent group of $R^5$ is optionally independently substituted with a substituent group selected from methyl, methoxy, fluoro, chloro, bromo, trifluoromethyl, heteroaryl, heterocyclyl, or amino wherein the nitrogen atom is optionally independently mono- or di-substituted by $C_1$-$C_5$ alkyl or aryl; and $R^6$ is $C_1$-$C_5$ alkyl, $C_2$-$C_5$ alkenyl, $C_3$-$C_6$ cycloalkyl, trifluoromethyl, phenyl, $C_3$-$C_6$ cycloalkyl-$C_1$-$C_3$ alkyl, phenyl-$C_1$-$C_3$ alkyl, phenyl-$C_1$-$C_3$ haloalkyl, $C_3$-$C_6$ cycloalkyl-$C_2$-$C_3$ alkenyl, phenyl-$C_2$-$C_3$ alkenyl, each optionally independently substituted with one to three substituent groups, wherein each substituent group of $R^6$ is independently $C_1$-$C_3$ alkyl, $C_2$-$C_3$ alkenyl, $C_2$-$C_3$ alkynyl, $C_1$-$C_3$ alkoxy, aminocarbonyl, $C_1$-$C_3$ alkylaminocarbonyl, $C_1$-$C_3$ dialkylaminocarbonyl, halogen, hydroxy, carboxy, cyano, trifluoromethyl, nitro, or $C_1$-$C_3$ alkylthio wherein the sulfur atom is optionally oxidized to a sulfoxide or sulfone, or a tautomer, prodrug, solvate, or salt thereof.

Yet another aspect of the invention includes compounds of Formula (IC), wherein:

$R^1$ is thienyl, phenyl, naphthyl, pyridyl, chromanyl, dihydrobenzofuranyl, or benzofuranyl, each optionally independently substituted with one or two substituent groups, wherein each substituent group of $R^1$ is independently methyl, ethyl, methoxy, ethoxy, fluoro, chloro, bromo, hydroxy, trifluoromethyl, cyano, or $C_1$-$C_5$ alkylthio wherein the sulfur atom is optionally oxidized to a sulfoxide or sulfone;

$R^2$ and $R^3$ are each methyl;

$R^4$ is $CH_2$;

$R^5$ is a N-linked pyrrole, pyrazole, or imidazole fused to a 5-7 membered saturated carbocyclic ring optionally and independently substituted with one to three substituent groups, wherein each substituent group of $R^5$ is independently methyl, phenyl, methoxycarbonyl, aminocarbonyl, methylaminocarbonyl, dimethylaminoaminocarbonyl, morpholinylcarbonyl, fluoro, chloro, bromo, cyano, hydroxy, oxo, or trifluoromethyl; and $R^6$ is $C_1$-$C_5$ alkyl, $C_3$-$C_6$ cycloalkyl, trifluoromethyl, $C_3$-$C_6$ cycloalkylmethyl-, or benzyl, each optionally independently substituted with one to three substituent groups, wherein each substituent group of $R^6$ is independently methyl, methoxy, fluoro, chloro, bromo, cyano, trifluoromethyl, or hydroxy, or a tautomer, prodrug, solvate, or salt thereof.

Another aspect of the invention includes compounds of Formula (IC), wherein:

$R^1$ is thienyl, phenyl, naphthyl, dihydrobenzofuranyl, benzofuranyl, chromanyl, dihydroindolyl, indolyl, dihydrobenzothienyl, benzothienyl, benzodioxolanyl, benzoxazolyl, benzisoxazolyl, benzpyrazolyl, benzimidazolyl, thienyl, quinolinyl, pyridinyl, pyrimidinyl, or pyrazinyl, each optionally independently substituted with one to three substituent groups, wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, aryl, heteroaryl, heterocyclyl, or $C_1$-$C_3$ alkylthio wherein the sulfur atom is optionally oxidized to a sulfoxide or sulfone, wherein each substituent group of $R^1$ is optionally independently substituted with a substituent group selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl;

$R^2$ and $R^3$ are each independently $C_1$-$C_3$ alkyl;

$R^4$ is $CH_2$;

$R^5$ is a N-linked heteroaryl with a fused 5-7 membered saturated carbocyclic ring optionally and independently substituted with one to three substituent groups, wherein each substituent group of $R^5$ is independently $C_1$-$C_3$ alkyl, $C_2$-$C_3$ alkenyl, phenyl, $C_1$-$C_3$ alkoxy, methoxycarbonyl, aminocarbonyl, $C_1$-$C_3$ alkylaminocarbonyl, $C_1$-$C_3$ dialkylaminocarbonyl, heterocyclylcarbonyl, fluoro, chloro, bromo, cyano, trifluoromethyl, hydroxyl, oxo, or $C_1$-$C_3$ alkylthio wherein the sulfur atom is optionally oxidized to a sulfoxide or sulfone, wherein each substituent group of $R^5$ is optionally independently substituted with a substituent group selected from methyl, methoxy, fluoro, chloro, bromo, trifluoromethyl, heteroaryl, heterocyclyl, or amino wherein the nitrogen atom is optionally independently mono- or di-substituted by $C_1$-$C_5$ alkyl or aryl; and $R^6$ is $C_1$-$C_5$ alkyl, $C_2$-$C_5$ alkenyl, $C_3$-$C_6$ cycloalkyl, trifluoromethyl, phenyl, $C_3$-$C_6$ cycloalkyl-$C_1$-$C_3$ alkyl, phenyl-$C_1$-$C_3$ alkyl, phenyl-$C_1$-$C_3$ haloalkyl, $C_3$-$C_6$ cycloalkyl-$C_2$-$C_3$ alkenyl, phenyl-$C_2$-$C_3$ alkenyl, each optionally independently substituted with one to three substituent groups, wherein each substituent group of $R^6$ is independently $C_1$-$C_3$ alkyl, $C_2$-$C_3$ alkenyl, $C_2$-$C_3$ alkynyl, $C_1$-$C_3$ alkoxy, aminocarbonyl, $C_1$-$C_3$ alkylaminocarbonyl, $C_1$-$C_3$ dialkylaminocarbonyl, halogen, hydroxy, carboxy, cyano, trifluoromethyl, nitro, or $C_1$-$C_3$ alkylthio wherein the sulfur atom is optionally oxidized to a sulfoxide or sulfone, or a tautomer, prodrug, solvate, or salt thereof.

Yet another aspect of the invention includes compounds of Formula (IC), wherein:

$R^1$ is thienyl, phenyl, naphthyl, pyridyl, chromanyl, dihydrobenzofuranyl, or benzofuranyl, each optionally independently substituted with one or two substituent groups, wherein each substituent group of $R^1$ is independently methyl, ethyl, methoxy, ethoxy, fluoro, chloro, bromo, hydroxy, trifluoromethyl, pyridinyl, pyrimidinyl, pyrazinyl, cyano, or $C_1$-$C_5$ alkylthio wherein the sulfur atom is optionally oxidized to a sulfoxide or sulfone;

wherein each substituent group of $R^1$ is optionally independently substituted with a substituent group selected from cyano or halogen;

$R^2$ and $R^3$ are each methyl;

$R^4$ is $CH_2$;

$R^5$ is a N-linked pyrrole, pyrazole, or imidazole fused to a 5-7 membered saturated carbocyclic ring optionally and independently substituted with one to three substituent groups, wherein each substituent group of $R^5$ is independently methyl, phenyl, methoxycarbonyl, aminocarbonyl, methylaminocarbonyl, dimethylaminoaminocarbonyl, morpholinylcarbonyl, fluoro, chloro, bromo, cyano, hydroxy, oxo, or trifluoromethyl; and $R^6$ is $C_1$-$C_5$ alkyl, $C_3$-$C_6$ cycloalkyl, trifluoromethyl, $C_3$-$C_6$ cycloalkylmethyl-, or benzyl, each optionally independently substituted with one to three substituent groups, wherein each substituent group of $R^6$ is independently methyl, methoxy, fluoro, chloro, bromo, cyano, trifluoromethyl, or hydroxy, or a tautomer, prodrug, solvate, or salt thereof.

Representative compounds of Formula (IC) according to the invention are appended hereto as Table IC, where column A is the compound name according to standard nomenclature and column B is the corresponding chemical structure.

Preferred compounds of Formula (IC) include the following:

1-[4-(5-Fluoro-2-methoxyphenyl)-2-hydroxy-4-methyl-2-trifluoromethylpentyl]-1,5,6,7-tetrahydroindol-4-one;

1-[4-(5-Fluoro-2-hydroxyphenyl)-2-hydroxy-4-methyl-2-trifluoromethylpentyl-1,5,6,7-tetrahydroindol-4-one;

1-[4-(2,3-Dihydrobenzofuran-7-yl)-2-hydroxy-4-methyl-2-trifluoromethylpentyl]-1,5,6,7-tetrahydroindol-4-one;

1-[4-(5-Fluoro-2-methylphenyl)-2-hydroxy-4-methyl-2-trifluoromethylpentyl]-1,5,6,7-tetrahydroindol-4-one;

1-[2-Hydroxy-4-methyl-4-(5-pyrimidin-5-yl-2,3-dihydrobenzofuran-7-yl)-2-trifluoromethylpentyl]-1,5,6,7-tetrahydroindol-4-one;

1-[2-Hydroxy-4-(2-methoxy-5-pyrimidin-5-ylphenyl)-4-methyl-2-trifluoromethylpentyl]-1,5,6,7-tetrahydroindol-4-one;

1-[2-Hydroxy-4-(2-hydroxy-5-pyrimidin-5-ylphenyl)-4-methyl-2-trifluoromethylpentyl]-1,5,6,7-tetrahydroindol-4-one;

1-[2-Hydroxy-4-(2-methoxy-5-pyridin-3-ylphenyl)-4-methyl-2-trifluoromethylpentyl]-1,5,6,7-tetrahydroindol-4-one;

1-[2-Hydroxy-4-(2-hydroxy-5-pyridin-3-ylphenyl)-4-methyl-2-trifluoromethylpentyl]-1,5,6,7-tetrahydroindol-4-one; and 1-[2-Hydroxy-4-(5-methanesulfonyl-2,3-dihydrobenzofuran-7-yl)-4-methyl-2-trifluoromethylpentyl]-1,5,6,7-tetrahydroindol-4-one,
or a tautomer, prodrug, solvate, or salt thereof.

More preferred compounds of Formula (IC) include the following:
1-[2-Hydroxy-4-methyl-4-(5-pyrimidin-5-yl-2,3-dihydrobenzofuran-7-yl)-2-trifluoromethylpentyl]-1,5,6,7-tetrahydroindol-4-one;
1-[2-Hydroxy-4-(2-methoxy-5-pyrimidin-5-ylphenyl)-4-methyl-2-trifluoromethylpentyl]-1,5,6,7-tetrahydroindol-4-one;
1-[2-Hydroxy-4-(2-hydroxy-5-pyrimidin-5-ylphenyl)-4-methyl-2-trifluoromethylpentyl]-1,5,6,7-tetrahydroindol-4-one;
1-[2-Hydroxy-4-(2-methoxy-5-pyridin-3-ylphenyl)-4-methyl-2-trifluoromethylpentyl]-1,5,6,7-tetrahydroindol-4-one; and
1-[2-Hydroxy-4-(2-hydroxy-5-pyridin-3-ylphenyl)-4-methyl-2-trifluoromethylpentyl]-1,5,6,7-tetrahydroindol-4-one,
or a tautomer, prodrug, solvate, or salt thereof.

The most preferred compounds of Formula (IC) include the following:
1-[2-Hydroxy-4-methyl-4-(5-pyrimidin-5-yl-2,3-dihydrobenzofuran-7-yl)-2-trifluoromethylpentyl]-1,5,6,7-tetrahydroindol-4-one;
1-[2-Hydroxy-4-(2-methoxy-5-pyrimidin-5-yphenyl)-4-methyl-2-trifluoromethylpentyl]-1,5,6,7-tetrahydroindol-4-one;
1-[2-Hydroxy-4-(2-hydroxy-5-pyrimidin-5-ylphenyl)-4-methyl-2-trifluoromethylpentyl]-1,5,6,7-tetrahydroindol-4-one;
1-[2-Hydroxy-4-(2-methoxy-5-pyridin-3-ylphenyl)-4-methyl-2-trifluoromethylpentyl]-1,5,6,7-tetrahydroindol-4-one; and
1-[2-Hydroxy-4-(2-hydroxy-5-pyridin-3-ylphenyl)-4-methyl-2-trifluoromethylpentyl]-1,5,6,7-tetrahydroindol-4-one,
or a tautomer, prodrug, solvate, or salt thereof.

The invention further provides methods of making a compound of Formula (IC)

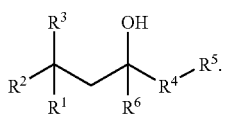
(IC)

One synthetic sequence for making a compound of Formula (IC) is shown below.

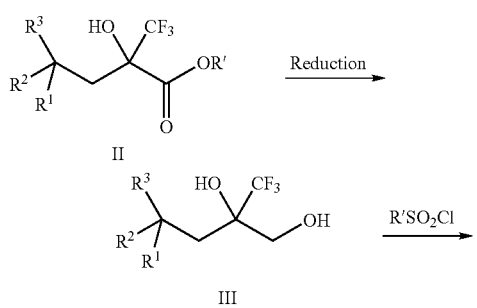

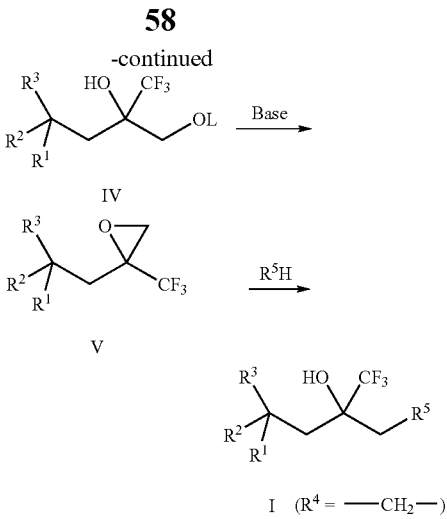

A second method of making a compound of Formula (IC) is shown below.

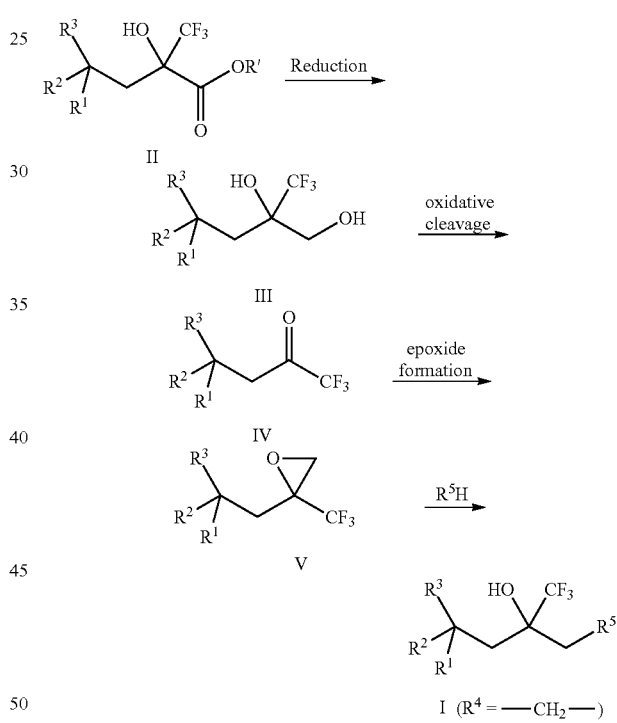

The instant invention is also directed to compounds of Formula (ID)

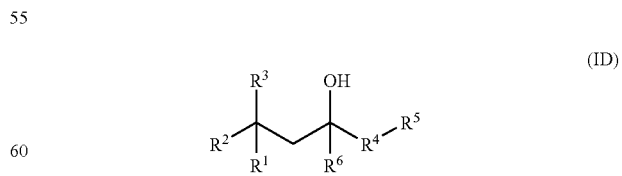
(ID)

wherein:
R$^1$ is an aryl or heteroaryl group, each optionally independently substituted with one to three substituent groups, wherein each substituent group of R$^1$ is independently C$_1$-C$_5$ alkyl, C$_2$-C$_5$ alkenyl, C$_2$-C$_5$ alkynyl, C$_3$-C$_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, $C_1$-$C_5$ alkanoyl, aroyl, aminocarbonyl, $C_1$-$C_5$ alkylaminocarbonyl, $C_1$-$C_5$ dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, nitro, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
  wherein each substituent group of $R^1$ is optionally independently substituted with one to three substituent groups selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl;
$R^2$ and $R^3$ are each independently $C_1$-$C_5$ alkyl, wherein one or both are independently substituted with hydroxy, $C_1$-$C_5$ alkoxy, $C_1$-$C_5$ alkylthio wherein the sulfur atom is optionally oxidized to a sulfoxide or sulfone, amino wherein the nitrogen atom is optionally independently mono- or di-substituted by $C_1$-$C_5$ alkyl or aryl;
$R^4$ is $C_1$-$C_5$ alkyl, $C_2$-$C_5$ alkenyl, or $C_2$-$C_5$ alkynyl, each optionally independently substituted with one to three substituent groups,
  wherein each substituent group of $R^4$ is independently $C_1$-$C_3$ alkyl, hydroxy, halogen, or oxo;
$R^5$ is a heteroaryl group optionally independently substituted with one to three substituent groups,
  wherein each substituent group of $R^5$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, $C_1$-$C_5$ alkylaminosulfonyl, $C_1$-$C_5$ dialkylaminosulfonyl, halogen, hydroxy, carboxy, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
  wherein each substituent group of $R^5$ is optionally independently substituted with one to three substituent groups selected from $C_1$-$C_3$ alkyl, $C_1$-$C_3$ alkoxy, halogen, hydroxy, oxo, cyano, heteroaryl, heterocyclyl, or amino wherein the nitrogen atom is optionally independently mono- or di-substituted by $C_1$-$C_5$ alkyl or aryl; or ureido wherein either nitrogen atom is optionally independently substituted with $C_1$-$C_5$ alkyl, or trifluoromethyl; and $R^6$ is hydrogen, $C_1$-$C_8$ alkyl, $C_2$-$C_8$ alkenyl, $C_2$-$C_8$ alkynyl, carbocycle, heterocyclyl, aryl, heteroaryl, trifluoromethyl, carbocycle-$C_1$-$C_8$ alkyl, carboxy, alkoxycarbonyl, aryl-$C_1$-$C_8$ alkyl, aryl-$C_1$-$C_8$ haloalkyl, heterocyclyl-$C_1$-$C_8$ alkyl, heteroaryl-$C_1$-$C_8$ alkyl, carbocycle-$C_2$-$C_8$ alkenyl, aryl-$C_2$-$C_8$ alkenyl, heterocyclyl-$C_2$-$C_8$ alkenyl, or heteroaryl-$C_2$-$C_8$ alkenyl, each optionally independently substituted with one to three substituent groups,
  wherein each substituent group of $R^6$ is independently $C_1$-$C_5$ alkyl, $C_2$-$C_5$ alkenyl, $C_2$-$C_5$ alkynyl, $C_3$-$C_8$ cycloalkyl, phenyl, $C_1$-$C_5$ alkoxy, phenoxy, $C_1$-$C_5$ alkanoyl, aroyl, $C_1$-$C_5$ alkoxycarbonyl, $C_1$-$C_5$ alkanoyloxy, aminocarbonyloxy, $C_1$-$C_5$ alkylaminocarbonyloxy, $C_1$-$C_5$ dialkylaminocarbonyloxy, aminocarbonyl, $C_1$-$C_5$ alkylaminocarbonyl, $C_1$-$C_5$ dialkylaminocarbonyl, $C_1$-$C_5$ alkanoylamino, $C_1$-$C_5$ alkoxycarbonylamino, $C_1$-$C_5$ alkylsulfonylamino, $C_1$-$C_5$ alkylaminosulfonyl, $C_1$-$C_5$ dialkylaminosulfonyl, halogen, hydroxy, carboxy, cyano, oxo, trifluoromethyl, nitro, amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone, or a tautomer, prodrug, solvate, or salt thereof.

Another aspect of the invention includes compounds of Formula (ID), wherein:

$R^1$ is thienyl, phenyl, naphthyl, dihydrobenzofuranyl, benzofuranyl, chromanyl, dihydroindolyl, indolyl, dihydrobenzothienyl, benzothienyl, benzodioxolanyl, benzoxazolyl, benzisoxazolyl, benzpyrazolyl, benzimidazolyl, thienyl, quinolinyl, pyridinyl, pyrimidinyl, or pyrazinyl, each optionally independently substituted with one to three substituent groups,
  wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, or $C_1$-$C_3$ alkylthio wherein the sulfur atom is optionally oxidized to a sulfoxide or sulfone,
    wherein each substituent group of $R^1$ is optionally independently substituted with a substituent group selected from methyl, methoxy, halogen, hydroxy, oxo, cyano, heteroaryl, heterocyclyl, or amino wherein the nitrogen atom is optionally independently mono- or di-substituted by $C_1$-$C_5$ alkyl or aryl;
$R^2$ and $R^3$ are each independently $C_1$-$C_3$ alkyl, wherein one or both are independently substituted with hydroxy, $C_1$-$C_5$ alkoxy;
$R^4$ is $CH_2$;
$R^5$ is an imidazolyl, pyridyl, indolyl, azaindolyl, diazaindolyl, benzofuranyl, furanopyridinyl, furanopyrimidinyl, benzothienyl, thienopyridinyl, thienopyrimidinyl, benzoxazolyl, oxazolopyridinyl, benzothiazolyl, thiazolopyridinyl, benzimidazolyl, imidazolopyridinyl, imidazolopyrimidinyl, imidazolopyridazinyl, imidazolopyrazinyl, quinolinyl, or isoquinolinyl group, each optionally independently substituted with one to three substituent groups,
  wherein each substituent group of $R^5$ is independently $C_1$-$C_3$ alkyl, $C_2$-$C_3$ alkenyl, phenyl, $C_1$-$C_3$ alkoxy, methoxycarbonyl, aminocarbonyl, $C_1$-$C_3$ alkylaminocarbonyl, $C_1$-$C_3$ dialkylaminocarbonyl, heterocyclylcarbonyl, fluoro, chloro, bromo, cyano, trifluoromethyl, or $C_1$-$C_3$ alkylthio wherein the sulfur atom is optionally oxidized to a sulfoxide or sulfone,
wherein each substituent group of $R^5$ is optionally independently substituted with a substituent group selected from methyl, methoxy, fluoro, chloro, bromo, trifluoromethyl, heteroaryl, heterocyclyl, or amino wherein the nitrogen atom is optionally independently mono- or di-substituted by $C_1$-$C_5$ alkyl or aryl; and $R^6$ is $C_1$-$C_5$ alkyl, $C_2$-$C_5$ alkenyl, $C_3$-$C_6$ cycloalkyl, trifluoromethyl, phenyl, $C_3$-$C_6$ cycloalkyl-$C_1$-$C_3$ alkyl, phenyl-$C_1$-$C_3$ alkyl, phenyl-$C_1$-$C_3$ haloalkyl, $C_3$-$C_6$ cycloalkyl-$C_2$-$C_3$ alkenyl, phenyl-$C_2$-$C_3$ alkenyl, each optionally independently substituted with one to three substituent groups,
wherein each substituent group of $R^6$ is independently $C_1$-$C_3$ alkyl, $C_2$-$C_3$ alkenyl, $C_2$-$C_3$ alkynyl, $C_1$-$C_3$ alkoxy, aminocarbonyl, $C_1$-$C_3$ alkylaminocarbonyl, $C_1$-$C_3$ dialkylaminocarbonyl, halogen, hydroxy, carboxy, cyano, trifluoromethyl, nitro, or $C_1$-$C_3$ alkylthio wherein the sulfur atom is optionally oxidized to a sulfoxide or sulfone, or a tautomer, prodrug, solvate, or salt thereof.

Yet another aspect of the invention includes compounds of Formula (ID), wherein:

$R^1$ is thienyl, phenyl, naphthyl, pyridyl, chromanyl, dihydrobenzofuranyl, or benzofuranyl, each optionally independently substituted with one or two substituent groups, wherein each substituent group of $R^1$ is independently methyl, ethyl, methoxy, ethoxy, fluoro, chloro, bromo, hydroxy, trifluoromethyl, cyano, or $C_1$-$C_5$ alkylthio wherein the sulfur atom is optionally oxidized to a sulfoxide or sulfone;

$R^2$ and $R^3$ are each methyl wherein one or both are independently substituted with hydroxy or methoxy;

$R^4$ is $CH_2$;

$R^5$ is a pyridyl, indolyl, azaindolyl, benzofuranyl, furanopyridinyl, thienopyridinyl, benzoxazolyl, benzimidazolyl, quinolinyl, or isoquinolinyl group, each optionally independently substituted with one to three substituent groups,
wherein each substituent group of $R^5$ is independently methyl, phenyl, methoxycarbonyl, aminocarbonyl, methylaminocarbonyl, dimethylaminoaminocarbonyl, morpholinylcarbonyl, fluoro, chloro, bromo, cyano, or trifluoromethyl; and $R^6$ is $C_1$-$C_5$ alkyl, $C_3$-$C_6$ cycloalkyl, $C_3$-$C_6$ cycloalkylmethyl-, trifluoromethyl, or benzyl, each optionally independently substituted with one to three substituent groups,
wherein each substituent group of $R^6$ is independently methyl, methoxy, fluoro, chloro, bromo, cyano, trifluoromethyl, or hydroxy, or a tautomer, prodrug, solvate, or salt thereof.

Yet another aspect of the invention includes compounds of Formula (ID), wherein:

$R^1$ is phenyl, dihydrobenzofuranyl, or benzofuranyl, each optionally independently substituted with one to three substituent groups,
wherein each substituent group of $R^1$ is independently $C_1$-$C_3$ alkyl, $C_2$-$C_3$ alkenyl, $C_2$-$C_3$ alkynyl, $C_1$-$C_3$ alkoxy, $C_2$-$C_3$ alkenyloxy, $C_1$-$C_3$ alkanoyl, $C_1$-$C_3$ alkoxycarbonyl, $C_1$-$C_3$ alkanoyloxy, halogen, hydroxy, carboxy, cyano, trifluoromethyl, nitro, or $C_1$-$C_3$ alkylthio wherein the sulfur atom is optionally oxidized to a sulfoxide or sulfone; and $R^2$ and $R^3$ are each independently $C_1$-$C_3$ alkyl each optionally independently substituted with hydroxy, $C_1$-$C_3$ alkoxy, or a tautomer, prodrug, solvate, or salt thereof.

Representative compounds of Formula (ID) according to the invention are appended hereto as Table ID, where column A is the compound name according to standard nomenclature and column B is the corresponding chemical structure.

Preferred compounds of Formula (ID) include the following:

1,1,1-Trifluoro-5-methoxy-4-methyl-4-phenyl-2-quinolin-4-ylmethylpentan-2-ol; and 5,5,5-Trifluoro-2-methyl-2-phenyl-4-quinolin-4-ylmethylpentane-1,4-diol, or a tautomer, prodrug, solvate, or salt thereof.

The invention further provides methods of making a compound of Formula (ID).

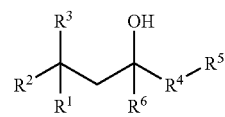

One method of making a compounds of Formula (ID) is via the intermediate aldehyde which is shown below.

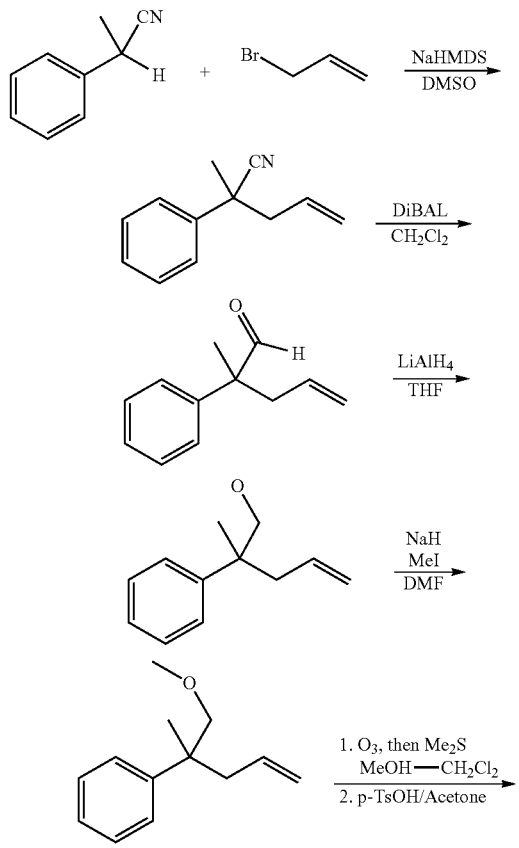

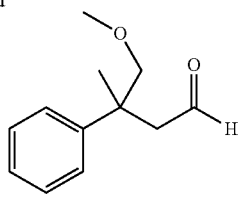

In another aspect of the invention, the compounds according to the invention are formulated into pharmaceutical compositions comprising an effective amount, preferably a pharmaceutically effective amount, of a compound according to the invention or a tautomer, prodrug, solvate, or salt thereof, and a pharmaceutically acceptable excipient or carrier.

The invention also provides a method of modulating the glucocorticoid receptor function in a patient, the method comprising administering to the patient an effective amount of a compound according to the invention or a tautomer, prodrug, solvate, or salt thereof.

The invention further provides a method of treating a disease-state or condition mediated by the glucocorticoid receptor function in a patient in need of such treatment, the method comprising administering to the patient an effective amount of a pharmaceutically acceptable compound according to the invention or a tautomer, prodrug, solvate, or salt thereof.

In addition, the invention also provides a method of treating a disease-state or condition selected from: type II diabetes, obesity, cardiovascular diseases, hypertension, arteriosclerosis, neurological diseases, adrenal and pituitary tumors, and glaucoma, in a patient in need of such treatment, the method comprising administering to the patient an effective amount of a pharmaceutically acceptable compound according to the invention or a tautomer, prodrug, solvate, or salt thereof.

The invention provides a method of treating a disease characterized by inflammatory, allergic, or proliferative processes, in a patient in need of such treatment, the method comprising administering to the patient an effective amount of a pharmaceutically acceptable compound according to the invention or a tautomer, prodrug, solvate, or salt thereof. In a preferred embodiment of the invention, the disease characterized by inflammatory, allergic, or proliferative processes is selected from: (i) lung diseases; (ii) rheumatic diseases or autoimmune diseases or joint diseases; (iii) allergic diseases; (iv) vasculitis diseases; (v) dermatological diseases; (vi) renal diseases; (vii) hepatic diseases; (viii) gastrointestinal diseases; (ix) proctological diseases; (x) eye diseases; (xi) diseases of the ear, nose, and throat (ENT) area; (xii) neurological diseases; (xiii) blood diseases; (xiv) tumor diseases; (xv) endocrine diseases; (xvi) organ and tissue transplantations and graft-versus-host diseases; (xvii) severe states of shock; (xviii) substitution therapy; and (xix) pain of inflammatory genesis. In another preferred embodiment of the invention, the disease characterized by inflammatory, allergic, or proliferative processes is selected from: type I diabetes, osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis, and syndromes associated with hemodialysis, leukopheresis, and granulocyte transfusion.

The invention further provides methods of treating the disease-states or conditions mentioned above, in a patient in need of such treatment, the methods comprising sequentially or simultaneously administering to the patient: (a) an effective amount of a pharmaceutically acceptable compound according to the invention or a tautomer, prodrug, solvate, or salt thereof; and (b) a pharmaceutically acceptable glucocorticoid.

The invention further provides a method of assaying the glucocorticoid receptor function in a sample, comprising: (a) contacting the sample with a selected amount of a compound according to the invention or a tautomer, prodrug, solvate, or salt thereof; and (b) detecting the amount of the compound according to the invention or a tautomer, prodrug, solvate, or salt thereof bound to glucocorticoid receptors in the sample. In a preferred embodiment of the invention, the compound according to the invention or a tautomer, prodrug, solvate, or salt thereof is labeled with a detectable marker selected from: a radiolabel, fluorescent tag, a chemiluminescent tag, a chromophore, and a spin label.

The invention also provides a method of imaging the glucocorticoid receptor distribution in a sample or patient, the method comprising: (a) contacting the sample or administering to a patient a compound according to the invention or a tautomer, prodrug, solvate, or salt thereof having a detectable marker; (b) detecting the spatial distribution and amount of the compound according to the invention or a tautomer, prodrug, solvate, or salt thereof having a detectable marker bound to glucocorticoid receptors in the sample or patient using an imaging means to obtain an image; and (c) displaying an image of the spatial distribution and amount of the compound according to the invention or a tautomer, prodrug, solvate, or salt thereof having a detectable marker bound to glucocorticoid receptors in the sample. In a preferred embodiment of the invention, the imaging means is selected from: radioscintigraphy, nuclear magnetic resonance imaging (MRI), computed tomography (CT scan), or positron emission tomography (PET).

The invention also provides a kit for the in vitro diagnostic determination of the glucocorticoid receptor function in a sample, comprising: (a) a diagnostically effective amount of a compound according to the invention or a tautomer, prodrug, solvate, or salt thereof; and (b) instructions for use of the diagnostic kit.

It is preferred that the compounds of Formula (IA), (IB), (IC), and (ID) exclude the compounds disclosed in U.S. patent application Pub. No. 2004/0023999.

BRIEF DESCRIPTION OF THE TABLES

Table IA lists representative compounds of Formula (IA);
Table IB lists representative compounds of Formula (IB);
Table IC lists representative compounds of Formula (IC); and
Table ID lists representative compounds of Formula (ID).

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1$-$C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk-(where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO-, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO-, where Ar is aryl. This term is exemplified by groups such as phenoxy, naphthoxy, and the like.

The term "oxo" means a double-bonded divalent oxygen radical of the formula (=O), for example, one example of an alkyl group substituted by an "oxo" would be a group of the formula Alk-C(O)-Alk, wherein each Alk is an alkyl.

The terms "alkylcarbonyl", "alkylcarbonyl group", "alkanoyl", or "alkanoyl group" mean a monovalent radical of the formula AlkC(O)—, where Alk is alkyl or hydrogen.

The terms "arylcarbonyl", "arylcarbonyl group", "aroyl" or "aroyl group" mean a monovalent radical of the formula ArC(O)—, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO—C(O)—, where Alk is alkyl. Exemplary alkoxycarbonyl groups include methoxycarbonyl, ethoxycarbonyl, tert-butyloxycarbonyl, and the like.

The terms "alkylaminocarbonyloxy" or "alkylaminocarbonyloxy group" mean a monovalent radical of the formula $R_2NC(O)O$—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido ($CH_3C(O)NH$—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an —$NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula $R_2NC(O)NH$—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "haloalkyl" or "haloalkyl group" mean a branched or straight-chain saturated aliphatic hydrocarbon monovalent radical, wherein one or more hydrogen atoms thereof are each independently replaced with halogen atoms. This term is exemplified by groups such as chloromethyl, 1,2-dibromoethyl, 1,1,1-trifluoropropyl, 2-iodobutyl, 1-chloro-2-bromo-3-fluoropentyl, and the like.

The terms "sulfanyl", "sulfanyl group", "thioether", or "thioether group" mean a divalent radical of the formula —S—.

The terms "alkylthio" or "alkylthio group" mean a monovalent radical of the formula AlkS—, where Alk is alkyl. Exemplary groups include methylthio, ethylthio, n-propylthio, isopropylthio, n-butylthio, and the like.

The terms "sulfonyl" or "sulfonyl group" mean a divalent radical of the formula —SO$_2$—.

The terms "sulfonylamino" or "sulfonylamino group" mean a divalent radical of the formula —SO$_2$NR—, where R is a hydrogen or a substituent group.

The terms "aminosulfonyl" or "aminosulfonyl group" mean a monovalent radical of the formula NR$_2$SO$_2$—, where R is each independently a hydrogen or a substituent group.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like.

The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornanyl, adamantyl, tetrahydronaphthyl (tetralin), 1-decalinyl, bicyclo[2.2.2]octanyl, 1-methylcyclopropyl, 2-methylcyclopentyl, 2-methylcyclooctyl, and the like.

The terms "cycloalkenyl" or "cycloalkenyl group" mean a stable aliphatic 3- to 15-membered monocyclic or polycyclic monovalent radical having at least one carbon-carbon double bond and consisting solely of carbon and hydrogen atoms which may comprise one or more fused or bridged ring(s), preferably a 5- to 7-membered monocyclic or 7- to 10-membered bicyclic ring. Unless otherwise specified, the cycloalkenyl ring may be attached at any carbon atom which results in a stable structure and, if substituted, may be substituted at any suitable carbon atom which results in a stable structure. Exemplary cycloalkenyl groups include cyclopentenyl, cyclohexenyl, cycloheptenyl, cyclooctenyl, cyclononenyl, cyclodecenyl, norbornenyl, 2-methylcyclopentenyl, 2-methylcyclooctenyl, and the like.

The terms "cycloalkynyl" or "cycloalkynyl group" mean a stable aliphatic 8- to 15-membered monocyclic or polycyclic monovalent radical having at least one carbon-carbon triple bond and consisting solely of carbon and hydrogen atoms which may comprise one or more fused or bridged ring(s), preferably a 8- to 10-membered monocyclic or 12- to 15-membered bicyclic ring. Unless otherwise specified, the cycloalkynyl ring may be attached at any carbon atom which results in a stable structure and, if substituted, may be substituted at any suitable carbon atom which results in a stable structure. Exemplary cycloalkynyl groups include, cyclooctynyl, cyclononynyl, cyclodecynyl, 2-methylcyclooctynyl, and the like.

The terms "cycloalkylene" or "cycloalkylene group" mean a stable saturated aliphatic 3- to 15-membered monocyclic or polycyclic divalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkylene groups include cyclopentylene, and the like.

The terms "cycloalkenylene" or "cycloalkenylene group" mean a stable aliphatic 5- to 15-membered monocyclic or polycyclic divalent radical having at least one carbon-carbon double bond and consisting solely of carbon and hydrogen atoms which may comprise one or more fused or bridged ring(s), preferably a 5- to 7-membered monocyclic or 7- to 10-membered bicyclic ring. Unless otherwise specified, the cycloalkenylene ring may be attached at any carbon atom which results in a stable structure and, if substituted, may be substituted at any suitable carbon atom which results in a stable structure. Exemplary cycloalkenylene groups include cyclopentenylene, cyclohexenylene, cycloheptenylene, cyclooctenylene, cyclononenylene, cyclodecenylene, norbornenylene, 2-methylcyclopentenylene, 2-methylcyclooctenylene, and the like.

The terms "cycloalkynylene" or "cycloalkynylene group" mean a stable aliphatic 8- to 15-membered monocyclic or polycyclic divalent radical having at least one carbon-carbon triple bond and consisting solely of carbon and hydrogen atoms which may comprise one or more fused or bridged ring(s), preferably a 8- to 10-membered monocyclic or 12- to 15-membered bicyclic ring. Unless otherwise specified, the cycloalkynylene ring may be attached at any carbon atom which results in a stable structure and, if substituted, may be substituted at any suitable carbon atom which results in a stable structure. Exemplary cycloalkynylene groups include cyclooctynylene, cyclononynylene, cyclodecynylene, 2-methylcyclooctynylene, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure. Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of Formula (I)" and equivalent expressions are mean to embrace compounds of Formula (IA), compounds of Formula (IB), compounds of Formula (IC), and compounds of Formula (ID), either individually, in some combination, or all of them, as the context permits.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

B. Salt, Prodrug, Derivative, and Solvate Terms and Conventions

The terms "prodrug" or "prodrug derivative" mean a covalently-bonded derivative or carrier of the parent compound or active drug substance which undergoes at least some biotransformation prior to exhibiting its pharmacological effect(s). In general, such prodrugs have metabolically cleavable groups and are rapidly transformed in vivo to yield the parent compound, for example, by hydrolysis in blood, and generally include esters and amide analogs of the parent compounds. The prodrug is formulated with the objectives of improved chemical stability, improved patient acceptance and compliance, improved bioavailability, prolonged duration of action, improved organ selectivity, improved formulation (e.g., increased hydrosolubility), and/or decreased side effects (e.g., toxicity). In general, prodrugs themselves have weak or no biological activity and are stable under ordinary conditions. Prodrugs can be readily prepared from the parent compounds using methods known in the art, such as those described in *A Textbook of Drug Design and Development*, Krogsgaard-Larsen and H. Bundgaard (eds.), Gordon & Breach, 1991, particularly Chapter 5: "Design and Applications of Prodrugs"; *Design of Prodrugs*, H. Bundgaard (ed.), Elsevier, 1985; *Prodrugs: Topical and Ocular Drug Delivery*, K. B. Sloan (ed.), Marcel Dekker, 1998; *Methods in Enzymology*, K. Widder et al. (eds.), Vol. 42, Academic Press, 1985, particularly pp. 309-396; *Burger's Medicinal Chemistry and Drug Discovery*, 5th Ed., M. Wolff (ed.), John Wiley & Sons, 1995, particularly Vol. I and pp. 172-178 and pp. 949-982; *Pro-Drugs as Novel Delivery Systems*, T. Higuchi and V. Stella (eds.), Am. Chem. Soc., 1975; *Bioreversible Carriers in Drug Design*, E. B. Roche (ed.), Elsevier, 1987, each of which is incorporated herein by reference in their entireties.

The term "pharmaceutically acceptable prodrug" as used herein means a prodrug of a compound of the invention which is, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible.

The term "salt" means an ionic form of the parent compound or the product of the reaction between the parent compound with a suitable acid or base to make the acid salt or base salt of the parent compound. Salts of the compounds of the present invention can be synthesized from the parent compounds which contain a basic or acidic moiety by conventional chemical methods. Generally, the salts are prepared by reacting the free base or acid parent compound with stoichiometric amounts or with an excess of the desired salt-forming inorganic or organic acid or base in a suitable solvent or various combinations of solvents.

The term "pharmaceutically acceptable salt" means a salt of a compound of the invention which is, within the scope of sound medical judgment, suitable for use in contact with the tissues of humans and lower animals without undue toxicity, irritation, allergic response, and the like, commensurate with a reasonable benefit/risk ratio, generally water or oil-soluble or dispersible, and effective for their intended use. The term includes pharmaceutically-acceptable acid addition salts and pharmaceutically-acceptable base addition salts. As the compounds of the present invention are useful in both free base and salt form, in practice, the use of the salt form amounts to use of the base form. Lists of suitable salts are found in, e.g., S. M. Birge et al., J. Pharm. Sci., 1977, 66, pp. 1-19, which is hereby incorporated by reference in its entirety.

The term "pharmaceutically-acceptable acid addition salt" means those salts which retain the biological effectiveness and properties of the free bases and which are not biologically or otherwise undesirable, formed with inorganic acids such as hydrochloric acid, hydrobromic acid, hydroiodic acid, sulfuric acid, sulfamic acid, nitric acid, phosphoric acid, and the like, and organic acids such as acetic acid, trichloroacetic acid, trifluoroacetic acid, adipic acid, alginic acid, ascorbic acid, aspartic acid, benzenesulfonic acid, benzoic acid, 2-acetoxybenzoic acid, butyric acid, camphoric acid, camphorsulfonic acid, cinnamic acid, citric acid, digluconic acid, ethanesulfonic acid, glutamic acid, glycolic acid, glycerophosphoric acid, hemisulfic acid, heptanoic acid, hexanoic acid, formic acid, fumaric acid, 2-hydroxyethanesulfonic acid (isethionic acid), lactic acid, maleic acid, hydroxymaleic acid, malic acid, malonic acid, mandelic acid, mesitylenesulfonic acid, methanesulfonic acid, naphthalenesulfonic acid, nicotinic acid, 2-naphthalenesulfonic acid, oxalic acid, pamoic acid, pectinic acid, phenylacetic acid, 3-phenylpropionic acid, picric acid, pivalic acid, propionic acid, pyruvic acid, pyruvic acid, salicylic acid, stearic acid, succinic acid, sulfanilic acid, tartaric acid, p-toluenesulfonic acid, undecanoic acid, and the like.

The term "pharmaceutically-acceptable base addition salt" means those salts which retain the biological effectiveness and properties of the free acids and which are not biologically or otherwise undesirable, formed with inorganic bases such as ammonia or hydroxide, carbonate, or bicarbonate of ammonium or a metal cation such as sodium, potassium, lithium, calcium, magnesium, iron, zinc, copper, manganese, aluminum, and the like. Particularly preferred are the ammonium, potassium, sodium, calcium, and magnesium salts. Salts derived from pharmaceutically-acceptable organic non-toxic bases include salts of primary, secondary, and tertiary amines, quaternary amine compounds, substituted amines including naturally occurring substituted amines, cyclic amines and basic ion-exchange resins, such as methylamine, dimethylamine, trimethylamine, ethylamine, diethylamine, triethylamine, isopropylamine, tripropylamine, tributylamine, ethanolamine, diethanolamine, 2-dimethylaminoethanol, 2-diethylaminoethanol, dicyclohexylamine, lysine, arginine, histidine, caffeine, hydrabamine, choline, betaine, ethylenediamine, glucosamine, methylglucamine, theobromine, purines, piperazine, piperidine, N-ethylpiperidine, tetramethylammonium compounds, tetraethylammonium compounds, pyridine, N,N-dimethylaniline, N-methylpiperidine, N-methylmorpholine, dicyclohexylamine, dibenzylamine, N,N-dibenzylphenethylamine, 1-ephenamine, N,N'-dibenzylethylenediamine, polyamine resins, and the like. Particularly preferred organic nontoxic bases are isopropylamine, diethylamine, ethanolamnine, trimethylamine, dicyclohexylamine, choline, and caffeine.

The term "solvate" means a physical association of a compound with one or more solvent molecules or a complex of variable stoichiometry formed by a solute (for example, a compound of Formula (I)) and a solvent, for example, water, ethanol, or acetic acid. This physical association may involve varying degrees of ionic and covalent bonding, including hydrogen bonding. In certain instances, the solvate will be capable of isolation, for example, when one or more solvent molecules are incorporated in the crystal lattice of the crystalline solid. In general, the solvents selected do not interfere with the biological activity of the solute. Solvates encompasses both solution-phase and isolatable solvates. Representative solvates include hydrates, ethanolates, methanolates, and the like.

The term "hydrate" means a solvate wherein the solvent molecule(s) is/are $H_2O$.

The compounds of the present invention as discussed below include the free base or acid thereof, their salts, solvates, and prodrugs and may include oxidized sulfur atoms or quatemized nitrogen atoms in their structure, although not explicitly stated or shown, particularly the pharmaceutically acceptable forms thereof. Such forms, particularly the pharmaceutically acceptable forms, are intended to be embraced by the appended claims.

C. Isomer Terms and Conventions

The term "isomers" means compounds having the same number and kind of atoms, and hence the same molecular weight, but differing with respect to the arrangement or configuration of the atoms in space. The term includes stereoisomers and geometric isomers.

The terms "stereoisomer" or "optical isomer" mean a stable isomer that has at least one chiral atom or restricted rotation giving rise to perpendicular dissymmetric planes (e.g., certain biphenyls, allenes, and spiro compounds) and can rotate plane-polarized light. Because asymmetric centers and other chemical structure exist in the compounds of the invention which may give rise to stereoisomerism, the invention contemplates stereoisomers and mixtures thereof. The compounds of the invention and their salts include asymmetric carbon atoms and may therefore exist as single stereoisomers, racemates, and as mixtures of enantiomers and diastereomers. Typically, such compounds will be prepared as a racemic mixture. If desired, however, such compounds can be prepared or isolated as pure stereoisomers, i.e., as individual enantiomers or diastereomers, or as stereoisomer-enriched mixtures. As discussed in more detail below, individual stereoisomers of compounds are prepared by synthesis from optically active starting materials containing the desired chiral centers or by preparation of mixtures of enantiomeric products followed by separation or resolution, such as conversion to a mixture of diastereomers followed by separation or recrystallization, chromatographic techniques, use of chiral resolving agents, or direct separation of the enantiomers on chiral chromatographic columns. Starting compounds of particular stereochemistry are either commercially available or are made by the methods described below and resolved by techniques well-known in the art.

The term "enantiomers" means a pair of stereoisomers that are non-superimposable mirror images of each other.

The terms "diastereoisomers" or "diastereomers" mean optical isomers which are not mirror images of each other.

The terms "racemic mixture" or "racemate" mean a mixture containing equal parts of individual enantiomers.

The term "non-racemic mixture" means a mixture containing unequal parts of individual enantiomers.

The term "geometrical isomer" means a stable isomer which results from restricted freedom of rotation about double bonds (e.g., cis-2-butene and trans-2-butene) or in a cyclic structure (e.g., cis-1,3-dichlorocyclobutane and trans-1,3-dichlorocyclobutane). Because carbon-carbon double (olefinic) bonds, C═N double bonds, cyclic structures, and the like may be present in the compounds of the invention, the invention contemplates each of the various stable geometric isomers and mixtures thereof resulting from the arrangement of substituents around these double bonds and in these cyclic structures. The substituents and the isomers are designated using the cisltrans convention or using the E or Z system, wherein the term "E" means higher order substituents on opposite sides of the double bond, and the term "Z" means higher order substituents on the same side of the double bond. A thorough discussion of E and Z isomerism is provided in J. March, *Advanced Organic Chemistry: Reactions, Mechanisms, and Structure*, 4th ed., John Wiley & Sons, 1992, which is hereby incorporated by reference in its entirety. Several of the following examples represent single E isomers, single Z isomers, and mixtures of E/Z isomers. Determination of the E and Z isomers can be done by analytical methods such as x-ray crystallography, $^1$H-NMR, and $^{13}$C-NMR.

Some of the compounds of the invention can exist in more than one tautomeric form. As mentioned above, the compounds of the invention include all such tautomers.

It is well-known in the art that the biological and pharmacological activity of a compound is sensitive to the stereochemistry of the compound. Thus, for example, enantiomers often exhibit strikingly different biological activity including differences in pharmacokinetic properties, including metabolism, protein binding, and the like, and pharmacological properties, including the type of activity displayed, the degree of activity, toxicity, and the like. Thus, one skilled in the art will appreciate that one enantiomer may be more active or may exhibit beneficial effects when enriched relative to the other enantiomer or when separated from the other enantiomer. Additionally, one skilled in the art would know how to separate, enrich, or selectively prepare the enantiomers of the compounds of the invention from this disclosure and the knowledge of the prior art.

Thus, although the racemic form of drug may be used, it is often less effective than administering an equal amount of enantiomerically pure drug; indeed, in some cases, one enantiomer may be pharmacologically inactive and would merely serve as a simple diluent. For example, although ibuprofen had been previously administered as a racemate, it has been shown that only the S-isomer of ibuprofen is effective as an anti-inflammatory agent (in the case of ibuprofen, however, although the R-isomer is inactive, it is converted in vivo to the S-isomer, thus, the rapidity of action of the racemic form of the drug is less than that of the pure S-isomer). Furthermore, the pharmacological activities of enantiomers may have distinct biological activity. For example, S-penicillamine is a therapeutic agent for chronic arthritis, while R-penicillamine is toxic. Indeed, some purified enantiomers have advantages over the racemates, as it has been reported that purified individual isomers have faster transdermal penetration rates compared to the racemic mixture. See U.S. Pat. Nos. 5,114,946 and 4,818,541.

Thus, if one enantiomer is pharmacologically more active, less toxic, or has a preferred disposition in the body than the other enantiomer, it would be therapeutically more beneficial to administer that enantiomer preferentially. In this way, the patient undergoing treatment would be exposed to a lower total dose of the drug and to a lower dose of an enantiomer that is possibly toxic or an inhibitor of the other enantiomer.

Preparation of pure enantiomers or mixtures of desired enantiomeric excess (ee) or enantiomeric purity are accomplished by one or more of the many methods of (a) separation or resolution of enantiomers, or (b) enantioselective synthesis known to those of skill in the art, or a combination thereof These resolution methods generally rely on chiral recognition and include, for example, chromatography using chiral stationary phases, enantioselective host-guest complexation, resolution or synthesis using chiral auxiliaries, enantioselective synthesis, enzymatic and nonenzymatic kinetic resolution, or spontaneous enantioselective crystallization. Such methods are disclosed generally *in Chiral Separation Techniques: A Practical Approach* (2nd Ed.), G. Subramanian (ed.), Wiley-VCH, 2000; T. E. Beesley and R. P. W. Scott, *Chiral Chromatography*, John Wiley & Sons, 1999; and Satinder Ahuja, *Chiral Separations by Chromatography*, Am. Chem. Soc., 2000. Furthermore, there are equally well-known methods for the quantitation of enantiomeric excess or purity, for example, GC, HPLC, CE, or NMR, and assignment of absolute configuration and conformation, for example, CD/ORD, X-ray crystallography, or NMR.

In general, all tautomeric forms and isomeric forms and mixtures, whether individual geometric isomers or stereoisomers or racemic or non-racemic mixtures, of a chemical structure or compound is intended, unless the specific stereochemistry or isomeric form is specifically indicated in the compound name or structure. Generally, one enantiomer is preferred, when a racemic mixtures is resolved.

D. Pharmaceutical Administration and Diagnostic and Treatment Terms and Conventions The term "patient" includes both human and non-human mammals.

The term "effective amount" means an amount of a compound according to the invention which, in the context of which it is administered or used, is sufficient to achieve the desired effect or result. Depending on the context, the term effective amount may include or be synonymous with a pharmaceutically effective amount or a diagnostically effective amount.

The terms "pharmaceutically effective amount" or "therapeutically effective amount" means an amount of a compound according to the invention which, when administered to a patient in need thereof, is sufficient to effect treatment for disease-states, conditions, or disorders for which the compounds have utility. Such an amount would be sufficient to elicit the biological or medical response of a tissue, system, or patient that is sought by a researcher or clinician. The amount of a compound of according to the invention which constitutes a therapeutically effective amount will vary depending on such factors as the compound and its biological activity, the composition used for administration, the time of administration, the route of administration, the rate of excretion of the compound, the duration of treatment, the type of disease-state or disorder being treated and its severity, drugs used in combination with or coincidentally with the compounds of the invention, and the age, body weight, general health, sex, and diet of the patient. Such a therapeutically effective amount can be determined routinely by one of ordinary skill in the art having regard to their own knowledge, the prior art, and this disclosure.

The term "diagnostically effective amount" means an amount of a compound according to the invention which, when used in a diagnostic method, apparatus, or assay, is sufficient to achieve the desired diagnostic effect or the desired biological activity necessary for the diagnostic method, apparatus, or assay. Such an amount would be sufficient to elicit the biological. or medical response in a diagnostic method, apparatus, or assay, which may include a biological or medical response in a patient or in a in vitro or in vivo tissue or system, that is sought by a researcher or clinician. The amount of a compound according to the invention which constitutes a diagnostically effective amount will vary depending on such factors as the compound and its biological activity, the diagnostic method, apparatus, or assay used, the composition used for administration, the time of administration, the route of administration, the rate of excretion of the compound, the duration of administration, drugs and other compounds used in combination with or coincidentally with the compounds of the invention, and, if a patient is the subject of the diagnostic administration, the age, body weight, general health, sex, and diet of the patient. Such a diagnostically effective amount can be determined routinely by one of ordinary skill in the art having regard to their own knowledge, the prior art, and this disclosure.

The term "modulate" means the ability of a compound to alter the function of the glucocorticoid receptor by, for example, binding to and stimulating or inhibiting the glucocorticoid receptor functional responses.

The term "modulator" in the context of describing compounds according to the invention means a compound that modulates the glucocorticoid receptor function. As such, modulators include, but are not limited to, agonists, partial agonists, antagonists, and partial antagonists.

The term "agonist" in the context of describing compounds according to the invention means a compound that, when bound to the glucocorticoid receptor, enhances or increases the glucocorticoid receptor function. As such, agonists include partial agonists and full agonists.

The term "full agonist" in the context of describing compounds according to the invention means a compound that evokes the maximal stimulatory response from the glucocorticoid receptor, even when there are spare (unoccupied) glucocorticoid receptors present.

The term "partial agonist" in the context of describing compounds according to the invention means a compound that is unable to evoke the maximal stimulatory response from the glucocorticoid receptor, even at concentrations sufficient to saturate the glucocorticoid receptors present.

The term "antagonist" in the context of describing compounds according to the invention means a compound that directly or indirectly inhibits or suppresses the glucocorticoid receptor function. As such, antagonists include partial antagonists and full antagonists.

The term "full antagonist" in the context of describing compounds according to the invention means a compound that evokes the maximal inhibitory response from the glucocorticoid receptor, even when there are spare (unoccupied) glucocorticoid receptors present.

The term "partial antagonist" in the context of describing compounds according to the invention means a compound that is unable to evoke the maximal inhibitory response from the glucocorticoid receptor, even at concentrations sufficient to saturate the glucocorticoid receptors present.

The terms "treating" or "treatment" mean the treatment of a disease-state in a patient, and include:
  (i) preventing the disease-state from occurring in a patient, in particular, when such patient is genetically or otherwise predisposed to the disease-state but has not yet been diagnosed as having it;
  (ii) inhibiting or ameliorating the disease-state in a patient, i.e., arresting or slowing its development; or
  (iii) relieving the disease-state in a patient, i.e., causing regression or cure of the disease-state.

General Synthetic Methods for Making Compounds of Formula (IA), Formula (IB), Formula (IC), and Formula (ID)

The invention also provides processes for making compounds of Formula (IA), Formula (IB), Formula (IC), and Formula (ID). In all schemes, unless specified otherwise, $R^1$ to $R^5$ in the formulas below shall have the meaning of $R^1$ to $R^5$ in the Formula (I) of the invention described hereinabove; and where appropriate, $R^1$ to $R^6$ in the formulas below shall have the meaning of $R^1$ to $R^6$ in the Formula (IB), Formula (IC), or Formula (ID) of the invention described hereinabove. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by thin layer chromatography (TLC), if desired, and intermediates and products may be purified by chromatography on silica gel and/or by recrystallization.

Compounds of Formula (IA), Formula (IC), and Formula (ID) may be prepared by the method outlined in Scheme I.

Scheme I

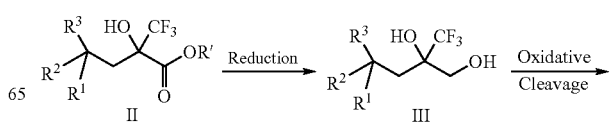

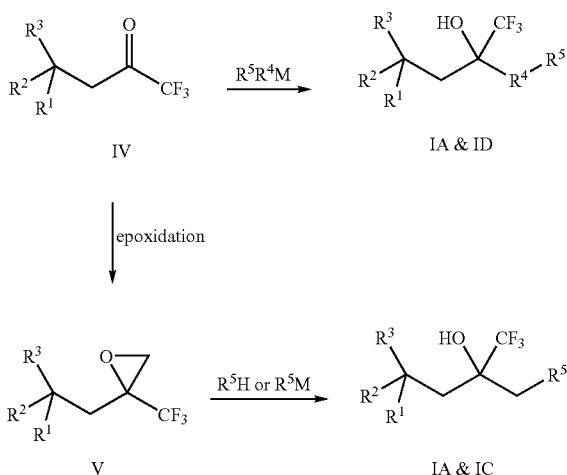

As illustrated in Scheme I, an ester intermediate of Formula (II), where R' is Me or Et, is reduced with a suitable reducing agent, such as lithium aluminum hydride, in a suitable solvent, such as THF or diethyl ether, to produce the 1,2-diol of Formula (III). Oxidative cleavage of 1,2-diols is well-known in the art and may be achieved with periodic acid or lead tetraacetate, for example, in a suitable solvent, such as methanol, to provide ketone (IV). Reaction of ketone (IV) with a suitable organometallic reagent $R^5R^4M$, such as a Grignard reagent (M is MgBr or MgCl) or an organolithium reagent (M is Li), in a suitable solvent such as THF or diethyl ether provides the desired compound of Formula (I). Such organolithium reagents or Grignard reagents are well-known in the art, for example, Grignard reagents are easily prepared by reacting the corresponding halides ($R^5R^4X$, where X is Br or Cl) with magnesium metal in a suitable solvent, such as diethyl ether or THF, under anhydrous conditions. The aforementioned organolithium reagents are readily prepared by reacting the $R^5R^4H$, where $R^5$ is heteroaryl, with alkyl lithium reagents such lithium diisopropylamide (LDA) in a suitable solvent, such as diethyl ether or THF, under anhydrous conditions.

Alternatively, ketone (IV) is reacted with a suitable reagent to provide epoxide (V). Reaction of epoxide (V) with the desired $R^5H$ or $R^5M$ (M is Na or Li), provides the desired product of Formula (I). The reaction may take place by heating $R^5H$ and epoxide (V) in a suitable solvent such as DMF, heating $R^5H$ and epoxide (V) together in a solvent in the presence of a suitable base such as sodium ethoxide in ethanol, or by reacting $R^5M$ and epoxide (V) in suitable solvents such as DMF or DMSO. Such organometallic reagents could be generated by treating $R^5H$ with NaH, LiH, or other reagents or methods known by one of ordinary skill in the art, in suitable solvents such as THF, DMF, or DMSO.

Scheme II outlines another approach that may be used to obtain compounds of Formula (IA).

Scheme II

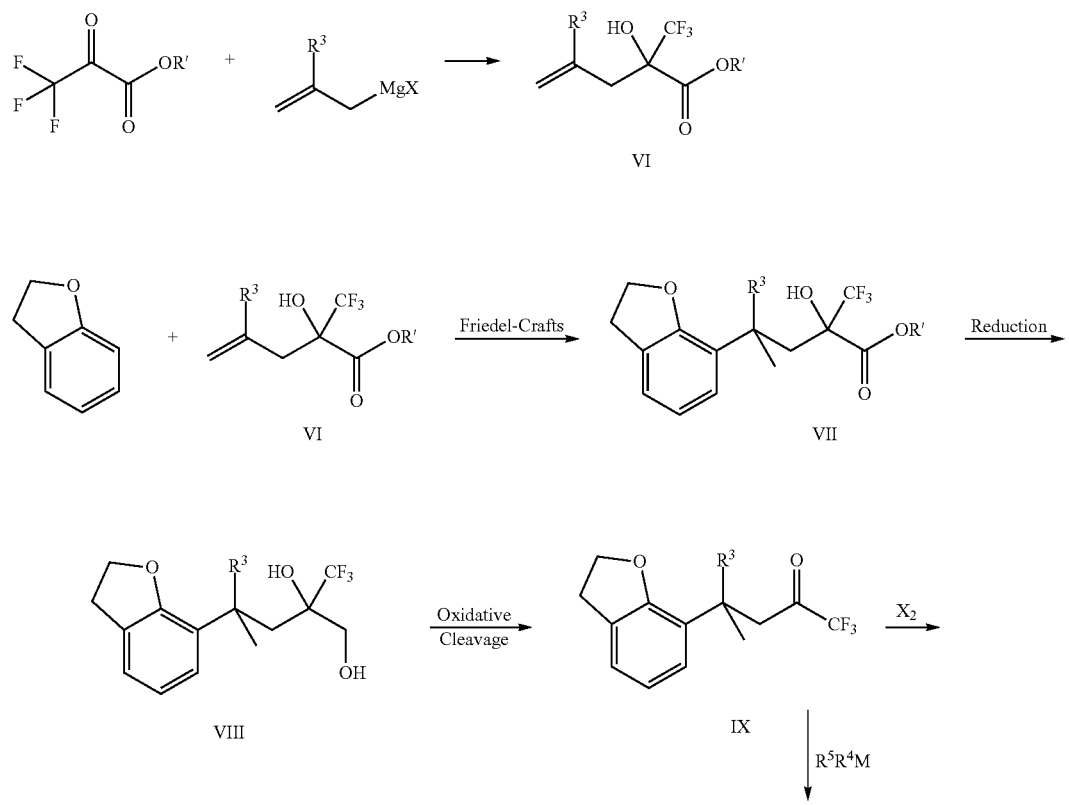

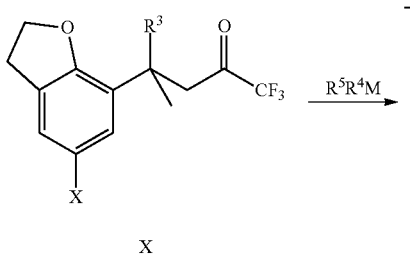 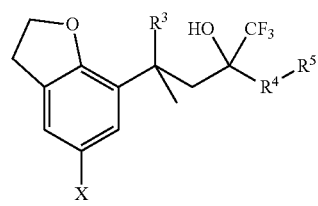

X

IA

X = H, I, Br, Cl
R² = Me

R¹ = 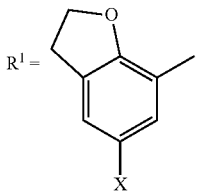

In Scheme II, ethyl trifluoropyruvate is reacted with a substituted allyl Grignard to provide olefin (VI). Reaction of olefin (VI) with 2,3-dihydrobenzofuran in the presence of a suitable Lewis acid such as AlCl₃, well-known in the art as the "Friedel-Crafts alkylation", gives ester (VII). Reduction of ester (VII) with a suitable reducing agent such as lithium aluminum hydride (LAH) in a solvent such as THF provides 1,2-diol (VIII). Oxidative cleavage of 1,2-diol (VIII) may be achieved with sodium periodate or lead tetraacetate, for instance, in a suitable solvent, such as methanol, to provide ketone (IX). Reaction of ketone (LX) with a suitable halogen (Cl₂, Br₂, or I₂) or halogenating reagents such as N-bromosuccinimide (NBS), affords ketone (X). Treatment of ketones (IX) or (X) with a suitable organometallic reagent R⁵R⁴M, where M is Li or MgX and X is Cl, Br, or I, provides the desired compound of Formula (I), where R¹ is an optionally substituted 2,3-dihydrobenzofuranyl group and R¹ is a methyl group.

Compounds of Formula (IA) may also be prepared by the method outlined in Scheme III.

Scheme III

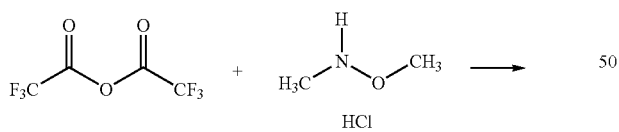

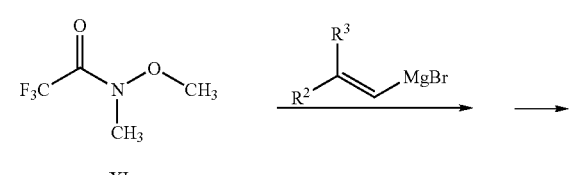 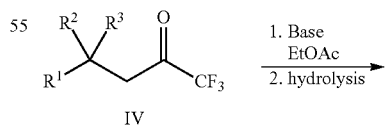

-continued

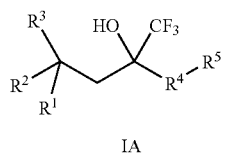

IA

In this approach, trifluoroacetic anhydride and N,O-dimethylhydroxylamine hydrochloride are coupled under basic conditions to afford trifluoroacetamide (XI) (Weinreb amide). Weinreb amide (XI) is reacted with a vinyl magnesium bromide bearing R² and R³ to afford trifluoromethylenone intermediate (XII). Trifluoromethylenone intermediate (XII) is treated with an organocopper reagent, derived from a Grignard or organolithium reagent by treating with a copper salt, to afford 1,4-addition product (IV). This trifluoroketone intermediate (IV) is reacted with an organometallic reagent R⁴R⁵M (as described in Scheme I) to afford the desired compound of Formula (IA).

Compounds of Formula (IA) where R⁴-R⁵ is an optionally substituted benzimidazol-2-ylmethyl group may be prepared by the procedure outlined in Scheme IV.

Scheme IV

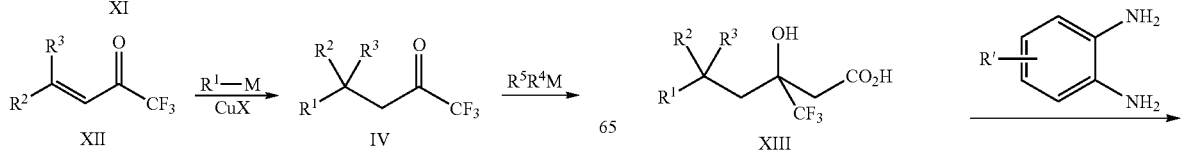 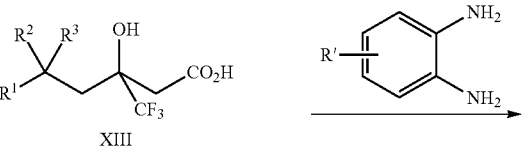

-continued

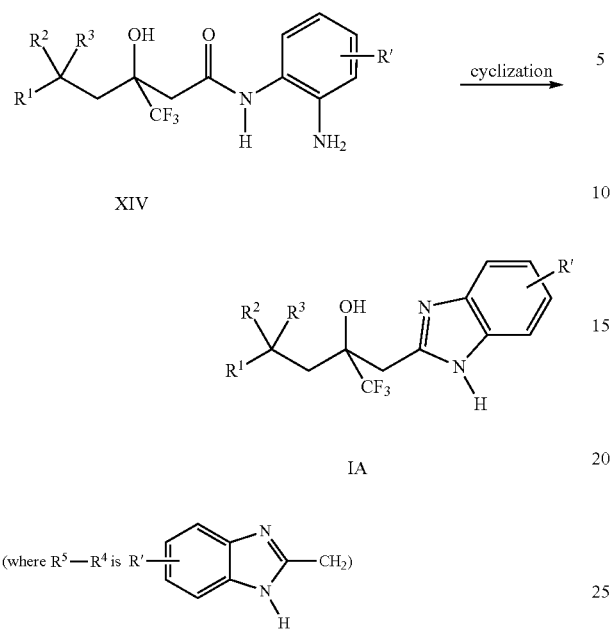

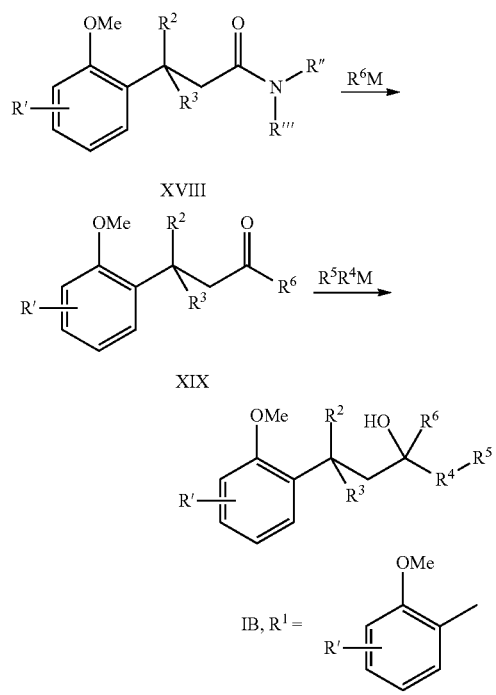

As illustrated in Scheme IV, trifluoromethylketone (IV) is reacted with ethyl acetate in the presence of a strong base such as lithium diisopropylamide (LDA) in a suitable solvent such as THF. The intermediate ester is hydrolyzed, for example, by treatment with aqueous base, to provide carboxylic acid intermediate (XIII). This carboxylic acid intermediate (XIII) is then coupled with an optionally substituted phenylenediamine under standard coupling conditions known in the art, for example, by treatment with 1-(3-dimethylaminopropyl)-3-ethylcarbodiimide (EDC) in the presence of 1-hydroxybenzotriazole in a suitable solvent such as N,N-dimethylformamide (DMF), to provide compound (XIV). Ring closure by methods known in the art, for example, acid catalyzed ring closure by treatment with polyphosphoric acid, provides the desired compound of Formula (IA).

Compounds of Formula (IB) may be prepared by the procedure illustrated in Scheme V.

Scheme V

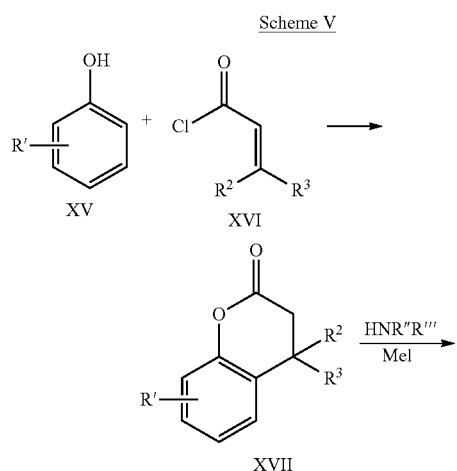

In Scheme V, substituted phenol (XV) is reacted with an acryloyl chloride bearing $R^2$ and $R^3$ (XVI) in the presence of a suitable base, such as triethylamine, to provide an intermediate ester which is cyclized by treatment with a Lewis acid, such as aluminum trichloride, in a suitable solvent, such as carbon disulfide, to provide lactone (XVII). Lactone (XVII) is treated with a suitable amine HNR"R'", such as morpholine, such that in the resulting amide (XVIII), —NR"R'" will function as a leaving group in the subsequent reaction. The intermediate phenol that forms is protected, for example, by reaction with methyl iodide in the presence of a suitable base such as potassium hydroxide to form protected phenol (XVIII), in this case having a methoxy group. Amide (XVIII) is then reacted with an organometallic reagent ($R^6M$), such as a Grignard reagent (M is MgBr or MgCl) or an organolithium reagent (M is Li), in a suitable solvent, such as THF or diethyl ether, to provide the ketone (XIX). Reaction of the ketone (XIX) with $R^5R^4M$ as described in the last step in Scheme I provides the desired compound of Formula (IB) where $R^1$ is an optionally substituted methoxyphenyl group.

In a more general procedure, suitable for a variety of $R^1$, one may use a method analogous to that described in Scheme III. As illustrated in Scheme VI, using a Weinreb amide bearing $R^6$ one may employ the method described in Scheme III to prepare the desired ketone (XX) and compound of Formula (IB).

Scheme VI

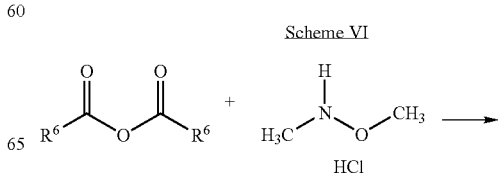

-continued

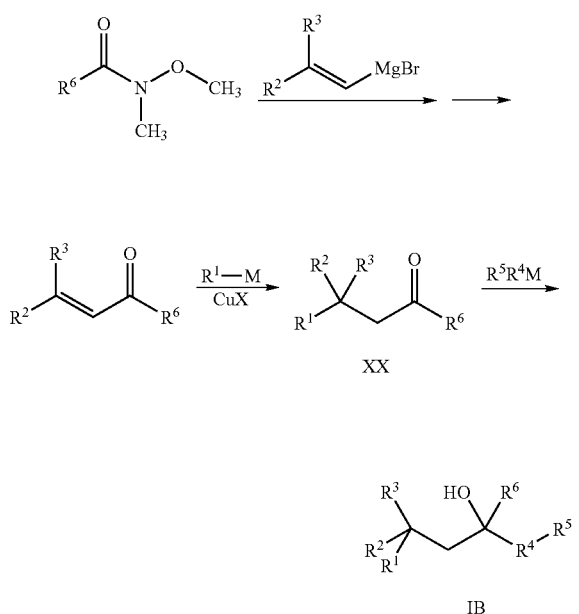

An alternative method to prepare intermediate (IV) in Schemes I, III, and IV, as well as ketone (XX) in Scheme VI, is illustrated in Scheme VII.

As illustrated in Scheme VII, a ketone bearing $R^1$ and $R^2$ (XXI) is condensed with cyanoacetic acid ester (XXII), where $R^1$ is Me or Et, in a reaction known in the art as a Knoevenagel condensation to provide olefin (XXIII). Reaction of olefin (XXIII) with a suitable organometallic reagent such as $R^1M$, where M is MgBr, MgCl, or Li, in the presence of a copper salt, such as CuI, affords ester (XXIV). Hydrolysis of ester (XXIV) followed by the concomitant decarboxylation of resulting acid in the presence of suitable reagent, such as sodium chloride, and in a suitable solvent mixture, such as DMSO and water, gives the corresponding nitrile (XXV). Reduction of nitrile (XXV), for example, by treatment with a suitable reducing agent, such as diusobutylaluminum hydride (DIBAL), in a suitable solvent such as dichloromethane, furnishes aldehyde (XXVD). Treatment of aldehyde (XXVI) with trimethyl(trifluoromethyl)silane in the presence of a suitable fluoride source, such as tetrabutylammonium fluoride, provides alcohol (XXVII). Oxidation of alcohol (XXVII) by methods known in the art, such as treatment with the Dess-Martin periodinane reagent, in a suitable solvent, such as dichloromethane, gives ketone (IV).

Alternatively, aldehyde (XXVI) is treated with a suitable organometallic reagent $R^6M$, such as a Grignard reagent (M is MgBr or MgCl) or an organolithium reagent (M is Li), in a suitable solvent such as THF or diethyl ether to provide alcohol (XXVIII). Subsequent oxidation of alcohol (XXVIII) by a method well-known in the art provides ketone (XX).

Additionally, ketone (XX) in Scheme VII may be prepared from ketone (IV) as depicted in Scheme VIII.

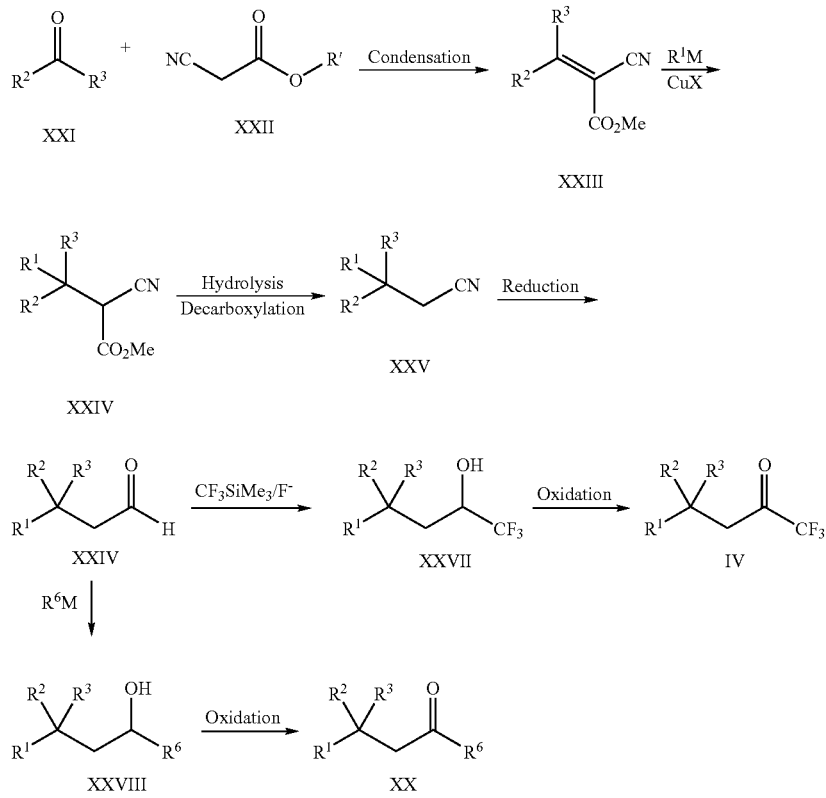

Scheme VIII

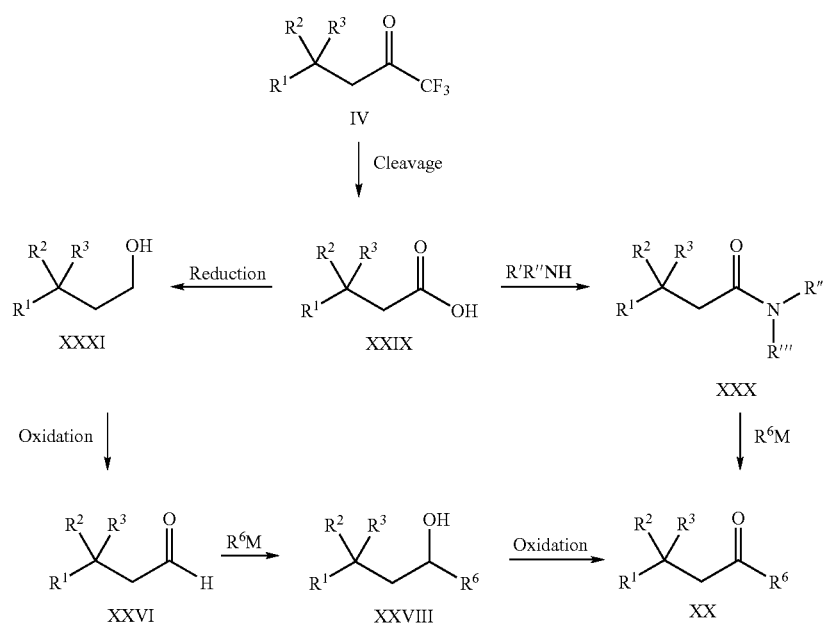

In Scheme VIII, ketone (IV) is cleaved in the presence of a suitable base, such as NaOH, and in a suitable solvent mixture, such as a mixture of water and ethanol, to provide acid (XXIX). Acid (XXIX) is treated with a suitable amine HNR"R'", such as morpholine, such that —NR"R'" will function as a leaving group in the subsequent reaction. The resulting amide (XXX), is then reacted with an organometallic reagent ($R^6M$), such as a Grignard reagent (M is MgBr or MgCl) or an organolithium reagent (M is Li), in a suitable solvent, such as THF or diethyl ether, to provide ketone (XX). Alternatively, acid (XXIX) is treated with a suitable reducing agent such as lithium aluminum hydride (LAH) in a solvent such as THF to give alcohol (XXXI). Oxidation of alcohol (XXXI) according to methods known by one of ordinary skills in the art, such as treatment with the Dess-Martin periodinane reagent, in a suitable solvent, such as dichloromethane, gives aldehyde (XXVI).

As previously illustrated in Scheme VII, reaction of aldehyde (XXVI) with a suitable organometallic reagent $R^6M$ (M is MgBr, MgCl, or Li), in a solvent such as THF or diethyl ether affords alcohol (XXVIII), which is oxidized to alcohol (XXVIII) by a method, such as Swern oxidation or treatment with the Dess-Martin periodinane, provides ketone (XX).

Compounds of Formula (IA) where $R^4-R^5$ is an optionally substituted indol-2-ylmethyl group may be synthesized by the procedure outlined in Scheme IX.

Scheme IX

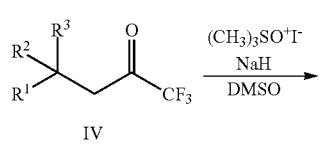

-continued

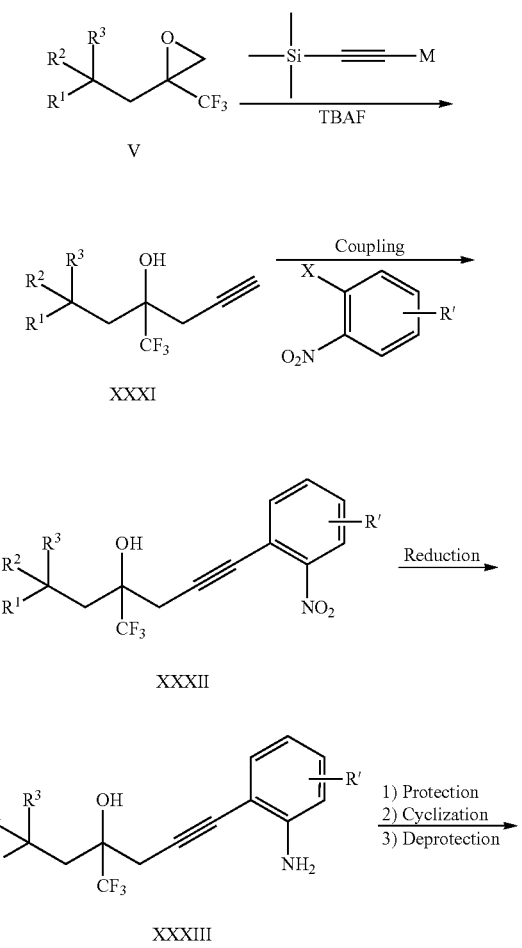

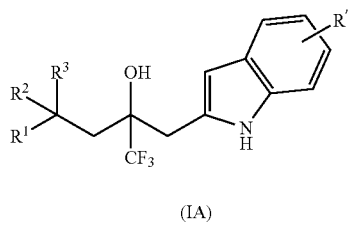

(IA)

As depicted in Scheme IX, reaction of ketone (IV) with sulfur ylide in a suitable solvent, such as DMSO, provides epoxide (V). Opening of epoxide (V) with a suitable acetylide reagent, such as lithium trimethylsilylacetylide (M is Li) in a suitable solvent, such as DMSO, followed by deprotection with a suitable fluoride source in a suitable solvent, affords alkyne (XXXI). Treatment of alkyne (XXXI) with a suitable coupling partner, such as optionally substituted aniline or nitrobenzene (X is OTf, I, or Br) in the presence of suitable catalysts, base and solvent (e.g., dichlorobis(triphenylphosphine)palladium (II), CuI, triethylamine, and DMF) provides alkyne (XXXII). Reduction of intermediate (XXXII) with a suitable metal reducing agent, such as iron, in a suitable solvent, such as acetic acid, affords aniline (XXXIII). Protection of aniline (XXXIII) with a suitable protecting group, such as trifluoroacetyl is well-known in the art and may be achieved by treatment with trifluoroacetic anhydride in a suitable solvent, such as dichloromethane. The resulting intermediate is cyclized with a suitable base, such as 1,1,3,3-tetramethyl guanidine, in a suitable solvent, such as methanol, provides the trifluoroacetyl-protected indole, which undergoes an in situ deprotection of the acyl group to afford compound of Formula (IA).

Additionally, compounds of Formula (IA) where $R^4$-$R^5$ is an optionally substituted azaindol-2-ylmethyl group may be prepared by the procedure illustrated in Scheme X.

Ketone (IV) is treated with a suitable propargylating reagent, such as propargyl aluminum sesquibromide, in a suitable solvent, such as THF, to furnish alkyne (XXXI). Reaction of homopropargyl alcohol (XXXI) with a suitable coupling partner, such as optionally substituted and protected amino pyridines, optionally substituted and protected amino pyrimidines or optionally substituted and protected amino pyridazines, wherein one or two atoms selected from A, W, Y, and Z are nitrogens and the remaining atoms are carbons, X is I or Br and PG is H or BOC (tert-butoxycarboyl), in the presence of suitable catalysts, base and solvent (e.g., dichlorobis(triphenylphosphine)palladium (II), CuI, triethylamine, and DMF) provides alkyne (XXXIV). Alkyne (XXXWV), where PG is H, is converted to the corresponding optionally protected azaindole or diazaindole of Formula (IA) by treatment with the suitable base such as potassium tert-butoxide, in a suitable solvent, such as N-methyl pyrrolidinone (NMP). In addition, alkyne (XXXWV) containing a N—BOC group is cyclized with a suitable base, such as 1,8-diazabicyclo[5.4.0]undec-7-ene (DBU), in a suitable solvent mixture, such as a mixture of water and methanol, to give the desired product of Formula (IA). Alternatively, the N—BOC protecting group of alkyne (XXXWV) may be removed by treatment with a suitable acid, such as HCl, in a suitable solvent, such as ethyl acetate, to provide the corresponding amine salt, which is cyclized in the presence of potassium tert-butoxide in NMP to provide the compound of Formula (IA).

Moreover, compounds of Formula (I) where $R^1$ is an optionally substituted aryl group may be converted by the sequence illustrated in Scheme XI to compounds of Formula (I) where $R^1$ is further optionally functionalized.

Scheme X

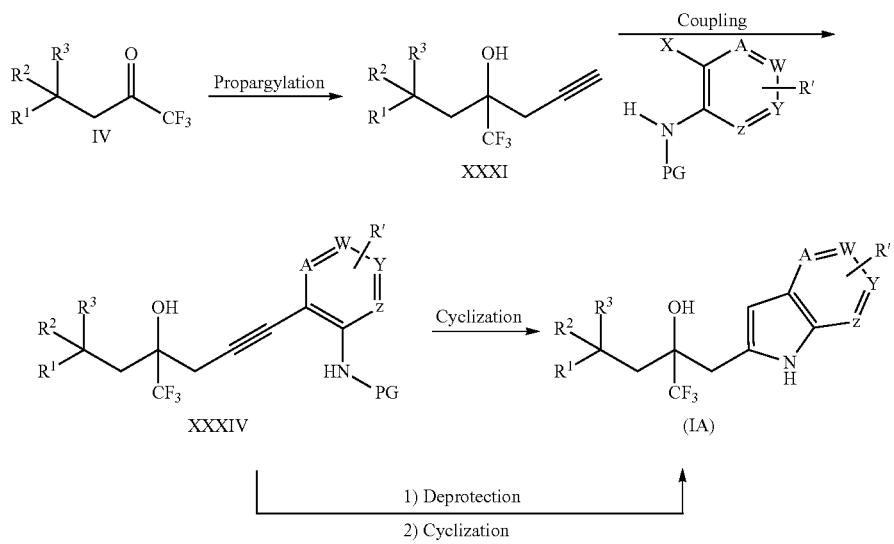

Scheme XI

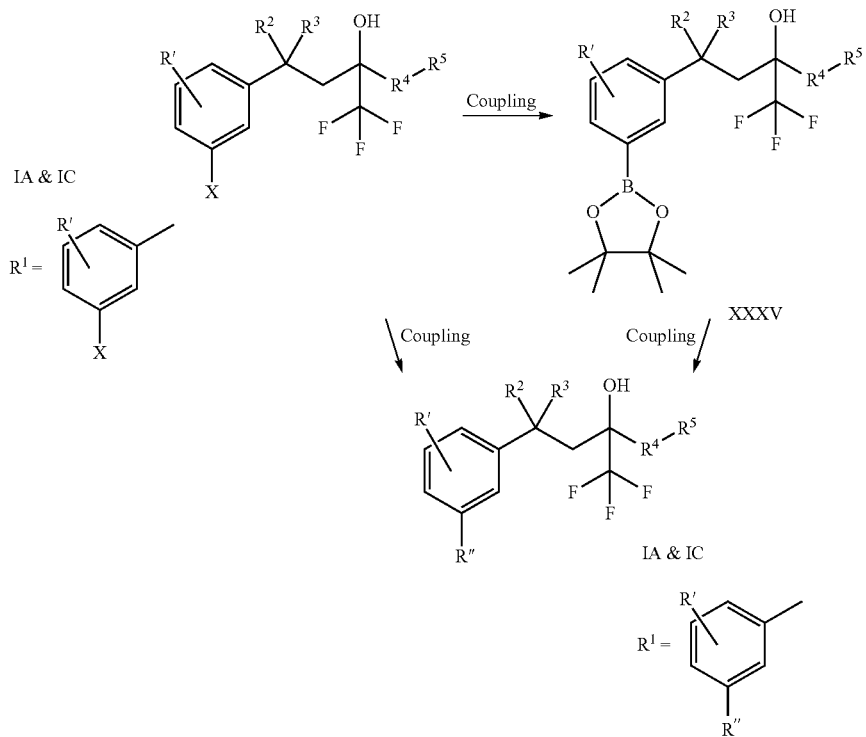

As outlined in Scheme XI, compounds of Formula (I) where $R^1$ is an optionally substituted aryl group in which one of the substituents is a suitable coupling group, such as Cl, Br, I, or OTf, may be treated with a suitable coupling partner, such as a boronic acid or a boronic ester, in a suitable solvent or a mixture of solvents, such as a mixture of DME, methanol, and DMF, in the presence of a suitable catalyst, such as tetrakis(triphenylphosphine)palladium (0), with an appropriate base, such as potassium carbonate, at a suitable temperature and under an appropriate atmospheric environment, such as argon, to give compounds of Formula (I) where $R^1$ is further optionally functionalized. Alternatively, compounds of Formula (I) where $R^1$ is an optionally substituted aryl group containing a suitable group, such as Cl, Br, I, or OTf, is converted to its corresponding boronic ester (XXXV) by reacting with an appropriate coupling partner, such as bis(pinacolato)diboron, under a suitable condition, such as heating at 100° C. in DME with potassium carbonate and in the presence of [1,1'-bis(diphenylphosphino)ferrocene]dichloropalladium (II). Subsequently, the boronic ester of formula (XXXV) may be converted to compounds of Formula (I) where $R^1$ is optionally functionalized by treating with a suitable aryl halide, and under a suitable, previously indicated, coupling condition. The choice between the two described methods depends on the commercial or synthetic availability of the coupling partner, which is up to the discretion of one skilled in the art.

As illustrated in Scheme XII, compounds of Formula (IA) where $R^4R^5$ is a cyano-substituted azaindol-2-ylmethyl or a cyano-substituted indol-2-ylmethyl may be converted to a compound of Formula (IA) where $R^4R^5$ is optionally functionalized.

Scheme XII

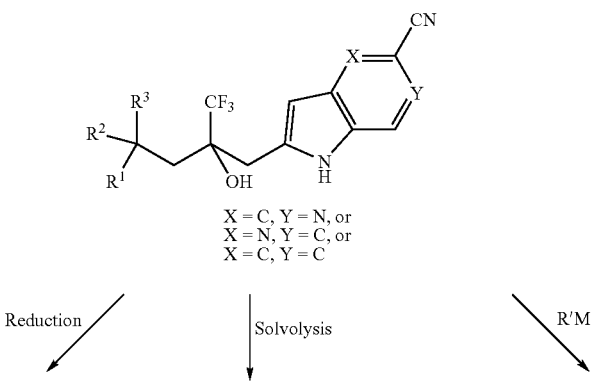

-continued

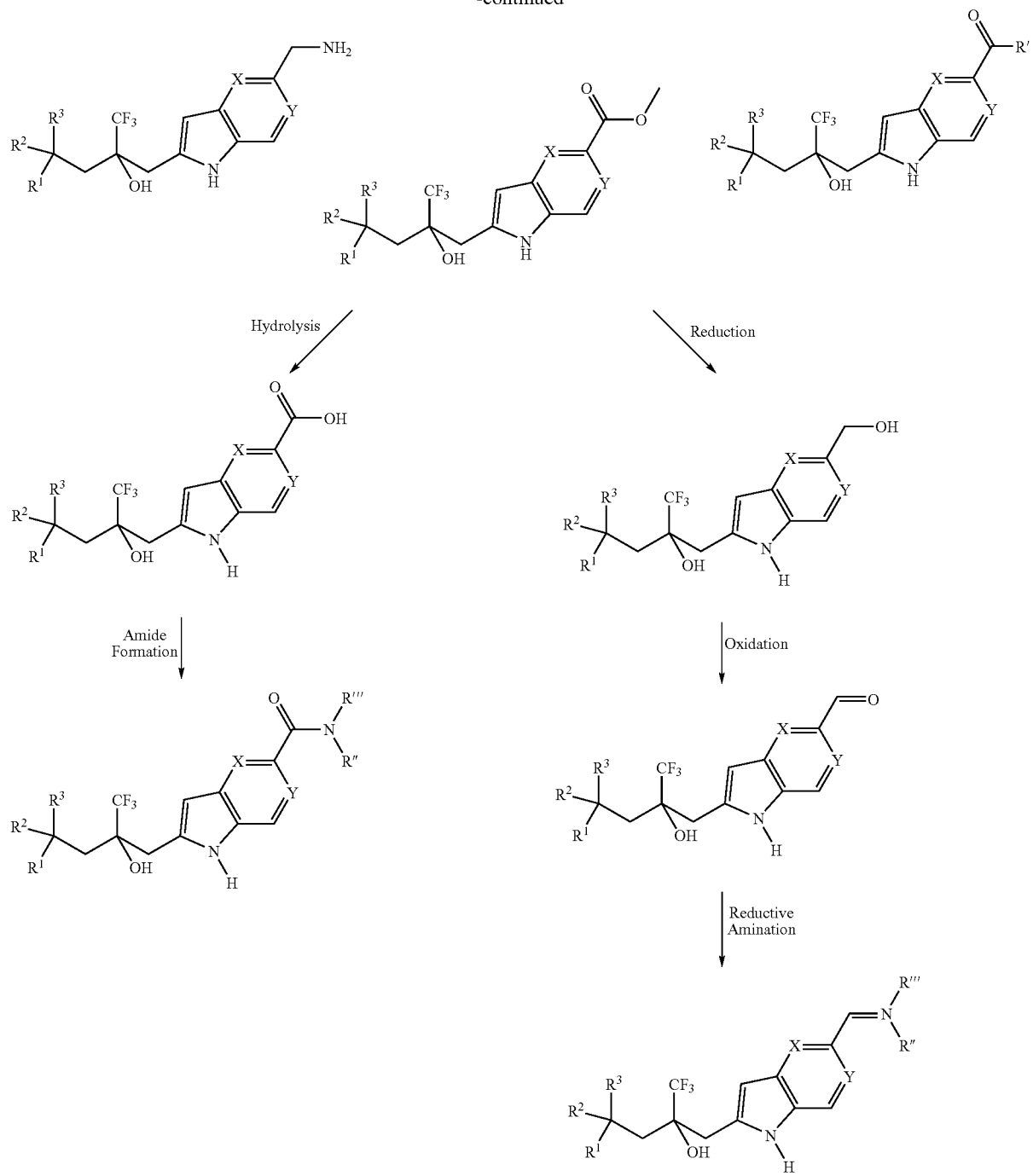

Compounds of Formula (IA) where $R^4R^5$ is a cyano-substituted azaindol-2-ylmethyl (X is a nitrogen and Y is a carbon, or X is a carbon and Y is a nitrogen) or a cyano-substituted indol-2-ylmethyl (X and Y are carbons), may be converted to the corresponding ketone by treatment with a suitable organometallic reagent such as R'M, where M is MgI, MgBr, MgCl, or Li, and R' is alkyl, cycloalkyl, aryl, heteroaryl, or heterocyclyl. Reduction of the cyano group with a suitable reducing agent, such as borane.methyl sulfide complex, in a suitable solvent such as THF, gives a compound of Formula (IA) bearing a 1° amine moiety. Moreover, the compound of Formula (IA) bearing a cyano group may be treated with an alcohol, such as methanol, in the presence of an acid catalyst, such as HCl, to afford the corresponding ester. The resulting ester may be hydrolyzed by treatment with a suitable base, such as lithium hydroxide, in a suitable mixture of solvents, such as a mixture of THF, water, and methanol, to provide a compound of Formula (IA) containing a carboxylic acid moiety. The resulting carboxylic acid of Formula (IA) can be converted to an amide using standard peptide coupling conditions known to one skilled in the art. This transformation may be affected by treatment with a suitable amine HNR"R'" and a suitable activating reagent, such as 1,3-dicyclohexylcarbodiimide (DCC), in the presence of a suitable base, such as N,N-diisopropylethyl amine, in an appropriate solvent, such as DMF or acetonitrile. Alternatively, the compound of Formula (IA) bearing an ester group may be reduced by treatment with a suitable reducing agent, such as lithium aluminum hydride (LAH), in a suitable solvent such as THF, to furnish the corresponding alcohol. Oxidation of the resulting alcohol with a suitable oxidizing agent, such as manganese (IV) oxide, in a suitable solvent, such as acetone, gives the desired compound of Formula (IA) containing an aldehyde group. Such aldehyde may be converted to the corresponding amine by a method well-known in the art as reductive amination. This functional group inter conversion may be performed by reaction of an aldehyde with a suitable amine HNR"R'" in the presence of a suitable reducing agent, such as sodium triacetoxyborohydride, and an appropriate acid catalyst, such as acetic acid, in a suitable solvent, such as 1,2-dichloroethane.

Compounds of Formula (ID) may be prepared according to the procedure shown in Scheme XIII.

In Scheme XIII, nitrile (XXXVIII) is treated with allyl bromide in the presence of a suitable base, such as sodium bis(trimethylsilyl)amide (NaHMDS), in a suitable solvent, such as DMSO, to provide the corresponding nitrile (XXXIX). Reduction of the nitrile (XXXIX) with a suitable reducing agent, such as DIBAL, in an appropriate solvent, such as dichloromethane, affords aldehyde (XL). Aldehyde (XL) is further reduced by reacting with a suitable reducing agent, such as lithium aluminum hydride (LAH), in a suitable solvent, such as THF, to give alcohol (XLI). Reaction of alcohol (XLI) with methyl iodide, in the presence of a suitable base, such as sodium hydride (NaH), in an appropriate solvent such as DMF, provides ether (XLII). Ether (XLII) is converted to aldehyde (XLIII) by oxidative cleavage methods well-known in the art, such as treatment with ozone. Reaction of aldehyde (XLIII) with a suitable nucleophilic trifluorom-

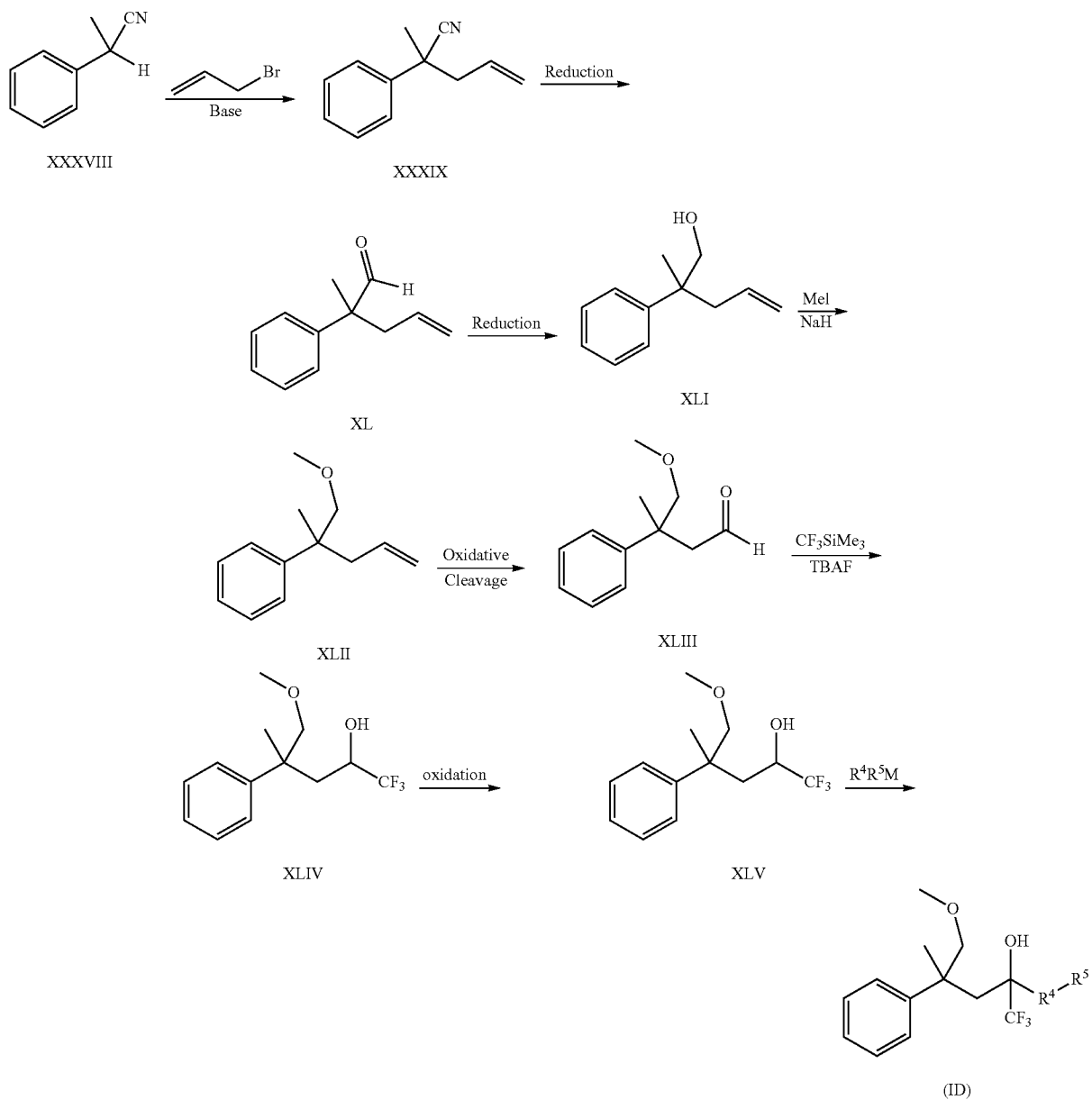

ethylating reagent, such as trimethyl(trifluoromethyl)silane, in the presence of a fluoride source, such as tetrabutylammonium fluoride (TBAF), provides alcohol (XLIV). Subsequent oxidation of alcohol (XLIV) with a suitable oxidizing reagent, such as Dess-Martin periodinane reagent, provides trifluoromethyl ketone (XLV). Reaction of ketone (XLV) with a suitable organometallic reagent $R^5R^4M$, where M is Li or MgX, and X is Cl, Br, or I, in a suitable solvent, such as THF, furnishes the compound of Formula (ID).

In order that this invention may be more fully understood, the following Examples are set forth. These Examples are for the purpose of illustrating embodiments of this invention, and are not to be construed as limiting the scope of the invention in any way since, as recognized by one skilled in the art, particular reagents or conditions could be modified as needed for individual compounds. Thus, while the Examples illustrate the synthesis of certain compounds of the invention or intermediates that may be used to synthesize compounds according to the invention, all of the compounds disclosed herein may be made by one or more methods disclosed herein, as one of skill in the art would appreciate. Starting materials used are either commercially available or easily prepared from commercially available materials by those skilled in the art.

EXPERIMENTAL EXAMPLES

Example 1

Syntheses of (3-Iodopyridin-4-yl)carbamic acid tert-butyl ester and (4-iodopyridin-3-yl)carbamic acid tert-butyl ester

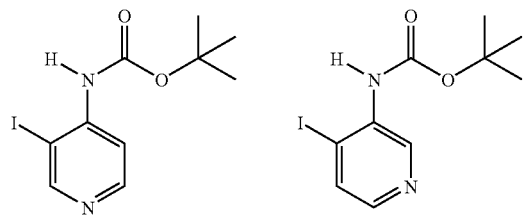

The title products were prepared according to the procedure described by T. A. Kelly et al., J. Org. Chem., 1995, 60, p. 1875.

Example 2

Synthesis of (2-Bromopyridin-3-yl)carbamic acid tert-butyl ester

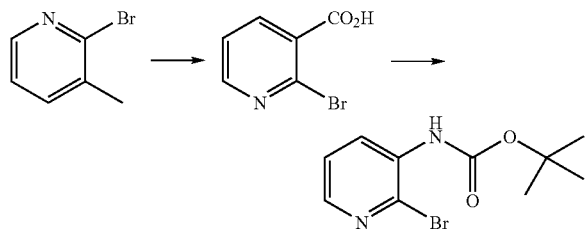

2-bromo-3-methylpyridine (25.0 mL, 213 mmol) was added to a solution of potassium permanganate (87.7 g, 555 mmol) in 800 mL of water and the mixture was stirred under reflux. After 5 hours, 600 mL of water was distilled off and the remaining suspension was filtered. The residue was washed with two 50 mL portions of hot water and the combined filtrates were acidified with concentrated HCl. The white precipitate was filtered and dried in a vacuum oven to give 26.8 g of 2-bromonicotinic acid (62% yield).

Diphenylphosphorylazide was added to a solution of 2-bromonicotinic acid (15.0 g, 74.0 mmol) and triethylamine (11.4 mL, 81.4 mmol) in 140 mL of anhydrous tert-butanol. The reaction mixture was stirred under reflux for 2 hours, cooled to room temperature, and concentrated in vacuo. The residue was dissolved in 150 mL of ethyl acetate and washed with three 50 mL portions of water, three 50 mL portions of saturated aqueous sodium bicarbonate, and with two 50 mL portions of brine. The organic layer was dried over magnesium sulfate (MgSO$_4$), filtered, and concentrated in vacuo. The residue crystallized upon standing to give 15.3 g of the title product (76% yield).

Example 3

Synthesis of 4-Amino-3-iodo-2-methylpyridine and 4-Amino-3-iodo-6-methylpyridine

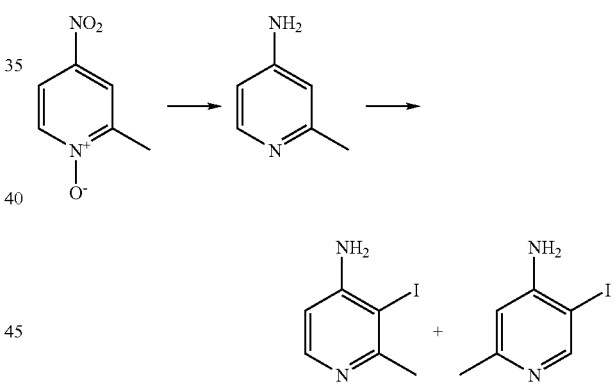

A solution of 2-methyl-4-nitropyridine-N-oxide (3.80 g, 24.6 mmol) in 100 mL of acetic acid was slowly heated with iron powder (6.89 g, 124 mmol) in a large flask (caution: the reaction becomes very exothermic upon turning brown). The resulting slurry was heated for 2 hours at 80° C. Excess acetic acid was removed in vacuo, the residue was taken up in 20% aqueous sodium hydroxide solution, and 100 mL of chloroform (CHCl$_3$) was added and the mixture filtered through CELITE® filter aid. The aqueous phase was extracted with two 200 mL portions of chloroform. The combined organic layers were dried over magnesium sulfate, filtered, and concentrated in vacuo. The crude product (2.2 g, 83% yield) was used without further purification.

A solution of KI (1.96 g, 11.9 mmol) and I$^2$ (1.87 g, 7.36 mmol) in 10 mL of water was added to a refluxing solution of the 2-methylpyridin-4-ylamine (1.00 g, 9.25 mmol) and sodium carbonate (683 mg, 6.44 mmol) in 5 mL of water. The mixture was heated at reflux for 2 hours, cooled to room temperature, and treated with 20 mL of ethyl acetate (EtOAc).

Phases were separated and the aqueous layer was extracted with three 20 mL portions of ethyl acetate. The combined organic layers were washed with a saturated aqueous sodium thiosulfate ($Na_2S_2O_3$) solution, dried over magnesium sulfate, and concentrated in vacuo. Flash chromatography (30% ethyl acetate in hexanes to 100% ethyl acetate, gradient) of the resulting residue yielded 4-amino-3-iodo-6-methylpyridine (first eluting: 226 mg, 11% yield) and 4-amino-3-iodo-2-methylpyridine (second eluting: 116 mg; 5% yield).

Example 4

Synthesis of
4-Amino-3-bromo-2,6-dimethylpyridine

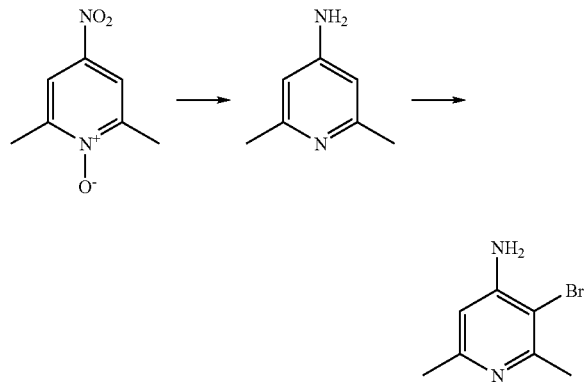

A solution of 4-nitro-2,6-dimethylpyridine-N-oxide (11.0 g, 65.4 mmol) in 50 mL of acetic acid was treated with iron powder (21.8 g, 390 mmol) in small portions while the mixture was rapidly stirred and gradually heated to 50° C. (caution: the reaction becomes very exothermic at this temperature). After the exotherm ceased, the mixture was heated for an additional hour at 80° C. The resulting solidified mixture was treated with 50 mL of water and the suspension was filtered through CELITE® filter aid. The filtrate was treated with ca. 200 mL of 6 N sodium hydroxide solution until the pH of the solution was basic (>12). The resulting green suspension was extracted with three 300 mL portions of chloroform. The extracts were combined, dried over magnesium sulfate, filtered, and concentrated in vacuo to give yellowish crystals (5.70 g, 71% yield).

A solution of 2,6-dimethylpyridin-4-ylamine (2.00 g, 16.4 mmol) in 5 mL of acetic acid was treated dropwise with a solution of bromine (0.84 mL, 16.3 mmol) in 2 mL of acetic acid at room temperature in a water bath over a period of 10 minutes. After 1 hour, the resulting slurry was treated with 40 mL of 20% sodium hydroxide solution and extracted with three 100 mL portions of dichloromethane ($CH_2Cl_2$). The combined extracts were dried over magnesium sulfate, filtered, and concentrated in vacuo. The resulting solid (starting material-desired product-dibromo byproduct (1:3:1)) was dissolved in 100 mL of hot hexanes and hot filtered to remove the insoluble starting material. The filtrate was allowed to cool to room temperature, which gave the title product as fine white needles (1.30 g, 40% yield).

Example 5

Synthesis of
4-Amino-3-bromo-6-cyano-2-methylpyridine

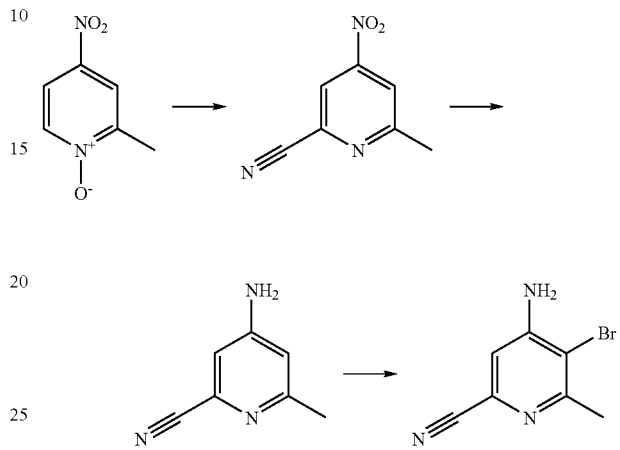

4-Nitropicoline-N-oxide (10.0 g, 64.9 mmol) and dimethylsulfate (6.39 mL, 64.5 mmol) were heated at 70° C. for 6 hours under a nitrogen gas ($N_2$) atmosphere. The dark brown mixture, which solidified upon cooling to room temperature was dissolved in 20 mL of water, cooled to −10° C. while vigorously stirring, and treated dropwise with a solution of KCN (5.04 g, 77.4 mmol) in 20 mL of water. The mixture was warmed to room temperature overnight. The resulting black heterogeneous mixture was dissolved in 50 mL of ethyl acetate and 50 mL of water. The phases were separated and the aqueous layer was extracted with two 50 mL portions of ethyl acetate. The combined organic layers were dried over magnesium sulfate, filtered, and concentrated in vacuo. Flash chromatography (20% to 50% ethyl acetate in hexanes, gradient) afforded the product as a brown solid (2.80 g, 27% yield).

2-Cyano-6-methyl-4-nitropyridine (1.9 g, 11.6 mmol) in a mixture of 50 mL of ethanol and 15 mL of saturated aqueous ammonium chloride ($NH_4Cl$) solution was heated with indium powder (7.00 g, 60.9 mmol) to 60° C. for 3 days. 20 mL of water was then added, and the slurry was filtered through CELITE® filter aid and the pad was washed with methanol. The filtrate was concentrated in vacuo to remove volatile organics and extracted with three 20 mL portions of dichloromethane. The combined extracts were dried over magnesium sulfate, filtered, and concentrated in vacuo. Chromatography on $SiO_2$ (30% ethyl acetate in hexanes to 100% ethyl acetate, gradient) gave the product as a tan solid (580 mg, 27% yield).

4-Amino-6-methylpyridine-2-carbonitrile was converted to the title product in 57% yield according to the procedure described for the preparation of 4-amino-3-bromo-2,6-dimethylpyridine.

Example 6

Synthesis of 5-Amino-6-bromopyridine-2-carbonitrile

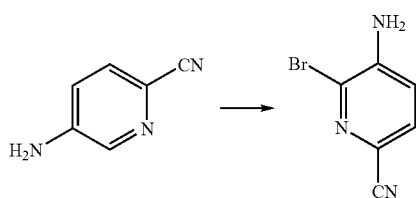 [SMILES: N#Cc1ccc(N)cn1 ; N#Cc1ccc(N)c(Br)n1]

5-Aminopyridine-2-carbonitrile (2.38 g, 20 mmol) was dissolved in 6 mL of glacial acetic acid. A solution of bromine (1 mL, 20 mmol) in 2.5 mL of glacial acetic acid was added dropwise over a period of 30 minutes while the room temperature was maintained with a water bath. The resulting slurry was stirred for 1 hour at room temperature, treated with 50 mL of aqueous 20% sodium hydroxide solution and extracted with three 160 mL portions of dichloromethane. The combined organic layers were dried over sodium sulfate ($Na_2SO_4$), filtered, and concentrated in vacuo. The residue was purified by crystallization from ethyl acetate-hexanes to give 5-amino-6-bromopyridine-2-carbonitrile (1.42 g, 35% yield).

Example 7

Synthesis of (6-Cyano-4-iodopyridin-3-yl)carbamic acid tert-butyl ester

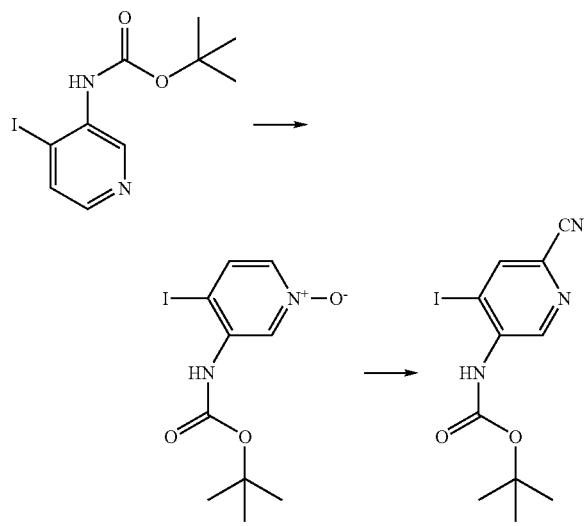

(4-Iodopyridin-3-yl)carbamic acid tert-butyl ester (3.2 g, 10 mmol) was dissolved in 100 mL of dimethoxyethane at room temperature. m-Chloroperoxybenzoic acid (77% by weight, 3.36 g, 15 mmol) was added and the reaction was stirred overnight at room temperature. The mixture was concentrated in vacuo, redissolved in 400 mL of ethyl acetate, and washed with two 200 mL portions of saturated sodium bicarbonate ($NaHCO_3$) solution. The phases were separated and the aqueous layer was extracted with two 100 mL portions of ethyl acetate. The combined organic layers were washed with brine, dried over magnesium sulfate, filtered, and concentrated in vacuo. Crystallization from ethyl acetate-hexanes gave (4-iodo-1-oxypyridin-3-yl)carbamic acid tert-butyl ester (2.65 g, 79% yield).

A mixture of (4-iodo-1-oxypyridin-3-yl)carbamic acid tert-butyl ester (2.65 g, 7.6 mmol), trimethylsilyl cyanide (4 mL, 30 mmol), triethylamine (2.6 mL, 18.9 mmol), and 40 mL of anhydrous acetonitrile was heated at 90° C. for 2.5 hours. The mixture was concentrated in vacuo, diluted with 500 mL of dichloromethane, and treated with saturated aqueous sodium carbonate ($Na_2CO_3$) solution until the aqueous layer was basic. After phases were separated, the organic layer was washed with brine, dried over sodium sulfate, filtered, and concentrated in vacuo. Chromatography on $SiO_2$ (2:98 to 8:92 ethyl acetate-hexanes, gradient) gave (6-cyano-4-iodopyridin-3-yl)carbamic acid tert-butyl ester (185 mg, 7% yield).

Example 8

Synthesis of (2-Cyano-3-iodopyridin4-yl)carbamic acid tert-butyl ester

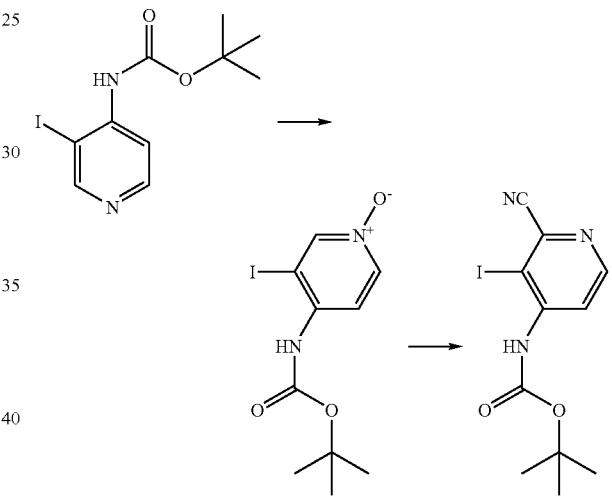

(3-Iodopyridin-4-yl)carbamic acid tert-butyl ester (3.2 g, 10 mmol) was dissolved in 100 mL of dimethoxyethane at room temperature. m-Chloroperoxybenzoic acid (77% by weight, 3.36 g, 15 mmol) was added and the reaction was stirred overnight at room temperature. After removing the solvent in vacuo, the residue was dissolved in 400 mL of ethyl acetate and washed with two 200 mL portions of saturated aqueous sodium bicarbonate solution. The phases were separated and the aqueous layer was extracted with two 100 mL portions of ethyl acetate. The combined organic layers were washed with brine, dried over magnesium sulfate, filtered, and concentrated in vacuo. Crystallization from ethyl acetate-hexanes gave (3-iodo-1-oxypyridin-4-yl)carbamic acid tert-butyl ester (1.95 g, 58% yield).

A mixture of (3-iodo-1-oxypyridin-4-yl)carbamic acid tert-butyl ester (1.95 g, 5.79 mmol), trimethylsilyl cyanide (3 mL, 23 mmol), and triethylamine (2 mL, 14.5 mmol) in 30 mL of anhydrous acetonitrile was heated to reflux at 90° C. for 2.5 hours. The solvent was then removed in vacuo. The residue was diluted with 500 mL of dichloromethane and treated with saturated aqueous sodium carbonate solution until the aqueous layer was basic. The phases were separated and the organic layer was washed with brine, dried over sodium sulfate, filtered, and concentrated in vacuo. Chromatography on SiO$_2$ (2:98 to 8:92 ethyl acetate-hexanes, gradient) gave (2-cyano-3-iodopyridin-4-yl)carbamic acid tert-butyl ester (1.22 g, 61% yield).

Example 9

Synthesis of 5-amino-6-bromo-2-methoxypyridine

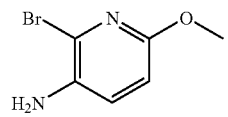

A stirred mixture of 2-methoxy-5-aminopyridine (10 g, 0.081 mol, 1.0 equiv) and sodium acetate (6.6 g, 0.081 mol, 1.0 equiv) in 60 mL of acetic acid was treated dropwise with bromine (12.9 g, 0.081 mol, 1.0 equiv). After 20 minutes, the reaction mixture was poured into 1000 mL of 10% aqueous sodium hydroxide solution and extracted with three 250 mL portions of ethyl acetate. The combined organic layers were dried over magnesium sulfate, filtered, and evaporated to dryness. Chromatography on SiO$_2$ (20% hexanes in dichloromethane) gave 5-amino-6-bromo-2-methoxypyridine (6.5 g, 40% yield) as a purple solid.

Example 10

Synthesis of (4-Iodo-6-phenylpyridin-3-yl)carbamic acid tert-butyl ester

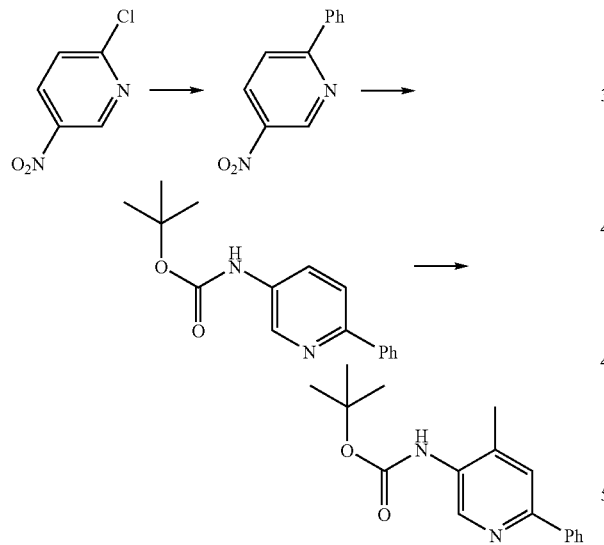

A mixture of Pd(PPh$_3$)$_4$ (354 mg, 1.58 mmol), 2-chloro-5-nitropyridine (5.00 g, 31.5 mmol), and phenylboronic acid (4.61 g, 37.8 mmol) was degassed and filled with nitrogen gas three times. The mixture was treated with 40 mL of DME and aqueous 2 M potassium carbonate (80.0 mmol) solution and heated to reflux. After 4 hours, the reaction mixture was cooled to room temperature and diluted with 100 mL of ethyl acetate and 50 mL of water. The phases were separated and the aqueous layer was extracted with three 100 mL portions of ethyl acetate. The combined organic layers were washed with 100 mL of brine, dried over magnesium sulfate, filtered, and concentrated in vacuo. Chromatography on SiO$_2$ (0% to 50% ethyl acetate in hexanes, gradient) give 4.60 g of 5-nitro-2-phenylpyridine (73% yield).

A solution of 5-nitro-2-phenylpyridine (4.60 g, 23.0 mumol) and BOC anhydride (15.0 g, 68.9 mmol) in a mixture of 25 mL of methanol and 25 mL of ethyl acetate was treated with palladium (10% on carbon, 500 mg). The resulting mixture was shaken under 50 psi of hydrogen gas (H$_2$) at room temperature. After 18 hours, the mixture was diluted with 20 mL of dichloromethane, filtered through a pad of CELITE® filter aid, and concentrated in vacuo. The resulting solid was triturated with ethyl acetate, filtered, and dried to give 5.54 g of (6-phenylpyridin-3-yl)carbamic acid tert-butyl ester as white solid (89% yield).

A solution of (6-phenylpyridin-3-yl)carbamic acid tert-butyl ester (5.54 g, 20.5 mmol) and TMEDA (6.49 mL, 43.0 mmol) in 100 mL of anhydrous diethyl ether was treated with n-BuLi at −78° C. After 15 minutes at −78° C., the mixture was warmed to −10° C. and stirred for an additional 3 hours. The reaction mixture was then cooled to −78° C. and a solution of iodine in a mixture of 10 mL of THF and 100 mL of diethyl ether was added dropwise. After 2 hours at −78° C., the mixture was allowed to warm to 0° C. and was quenched with 400 mL of saturated aqueous ammonium chloride solution. The organic layer was washed with five 100 mL portions of saturated aqueous sodium thiosulfate. The combined aqueous layers extracted with three 200 mL portions of ethyl acetate. The combined organic layers were dried over magnesium sulfate, filtered, and concentrated in vacuo. Chromatography on SiO$_2$ (0% to 70% ethyl acetate in hexanes, gradient) afforded 900 mg of the title product as yellow oil that solidified over time (11% yield).

Example 11

Synthesis of (4'-Iodo-3,4,5,6-tetrahydro-2H-[1,2] bipyridinyl-5'-yl)carbamic acid tert-butyl ester

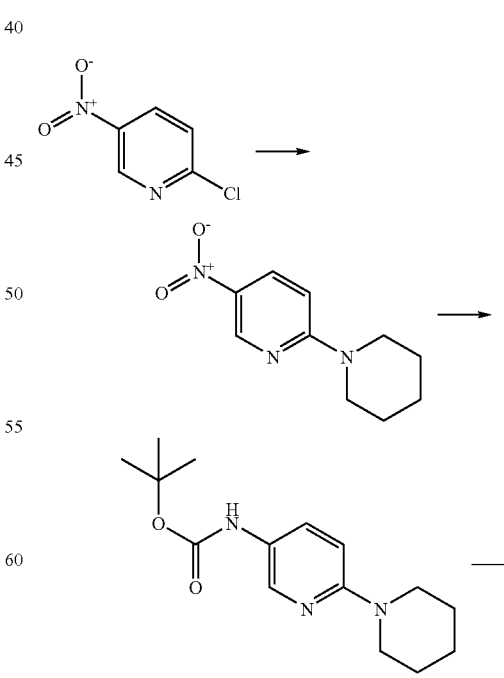

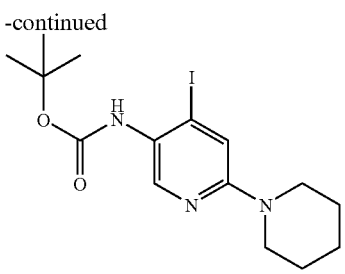

2-Chloro-5-nitropyridine (10 g, 63.3 mmol) was dissolved in 150 mL of THF. 20 mL of piperidine was then added and the resulting mixture was stirred for 18 hours at room temperature. The reaction mixture with copious precipitate was then diluted with 200 mL of water and 100 mL of diethyl ether. The layers were thoroughly mixed and separated. The organic layer was dried over sodium sulfate and concentrated in vacuo. The bright yellow solid was redissolved in 35 mL of dichloromethane and, with vigorous stirring, hexanes were added until the product began to precipitate. The bright yellow solid was collected by filtration and dried to afford 12.5 g of 5'-nitro-3,4,5,6-tetrahydro-2H-[1,2']bipyridinyl.

5'-Nitro-3,4,5,6-tetrahydro-2H-[1,2']bipyridinyl (12.5 g, 60.4 mmol) was suspended in 125 mL of methanol in a Parr shaker bottle and 16 g of di-tert-butyldicarbonate was added, followed by 500 mg of platinum oxide. The resulting mixture was shaken under 55 psi of hydrogen gas for 2 hours, followed by stirring under argon overnight. After 16 hours, the mixture was filtered through a pad of diatomaceous earth and concentrated in vacuo. The crude residue was triturated with hexanes and filtered. Chromatography on silica gel (100% dichloromethane to 30% ethyl acetate in dichloromethane, gradient) provided 6.9 g (41.2% yield) of (3,4,5,6-tetrahydro-2H-[1,2']bipyridinyl-5'-yl)carbamic acid tert-butyl ester as a white solid.

The title product was prepared from (3,4,5,6-tetrahydro-2H-[1,2']bipyridinyl-5'-yl)carbamic acid tert-butyl ester in the same manner as described in the preparation of (4-iodo-6-phenylpyridin-3-yl)carbamic acid tert-butyl ester.

Example 12

Synthesis of 4-[(tert-Butoxycarbonyl)amino]-3-iodo-2-methoxypyridine

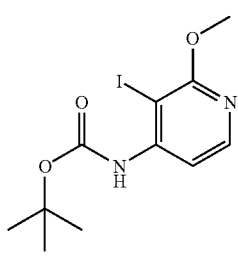 [SMILES: COc1nccc(NC(=O)OC(C)(C)C)c1I]

4-Amino-2-chloropyridine (15 g, 117 mmol, 1.0 equiv) was dissolved in 100 mL of THF. A solution of sodium methoxide in methanol (1.0 M, 234 mL, 234 mmol, 2.0 equiv) was added and the resulting solution was refluxed for 16 hours. The reaction mixture was poured into 500 mL of a rapidly stirring saturated sodium bicarbonate solution. 500 mL of ethyl acetate was added and the layers were separated. The organic layer was dried over sodium sulfate, decanted, and concentrated in vacuo. Chromatography on SiO$_2$ (30% ethyl acetate in hexanes) provided the titled compound as a yellow solid (2.1 g).

4-amino-2-methoxypyridine (2.1 g, 16.9 mmol, 1.0 equiv) was dissolved in 35 mL of ethyl acetate. BOC anhydride (5.4 g, 25.4 mmol, 1.5 equiv) was added and the resulting solution was refluxed for 3 hours. The reaction was cooled and concentrated in vacuo. The residue was triturated with 100 mL of hexanes to give an off-white precipitate that was collected and dried under vacuum to give the titled product (1.8 g).

A solution of 4-[(tert-butoxycarbonyl)amino]-2-methoxypyridine (1.8 g, 8.03 mmol, 1.0 equiv) in 100 mL of anhydrous diethyl ether was treated with 2.79 mL of N,N,N',N'-tetramethylethylenediamine (18.5 mmol, 2.3 equiv) under an inert atmosphere. The resulting solution was cooled to –78° C., treated with n-BuLi (2.5 M, 7.2 mL, 18.0 mmol, 2.24 equiv) and warmed to –7° C. The reaction was stirred at –7° C. to 0° C. for 3 hours, cooled to –78° C. and treated with a solution of iodine (3.05 g, 12 mmol) in 30 mL of anhydrous THF. The resulting mixture was stirred to room temperature for 16 hours. 200 mL of saturated ammonium chloride solution and 100 mL of diethyl ether were added. The phases were separated and the organic layer was washed with 100 mL of sodium thiosulfate (10% aqueous solution), dried over sodium sulfate, decanted, and concentrated in vacuo. Chromatography on SiO$_2$ (100% dichloromethane to 5% methanol in dichloromethane, gradient) provided the title product (650 mg, 23% yield) as a white wax.

Example 13

Synthesis of 5-[(tert-Butoxycarbonyl)amino]-4-iodo-2-(isopropoxy)pyridine

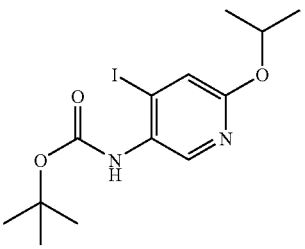 [SMILES: CC(C)Oc1cc(I)c(NC(=O)OC(C)(C)C)cn1]

A mixture of 2-chloro-5-nitropyridine (15 g, 95 mmol) and 28 mL of isopropyl alcohol (366 mmol) in 100 mL of anhydrous THF was stirred until the solids dissolved. The resulting solution was cooled in an ice bath and treated dropwise with potassium tert-butoxide (1 M in THF, 115 mL, 115 mmol) over 45 minutes. The reaction was quenched with 75 mL of saturated aqueous ammonium chloride solution and diluted with 100 mL of ethyl acetate. The phases were separated and the organic layer was dried over magnesium sulfate, filtered, and concentrated in vacuo. This residue was triturated with hexanes and stirred at room temperature overnight. The mixture was filtered and the filtrate was concentrated in vacuo to yield 15.7 g of dark orange oil that was used in the next step without further purification.

5-nitro-2-isopropoxypyridine (15.7 g, 86 mmol) was dissolved in 125 mL of methanol and transferred to a Parr bottle. Palladium (10% on carbon, 1.57 g) and BOC anhydride (28.2 g, 129 mmol) were added. The resulting mixture was shaken on a Parr shaker under 50 psi of hydrogen gas overnight. The mixture was treated with 5 g of CELITES filter aid, filtered through a pad of CELITE® filter aid and concentrated in vacuo. Chromatography on SiO₂ (hexanes-ethyl acetate (9:1)) yielded a pink solid (16.1 g). This solid was dissolved in dichloromethane, treated with hexanes, and filtered to give 13.7 g of the title product as a white solid.

A solution of 13.7 g of 5-[(tert-butoxycarbonyl)amino]-2-(isopropoxy)pyridine (54.3 mmol) and 18.1 mL of N,N,N'-tetramethylethylenediamine (120 mmol) in 200 mL of anhydrous diethyl ether was cooled to −78° C. and treated with n-BuLi (2.5 M in hexanes, 48 mL, 120 mmol) under an inert atmosphere. The mixture was placed in a −8° C. bath for 1 hour and allowed to slowly warm to room temperature. After 40 minutes, the flask was cooled to −8° C. and stirred for 4 hours. The mixture was then cooled to −78° C., treated with a solution of iodine (19.0 g, 75 mmol) in 100 mL of anhydrous THF, and the resulting mixture was stirred for 16 hours while allowing the bath to warm to 11° C. The reaction mixture was poured into a rapidly stirring aqueous saturated ammonium chloride solution (200 mL) and diluted with 100 mL of water and 300 mL of diethyl ether. The phases were separated and the aqueous layer was extracted with 200 mL of diethyl ether. The combined organic layers were washed with two 200 mL portions of sodium thiosulfate (10% aqueous solution), dried over sodium sulfate, decanted, and concentrated in vacuo. Chromatography on SiO₂ (10% to 50% ethyl acetate in hexanes, gradient) gave the title product as an oil, which solidified on standing (13 g, 63% yield).

Example 14

Synthesis of 4-Amino-3-bromopyridazine and 4-Amino-5-bromopyridazine

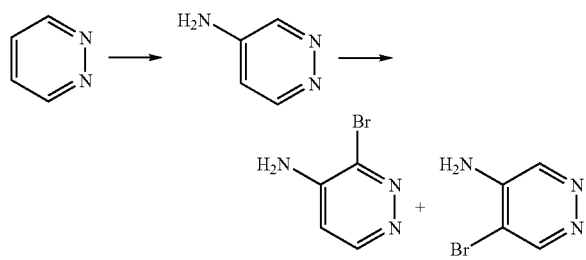

50 mL of ammonia was condensed in a 200 mL, 3-neck flask equipped with dry ice condenser. After the addition of a crystal of Fe(NO₃)₃, potassium (468 mg, 12.0 mmol) was added in small pieces at −78° C. The cooling bath was removed and the intense dark blue mixture was brought to a gentle reflux until a light grey slurry was obtained. After cooling to −78° C., 0.35 mL (4.80 mmol) of pyridazine was added and the mixture was stirred for 10 minutes. Solid KMnO₄ (2.65 g, 16.8 mmol) was added in small portions, the cooling bath was removed, and the mixture was stirred for 10 minutes. The reaction was carefully quenched with 1.2 g of solid ammonium chloride. 20 mL of methanol was added and the ammonia was left to evaporate in the hood. The black mixture was filtered through CELITE® filter aid, the filtrate was concentrated in vacuo, and the resulting black solid was purified on SiO₂ (100% CH₂Cl₂ to 10% MeOH in CH₂Cl₂, gradient) to yield pyridazin-4-ylamine as a brownish solid (380 mg; 83% yield).

Bromination of pyridazin-4-ylamine was performed in the same manner as for the preparation of 4-amino-3-bromo-2,6-dimethylpyridine. Chromatography on SiO₂ (20% ethyl acetate in hexanes to 100% ethyl acetate, gradient, followed by 2% methanol in ethyl acetate) yielded 4-amino-3-bromopyridazine (first eluting: 15% yield) and 4-amino-5-bromopyridazine (second eluting: 5% yield) as tan solids.

Example 15

Synthesis of 5-Amino-4-bromopyrimidine

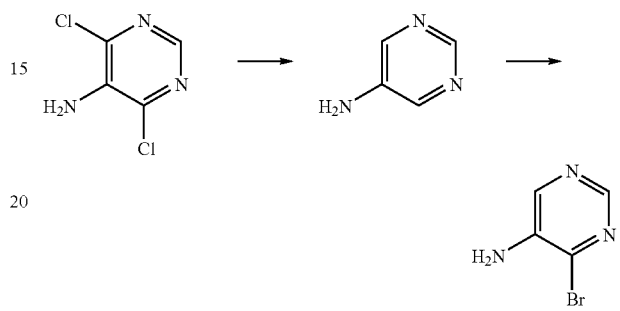

A solution of 5-amino-4,6-dichloropyrimidine (5.0 g, 30.5 mmol) in 250 mL of diethyl ether was treated with sodium hydroxide solution (20.0 g, 0.50 mol, in 60 mL of water) and palladium (10% on carbon, 400 mg). The mixture was shaken at room temperature on a Parr shaker under 50 psi of hydrogen gas for 20 hours. The mixture was filtered through CELITE® filter aid. The phases were separated and the aqueous layer was extracted with three 100 mL portions of ethyl acetate. The combined organic layers were dried over magnesium sulfate, filtered, and concentrated in vacuo. Crystallization of the crude from ethyl acetate gave pyrimidin-5-ylamine as white crystalline solid (2.8 g; 95% yield).

Bromination of pyrimidin-5-ylamine was performed in the same manner as for the preparation of 4-amino-3-bromo-2,6-dimethylpyridine. The resulting crude product (300 mg, 35% yield) was deemed pure and used without further purification.

Alternatively, 5-amino-4-bromopyrimidine can be synthesized according to the following procedure: A solution of 4,6-dichloro-5-aminopyrimidine (21 g, 128 mmol) in 250 mL of MeOH was sequentially treated with ammonium formate (45 g, 714 mmol) and palladium (10% on charcoal, 1 g, 0.943 mmol) at 0° C. The mixture was stirred overnight at room temperature and was filtered through CELITE® filter aid. The filtrate was concentrated to give a yellow solid. 100 mL of water and 250 mL of ethyl acetate were added. The organic phase was separated and the aqueous layer was extracted with eight 250 mL portions of ethyl acetate. The combined organic layers were dried over magnesium sulfate, filtered, and concentrated in vacuo to yield off-white crystals (8.1 g, 67%).

A stirred solution of 5-aminopyrimidine (3.0 g, 31.5 mmol) in 150 mL of dichlromethane and 30 mL of methanol was cooled to 0° C. Benzyltrimethylammonium tribromide (13.5 g, 34.7 mmol) was added in portions over a period of 10 minutes. Stirring was continued at 0° C. for 15 minutes and at room temperature for 90 minutes. The reaction mixture was treated with aqueous sodium bicarbonate solution until the solution was pH 8. The organic layer was separated and aqueous layer was extracted with three 30 mL portions of ethyl acetate. The combined organic extracts were dried over sodium sulfate, filtered, and concentrated in vacuo. An off-white solid (2.8 g; 51%) was obtained, which was used without further purification.

Example 16

Synthesis of 4-Amino-5-iodopyrimidine

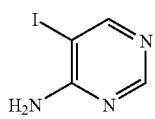

A solution of 4-aminopyrimidine (0.970 g, 10.3 mmol) in 20 mL of acetic acid was treated with iodine monochloride (1.67 g, 10.3 mmol, 1.01 equiv), which gave a copious precipitate of the N-iodo intermediate. The resulting mixture was refluxed for 3 hours under argon and cooled to about 10° C. with water bath. A precipitate formed that was collected and dried to provide the title compound as a yellowish solid (1.4 g, 62% yield).

Example 17

Synthesis of 2,2,2-Trifluoro-N-(4-iodo-2-isopropylpyrimidin-5-yl)acetamide

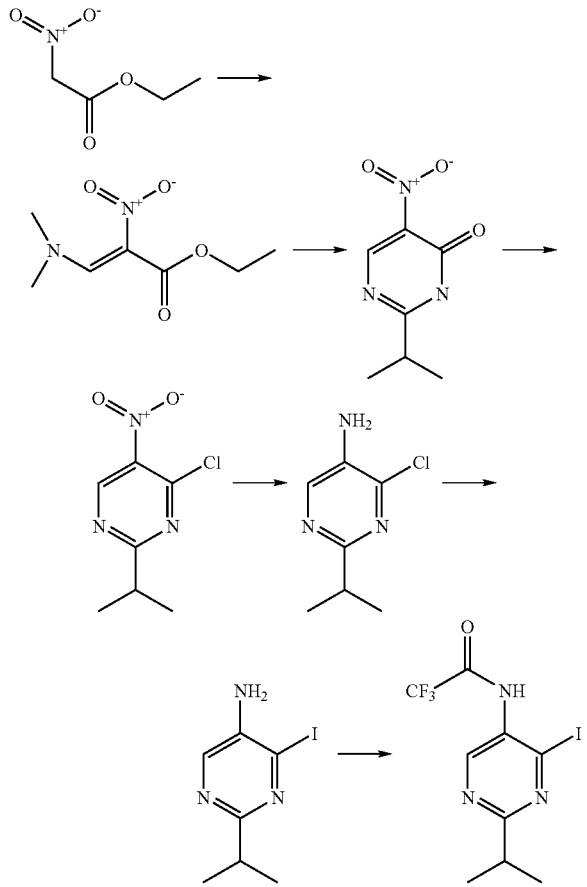

Ethylnitroacetate (11.7 mL, 105 mmol) was added slowly to a stirred solution of dimethyl formamide dimethyl acetal (29.2 mL, 220 mmol). The resulting reddish mixture was kept at room temperature for 2 hours, heated in an oil bath at 100° C. for 90 minutes, and cooled to room temperature. The mixture was concentrated in vacuo to remove volatile organics and the resulting residue was heated at 60° C. for 1 hour. A reddish orange liquid was obtained (18 g, ~100% yield), which was used in the next step without purification.

To a stirred solution of 3-dimethylamino-2-nitroacrylic acid ethyl ester (3.8 g, 20 mmol) in 50 mL of anhydrous ethanol was added isopropyl amidine hydrochloride (3.1 g, 25 mmol) followed by triethylamine (2.5 mL, 25 mmol). The resulting mixture was heated at 90° C. for 6 hours. After cooling to room temperature, the mixture was concentrated in vacuo and the crude was purified on $SiO_2$ (3% methanol in dichloromethane) to give 3.1 g of a brownish oil (84% yield).

A suspension of 2-isopropyl-5-nitro-3H-pyrimidin-4-one (1.55 g, 8.5 mmol) and triethylamine (1.4 mL, 10 mmol) in 10 mL of dichloromethane was cooled in an ice bath. A solution of phosphorus oxychloride (1.9 mL, 20 mmol) in 5 mL of dichloromethane was added slowly over a period of 5 minutes, and the resulting mixture was stirred for 90 minutes. The resulting mixture was diluted with dichloromethane, quenched with ice, sequentially washed with a saturated sodium bicarbonate solution and water, dried over sodium sulfate, filtered, and concentrated in vacuo to give 0.7 g of brownish oil (41% yield), which was used without further purification.

A stirred solution of 4-chloro-2-isopropyl-5-nitropyrimidine (0.7 g, 3.5 mmol) in 10 mL of absolute alcohol and 5 mL of glacial acetic acid was treated with iron powder and the mixture was heated at 90° C. for 20 minutes. After cooling to room temperature, the reaction mixture was diluted with 200 mL of dichloromethane, sequentially washed with a saturated sodium bicarbonate solution and water, dried over sodium sulfate, filtered, and concentrated in vacuo to give 450 mg of light brownish oil, which was used without further purification (75% yield).

A stirred mixture of 4-chloro-2-isopropylpyrimidin-5-ylamine (450 mg, 2.6 mmol) in 10 mL of a solution of HI (40% aqueous) was treated with NaI (1.97 g, 13.1 mmol). The resulting mixture was stirred at room temperature for 2 hours and poured onto dichloromethane. The phases were separated. The organic layer was washed with aqueous sodium carbonate solution, aqueous sodium bisulfite solution, and water, dried over sodium sulfate, filtered, and concentrated in vacuo to give 600 mg of brownish oil, which was used without further purification (87% yield).

A stirred solution of 4-iodo-2-isopropylpyrimidin-5-ylamine (600 mg, 2.28 mmol) in 4 mL of anhydrous dichloromethane was treated with a solution of trifluoroacetic anhydride (0.43 mL, 3 mmol) in 2 mL of dichloromethane at room temperature. After 15 minutes, the mixture was concentrated in vacuo to give 0.8 g of brownish oil which solidified upon standing and was used without purification (quantitative yield).

Example 18

Synthesis of 4-Bromo-6-phenylpyridazin-3-ylamine

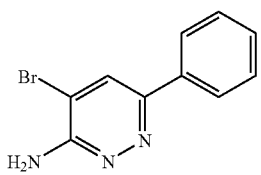 [SMILES: Nc1nnc(-c2ccccc2)cc1Br]

4-Bromo-6-phenylpyridazin-3-ylamine was prepared according to the procedure described in M. Bourotte, N. Pellegrini, M. Schmitt, and J.-J. Bourguignon, Syn. Lett., 2003, 10, pp. 1482-1484.

Example 19

Synthesis of (4-Iodo-6-trifluoromethylpyridin-3-yl)carbamic acid tert-butyl ester

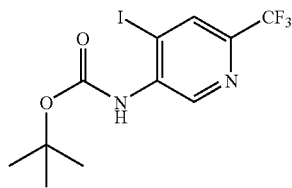 [SMILES: CC(C)(C)OC(=O)Nc1cnc(C(F)(F)F)cc1I]

A solution of 6-trifluoromethylnicotinic acid (1.0 g, 5.23 mmol), diphenylphosphorylazide (1.36 mL, 6.3 mmol), and triethylamine (1.83 mL, 13.1 mmol) in 15 mL of anhydrous tert-butanol was heated at reflux under nitrogen gas for 5 hours. The reaction was cooled to room temperature and concentrated in vacuo. 150 mL of water was added and the mixture was extracted with two 150 mL portions of ethyl acetate. The combined organic layers were washed with 150 mL of water, 150 mL of saturated aqueous sodium bicarbonate solution, dried over sodium sulfate, filtered, and concentrated in vacuo. The crude mixture was purified on SiO$_2$ (10% ethyl acetate in hexanes) to yield the title product (0.90 g, 66% yield).

A solution of (6-trifluoromethylpyridin-3-yl)carbamic acid tert-butyl ester (0.90 g, 3.43 mmol) and N,N,N',N'-tetramethylethylenediamine (1.29 mL, 8.55 mmol) in 25 mL of anhydrous diethyl ether was cooled to −78° C. under an argon atmosphere. The resulting mixture was treated dropwise with n-BuLi (2.5 M in hexanes, 3.42 mL, 8.55 mmol) over 5 minutes, and the mixture was allowed to warm to −10° C. After 30 minutes, the mixture was cooled to −78° C. and a solution of I$_2$ (1.14 g, 4.5 mmol) in 5 mL of anhydrous THF was added rapidly. The resulting mixture was warmed to room temperature, stirred for 1 hour, and quenched with 50 mL of water. The organic layer was dried over sodium sulfate, filtered, and concentrated in vacuo. The crude mixture was purified on SiO$_2$ (10% ethyl acetate in dichloromethane) to afford the title compound (150 mg, 11.3% yield).

Example 20

Synthesis of (4-Iodo-2,6-dimethoxypyridin-3-yl)carbamic acid tert-butyl ester

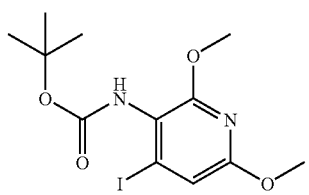 [SMILES: COc1cc(I)c(NC(=O)OC(C)(C)C)c(OC)n1]

The title product was prepared from 2,6-dimethoxynicotinic acid in the same manner as in the preparation of (4-iodo-6-trifluoromethylpyridin-3-yl)carbamic acid tert-butyl ester.

Example 21

Synthesis of (6-Chloro-4-iodopyridin-3-yl)carbamic acid tert-butyl ester

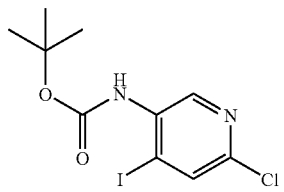 [SMILES: CC(C)(C)OC(=O)Nc1cnc(Cl)cc1I]

The title product was prepared from 6-chloronicotinic acid in the same manner as in the preparation of (4-iodo-6-trifluoromethylpyridin-3-yl)carbamic acid tert-butyl ester.

Example 22

Synthesis of (2,6-Dichloro-4-iodopyridin-3-yl)carbamic acid tert-butyl ester

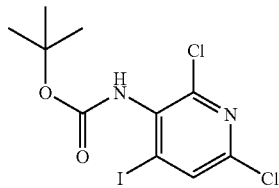 [SMILES: CC(C)(C)OC(=O)Nc1c(I)cc(Cl)nc1Cl]

The title product was prepared from 2,6-dichloronicotinic acid in the same manner as in the preparation of (4-iodo-6-trifluoromethylpyridin-3-yl)carbamic acid tert-butyl ester.

Example 23

Synthesis of (4-Iodo-5-methylpyridin-3-yl)carbamic acid tert-butyl ester

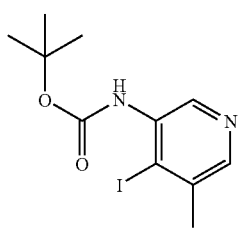 [SMILES: Cc1cncc(NC(=O)OC(C)(C)C)c1I]

The title product was prepared from 5-methylnicotinic acid in the same manner as in the preparation of (4-iodo-6-trifluoromethylpyridin-3-yl)carbamic acid tert-butyl ester.

Example 24

Synthesis of (2-Fluoro-4-iodopyridin-3-yl)carbamic acid tert-butyl ester

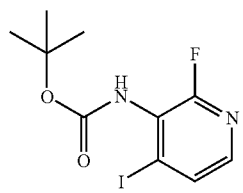 [SMILES: CC(C)(C)OC(=O)Nc1c(I)ccnc1F]

The title product was prepared from 2-fluoronicotinic acid in the same manner as in the preparation of (4-iodo-6-trifluoromethylpyridin-3-yl)carbamic acid tert-butyl ester.

Example 25

Synthesis of N-(4-Bromo-2-iodophenyl)benzenesulfonamide

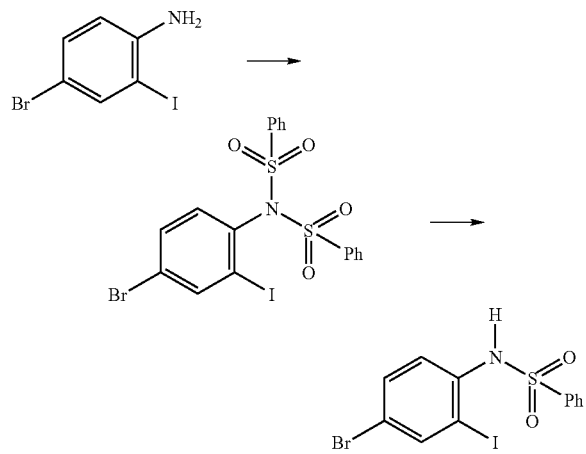

A solution of 4-bromo-2-iodoaniline (8.5 g, 28.5 mmol) in 200 mL of dichloromethane was sequentially treated with benzenesulfonyl chloride (15 mL, 117.5 mmol) and triethylamine (25 mL, 179.6 mmol). After 4 days, the mixture was diluted with 100 mL of saturated aqueous sodium bicarbonate solution and extracted with three 100 mL portions of ethyl acetate. The combined organic layers were washed with 50 mL of brine, three 60 mL portions of saturated aqueous ammonium chloride solution, dried over magnesium sulfate, filtered, and concentrated in vacuo. The crude product was triturated with diethyl ether to afford 5.74 g (35% yield) of N,N-bisbenzenesulfonyl-(4-bromo-2-iodoaniline).

A solution of tetrabutylammonium fluoride (1 M in THF, 11 mL) in 30 mL of THF was treated with N,N-bisbenzenesulfonyl-(4-bromo-2-iodoaniline) (5.78 g, 10 mmol) in several portions. After 18 hours, the mixture was diluted with of 40 mL of ethyl acetate and 40 mL of 1 N HCl. The phases were separated and the aqueous layer was extracted with two 40 mL portions of ethyl acetate. The combined organic layers were washed with two 20 mL portions of 1 N HCl, two 20 mL portions of saturated aqueous sodium bicarbonate solution, 20 mL of brine, dried over magnesium sulfate, filtered, and concentrated in vacuo to afford 3.95 g (90% yield) of the title compound as a solid, which was used without further purification.

Example 26

Synthesis of Trifluoromethanesulfonic acid 3-fluoro-2-nitrophenyl ester

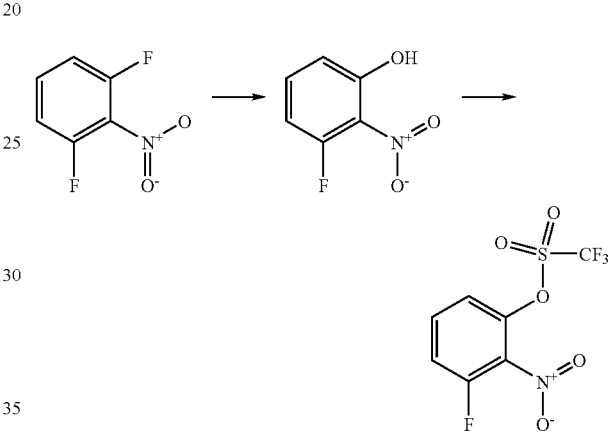

A solution of potassium tert-butoxide (1.23 g, 11 mmol) in 25 mL of anhydrous DMSO was stirred at room temperature for 30 minutes and treated with 1,3-difluoro-2-nitrobenzene (1.59 g, 10 mmol). After 18 hours, the mixture was diluted with 150 mL of 1 N aqueous sulfuric acid and extracted with three 50 mL portions of diethyl ether. The combined organic layers were washed with water, dried over sodium sulfate, filtered, and concentrated in vacuo. The residue was dissolved in 50 mL of trifluoroacetic acid. After 30 minutes at room temperature, the mixture was concentrated in vacuo, treated with 50 mL of 1 N aqueous sodium hydroxide, and extracted with three 30 mL portions of diethyl ether. The aqueous layer was acidified with 1 N aqueous sulfuric acid and extracted with two 50 mL portions of dichloromethane. The combined dichloromethane layers were washed with water, dried over sodium sulfate, filtered, and concentrated in vacuo to give 1.3 g of 3-fluoro-2-nitrophenol as orange oil (61% yield).

An solution of 3-fluoro-2-nitrophenol (1.13 g, 7.2 mmol) and pyridine (0.65 mL, 8 mmol) in 15 mL of anhydrous dichloromethane was cooled in an ice bath and treated with a solution of triflic anhydride (1.33 mL, 7.9 mmol) in 3 mL of anhydrous dichloromethane. After 4 hours, the reaction mixture was diluted with 100 mL of dichloromethane, washed with two 30 mL portions of saturated aqueous sodium bicarbonate, two 30 mL portions of 1 N aqueous sulfuric acid, and two 30 mL portions of water, dried over sodium sulfate, filtered, and concentrated in vacuo to give 2 g of the title product as a light brown oil (96% yield).

Example 27

Synthesis of Trifluoromethanesulfonic acid 4-cyano-2-methyl-6-nitrophenyl ester

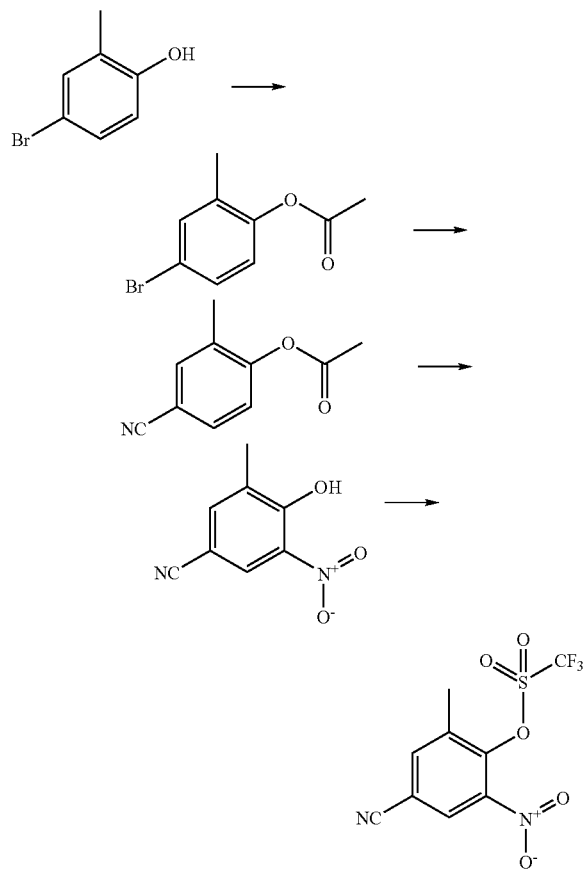

An ice-cold solution of 4-bromo-2-methylphenol (5.6 g, 30 mmol) and pyridine (6.1 mL, 75 mmol) in 50 mL of anhydrous dichloromethane was treated with a solution of acetyl chloride (2.8 mL, 26 mmol) in 5 mL of anhydrous dichloromethane. After 2 hours, the reaction mixture was concentrated in vacuo. The resulting residue was treated with crushed ice, diluted with 150 mL of dichloromethane, washed with water, dried over sodium sulfate, filtered, and concentrated in vacuo to give 6.9 g of 4-bromo-2-methylphenyl acetate as a light brown oil (quantitative yield).

A solution of 4-bromo-2-methylphenyl acetate (6.9 g, 30 mol) in 75 mL of anhydrous dimethyl acetamide was treated with zinc cyanide (3 g, 25.6 mmol) and tetrakis(triphenylphosphine)palladium(0) (4.5 g, 3.9 mmol). The reaction mixture was heated at 100° C. for 2 hours, cooled to room temperature, and treated with 300 mL of cold water. The resulting precipitate was filtered, washed with water, and air dried. Chromatography on $SiO_2$ (100% dichloromethane) afforded 5.2 g of 4-cyano-2-methylphenyl acetate as a colorless oil (99% yield), which solidified on standing.

A stirred solution of 4-cyano-2-methylphenyl acetate (5.2 g, 29.7 mmol) in 75 mL of methanol was treated with a solution of potassium carbonate (30 mmol, 4.15 g) in 25 mL of water at room temperature. After 30 minutes, the mixture was concentrated in vacuo and treated with 1 N sulfuric acid. The resulting precipitate was filtered, washed with water, and dried to give 3.1 g of 4-hydroxy-3-methylbenzonitrile as a white solid (78% yield).

A stirred solution of 4-hydroxy-3-methylbenzonitrile (3.1 g, 23.3 mmol) in 60 mL of anhydrous acetonitrile was cooled to −30° C. and treated with nitronium tetrafluoroborate (3.4 g, 25.6 mmol) in portions. After 60 minutes, the reaction mixture was diluted with 100 mL of water. The resulting light yellow precipitate was filtered, washed with water, and dried to give 3.9 g of 4-hydroxy-3-methyl-5-nitrobenzonitrile (94% yield).

4-Hydroxy-3-methyl-5-nitrobenzonitrile was converted to the title product according to the procedure described for the preparation of trifluoromethanesulfonic acid 3-fluoro-2-nitrophenyl ester.

Example 28

Synthesis of 3-Fluoro-6-methyl-2-nitrophenol

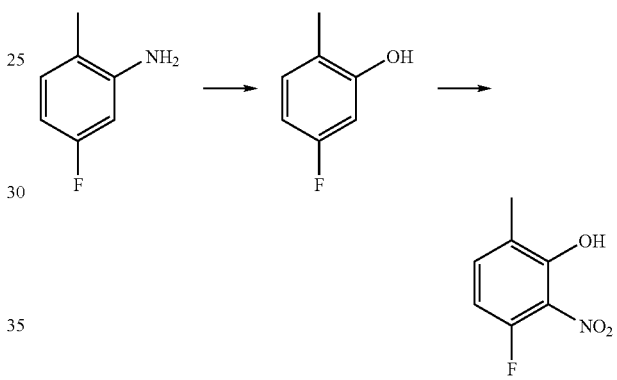

7 mL of a hot solution of concentrated sulfuric acid in 21 mL of water was added to 5-fluoro-2-methylphenylamine (5 g, 40 mmol). The mixture was cooled in an ice bath for 30 minutes and treated with a solution of sodium nitrite (3.38 g, 48 mmol) in 10 mL of water over a period of 10 minutes. After stirring at 0° C. for 45 minutes, the reaction was diluted with 20 mL of cold water and treated with 0.3 g of urea. The resulting mixture was added to a stirred solution of 11 mL of concentrated sulfuric acid in 10 mL of water containing 15 g of anhydrous sodium sulfate at 130° C. over 10 minutes. After an additional 5 minutes at 130° C., the reaction was allowed to cool to room temperature and was extracted with three 100 mL portions of dichloromethane. The combined organic layers were washed with two 50 mL portions of water and concentrated in vacuo. The reddish oil was dissolved in 250 mL of diethyl ether and washed with three 50 mL portions of 10% aqueous sodium hydroxide. The combined aqueous sodium hydroxide extracts were washed with two 50 mL portions of diethyl ether. The basic layer was acidified with 1 N aqueous HCl and extracted with three 100 mL portions of dichloromethane. The combined dichloromethane layers were washed with two 50 mL portions of brine, dried over sodium sulfate, filtered, and concentrated in vacuo to give a light reddish liquid. The crude was purified by chromatography on $SiO_2$ (10% ethyl acetate in hexanes) to give 5 g of 5-fluoro-2-methylphenol as a light brownish oil (99% yield).

A stirred solution of 5-fluoro-2-methylphenol (640 mg, 5 mmol) in 20 mL of anhydrous acetonitrile was cooled to −30° C. to −40° C. and treated with nitronium tetrafluoroborate (740 mg, 5.5 mmol). After 45 minutes, the reaction mixture was diluted with 100 mL of cold water and extracted with three 50 mL portions of dichloromethane. The combined organic layers were washed with three 25 mL portions of water, dried over sodium sulfate, and concentrated in vacuo to give a reddish crystalline solid. Chromatography over SiO$_2$ (5% ethyl acetate in hexanes) gave 0.58 g of the title product as bright yellow solid (68% yield).

The title compound was converted to the corresponding trifluoromethane sulfonate according to the procedure described in Example 26.

Example 29

Synthesis of 4-Amino-3-fluoro-5-iodobenzonitrile

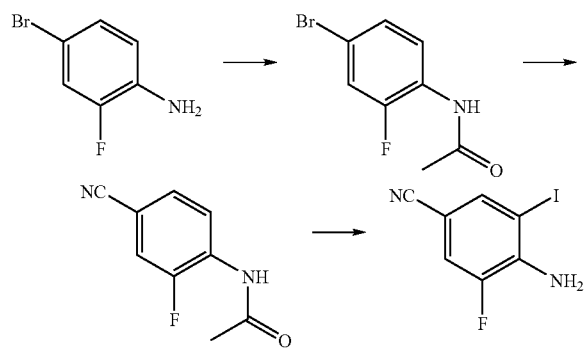

A solution of 4-bromo-2-fluorophenylamine (10.9 g, 57.4 mmol) and pyridine (9.4 mL, 115 mmol) in 50 mL of anhydrous dichloromethane was treated with acetyl chloride (3.33 mL, 63.1 mmol) at 0° C. After 10 minutes at 0° C. and 10 minutes at room temperature, the mixture was concentrated in vacuo and the residue was treated with 300 mL of 1 N aqueous sulfuric acid. The organic layer was concentrated in vacuo to give 12.9 g of N-(4-bromo-2-fluorophenyl)acetamide as a light greyish solid (97% yield).

A solution of N-(4-bromo-2-fluorophenyl)acetamide (12.9 g, 55.4 mmol) in 125 mL of anhydrous dimethyl acetamide was heated in the presence of zinc cyanide (5.53 g, 47.1 mmol) and tetrakis(triphenylphosphine)palladium (0) (5.2 g, 4.5 mmol) at 100° C. for 3 hours. The mixture was diluted with 300 mL of cold water, the resulting solid was filtered, washed with water, and dried. The filtrate was extracted with three 100 mL portions of ethyl acetate and the combined extracts were dried over sodium sulfate, filtered, and concentrated in vacuo. The resulting residue was combined with the solid from the filtration. This combined material was filtered through a silica gel column (100% dichloromethane followed by 100% ethyl acetate) to give 8.5 g of N-(4-cyano-2-fluorophenyl)acetamide as a light cream solid (86% yield).

A solution of sodium perborate (4.2 g, 27.3 mmols) and sodium tungstate (450 mg, 1.4 mmol) in a mixture of 20 mL of glacial acetic acid and 15 mL of acetic anhydride was treated with a solution of potassium iodide (2.3 g, 13.9 mmols) in 15 mL of water. The mixture was treated with 7.5 mL of concentrated sulfuric acid over 15 minutes. A suspension of N-(4-cyano-2-fluorophenyl)acetamide (1.79 g, 10 mmols) in 15 mL of glacial acetic acid was added to and the resulting mixture was heated at 50° C. After 1 hour, the mixture was poured into 300 mL of crushed ice and treated with 100 mL of a saturated solution of sodium thiosulfate followed by 100 mL of a sodium bisulfite solution. The mixture was extracted with three 100 mL portions of dichloromethane and the combined organic layers were washed with three 50 mL portions of sodium bicarbonate solution, three 50 mL portions of water, dried over sodium sulfate, and concentrated in vacuo to give a light brownish solid. Chromatography on SiO$_2$ (50% ethyl acetate in hexanes) afforded 400 mg of the title product as a light brownish solid (15% yield).

Example 30

Synthesis of 2-Fluoro-6-iodo-4-methylphenylamine

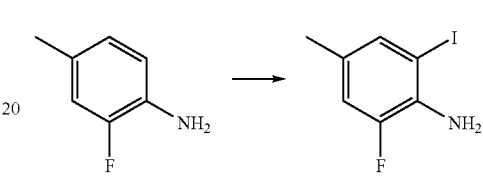

A solution of 2-fluoro-4-methylphenylamine (1.25 g, 10 mmol) in 5 mL of methanol was treated with a solution of iodine (1.27 g, 5 mmol) in a mixture of 25 mL of methanol and 3 mL of hydrogen peroxide over a period of 15 minutes at room temperature. After 18 hours, the reaction mixture was quenched with 30 mL of saturated aqueous sodium thiosulfate and extracted with three 50 mL portions of dichloromethane. The combined organic layers were washed with two 30 mL portions of saturated sodium bisulfite solution, three 50 mL portions of water, dried over sodium sulfate, and concentrated in vacuo. Chromatography on SiO$_2$ (10% ethyl acetate in hexanes) gave 1.1 g of the title product as a light brownish oil (44% yield).

Example 31

Synthesis of 2-Iodo-4-trifluoromethylphenylamine

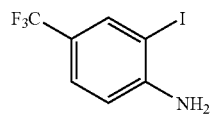

The title compound was prepared in the same manner as indicated for the synthesis of 2-fluoro-6-iodo-4-methylphenylamine.

Example 32

Synthesis of 2-Iodo-4-nitrophenylamine

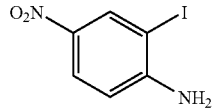 [SMILES: Nc1ccc([N+](=O)[O-])cc1I]

The title compound was prepared in the same manner as indicated for the synthesis of 2-fluoro-6-iodo-4-methylphenylamine.

Example 33

Synthesis of N-(4-Amino-3-iodophenyl)acetamide

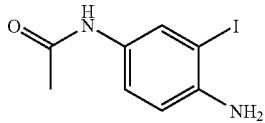

The title compound was prepared in the same manner as indicated for the synthesis of 2-fluoro-6-iodo-4-methylphenylamine.

Example 34

Synthesis of 2-Ethyl-6-nitrophenol

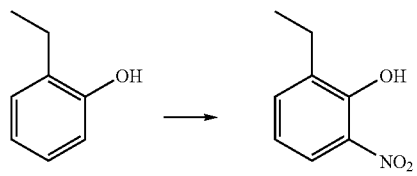

A solution of 2-ethylphenol (2.44 g, 20 mmol) in 80 mL of anhydrous acetonitrile was treated with nitronium tetrafluoroborate (2.93 g, 22 mmols) in portions over a period of 5 minutes at −30° C. to −40° C. After 20 minutes, the mixture was quenched with ice, treated with cold water and extracted with three 100 mL portions of dichloromethane. The combined organic layers were washed with two 30 mL portions of water, dried over sodium sulfate, filtered, and concentrated in vacuo. Chromatography on SiO$_2$ (20% ethyl acetate in hexanes) gave 2.0 g of 2-ethyl-6-nitrophenol as a yellow oil (60% yield).

The title compound was converted to the corresponding trifluoromethane sulfonate according to the procedure described in Example 26.

Example 35

Synthesis of 2-Methyl-6-nitrophenol

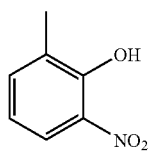

The title compound was prepared in the same manner as indicated for the synthesis of 2-ethyl-6-nitrophenol and was converted to the corresponding trifluoromethane sulfonate according to the procedure described in Example 26.

Example 36

Synthesis of 4-Iodo-3-(2,2,2-trifluoroacetylamino)benzoic acid methyl ester

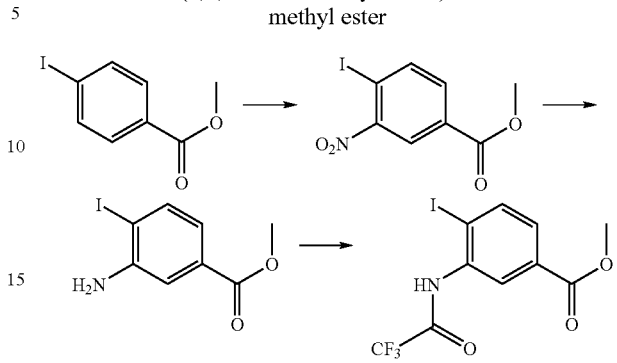

A solution of 4-iodobenzoic acid methyl ester (5.24 g, 20.0 mmol) in sulfuric acid was treated with 1.43 mL of concentrated nitric acid in a dropwise fashion at 0° C. After 5 hours at room temperature, the reaction mixture was heated to 40° C. for 1 hour. The resulting orange solution was added to 100 g of ice, treated with 200 mL of ethyl acetate, shaken for 30 minutes, and filtered. The phases were separated and the aqueous layer was extracted with 200 mL of ethyl acetate. The combined organic layers were washed with saturated sodium bicarbonate solution and brine, dried over magnesium sulfate, filtered, and concentrated in vacuo. The residue was passed through a column of silica gel (100% ethyl acetate) to give 2.0 g of 4-iodo-3-nitrobenzoic acid methyl ester as a yellow solid (33% yield).

A solution of 4-iodo-3-nitrobenzoic acid methyl ester (2.0 g, 6.50 mmol) in 25 mL of absolute alcohol and 15 mL of glacial acetic acid was treated with iron powder (3.6 g, 65.0 mmol) and the mixture was heated at 80° C. After 1 hour, the reaction mixture was filtered through a pad of silica, washed with ethanol, and concentrated in vacuo. The residue was diluted with a solution of potassium carbonate and extracted with ethyl acetate. The combined organic layers were washed with brine, dried over sodium sulfate, filtered, and concentrated in vacuo to give 1.6 g of 3-amino-4-iodobenzoic acid methyl ester as a white solid (88% yield).

A solution of 3-amino-4-iodobenzoic acid methyl ester (1.59 g, 5.74 mmols) in 40 mL of dichloromethane was reacted with trifluoroacetic anhydride (3 mL, 21 mmol) at room temperature. After 30 minutes, the reaction mixture was concentrated in vacuo and the residue was taken up in cold water, filtered, and dried to give 2.1 g of the title product as an off-white solid (quantitative yield).

Example 37

Synthesis of 2-Methyl-5-phenyl-1H-pyrrolo[2,3-c]pyridine

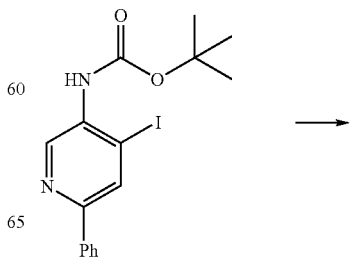

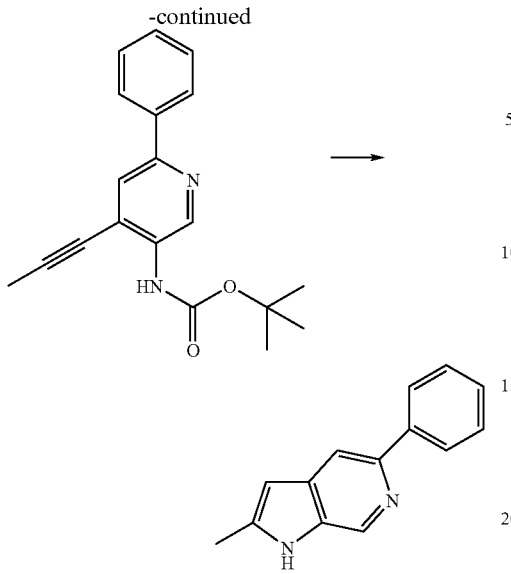

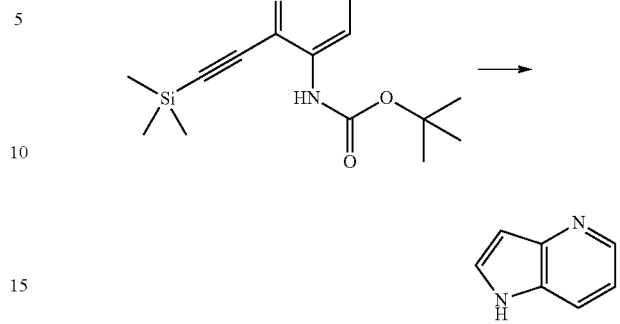

Propyne (0.60 mL, 11.4 mmol) was condensed in a pressure tube at −78° C. A solution of (4-iodo-6-phenylpyridin-3-yl)carbamic acid tert-butyl ester (900 mg, 2.27 mmol) in 2 mL of DMF, 6 mL of triethylamine, dichlorobis(triphenylphosphine)palladium (II) (80.2 mg, 0.114 mmol), and CuI (43.0 mg, 0.227 mmol) were added, the tube was sealed, and the mixture was stirred at room temperature overnight. The mixture was cooled to −78° C., the sealed tube was opened, and 20 mL of ethyl acetate and 10 mL of saturated aqueous ammonium chloride solution were added. The phases were separated and the aqueous layer was extracted with three 10 mL portions of ethyl acetate. The combined organic layers were dried over magnesium sulfate, filtered, and concentrated in vacuo. The crude product was purified on $SiO_2$ (0 to 40% ethyl acetate in hexanes, gradient) to give 670 mg of (6-phenyl-4-prop-1-ynylpyridin-3-yl)carbamic acid tert-butyl ester (96% yield).

A solution of (6-phenyl-4-prop-1-ynylpyridin-3-yl)carbamic acid tert-butyl ester (670 mg, 2.17 mmol) in a mixture of 33 mL of methanol and 11 mL of water was treated with DBU (2.0 mL, 13.4 mmol). The resulting mixture was heated at 60° C. After 24 hours, the mixture was concentrated in vacuo, 50 mL of water was added, the mixture was sonicated, and the resulting solid was filtered. The solid was dried over $P_2O_5$ in vacuum to give 450 mg of the title product as a yellow solid (99% yield), which was used without further purification.

Example 38

Synthesis of 1H-Pyrrolo[3,2-b]pyridine

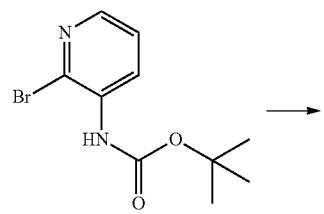

A mixture of (2-bromopyridin-3-yl)carbamic acid tert-butyl ester (1.09 mg, 4.00 mmol), (trimethylsilyl)acetylene (2.83 mL, 20.0 mmol), CuI (75.8 mg, 0.400 mmol), and dichlorobis(triphenylphosphine)palladium (II) (141 mg, 0.200 mmol) in a mixture of 12 mL of triethylamine and 3.0 mL of anhydrous DMF were stirred at room temperature overnight. The reaction was diluted with 50 mL of diethyl ether and quenched with 50 mL of saturated aqueous ammonium chloride solution. The organic layer was washed with 20 mL of saturated aqueous ammonium chloride solution and the combined aqueous layers were extracted with three 20 mL portions of diethyl ether. The combined organic layers were then washed with 20 mL of brine, dried over magnesium sulfate, filtered, and concentrated in vacuo. Chromatography on $SiO_2$ (20% to 30% ethyl acetate in hexanes, gradient) gave 500 mg of (2-trimethylsilanylethynylpyridin-3-yl)carbamic acid tert-butyl ester (43% yield).

A mixture of (2-trimethylsilanylethynylpyridin-3-yl)carbamic acid tert-butyl ester (500 mg, 1.72 mmol) in 5 mL of THF was treated with TBAF (1 M in THF, 10.3 mL) at room temperature. The mixture was heated at reflux for 8 hours, cooled to room temperature, diluted with 100 mL of diethyl ether, and quenched with 100 mL of water. The aqueous layer was extracted with three 50 mL portions of diethyl ether, and the combined organic layers were washed with 500 mL of brine, dried over magnesium sulfate, filtered, and concentrated in vacuo. Chromatography on $SiO_2$ (100% $CH_2Cl_2$ to 10% MeOH in $CH_2Cl_2$, gradient) gave 160 mg of the title product as tan solid (79% yield).

Example 39

Synthesis of 2-Methyl-1H-pyrrolo[2,3-c]pyridine

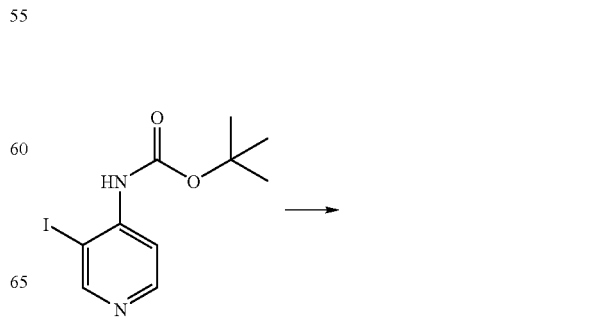

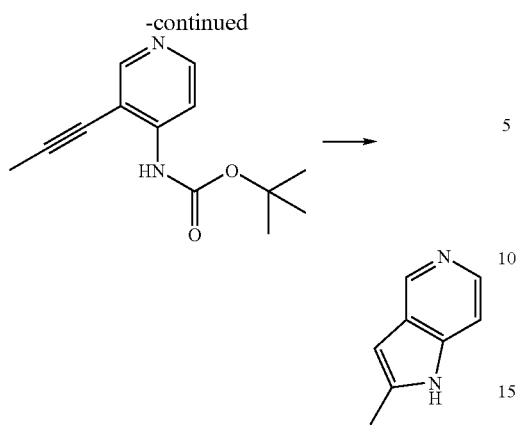

Propyne (6.3 mL, 124 mmol) was condensed in a pressure tube at −78° C. A solution of (3-iodopyridin-4-yl)carbamic acid tert-butyl ester (7.98 g, 24.9 mmol) in 15 mL of DMF, 60 mL of triethylamine, dichlorobis(triphenylphosphine)palladium (II) (877 mg, 1.25 mmol), and CuI (472 mg, 2.49 mmol) were added, and the tube was sealed and stirred at room temperature overnight. 200 mL of ethyl acetate and 100 mL of saturated aqueous ammonium chloride solution were added, the phases were separated and the aqueous layer was extracted with three 100 mL portions of ethyl acetate. The combined organic layers were dried over magnesium sulfate, filtered, and concentrated in vacuo. Chromatography on $SiO_2$ (25% to 40% ethyl acetate in hexanes, gradient) afforded 5.65 g of (3-prop-1-ynylpyridin-4-yl)carbamic acid tert-butyl ester (98% yield).

(3-Prop-1-ynylpyridin-4-yl)carbamic acid tert-butyl ester (5.65 g, 24.3 mmol) was treated with 30.4 mL of 4 M HCl in dioxane. The mixture was sonicated until the compound completely dissolved. After 15 hours, the mixture was concentrated in vacuo. The resulting brown solid (4.10 g) was dissolved in 65 mL of 1-methyl-2-pyrrolidinone (NMP) and treated with tert-BuOK (7.08 g, 63.2 mmol) at room temperature. After 18 hours, 300 mL of ethyl acetate and 300 mL of water were added. The phases were separated and the aqueous layer was extracted with five 100 mL portions of ethyl acetate. The combined organic layers were washed with two 20 mL portions of water, dried over magnesium sulfate, filtered, and concentrated in vacuo. Chromatography on $SiO_2$ (10% methanol in dichloromethane) yielded 2.85 g of the title product as yellow solid (89% yield).

Example 40

Synthesis of 2,3-Dimethyl-1H-pyrrolo[2,3-c]pyridine

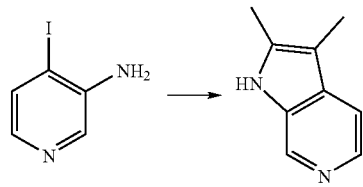

In a pressure tube, a solution of iodopyridine (1.80 g, 8.18 mmol) in 20 mL of DMF was treated with 2-butyne (1.5 mL, 19.1 mmol), $Pd(dppf)_2Cl_2 \cdot CH_2Cl_2$ (357 mg, 0.438 mmol), lithium chloride (367 mg, 8.71 mmol), and sodium carbonate (1.82 g, 17.2 mmol). The tube was sealed and heated to 90° C. After 24 hours, the tube was cooled and opened. The resulting mixture was diluted with 20 mL of ethyl acetate and 20 mL of saturated aqueous ammonium chloride solution. The phases were separated and the aqueous layer was extracted with three 50 mL portions of ethyl acetate. The combined organic layers were dried over magnesium sulfate, filtered, and concentrated in vacuo. Flash chromatography ($CH_2Cl_2$ to 10% MeOH in $CH_2Cl_2$, gradient) afforded the title product as a brown solid (920 mg, 77% yield).

Example 41

Synthesis of 2-Methyl-5-methylsulfanyl-1H-indole

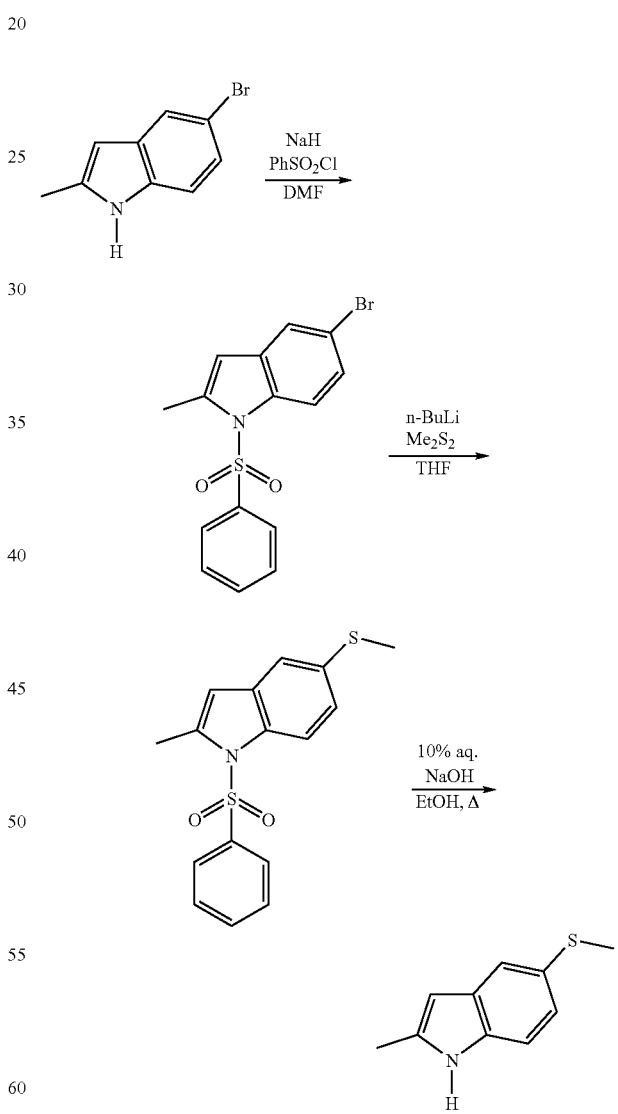

To a solution of 5-bromo-2-methyl-1H-indole (1.5 g, 7.14 mmol) in 10 mL of DMF was added 60% sodium hydride in mineral oil (189 mg, 7.9 mmol). Once hydrogen gas evolution ceased, the mixture stirred for 10 minutes and was then treated with 1 mL (7.83 mmol) of benzene sulfonyl chloride.

The reaction was monitored by TLC (ethyl acetate-hexanes (5:95)) to afford a major new slightly less polar product than starting material. After 2 hours, the mixture was poured into 50 mL of saturated aqueous ammonium chloride solution and extracted with three 50 mL portions of ethyl acetate. The combined organic layers were washed with four 25 mL portions of brine, dried over magnesium sulfate, treated with activated carbon (NORIT A™), filtered through diatomaceous earth, and concentrated in vacuo. The residue was adsorbed onto silica gel and chromatographed on silica gel using ethyl acetate-hexanes (1:99, then 2:98, then 3:97) to afford 1.71 g (68.4% yield) of 1-benzenesulfonyl-5-bromo-2-methyl-1H-indole as a clear oil.

To a chilled solution of 1-benzenesulfonyl-5-bromo-2-methyl-1H-indole (350 mg, 0.99 mmol) in 4 mL of THF was added 440 µL (1.10 mmol) of n-BuLi (2.5 M solution in hexanes), followed by dimethyl disulfide (100 µL, 1.11 mmol). The mixture was stirred as it warmed to room temperature and was then quenched with ammonium chloride and extracted with three 15 mL portions of ethyl acetate. The combined organic layers were washed with three 15 mL portions of brine, dried over magnesium sulfate, filtered, and concentrated in vacuo. The crude material was adsorbed onto silica gel and chromatographed on silica gel using ethyl acetate-hexanes (1:99, then 2:98) to afford 156 mg (44.3% yield) of 1-benzenesulfonyl-2-methyl-5-methylsulfanyl-1H-indole as a clear oil.

To a solution of 1-benzenesulfonyl-2-methyl-5-methylsulfanyl-1H-indole (156 mg, 0.49 mmol) in 10 mL of ethanol was added 10 mL of 10% aqueous sodium hydroxide solution. The mixture was warmed at reflux for 18 hours. The mixture was then diluted with 10 mL of brine and extracted with three 20 mL portions of ethyl acetate. The combined organic layers were washed with two 10 mL portions of 10% aqueous sodium hydroxide solution, two 20 mL portions of saturated aqueous ammonium chloride, two 20 mL portions of brine, dried over magnesium sulfate, filtered, and concentrated in vacuo. The crude product was adsorbed onto silica gel and chromatographed on silica gel using ethyl acetate-hexanes (1:99, then 2:98, then 3:97, then 5:96) to afford 62 mg (71.2% yield) of 2-methyl-5-methylsulfanyl-1H-indole.

Example 42

Synthesis of 1-Benzenesulfonyl-2-methyl-5-phenyl-1H-indole

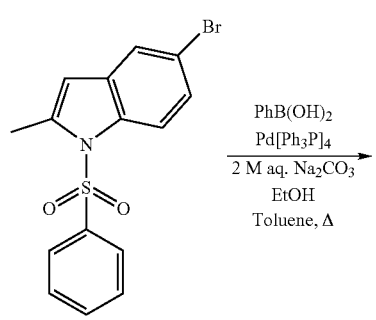

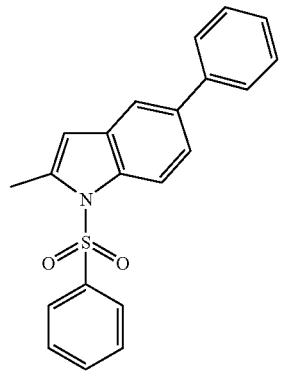

A mixture of 1-benzenesulfonyl-5-bromo-2-methyl-1H-indole (810 mg, 2.31 mmol), phenylboronic acid (850 mg, 6.97 mmol) and tetrakis(triphenylphosphine)palladium(0) (55 mg, 0.029 mmol) in 20 mL of toluene, 10 mL of ethanol, and 5 mL of 2 M sodium carbonate was warmed at reflux for 4 hours. The reaction was monitored by TLC (ethyl acetate-hexanes (5:95), 2× developed; and toluene-hexanes (1:1)) indicating a slightly more polar product. The mixture was cooled and diluted with 12% aqueous ammonium hydroxide solution and extracted with three 15 mL portions of ethyl acetate. The combined organic layers were washed with three 15 mL portions of brine, dried over magnesium sulfate, filtered, and concentrated in vacuo. The crude mixture was adsorbed onto silica gel and chromatographed on silica gel using ethyl acetate-hexanes (1:99, then 2:98, then 3:97) to afford 731 mg (91% yield) of 1-benzenesulfonyl-2-methyl-5-phenyl-1H-indole.

Removal of the phenyl sulfonyl group as described in Example 41 gave 2-methyl-5-phenyl-1H-indole.

Example 43

Synthesis of 1-Benzenesulfonyl-2-methyl-1H-indole-5-sulfonic acid dimethylamide

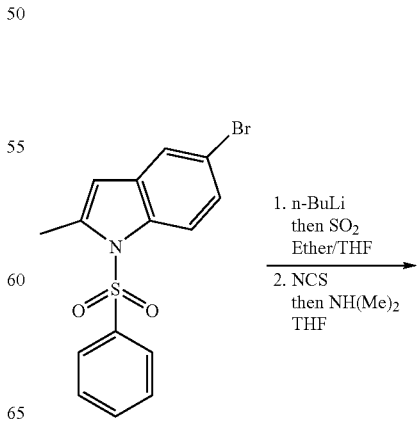

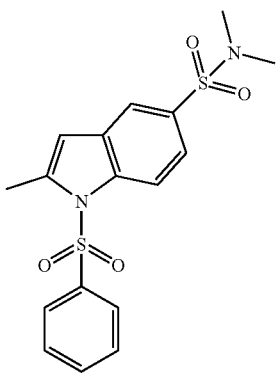

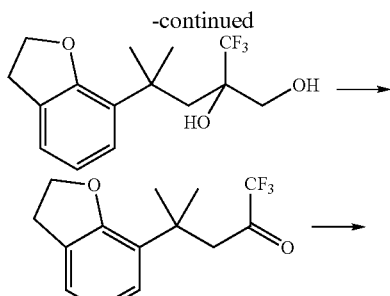

To a chilled (−78° C.) solution of 1-benzenesulfonyl-5-bromo-2-methyl-1H-indole (505 mg, 1.44 mmol) in 5 mL of diethyl ether and 2 mL of THF was added 650 µL (1.63 mmol) of n-BuLi (2.5 M solution in hexanes). The mixture was stirred of 10 minutes and then sulfur dioxide ($SO_2$) gas was bubbled through the solution, resulting in a precipitate. The mixture was warmed to room temperature and filtered to afford 468 mg of the lithium sulfonate. This material was dissolved in 10 mL of THF and then N-chlorosuccinimide (200 mg, 1.49 mmol) was added. The mixture was stirred for 15 minutes and then 4 mL (8 mmol) of a 2 M solution of dimethylamine in THF was added. The mixture was then stirred for 1 hour and was diluted with saturated aqueous ammonium chloride solution and extracted with three 10 mL portions of ethyl acetate. The combined organics were washed with three 10 mL portions of brine, dried over magnesium sulfate, filtered, and concentrated in vacuo to afford 365 mg of 1-benzenesulfonyl-2-methyl-1H-indole-5-sulfonic acid dimethylamide.

Removal of the phenylsulfonyl group as described in Example 41 gave 2-methyl-1H-indole-5-sulfonic acid dimethylamide.

Example 44

Synthesis of 4-(5-Chloro-2,3-dihydrobenzofuran-7-yl)-1,1,1-trifluoro-4-methylpentan-2-one

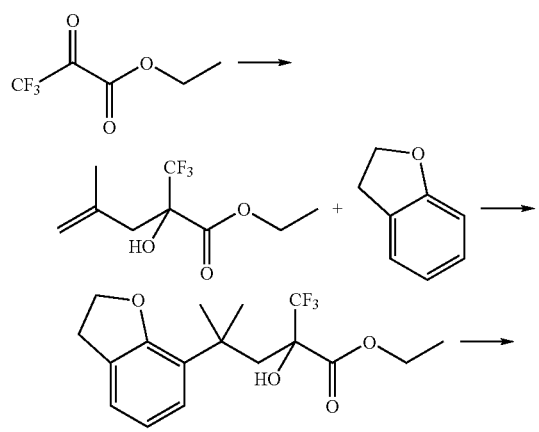

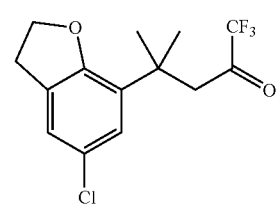

A solution of ethyl trifluoropyruvate (124.84 g, 0.734 mol) in 2.0 L of THF was treated with methylallyl magnesium chloride (0.5 M in THF, 1.90 L, 0.954 mol) over 4 hours while the internal temperature was maintained below −60° C. The reaction mixture was allowed to reach room temperature overnight, concentrated in vacuo to remove THF, quenched with 1 L of saturated ammonium chloride solution, and extracted with three 1 L portions of diethyl ether. The combined organic phases were washed with 100 mL of brine, dried over magnesium sulfate, filtered, and concentrated in vacuo. Vacuum distillation at 60 mmHg afforded 100.1 g of 2-hydroxy-4-methyl-2-trifluoromethylpent-4-enoic acid ethyl ester as a clear oil (b.p. 97° C.-103° C., 60% yield).

A solution of 2-hydroxy-4-methyl-2-trifluoromethylpent-4-enoic acid ethyl ester (100 g, 442 mmol) and 2,3-dihydrobenzofuran (57.7 g, 480 mmol) in 500 mL of dichloroethane was treated with $AlCl_3$ (87.8 g, 660 mmol) while maintaining the internal temperature below 10° C. The reaction was allowed to warm to room temperature overnight and quenched with 1 L of cold 1 N HCl. The mixture was then extracted with three 1 L portions of ethyl acetate. The combined organic layers were washed with 1 L of saturated aqueous sodium bicarbonate solution, 1 L of brine, dried over magnesium sulfate, filtered, and concentrated in vacuo. The residue was purified on $SiO_2$ (10% diethyl ether in hexanes). The resulting solid was recrystallized in hot hexanes to afford 39.5 g of 4-(2,3-dihydrobenzofuran-7-yl)-2-hydroxy-4-methyl-2-trifluoromethylpentanoic acid ethyl ester as a white solid (26% yield).

A suspension of LAH (4.52 g, 119 mmol) in 230 mL of THF was treated with a solution of 4-(2,3-dihydrobenzofuran-7-yl)-2-hydroxy-4-methyl-2-trifluoromethylpentanoic acid ethyl ester (27.5 g, 79.4 mmol) in 40 mL of THF at 0° C. over 30 minutes. After stirring overnight, the reaction was cooled to 0° C., quenched with 3 mL of water, and treated with 3 mL of 4 M sodium hydroxide solution. After 10 minutes, the mixture was treated with additional 18 mL portion of water and the resulting mixture was warmed to room temperature for 4 hours. The mixture was filtered and the filter cake was washed with five 100 mL portions of diethyl ether. The filtrate was concentrated in vacuo to give 24.0 g of 4-(2,3-dihydrobenzofuran-7-yl)-4-methyl-2-trifluoromethylpentane-1,2-diol as an oil (99% yield).

A solution of 4-(2,3-dihydrobenzofuran-7-yl)-4-methyl-2-trifluoromethylpentane-1,2-diol (24.0 g, 78.9 mmol) and $NaIO_4$ (84.3 g, 394 mmol) in 360 mL of methanol was stirred at room temperature overnight. The resulting mixture was filtered through pad of CELITE® filter aid and the filter cake was washed with three 100 mL portions of methanol. The filtrate was concentrated in vacuo, taken up in hexanes, filtered again, and concentrated in vacuo to give 21.4 g of 4-(2,3-dihydrobenzofuran-7-yl)-1,1,1-trifluoro-4-methylpentan-2-one as colorless oil (quantitative yield), which was used without purification.

A solution of 4-(2,3-dihydrobenzofuran-7-yl)-1,1,1-trifluoro-4-methylpentan-2-one (20.8 g, 76.2 mmol) in 200 mL of acetic acid was treated with a solution of chlorine gas ($Cl_2$) in acetic acid (prepared by bubbling chlorine gas into acetic acid, ~1.19 M). The reaction was monitored by $^1$H-NMR. The ratio of the starting material to product was determined based on the integration of $CH_2$ signal of the respective ketones (starting material: δ=3.32 ppm; product: δ=3.32 ppm). The concentration of the $Cl_2$ solution was recalculated based on the NMR ratios and an additional portion of $Cl_2$ solution was added (this process was repeated until NMR showed the complete consumption of the starting material). The mixture was quenched with 500 mL of water and solid sodium bicarbonate (~500 g) was added carefully during 1 hour. The mixture was poured onto 500 mL of ethyl acetate. The phases were separated and the aqueous layer was extracted with three 500 mL portions of ethyl acetate. The combined organic layers were washed with two 100 mL portions of brine, dried over magnesium sulfate, filtered, and concentrated in vacuo to afford 23.4 g of the title product (quantitative yield), which was used without purification.

Example 45

Synthesis of 4-(5-Chloro-2,3-dihydrobenzofuran-7-yl)-1,1-difluoro-4-methylpentan-2-one

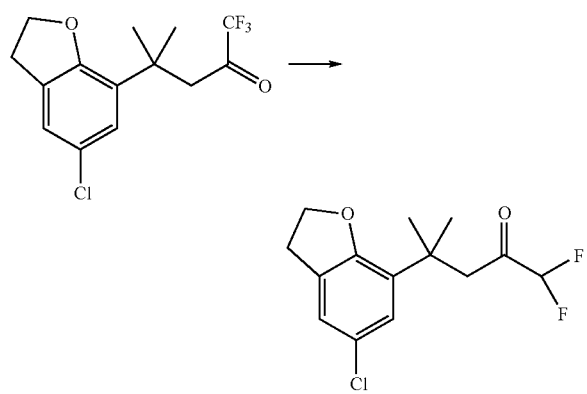

A mixture of magnesium turnings (204 mg, 8.40 mmol) and trimethylsilyl chloride (2.13 mL, 16.8 mmol) in 10 mL of DMF was treated with 4-(5-chloro-2,3-dihydrobenzofuran-7-yl)-1,1,1-trifluoro-4-methylpentan-2-one (1.23 g, 4.00 mmol) in 10 mL of DMF at 0° C. The resulting mixture was stirred at room temperature overnight. The mixture was filtered and concentrated in vacuo. The residue was suspended in 20 mL of THF and treated with TBAF (1 M in THF, 4.0 mL) at room temperature. After 15 minutes, the reaction was quenched with 25 mL of saturated aqueous ammonium chloride solution and diluted with 50 mL of diethyl ether. The phases were separated and the aqueous layer was extracted with three 50 mL portions of diethyl ether. The combined organic layers were washed with brine, dried over magnesium sulfate, filtered, and concentrated in vacuo. Chromatography on $SiO_2$ (100% hexanes to 10% diethyl ether in hexanes, gradient) afforded 550 mg of the title product (48% yield).

Example 46

Synthesis of 5-(5-Fluoro-2-methylphenyl)-2,5-dimethylhexan-3-one

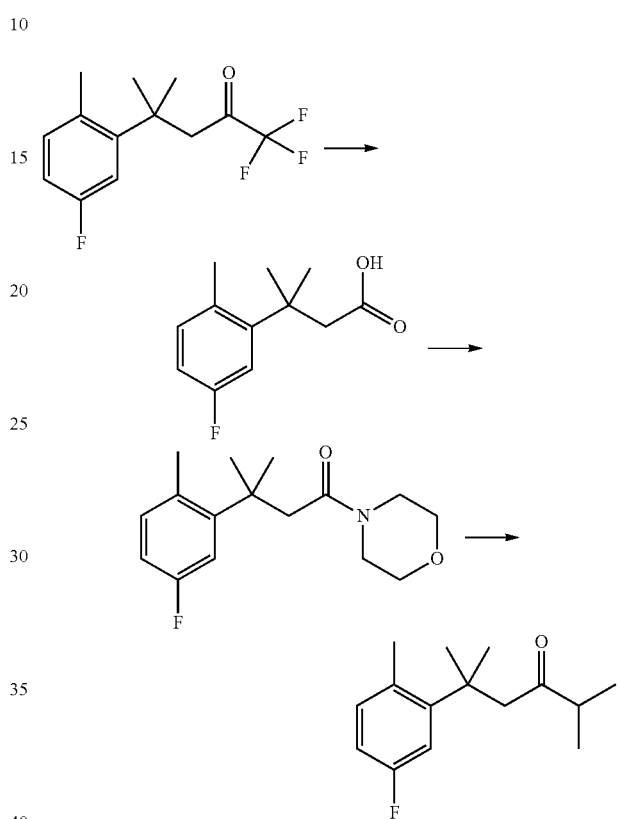

A solution of 1,1,1-trifluoro-4-(5-fluoro-2-methylphenyl)-4-methylpentan-2-one (4.88 g, 18.6 mmol) was treated with sodium hydroxide solution (4 M in a mixture of 30% water in ethanol, 40 mL) at room temperature. The mixture was heated to 80° C. for 1 hour. After cooling to room temperature, the mixture was diluted with 100 mL of water and extracted with three 100 mL portions of diethyl ether. The aqueous layer was treated with 150 mL of ethyl acetate and the resulting mixture was treated with 6 M HCl dropwise until the solution had a pH of 2. The phases were separated and the aqueous layer was extracted with three 100 mL portions of ethyl acetate. The combined organic layers were dried over magnesium sulfate, filtered, and concentrated in vacuo to yield 3.92 g of 3-(5-fluoro-2-methylphenyl)-3-methylbutyric acid as an oil, which solidified upon standing and was used without further purification (quantitative yield).

A mixture of 3-(5-fluoro-2-methylphenyl)-3-methylbutyric acid (3.80 g, 18.0 mmol) in 15 mL of dichloromethane was treated with $SOCl_2$ (1.98 mL, 27.1 mmol) at 0° C. After 30 minutes, a mixture of morpholine (2.36 mL, 27.1 mmol) and pyridine (4.4 mL, 54.2 mmol) in 10 mL of dichloromethane was added to the reaction mixture at 0° C. After an additional 90 minutes, 60 mL of 2 M aqueous HCl solution was added, phases were separated and the aqueous layer was extracted with three 50 mL portions of dichloromethane. The combined organic phases were dried over magnesium sulfate, filtered, and concentrated in vacuo to give 5.03 g of 3-(5-fluoro-2-methylphenyl)-3-methyl-1-morpholin-4-ylbutan-1-one as an oil, which was used without further purification (quantitative yield).

A solution of 3-(5-fluoro-2-methylphenyl)-3-methyl-1-morpholin-4-ylbutan-1-one (200 mg, 0.716 mmol) in 2 mL of THF was treated with i-PrLi (0.7 M in pentane, 1.28 mL) at −78° C. The reaction mixture was stirred at −78° C. for 1 hour, allowed to warm to room temperature, quenched with 1 mL of methanol and 5 mL of saturated aqueous ammonium chloride solution, and extracted with three 50 mL portions of ethyl acetate. The combined organic layers were dried over magnesium sulfate, filtered, and concentrated in vacuo. Chromatography on SiO$_2$ (100% hexanes to 25% ethyl acetate in hexanes, gradient) afforded 80.4 mg of the title product (48% yield).

Example 47

Synthesis of 4-(3-[1,3]Dioxan-2-ylphenyl)-1,1,1-trifluoro-4-methylpentan-2-one

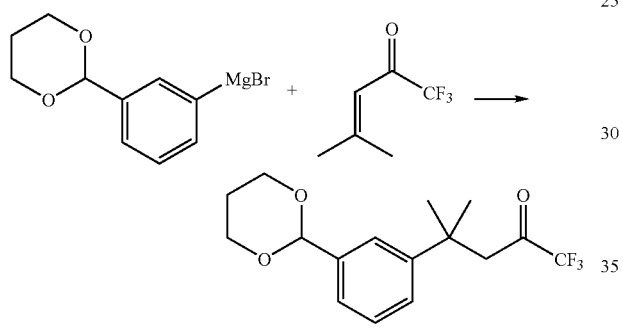

A solution of the Grignard reagent (generated from the reaction of 2-(3-bromophenyl)-[1,3]dioxane with magnesium turnings in THF, 0.25 M, 52.6 mL, 13.1 mmol) was treated with copper (I) iodide (2.5 g, 13.1 mmol) at 0° C. After 45 minutes, 1,1,1-trifluoro-4-methylpent-3-en-2-one (2 g, 13.1 mmol) was added, and the reaction mixture was slowly warmed to room temperature and stirred overnight. The mixture was quenched with aqueous saturated ammonium chloride solution and extracted with ethyl acetate. The combined organic layers were washed with aqueous saturated sodium chloride solution, dried with sodium sulfate, filtered, and concentrated in vacuo. The residue was triturated with hexanes and filtered. The filtrate was concentrated in vacuo to give 1.78 g of the crude product, which was used without purification.

Example 48

Synthesis of (1-Fluorovinyl)dimethylphenylsilane

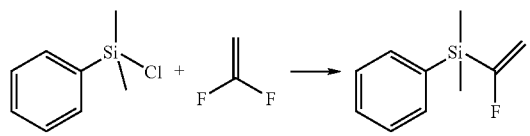

To a suspension of 4.4 g of lithium wire cut into small pieces in 200 mL of anhydrous THF stirred under argon and cooled on ice (internal temperature <10° C.) was added dimethylphenyl-chlorosilane in 5 mL portions over 1 hour. The deep red color of the silyl lithium reagent appeared after approximately 0.75 hour. The mixture was stirred on ice for an additional 5 hours (internal temperature remained between 5° C. and 10° C.). The mixture was cooled on a dry ice/acetone bath and 1,1-difluoroethylene was introduced by filling a balloon connected to the reaction mixture and the reagent cylinder using a three-way valve. The balloon was filled with 1,1-difluoroethylene and emptied into the reaction mixture 10 times. The mixture was allowed to warm to room temperature (effervescence observed, probably from unreacted 1,1-difluoroethylene). The mixture was diluted with 200 mL of hexanes and filtered through a cotton wool plug. The filtrate was washed with water, dried, filtered, and concentrated in vacuo. Four fractional distillations under vacuum through a Vigreux column gave 4.6 g of product.

Example 49

Synthesis of 1-(1-Fluorocyclopropyl)-3-(4-fluorophenyl)-3-methylbutan-1-one

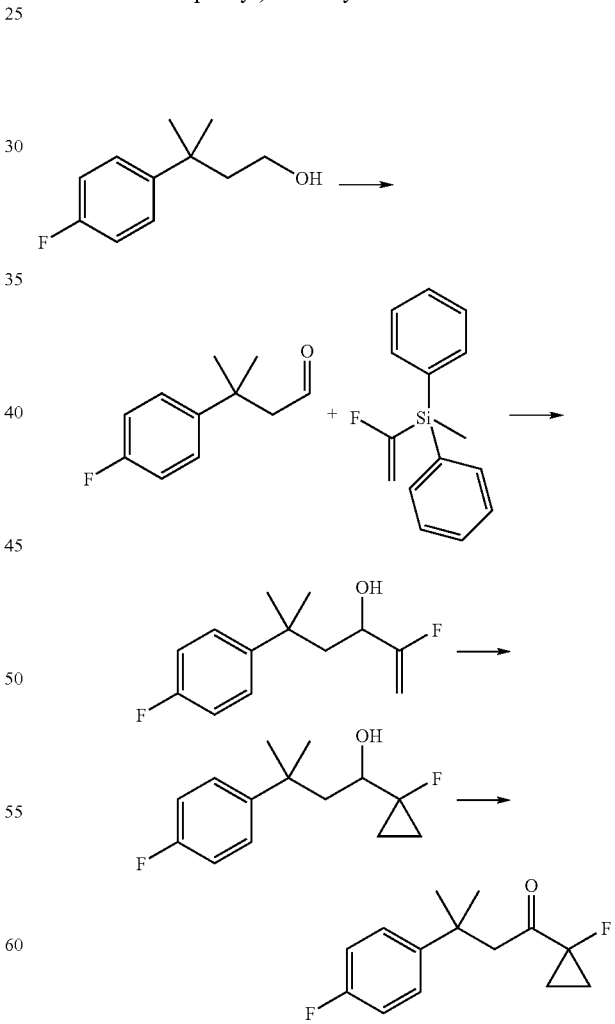

12 mL of a 2 M solution of oxalyl chloride in dichloromethane was diluted with 19 mL of dichloromethane and cooled on a dry ice/acetone bath. To this solution was added a dropwise a solution of 3.6 mL of DMSO in 16 mL of dichloromethane. After 10 minutes, a solution of 3-(4-fluorophenyl)-3-methylbutan-1-ol (3.6 g, 19.8 mmol) in 12 mL of dichloromethane was added and the mixture was stirred for 15 minutes. 14 mL of triethylamine was then added, the cooling bath was removed, and the reaction mixture was allowed to warm to room temperature and was quenched with water and diluted with hexanes. The organic layer was separated, washed with water, dried, filtered, and concentrated in vacuo. The residue was purified by chromatography over silica gel (eluent: hexanes to hexanes-dichloromethane (9:1), gradient) to give 1.2 g of 3-(4-fluorophenyl)-3-methylbutyraldehyde as an oil.

To a mixture of 3-(4-fluorophenyl)-3-methylbutyraldehyde (1.2 g, 6.6 mmol) and (1-fluorovinyl)methyldiphenylsilane in 5 mL of THF cooled on ice under nitrogen gas was added 1 mL of TBAF (1 M in THF). The mixture was allowed to warm to room temperature and left overnight. The solvent was evaporated and the residue was taken up in hexanes. The hexane soluble material was fractionated over silica gel (eluent: hexanes to hexanes-ethyl acetate (98:2)) to give a fraction (3.1 g) containing silylated product along with other silanes. This fraction was dissolved in 5 mL of THF and 10 mL of TBAF solution (1 M in THF) was added. The mixture was left at room temperature for 20 minutes, diluted with hexanes-ethyl acetate, and washed with water, dried, filtered, and concentrated in vacuo. Fractionation of the residue over silica gel (eluent: hexanes-ethyl acetate (99:1 to 9:1 gradient)) gave 1.73 g of the crude 2-fluoro-5-(4-fluorophenyl)-5-methyl-hex-1-en-3-ol as an oil which was used without additional purification.

To the above crude 2-fluoro-5-(4-fluorophenyl)-5-methyl-hex-1-en-3-ol (1.73 g, 7.65 mmol) stirred under nitrogen gas and cooled on ice, was added diethyl zinc (1.1 M in toluene, 8.0 mL). After 5 minutes, 1.0 mL of diiodomethane was added dropwise over 20 minutes and the mixture was stirred and allowed to come to room temperature and then stirred at room temperature for 4 days. 0.5 mL of water was then added to the reaction mixture, followed by ethyl acetate. The resulting mixture was then filtered through diatomaceous earth and the solvent was removed in vacuo and the residue was fractionated over silica gel (hexanes-dichloromethane (1:1) to dichloromethane gradient) to give 1-(1-fluorocyclopropyl)-3-(4-fluorophenyl)-3-methylbutan-1-ol as an oil.

2.2 mL of a 2 M solution of oxalyl chloride in dichloromethane was diluted with 2.5 mL of dichloromethane and cooled on dry ice/acetone bath. To this solution was added a dropwise a solution of 0.7 mL of DMSO in 2.5 mL of dichloromethane. After 10 minutes, a solution of the above crude 1-(1-fluorocyclopropyl)-3-(4-fluorophenyl)-3-methylbutan-1-ol (0.72 g, 3.0 mmol) in 2 mL of dichloromethane was added and the mixture was stirred for 15 minutes. 4 mL of triethylamine was added, the cooling bath was removed, the mixture was allowed to warm to room temperature and was then quenched with water and diluted with hexanes. The organic layer was separated, washed with water, dried, filtered, and concentrated in vacuo. The residue was purified by chromatography over silica gel (eluent: hexanes to hexanes-dichloromethane (4:1) gradient) to give 0.37 g of the title product as an oil.

Example 50

Synthesis of 1-(1-Fluorocyclopropyl)-3-(5-fluoro-2-methoxyphenyl)-3-methylbutan-1-one

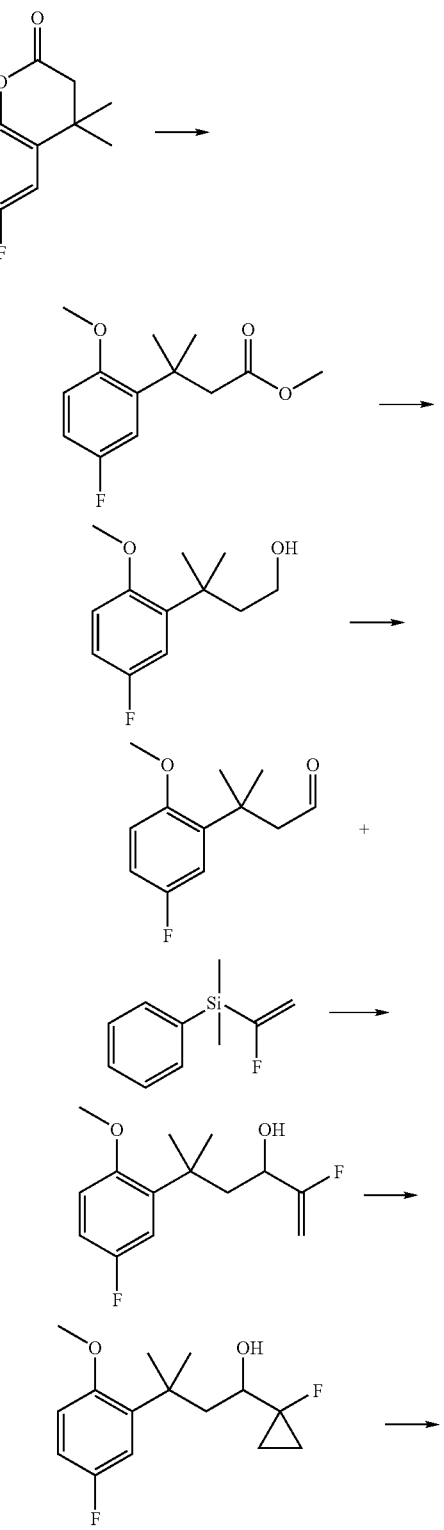

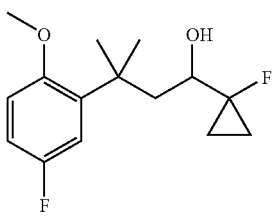

To a solution of 6-fluoro-4,4-dimethylchroman-2-one in 40 mL of DMSO was added a solution of 5.5 g of sodium hydroxide in 5 mL of water over 5 minutes (an exothermic reaction). After 20 minutes, methyl iodide (20 g) was added portionwise over 15 minutes and the mixture was stirred at room temperature overnight. The mixture was diluted with hexanes, washed with water, dried, filtered, and concentrated in vacuo to give 12.4 g of the ester which was used without additional purification.

To a suspension of LAH (1.64 g) in 100 mL of THF stirred under argon was added dropwise over 30 minutes a solution of the above 3-(5-fluoro-2-methoxyphenyl)-3-methylbutyric acid methyl ester in 10 mL of THF (vigorous reaction). The mixture was stirred at room temperature overnight. The reaction was diluted with 200 mL of diethyl ether and quenched by the addition of 3 mL of water (added cautiously) and 3 mL of acetic acid. The mixture was filtered through diatomaceous earth and washed through with diethyl ether. Evaporation of the solvent gave 10.8 g of 3-(5-fluoro-2-methoxyphenyl)-3-methylbutan-1-ol, which was used without additional purification.

A solution of 3-(5-fluoro-2-methoxyphenyl)-3-methylbutan-1-ol (3.30 g, 15.5 mmol) in 40 mL of dichloromethane was treated with pyridinium chlorochromate (4.2 g, 19.5 mmol) portionwise over 5 minutes. The mixture was stirred for 3 hours, filtered through pad of CELITE® filter aid and the pad was wash with hexanes. The filtrate was concentrated in vacuo. Chromatography on $SiO_2$ (30% to 50% dichloromethane in hexanes, gradient) gave 2.5 g of 3-(5-Fluoro-2-methoxyphenyl)-3-methylbutyraldehyde as an oil (77% yield).

To a solution of 3-(5-fluoro-2-methoxyphenyl)-3-methylbutyraldehyde (1.1 g, 5.2 mmol) and the above (1-fluorovinyl)dimethylphenylsilane (2.2 g, 12.2 mmol) in 5 mL of THF was added 0.6 mL of tetrabutylammonium fluoride (1 M in THF) and the mixture was stirred at room temperature overnight. TLC showed partial conversion to product. Cesium fluoride (0.22 g) was added and the mixture was stirred at room temperature for 3 days. 2 mL of water and 2 mL of acetic acid were added and the mixture was warmed at 60° C. for 2 hours to effect desilylation of any silylated product. The mixture was diluted with ethyl acetate, washed with water, dried, filtered and concentrated in vacuo. Fractionation of the residue over silica gel (eluent: hexanes-dichloromethane (3:1 to 1:3 gradient) gave 0.798 g (59.5% yield) of 2-fluoro-5-(5-fluoro-2-methoxyphenyl)-5-methylhex-1-en-3-ol as an oil which was used without additional purification.

To 2-fluoro-5-(5-fluoro-2-methoxyphenyl)-5-methylhex-1-en-3-ol, stirred under nitrogen gas and cooled on ice, was added 8.0 mL of diethyl zinc (1.1 M in toluene). After 5 minutes, 1.0 mL of diiodomethane was added dropwise over 20 minutes, and the mixture was stirred and allowed to come to room temperature and then stirred at room temperature for 2 days. Then 0.5 mL of water was added, followed by ethyl acetate, and the mixture was filtered through diatomaceous earth. The product was concentrated in vacuo and the residue was fractionated over silica gel (hexanes-dichloromethane (1:1) to dichloromethane, gradient) to give 0.8 g of 1-(1-fluorocyclopropyl)-3-(5-fluoro-2-methoxyphenyl)-3-methylbutan-1-ol as an oil which was used without additional purification.

6 mL of a 2 M solution of oxalyl chloride in dichloromethane was diluted with 5 mL of dichloromethane and cooled on dry ice/acetone bath. To this solution was added dropwise a solution of 1.5 mL of DMSO in 5 mL of dichloromethane. After 10 minutes, a solution of the crude 1-(1-fluorocyclopropyl)-3-(5-fluoro-2-methoxyphenyl)-3-methylbutan-1-ol (0.8 g, 3 mmol) in 4 mL of dichloromethane was added and the mixture was stirred for 15 minutes. 4 mL of triethylamine was added, the cooling bath was removed, and the reaction mixture was allowed to warm to room temperature, quenched with water, and diluted with hexanes. The organic layer was separated, washed with water, dried, filtered, and concentrated in vacuo. The residue was purified by chromatography over silica gel (eluent: hexanes to hexanes-ethyl acetate (10:1), gradient) to give 0.68 g of the title product as an oil which was used without additional purification.

Example 51

Synthesis of 1,1,1-Trifluoro-4-(5-methanesulfonyl-2,3-dihydrobenzofuran-7-yl)-4-methylpentan-2-one

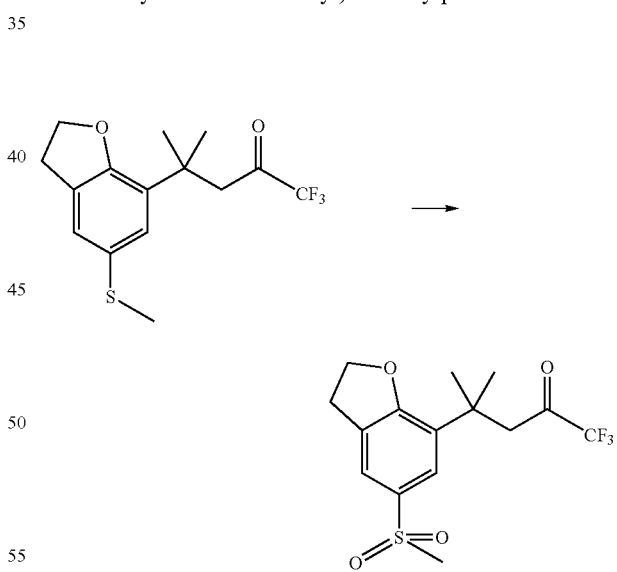

A stirred solution of 1,1,1-trifluoro-4-methyl-4-(5-methylsulfanyl-2,3-dihydrobenzofuran-7-yl)pentan-2-one (5.3 g, 16.7 mmol) in acetonitrile was slowly added a solution of $NaIO_4$ (10.7 g, 50 mmol) in 70 mL of water. After 10 minutes, $RuCl_3$ (50 mg, 0.24 mmol) was added and the stirring was continued at room temperature for 30 minutes. The mixture was concentrated in vacuo, and the resulting greyish solid was filtered, washed with water, and dried to give 5.4 g of the title product, which was used without further purification (93% yield).

Example 52

Synthesis of 1,1,1-Trifluoro-4-(2-methoxy-5-methyl-sulfanylphenyl)-4-methylpentan-2-one

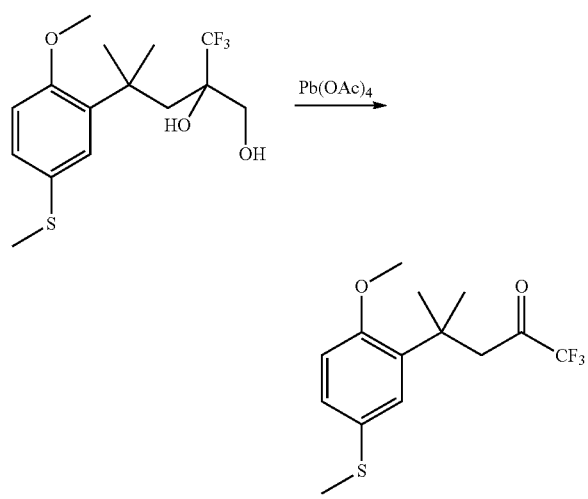

To a solution of 4-(2-methoxy-5-methylsulfanylphenyl)-4-methyl-2-trifluoromethylpentane-1,2-diol (1.5 g, 5.3 mmol) in 25 mL of methanol was added 2.4 g of lead (IV) acetate (Pb(OAc)$_4$) and the reaction mixture was stirred until TLC indicated the reaction was complete, after several hours. The reaction mixture was then filtered through a bed of diatomaceous earth and the filtrate was concentrated in vacuo to afford 1.12 g (83.8% yield) of 1,1,1-trifluoro-4-(2-methoxy-5-methylsulfanylphenyl)-4-methylpentan-2-one.

Example 53

Synthesis of 4-(2-Benzyloxy-5-tert-butylphenyl)-1,1,1-trifluoro-4-methylpentan-2-one

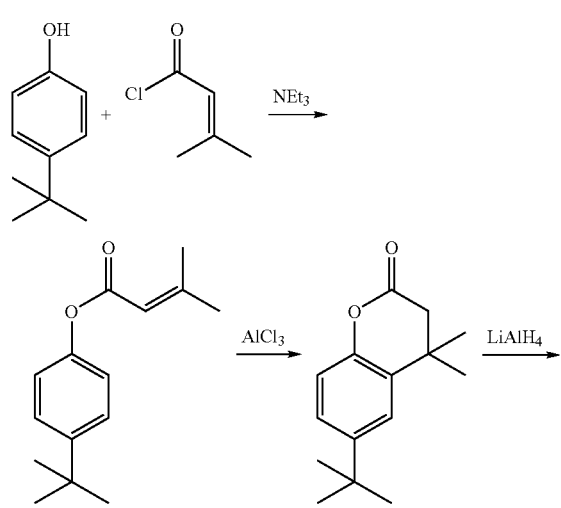

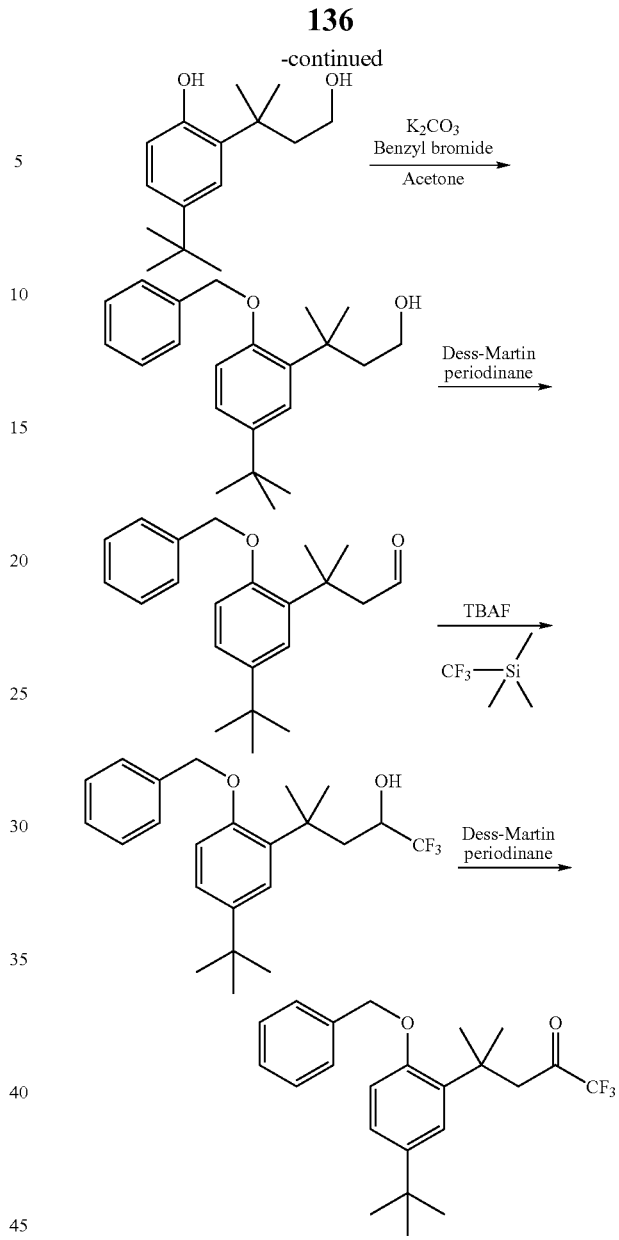

To a chilled solution of 4-tert-butylphenol (15 g, 100 mmol) and 11.12 mL of 3-methylbut-2-enoyl chloride in 200 mL of diethyl ether at 0° C. was added 13.9 mL of triethylamine by addition funnel. The reaction mixture was warmed to room temperature and stirred until TLC indicated the reaction was complete. The reaction mixture was then filtered through diatomaceous earth, and the diethyl ether layer was washed two times with water, washed with brine, dried over magnesium sulfate, and concentrated in vacuo to leave 23 g of 3-methylbut-2-enoic acid 4-tert-butylphenyl ester as a brown oil that partially crystallized upon standing.

To a solution of 3-methylbut-2-enoic acid 4-tert-butylphenyl ester (23 g, 99 mmol) in 50 mL of carbon disulfide (CS$_2$) was added 19.8 g of aluminum chloride (AlCl$_3$) portionwise over the course of 1 hour, a very exothermic reaction. After stirring for several hours, TLC showed the reaction was complete. The reaction mixture was concentrated under a stream of nitrogen gas, and the residue poured over ice and extracted with ethyl acetate. The organics were combined, dried over magnesium sulfate, and concentrated in vacuo. The residue was purified on silica pad (0% to 5% ethyl acetate-hexanes) to give 8.1 g of 6-tert-butyl-4,4-dimethylchroman-2-one as an oil.

To a chilled suspension of 1.99 g of LAH in 60 mL of THF at 0° C. was added a solution of 6-tert-butyl-4,4-dimethyl-chroman-2-one (8.1 g, 34.9 mmol) in 10 mL of THF by addition funnel. The reaction mixture was warmed to room temperature and stirred until TLC indicated the reaction was complete. After 1 hour, the reaction mixture was cooled in ice bath and carefully quenched with a minimum amount of water. The reaction mixture was then dried over magnesium sulfate and filtered through diatomaceous earth. The filtrate was concentrated in vacuo, the residue was taken up in hexanes, and the solids isolated by filtration to afford 5 g of 4-tert-butyl-2-(3-hydroxy-1,1-dimethylpropyl)phenol.

To a solution of 4-tert-butyl-2-(3-hydroxy-1,1-dimethyl-propyl)phenol (2 g, 8.5 mmol) and 1.1 mL benzyl bromide in 10 mL of DMF was added 1.75 g of potassium carbonate ($K_2CO_3$) and the reaction mixture stirred at room temperature until TLC indicated that the reaction was complete. After stirring overnight, the reaction mixture was diluted with ice and extracted with diethyl ether. The organics were combined, washed four times with water, washed with brine, dried over magnesium sulfate, and concentrated in vacuo. The residue was purified on COMBIFLASH® apparatus (0% to 30% ethyl acetate-hexanes) to give 1.7 g of 3-(2-benzyloxy-5-tert-butylphenyl)-3-methylbutan-1-ol as an oil.

To a solution of 3-(2-benzyloxy-5-tert-butylphenyl)-3-methylbutan-1-ol (1.7 g, 5.2 mmol) in 20 mL of dichloromethane was added 3.27 g of Dess-Martin periodinane and reaction stirred until TLC indicated the reaction was complete. After 2 hours, the reaction mixture was passed through a pad of silica, eluting with 5% ethyl acetate-hexanes to afford 1.67 g of 3-(2-benzyloxy-5-tert-butylphenyl)-3-methylbutyraldehyde as an oil.

3-(2-Benzyloxy-5-tert-butylphenyl)-3-methylbutyraldehyde was converted to 4-(2-benzyloxy-5-tert-butylphenyl)-1,1,1-trifluoro-4-methylpentan-2-one using similar procedures as in Example 4 of U.S. patent application Pub. No. 2004/0023999.

Example 54

Synthesis of 4-(2-Benzyloxy-5-isopropylphenyl)-1,1,1-trifluoro-4-methylpentan-2-one

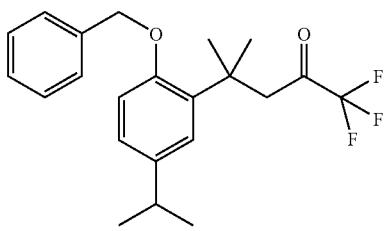 [SMILES: CC(C)c1ccc(OCc2ccccc2)c(C(C)(C)CC(=O)C(F)(F)F)c1]

4-(2-Benzyloxy-5-isopropylphenyl)-1,1,1-trifluoro-4-methylpentan-2-one was prepared from 4-isopropylphenol in the same manner as described in the synthesis of 4-(2-benzyloxy-5-tert-butylphenyl)-1,1,1-trifluoro-4-methylpentan-2-one.

Example 55

Synthesis of 7-(4,4,4-Trifluoro-3-hydroxy-3-hydroxymethyl-1,1-dimethylbutyl)-2,3-dihydrobenzofuran-5-sulfonic acid dimethylamide

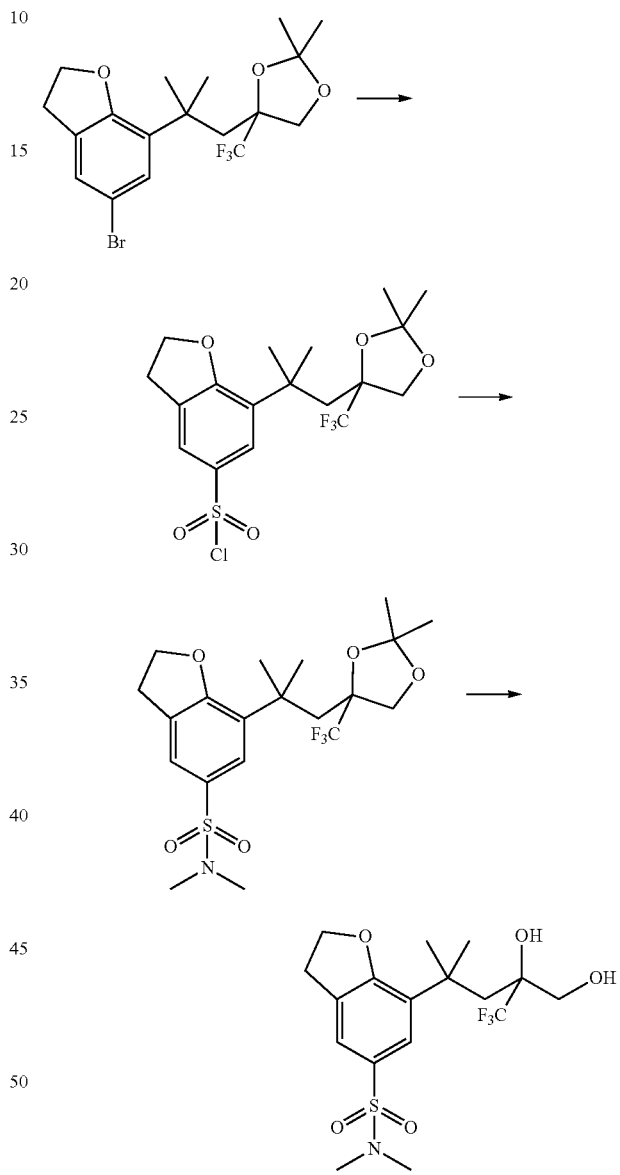

A solution of 5-bromo-7-[2-(2,2-dimethyl-4-trifluoromethyl-[1,3]dioxolan-4-yl)-1,1-dimethylethyl]-2,3-dihydrobenzofuran (4.0 g, 9.4 mmol) in 8 mL of THF was treated with n-BuLi (2.5 M in hexanes, 4.2 mL, 10.5 mmol) at −78° C. After 15 minutes, an excess of $SO_2$ gas was bubbled into the mixture and the reaction was monitored for the disappearance of the starting material. Next, the reaction mixture was concentrated under a stream of nitrogen gas, diluted with THF, and treated with N-chlorosuccinimide (1.48 g, 11.1 mmol). The mixture was stirred for 15 minutes and divided into three equal portions. A stock solution of sulfonyl chloride (⅓ of the mixture) in 8 mL of THF was treated with dimethylamine (2 M in THF, 10 mL, 20 mmol). After 30 minutes, the mixture was diluted with 20 mL of saturated aqueous ammonium chloride solution and extracted with three 10 mL portions of ethyl acetate. The combined organic layers were washed with three 10 mL portions of saturated aqueous ammonium chloride solution, two 10 mL portions of brine, dried over magnesium sulfate, filtered, and concentrated in vacuo. The crude material was purified on silica gel (3% to 30% ethyl acetate in hexanes, gradient) to afford 1.18 g (83% yield) of 7-[2-(2,2-dimethyl-4-trifluoromethyl-[1,3]dioxolan-4-yl)-1,1-dimethyl-ethyl]-2,3-dihydrobenzofuran-5-sulfonic acid dimethylamide, which was used without further purification.

A mixture of 1.18 g (2.61 mmol) of 7-[2-(2,2-dimethyl-4-trifluoromethyl-[1,3]dioxolan-4-yl)-1,1-dimethyl-ethyl]-2,3-dihydrobenzofuran-5-sulfonic acid dimethylamide and 303 mg (1.59 mmol) of p-toluenesulfonic acid monohydrate in 20 mL of methanol was warmed at reflux for 3 days. The mixture was then cooled and diluted with 15 mL of saturated aqueous sodium bicarbonate and extracted with three 15 mL portions of ethyl acetate. The combined organic layers were washed with two 15 mL portions of saturated aqueous sodium bicarbonate, two 15 mL portions of brine, dried over magnesium sulfate, filtered, and concentrated in vacuo. The residue was triturated with ether to afford 845 mg (78% yield) of the title compound as a white solid.

7-(4,4,4-Trifluoro-3-hydroxy-3-hydroxymethyl-1,1-dimethylbutyl)-2,3-dihydrobenzofuran-5-sulfonic acid dimethylamide was converted to the corresponding trifluoromethyl ketone according to the method disclosed in U.S. patent application Pub. No. 2004/0029932, which is hereby incorporated by reference.

Example 56

Synthesis of 7-(4,4,4-Trifluoro-3-hydroxy-3-hydroxymethyl-1,1-dimethylbutyl)-2,3-dihydrobenzofuran-5-sulfonic acid amide

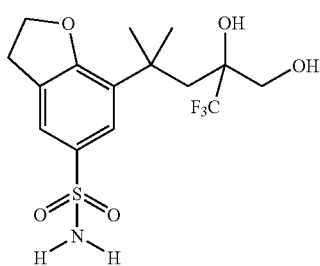 [SMILES: CC(C)(CC(O)(CO)C(F)(F)F)c1cc(S(N)(=O)=O)cc2c1OCC2]

7-(4,4,4-Trifluoro-3-hydroxy-3-hydroxymethyl-1,1-dimethylbutyl)-2,3-dihydrobenzofuran-5-sulfonic acid amide was prepared from 5-bromo-7-[2-(2,2-dimethyl-4-trifluoromethyl-[1,3]dioxolan-4-yl)-1,1-dimethylethyl]-2,3-dihydrobenzofuran in the same manner as in the preparation of 7-(4,4,4-trifluoro-3-hydroxy-3-hydroxymethyl-1,1-dimethylbutyl)-2,3-dihydrobenzofuran-5-sulfonic acid dimethylamide.

Example 57

Synthesis of 7-(4,4,4-Trifluoro-1,1-dimethyl-3-oxobutyl)-2,3-dihydrobenzofuran-5-sulfonic acid 1-dimethylaminometh-(E)-ylideneamide

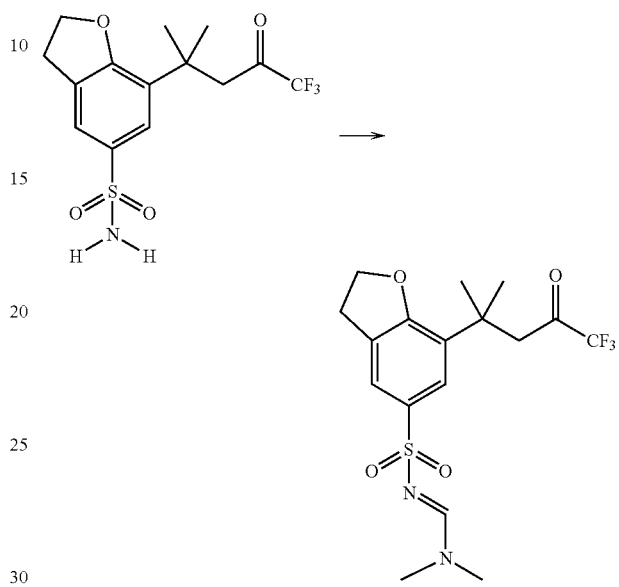

A solution of 7-(4,4,4-trifluoro-1,1-dimethyl-3-oxobutyl)-2,3-dihydrobenzofuran-5-sulfonic acid amide (870 mg, 2.47 mmol) in 30 mL of dichloromethane was reacted with N,N-dimethylformamide dimethyl acetal (580 mg, 4.86 mmol). After 30 minutes, the mixture was concentrated in vacuo to dryness. The resulting solid was triturated with diethyl ether and collected to afford 950 mg of the title compound (94% yield).

Example 58

Synthesis of 1,1-Difluoro-4-(5-methanesulfonyl-2,3-dihydrobenzofuran-7-yl)-4-methylpentan-2-one

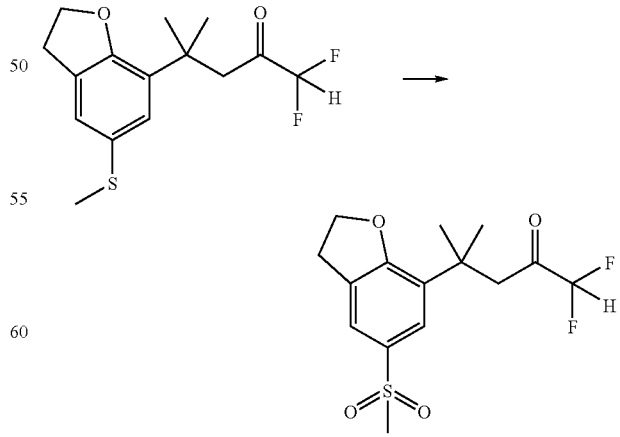

To a solution of 1,1-difluoro-4-methyl-4-(5-methylsulfanyl-2,3-dihydrobenzofuran-7-yl)pentan-2-one (840 mg, 2.8 mmol) in 12 mL of MeCN and 4 mL of water was added sodium periodate (1.79 g, 8.4 mmol) followed by a crystal of ruthenium (III) chloride hydrate. The reaction was monitored by TLC until the thiol ether was no longer evident. After 1 hour, the reaction was concentrated in vacuo, diluted with water, and extracted with ethyl acetate. The combined organic layers were dried over magnesium sulfate, treated with carbon, filtered, and concentrated in vacuo to afford 910 mg (98% yield) of the title compound as a white solid.

Example 59

Synthesis of
4-Methoxy-3-methyl-3-phenylbutyraldehyde

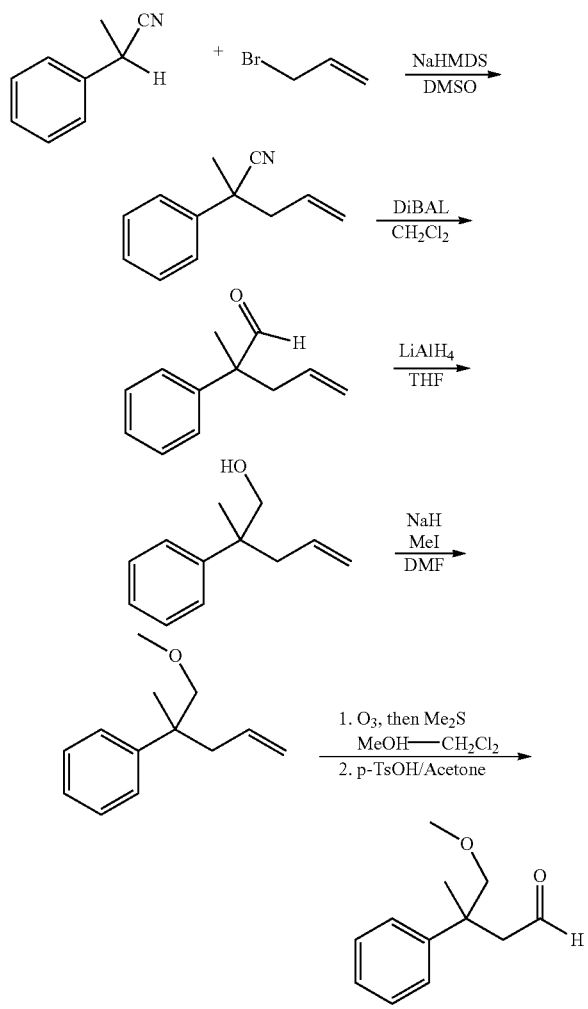

To a solution of 2-phenylpropionitrile (4.04 g, 30.79 mmol) in 40 mL of DMSO was added 34 mL (34 mmol) of a 1 M solution of sodium bis(trimethylsilyl)amide (NaHMDS) in THF over a 5 minute period. After 10 minutes, allyl bromide (6 mL, 69.33 mmol) was added dropwise (exothermic). The mixture was cooled with an ice-water bath. The mixture stirred for 20 minutes, becoming a solid mass. An additional 20 mL of DMSO was added. After 10 minutes, the mixture was diluted with 200 mL of ammonium chloride and extracted with three 100 mL portions of ethyl acetate. The combined organic layers were washed with six 75 mL portions of brine, dried over magnesium sulfate, filtered, and concentrated in vacuo to afford 5.25 g (99.5% yield) of 2-methyl-2-phenylpent-4-enenitrile as yellow oil which was used without further purification.

To a solution of 2-methyl-2-phenylpent-4-enenitrile (5.25 g, 30.65 mmol) in 150 mL of dichloromethane was added a 1 M solution of diisobutylaluminum hydride (DIBAL) (38 mL, 38 mmol) in dichloromethane over a 15 minute period. The reaction was monitored by TLC; after 1 hour, TLC (ethyl acetate-hexanes (1:9)) indicated a slightly less polar product. The reaction was poured into ice-cold 1 N aqueous HCl and the dichloromethane layer separated. The aqueous was extracted with two 50 mL portions of dichloromethane. The combined organic layers were washed with 50 mL of brine, two 50 mL portions of saturated aqueous sodium bicarbonate, 50 mL of brine, dried over magnesium sulfate, filtered through diatomaceous earth, and concentrated in vacuo to afford 4.6 g (86.1% yield) of 2-methyl-2-phenylpent-4-enal which was used without further purification.

To a solution of 2-methyl-2-phenylpent-4-enal (4.6 g, 26.4 mmol) in 100 mL of THF was added of lithium aluminum hydride (LAH) (2.6 g, 68.51 mmol) in several portions. The mixture stirred for 3 hours at room temperature and was then refluxed for 2 hours. The reaction was monitored by TLC with ethyl acetate-hexanes (1:9) indicating a new more polar product. The reaction was cooled and the excess LAH was cautiously quenched with water dropwise. The mixture was then diluted with 1N aqueous HCl and extracted with 100 mL of hexanes and two 100 mL portions of ethyl acetate. The combined organic layers were washed with 50 mL of 1 N aqueous HCl, two 50 mL portions of brine, two 50 mL portions of saturated aqueous sodium bicarbonate, 50 mL of brine, dried over magnesium sulfate, filtered, and concentrated in vacuo. The crude material was chromatographed on silica gel using hexanes to load the sample and then eluting with 1% to 15% ethyl acetate-hexanes to afford 3.2 g (68.8) of 2-methyl-2-phenylpent-4-en-1-ol.

To a solution of 2-methyl-2-phenylpent-4-en-1-ol (3.2 g, 18.15 mmol) in 17 mL of DMF was added sodium hydride (1.25 g, 31.25 mmol, 60% in mineral oil). The mixture was stirred until foaming ceased and then methyl iodide (6 mL, 96 mmol) was added. After 2 hours, the mixture was quenched with 50 mL of saturated aqueous ammonium chloride solution and extracted with three 50 mL portions of ethyl acetate. The combined organic layers were washed with 30 mL of saturated aqueous ammonium chloride solution, five 25 mL portions of brine, dried over magnesium sulfate, filtered, and concentrated in vacuo to afford 3.4 g (98.4% yield) of (1-methoxymethyl-1-methylbut-3-enyl)benzene which was used without further purification.

To a chilled (−78° C.) solution of (1-methoxymethyl-1-methylbut-3-enyl)benzene (1.67 g, 8.77 mmol) in methanol-dichloromethane was bubbled ozone gas until the solution turned blue. The excess ozone was then purged from the mixture with oxygen and then dimethyl sulfide (5 mL, 68 mmol) was added and the mixture was warmed to room temperature and stirred overnight. The mixture was then concentrated in vacuo to remove the excess dimethyl sulfide and diluted with 20 mL of ammonium chloride and extracted with three 15 mL portions of ethyl acetate. The combined organic layers were washed with three 15 mL portions of brine, dried over magnesium sulfate, filtered, and concentrated in vacuo to afford an oil which corresponded to the dimethyl acetal by $^1$H-NMR. The crude product was diluted with 40 mL of acetone and p-TsOH (300 mg, 1.57 mmol) was added and the mixture was stirred at room temperature for 2 hours. The reaction was monitored by $^1$H-NMR and indicated the presence of aldehyde and dimethyl acetal. The reaction was refluxed for 4 hours and monitored by TLC (ethyl acetate-hexanes (1:9)) and then cooled and diluted with saturated aqueous sodium bicarbonate solution and extracted with three 15 mL portions of ethyl acetate. The combined organic layers were washed with two 10 mL portions of saturated aqueous sodium bicarbonate solution, two 10 mL portions of brine, dried over magnesium sulfate, filtered, and concentrated in vacuo to afford 1.45 g (85.9% yield) of 4-methoxy-3-methyl-3-phenylbutyraldehyde.

4-Methoxy-3-methyl-3-phenylbutyraldehyde was converted to 1,1,1-trifluoro-5-methoxy-4-methyl-4-phenylpentan-2-one as described previously in Example 26 of U.S. Patent Application Pub. No. 2004/0023999.

Example 60

Synthesis of 1-Benzo[1,3]dioxol-4-ylethanone

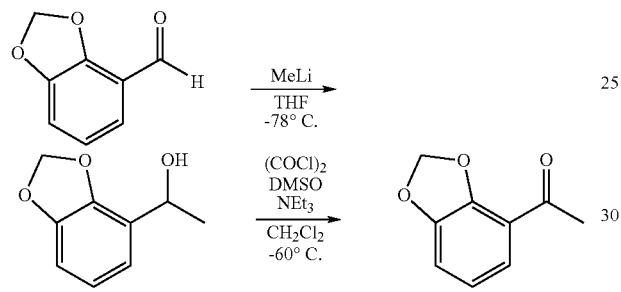

To a solution of benzo[1,3]dioxole-4-carbaldehyde (10 g, 66.7 mmol) in 200 mL THF at −78° C. was added, via addition funnel, 43.7 mL of a 1.6 M MeLi solution in diethyl ether. The reaction was slowly warmed to room temperature and stirred overnight. A TLC of an aliquot showed reaction was complete. The reaction was then cooled to −78° C. and quenched with saturated aqueous ammonium chloride and concentrated in vacuo. The residue was then extracted with ethyl acetate. The organics were combined, dried over magnesium sulfate, and concentrated in vacuo to give 11 g (99.4% yield) of 1-benzo[1,3]dioxol-4-ylethanol as a brown oil that crystallized upon standing.

To a solution of 1-benzo[1,3]dioxol-4-ylethanol (11 g, 66.3 mmol) in 100 mL of THF was added 17.26 g of manganese dioxide (MnO$_2$) in one portion and reaction was monitored by TLC. After several hours, TLC showed some product but significant alcohol left. More manganese dioxide was added and the solution stirred. TLC then showed mostly product but a significant amount of alcohol. The reaction mixture was then filtered through a bed of diatomaceous earth and the filtrate was concentrated in vacuo to give an oil that mostly crystallized on standing. To 9.24 mL of a solution of oxalyl chloride in 120 mL of dichloromethane at −60° C. was added a solution of 15 mL of DMSO in 20 mL of dichloromethane. After 10 minutes, a solution of above alcohol/ketone mixture (53 mmol) in 20 mL of dichloromethane was added, followed 15 minutes later by 44.3 mL of triethylamine. The reaction was allowed to slowly warm to room temperature overnight. The reaction mixture was then poured onto ice and the organic layer was washed with five 100 mL portions of water, then brine, and then dried over magnesium sulfate. The organics were concentrated in vacuo to leave tan solids and the solids were triturated with hexanes, collected by filtration, and dried to give 9.33 g (85.8% yield) of 1-benzo[1,3]dioxol-4-ylethanone.

1-Benzo[1,3]dioxol-4-ylethanone was converted to 4-benzo[1,3]dioxol-4-yl-1,1,1-trifluoro-4-methylpentan-2-one according to Example 26 of U.S. Patent Application Pub. No. 2004/0023999.

Example 61

Synthesis of 2-Hydroxy-4-methyl-4-phenyl-2-trifluoromethylhexanoic acid ethyl esters

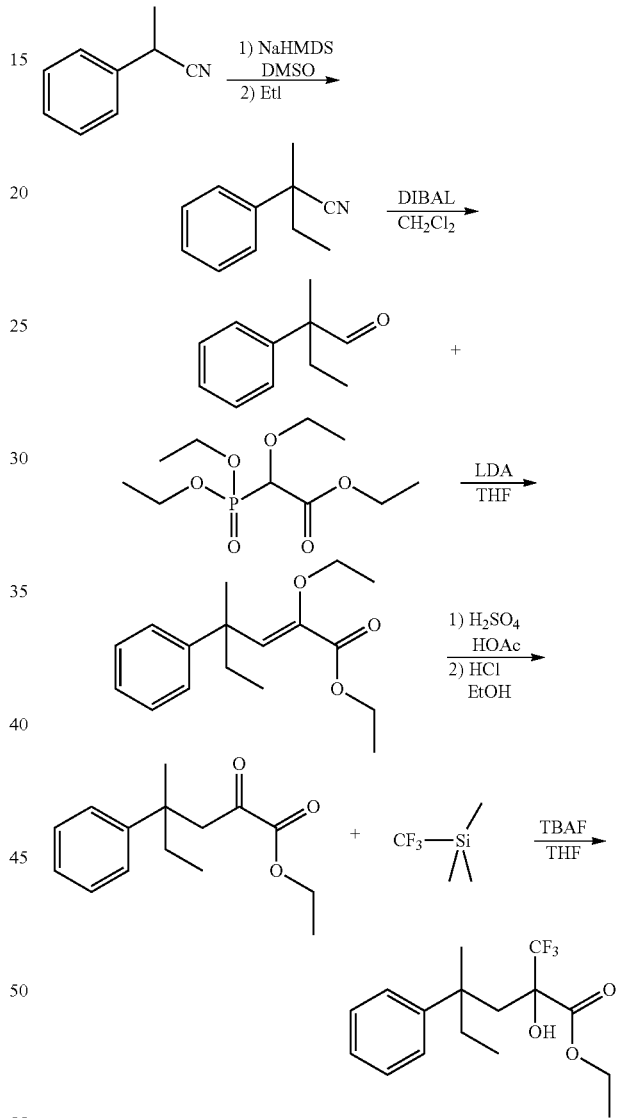

To a solution of 2-phenylpropionitrile (5 g, 38 mmol) in 50 mL of DMSO was added 42 mL of 1 M THF solution of sodium bis(trimethylsilyl)amide (NaHMDS). After 15 minutes, the reaction was cooled to 0° C. and 4.6 mL of ethyl iodide was added. The reaction was then stirred for 30 minutes. As TLC showed the reaction was complete, the reaction mixture was poured into water and extracted with diethyl ether. The organics were combined, washed four times with water, washed with brine, dried over magnesium sulfate, and concentrated in vacuo to give 6.1 g of 2-methyl-2-phenylbutyronitrile as an oil.

To a solution of 2-methyl-2-phenylbutyronitrile (6.1 g, 38.3 mmol) in 50 mL of dichloromethane at room temperature was added 57 mL of 1 M DIBAL in dichloromethane via syringe. The reaction was stirred for 30 minutes, at which time TLC of aliquot showed the reaction was complete. The reaction mixture was carefully poured into 100 mL of 1N HCl and the layers were separated. The organics were concentrated in vacuo and taken up in diethyl ether, combined with the aqueous layer, and extracted with diethyl ether. The organics were then combined, dried over magnesium sulfate, and concentrated in vacuo. The residue was purified on silica gel column (0% to 2% ethyl acetate in hexanes) to give 4.2 g of 2-methyl-2-phenylbutyraldehyde as colorless oil.

To a solution of (diethoxyphosphoryl)ethoxyacetic acid ethyl ester (7.4 g, 27.6 mmol) in 30 mL of THF, at 0° C., was added 16 mL of 1.8 M LDA in heptane/THF/ethylbenzene. The reaction mixture was stirred for 30 minutes and then a solution of 2-methyl-2-phenylbutyraldehyde (4.2 g, 25.9 mmol) in 30 mL of THF was added dropwise by syringe. The reaction mixture was then warmed to room temperature, quenched with saturated aqueous ammonium chloride solution, and extracted with diethyl ether. The organics were combined, dried over magnesium sulfate and concentrated in vacuo to give 8.3 g of a 2:1 mixture of E and Z isomers of 2-ethoxy-4-methyl-4-phenylhex-2-enoic acid ethyl ester as orange oil.

To a solution of 2-ethoxy-4-methyl-4-phenylhex-2-enoic acid ethyl ester (8.3 g, 30 mmol) in 25 mL of HOAc was added 116.5 mL of aqueous 1 M sulfuric acid solution. The reaction mixture was stirred at room temperature for several hours. As TLC showed no reaction, the reaction mixture was placed in a 100° C. oil bath and stirred overnight. As TLC was then inconclusive, 2 mL more aqueous 1 M sulfuric acid and 20 mL of HOAc were added. After 1 hour, TLC of an aliquot showed major olefin isomer (more polar spot) consumed and minor isomer spot remaining (product may co-spot with minor isomer). The reaction mixture was then cooled to room temperature and extracted with diethyl ether. Organics were combined, washed with four portions of water, washed with brine, dried over magnesium sulfate, and concentrated in vacuo to afford 2.5 g of an orange oil. $^1$H-NMR showed 1:1 mixture of minor isomer and aldehyde. The aqueous layer was extracted with ethyl acetate and the ethyl acetate extracts were combined, dried over magnesium sulfate, and concentrated in vacuo to leave a brown liquid. $^1$H-NMR showed significant ethyl acetate and HOAc and desired product as the ketoacid. The ketoacid solution was taken up in 200 mL of ethanol, treated with 1 mL of concentrated HCl, and heated to reflux overnight. TLC then showed a new, less polar spot. The reaction mixture was cooled to room temperature and concentrated in vacuo. The residue was then diluted with water and extracted with diethyl ether. The organics were combined, dried over magnesium sulfate, and concentrated in vacuo to leave 4.3 g of 4-methyl-2-oxo-4-phenylhexanoic acid ethyl ester as an orange oil.

To a solution of 4-methyl-2-oxo-4-phenylhexanoic acid ethyl ester (4.3 g, 17.3 mmol) and 3.6 mL of trifluoromethyltrimethylsilane in 50 mL of THF was added 1.5 mL (0.1 equiv) of 1 M TBAF solution and reaction stirred at room temperature until the ketoester was shown to be consumed by TLC, about 30 minutes. The remainder of the TBAF (17.5 mL) was then added and the reaction mixture stirred for 1 hour. TLC then showed the reaction was complete. The reaction mixture was concentrated in vacuo, the residue diluted with 1 N HCl and extracted with diethyl ether. The organics were combined, dried over magnesium sulfate, and concentrated in vacuo to leave a brown oil. The oil was taken up in hexanes (cloudy appearance), activated charcoal was added, and the resulting solution filtered through diatomaceous earth and concentrated in vacuo to leave 3.8 g (83% yield) of a diastereomeric mixture of 2-hydroxy-4-methyl-4-phenyl-2-trifluoromethylhexanoic acid ethyl esters as a light green oil.

The diastereomeric mixture of esters was converted to the corresponding trifluoromethyl ketone according to Example 1 of U.S. Patent Application Pub. No. 2004/0023999.

Example 62

Synthesis of 1,1,1-Trifluoro-4-(2-methoxy-5-methylphenyl)-4-methylpentan-2-one

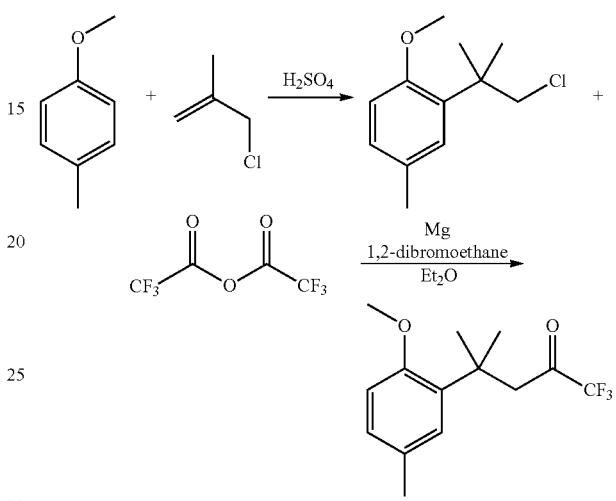

To a yellow solution of 4-methylanisole (20 g, 183.5 mmol) and 1.7 mL of concentrated sulfuric acid was added 19.17 mL of 3-chloro-2-methylpropene by addition funnel. The reaction became warm and turned dark purple. After 20 minutes, solids began to precipitate. TLC of an aliquot showed some starting anisole left and a new, slightly less polar spot forming. The reaction mixture was stirred overnight and TLC then showed that the reaction was complete. The reaction mixture was poured onto ice and extracted with diethyl ether. The organics were combined, dried over magnesium sulfate, and concentrated in vacuo to leave an oil. The residue was taken up in hexanes, cooled to −78° C., and the solids collected by filtration to give 14 g of 2-(2-chloro-1,1-dimethylethyl)-1-methoxy-4-methylbenzene as an oil upon warming. The filtrate was concentrated in vacuo to give 15.5 g of a 4:1 mixture of product and starting anisole.

To a suspension of magnesium turnings (1.87 g) in 30 mL of anhydrous diethyl ether under argon in a water bath was added 1.62 mL of dibromoethane slowly by syringe such that the internal reaction temperature did not go above 27° C. A solution of 2-(2-chloro-1,1-dimethylethyl)-1-methoxy-4-methylbenzene (4 g, 18.9 mmol) and additional dibromoethane (1.62 mL) in 20 mL of diethyl ether was added by addition funnel at a rate that kept the internal temperature below 25° C. The reaction mixture became green and a fine precipitate formed. After 1 hour, the reaction mixture was cooled to −78° C.; solids clumped on the bottom of the reaction mixture and stirring was stopped. A solution of 3.98 mL of trifluoroacetic anhydride in 4 mL of diethyl ether was added to the reaction mixture by addition funnel while swirling the reaction mixture by hand. The reaction mixture was then warmed to room temperature, stirring resumed above −40° C. TLC of an aliquot showed a new slightly more polar spot and starting material. The reaction mixture was then poured onto cold 1 N HCl and extracted with diethyl ether. The organics were combined, dried over magnesium sulfate, and concentrated in vacuo. The residue was purified on silica gel column (0% to 5% ethyl acetate-hexanes) to give 1.7 g (41% yield) of 1,1,1-trifluoro-4-(2-methoxy-5-methylphenyl)-4-methylpentan-2-one as a clear oil.

Example 63

Synthesis of 1,1,1-Trifluoro-4-(2-methoxy-3,5-dimethylphenyl)-4-methylpentan-2-one

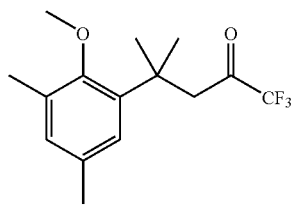 [SMILES: COc1c(C)cc(C)cc1C(C)(C)CC(=O)C(F)(F)F]

The title product was prepared from 1-methoxy-2,4-dimethylbenzene according to the same procedure described in the synthesis of 1,1,1-trifluoro-4-(2-methoxy-5-methylphenyl)-4-methylpentan-2-one.

Example 64

Synthesis of 1,1,1-Trifluoro-4-(5-methoxy-2,4-dimethylphenyl)-4-methylpentan-2-one

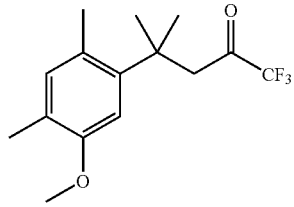 [SMILES: COc1cc(C(C)(C)CC(=O)C(F)(F)F)c(C)cc1C]

The title product was prepared from 1-methoxy-2,4-dimethylbenzene according to the same procedure described in the synthesis of 1,1,1-trifluoro-4-(2-methoxy-5-methylphenyl)-4-methylpentan-2-one.

Example 65

4-(2-benzyloxy-5-methylsulfanylphenyl)-1,1,1-trifluoro-4-methylpentan-2-one

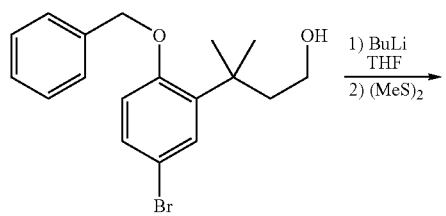

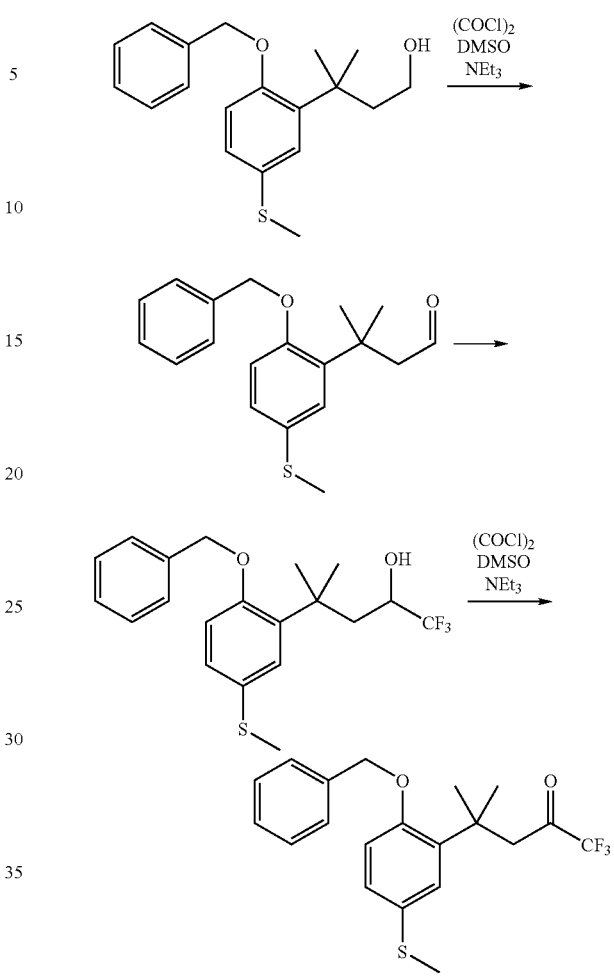

To a solution of 3-(2-benzyloxy-5-bromophenyl)-3-methylbutan-1-ol (3 g, 8.6 mmol) in 50 mL of THF at −78° C. was added 7.56 mL of n-BuLi (2.5 M solution in hexanes) and the reaction mixture was stirred for 10 minutes. Then 1.55 mL of dimethyldisulfide was added and the reaction mixture was warmed to room temperature. After 20 minutes, TLC showed a new, slightly more polar spot (major) with very little else. The reaction mixture was then quenched with saturated aqueous ammonium chloride solution and extracted with diethyl ether. The organics were combined, dried over magnesium sulfate, and concentrated in vacuo to 2.84 g of 3-(2-benzyloxy-5-methylsulfanylphenyl)-3-methylbutan-1-ol as an oil.

To a solution of 1.57 mL of oxalyl chloride in 15 mL of dichloromethane at −60° C. was added a solution of 2.55 mL of DMSO in 5 mL of dichloromethane. After 10 minutes, a solution of 3-(2-benzyloxy-5-methylsulfanylphenyl)-3-methylbutan-1-ol (2.84 g, 8.9 mmol) in 5 mL of dichloromethane was added (solids quickly precipitated), followed 15 minutes later by 7.5 mL triethylamine and the reaction mixture became very thick with solids. The reaction mixture was then warmed to room temperature and monitored by TLC. After 1 hour, TLC of an aliquot showed reaction was complete, so water was added to the reaction mixture and the resulting layers were separated. The aqueous layer was washed with dichloromethane and the organics were combined, washed four times with water, washed with brine, dried over magnesium sulfate, and concentrated in vacuo to afford a yellow oil. The residue was purified on SiO₂ (0% to 10% ethyl acetate-hexanes) to give 2.2 g (78.7% yield) of 3-(2-benzyloxy-5-methylsulfanylphenyl)-3-methylbutyraldehyde as a colorless oil that slowly crystallized upon standing.

3-(2-Benzyloxy-5-methylsulfanylphenyl)-3-methylbutyraldehyde was converted to 4-(2-benzyloxy-5-methylsulfanylphenyl)-1,1,1-trifluoro-4-methylpentan-2-ol as in Example 26 of U.S. patent application Pub. No. 2004/0023999.

4-(2-Benzyloxy-5-methylsulfanylphenyl)-1,1,1-trifluoro-4-methylpentan-2-ol was oxidized to 4-(2-benzyloxy-5-methylsulfanylphenyl)-1,1,1-trifluoro-4-methylpentan-2-one using Swern conditions as above.

Example 66

Synthesis of 1,1,1-Trifluoro-4-methyl-4-(5-pyrimidin-5-yl-2,3-dihydrobenzofuran-7-yl)pentan-2-one

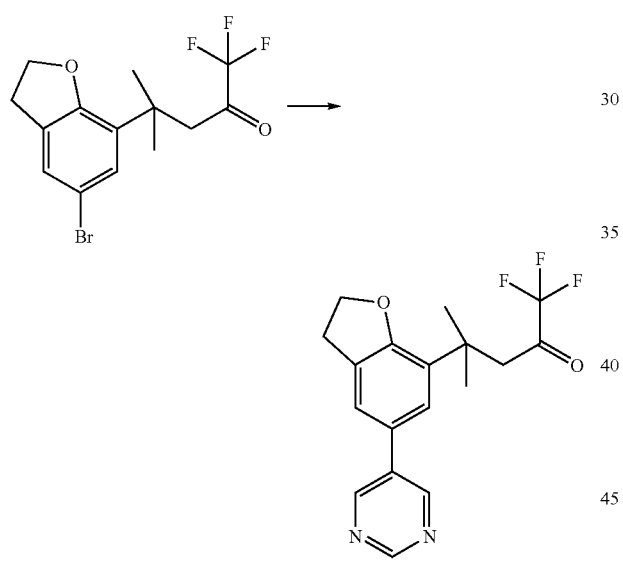

To a mixture of 4-(5-bromo-2,3-dihydrobenzofuran-7-yl)-1,1,1-trifluoro-4-methylpentan-2-one (1.00 g, 2.8 mmol), pyrimidine-5-boronic acid (529 mg, 4.3 mmol) and potassium carbonate (787 mg) in a sealed tube was added 20 mL of MeOH-DME-DMF (3:2:1). After stirring at room temperature for 10 minutes, tetrakis(triphenylphosphine)palladium (0) (329 mg) was added and the reaction mixture was heated at 120° C. for 40 minutes. After cooling to room temperature, the crude mixture was filtered through a cotton plug with the aid of ethyl acetate. The filtrate was concentrated in vacuo to remove most of the methanol, redissolved in 160 mL of ethyl acetate, and washed with 80 mL of aqueous 1 N sodium hydroxide solution, 80 mL of water, and 80 mL of brine respectively. The organic phase was dried over anhydrous sodium sulfate, filtered, and concentrated in vacuo. Purification by column chromatography with 20% to 30% ethyl acetate-hexanes afforded 620 mg (62% yield) of the title compound.

Example 67

Synthesis of 5-{7-[1,1-Dimethyl-2-(2-trifluoromethyloxiranyl)ethyl]-2,3-dihydrobenzofuran-5-yl}pyrimidine

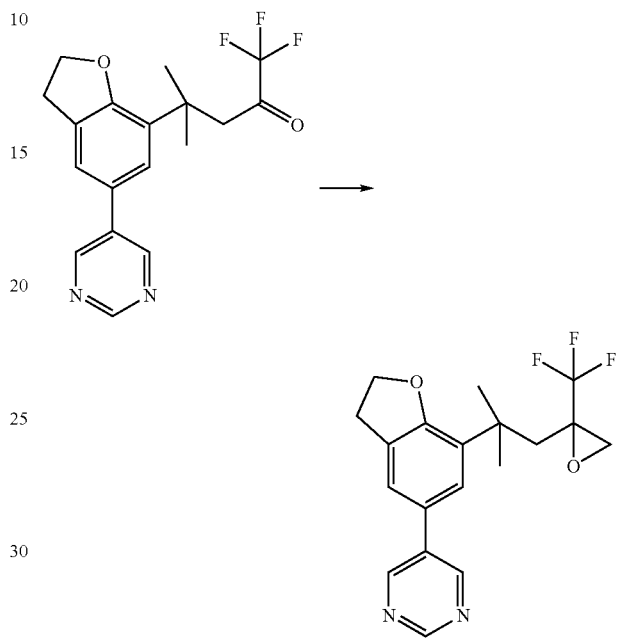

To a solution of 1,1,1-trifluoro-4-methyl-4-(5-pyrimidin-5-yl-2,3-dihydrobenzofuran-7-yl)pentan-2-one (620 mg, 1.8 mmol) in 5 mL of anhydrous DMSO-THF (1:1) was added 2.64 mL of a trimethylsulfoxonium ylide solution (stock solution prepared by reaction of NaH (242 mg, 60% dispersion in mineral oil) with trimethylsulfoxonium iodide (1.33 g, 6.0 mmol) in 7.50 mL of anhydrous DMSO for 30 minutes) dropwise over 5 minutes. After stirring for 2 hour at room temperature, the reaction mixture was poured into 40 mL of water and extracted with diethyl ether (200 mL total volume). The combined organic phases were washed with water, brine, dried over magnesium sulfate, filtered, and concentrated in vacuo to afford 651 mg (99% yield) of the title compound as a pale yellow oil which was used without further purification.

Example 68

Synthesis of 5-Chloro-7-[1,1-dimethyl-2-(2-trifluoromethyloxiranyl)ethyl]-2,3-dihydrobenzofuran

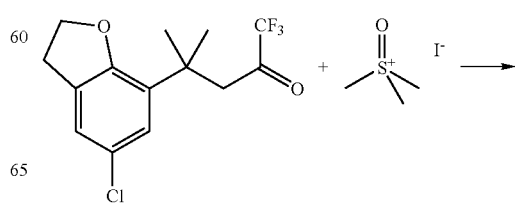

-continued

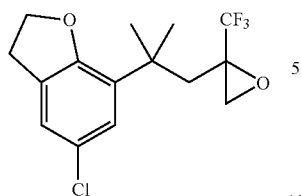

To a solution of trimethylsulfoxonium iodide (343 mg, 1.56 mmol) in 3 mL of anhydrous DMSO was treated with NaH (60% in mineral oil, 66.0 mg, 1.65 mmol) in portions and the mixture was stirred at room temperature for 30 minutes. The mixture was transferred to a solution of 4-(5-chloro-2,3-dihydrobenzofuran-7-yl)-1,1,1-trifluoro-4-methylpentan-2-one (400 mg, 1.30 mmol) in 1 mL of anhydrous DMSO over 5 minutes and the resulting mixture was stirred overnight. The mixture was quenched with water and extracted with three 20 mL portions of ethyl acetate. The combined organic layers were washed with two 5 mL portions of water, dried over magnesium sulfate, filtered, and concentrated in vacuo to afford 380 mg (91% yield) of the title product as a yellow oil. The crude product was sufficiently pure and used without further purification.

Example 69

Synthesis of 7-[1,1-Dimethyl-2-(2-trifluoromethyloxiranyl)ethyl]-5-methylsulfanyl-2,3-dihydrobenzofuran

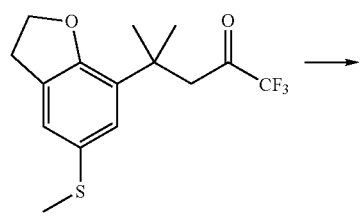

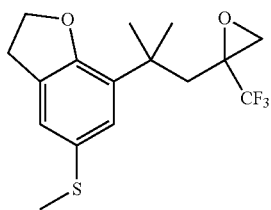

To a suspension of trimethylsulfoxonium iodide (1.36 g, 6.1 mmol) in 7.7 mL of anhydrous DMSO was added sodium hydride (60% dispersion in mineral oil, 246 mg). The resulting solution was stirred at room temperature for 30 minutes and was then added dropwise to a solution of 1,1,1-trifluoro-4-methyl-4-(5-methylsulfanyl-2,3-dihydrobenzofuran-7-yl)pentan-2-one (1.63 g, 6.2 mmol) in 6.5 mL of anhydrous DMSO. After 2 hours, 100 mL of water was added and the resulting mixture was extracted with three 100 mL portions of diethyl ether. The combined organic phases were washed twice with water, aqueous saturated sodium chloride solution, dried over magnesium sulfate, filtered, and concentrated in vacuo to afford the title compound, 1.64 g (95% yield) which was used without further purification.

Example 70

Synthesis of 7-[1,1-Dimethyl-2-(2-trifluoromethyloxiranyl)ethyl]-5-methanesulfonyl-2,3-dihydrobenzofuran

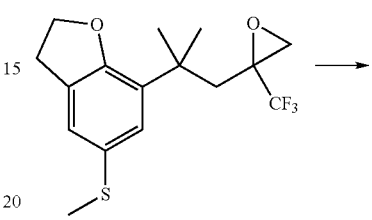

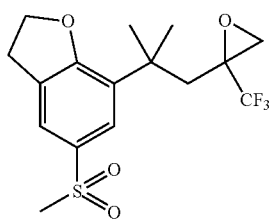

To a solution of 7-[1,1-dimethyl-2-(2-trifluoromethyloxiranyl)ethyl]-5-methylsulfanyl-2,3-dihydrobenzofuran (535 mg, 1.9 mmol) in 30 mL of acetonitrile and 10 mL of water was added sodium periodate (1.03 g, 4.8 mmol) followed by ruthenium (III) chloride (1 mg). After 2 hours, the reaction mixture was diluted with water and extracted with ethyl acetate. The combined organic phases were dried over magnesium sulfate, filtered, and concentrated in vacuo to afford the title compound as a tan solid, 568 mg (95% yield) which was used without further purification.

Example 71

Synthesis of 6-(5-Chloro-2,3-dihydrobenzofuran-7-yl)-4-difluoromethyl-6-methylhept-1-yn-4-ol

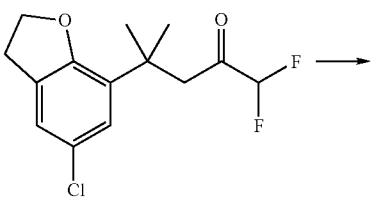

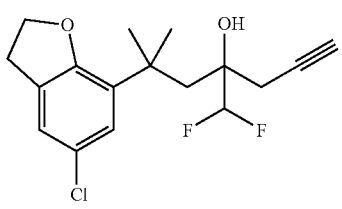

Aluminum foil (108 mg, 4.00 mmol) and mercuric chloride (ca. 1 mg, 0.01 mmol) in 3.5 mL of anhydrous THF were vigorously stirred for 20 minutes. Propargyl bromide (80% in toluene, 0.45 mL, 4.00 mmol) was added slowly (the reaction mixture became warm) and the resulting mixture was stirred at 40° C. for 1 hour. The dark gray propargyl aluminum sesquibromide solution was added to a solution of 4-(5-chloro-2,3-dihydrobenzofuran-7-yl)-1,1-difluoro-4-methyl-pentan-2-one (380 mg, 1.32 mmol) in 10 mL of anhydrous THF at 0° C. and the reaction was allowed to slowly warmed to room temperature and stirred overnight. The mixture was concentrated in vacuo, quenched with ice and water, and the aqueous layer was extracted with ethyl acetate. The combined organic extracts were dried over magnesium sulfate and concentrated in vacuo to give 420 mg of the title product as an oil (97% yield), which was used without further purification.

Example 72

Synthesis of 6-(3-[1,3]Dioxan-2-ylphenyl)-6-methyl-4-trifluoromethylhept-1-yn-4-ol

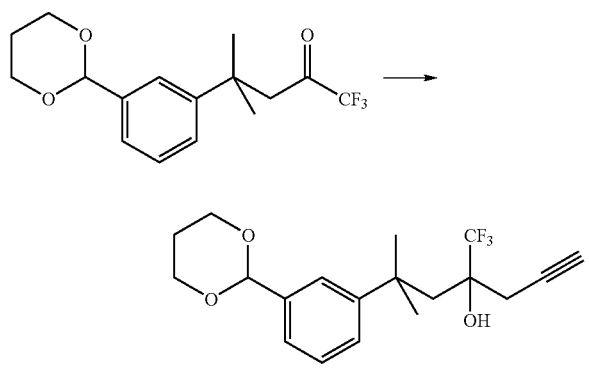

Aluminum amalgam was prepared from aluminum foil (1.16 g, 14.4 mmol) and mercuric chloride (12 mg, catalytic amount) in 20 mL of anhydrous THF by vigorously stirring the mixture at room temperature for 1 hour under an argon atmosphere. A solution of propargyl bromide (4.80 mL, 80 wt. % in toluene, 43.1 mmol) in 25 mL of anhydrous THF was slowly added to a stirred suspension maintaining a temperature of 30° C.-40° C., and after addition, stirring at 40° C. was continued until a dark gray solution was obtained (ca. 1 hour). The propargyl aluminum sesquibromide solution was added to a solution of 4-(3-[1,3]dioxan-2-ylphenyl)-1,1,1-trifluoro-4-methylpentan-2-one (5.6 g, 14.2 mmol) in 100 mL of anhydrous diethyl ether at −78° C. The reaction mixture was stirred at this temperature for 3 hours, and then was allowed to warm to room temperature, at which time it was stirred for 12 hours. The reaction mixture was then poured into 20 mL of ice-water and extracted with four 30 mL portions of diethyl ether. The combined extracts were washed with 20 mL of brine, dried over magnesium sulfate, and concentrated in vacuo. Chromatography on silica gel (100% hexanes to 40% ethyl acetate in hexanes, gradient) afforded 2.5 g of the title compound as an oil (50% yield).

Example 73

Synthesis of 6-(5-Methanesulfonyl-2,3-dihydrobenzofuran-7-yl)-6-methyl-4-trifluoromethylhept-1-yn-4-ol

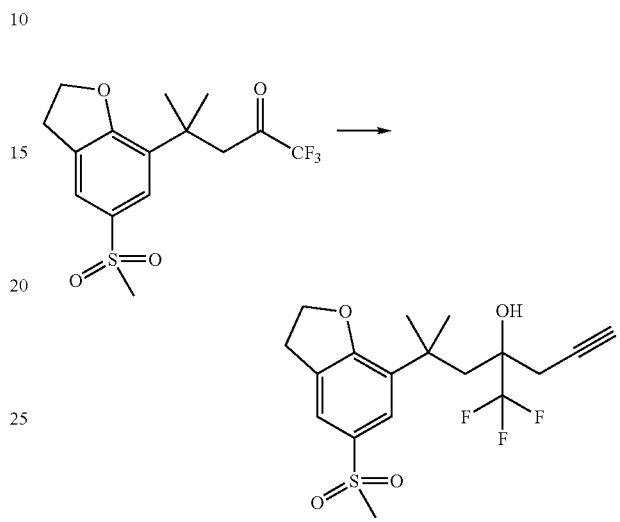

40 mL of anhydrous THF was added to a mixture of aluminum foil (1.25 g, 4.6 mmol) and mercuric chloride (100 mg, 0.37 mmol). The resulting mixture was vigorously stirred for 1 hour, cooled in an ice bath, and treated with propargyl bromide (80% by wt. solution in toluene, 62.9 mmol, 7 mL). The reaction mixture was stirred at 0° C. for 1 hour and at room temperature for 30 minutes.

A solution of 1,1,1-trifluoro-4-(5-methanesulfonyl-2,3-dihydrobenzofuran-7-yl)-4-methylpentan-2-one (5.4 g, 15.4 mmol) in a mixture of 10 mL of anhydrous diethyl ether and 10 mL of anhydrous THF was treated with the organoaluminum reagent at −78° C. After 1 hour at −78° C. and 1 hour at room temperature, the reaction mixture was quenched with saturated ammonium chloride solution and diluted with water. The aqueous layer was extracted with three 100 mL portions of ethyl acetate. The combined organic layers were washed with brine, dried over sodium sulfate, filtered, and concentrated in vacuo to give 6.3 g of the title product as a solid, which was used without further purification (quantitative yield).

Example 74

Synthesis of {4-[6-(3-[1,3]Dioxan-2-ylphenyl)-4-hydroxy-6-methyl-4-trifluoromethylhept-1-ynyl]pyridin-3-yl}carbamic acid tert-butyl ester

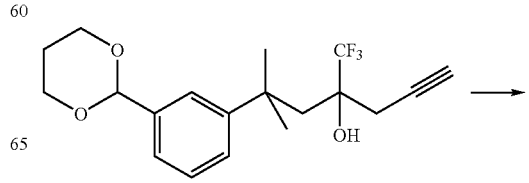

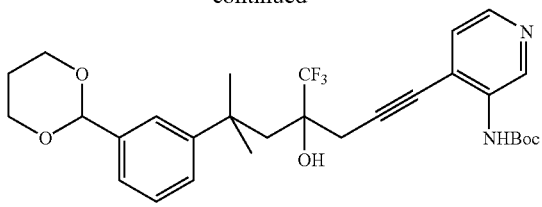

A mixture of 6-(3-[1,3]dioxan-2-ylphenyl)-6-methyl-4-trifluoromethylhept-1-yn-4-ol (300 mg, 0.84 mmol), (4-iodopyridin-3-yl)carbamic acid tert-butyl ester (270 mg, 0.84 mmol), bis(triphenylphosphine)palladium(II) chloride catalyst (29.6 mg, 0.04 mmol) and copper (I) iodide (16 mg, 0.08 mmol) in 4 mL of anhydrous triethylamine and 1 mL of anhydrous DMF was stirred at room temperature for 12 hours. The reaction mixture was then diluted with 30 nL of diethyl ether and washed with 20 mL of aqueous saturated ammonium chloride solution and 20 mL of brine. The organic layer was dried over magnesium sulfate and concentrated in vacuo. Column chromatography over silica gel with hexanes-ethyl acetate (5:1 to 1:1) provided 250 mg of the title compound as a foam (54% yield).

Example 75

Synthesis of N-{4-[6-(5-Chloro-2,3-dihydrobenzofuran-7-yl)-4-hydroxy-6-methyl-4-trifluoromethylhept-1-ynyl]-2-isopropylpyrimidin-5-yl}-2,2,2-trifluoroacetamide

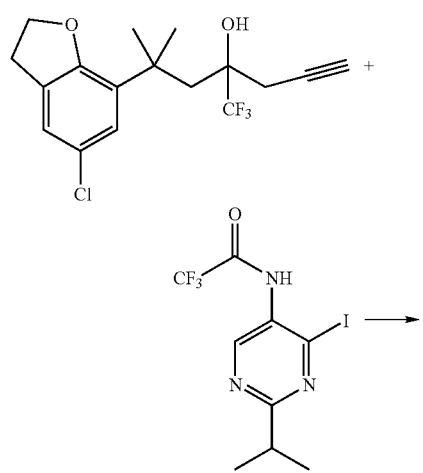

A mixture of chlorodihydrobenzofuran alkyne (185 mg, 0.533 mmol), iodopyrimidine (144 mg, 0.4 mmol), copper (I) iodide (9.5 mg, 0.05 mmol), and dichlorobis(triphenylphosphine)palladium (II) (17.5 mg, 0.025 mmol) in 0.8 mL of anhydrous acetonitrile and 0.25 mL of anhydrous triethylamine was stirred at room temperature. After 1 hour, LC-MS indicated no starting alkyne but showed a major peak at M+H=578 corresponding to the desired compound and a minor peak for the dimer at M+H=691. The crude reaction mixture was purified by silica gel column chromatography eluting with a gradient of 0%-25% ethyl acetate in hexanes to give the title compound as a brownish oil, (120 mg, 52% yield), M+H=577.

Example 76

Synthesis of 6-(5-Fluoro-2-methylphenyl)-1-(3-fluoro-2-nitrophenyl)-6-methyl-4-trifluoromethyl-hept-1-yn-4-ol

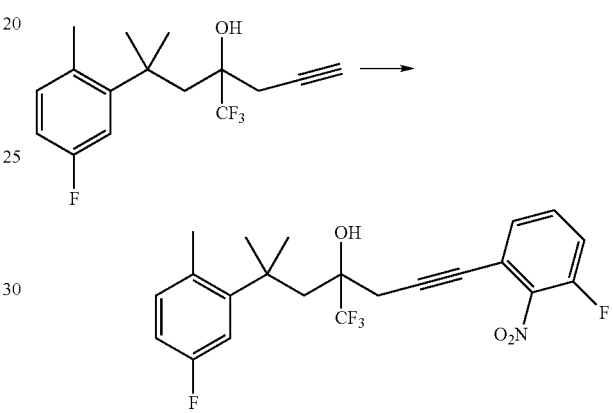

A mixture of trifluoromethanesulfonic acid 3-fluoro-2-nitrophenyl ester (149 mg, 0.52 mmol), dichlorobis(triphenylphosphine)palladium (II) (20 mg, 0.028 mmol), copper (I) iodide (14 mg, 0.074 mmol), tetrabutyl ammonium iodide (200 mg, 0.54 mmol), 0.25 mL of anhydrous triethylamine, 0.5 mL of anhydrous acetonitrile, and 0.5 mL of anhydrous tetrahydrofuran was stirred at room temperature for 30 minutes. The resulting mixture was treated with 6-(5-fluoro-2-methylphenyl)-6-methyl-4-trifluoromethylhept-1-yn-4-ol (145 mg, 0.48 mmol) and stirred at room temperature for 18 hours. The crude product was purified by chromatography on SiO$_2$ (50% hexanes in dichloromethane) to give 96 mg of the title product as light yellow oil, (45% yield).

Example 77

Synthesis of 4-[4-Hydroxy-6-(5-methanesulfonyl-2,3-dihydrobenzofuran-7-yl)-6-methyl-4-trifluoromethylhept-1-ynyl]-3-methyl-5-nitrobenzonitrile

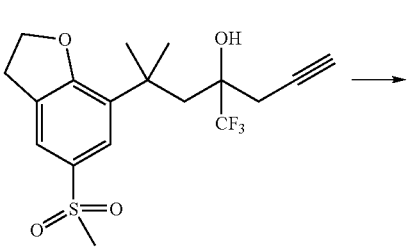

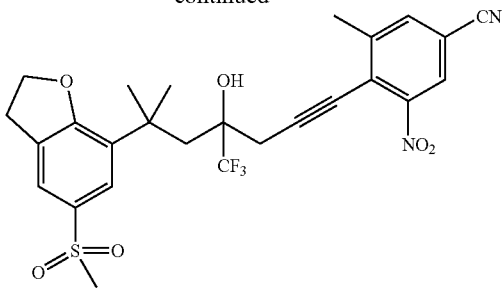

A mixture of trifluoromethanesulfonic acid 4-cyano-2-methyl-6-nitrophenyl ester (217 mg, 0.7 mmol), dichlorobis(triphenylphosphine)palladium (II) (24.6 mg, 0.035 mmol), copper (I) iodide (13.3 mg, 0.7 mmol), and 6-(5-methanesulfonyl-2,3-dihydrobenzofuran-7-yl)-6-methyl-4-trifluoromethylhept-1-yn-4-ol (273 mg, 0.7 mmol) in a mixture of 0.8 mL of anhydrous toluene and 0.3 mL of anhydrous triethylamine was heated in a microwave at 60° C. for 10 minutes. The reaction mixture was applied to a column of SiO₂ (50% ethyl acetate in hexanes) to give 165 mg of the title product as a light yellow oil (43% yield).

Example 78

Synthesis of 2-(1-Benzenesulfonyl-5-bromo-1H-indol-2-ylmethyl)-4-(5-chloro-2,3-dihydrobenzofuran-7-yl)-1,1,1-trifluoro-4-methylpentan-2-ol

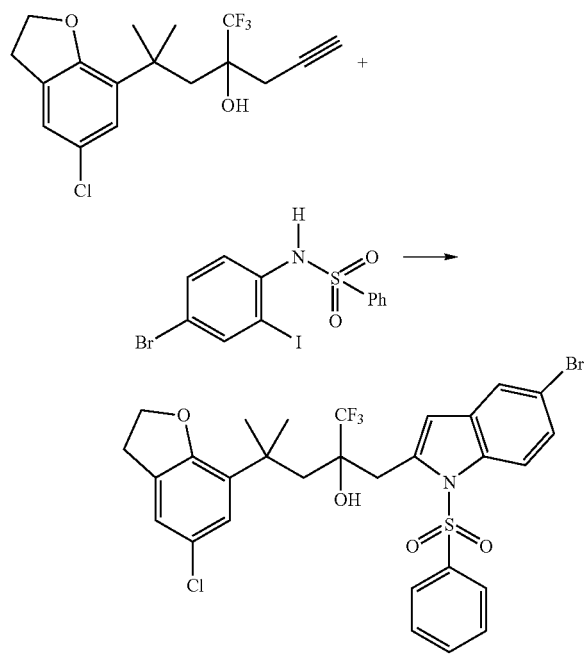

A mixture of 6-(5-chloro-2,3-dihydrobenzofuran-7-yl)-6-methyl-4-trifluoromethylhept-1-yn-4-ol (170 mg, 0.49 mmol), N-(4-bromo-2-iodophenyl)benzenesulfonamide (220 mg, 0.50 mmol), dichlorobis(triphenylphosphine)palladium (II) (20 mg, 0.03 mmol), and copper (I) iodide (10 mg, 0.05 mmol) in 1 nL of DMF and 0.7 mL of triethylamine was warmed at 70° C. After 45 minutes, the mixture was cooled and diluted with 7 mL of saturated aqueous ammonium chloride solution and extracted with three 7 mL portions of ethyl acetate. The combined organic layers were washed with two 7 mL portions of saturated aqueous ammonium chloride solution, four 7 mL portions of brine, dried over magnesium sulfate, filtered and concentrated in vacuo. The crude residue was purified on silica gel eluting with ethyl acetate-hexanes (0-30% gradient) to afford 126 mg (39% yield) of the title compound.

Example 79

Synthesis of 4-(3-[1,3]dioxan-2-ylphenyl)-1,1,1-trifluoro-4-methyl-2-(1H-pyrrolo[2,3-c]pyridin-2-ylmethyl)pentan-2-ol

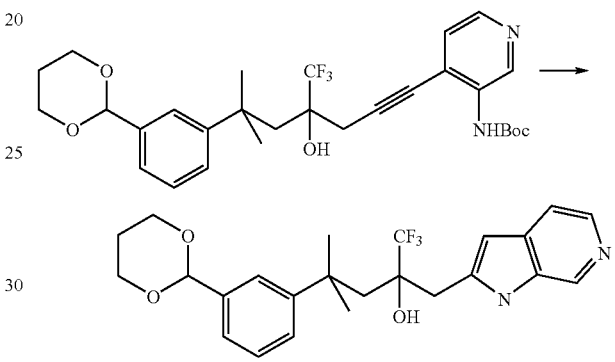

To a solution of {4-[6-(3-[1,3]dioxan-2-ylphenyl)-4-hydroxy-6-methyl-4-trifluoromethyl 1-ynyl]pyridin-3-yl}carbamic acid tert-butyl ester (250 mg, 0.46 mmol) in 5 mL of methanol-water (4:1) was added DBU (0.7 mL, 4.6 mmol) and the reaction mixture heated to 65° C. for 2 hour. The solution was concentrated in vacuo and the product precipitated from water. The precipitation was filtered and dried to give 176 mg of the title compound as a white solid (86% yield).

Example 80

Synthesis of 4-(5-Chloro-2,3-dihydrobenzofuran-7-yl)-1,1,1-trifluoro-2-(2-isopropyl-5H-pyrrolo[3,2-d]pyrimidin-6-ylmethyl)-4-methylpentan-2-ol

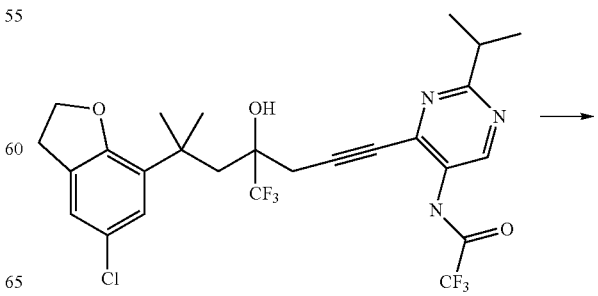

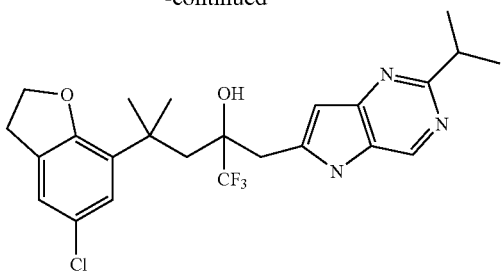

To a solution of N-{4-[6-(5-chloro-2,3-dihydrobenzofuran-7-yl)-4-hydroxy-6-methyl-4-trifluoromethylhept-1-ynyl]-2-isopropylpyrimidin-5-yl}-2,2,2-trifluoroacetamide (58 mg, 0.1 mmol) in 1 mL of anhydrous dioxane was added tetramethylguanidine (0.05 mL, 0.4 mmol) and the reaction mixture stirred and heated in oil bath maintained at 100° C. for 1 hour. Purification by preparative TLC over silica gel eluting with 5% methanol in dichloromethane provided the title compound as a light cream colored solid, (25 mg, 52% yield) M+H=482.

Example 81

Synthesis of 2-[2-Hydroxy-4-(5-methanesulfonyl-2,3-dihydrobenzofuran-7-yl)-4-methyl-2-trifluoromethylpentyl]-4-methyl-1H-indole-6-carbonitrile

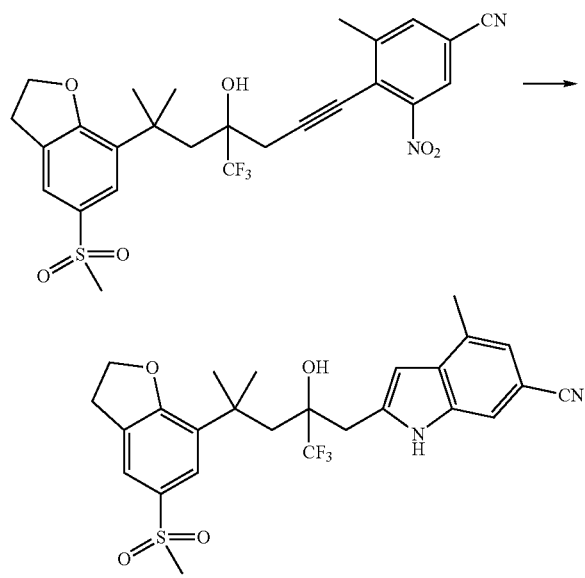

A stirred solution of 4-[4-hydroxy-6-(5-methanesulfonyl-2,3-dihydrobenzofuran-7-yl)-6-methyl-4-trifluoromethylhept-1-ynyl]-3-methyl-5-nitrobenzonitrile. (165 mg, 0.3 mmol) in 6 mL of absolute ethanol was treated with 4 mL of glacial acetic acid and iron powder (335 mg, 6 mmol). The resulting mixture was heated at 90° C. for 30 minutes, cooled to room temperature, diluted with 200 mL of dichloromethane, and filtered through a pad of CELITE® filter aid. The filtrate was washed with three 50 mL portions of saturated aqueous sodium carbonate solution and two 25 mL portions of brine, dried over sodium sulfate, filtered, and concentrated in vacuo to give 140 mg of 3-amino-4-[4-hydroxy-6-(5-methanesulfonyl-2,3-dihydrobenzofuran-7-yl)-6-methyl-4-trifluoromethylhept-1-ynyl]-5-methylbenzonitrile as a light brownish oil (90% yield).

A stirred solution of 3-amino-4-[4-hydroxy-6-(5-methanesulfonyl-2,3-dihydrobenzofuran-7-yl)-6-methyl-4-trifluoromethylhept-1-ynyl]-5-methylbenzonitrile (140 mg, 0.27 mmol) in 5 mL of anhydrous dichloromethane was cooled in an ice bath and treated with trifluoroacetic anhydride (0.075 mL, 0.54 mmol). After 5 minutes, the mixture was concentrated in vacuo. Chromatography on SiO₂ (100% dichloromethane) gave 155 mg of N-{5-cyano-2-[4-hydroxy-6-(5-methanesulfonyl-2,3-dihydrobenzofuran-7-yl)-6-methyl-4-trifluoromethylhept-1-ynyl]-3-methylphenyl}-2,2,2-trifluoroacetamide as a light brownish oil (93% yield).

A solution of N-{5-cyano-2-[4-hydroxy-6-(5-methanesulfonyl-2,3-dihydrobenzofuran-7-yl)-6-methyl-4-trifluoromethylhept-1-ynyl]-3-methylphenyl}-2,2,2-trifluoroacetamide (154 mg, 0.25 mmol) in 0.6 mL of anhydrous DMSO was heated in the presence of 1,1,3,3-tetramethylguanidine (0.094 mL, 0.75 mmol) in a microwave at 140° C. for 10 minutes. The reaction was quenched with a mixture of 1 N sulfuric acid and 10 mL of crushed ice. The resulting precipitate was filtered, washed with water, and dried. Preparative TLC chromatography (50% ethyl acetate in hexanes, followed by 15% ethyl acetate in dichloromethane) gave 23 mg of the title product as an off-white solid (18% yield).

Example 82

Synthesis of 1,1,1-Trifluoro-2-(7-fluoro-1H-indol-2-ylmethyl)-4-(5-fluoro-2-methylphenyl)-4-methylpentan-2-ol

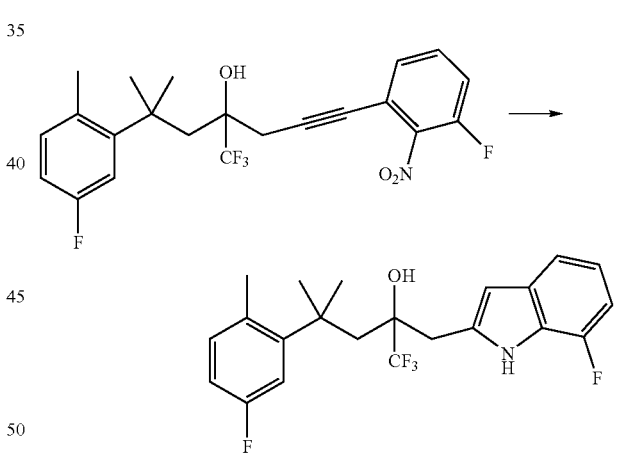

A stirred solution of 6-(5-fluoro-2-methylphenyl)-1-(3-fluoro-2-nitrophenyl)-6-methyl-4-trifluoromethylhept-1-yn-4-ol (1.05 g, 2.4 mmol) in 6 mL of absolute ethanol and 2 mL of glacial acetic acid was treated with iron powder (800 mg, 14.3 mmol). The resulting mixture was heated at 80° C. for 2 hours, cooled to room temperature, diluted with diethyl ether, filtered through a pad of CELITE® filter aid, and concentrated in vacuo. The residue was dissolved in diethyl ether, treated with anhydrous potassium carbonate, filtered, and concentrated in vacuo to give 900 mg of 1-(2-amino-3-fluorophenyl)-6-(5-fluoro-2-methylphenyl)-6-methyl-4-trifluoromethylhept-1-yn-4-ol as a light brownish oil (92% yield), which was used without purification.

A solution of 1-(2-amino-3-fluorophenyl)-6-(5-fluoro-2-methylphenyl)-6-methyl-4-trifluoromethylhept-1-yn-4-ol (900 mg, 2.2 mmol) in 10 mL of anhydrous dioxane was treated with dichlorobis(triphenylphosphine)palladium (II) (250 mg, 0.36 mmol) and the mixture was heated at 100° C. for 60 hours. The crude reaction mixture was purified on SiO$_2$ (20% dichloromethane in hexanes) to afford 700 mg of the title product as a yellow oil (78% yield).

Example 83

Synthesis of 4-(5-Chloro-2,3-dihydrobenzofuran-7-yl)-1,1,1-trifluoro-4-methyl-2-(5-pyridin-2-yl-1H-indol-2-ylmethyl)pentan-2-ol

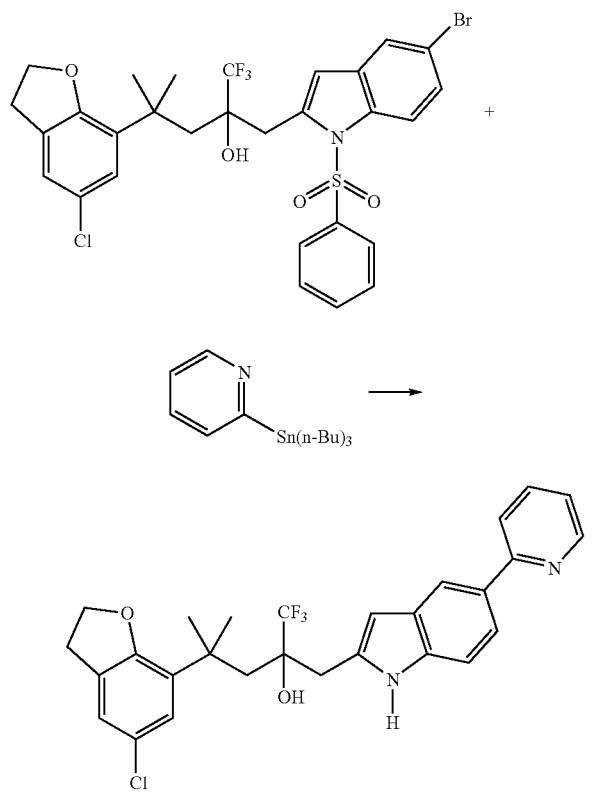

A mixture of 2-(1-benzenesulfonyl-5-bromo-1H-indol-2-ylmethyl)-4-(5-chloro-2,3-dihydrobenzofuran-7-yl)-1,1,1-trifluoro-4-methylpentan-2-ol (30 mg, 0.046 mmol), 2-tributylstannanylpyridine (72 mg, 0.196 mmol) and dichlorobis(triphenylphosphine)palladium (II) (10 mg) was warmed at reflux for 2 hours. The mixture was then cooled and diluted with diethyl ether, a few drops of DBU were added, and the mixture was diluted with water and extracted with ethyl acetate. The crude material was partially purified on silica gel by preparative TLC eluting with ethyl acetate-hexanes (35:65) to afford partially purified product contaminated with tin byproducts.

A mixture of the above 2-(1-benzenesulfonyl-5-pyridin-2-yl-1H-indol-2-ylmethyl)-4-(5-chloro-2,3-dihydrobenzofuran-7-yl)-1,1,1-trifluoro-4-methylpentan-2-ol (30.1 mg, 0.046 mmol, theoretical maximum from above) in 5 mL of methanol and 5 mL of 10% aqueous sodium hydroxide solution was warmed at reflux. After 4 hours, the mixture was diluted with 7 mL of brine and extracted with three 5 mL portions of ethyl acetate. The combined organic layers were washed with three 5 mL portions of saturated aqueous sodium bicarbonate solution, 5 mL of brine, two 5 mL portions of saturated aqueous ammonium chloride solution, 5 mL of brine, dried over magnesium sulfate, filtered and concentrated in vacuo. The crude material was purified by silica gel preparative TLC using ethyl acetate-hexanes (1:1). The material from the preparative TLC plate when concentrated in vacuo from diethyl ether-hexanes afforded 10 mg (42% yield) of the title compound.

Example 84

Synthesis of 1,1,1-Trifluoro-4-(5-fluoro-2,3-dihydrobenzofuran-7-yl)-4-methyl-2-(5-pyridin-3-yl-1H-indol-2-ylmethyl)pentan-2-ol

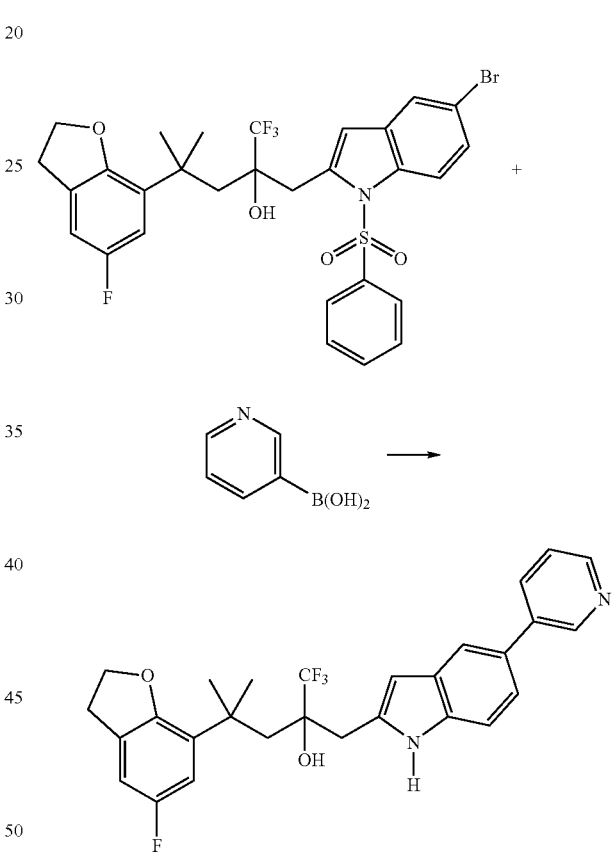

A mixture of 2-(1-benzenesulfonyl-5-bromo-1H-indol-2-ylmethyl)-1,1,1-trifluoro-4-(5-fluoro-2,3-dihydrobenzofuran-7-yl)-4-methylpentan-2-ol (100 mg, 0.156 mmol), pyridine-3-boronic acid (80 mg, 0.65 mmol), and tetrakis(triphenylphosphine)palladium (0) (25 mg, 0.022 mmol) in 6 mL of toluene, 3 mL of ethanol, and 1.5 mL of 2 M aqueous sodium carbonate solution was heated at reflux. The reaction was monitored by TLC (ethyl acetate-hexanes (6:4)). The mixture was then diluted with saturated aqueous ammonium chloride solution and extracted with three 10 mL portions of ethyl acetate. The combined organic layers were washed with three 10 mL portions of brine, dried over magnesium sulfate, filtered, and concentrated in vacuo. The crude material was purified on silica gel using ethyl acetate-hexanes (gradient 10-60%) to afford 88 mg (88% yield) of material. Recrystallization from diethyl ether-hexanes afforded 76 mg (76% yield) of 2-(1-benzenesulfonyl-5-pyridin-3-yl-1H-indol-2-ylmethyl)-1,1,1-trifluoro-4-(5-fluoro-2,3-dihydrobenzofuran-7-yl)-4-methylpentan-2-ol.

To a solution of the above 2-(1-benzenesulfonyl-5-pyridin-3-yl-1H-indol-2-ylmethyl)-1,1,1-trifluoro-4-(5-fluoro-2,3-dihydrobenzofuran-7-yl)-4-methylpentan-2-ol (71 mg, 0.11 mmol) in 5 mL of THF was added a 1 M solution of tetrabutylammonium fluoride (0.5 mL, 0.5 mmol) in THF and the mixture was warmed at 80° C. After 18 hours, the mixture was concentrated in vacuo and diluted with 1 N aqueous sodium hydroxide solution and extracted with three 5 mL portions of ethyl acetate. The combined organic layers were washed with two 5 mL portions of 1 N aqueous sodium hydroxide solution, 5 mL of brine, three 5 mL portions of saturated aqueous ammonium chloride solution, dried over magnesium sulfate, filtered, and concentrated in vacuo. The residue was purified on silica gel eluting with methanol-dichloromethane (0:100, then 0.5:99.5, then 1:99) to afford 46 mg (83% yield) of the title compound.

Example 85

Synthesis of 1,1,1-Trifluoro-4-(2-methoxy-5-pyridin-3-ylphenyl)-4-methyl-2-(1H-pyrrolo[2,3-c]pyridin-2-ylmethyl)pentan-2-ol

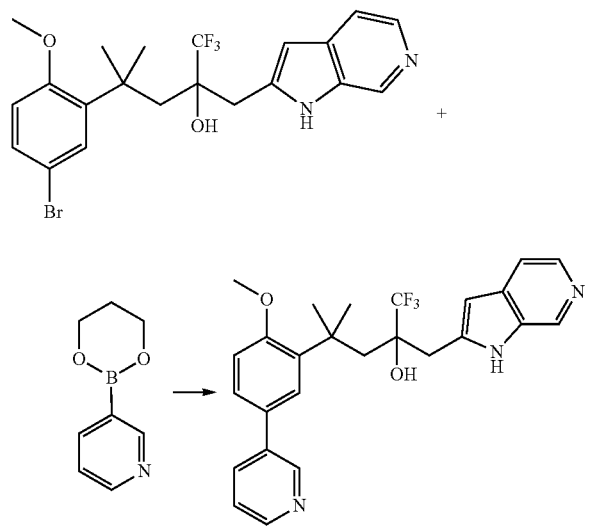 [SMILES: COc1ccc(Br)cc1C(C)(C)CC(O)(Cc1cc2ccncc2[nH]1)C(F)(F)F ; c1cncc(B2OCCCO2)c1 ; COc1ccc(-c2cccnc2)cc1C(C)(C)CC(O)(Cc1cc2ccncc2[nH]1)C(F)(F)F]

A mixture of 4-(5-bromo-2-methoxyphenyl)-1,1,1-trifluoro-4-methyl-2-(1H-pyrrolo[2,3-c]pyridin-2-ylmethyl)pentan-2-ol (188 mg, 0.4 mmol), pyridine 3-boronic acid 1,3-propanediol cyclic ester (89 mg, 0.6 mmol), potassium carbonate ($K_2CO_3$; 166 mg, 1.2 mmol), and $Pd(PPh_3)_4$ (46.2 mg, 0.04 mmol) in 3.0 mL of DME-MeOH-DMF (1:1.5:0.5) was microwaved for 20 minutes at 120° C., cooled to room temperature, diluted with 20 mL of ethyl acetate and filtered through diatomaceous earth. The filtrate was washed with 5 mL of 1.0 M aqueous sodium hydroxide solution, water, and brine, dried over magnesium sulfate, and concentrated in vacuo. The residue was purified by silica gel chromatography to yield 90 mg (48% yield) of the title compound as a white foam.

Example 86

Synthesis of 1,1,1-Trifluoro-4-(4-methoxybiphenyl-3-yl)4-methyl-2-(1H-pyrrolo[2,3-c]pyridin-2-ylmethyl)pentan-2-ol

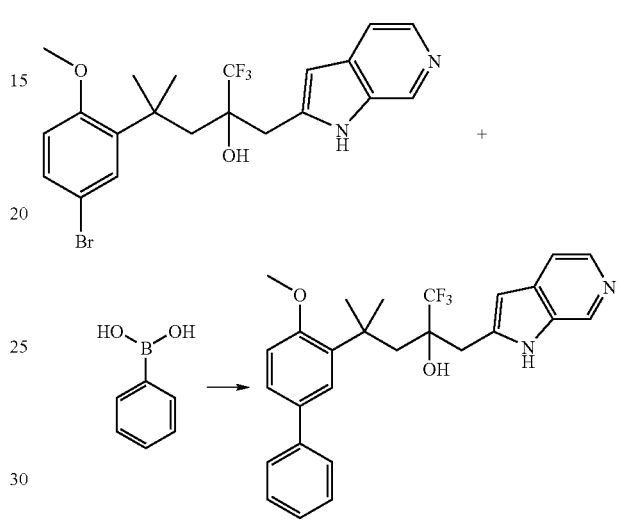

A mixture of 4-(5-bromo-2-methoxyphenyl)-1,1,1-trifluoro-4-methyl-2-(1H-pyrrolo[2,3-c]pyridin-2-ylmethyl) pentan-2-ol (188 mg, 0.4 mmol), $Pd(OAc)_2$ (9 mg, 0.04 mmol), DCyBPP ((2-dicyclohexylphosphino)biphenyl, 28 mg, 0.08 mmol), and KF (93 mg, 1.6 mmol) in 3 mL of THF at room temperature was treated with phenylboronic acid (74 mg, 0.6 mmol). The reaction mixture was microwaved for 20 minutes at 120° C., cooled to room temperature, diluted with 20 mL of ethyl acetate and filtered through diatomaceous earth. The filtrate was washed with 5 mL of 1.0 M aqueous sodium hydroxide solution, water, and 5 mL of brine. The organic phase was dried over magnesium sulfate, filtered, and the solvent evaporated in vacuo. The residue was purified silica gel chromatography to provide 75 mg (40% yield) of the title compound as a white solid.

Example 87

Synthesis of 2-(3-Chloro-1H-pyrrolo[3,2-c]pyridin-2-ylmethyl)-1,1,1-trifluoro-4-(5-fluoro-2-methoxyphenyl)-4-methylpentan-2-ol

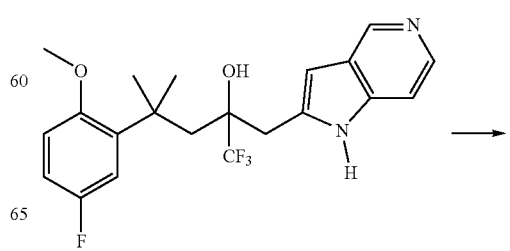

-continued

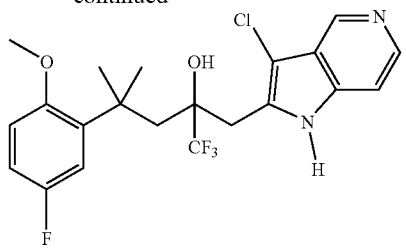

A solution of trichloroacetyl chloride (0.045 mL, 0.403 mmol) in 0.5 mL of DMF was treated with a solution of 1,1,1-trifluoro-4-(5-fluoro-2-methoxyphenyl)-4-methyl-2-(1H-pyrrolo[3,2-c]pyridin-2-ylmethyl)pentan-2-ol (33.0 mg, 0.081 mmol) in 0.5 mL of DMF at room temperature. After 2 days, the reaction was quenched with 2 mL of ice-water and 2 mL of cold 1 N sodium hydroxide solution. The resulting mixture was extracted with three 5 mL portions of ethyl acetate. The combined organic layers were dried over magnesium sulfate, filtered, and concentrated in vacuo. Chromatography on SiO$_2$ (100% dichloromethane to 10% methanol in dichloromethane, gradient) gave 20.0 mg of the title product (56% yield).

Example 88

Synthesis of 2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid methyl ester

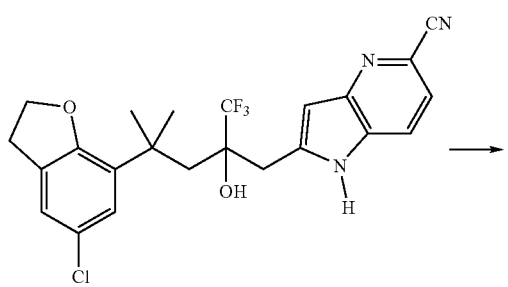

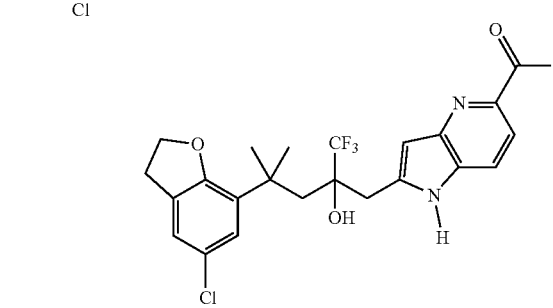

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile (300 mg, 0.65 mmol) was dissolved in 10 mL of methanol at room temperature. HCl gas was introduced for 2 minutes. The mixture was heated to reflux overnight. The solvent was removed in vacuo. The residue was diluted with 50 mL of ethyl acetate and neutralized with 30 mL of a saturated sodium carbonate solution. The organic layer was separated. The aqueous layer was extracted with three 50 mL portions of ethyl acetate. The organic layers were combined, washed with brine, dried over sodium sulfate, and the solvent was removed in vacuo. The residue was purified by flash chromatography (deactivated SiO$_2$ with 2% triethylamine, eluting with CH$_2$Cl$_2$ to CH$_2$Cl$_2$-MeOH (95:5)) to give the title compound (263 mg, 82% yield).

Example 89

Synthesis of 2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid

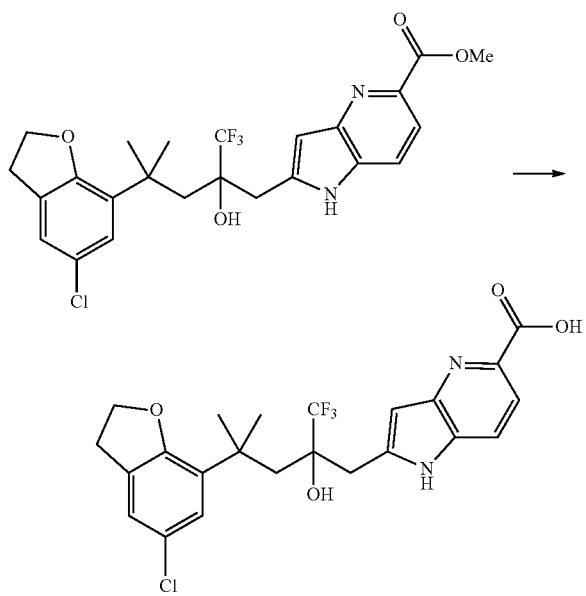

2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid methyl ester (100 mg, 0.2 mmol) was dissolved in 2 mL of THF-MeOH-water (3:1:1). Lithium hydroxide monohydrate (25 mg, 0.6 mmol) was added. The reaction was stirred at room temperature for 4 hours. The mixture was diluted with 5 mL of water and 6 N HCl solution was used to adjust the pH to about 2. The organic was extracted with three 50 mL portions of ethyl acetate, washed with brine, and dried over anhydrous sodium sulfate. The solvent was removed in vacuo to give the title compound (13.5 mg, 14% yield).

Example 90

Synthesis of 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}ethanone

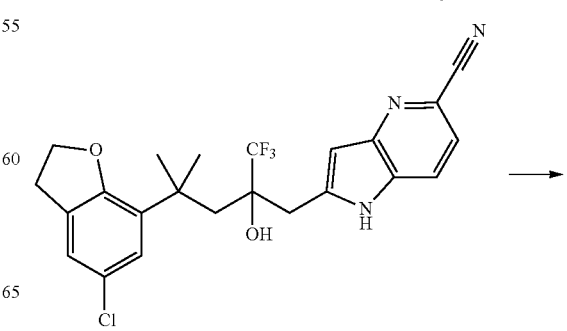

-continued

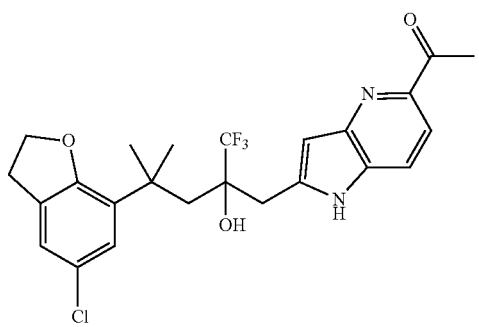

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile (100 mg, 0.22 mmol) was dissolved in 6 mL of THF. The solution was cooled to −78° C. Methyl magnesium iodide (3 M in diethyl ether, 1.2 mL, 3.6 mmol) was added. The reaction was stirred overnight and the temperature was allowed to come to room temperature. The reaction was quenched with 10 mL of saturated aqueous ammonium chloride solution and extracted with three 50 mL portions of ethyl acetate. The organic layers were combined and dried over magnesium sulfate. The solvent was removed in vacuo. The residue was purified by flash chromatography (eluting with CH$_2$Cl$_2$ to 95:5 CH$_2$Cl$_2$-MeOH) to give the title compound (36 mg, 35% yield).

Example 91

Synthesis of 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2-methylpropan-1-one

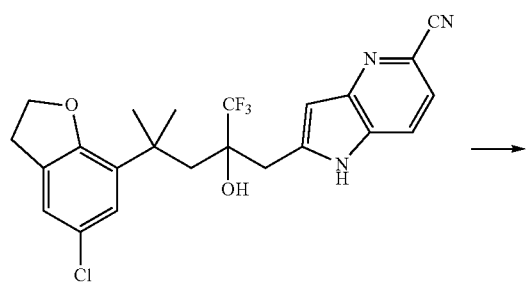

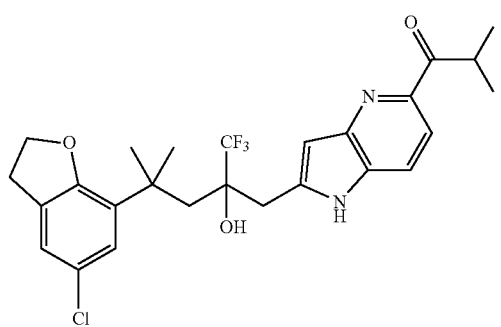

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile (50 mg, 0.11 mmol) was dissolved in 3 mL of THF. Isopropyl magnesium chloride (2 M in THF, 0.15 mL, 0.3 mmol) was added, followed by CuBr (7 mg, 0.05 mmol). The reaction was stirred at reflux (75° C.) for 30 minutes. The mixture was cooled to room temperature. The reaction was quenched with 1 mL of water, followed by 3 drops of concentrated HCl. The mixture was stirred for 10 minutes, and neutralized with saturated sodium carbonate solution until the pH was 8. The reaction mixture was extracted with ethyl acetate and washed with brine. The solvent was removed in vacuo. The residue was purified by preparative HPLC (medium polar condition) to give the title compound (39 mg, 70% yield).

Example 92

Synthesis of 2-(5-Aminomethyl-1H-pyrrolo[3,2-b]pyridin-2-ylmethyl)-4-(5-chloro-2,3-dihydrobenzofuran-7-yl)-1,1,1-trifluoro-4-methylpentan-2-ol

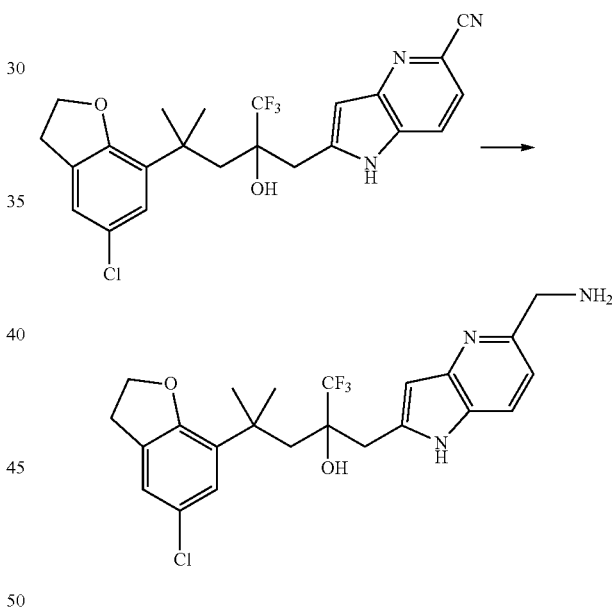

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile (100 mg, 0.22 mmol) was dissolved in 3 mL of THF and borane-methyl sulfide (10 M, 0.065 mL, 0.648 mmol) was added. The reaction was heated at reflux for 1 hour and then cooled to room temperature. 1 mL of a 6 N HCl solution was then added. The reaction was heated at reflux overnight. The reaction was cooled to room temperature, diluted with 50 mL of ethyl acetate, and then quenched with saturated sodium carbonate solution until the pH was 12. The organic layer was separated and aqueous layer was extracted with three 50 mL portions of ethyl acetate. The combined organic fractions were dried over sodium sulfate and the solvent was removed in vacuo. The residue was purified by preparative HPLC (polar condition) to give the title compound (49 mg, 49% yield).

Example 93

Synthesis of 4-(5-chloro-2,3-dihydrobenzofuran-7-yl)-1,1,1-trifluoro-2-(5-hydroxymethyl-1H-pyrrolo[3,2-b]pyridin-2-ylmethyl)-4-methylpentan-2-ol

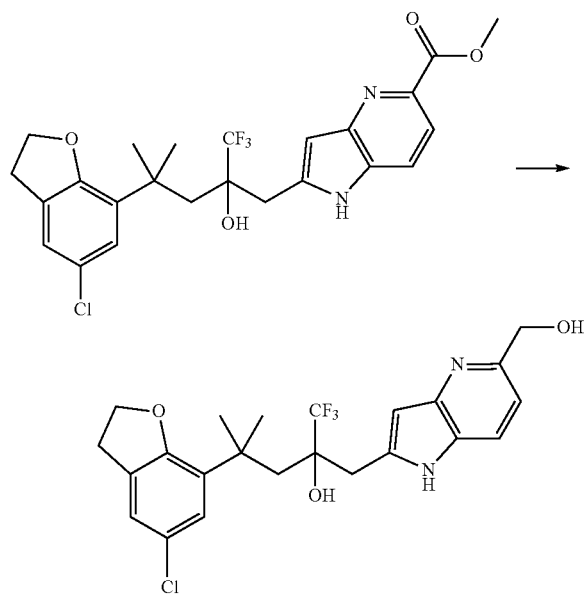

To a solution of the starting ester (0.995 g, 2.00 mmol) in 35.0 mL of THF was added lithium aluminum hydride (2.40 mL, 2.40 mmol) dropwise at 0° C. The reaction was allowed to come to room temperature then stirred for 2 hours. TLC analysis (5% MeOH—CH$_2$Cl$_2$, 0.5% NH$_4$OH) showed the appearance of one product spot and consumption of all starting material. The solution was diluted with 50 mL of THF and quenched with a water-THF solution (3.0 mL of water and 50 mL of THF). To this magnesium sulfate was added and the resulting slurry was stirred for 30 minutes. The suspension was filtered through diatomaceous earth and the THF was evaporated to give the title compound as a yellow foam (0.882 g, 94.0% yield).

Example 94

Synthesis of 2-[4-(5-Chloro-2,3-dihydrobenzofuran-7-yl)-2-hydroxy-4-methyl-2-trifluoromethylpentyl]-1H-pyrrolo[3,2-b]pyridine-5-carbaldehyde

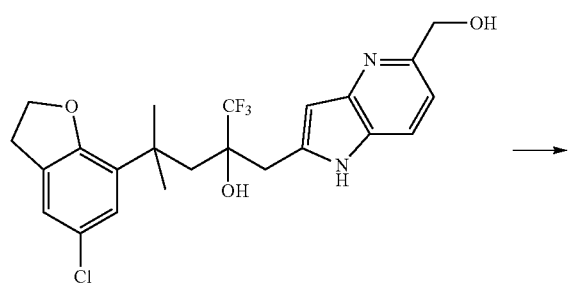

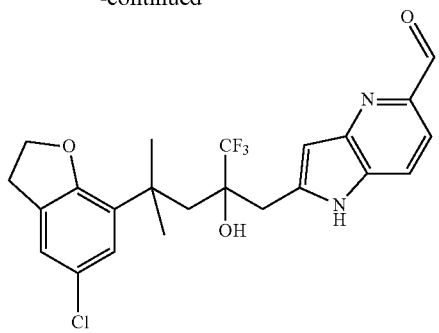

To a solution of alcohol of Example 93 (0.882 g, 1.88 mmol) in 25 mL of acetone was added manganese (IV) oxide (3.99 g, 9.41 mmol). The black suspension was stirred at room temperature for 1 hour. The solution was filtered through diatomaceous earth and the acetone was evaporated in vacuo to give the title compound (0.625 g, 74.0% yield) as a yellow foam.

Example 95

Synthesis of 4-(5-Chloro-2,3-dihydrobenzofuran-7-yl)-1,1,1-trifluoro-4-methyl-2-(5-morpholin-4-ylmethyl-1H-pyrrolo[3,2-b]pyridin-2-ylmethyl)pentan-2-ol

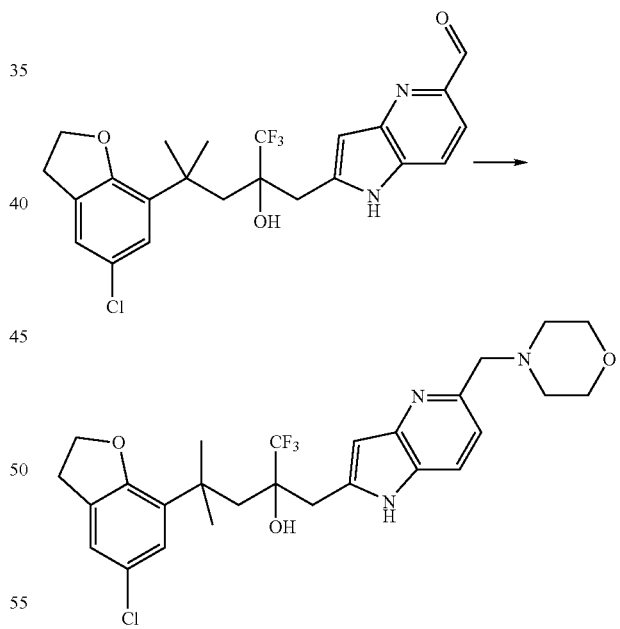

To a solution of the aldehyde of Example 94 (0.050 g, 0.107 mmol) and 0.078 mL of acetic acid in 3.0 mL of dichloroethane was added morpholine (0.233 mL, 2.68 mmol) at 0° C. The reaction was allowed to stir at room temperature for 30 minutes. To this yellow solution was added triacetoxy sodium borohydride (0.057 mg, 0.268 mmol), then continued stirring at room temperature for 14 hours. The reaction mixture was diluted with 10 mL of ethyl acetate and 2 mL of 3% ammonium hydroxide solution. The biphasic system was separated and the aqueous phase was extracted with ethyl acetate. The

Example 96

Synthesis of 3-[4,4,4-Trifluoro-3-hydroxy-1,1-dimethyl-3-(1H-pyrrolo[2,3-c]pyridin-2-ylmethyl)butyl]benzaldehyde

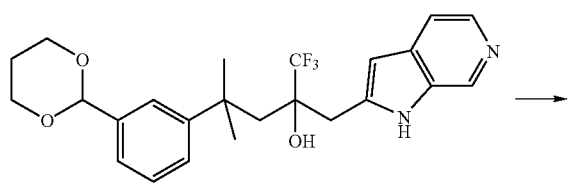

A mixture of 4-(3-[1,3]dioxan-2-ylphenyl)-1,1,1-trifluoro-4-methyl-2-(1H-pyrrolo[2,3-c]pyridin-2-ylmethyl)pentan-2-ol (160 mg, 0.36 mmol), 2 mL of ethanol, 1 mL of water, and pyridinium p-toluenesulfonic acid (200 mg, 0.8 mmol) was stirred at room temperature for 14 hours and then concentrated in vacuo to remove ethanol. The residue was diluted with ethyl acetate and water. The aqueous layer was extracted with ethyl acetate. The combined organic layers were washed with aqueous saturated sodium bicarbonate solution and brine, and dried over sodium sulfate. Removal of the solvent in vacuo afforded 134 mg (95% yield) of the title compound.

Example 97

Synthesis of 1,1,1-Trifluoro-4-methyl-4-(3-morpholin-4-ylmethylphenyl)-2-(1H-pyrrolo[2,3-c]pyridin-2-ylmethyl)pentan-2-ol

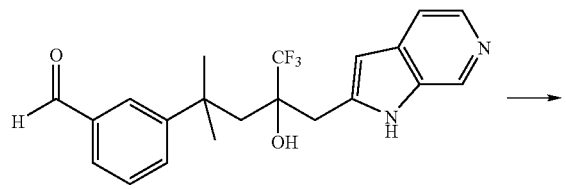

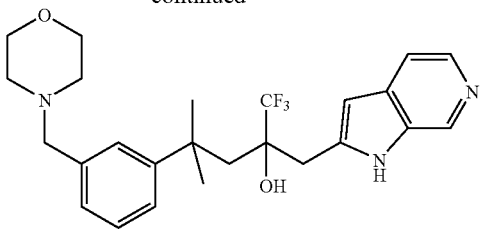

To a solution of 3-[4,4,4-trifluoro-3-hydroxy-1,1-dimethyl-3-(1H-pyrrolo[2,3-c]pyridin-2-ylmethyl)butyl]benzaldehyde (50 mg, 0.13 mmol), 3 mL of dichloroethane, and acetic acid (0.1 mL, 1.6 mmol) in an ice bath was added morpholine (0.28 mL, 3.20 mmol) in one batch. The solution was warmed to room temperature and stirred for 0.5 hours. Triacetoxy sodium borohyride (68 g, 0.32 mmol) was added in a single portion and the reaction stirred at room temperature for 3.0 hours. The solution was diluted with ethyl acetate and 3 mL of 3% ammonium hydroxide solution was added. The biphasic system was transferred to a separatory funnel and the aqueous layer was removed and back-extracted with ethyl acetate. The combined organic layers were washed with brine, dried over magnesium sulfate, filtered, and the solvent was evaporated in vacuo. The product was eluted from a flash chromatography column with dichloromethane-methanol, and evaporation of the solvent in vacuo yielded the title compound (27 mg, 45% yield).

Example 98

Synthesis of 7-[3-(5-Bromo-1H-indol-2-ylmethyl)-4,4,4-trifluoro-3-hydroxy-1,1-dimethylbutyl]-2,3-dihydrobenzofuran-5-sulfonic acid amide

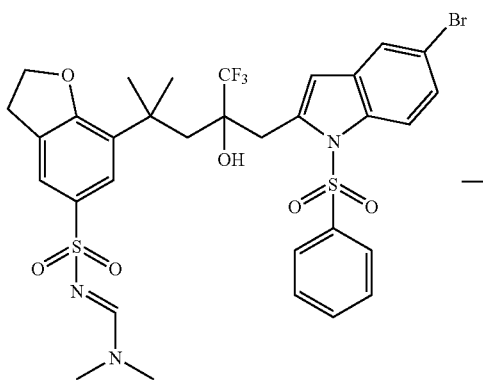

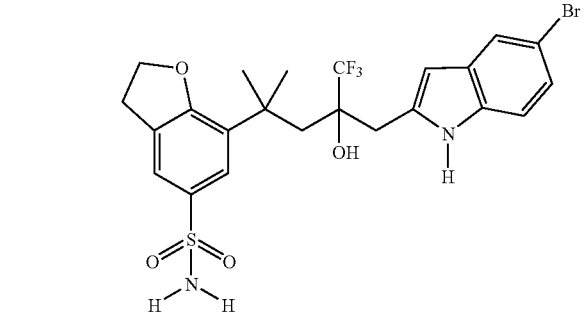

A mixture of 7-[3-(1-benzenesulfonyl-5-bromo-1H-indol-2-ylmethyl)-4,4,4-trifluoro-3-hydroxy-1,1-dimethylbutyl]-

2,3-dihydrobenzofuran-5-sulfonic acid 1-dimethylaminometh(E)-ylideneamide (167 mg, 0.22 mmol) in 10 mL of methanol and 3 mL of 10% aqueous sodium hydroxide solution was warmed at reflux. After 24 hours, the mixture was diluted with 10 mL of brine and extracted with three 10 mL portions of ethyl acetate. The combined organic layers were washed with two 5 mL portions of saturated aqueous sodium bicarbonate solution, 5 mL of brine, three 5 mL portions of saturated aqueous ammonium chloride solution, 5 mL of brine, dried over magnesium sulfate, filtered, and concentrated in vacuo. The crude material was chromatographed on silica gel using ethyl acetate-hexanes (0-50% gradient) and then triturated with diethyl ether-hexanes to afford 79 mg (64% yield) of the title compound.

Example 99

Synthesis of 2-(5-Bromo-1H-indol-2-ylmethyl)-4-(5-chloro-2,3-dihydrobenzofuran-7-yl)-1,1,1-trifluoro-4-methylpentan-2-ol

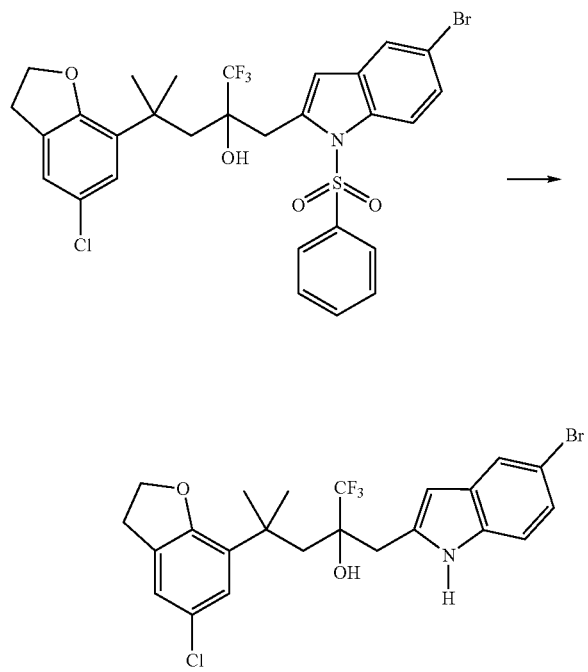

A mixture of 2-(1-benzenesulfonyl-5-bromo-1H-indol-2-ylmethyl)-4-(5-chloro-2,3-dihydrobenzofuran-7-yl)-1,1,1-trifluoro-4-methylpentan-2-ol (30 mg, 0.046 mmol) in 5 mL of methanol and 5 mL of 10% aqueous sodium hydroxide solution was warmed at reflux. After 18 hours, the mixture was diluted with brine and extracted with three 7 mL portions of ethyl acetate. The combined organic layers were washed with three 5 mL portions of brine, three 5 mL portions of saturated aqueous ammonium chloride solution, 5 mL of brine, dried over magnesium sulfate, filtered, and concentrated in vacuo. The crude material was purified by preparative TLC (1 mm, silica gel, ethyl acetate-hexanes (3:7)) to afford 15 mg (63% yield) of the title compound.

Example 100

Synthesis of 1,1,1-Trifluoro-4-(5-fluoro-2,3-dihydrobenzofuran-7-yl)-2-(5-methanesulfinyl-1H-indol-2-ylmethyl)-4-methylpentan-2-ol

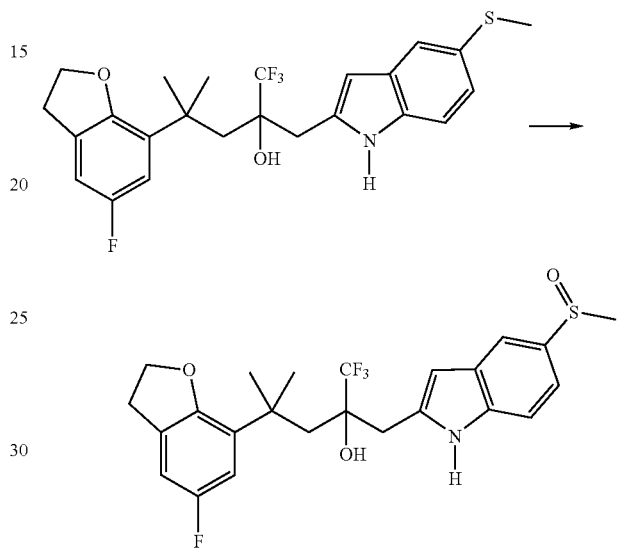

To a solution of 1,1,1-trifluoro-4-(5-fluoro-2,3-dihydrobenzofuran-7-yl)-4-methyl-2-(5-methylsulfanyl-1H-indol-2-ylmethyl)pentan-2-ol (25 mg, 0.053 mmol) in 10 mL of methanol was added sodium periodate (150 mg, 0.70 mmol). After 1 hour, the mixture was diluted with brine and extracted with three 10 mL portions of ethyl acetate. The combined organic layers were washed with three 7 mL portions of brine, dried over magnesium sulfate, filtered, and concentrated in vacuo. The crude residue was purified by preparative TLC on silica gel eluting with ethyl acetate to afford 19.8 mg (77% yield) of the title compound.

Example 101

Synthesis of 2-(1-Fluorocyclopropyl)-4-(5-fluoro-2-methoxyphenyl)-4-methyl-1-(1H-pyrrolo[2,3-c]pyridin-2-yl)pentan-2-ol

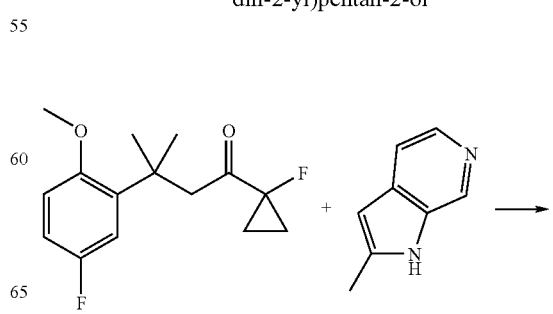

-continued

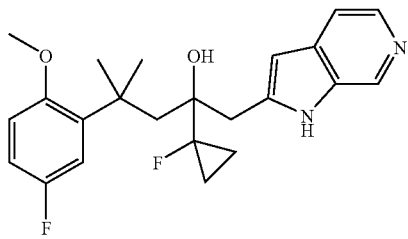

To a solution of 2-methyl-1H-pyrrolo[2,3-c]pyridine (80.0 mg, 0.605 mmol) in 2 mL of THF cooled to −78° C. was added 0.70 mL of n-BuLi (1.6 M in hexanes). After 5 minutes, tert-BuOK (1 M in THF, 0.75 mL) was added and the mixture was warmed to room temperature for 1 hour. The mixture was cooled to −78° C. and the above 1-(1-fluorocyclopropyl)-3-(5-fluoro-2-methoxyphenyl)-3-methylbutan-1-one (150 mg, 0.600 mmol) was added as a solution in 0.5 mL of THF. The mixture was stirred for 30 minutes at −78° C. and warmed to room temperature. 5 mL of ethyl acetate was added and the organic phase was washed with water, dried, filtered, and evaporated. Preparative layer chromatography (developer: dichloromethane-ethanol (95:5)) gave 100 mg of the title compound as an oil that solidified on standing (45% yield).

Example 102

Synthesis of 2-(1-Fluorocyclopropyl)-4-(4-fluorophenyl)-4-methyl-1-quinolin-4-ylpentan-2-ol

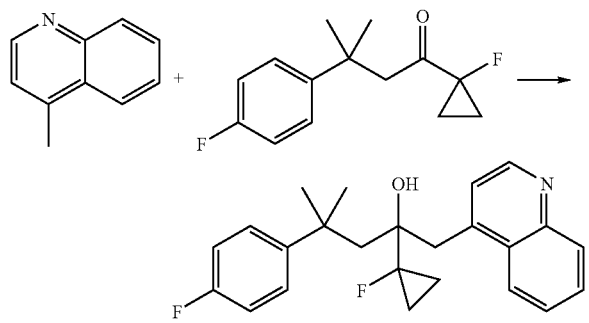

To a solution of 4-methylquinoline (69 mg, 0.482 mmol) in THF cooled on dry ice/acetone was added 0.4 mL of lithium diisopropylamide (1.5 M in hexanes). The mixture was placed in a cold bath at −20° C. to −30° C. for 15 minutes and then cooled to −78° C. 1-(1-Fluorocyclopropyl)-3-(4-fluorophenyl)-3-methylbutan-1-one (49 mg, 0.206 mmol) was added dropwise as a solution in 0.5 mL of THF. The cold bath was then removed and the mixture stirred for 1 hour. The reaction was quenched by addition of 0.5 mL of water and diluted with ethyl acetate. The organic phase was separated, washed with water, dried, filtered, and the solvent evaporated in vacuo. Fractionation of the residue by preparative layer chromatography (developer: ethyl acetate-hexanes (2:1)) gave the title compound (0.019 g, 24% yield) (slightly less polar than lepidine) as an oil that crystallized on standing in hexanes, m.p. 152° C.-155° C.

Example 103

Synthesis of 1,1,1-Trifluoro-4-(5-fluoro-2-methoxyphenyl)-2-furo[3,2-c]pyridin-2-ylmethyl-4-methylpentan-2-ol

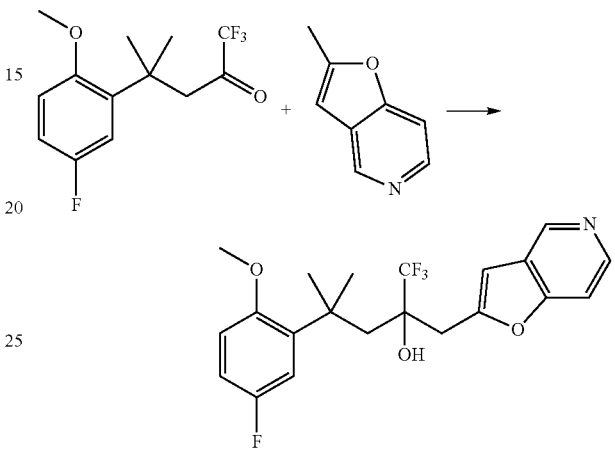

A solution of 2-methylfuro[3,2-c]pyridine (prepared according to the procedure by T. Kitamura, K. Tsuda, and Y. Fujiwara, Tetrahedron Lett. 1998, 39, pp. 5375-5376) (26.0 mg, 0.195 mmol) in 2 mL of THF was treated with lithium diisopropylamide (LDA; 1.5 M in cyclohexane, 195 μL) dropwise at −78° C. The mixture was stirred for 30 minutes (the color changed from yellow to orange-red) and was slowly treated with a solution of 1,1,1-trifluoro-4-(5-fluoro-2-methoxyphenyl)-4-methylpentan-2-one (81.5 mg, 0.293 mmol) in 1 mL of THF. The reaction was stirred at −78° C. for 4.5 hours, quenched with 5 mL of saturated ammonium chloride solution, and diluted with 20 mL of ethyl acetate. The phases were separated and the aqueous layer was extracted with three 10 mL portions of ethyl acetate. The combined organic layers were washed with brine, dried over magnesium sulfate, and concentrated in vacuo. Flash chromatography (ethyl acetate-hexanes, 5% to 50% gradient) gave 36.0 mg (45% yield) of the title product as a clear oil.

Example 104

Synthesis of 4-(5-Chloro-2,3-dihydrobenzofuran-7-yl)-1,1,1-trifluoro-4-methyl-2-thieno[3,2-c]pyridin-2-ylmethylpentan-2-ol

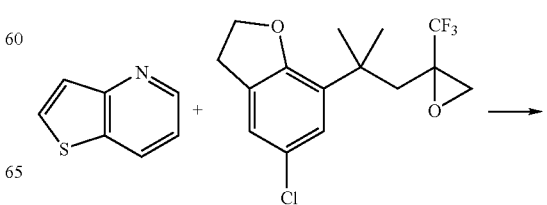

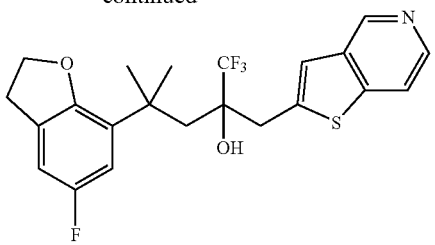

A solution of thieno[3,2-c]pyridine (prepared according to the procedure by J. H. Wikel, M. L. Denney, and R. T. J. Vasileff, Heterocyclic Chem. 1993, 30, pp. 289-290) (152 mg, 1.12 mmol) in 2 mL of THF was treated with 450 μL of n-BuLi (2.5 M in hexanes) in a dropwise manner at −78° C. The resulting dark reaction mixture was stirred for 30 minutes and treated with a solution of 5-chloro-7-[1,1-dimethyl-2-(2-trifluoromethyloxiranyl)ethyl]-2,3-dihydrobenzofuran (180 mg, 0.561 mmol) in 0.5 mL of THF. The reaction was allowed to warm to room temperature overnight and quenched with a mixture of 5 mL of saturated ammonium chloride solution and 10 mL of ethyl acetate. The phases were separated and the aqueous layer was extracted with three 10 mL portions of ethyl acetate. The combined organic layers were washed with brine, dried over magnesium sulfate, and concentrated in vacuo. Flash chromatography (ethyl acetate-hexanes, 20%-30% gradient) gave 33.5 mg (13% yield) of the title product as yellow foam.

Example 105

Synthesis of 5-(5-Fluoro-2-methoxyphenyl)-2,5-dimethyl-3-(1H-pyrrolo[3,2-c]pyridin-2-ylmethyl)hexan-3-ol

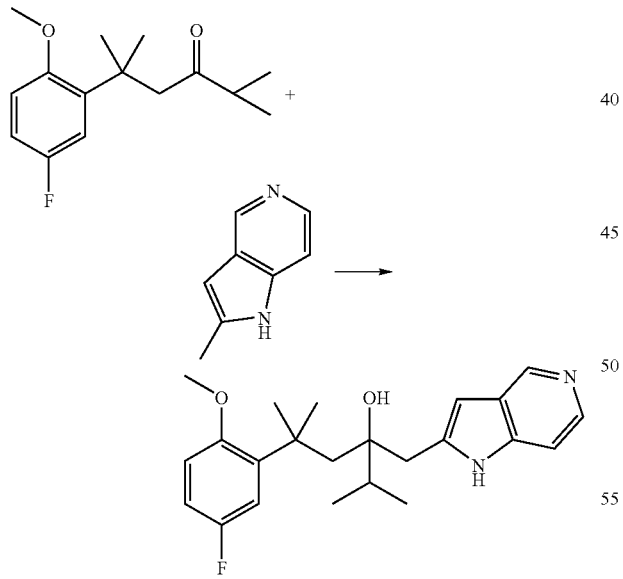

A solution of 2-methyl-1H-pyrrolo[3,2-c]pyridine (69 mg, 0.52 mmol) in 4 mL of THF was treated with 610 μL of n-BuLi (2.5 M in hexanes) at −78° C. After 5 minutes, tert-BuOK (1 M in THF, 1.0 mL) was added and the mixture was warmed to room temperature for 1.5 hours. The orange reaction mixture was cooled to −78° C. and 5-(5-fluoro-2-methoxyphenyl)-2,5-dimethylhexan-3-one (110 mg, 0.436 mmol) in 2 mL of THF was added dropwise. The mixture was stirred at −78° C. for 30 minutes, warmed to room temperature, quenched with 10 mL of saturated ammonium chloride solution, and diluted with 20 mL of ethyl acetate. The phases were separated and the aqueous layer was extracted with two 10 mL portions of ethyl acetate. The combined organic layers were dried over magnesium sulfate and concentrated in vacuo. Chromatography on SiO₂ (MeOH in CH₂Cl₂, gradient, 0% to 10%) afforded 71.4 mg (43% yield) of the product as a white solid.

Example 106

Synthesis of 4-(5-Chloro-2,3-dihydrobenzofuran-7-yl)-1,1,1-trifluoro-4-methyl-2-pyrrolo[3,2-b]pyridin-1-ylmethylpentan-2-ol

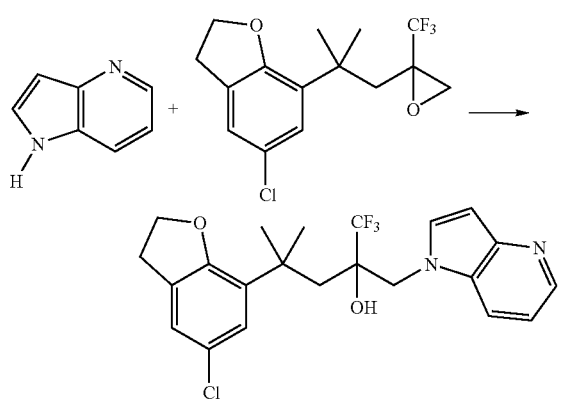

A solution of 1H-pyrrolo[3,2-b]pyridine (33.0 mg, 0.279 mmol) in 4 mL of DMF was treated with NaH (60% in mineral oil, 16.8 mg, 0.419 mmol) at room temperature. After 30 minutes, 5-chloro-7-[1,1-dimethyl-2-(2-trifluoromethyloxiranyl)ethyl]-2,3-dihydrobenzofuran (188 mg, 0.558 mmol) was added and the resulting mixture was stirred overnight. The reaction was then diluted with 5 mL of ethyl acetate and quenched with 5 mL of saturated ammonium chloride solution. The aqueous layer was extracted with 5 mL of ethyl acetate. The combined organic layers were dried over magnesium sulfate, filtered, and concentrated in vacuo. The residue was triturated with diethyl ether to afford 55.0 mg (45% yield) of the title product as white solid.

Example 107

Synthesis of 1-[4-(2,3-Dihydrobenzofuran-7-yl)-2-hydroxy-4-methyl-2-trifluoromethylpentyl]-1,5,6,7-tetrahydroindol-4-one

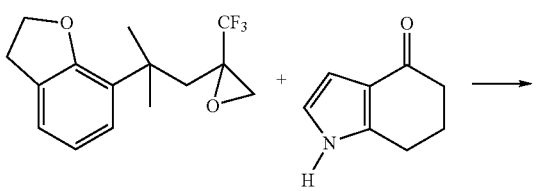

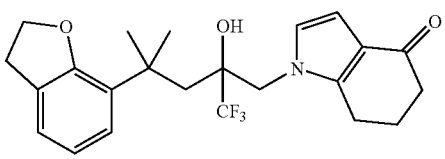

To a suspension of 7-[1,1-dimethyl-2-(2-trifluoromethyloxiranyl)ethyl]-2,3-dihydrobenzofuran (59.2 mg, 0.21 mmol) and 1,5,6,7-tetrahydroindol-4-one (56.0 mg, 0.41 mmol) in 0.4 mL of anhydrous ethanol was added 0.077 mL of sodium ethoxide solution (21 wt % in ethanol). The reaction mixture was then heated at 85° C. for 16 hours. The resulting mixture was poured into half-saturated sodium bicarbonate and extracted with ethyl acetate. The combined organic phases were dried over sodium sulfate, filtered, and concentrated in vacuo. The residue was purified by silica gel chromatography (eluted with 35% ethyl acetate-hexanes) to give 58.4 mg (66% yield) of the title compound as a white solid, m.p. 145° C.-146° C.

Example 108

Synthesis of 1-[2-Hydroxy-4-(5-methanesulfonyl-2,3-dihydrobenzofuran-7-yl)-4-methyl-2-trifluoromethylpentyl]-1,5,6,7-tetrahydroindol-4-one

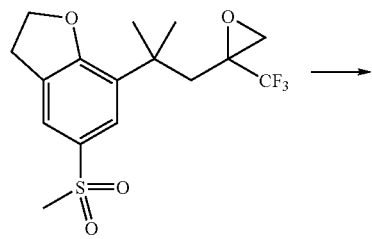

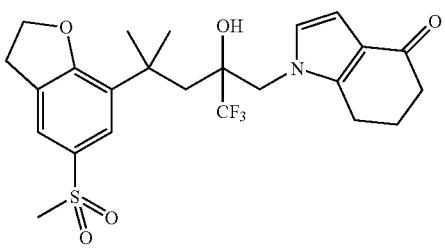

To a suspension of 7-[1,1-dimethyl-2-(2-trifluoromethyloxiranyl)ethyl]-5-methanesulfonyl-2,3-dihydrobenzofuran (101 mg, 0.33 mmol) and 1,5,6,7-tetrahydroindol-4-one (74.9 mg, 0.56 mmol) in 0.75 mL of anhydrous ethanol was added sodium ethoxide (21 wt. % solution in ethanol, 103 µL). After heating at 85° C. for 16 hours, the reaction mixture was diluted with ethyl acetate, dried over sodium sulfate, filtered, and concentrated in vacuo. The residue was purified by column chromatography with silica gel (eluted with 50% to 60% ethyl acetate-hexanes) to give 80.0 mg (58% yield) of the title compound as a white solid, m.p. 207° C.-208° C.

Example 109

Synthesis of 1-[2-Hydroxy-4-methyl-4-(5-pyrimidin-5-yl-2,3-dihydrobenzofuran-7-yl)-2-trifluoromethylpentyl]-1,5,6,7-tetrahydroindol-4-one

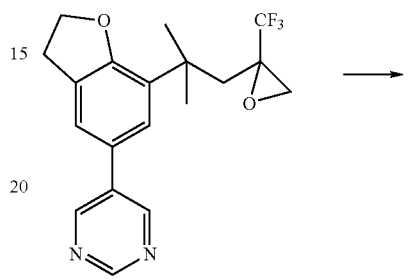

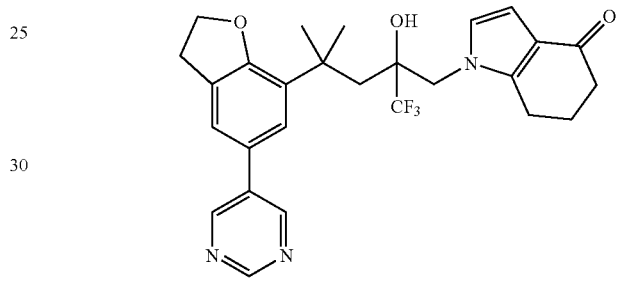

To a suspension of 5-{7-[1,1-dimethyl-2-(2-trifluoromethyloxiranyl)ethyl]-2,3-dihydrobenzofuran-5-yl}pyrimidine (56.0 mg, 0.15 mmol) and 1,5,6,7-tetrahydroindol-4-one (41.6 mg, 0.31 mmol) in 1.0 mL of anhydrous ethanol was added sodium ethoxide solution (0.057 mL, 21 wt. % in ethanol). The reaction mixture was heated at 85° C. for 15 hours. After cooling to room temperature, the reaction mixture was concentrated onto silica gel (for dry loading) and purified by silica gel chromatography (eluted with 40% to 70% ethyl acetate-hexanes) to give 42.0 mg (55% yield) of the title compound as a white solid, m.p. 213° C.-214° C.

Example 110

2-[2-Hydroxy-4-(5-methanesulfonyl-2-methoxyphenyl)-4-methyl-2-trifluoromethylpentyl]-1H-indole-3-carbonitrile

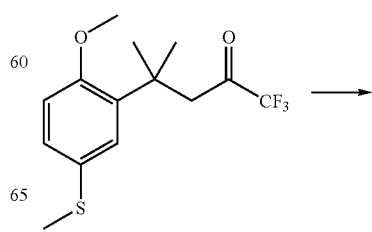

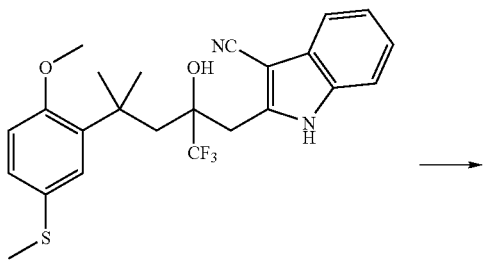

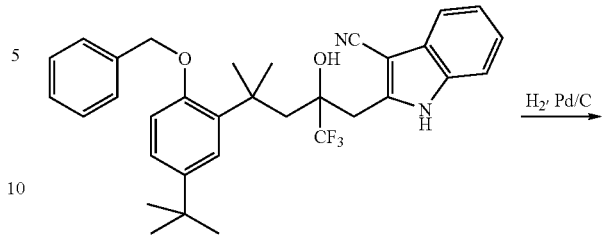

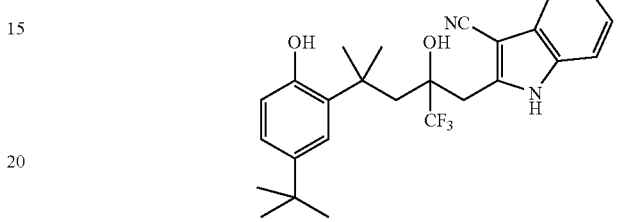

4-(2-Benzyloxy-5-tert-butylphenyl)-1,1,1-trifluoro-4-methylpentan-2-one was converted to 2-[4-(5-tert-butyl-2-hydroxyphenyl)-2-hydroxy-4-methyl-2-trifluoromethylpentyl]-1H-indole-3-carbonitrile using similar procedures as in Example 4 of U.S. patent application Pub. No. 2004/0023999.

1,1,1-Trifluoro-4-(2-methoxy-5-methylsulfanylphenyl)-4-methylpentan-2-one was converted to 2-[2-Hydroxy-4-(2-methoxy-5-methylsulfanylphenyl)-4-methyl-2-trifluoromethylpentyl]-1H-indole-3-carbonitrile in a similar manner to Example 4 of U.S. patent application Pub. No. 2004/0023999.

2-[2-Hydroxy-4-(2-methoxy-5-methylsulfanylphenyl)-4-methyl-2-trifluoromethylpentyl]-1H-indole-3-carbonitrile was oxidized to 2-[2-hydroxy-4-(5-methanesulfonyl-2-methoxyphenyl)-4-methyl-2-trifluoromethylpentyl]-1H-indole-3-carbonitrile according to Example 4 of U.S. patent application Pub. No. 2004/0023999.

Example 111

Synthesis of 2-[4-(5-tert-butyl-2-hydroxyphenyl)-2-hydroxy-4-methyl-2-trifluoromethylpentyl]-1H-indole-3-carbonitrile

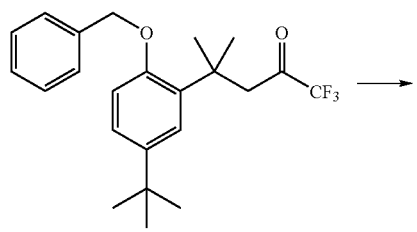

Example 112

Synthesis of 2-[2-Hydroxy-4-(2-hydroxy-5-isopropylphenyl)-4-methyl-2-trifluoromethylpentyl]-1H-indole-3-carbonitrile

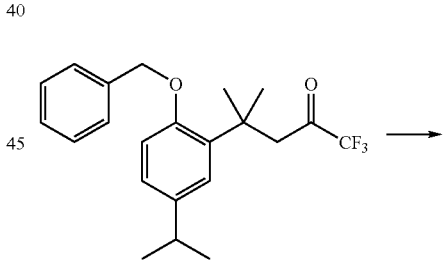

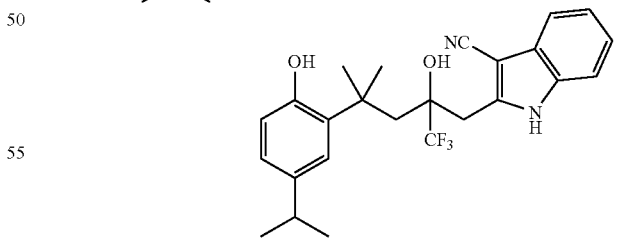

4-(2-Benzyloxy-5-isopropylphenyl)-1,1,1-trifluoro-4-methylpentan-2-one was converted to 2-[2-hydroxy-4-(2-hydroxy-5-isopropylphenyl)-4-methyl-2-trifluoromethylpentyl]-1H-indole-3-carbonitrile using a similar procedure as described in the synthesis of 2-[4-(5-tert-butyl-2-hydroxyphenyl)-2-hydroxy-4-methyl-2-trifluoromethylpentyl]-1H-indole-3-carbonitrile.

Example 113

Synthesis of 2-[4-(5-tert-Butyl-2-methoxyphenyl)-2-hydroxy-4-methyl-2-trifluoromethylpentyl]-1H-indole-3-carbonitrile and 2-[4-(5-tert-Butyl-2-methoxyphenyl)-2-hydroxy-4-methyl-2-trifluoromethylpentyl]-1-methyl-1H-indole-3-carbontrile

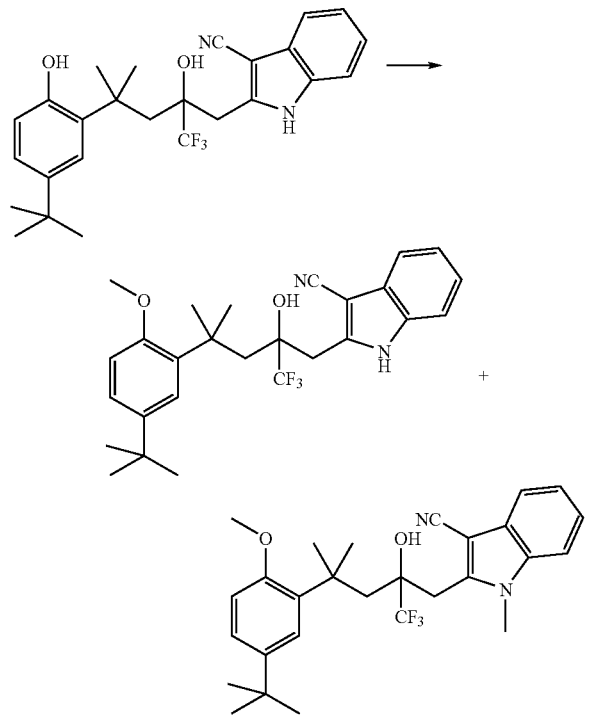

2-[4-(5-tert-Butyl-2-hydroxyphenyl)-2-hydroxy-4-methyl-2-trifluoromethylpentyl]-1H-indole-3-carbonitrile was alkylated to give 2-[4-(5-tert-butyl-2-methoxyphenyl)-2-hydroxy-4-methyl-hydroxy-4-methyl-2-trifluoromethylpentyl]-1-methyl-1H-indole-3-carbonitrile in a similar manner described for the alkylation of 3-(2-benzyloxy-5-tert-butylphenyl)-3-methylbutan-1-ol in Example 53.

Example 114

Synthesis of 2-[2-Hydroxy-4-(5-isopropyl-2-methoxyphenyl)-4-methyl-2-trifluoromethylpentyl]-1H-indole-3-carbonitrile and 2-[2-Hydroxy-4-(5-isopropyl-2-methoxyphenyl)-4-methyl-2-trifluoromethylpentyl]-1-methyl-1H-indole-3-carbonitrile

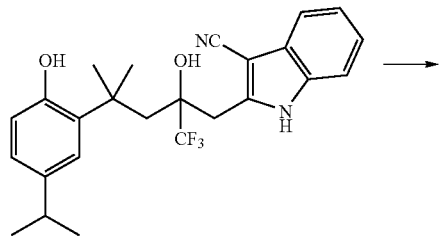

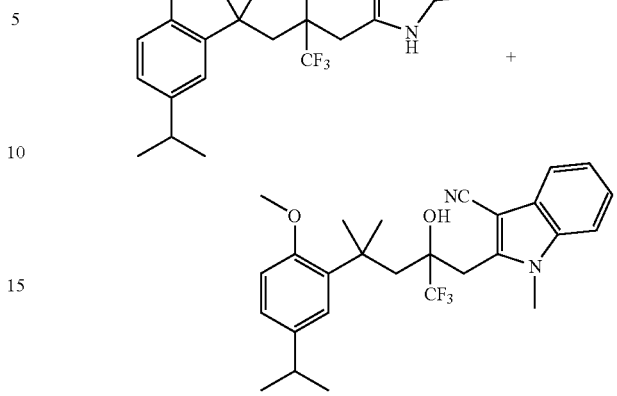

2-[2-Hydroxy-4-(2-hydroxy-5-isopropylphenyl)-4-methyl-2-trifluoromethylpentyl]-1H-indole-3-carbonitrile was alkylated to give 2-[2-hydroxy-4-(5-isopropyl-2-methoxyphenyl)-4-methyl-2-trifluoromethylpentyl]-1H-indole-3-carbonitrile and 2-[2-Hydroxy-4-(5-isopropyl-2-methoxyphenyl)-4-methyl-2-trifluoromethylpentyl]-1-methyl-1H-indole-3-carbonitrile in a similar manner described for the alkylation of 3-(2-benzyloxy-5-tert-butylphenyl)-3-methylbutan-1-ol in Example 53.

Example 115

Synthesis of 2-[2-Hydroxy-4-(2-methoxy-5-methylphenyl)-4-methyl-2-trifluoromethylpentyl]-4-methyl-1H-indole-6-carbonitrile

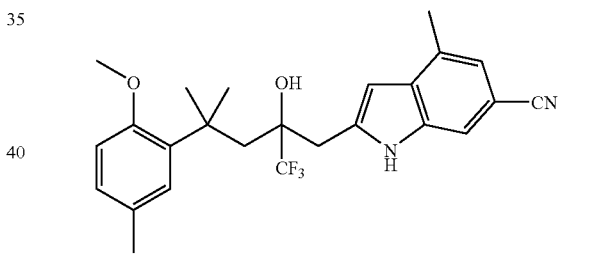

1,1,1-Trifluoro-4-(2-methoxy-5-methylphenyl)-4-methylpentan-2-one was converted to 2-[2-hydroxy-4-(2-methoxy-5-methylphenyl)-4-methyl-2-trifluoromethylpentyl]-4-methyl-1H-indole-6-carbonitrile as in Example 8 of U.S. patent application Pub. No. 2004/0023999.

Example 116

Synthesis of 2-[2-Hydroxy-4-(2-hydroxy-5-methylphenyl)-4-methyl-2-trifluoromethylpentyl]-4-methyl-1H-indole-6-carbonitrile

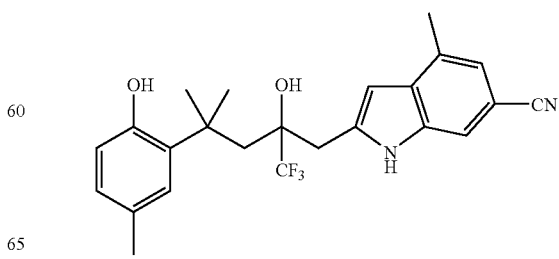

2-[2-Hydroxy-4-(2-methoxy-5-methylphenyl)-4-methyl-2-trifluoromethylpentyl]-4-methyl-1H-indole-6-carbonitrile was converted to 2-[2-hydroxy-4-(2-hydroxy-5-methylphenyl)-4-methyl-2-trifluoromethylpentyl]-4-methyl-1H-indole-6-carbonitrile as in Example 8 of U.S. patent application Pub. No. 2004/0023999.

Example 117

Synthesis of 2-[4-(5-fluoro-2-methoxyphenyl)-2-hydroxy-4-methyl-2-trifluoromethylpentyl]-1H-indole-4-carboxylic acid

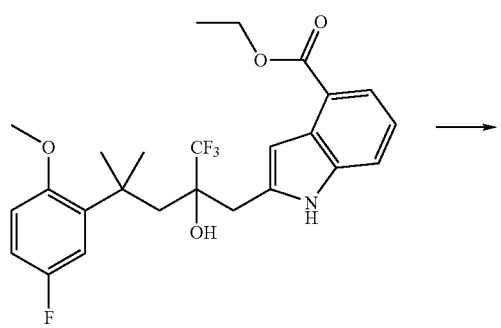

A solution of 2-[4-(5-fluoro-2-methoxyphenyl)-2-hydroxy-4-methyl-2-trifluoromethylpentyl]-1H-indole-4-carboxylic acid ethyl ester (220 mg, 0.470 mmol) in 10 mL of methanol was treated with a solution of potassium hydroxide (85 mg, 1.5 mmol) in 3 mL of water. The resulting mixture was stirred at room temperature for 4 hours, refluxed for 6 hours, cooled to room temperature, and concentrated in vacuo. The residue was treated with cold 1 N sulfuric acid and extracted with three 30 mL portions of dichloromethane. The combined organic layers were washed with water, dried over sodium sulfate, filtered, and concentrated in vacuo to give 190 mg of the title product as a light cream solid (89% yield).

Example 118

Synthesis of 2-[4-(5-Fluoro-2-methoxyphenyl)-2-hydroxy-4-methyl-2-trifluoromethylpentyl]-1H-indole-4-carboxylic acid amide

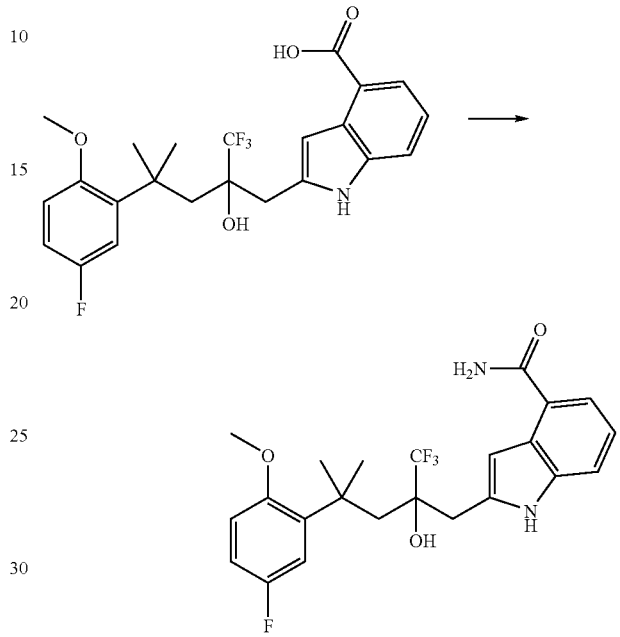

A solution 2-[4-(5-fluoro-2-methoxyphenyl)-2-hydroxy-4-methyl-2-trifluoromethylpentyl]-1H-indole-4-carboxylic acid (170 mg, 0.375 mmol) in 2 mL of acetonitrile was treated with 105 mL of triethylamine and TBTU (133 mg, 0.413 mmol). After 15 minutes, 53.6 mL of ammonium hydroxide solution was added. The resulting reaction mixture was diluted with water and extracted with dichloromethane. The organic layer was dried over sodium sulfate, filtered, and concentrated in vacuo. Chromatography on SiO$_2$ (50% ethyl acetate in hexanes) gave 170 mg of the title product as an off-white solid (quantitative yield).

Example 119

Synthesis of 2-[4-(5-Fluoro-2-methoxyphenyl)-2-hydroxy-4-methyl-2-trifluoromethylpentyl]-1H-indole-4-carbonitrile

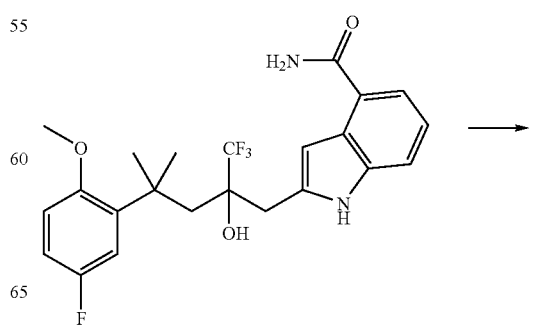

-continued

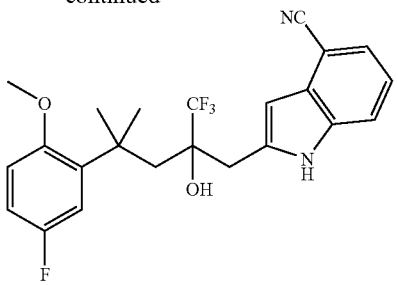

A solution 2-[4-(5-fluoro-2-methoxyphenyl)-2-hydroxy-4-methyl-2-trifluoromethylpentyl]-1H-indole-4-carboxylic acid amide (95 mg, 0.21 mmol) in 1 mL of DMF was reacted with cyanuric chloride (46 mg, 0.25 mmol). After 3 hours, the mixture was treated with sodium bicarbonate, extracted with dichloromethane. The organic layer was dried over sodium sulfate, filtered, and concentrated in vacuo to give 33 mg of the title product as off-white solid (36% yield).

Resolution to the (+)- and (−)-enantiomers was accomplished by chiral HPLC on a CHIRALCEL™ OD column, eluting with 15% to 25% isopropanol-hexanes.

Assessment of Biological Properties

Compounds of the invention were evaluated for binding to the steroid receptor by a fluorescence polarization competitive binding assay. Detailed descriptions for preparation of recombinant glucocorticoid receptor (GR) complex used in the assay is described in U.S. patent application Pub. No. 2003/0017503, which is incorporated herein by reference in its entirety. Preparation of the tetramethyl rhodamine (TAMRA)-labeled dexamethasone probe was accomplished using a standard literature procedure (M. Pons et al., J. Steroid Biochem., 1985, 22, pp. 267-273).

A. Glucocorticoid Receptor Competitive Binding Assay

Step 1. Characterization of the Fluorescent Probe

The wavelengths for maximum excitation and emission of the fluorescent probe should first be measured. An example of such a probe is rhodamine (TAMRA)-labeled dexamethasone.

The affinity of the probe for the steroid receptor was then determined in a titration experiment. The fluorescence polarization value of the probe in assay buffer was measured on an SLM-8100 fluorometer using the excitation and emission maximum values described above. Aliquots of expression vector lysate were added and fluorescence polarization was measured after each addition until no further change in polarization value was observed. Non-linear least squares regression analysis was used to calculate the dissociation constant of the probe from the polarization values obtained for lysate binding to the probe.

Step 2. Screening for Inhibitors of Probe Binding

This assay uses fluorescence polarization (FP) to quantitate the ability of test compounds to compete with tetramethyl rhodamine (TAMRA)-labeled dexamethasone for binding to a human glucocorticoid receptor (GR) complex prepared from an insect expression system. The assay buffer was: 10 mM TES, 50 mM KCl, 20 mM $Na_2MoO_4.2H_2O$, 1.5 mM EDTA, 0.04% w/v CHAPS, 10% v/v glycerol, 1 mM dithiothreitol, pH 7.4. Test compounds were dissolved to 1 mM in neat DMSO and then further diluted to 10× assay concentration in assay buffer supplemented with 10% v/v DMSO. Test compounds were serially diluted at 10× assay concentrations in 10% DMSO-containing buffer in 96-well polypropylene plates. Binding reaction mixtures were prepared in 96-well black Dynex microtiter plates by sequential addition of the following assay components to each well: 15 μL of 10× test compound solution, 85 μL of GR-containing baculovirus lysate diluted 1:170 in assay buffer, and 50 μL of 15 nM TAMRA-labeled dexamethasone. Positive controls were reaction mixtures containing no test compound; negative controls (blanks) were reaction mixtures containing 0.7 μM to 2 μM dexamethasone. The binding reactions were incubated for 1 hour at room temperature and then read for fluorescence polarization in the LJL Analyst set to 550 nm excitation and 580 nm emission, with the Rhodamine 561 dichroic mirror installed. $IC_{50}$ values were determined by iterative non-linear curve fitting of the FP signal data to a 4-parameter logistic equation.

Compounds found to bind to the glucocorticoid receptor may be evaluated for binding to the progesterone receptor (PR), estrogen receptor (ER), and mineralocorticoid receptors (MR) to evaluate the compound's selectivity for GR. The protocols for PR and MR are identical to the above GR method, with the following exceptions: PR insect cell lysate is diluted 1:7.1 and MR lysate diluted 1:9.4. PR probe is TAMRA-labeled mifepristone, used at a final concentration of 5 nM in the assay, and the negative controls (blanks) were reactions containing mifepristone at 0.7 μM to 2 μM.

The ER protocol is similar to the above protocols, but uses PanVera kit receptor, fluorescein-labeled probe. The assay components are made in the same volumes as above, to produce final assay concentrations for ER of 15 nM and ES2 probe of 1 nM. In addition, the component order of addition is modified from the above assays: probe is added to the plate first, followed by receptor and test compound. The plates are read in the LJL Analyst set to 485 nm excitation and 530 nm emission, with the Fluorescein 505 dichroic mirror installed.

Compounds found to bind to the glucocorticoid receptor may be evaluated for dissociation of transactivation and transrepression by assays cited in the Background of the Invention (C. M. Bamberger and H. M. Schulte, Eur. J. Clin. Invest., 2000, 30 (suppl. 3) pp. 6-9) or by the assays described below.

B. Glucocorticoid Receptor Cell Assays

1. Induction of Aromatase in Fibroblasts (Cell Assay for Transactivation)

Dexamethasone, a synthetic ligand to the glucocorticoid receptor (GR), induces expression of aromatase in human foreskin fibroblast cells. The activity of aromatase is measured by the conversion of testosterone to estradiol in culture media. Compounds that exhibit binding to GR are evaluated for their ability to induce aromatase activity in human foreskin fibroblasts.

Human foreskin fibroblast cells (ATCC Cat. No. CRL-2429, designation CCD112SK) are plated on 96 well plates at 50,000 cells per well 5 days before use, in Iscove's Modified Dulbecco's Media (GibcoBRL Life Technologies Cat No. 12440-053) supplemented with 10% charcoal filtered FBS (Clonetech Cat No. SH30068) and Gentamycin (GibcoBRL Life Technologies Cat. No. 15710-064). On the day of the experiment, the media in the wells is replaced with fresh media. Cells are treated with test compounds to final concentrations of $10^{-5}$ M to $10^{-8}$ M, and testosterone to a final concentration of 300 ng/mL. Each well has a total volume of 100 μL. Samples are made in duplicates. Control wells include: (a) wells that receive testosterone only, and (b) wells that receive testosterone plus 2 μM of dexamethasone to provide maximum induction of aromatase. Plates are incubated at 37° C. overnight (15 to 18 hours), and supernatants are harvested at the end of incubation. Estradiol in the supernatant is measured using ELISA kits for estradiol (made by ALPCO, obtained from American Laboratory Products Cat. No. 020-DR-2693) according to the manufacture's instruction. The amount of estradiol is inversely proportional to the ELISA signals in each well. The extent of aromatase induction by test compounds is expressed as a relative percentage to dexamethasone. $EC_{50}$ values of test compounds are derived by non-linear curve fitting.

2. Inhibition of IL-6 Production in Fibroblasts (Cell Assay for Transrepression)

Human foreskin fibroblast cells produce IL-6 in response to stimulation by proinflammatory cytokine IL-1. This inflammatory response, as measured by the production of IL-6, can be effectively inhibited by dexamethasone, a synthetic ligand to the glucocorticoid receptor (GR). Compounds that exhibit binding to GR are evaluated for their ability to inhibit IL-6 production in human foreskin fibroblasts.

Human foreskin fibroblast cells (ATCC Cat. No. CRL-2429) are plated on 96 well plates at 5,000 cells per well the day before use, in Iscove's Modified Dulbecco's Media (GibcoBRL Life Technologies Cat. No. 12440-053) supplemented with 10% charcoal filtered FBS (Clonetech Cat. No. SH30068) and Gentamycin (GibcoBRL Life Technologies Cat. No. 15710-064). On the next day, media in the wells is replaced with fresh media. Cells are treated with IL-1 (rhIL-1α, R&D Systems Cat. No. 200-LA) to a final concentration of 1 ng/mL, and with test compounds to final concentrations of $10^{-5}$ M to $10^{-8}$ M, in a total volume of 200 μL per well. Samples are done in duplicates. Background control wells do not receive test compounds or IL-1. Positive control wells receive IL-1 only and represent maximum (or 100%) amount of IL-6 production. Plates are incubated at 37° C. overnight (15 to 18 hours), and supernatants are harvested at the end of incubation. IL-6 levels in the supernatants are determined by the ELISA kits for IL-6 (MedSystems Diagnostics GmbH, Vienna, Austria, Cat. No. BMS213TEN) according to manufacture's instructions. The extent of inhibition of IL-6 by test compounds is expressed in percentage relative to positive controls. $IC_{50}$ values of test compounds are derived by non-linear curve fitting.

Evaluation of agonist or antagonist activity of compounds binding to the glucocorticoid receptor may be determined by any of the assays.

3. Modulation of Tyrosine Aminotransferase (TAT) Induction in Rat Hepatoma Cells Testing of compounds for agonist or antagonist activity in induction of tyrosine aminotransferase (TAT) in rat hepatoma cells.

H4-II-E-C3 cells were incubated overnight in 96 well plates (20,000 cells/100 μL/well) in MEM medium containing 10% heat inactivated FBS and 1% nonessential amino acids. On the next day, cells were stimulated with the indicated concentrations of dexamethasone or test compound (dissolved in DMSO, final DMSO concentration 0.2%) for 18 hours. Control cells were treated with 0.2% DMSO. After 18 hours, the cells were lysed in a buffer containing 0.1% Triton X-100 and the TAT activity was measured in a photometric assay using tyrosine and alpha-ketoglutarate as substrates.

For measuring antagonist activity, the hepatoma cells were pre-stimulated by addition of dexamethasone (concentration ranges from $3 \times 10^{-9}$ M to $3 \times 10^{-8}$ M) shortly before the test compound was applied to the cells. The steroidal non-selective GR/PR antagonist mifepristone was used as control.

4. Modulation of MMTV-Luc Induction in HeLa Cells

Testing of compounds for agonist or antagonist activity in stimulation of MMTV-(mouse mammary tumor virus) promoter in HeLa cells.

HeLa cells were stably co-transfected with the pHHLuc-plasmid containing a fragment of the MMTV-LTR (−200 to +100 relative to the transcription start site) cloned in front of the luciferase gene (Norden, 1988) and the pcDNA3.1 plasmid (Invitrogen) constitutively expressing the resistance for the selective antibiotic GENETICIN®. Clones with best induction of the MMTV-promoter were selected and used for further experiments.

Cells were cultured overnight in DMEM medium without phenol red, supplemented with 3% CCS (charcoal treated calf serum) and then transferred to 96 well plates (15,000 cells/100 μL/well). On the next day, activation of the MMTV-promoter was stimulated by addition of test compound or dexamethasone dissolved in DMSO (final concentration 0.2%). Control cells were treated with DMSO only. After 18 hours, the cells were lysed with cell lysis reagent (Promega, Cat. No. E1531), luciferase assay reagent (Promega, Cat. No. E1501) was added and the glow luminescence was measured using a luminometer (BMG, Offenburg).

For measuring antagonist activity, the MMTV-promoter was pre-stimulated by adding dexamethasone ($3 \times 10^{-9}$ M to $3 \times 10^{-8}$ M) shortly before the test compound was applied to the cells. The steroidal non-selective GR/PR antagonist mifepristone was used as control.

5. Modulation of IL-8 Production in U937 Cells

Testing of compounds for agonist or antagonist activity in GR-mediated inhibition of LPS-induced IL-8 secretion in U-937 cells.

U-937 cells were incubated for 2 to 4 days in RPM11640 medium containing 10% CCS (charcoal treated calf serum). The cells were transferred to 96 well plates (40,000 cells/100 μL/well) and stimulated with 1 μg/mL LPS (dissolved in PBS) in the presence or absence of dexamethasone or test compound (dissolved in DMSO, final concentration 0.2%). Control cells were treated with 0.2% DMSO. After 18 hours, the IL-8 concentration in the cell supernatant was measured by ELISA, using the "OptEIA human IL-8 set" (Pharmingen, Cat. No. 2654KI).

For measuring antagonist activity, the LPS-induced IL-8 secretion was inhibited by adding dexamethasone ($3 \times 10^{-9}$ M to $3 \times 10^{-8}$ M) shortly before the test compound was applied to the cells. The steroidal non-selective GR/PR antagonist mifepristone was used as control.

6. Modulation of ICAM-Luc Expression in HeLa Cells

Testing of compounds for agonist or antagonist activity in inhibition of TNF-alpha-induced activation of the ICAM-promoter in HeLa cells.

HeLa cells were stably co-transfected with a plasmid containing a 1.3 kb fragment of the human ICAM-promoter (−1353 to −9 relative to the transcription start site, Ledebur and Parks, 1995) cloned in front of the luciferase gene and the pcDNA3.1 plasmid (Invitrogen) which constitutively expresses the resistance for the antibiotic GENETICIN®. Clones with best induction of the ICAM-promoter were selected and used for further experiments. Cells were transferred to 96 well plates (15,000 cells/100 μL/well) in DMEM medium supplemented with 3% CCS. On the following day the activation of the ICAM-promoter was induced by addition of 10 ng/mL recombinant TNF-alpha (R&D System, Cat. No. 210-TA). Simultaneously the cells were treated with the test compound or dexamethasone (dissolved in DMSO, final concentration 0.2%). Control cells were treated with DMSO only. After 18 hours, the cells were lysed with cell lysis reagent (Promega, Cat. No. E1531), luciferase assay reagent (Promega, Cat. No. E1501) was added and glow luminescence was measured using a luminometer (BMG, Offenburg).

For measuring antagonist activity, the TNF-alpha-induced activation of the ICAM-promoter was inhibited by adding dexamethasone ($3 \times 10^{-9}$ M to $3 \times 10^{-8}$ M) shortly before the test compound was applied to the cells. The steroidal non-selective GR/PR antagonist mifepristone was used as control.

In general, the preferred potency range in the above assays is between 0.1 nM and 10 μM, the more preferred potency range is 0.1 nM to 1 μM, and the most preferred potency range is 0.1 nM to 100 nM.

Representative compounds of the invention have been tested and have shown activity as modulators of the glucocorticoid receptor function in one or more of the above assays. For example, the following compounds of the invention of Formula (IA) have demonstrated potent activity in the GR binding assay:

1,1,1-Trifluoro-4-(5-fluoro-2-methoxyphenyl)-4-methyl-2-(3-methyl-1H-pyrrolo[3,2-c]pyridin-2-ylmethyl)pentan-2-ol;
1,1,1-Trifluoro-4-(5-fluoro-2,3-dihydrobenzofuran-7-yl)-4-methyl-2-(1H-pyrrolo[3,2-c]pyridin-2-ylmethyl)pentan-2-ol;
1,1,1-Trifluoro-4-(5-fluoro-2-methylphenyl)-4-methyl-2-(3-methyl-1H-pyrrolo[2,3-c]pyridin-2-ylmethyl)pentan-2-ol;
2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol;
2-[4-(5-Fluoro-2-methoxyphenyl)-2-hydroxy-4-methyl-2-trifluoromethylpentyl]-1H-pyrrolo[3,2-b]pyridine-5-carbonitrile;
1,1,1-Trifluoro-4-(5-fluoro-2-methoxyphenyl)-4-methyl-2-(6-methyl-1H-pyrrolo[3,2-c]pyridin-2-ylmethyl)pentan-2-ol;
1,1,1-Trifluoro-4-(5-fluoro-2-methoxyphenyl)-4-methyl-2-(4-methyl-1H-pyrrolo[3,2-c]pyridin-2-ylmethyl)pentan-2-ol;
2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile;
2-[4-(5-Fluoro-2-methoxyphenyl)-2-hydroxy-4-methyl-2-trifluoromethylpentyl]-1H-pyrrolo[2,3-c]pyridine-5-carbonitrile;
2-[4-(5-Fluoro-2-methoxyphenyl)-2-hydroxy-4-methyl-2-trifluoromethylpentyl]-1H-pyrrolo[3,2-c]pyridine-4-carbonitrile;
1,1,1-Trifluoro-4-(5-fluoro-2-methoxyphenyl)-4-methyl-2-(5H-pyrrolo[3,2-d]pyrimidin-6-ylmethyl)pentan-2-ol;
1,1,1-Trifluoro-4-(5-fluoro-2-methoxyphenyl)-4-methyl-2-thieno[2,3-d]pyridazin-2-ylmethylpentan-2-ol;
1,1,1-Trifluoro-4-(5-fluoro-2-methoxyphenyl)-4-methyl-2-(5H-pyrrolo[3,2-c]pyridazin-6-ylmethyl)pentan-2-ol;
1,1,1-Trifluoro-4-(5-fluoro-2-methoxyphenyl)-4-methyl-2-(2-methyl-5H-pyrrolo[3,2-d]pyrimidin-6-ylmethyl)pentan-2-ol;
1,1,1-Trifluoro-4-(5-fluoro-2-methylphenyl)-4-methyl-2-(1H-pyrrolo[2,3-d]pyridazin-2-ylmethyl)pentan-2-ol;
2-(4,6-Dimethyl-1H-pyrrolo[3,2-c]pyridin-2-ylmethyl)-1,1,1-trifluoro-4-(5-fluoro-2-methylphenyl)-4-methylpentan-2-ol;
4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol;
4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol;
1,1,1-Trifluoro-4-(5-fluoro-2-methylphenyl)-4-methyl-2-(6-methyl-1H-pyrrolo[3,2-c]pyridin-2-ylmethyl)pentan-2-ol;
2-[4-(5-Fluoro-2-methylphenyl)-2-hydroxy-4-methyl-2-trifluoromethylpentyl]-1H-pyrrolo[3,2-b]pyridine-5-carbonitrile;
2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile;
1,1,1-Trifluoro-4-(5-fluoro-2-methylphenyl)-4-methyl-2-(5H-pyrrolo[3,2-d]pyrimidin-6-ylmethyl)pentan-2-ol;
4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol;
4-(5-Chloro-2,3-dihydrobenzofuran-7-yl)-1,1,1-trifluoro-4-methyl-2-(3-methyl-1H-pyrrolo[2,3-c]pyridin-2-ylmethyl)pentan-2-ol;
1,1,1-Trifluoro-4-(5-fluoro-2-methylphenyl)-4-methyl-2-(5H-pyrrolo[3,2-c]pyridazin-6-ylmethyl)pentan-2-ol;
1,1,1-Trifluoro-4-(5-fluoro-2-methoxyphenyl)-2-(7-fluoro-1H-pyrrolo[2,3-c]pyridin-2-ylmethyl)-4-methylpentan-2-ol;
1,1,1-Trifluoro-4-(5-fluoro-2-methoxyphenyl)-4-methyl-2-(4-methyl-1H-pyrrolo[2,3-c]pyridin-2-ylmethyl)pentan-2-ol;
2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol;
1,1,1-Trifluoro-4-(5-fluoro-2-methoxyphenyl)-4-methyl-2-(5-trifluoromethyl-1H-pyrrolo[2,3-c]pyridin-2-ylmethyl)pentan-2-ol;
1,1,1-Trifluoro-4-(5-fluoro-2-methoxyphenyl)-2-(5-methoxy-1H-pyrrolo[2,3-c]pyridin-2-ylmethyl)-4-methylpentan-2-ol;
1,1,1-Trifluoro-4-(5-fluoro-2-methylphenyl)-4-methyl-2-(4-methyl-1H-pyrrolo[2,3-c]pyridin-2-ylmethyl)pentan-2-ol;
1,1,1-Trifluoro-4-(5-fluoro-2-methylphenyl)-2-(5-isopropoxy-1H-pyrrolo[2,3-c]pyridin-2-ylmethyl)-4-methylpentan-2-ol;
1,1,1-Trifluoro-4-(5-fluoro-2-methylphenyl)-2-(5-methoxy-1H-pyrrolo[2,3-c]pyridin-2-ylmethyl)-4-methylpentan-2-ol;
4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol;
1,1,1-Trifluoro-4-(5-fluoro-2-methylphenyl)-2-(7-fluoro-1H-pyrrolo[2,3-c]pyridin-2-ylmethyl)-4-methylpentan-2-ol;
4-(5-Chloro-2,3-dihydrobenzofuran-7-yl)-1,1,1-trifluoro-4-methyl-2-(5-trifluoromethyl-1H-pyrrolo[2,3-c]pyridin-2-ylmethyl)pentan-2-ol;
2-(5-Dimethylamino-1H-pyrrolo[2,3-c]pyridin-2-ylmethyl)-1,1,1-trifluoro-4-(5-fluoro-2-methylphenyl)-4-methylpentan-2-ol;
1,1,1-Trifluoro-4-(5-fluoro-2-methoxyphenyl)-2-(5-chloro-1H-pyrrolo[2,3-c]pyridin-2-ylmethyl)-4-methylpentan-2-ol;
4-(5-Bromo-2,3-dihydrobenzofuran-7-yl)-1,1,1-trifluoro-4-methyl-2-(1H-pyrrolo[2,3-c]pyridin-2-ylmethyl)pentan-2-ol;
1,1,1-Trifluoro-4-methyl-4-(5-methyl-2,3-dihydrobenzofuran-7-yl)-2-(1H-pyrrolo[2,3-c]pyridin-2-ylmethyl)pentan-2-ol;
4-(5-Chloro-2,3-dihydrobenzofuran-7-yl)-1,1,1-trifluoro-4-methyl-2-(1H-pyrrolo[2,3-c]pyridin-2-ylmethyl)pentan-2-ol;
1,1,1-Trifluoro-4-(5-fluoro-2-methoxyphenyl)-4-methyl-2-pyrrolo[2,3-b]pyridin-1-ylmethylpentan-2-ol;

2-Benzo[b]thiophen-2-ylmethyl-1,1,1-trifluoro-4-(5-fluoro-2-methoxyphenyl)-4-methylpentan-2-ol;
1,1,1-Trifluoro-4-(5-fluoro-2-methoxyphenyl)-4-methyl-2-thieno[2,3-c]pyridin-2-ylmethylpentan-2-ol;
1,1,1-Trifluoro-4-(5-fluoro-2-methoxyphenyl)-4-methyl-2-[4-((Z)propenyl)-3-vinylpyrazol-1-ylmethyl]pentan-2-ol;
4-(5-Chloro-2,3-dihydrobenzofuran-7-yl)-2,4-dimethyl-1-thieno[2,3-c]pyridin-2-ylpentan-2-ol;
4-(5-Fluoro-2-methylphenyl)-2,4-dimethyl-1-thieno[2,3-c]pyridin-2-ylpentan-2-ol;
1,1,1-Trifluoro-4-(5-fluoro-2-methylphenyl)-4-methyl-2-(1H-pyrrolo[3,2-c]pyridin-2-ylmethyl)pentan-2-ol;
1,1,1-Trifluoro-4-methyl-4-(5-methyl-2,3-dihydrobenzofuran-7-yl)-2-(1H-pyrrolo[3,2-c]pyridin-2-ylmethyl)pentan-2-ol;
4-(5-Chloro-2,3-dihydrobenzofuran-7-yl)-1,1,1-trifluoro-4-methyl-2-(1H-pyrrolo[3,2-c]pyridin-2-ylmethyl)pentan-2-ol;
4-(5-Bromo-2,3-dihydrobenzofuran-7-yl)-1,1,1-trifluoro-4-methyl-2-(1H-pyrrolo[3,2-c]pyridin-2-ylmethyl)pentan-2-ol;
2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol;
1,1,1-Trifluoro-4-(5-fluoro-2-methoxyphenyl)-4-methyl-2-pyrrolo[3,2-c]pyridin-1-ylmethylpentan-2-ol;
1,1,1-Trifluoro-4-(5-fluoro-2-methoxyphenyl)-4-methyl-2-pyrrolo[3,2-b]pyridin-1-ylmethylpentan-2-ol;
1,1,1-Trifluoro-4-(5-fluoro-2-methoxyphenyl)-2-furo[3,2-c]pyridin-2-ylmethyl-4-methylpentan-2-ol;
4-(5-Chloro-2,3-dihydrobenzofuran-7-yl)-1,1,1-trifluoro-4-methyl-2-pyrrolo[3,2-b]pyridin-1-ylmethylpentan-2-ol;
1,1-Difluoro-4-(5-fluoro-2-methoxyphenyl)-4-methyl-2-(1H-pyrrolo[3,2-c]pyridin-2-ylmethyl)pentan-2-ol;
1,1,1-Trifluoro-4-(5-fluoro-2-methoxyphenyl)-4-methyl-2-thieno[3,2-c]pyridin-2-ylmethylpentan-2-ol;
4-(5-Chloro-2,3-dihydrobenzofuran-7-yl)-1,1,1-trifluoro-4-methyl-2-thieno[3,2-c]pyridin-2-ylmethylpentan-2-ol;
1,1,1-Trifluoro-4-(5-fluoro-2-methylphenyl)-4-methyl-2-pyrrolo[3,2-b]pyridin-1-ylmethylpentan-2-ol;
1,1,1-Trifluoro-4-(5-fluoro-2-methylphenyl)-4-methyl-2-thieno[3,2-c]pyridin-2-ylmethylpentan-2-ol;
2-[4-(5-Fluoro-2-hydroxyphenyl)-2-hydroxy-4-methyl-2-trifluoromethylpentyl]-1H-indole-6-carboxylic acid dimethylamide;
{2-[4-(5-Fluoro-2-hydroxyphenyl)-2-hydroxy-4-methyl-2-trifluoromethylpentyl]-1H-indol-6-yl}morpholin-4-ylmethanone;
2-[4-(5-Fluoro-2-methoxyphenyl)-2-hydroxy-4-methyl-2-trifluoromethylpentyl]-1H-indole-6-carboxylic acid dimethylamide;
2-[4-(5-Fluoro-2-methoxyphenyl)-2-hydroxy-4-methyl-2-trifluoromethylpentyl]-1H-indole-6-carboxylic acid dimethylamide;
{2-[4-(5-Fluoro-2-methoxyphenyl)-2-hydroxy-4-methyl-2-trifluoromethylpentyl]-1H-indol-6-yl}morpholin-4-ylmethanone;
2-[4-(2,3-Dihydrobenzofuran-7-yl)-2-hydroxy-4-methyl-2-trifluoromethylpentyl]-4-methyl-1H-indole-6-carbonitrile;
2-[4-(5-Fluoro-2-hydroxyphenyl)-2-hydroxy-4-methyl-2-trifluoromethylpentyl]-1H-indole-6-carboxylic acid amide;
2-[4-(5-Fluoro-2-methoxyphenyl)-2-hydroxy-4-methyl-2-trifluoromethylpentyl]-1H-indole-6-carboxylic acid amide;
4-Fluoro-2-[4,4,4-trifluoro-3-hydroxy-1,1-dimethyl-3-(5-nitro-1H-indol-2-ylmethyl)butyl]phenol;
2-[4-(5-Fluoro-2-methoxyphenyl)-2-hydroxy-4-methyl-2-trifluoromethylpentyl]-1H-indole-6-carbonitrile;
2-[4-(5-Fluoro-2-hydroxyphenyl)-2-hydroxy-4-methyl-2-trifluoromethylpentyl]-1H-indole-6-carbonitrile;
N-{2-[4-(5-Fluoro-2-methoxyphenyl)-2-hydroxy-4-methyl-2-trifluoromethylpentyl]-1H-indol-5-yl}acetamide;
1,1,1-Trifluoro-4-(4-fluoro-2-methoxyphenyl)-2-(7-fluoro-4-methyl-1H-indol-2-ylmethyl)-4-methylpentan-2-ol;
5-Fluoro-2-[4,4,4-trifluoro-3-(7-fluoro-4-methyl-1H-indol-2-ylmethyl)-3-hydroxy-1,1-dimethylbutyl]phenol;
2-[4-(3-[1,3]Dioxolan-2-ylphenyl)-2-hydroxy-4-methyl-2-trifluoromethylpentyl]-1H-indole-5-carbonitrile;
2-[4-(5-Fluoro-2-methoxyphenyl)-2-hydroxy-4-methyl-2-trifluoromethylpentyl]-1H-indole-5-carboxylic acid-2-trimethylsilanylethyl ester;
2-[4-(4-Fluoro-2-hydroxyphenyl)-2-hydroxy-4-methyl-2-trifluoromethylpentyl]-4-methyl-1H-indole-6-carbonitrile;
{2-[4-(5-Fluoro-2-methoxyphenyl)-2-hydroxy-4-methyl-2-trifluoromethylpentyl]-1H-indol-5-yl}piperidin-1-ylmethanone;
2-[4-(5-Fluoro-2-methoxyphenyl)-2-hydroxy-4-methyl-2-trifluoromethylpentyl]-1H-indole-5-carboxylic acid methylamide;
{2-[4-(5-Fluoro-2-methoxyphenyl)-2-hydroxy-4-methyl-2-trifluoromethylpentyl]-1H-indol-5-yl}pyrrolidin-1-ylmethanone;
1-{2-[4-(5-Fluoro-2-methoxyphenyl)-2-hydroxy-4-methyl-2-trifluoromethylpentyl]-1H-indole-5-carbonyl}piperidin-4-one;
2-[4-(5-Fluoro-2-methoxyphenyl)-2-hydroxy-4-methyl-2-trifluoromethylpentyl]-1H-indole-5-carboxylic acid (2-hydroxyethyl)amide;
{2-[4-(5-Fluoro-2-methoxyphenyl)-2-hydroxy-4-methyl-2-trifluoromethylpentyl]-1H-indol-5-yl}(4-hydroxypiperidin-1-yl)methanone;
{2-[4-(5-Fluoro-2-methoxyphenyl)-2-hydroxy-4-methyl-2-trifluoromethylpentyl]-1H-indol-5-yl}(3-hydroxypyrrolidin-1-yl)methanone;
2-[4-(5-Fluoro-2-methoxyphenyl)-2-hydroxy-4-methyl-2-trifluoromethylpentyl]-1H-indole-5-carboxylic acid cyanomethylamide;
({2-[4-(5-Fluoro-2-methoxyphenyl)-2-hydroxy-4-methyl-2-trifluoromethylpentyl]-1H-indole-5-carbonyl}amino)acetic acid methyl ester;
2-[4-(5-Fluoro-2-methoxyphenyl)-2-hydroxy-4-methyl-2-trifluoromethylpentyl]-1H-indole-5-carboxylic acid carbamoylmethylamide;
4-({2-[4-(5-Fluoro-2-methoxyphenyl)-2-hydroxy-4-methyl-2-trifluoromethylpentyl]-1H-indole-5-carbonyl}amino)butyric acid methyl ester;
({2-[4-(5-Fluoro-2-methoxyphenyl)-2-hydroxy-4-methyl-2-trifluoromethylpentyl]-1H-indole-5-carbonyl}amino)acetic acid;
4-({2-[4-(5-Fluoro-2-methoxyphenyl)-2-hydroxy-4-methyl-2-trifluoromethylpentyl]-1H-indole-5-carbonyl}amino)butyric acid;
2-[4-(3-Dimethylaminomethylphenyl)-2-hydroxy-4-methyl-2-trifluoromethylpentyl]-1H-indole-5-carbonitrile;
4-Fluoro-2-[4,4,4-trifluoro-3-hydroxy-1,1-dimethyl-3-(5-trifluoromethyl-1H-indol-2-ylmethyl)butyl]phenol;
2-[4-(5-Bromo-2,3-dihydrobenzofuran-7-yl)-2-hydroxy-4-methyl-2-trifluoromethylpentyl]-4-methyl-1H-indole-6-carbonitrile;

2-[2-Hydroxy-4-(5-methane sulfonyl-2,3-dihydrobenzofuran-7-yl)-4-methyl-2-trifluoromethylpentyl]-4-methyl-1H-indole-6-carbonitrile;
2-[4-(5-Bromo-2,3-dihydrobenzofuran-7-yl)-2-hydroxy-4-methyl-2-trifluoromethylpentyl]-1H-indole-5-carboxylic acid;
2-[4-(5-Bromo-2,3-dihydrobenzofuran-7-yl)-2-hydroxy-4-methyl-2-trifluoromethylpentyl]-1H-indole-5-carboxylic acid amide;
2-[4-(5-Bromo-2,3-dihydrobenzofuran-7-yl)-2-hydroxy-4-methyl-2-trifluoromethylpentyl]-1H-indole-5-carboxylic acid dimethylamide;
2-[4-(5-Bromo-2,3-dihydrobenzofuran-7-yl)-2-hydroxy-4-methyl-2-trifluoromethylpentyl]-1H-indole-5-carboxylic acid cyanomethylamide;
{2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone;
{2-[4-(5-Bromo-2,3-dihydrobenzofuran-7-yl)-2-hydroxy-4-methyl-2-trifluoromethylpentyl]-1H-indol-5-yl}morpholin-4-ylmethanone;
2-[4-(5-Fluoro-2-methoxyphenyl)-2-hydroxy-4-methyl-2-trifluoromethylpentyl]-1H-indole-5-carboxylic acid amide;
{2-[4-(5-Fluoro-2-methoxyphenyl)-2-hydroxy-4-methyl-2-trifluoromethylpentyl]-1H-indol-5-yl}morpholin-4-ylmethanone;
2-(4-Benzo[1,3]dioxol-4-yl-2-hydroxy-4-methyl-2-trifluoromethylpentyl)-4-methyl-1H-indole-6-carbonitrile;
1,1,1-Trifluoro-4-methyl-4-phenyl-2-quinolin-4-ylmethylhexan-2-ol;
2-[2-Hydroxy-4-methyl-4-(5-methylsulfanyl-2,3-dihydrobenzofuran-7-yl)-2-trifluoromethylpentyl]-1H-indole-3-carbonitrile;
7-(4,4,4-Trifluoro-3-hydroxy-1,1-dimethyl-3-quinolin-4-ylmethylbutyl)-2,3-dihydrobenzofuran-5-carbonitrile;
2-[2-Hydroxy-4-(2-hydroxy-5-methylphenyl)-4-methyl-2-trifluoromethylpentyl]-4-methyl-1H-indole-6-carbonitrile;
1,1,1-Trifluoro-4-(5-fluoro-2,3-dihydrobenzofuran-7-yl)-4-methyl-2-(5-methylsulfanyl-1H-indol-2-ylmethyl)pentan-2-ol;
2-[2-Hydroxy-4-(5-methanesulfonyl-2-methoxyphenyl)-4-methyl-2-trifluoromethylpentyl]-1H-indole-3-carbonitrile;
1,1,1-Trifluoro-4-(5-fluoro-2,3-dihydrobenzofuran-7-yl)-4-methyl-2-(5-phenyl-1H-indol-2-ylmethyl)pentan-2-ol;
2-[4-(5-tert-Butyl-2-hydroxyphenyl)-2-hydroxy-4-methyl-2-trifluoromethylpentyl]-1H-indole-3-carbonitrile;
2-[2-Hydroxy-4-(2-hydroxy-5-isopropylphenyl)-4-methyl-2-trifluoromethylpentyl]-1H-indole-3-carbonitrile;
2-[2-Hydroxy-4-(2-hydroxy-3,5-dimethylphenyl)-4-methyl-2-trifluoromethylpentyl]-1H-indole-3-carbonitrile;
2-[2-Hydroxy-4-(5-hydroxy-2,4-dimethylphenyl)-4-methyl-2-trifluoromethylpentyl]-1H-indole-3-carbonitrile;
2-[4-(5-tert-Butyl-2-methoxyphenyl)-2-hydroxy-4-methyl-2-trifluoromethylpentyl]-1H-indole-3-carbonitrile;
2-[2-Hydroxy-4-(5-isopropyl-2-methoxyphenyl)-4-methyl-2-trifluoromethylpentyl]-1H-indole-3-carbonitrile;
2-[2-Hydroxy-4-(2-methoxy-5-methylphenyl)-4-methyl-2-trifluoromethylpentyl]-4-methyl-1H-indole-6-carbonitrile;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
1,1,1-Trifluoro-4-(2-fluorophenyl)-2-(1H-indol-2-ylmethyl)-4-methylpentan-2-ol;
1,1,1-Trifluoro-4-(2-fluorophenyl)-4-methyl-2-quinolin-4-ylmethylpentan-2-ol;
1,1,1-Trifluoro-4-(3-fluorophenyl)-2-(1H-indol-2-ylmethyl)-4-methylpentan-2-ol;
1,1,1-Trifluoro-4-(3-fluorophenyl)-4-methyl-2-quinolin-4-ylmethylpentan-2-ol;
1,1,1-Trifluoro-4-(4-fluorophenyl)-2-(1H-indol-2-ylmethyl)-4-methylpentan-2-ol;
1,1,1-Trifluoro-4-(4-fluorophenyl)-4-methyl-2-quinolin-4-ylmethylpentan-2-ol;
3-(4,4,4-Trifluoro-3-hydroxy-1,1-dimethyl-3-quinolin-4-ylmethylbutyl)phenol;
1,1,1-Trifluoro-4-methyl-2-quinolin-4-ylmethyl-4-(2-trifluoromethylphenyl)pentan-2-ol;
1,1,1-Trifluoro-2-(1H-indol-2-ylmethyl)-4-methyl-4-(4-trifluoromethylphenyl)pentan-2-ol;
1,1,1-Trifluoro-4-methyl-2-quinolin-4-ylmethyl-4-(4-trifluoromethylphenyl)pentan-2-ol;
4-(3-Chlorophenyl)-1,1,1-trifluoro-2-(1H-indol-2-ylmethyl)-4-methylpentan-2-ol;
4-(3-Chlorophenyl)-1,1,1-trifluoro-4-methyl-2-quinolin-4-ylmethylpentan-2-ol;
4-(4-Dimethylaminophenyl)-1,1,1-trifluoro-2-(1H-indol-2-ylmethyl)-4-methylpentan-2-ol;
4-Biphenyl-3-yl-1,1,1-trifluoro-4-methyl-2-quinolin-4-ylmethylpentan-2-ol;
4-(3-Bromophenyl)-1,1,1-trifluoro-2-(1H-indol-2-ylmethyl)-4-methylpentan-2-ol;
4-(2-Difluoromethoxy-5-fluorophenyl)-1,1,1-trifluoro-2-(1H-indol-2-ylmethyl)-4-methylpentan-2-ol;
4-Biphenyl-3-yl-1,1,1-trifluoro-2-(1H-indol-2-ylmethyl)-4-methylpentan-2-ol;
4-(4-Dimethylaminophenyl)-1,1,1-trifluoro-4-methyl-2-quinolin-4-ylmethylpentan-2-ol;
2-[4-(5-Fluoro-2-methylphenyl)-2-hydroxy-4-methyl-2-trifluoromethylpentyl]-1,6-dihydropyrrolo[2,3-c]pyridin-5-one;
2-[4-(5-Fluoro-2-methylphenyl)-2-hydroxy-4-methyl-2-trifluoromethylpentyl]-6-methyl-1,6-dihydropyrrolo[2,3-c]pyridin-5-one;
1,1,1-Trifluoro-4-(5-fluoro-2-methylphenyl)-2-(5-methoxy-1H-pyrrolo[3,2-b]pyridin-2-ylmethyl)-4-methylpentan-2-ol;
2-[4-(3-Dimethylaminomethylphenyl)-2-hydroxy-4-methyl-2-trifluoromethylpentyl]-1H-indole-5-carbonitrile;
1,1,1-Trifluoro-2-(1H-indol-2-ylmethyl)-4-methyl-4-pyridin-2-ylpentan-2-ol;
1,1,1-Trifluoro-4-methyl-4-pyridin-4-yl-2-quinolin-4-ylmethylpentan-2-ol;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
1,1,1-Trifluoro-4-(5-fluoro-2-methoxyphenyl)-4-methyl-2-pyridin-4-ylmethylpentan-2-ol;
4-Fluoro-2-[4,4,4-trifluoro-3-(2-fluoropyridin-4-ylmethyl)-3-hydroxy-1,1-dimethylbutyl]phenol;
2-[3-(2-Bromopyridin-4-ylmethyl)-4,4,4-trifluoro-3-hydroxy-1,1-dimethylbutyl]-4-fluorophenol;
2-(6,8-Dimethylquinolin-4-ylmethyl)-1,1,1-trifluoro-4-(5-fluoro-2-methoxyphenyl)-4-methylpentan-2-ol;
4-[4-(5-Fluoro-2-methoxyphenyl)-2-hydroxy-4-methyl-2-trifluoromethylpentyl]pyridine-2-carbonitrile;
2,6-Dichloro-4-[4-(5-fluoro-2-methoxyphenyl)-2-hydroxy-4-methyl-2-trifluoromethylpentyl]nicotinonitrile;

2,6-Dichloro-4-[4-(5-fluoro-2-hydroxyphenyl)-2-hydroxy-4-methyl-2-trifluoromethylpentyl]nicotinonitrile;
2-(2,6-Dichloroquinolin-4-ylmethyl)-1,1,1-trifluoro-4-(5-fluoro-2-methoxyphenyl)-4-methylpentan-2-ol;
2-[3-(2-Chloro-8-methylquinolin-4-ylmethyl)-4,4,4-trifluoro-3-hydroxy-1,1-dimethylbutyl]-4-fluorophenol;
2-[3-(2,6-Dichloroquinolin-4-ylmethyl)-4,4,4-trifluoro-3-hydroxy-1,1-dimethylbutyl]-4-fluorophenol;
4-(2,3-Dihydrobenzofuran-7-yl)-2-(2,6-dimethylpyridin-4-ylmethyl)-1,1,1-trifluoro-4-methylpentan-2-ol;
2-(2,6-Dimethylpyridin-4-ylmethyl)-1,1,1-trifluoro-4-(3-fluorophenyl)-4-methylpentan-2-ol;
2-(2,6-Dimethylpyridin-4-ylmethyl)-1,1,1-trifluoro-4-(4-fluorophenyl)-4-methylpentan-2-ol;
1,1,1-Trifluoro-4-(5-fluoro-2-methylphenyl)-4-methyl-2-quinolin-4-ylmethylpentan-2-ol;
2-(2,6-Dimethylpyridin-4-ylmethyl)-1,1,1-trifluoro-4-(5-fluoro-2-methylphenyl)-4-methylpentan-2-ol;
2-(2,6-Dimethylpyridin-4-ylmethyl)-1,1,1-trifluoro-4-methyl-4-m-tolylpentan-2-ol;
1,1,1-Trifluoro-4-(5-fluoro-2-methoxyphenyl)-4-methyl-2-(2-methylquinolin-4-ylmethyl)pentan-2-ol;
4-Fluoro-2-(4,4,4-trifluoro-3-hydroxy-1,1-dimethyl-3-quinolin-4-ylmethylbutyl)phenol;
4-Fluoro-2-[4,4,4-trifluoro-3-hydroxy-1,1-dimethyl-3-(2-methylquinolin-4-ylmethyl)butyl]phenol;
2-(2,6-Dimethylpyridin-4-ylmethyl)-1,1,1-trifluoro-4-(4-fluoro-2-methoxyphenyl)-4-methylpentan-2-ol;
1,1,1-Trifluoro-4-(5-fluoro-2-methoxyphenyl)-4-methyl-2-(7-methylquinolin-4-ylmethyl)pentan-2-ol;
2-[3-(2,6-Dimethylpyridin-4-ylmethyl)-4,4,4-trifluoro-3-hydroxy-1,1-dimethylbutyl]-5-fluorophenol;
1,1,1-Trifluoro-4-(4-fluorophenyl)-4-methyl-2-(2-methylquinolin-4-ylmethyl)pentan-2-ol;
1,1,1-Trifluoro-4-(3-fluorophenyl)-4-methyl-2-(3-methyl-1H-indol-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-2-(7-fluoro-4-methylquinolin-8-yl)-4-methylpentan-2-ol;
4-(2,6-Dimethylphenyl)-1,1,1-trifluoro-2-(1H-indol-2-ylmethyl)-4-methylpentan-2-ol;
2-(3-Bromo-1H-indol-2-ylmethyl)-1,1,1-trifluoro4-(3-fluorophenyl)-4-methylpentan-2-ol;
4-(3,4-Dimethylphenyl)-1,1,1-trifluoro-2-(1H-indol-2-ylmethyl)-4-methylpentan-2-ol;
1,1,1-Trifluoro-4-(3-fluoro-4-methylphenyl)-2-(1H-indol-2-ylmethyl)-4-methylpentan-2-ol;
1,1,1-Trifluoro-4-(4-fluoro-3-methylphenyl)-2-(1H-indol-2-ylmethyl)-4-methylpentan-2-ol;
1,1,1-Trifluoro-4-(3-fluoro-4-methylphenyl)-4-methyl-2-quinolin-4-ylmethylpentan-2-ol;
1,1,1-Trifluoro-4-(4-fluoro-2-methylphenyl)-4-methyl-2-quinolin-4-ylmethylpentan-2-ol;
4-(3,4-Dimethylphenyl)-1,1,1-trifluoro-4-methyl-2-quinolin-4-ylmethylpentan-2-ol;
4-(2,5-Dimethylphenyl)-1,1,1-trifluoro-2-(1H-indol-2-ylmethyl)-4-methylpentan-2-ol;
1,1,1-Trifluoro-2-(1H-indol-2-ylmethyl)-4-(2-methoxy-5-methylphenyl)-4-methylpentan-2-ol;
4-Methyl-2-[4,4,4-trifluoro-3-hydroxy-3-(1H-indol-2-ylmethyl)-1,1-dimethylbutyl]phenol;
4-(2,5-Dimethylphenyl)-1,1,1-trifluoro-4-methyl-2-quinolin-4-ylmethylpentan-2-ol;
1,1,1-Trifluoro-4-(2-methoxy-5-methylphenyl)-4-methyl-2-quinolin-4-ylmethylpentan-2-ol;
4-(2,5-Dimethoxyphenyl)-1,1,1-trifluoro-4-methyl-2-(1H-pyrrolo[2,3-c]pyridin-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-4-methyl-2-(7H-pyrrolo[2,3-d]pyrimidin-6-ylmethyl)pentan-2-ol;
1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol;
2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol;
2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol; and
2-(5-Chloro-1H-pyrrolo[2,3-c]pyridin-2-ylmethyl)-1,1,1-trifluoro-4-(5-fluoro-2-methylphenyl)-4-methylpentan-2-ol,
or a tautomer, prodrug, solvate, or salt thereof.

In addition, the following compounds of the invention of Formula (IA) have been tested and have shown activity as potent agonists of the glucocorticoid receptor function in one or more of the above assays:
4-Pyrimidin-5-yl-2-[4,4,4-trifluoro-3-hydroxy-1,1-dimethyl-3-(1H-pyrrolo[2,3-c]pyridin-ylmethyl)butyl]phenol;
1,1,1-Trifluoro-4-(5-fluoro-2-methoxyphenyl)-4-methyl-2-(3-methyl-1H-pyrrolo[3,2-c]pyridin-2-ylmethyl)pentan-2-ol;
1,1,1-Trifluoro-4-(5-fluoro-2,3-dihydrobenzofuran-7-yl)-4-methyl-2-(1H-pyrrolo[3,2-c]pyridin-2-ylmethyl)pentan-2-ol;
1,1,1-Trifluoro-4-(5-fluoro-2-methylphenyl)-4-methyl-2-(3-methyl-1H-pyrrolo[2,3-c]pyridin-2-ylmethyl)pentan-2-ol;
2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol;
2-[4-(5-Fluoro-2-methoxyphenyl)-2-hydroxy-4-methyl-2-trifluoromethylpentyl]-1H-pyrrolo[3,2-b]pyridine-5-carbonitrile;
1,1,1-Trifluoro-4-(5-fluoro-2-methoxyphenyl)-4-methyl-2-(6-methyl-1H-pyrrolo[3,2-c]pyridin-2-ylmethyl)pentan-2-ol;
1,1,1-Trifluoro-4-(5-fluoro-2-methoxyphenyl)-4-methyl-2-(4-methyl-1H-pyrrolo[3,2-c]pyridin-2-ylmethyl)pentan-2-ol;
2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile;
2-[4-(5-Fluoro-2-methoxyphenyl)-2-hydroxy-4-methyl-2-trifluoromethylpentyl]-1H-pyrrolo[2,3-c]pyridine-5-carbonitrile;
2-[4-(5-Fluoro-2-methoxyphenyl)-2-hydroxy-4-methyl-2-trifluoromethylpentyl]-1H-pyrrolo[3,2-c]pyridine-4-carbonitrile;
1,1,1-Trifluoro-4-(5-fluoro-2-methoxyphenyl)-4-methyl-2-(5H-pyrrolo[3,2-d]pyrimidin-6-ylmethyl)pentan-2-ol;
1,1,1-Trifluoro-4-(5-fluoro-2-methoxyphenyl)-4-methyl-2-thieno[2,3-d]pyridazin-2-ylmethylpentan-2-ol;
1,1,1-Trifluoro-4-(5-fluoro-2-methoxyphenyl)-4-methyl-2-(5H-pyrrolo[3,2-c]pyridazin-6-ylmethyl)pentan-2-ol;
1,1,1-Trifluoro-4-(5-fluoro-2-methoxyphenyl)-4-methyl-2-(1H-pyrrolo[2,3-d]pyridazin-2-ylmethyl)pentan-2-ol;
2-(4,6-Dimethyl-1H-pyrrolo[3,2-c]pyridin-2-ylmethyl)-1,1,1-trifluoro-4-(5-fluoro-2-methylphenyl)-4-methylpentan-2-ol;

4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol;

4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol;

1,1,1-Trifluoro-4-(5-fluoro-2-methylphenyl)-4-methyl-2-(6-methyl-1H-pyrrolo[3,2-c]pyridin-2-ylmethyl)pentan-2-ol;

2-[4-(5-Fluoro-2-methylphenyl)-2-hydroxy-4-methyl-2-trifluoromethylpentyl]-1H-pyrrolo[3,2-b]pyridine-5-carbonitrile;

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile;

1,1,1-Trifluoro-4-(5-fluoro-2-methylphenyl)-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(3-methyl-1H-pyrrolo[2,3-c]pyridin-2-ylmethyl)pentan-2-ol;

1,1,1-Trifluoro-4-(5-fluoro-2-methylphenyl)-4-methyl-2-(5H-pyrrolo[3,2-c]pyridazin-6-ylmethyl)pentan-2-ol;

1,1,1-Trifluoro-4-(5-fluoro-2-methoxyphenyl)-2-(7-fluoro-1H-pyrrolo[2,3-c]pyridin-2-ylmethyl)-4-methylpentan-2-ol;

1,1,1-Trifluoro-4-(5-fluoro-2-methoxyphenyl)-4-methyl-2-(4-methyl-1H-pyrrolo[2,3-c]pyridin-2-ylmethyl)pentan-2-ol;

2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol;

1,1,1-Trifluoro-4-(5-fluoro-2-methoxyphenyl)-4-methyl-2-(5-trifluoromethyl-1H-pyrrolo[2,3-c]pyridin-2-ylmethyl)pentan-2-ol;

1,1,1-Trifluoro-4-(5-fluoro-2-methoxyphenyl)-2-(5-methoxy-1H-pyrrolo[2,3-c]pyridin-2-ylmethyl)-4-methylpentan-2-ol;

1,1,1-Trifluoro-4-(5-fluoro-2-methylphenyl)-4-methyl-2-(4-methyl-1H-pyrrolo[2,3-c]pyridin-2-ylmethyl)pentan-2-ol;

1,1,1-Trifluoro-4-(5-fluoro-2-methylphenyl)-2-(5-isopropoxy-1H-pyrrolo[2,3-c]pyridin-2-ylmethyl)-4-methylpentan-2-ol;

1,1,1-Trifluoro-4-(5-fluoro-2-methylphenyl)-2-(5-methoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol;

1,1,1-Trifluoro-4-(5-fluoro-2-methylphenyl)-2-(7-fluoro-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(5-trifluoromethyl-1H-pyrrolo[2,3-c]pyridin-2-ylmethyl)pentan-2-ol;

2-(5-Dimethylamino-1H-pyrrolo[2,3-c]pyridin-2-ylmethyl)-1,1,1-trifluoro-4-(5-fluoro-2-methylphenyl)-4-methylpentan-2-ol;

1,1,1-Trifluoro-4-(5-fluoro-2-methoxyphenyl)-2-(5-chloro-1H-pyrrolo[2,3-c]pyridin-2-ylmethyl)-4-methylpentan-2-ol;

4-(5-Bromo-2,3-dihydrobenzofuran-7-yl)-1,1,1-trifluoro-4-methyl-2-(1H-pyrrolo[2,3-c]pyridin-2-ylmethyl)pentan-2-ol;

1,1,1-Trifluoro-4-methyl-4-(5-methyl-2,3-dihydrobenzofuran-7-yl)-2-(1H-pyrrolo[2,3-c]pyridin-2-ylmethyl)pentan-2-ol;

4-(5-Chloro-2,3-dihydrobenzofuran-7-yl)-1,1,1-trifluoro-4-methyl-2-(1H-pyrrolo[2,3-c]pyridin-2-ylmethyl)pentan-2-ol;

1,1,1-Trifluoro-4-(5-fluoro-2-methoxyphenyl)-4-methyl-2-thieno[2,3-c]pyridin-2-ylmethylpentan-2-ol;

4-(5-Chloro-2,3-dihydrobenzofuran-7-yl)-2,4-dimethyl-1-thieno[2,3-c]pyridin-2-ylpentan-2-ol;

4-(5-Fluoro-2-methylphenyl)-2,4-dimethyl-1-thieno[2,3-c]pyridin-2-ylpentan-2-ol;

1,1,1-Trifluoro-4-(5-fluoro-2-methylphenyl)-4-methyl-2-(1H-pyrrolo[3,2-c]pyridin-2-ylmethyl)pentan-2-ol;

1,1,1-Trifluoro-4-methyl-4-(5-methyl-2,3-dihydrobenzofuran-7-yl)-2-(1H-pyrrolo[3,2-c]pyridin-2-ylmethyl)pentan-2-ol;

4-(5-Chloro-2,3-dihydrobenzofuran-7-yl)-1,1,1-trifluoro-4-methyl-2-(1H-pyrrolo[3,2-c]pyridin-2-ylmethyl)pentan-2-ol;

4-(5-Bromo-2,3-dihydrobenzofuran-7-yl)-1,1,1-trifluoro-4-methyl-2-(1H-pyrrolo[3,2-c]pyridin-2-ylmethyl)pentan-2-ol;

2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol;

4-(5-Chloro-2,3-dihydrobenzofuran-7-yl)-1,1,1-trifluoro-4-methyl-2-pyrrolo[3,2-b]pyridin-1-ylmethylpentan-2-ol;

1,1-Difluoro-4-(5-fluoro-2-methoxyphenyl)-4-methyl-2-(1H-pyrrolo[3,2-c]pyridin-2-ylmethyl)pentan-2-ol;

1,1,1-Trifluoro-4-(5-fluoro-2-methylphenyl)-4-methyl-2-pyrrolo[3,2-b]pyridin-1-ylmethylpentan-2-ol;

1,1,1-Trifluoro-4-(5-fluoro-2-methylphenyl)-4-methyl-2-thieno[3,2-c]pyridin-2-ylmethylpentan-2-ol;

2-[4-(2,3-Dihydrobenzofuran-7-yl)-2-hydroxy-4-methyl-2-trifluoromethylpentyl]-4-methyl-1H-indole-6-carbonitrile;

4-Fluoro-2-[4,4,4-trifluoro-3-hydroxy-1,1-dimethyl-3-(5-nitro-1H-indol-2-ylmethyl)butyl]phenol;

2-[4-(5-Fluoro-2-methoxyphenyl)-2-hydroxy-4-methyl-2-trifluoromethylpentyl]-1H-indole-6-carbonitrile;

2-[4-(5-Fluoro-2-hydroxyphenyl)-2-hydroxy-4-methyl-2-trifluoromethylpentyl]-1H-indole-6-carbonitrile;

N-{2-[4-(5-Fluoro-2-methoxyphenyl)-2-hydroxy-4-methyl-2-trifluoromethylpentyl]-1H-indol-5-yl}acetamide;

1,1,1-Trifluoro-4-(4-fluoro-2-methoxyphenyl)-2-(7-fluoro-4-methyl-1H-indol-2-ylmethyl)-4-methylpentan-2-ol;

5-Fluoro-2-[4,4,4-trifluoro-3-(7-fluoro-4-methyl-1H-indol-2-ylmethyl)-3-hydroxy-1,1-dimethylbutyl]phenol;

2-[4-(3-[1,3]Dioxolan-2-ylphenyl)-2-hydroxy-4-methyl-2-trifluoromethylpentyl]-1H-indole-5-carbonitrile;

2-[4-(4-Fluoro-2-hydroxyphenyl)-2-hydroxy-4-methyl-2-trifluoromethylpentyl]-4-methyl-1H-indole-6-carbonitrile;

2-[4-(1-Fluoro-2-methoxyphenyl)-2-hydroxy-4-methyl-2-trifluoromethylpentyl]-1H-indole-5-carboxylic acid methylamide;

{2-[4-(5-Fluoro-2-methoxyphenyl)-2-hydroxy-4-methyl-2-trifluoromethylpentyl]-1H-indol-5-yl}pyrrolidin-1-ylmethanone;

{2-[4-(5-Fluoro-2-methoxyphenyl)-2-hydroxy-4-methyl-2-trifluoromethylpentyl]-1H-indol-5-yl}(3-hydroxypyrrolidin-1-yl)methanone;

2-[4-(5-Fluoro-2-methoxyphenyl)-2-hydroxy-4-methyl-2-trifluoromethylpentyl]-1H-indole-5-carboxylic acid cyanomethylamide;

({2-[4-(5-Fluoro-2-methoxyphenyl)-2-hydroxy-4-methyl-2-trifluoromethylpentyl]-1H-indole-5-carbonyl}amino)acetic acid methyl ester;
2-[4-(5-Fluoro-2-methoxyphenyl)-2-hydroxy-4-methyl-2-trifluoromethylpentyl]-1H-indole-5-carboxylic acid carbamoylmethylamide;
4-({2-[4-(5-Fluoro-2-methoxyphenyl)-2-hydroxy-4-methyl-2-trifluoromethylpentyl]-1H-indole-5-carbonyl}amino)butyric acid methyl ester;
4-Fluoro-2-[4,4,4-trifluoro-3-hydroxy-1,1-dimethyl-3-(5-trifluoromethyl-1H-indol-2-ylmethyl)butyl]phenol;
2-[4-(5-Bromo-2,3-dihydrobenzofuran-7-yl)-2-hydroxy-4-methyl-2-trifluoromethylpentyl]-4-methyl-1H-indole-6-carbonitrile;
2-[2-Hydroxy-4-(5-methanesulfonyl-2,3-dihydrobenzofuran-7-yl)-4-methyl-2-trifluoromethylpentyl]-4-methyl-1H-indole-6-carbonitrile;
2-[4-(5-Bromo-2,3-dihydrobenzofuran-7-yl)-2-hydroxy-4-methyl-2-trifluoromethylpentyl]-1H-indole-5-carboxylic acid amide;
2-[4-(5-Bromo-2,3-dihydrobenzofuran-7-yl)-2-hydroxy-4-methyl-2-trifluoromethylpentyl]-1H-indole-5-carboxylic acid dimethylamide;
2-[4-(5-Bromo-2,3-dihydrobenzofuran-7-yl)-2-hydroxy-4-methyl-2-trifluoromethylpentyl]-1H-indole-5-carboxylic acid cyanomethylamide;
{2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone;
{2-[4-(5-Bromo-2,3-dihydrobenzofuran-7-yl)-2-hydroxy-4-methyl-2-trifluoromethylpentyl]-1H-indol-5-yl}morpholin-4-ylmethanone;
2-[4-(5-Fluoro-2-methoxyphenyl)-2-hydroxy-4-methyl-2-trifluoromethylpentyl]-1H-indole-5-carboxylic acid amide;
{2-[4-(5-Fluoro-2-methoxyphenyl)-2-hydroxy-4-methyl-2-trifluoromethylpentyl]-1H-indol-5-yl}morpholin-4-ylmethanone;
2-(4-Benzo[1,3]dioxol-4-yl-2-hydroxy-4-methyl-2-trifluoromethylpentyl)-4-methyl-1H-indole-6-carbonitrile;
1,1,1-Trifluoro-4-methyl-4-phenyl-2-quinolin-4-ylmethylhexan-2-ol;
2-[2-Hydroxy-4-methyl-4-(5-methylsulfanyl-2,3-dihydrobenzofuran-7-yl)-2-trifluoromethylpentyl]-1H-indole-3-carbonitrile;
7-(4,4,4-Trifluoro-3-hydroxy-1,1-dimethyl-3-quinolin-4-ylmethylbutyl)-2,3-dihydrobenzofuran-5-carbonitrile;
2-[2-Hydroxy-4-(2-hydroxy-5-methylphenyl)-4-methyl-2-trifluoromethylpentyl]-4-methyl-1H-indole-6-carbonitrile;
1,1,1-Trifluoro-4-(5-fluoro-2,3-dihydrobenzofuran-7-yl)-4-methyl-2-(5-methylsulfanyl-1H-indol-2-ylmethyl)pentan-2-ol;
2-[2-Hydroxy-4-(5-methanesulfonyl-2-methoxyphenyl)-4-methyl-2-trifluoromethylpentyl]-1H-indole-3-carbonitrile;
2-[4-(5-tert-Butyl-2-hydroxyphenyl)-2-hydroxy-4-methyl-2-trifluoromethylpentyl]-1H-indole-3-carbonitrile;
2-[2-Hydroxy-4-(2-hydroxy-5-isopropylphenyl)-4-methyl-2-trifluoromethylpentyl]-1H-indole-3-carbonitrile;
2-[2-Hydroxy-4-(2-hydroxy-3,5-dimethylphenyl)-4-methyl-2-trifluoromethylpentyl]-1H-indole-3-carbonitrile;
2-[2-Hydroxy-4-(5-hydroxy-2,4-dimethylphenyl)-4-methyl-2-trifluoromethylpentyl]-1H-indole-3-carbonitrile;
2-[4-(5-tert-Butyl-2-methoxyphenyl)-2-hydroxy-4-methyl-2-trifluoromethylpentyl]-1H-indole-3-carbonitrile;
2-[2-Hydroxy-4-(5-isopropyl-2-methoxyphenyl)-4-methyl-2-trifluoromethylpentyl]-1H-indole-3-carbonitrile;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
1,1,1-Trifluoro-4-(2-fluorophenyl)-2-(1H-indol-2-ylmethyl)-4-methylpentan-2-ol;
1,1,1-Trifluoro-4-(2-fluorophenyl)-4-methyl-2-quinolin-4-ylmethylpentan-2-ol;
1,1,1-Trifluoro-4-(3-fluorophenyl)-2-(1H-indol-2-ylmethyl)-4-methylpentan-2-ol;
1,1,1-Trifluoro-4-(3-fluorophenyl)-4-methyl-2-quinolin-4-ylmethylpentan-2-ol;
1,1,1-Trifluoro-4-(4-fluorophenyl)-2-(1H-indol-2-ylmethyl)-4-methylpentan-2-ol;
1,1,1-Trifluoro-4-(4-fluorophenyl)-4-methyl-2-quinolin-4-ylmethylpentan-2-ol;
3-(4,4,4-Trifluoro-3-hydroxy-1,1-dimethyl-3-quinolin-4-ylmethylbutyl)phenol;
1,1,1-Trifluoro-4-methyl-2-quinolin-4-ylmethyl-4-(2-trifluoromethylphenyl)pentan-2-ol;
1,1,1-Trifluoro-4-methyl-2-quinolin-4-ylmethyl-4-(4-trifluoromethylphenyl)pentan-2-ol;
4-(3-Chlorophenyl)-1,1,1-trifluoro-2-(1H-indol-2-ylmethyl)-4-methylpentan-2-ol;
4-(3-Chlorophenyl)-1,1,1-trifluoro-4-methyl-2-quinolin-4-ylmethylpentan-2-ol;
4-Biphenyl-3-yl-1,1,1-trifluoro-4-methyl-2-quinolin-4-ylmethylpentan-2-ol;
4-(3-Bromophenyl)-1,1,1-trifluoro-2-(1H-indol-2-ylmethyl)-4-methylpentan-2-ol;
4-(2-Difluoromethoxy-5-fluorophenyl)-1,1,1-trifluoro-2-(1H-indol-2-ylmethyl)-4-methylpentan-2-ol;
4-(4-Dimethylaminophenyl)-1,1,1-trifluoro-4-methyl-2-quinolin-4-ylmethylpentan-2-ol;
1,1,1-Trifluoro-4-(5-fluoro-2-methylphenyl)-2-(5-methoxy-1H-pyrrolo[3,2-b]pyridin-2-ylmethyl)-4-methylpentan-2-ol;
2-[4-(3-Dimethylaminomethylphenyl)-2-hydroxy-4-methyl-2-trifluoromethylpentyl]-1H-indole-5-carbonitrile;
1,1,1-Trifluoro-2-(1H-indol-2-ylmethyl)-4-methyl-4-pyridin-2-ylpentan-2-ol;
1,1,1-Trifluoro-4-methyl-2-quinolin-4-ylmethyl-4-o-tolylpentan-2-ol;
1,1,1-Trifluoro-4-methyl-2-quinolin-4-ylmethyl-4-m-tolylpentan-2-ol;
4-Fluoro-2-[4,4,4-trifluoro-3-(2-fluoropyridin-4-ylmethyl)-3-hydroxy-1,1-dimethylbutyl]phenol;
2-[3-(2-Bromopyridin-4-ylmethyl)-4,4,4-trifluoro-3-hydroxy-1,1-dimethylbutyl]-4-fluorophenol;
2-(6,8-Dimethylquinolin-4-ylmethyl)-1,1,1-trifluoro-4-(5-fluoro-2-methoxyphenyl)-4-methylpentan-2-ol;
4-[4-(5-Fluoro-2-methoxyphenyl)-2-hydroxy-4-methyl-2-trifluoromethylpentyl]pyridine-2-carbonitrile;
2,6-Dichloro-4-[4-(5-fluoro-2-methoxyphenyl)-2-hydroxy-4-methyl-2-trifluoromethylpentyl]nicotinonitrile;
2,6-Dichloro-4-[4-(5-fluoro-2-hydroxyphenyl)-2-hydroxy-4-methyl-2-trifluoromethylpentyl]nicotinonitrile;
2-[3-(2,6-Dichloroquinolin-4-ylmethyl)-4,4,4-trifluoro-3-hydroxy-1,1-dimethylbutyl]-4-fluorophenol;
4-(2,3-Dihydrobenzofuran-7-yl)-2-(2,6-dimethylpyridin-4-ylmethyl)-1,1,1-trifluoro-4-methylpentan-2-ol;
2-(2,6-Dimethylpyridin-4-ylmethyl)-1,1,1-trifluoro-4-(3-fluorophenyl)-4-methylpentan-2-ol;
2-(2,6-Dimethylpyridin-4-ylmethyl)-1,1,1-trifluoro-4-(4-fluorophenyl)-4-methylpentan-2-ol;

1,1,1-Trifluoro-4-(5-fluoro-2-methylphenyl)-4-methyl-2-quinolin-4-ylmethylpentan-2-ol;
2-(2,6-Dimethylpyridin-4-ylmethyl)-1,1,1-trifluoro-4-(5-fluoro-2-methylphenyl)-4-methylpentan-2-ol;
2-(2,6-Dimethylpyridin-4-ylmethyl)-1,1,1-trifluoro-4-methyl-4-m-tolylpentan-2-ol;
1,1,1-Trifluoro-4-(5-fluoro-2-methoxyphenyl)-4-methyl-2-(2-methylquinolin-4-ylmethyl)pentan-2-ol;
4-Fluoro-2-(4,4,4-trifluoro-3-hydroxy-1,1-dimethyl-3-quinolin-4-ylmethylbutyl)phenol;
4-Fluoro-2-[4,4,4-trifluoro-3-hydroxy-1,1-dimethyl-3-(2-methylquinolin-4-ylmethyl)butyl]phenol;
2-(2,6-Dimethylpyridin-4-ylmethyl)-1,1,1-trifluoro-4-(4-fluoro-2-methoxyphenyl)-4-methylpentan-2-ol;
1,1,1-Trifluoro-4-(5-fluoro-2-methoxyphenyl)-4-methyl-2-(7-methylquinolin-4-ylmethyl)pentan-2-ol;
2-[3-(2,6-Dimethylpyridin-4-ylmethyl)-4,4,4-trifluoro-3-hydroxy-1,1-dimethylbutyl]-5-fluorophenol;
1,1,1-Trifluoro-4-(4-fluorophenyl)-4-methyl-2-(2-methylquinolin-4-ylmethyl)pentan-2-ol;
1,1,1-Trifluoro-4-(3-fluorophenyl)-4-methyl-2-(3-methyl-1H-indol-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-2-(7-fluoro-4-methylquinolin-8-yl)-4-methylpentan-2-ol;
4-(2,6-Dimethylphenyl)-1,1,1-trifluoro-2-(1H-indol-2-ylmethyl)-4-methylpentan-2-ol;
2-(3-Bromo-1H-indol-2-ylmethyl)-1,1,1-trifluoro-4-(3-fluorophenyl)-4-methylpentan-2-ol;
4-(3,4-Dimethylphenyl)-1,1,1-trifluoro-2-(1H-indol-2-ylmethyl)-4-methylpentan-2-ol;
1,1,1-Trifluoro-4-(3-fluoro-4-methylphenyl)-2-(1H-indol-2-ylmethyl)-4-methylpentan-2-ol;
1,1,1-Trifluoro-4-(4-fluoro-3-methylphenyl)-2-(1H-indol-2-ylmethyl)-4-methylpentan-2-ol;
1,1,1-Trifluoro-4-(3-fluoro-4-methylphenyl)-4-methyl-2-quinolin-4-ylmethylpentan-2-ol;
1,1,1-Trifluoro-4-(4-fluoro-2-methylphenyl)-4-methyl-2-quinolin-4-ylmethylpentan-2-ol;
4-(3,4-Dimethylphenyl)-1,1,1-trifluoro-4-methyl-2-quinolin-4-ylmethylpentan-2-ol;
4-(2,5-Dimethylphenyl)-1,1,1-trifluoro-2-(1H-indol-2-ylmethyl)-4-methylpentan-2-ol;
1,1,1-Trifluoro-2-(1H-indol-2-ylmethyl)-4-(2-methoxy-5-methylphenyl)-4-methylpentan-2-ol;
4-Methyl-2-[4,4,4-trifluoro-3-hydroxy-3-(1H-indol-2-ylmethyl)-1,1-dimethylbutyl]phenol;
4-(2,5-Dimethylphenyl)-1,1,1-trifluoro-4-methyl-2-quinolin-4-ylmethylpentan-2-ol;
1,1,1-Trifluoro-4-(2-methoxy-5-methylphenyl)-4-methyl-2-quinolin-4-ylmethylpentan-2-ol;
4-(2,5-Dimethoxyphenyl)-1,1,1-trifluoro-4-methyl-2-(1H-pyrrolo[2,3-c]pyridin-2-ylmethyl)pentan-2-ol;
1,1,1-Trifluoro-2-(1H-indol-2-ylmethyl)-4-methyl-4-(2-trifluoromethylphenyl)pentan-2-ol;
1,1,1-Trifluoro-4-(5-fluoro-2-methoxyphenyl)-4-methyl-2-(7H-pyrrolo[2,3-d]pyrimidin-6-ylmethyl)pentan-2-ol;
1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol;
2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol;
2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol;
2-(5-Chloro-1H-pyrrolo[2,3-c]pyridin-2-ylmethyl)-1,1,1-trifluoro-4-(5-fluoro-2-methylphenyl)-4-methylpentan-2-ol;
4-(5-Bromo-2-methoxyphenyl)-1,1,1-trifluoro-4-methyl-2-(5-piperidin-1-yl-1H-pyrrolo[2,3-c]pyridin-2-ylmethyl)pentan-2-ol;
1,1,1-Trifluoro-4-(5-fluoro-2-methoxyphenyl)-4-methyl-2-(5-morpholin-4-yl-1H-pyrrolo[2,3-c]pyridin-2-ylmethyl)pentan-2-ol;
4-(5-Bromo-2-methoxyphenyl)-1,1,1-trifluoro-4-methyl-2-(5-morpholin-4-yl-1H-pyrrolo[2,3-c]pyridin-2-ylmethyl)pentan-2-ol;
1,1,1-Trifluoro-4-(5-fluoro-2-methylphenyl)-4-methyl-2-(5-morpholin-4-yl-1H-pyrrolo[2,3-c]pyridin-2-ylmethyl)pentan-2-ol;
1,1,1-Trifluoro-4-(5-methanesulfonyl-2,3-dihydrobenzofuran-7-yl)-4-methyl-2-(5-piperidin-1-yl-1H-pyrrolo[2,3-c]pyridin-2-ylmethyl)pentan-2-ol;
2-(5-Dimethylamino-1H-pyrrolo[2,3-c]pyridin-2-ylmethyl)-1,1,1-trifluoro-4-(5-fluoro-2-methylphenyl)-4-methylpentan-2-ol;
2-[5-(Ethylmethylamino)-1H-pyrrolo[2,3-c]pyridin-2-ylmethyl]-1,1,1-trifluoro-4-(5-fluoro-2-methylphenyl)-4-methylpentan-2-ol;
4-(5-Chloro-2,3-dihydrobenzofuran-7-yl)-2-[5-(ethylmethylamino)-1H-pyrrolo[2,3-c]pyridin-2-ylmethyl]-1,1,1-trifluoro-4-methylpentan-2-ol;
2-[5-(Ethylmethylamino)-1H-pyrrolo[2,3-c]pyridin-2-ylmethyl]-1,1,1-trifluoro-4-(5-fluoro-2-methoxyphenyl)-4-methylpentan-2-ol;
1,1,1-Trifluoro-4-methyl-2-(5-morpholin-4-yl-1H-pyrrolo[2,3-c]pyridin-2-ylmethyl)-4-phenylpentan-2-ol;
1,1,1-Trifluoro-4-(3-fluorophenyl)-4-methyl-2-(5-morpholin-4-yl-1H-pyrrolo[2,3-c]pyridin-2-ylmethyl)pentan-2-ol;
1,1,1-Trifluoro-4-(5-fluoro-2-methylphenyl)-4-methyl-2-(5-pyrrolidin-1-yl-1H-pyrrolo[2,3-c]pyridin-2-ylmethyl)pentan-2-ol;
4'-Methoxy-3'-[4,4,4-trifluoro-3-hydroxy-1,1-dimethyl-3-(5-morpholin-4-yl-1H-pyrrolo[2,3-c]pyridin-2-ylmethyl)butyl]biphenyl-2-carbonitrile;
2-(5-Diethylamino-1H-pyrrolo[2,3-c]pyridin-2-ylmethyl)-1,1,1-trifluoro-4-(5-fluoro-2-methylphenyl)-4-methylpentan-2-ol;
1,1,1-Trifluoro-4-(5-fluoro-2-methylphenyl)-2-[5-(isopropylmethylamino)-1H-pyrrolo[2,3-c]pyridin-2-ylmethyl]-4-methylpentan-2-ol;
4-(3-Bromophenyl)-1,1,1-trifluoro-4-methyl-2-(5-morpholin-4-yl-1H-pyrrolo[2,3-c]pyridin-2-ylmethyl)pentan-2-ol;
1,1,1-Trifluoro-4-(4-fluorophenyl)-4-methyl-2-(5-morpholin-4-yl-1H-pyrrolo[2,3-c]pyridin-2-ylmethyl)pentan-2-ol;
1,1,1-Trifluoro-4-methyl-2-(5-morpholin-4-yl-1H-pyrrolo[2,3-c]pyridin-2-ylmethyl)-4-(3-pyrimidin-5-ylphenyl)pentan-2-ol;
3'-{3-[5-(Ethylmethylamino)-1H-pyrrolo[2,3-c]pyridin-2-ylmethyl]-4,4,4-trifluoro-3-hydroxy-1,1-dimethylbutyl}-4'-hydroxybiphenyl-2-carbonitrile;
4'-Hydroxy-3'-[4,4,4-trifluoro-3-hydroxy-1,1-dimethyl-3-(5-morpholin-4-yl-1H-pyrrolo[2,3-c]pyridin-2-ylmethyl)butyl]biphenyl-2-carbonitrile;
1,1,1-Trifluoro-4-(5-fluoro-2-methylphenyl)-4-methyl-2-(5-morpholin-4-ylmethyl-1H-pyrrolo[3,2-b]pyridin-2-ylmethyl)pentan-2-ol;

4-(5-Chloro-2,3-dihydrobenzofuran-7-yl)-1,1,1-trifluoro-4-methyl-2-(5-morpholin-4-ylmethyl-1H-pyrrolo[3,2-b]pyridin-2-ylmethyl)pentan-2-ol;

4-Chloro-2-[4,4,4-trifluoro-3-hydroxy-1,1-dimethyl-3-(5-morpholin-4-ylmethyl-1H-pyrrolo[3,2-b]pyridin-2-ylmethyl)butyl]phenol;

1,1,1-Trifluoro-4-(5-fluoro-2-methylphenyl)-4-methyl-2-(4-methyl-1H-pyrrolo[3,2-c]pyridin-2-ylmethyl)pentan-2-ol;

4-(5-Chloro-2,3-dihydrobenzofuran-7-yl)-1,1,1-trifluoro-4-methyl-2-(4-methyl-1H-pyrrolo[3,2-c]pyridin-2-ylmethyl)pentan-2-ol;

2-[2-Hydroxy-4-(5-methanesulfonyl-2,3-dihydrobenzofuran-7-yl)-4-methyl-2-trifluoromethylpentyl]-4-methyl-1H-pyrrolo[3,2-c]pyridine-6-carbonitrile;

2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile;

1,1,1-Trifluoro-4-(5-fluoro-2-methylphenyl)-4-methyl-2-(5H-pyrrolo[3,2-d]pyrimidin-6-ylmethyl)pentan-2-ol;

2-[4-(5-Chloro-2,3-dihydrobenzofuran-7-yl)-2-hydroxy-4-methyl-2-trifluoromethylpentyl]-1H-pyrrolo[2,3-c]pyridine-5-carbonitrile;

1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}ethanone;

2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid amide;

4-(5-Chloro-2,3-dihydrobenzofuran-7-yl)-1,1,1-trifluoro-2-(5-hydroxymethyl-1H-pyrrolo[3,2-b]pyridin-2-ylmethyl)-4-methylpentan-2-ol;

2-(5-Aminomethyl-1H-pyrrolo[3,2-b]pyridin-2-ylmethyl)-4-(5-chloro-2,3-dihydrobenzofuran-7-yl)-1,1,1-trifluoro-4-methylpentan-2-ol;

1,1,1-Trifluoro-4-(5-fluoro-2-methylphenyl)4-methyl-2-(5H-pyrrolo[3,2-c]pyridazin-6-ylmethyl)pentan-2-ol;

4-Fluoro-2-[4,4,4-trifluoro-3-hydroxy-1,1-dimethyl-3-(5H-pyrrolo[3,2-c]pyridazin-6-ylmethyl)butyl]phenol;

4-Fluoro-2-[4,4,4-trifluoro-3-hydroxy-1,1-dimethyl-3-(5H-pyrrolo[3,2-d]pyrimidin-6-ylmethyl)butyl]phenol;

1,1,1-Trifluoro-4-(4-fluoro-2-methoxyphenyl)-4-methyl-2-(3-methyl-1H-pyrrolo[2,3-c]pyridin-2-ylmethyl)pentan-2-ol;

1,1,1-Trifluoro-4-(3-fluorophenyl)-4-methyl-2-(3-methyl-1H-pyrrolo[2,3-c]pyridin-2-ylmethyl)pentan-2-ol;

5-Fluoro-2-[4,4,4-trifluoro-3-hydroxy-1,1-dimethyl-3-(3-methyl-1H-pyrrolo[2,3-c]pyridin-2-ylmethyl)butyl]phenol;

4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol;

4-(5-Chloro-2,3-dihydrobenzofuran-7-yl)-1,1,1-trifluoro-4-methyl-2-(3-phenyl-7H-pyrrolo[2,3-c]pyridazin-6-ylmethyl)pentan-2-ol;

1,1,1-Trifluoro-4-(5-fluoro-2-methylphenyl)-4-methyl-2-(3-phenyl-7H-pyrrolo[2,3c]-pyridazin-6-ylmethyl)pentan-2-ol;

4-(5-Chloro-2,3-dihydrobenzofuran-7-yl)-1,1,1-trifluoro-4-methyl-2-(4-methyl-1H-pyrrolo[3,2-c]pyridin-2-ylmethyl)pentan-2-ol;

1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}propan-1-one;

1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2-methylpropan-1-one;

1,1,1-Trifluoro-4-(4-fluoro-2-methoxyphenyl)-4-methyl-2-(4-methyl-1H-pyrrolo[3,2-c]pyridin-2-ylmethyl)pentan-2-ol;

1,1,1-Trifluoro-4-(2-methoxy-5-thiophen-3-ylphenyl)-4-methyl-2-(4-methyl-1H-pyrrolo[3,2-c]pyridin-2-ylmethyl)pentan-2-ol;

1,1,1-Trifluoro-4-(4-methoxybiphenyl-3-yl)-4-methyl-2-(4-methyl-1H-pyrrolo[3,2-c]pyridin-2-ylmethyl)pentan-2-ol;

5-Fluoro-2-[4,4,4-trifluoro-3-hydroxy-1,1-dimethyl-3-(4-methyl-1H-pyrrolo[3,2-c]pyridin-2-ylmethyl)butyl]phenol;

4-Thiophen-3-yl-2-[4,4,4-trifluoro-3-hydroxy-1,1-dimethyl-3-(4-methyl-1H-pyrrolo[3,2-c]pyridin-2-ylmethyl)butyl]phenol;

3-[4,4,4-Trifluoro-3-hydroxy-1,1-dimethyl-3-(4-methyl-1H-pyrrolo[3,2-c]pyridin-2-ylmethyl)butyl]biphenyl-4-ol;

1,1,1-Trifluoro-4-methyl-2-(3-methyl-1H-pyrrolo[2,3-c]pyridin-2-ylmethyl)-4-(5-pyrimidin-5-yl-2,3-dihydrobenzofuran-7-yl)pentan-2-ol;

1,1,1-Trifluoro-4-(2-methoxy-5-pyridin-3-ylphenyl)-4-methyl-2-(3-methyl-1H-pyrrolo[2,3-c]pyridin-2-ylmethyl)pentan-2-ol;

4-Pyridin-3-yl-2-[4,4,4-trifluoro-3-hydroxy-1,1-dimethyl-3-(3-methyl-1H-pyrrolo[2,3-c]pyridin-2-ylmethyl)butyl]phenol;

1,1,1-Trifluoro-4-(5-fluoro-2,3-dihydrobenzofuran-7-yl)-4-methyl-2-(5H-pyrrolo[3,2-d]pyrimidin-6-ylmethyl)pentan-2-ol;

1,1,1-Trifluoro-4-(2-methoxy-5-pyridin-3-ylphenyl)-4-methyl-2-(5-phenoxy-1H-pyrrolo[2,3-c]pyridin-2-ylmethyl)pentan-2-ol;

1,1,1-Trifluoro-4-methyl-4-phenyl-2-(3-phenyl-7H-pyrrolo[2,3-c]pyridazin-6-ylmethyl)pentan-2-ol;

1,1,1-Trifluoro-4-(3-fluorophenyl)-4-methyl-2-(3-phenyl-7H-pyrrolo[2,3-c]pyridazin-6-ylmethyl)pentan-2-ol;

4-Pyridin-3-yl-2-[4,4,4-trifluoro-3-hydroxy-1,1-dimethyl-3-(5-phenoxy-1H-pyrrolo[2,3-c]pyridin-2-ylmethyl)butyl]phenol;

1,1,1-Trifluoro-4-methyl-2-(4-methyl-1H-pyrrolo[3,2-c]pyridin-2-ylmethyl)-4-(5-yl-2,3-dihydrobenzofuran-7-yl)pentan-2-ol;

4-Pyridin-3-yl-2-[4,4,4-trifluoro-3-hydroxy-1,1-dimethyl-3-(4-methyl-1H-pyrrolo[3,2-c]pyridin-2-ylmethyl)butyl]phenol;

5-Fluoro-2-[4,4,4-trifluoro-3-hydroxy-1,1-dimethyl-3-(5H-pyrrolo[3,2-d]pyrimidin-6-ylmethyl)butyl]phenol;

1,1,1-Trifluoro-4-methyl-4-(3-morpholin-4-ylmethylphenyl)-2-(5-phenyl-1H-pyrrolo[2,3-c]pyridin-2-ylmethyl)pentan-2-ol;

1,1,1-Trifluoro-4-(3-fluorophenyl)-2-[5-(4-fluorophenyl)-1H-pyrrolo[2,3-c]pyridin-2-ylmethyl]-4-methylpentan-2-ol;

2-(5-Dimethylamino-1H-pyrrolo[2,3-c]pyridin-2-ylmethyl)-1,1,1-trifluoro-4-(5-fluoro-2-methoxyphenyl)-4-methylpentan-2-ol;

2-(5-Dimethylamino-1H-pyrrolo[2,3-c]pyridin-2-ylmethyl)-1,1,1-trifluoro-4-(4-fluoro-2-methoxyphenyl)-4-methylpentan-2-ol;

1,1,1-Trifluoro-4-(3-fluorophenyl)-4-methyl-2-(4-methyl-1H-pyrrolo[2,3-c]pyridin-2-ylmethyl)pentan-2-ol;

1,1,1-Trifluoro-4-(4-fluoro-2-methoxyphenyl)-4-methyl-2-(4-methyl-1H-pyrrolo[2,3-c]pyridin-2-ylmethyl)pentan-2-ol;

2-[3-(5-Dimethylamino-1H-pyrrolo[2,3-c]pyridin-2-ylmethyl)-4,4,4-trifluoro-3-hydroxy-1,1-dimethylbutyl]-4-fluorophenol;

2-[3-(5-Dimethylamino-1H-pyrrolo[2,3-c]pyridin-2-ylmethyl)-4,4,4-trifluoro-3-hydroxy-1,1-dimethylbutyl]-5-fluorophenol;

5-Fluoro-2-[4,4,4-trifluoro-3-hydroxy-1,1-dimethyl-3-(4-methyl-1H-pyrrolo[2,3-c]pyridin-2-ylmethyl)butyl]phenol;

4-(5-Bromo-2-methoxyphenyl)-1,1,1-trifluoro-4-methyl-2-(1H-pyrrolo[2,3-c]pyridin-2-ylmethyl)pentan-2-ol;

4-Bromo-2-[4,4,4-trifluoro-3-hydroxy-1,1-dimethyl-3-(1H-pyrrolo[2,3-c]pyridin-2-ylmethyl)butyl]phenol;

1,1,1-Trifluoro-4-(2-methoxy-5-pyrimidin-5-ylphenyl)-4-methyl-2-(1H-pyrrolo[2,3-c]pyridin-2-ylmethyl)pentan-2-ol;

4-(3-[1,3]Dioxan-2-ylphenyl)-1,1,1-trifluoro-4-methyl-2-(1H-pyrrolo[2,3-c]pyridin-2-ylmethyl)pentan-2-ol;

1,1,1-Trifluoro-4-(4-methoxybiphenyl-3-yl)-4-methyl-2-(1H-pyrrolo[2,3-c]pyridin-2-ylmethyl)pentan-2-ol;

1,1,1-Trifluoro-4-(2-methoxy-5-pyridin-3-ylphenyl)-4-methyl-2-(1H-pyrrolo[2,3-c]pyridin-2-ylmethyl)pentan-2-ol;

1,1,1-Trifluoro-4-(2-methoxy-5-thiophen-3-ylphenyl)-4-methyl-2-(1H-pyrrolo[2,3-c]pyridin-2-ylmethyl)pentan-2-ol;

1,1,1-Trifluoro-4-methyl-4-(3-morpholin-4-ylmethylphenyl)-2-(1H-pyrrolo[2,3-c]pyridin-2-ylmethyl)pentan-2-ol;

3-[4,4,4-Trifluoro-3-hydroxy-1,1-dimethyl-3-(1H-pyrrolo[2,3-c]pyridin-2-ylmethyl)butyl]biphenyl-4-ol;

4-Thiophen-3-yl-2-[4,4,4-trifluoro-3-hydroxy-1,1-dimethyl-3-(1H-pyrrolo[2,3-c]pyridin-2-ylmethyl)butyl]phenol;

4-Thiophen-3-yl-2-[4,4,4-trifluoro-3-hydroxy-1,1-dimethyl-3-(1H-pyrrolo[2,3-c]pyridin-2-ylmethyl)butyl]phenol;

4-Thiophen-3-yl-2-[4,4,4-trifluoro-3-hydroxy-1,1-dimethyl-3-(1H-pyrrolo[2,3-c]pyridin-2-ylmethyl)butyl]phenol;

4'-Methoxy-3'-[4,4,4-trifluoro-3-hydroxy-1,1-dimethyl-3-(4-methyl-1H-pyrrolo[2,3-c]pyridin-2-ylmethyl)butyl]biphenyl-2-carbonitrile;

4'-Methoxy-3'-[4,4,4-trifluoro-3-hydroxy-1,1-dimethyl-3-(1H-pyrrolo[2,3-c]pyridin-2-ylmethyl)butyl]biphenyl-3-carbonitrile;

1,1,1-Trifluoro-4-(2-methoxy-5-pyridin-3-ylphenyl)-4-methyl-2-(4-methyl-1H-pyrrolo[2,3-c]pyridin-2-ylmethyl)pentan-2-ol;

4-(3-Chlorophenyl)-1,1,1-trifluoro-4-methyl-2-(1H-pyrrolo[3,2-c]pyridin-2-ylmethyl)pentan-2-ol;

1,1,1-Trifluoro-4-(2-methoxy-5-pyrimidin-5-ylphenyl)-4-methyl-2-(1H-pyrrolo[3,2-c]pyridin-2-ylmethyl)pentan-2-ol;

4-Pyridin-3-yl-2-[4,4,4-trifluoro-3-hydroxy-1,1-dimethyl-3-(1H-pyrrolo[3,2-c]pyridin-2-ylmethyl)butyl]phenol;

1,1,1-Trifluoro-4-methyl-4-(3-morpholin-4-ylmethylphenyl)-2-(1H-pyrrolo[3,2-c]pyridin-2-ylmethyl)pentan-2-ol;

1,1,1-Trifluoro-4-(2-methoxy-5-pyridin-3-ylphenyl)-4-methyl-2-(1H-pyrrolo[3,2-c]pyridin-2-ylmethyl)pentan-2-ol;

1,1,1-Trifluoro-4-methyl-4-(3-pyridin-3-ylphenyl)-2-(1H-pyrrolo[3,2-c]pyridin-2-ylmethyl)pentan-2-ol;

1,1,1-Trifluoro-4-methyl-4-(3-pyrimidin-5-ylphenyl)-2-(1H-pyrrolo[3,2-c]pyridin-2-ylmethyl)pentan-2-ol;

4-(5-Chloro-2,3-dihydrobenzofuran-7-yl)-1,1,1-trifluoro-4-methyl-2-(5-pyridin-2-yl-1H-indol-2-ylmethyl)pentan-2-ol;

2-(5-Bromo-1H-indol-2-ylmethyl)-4-(5-chloro-2,3-dihydrobenzofuran-7-yl)-1,1,1-trifluoro-4-methylpentan-2-ol;

1,1,1-Trifluoro-4-(5-fluoro-2,3-dihydrobenzofuran-7-yl)-2-(5-methanesulfinyl-1H-indol-2-ylmethyl)-4-methylpentan-2-ol;

3-{2-[4-(5-Fluoro-2,3-dihydrobenzofuran-7-yl)-2-hydroxy-4-methyl-2-trifluoromethylpentyl]-1H-indol-5-yl}benzonitrile;

1,1,1-Trifluoro-4-(5-fluoro-2,3-dihydrobenzofuran-7-yl)-4-methyl-2-(5-pyridin-4-yl-1H-indol-2-ylmethyl)pentan-2-ol;

1,1,1-Trifluoro-4-(5-fluoro-2,3-dihydrobenzofuran-7-yl)-4-methyl-2-(5-pyridin-3-yl-1H-indol-2-ylmethyl)pentan-2-ol;

1,1,1-Trifluoro4-(5-fluoro-2,3-dihydrobenzofuran-7-yl)-4-methyl-2-(5-pyrimidin-5-yl-1H-indol-2-ylmethyl)pentan-2-ol;

2-[5-(4-Dimethylaminophenyl)-1H-indol-2-ylmethyl]-1,1,1-trifluoro-4-(5-fluoro-2,3-dihydrobenzofuran-7-yl)-4-methylpentan-2-ol;

1,1,1-Trifluoro-2-(7-fluoro-4-methyl-1H-indol-2-ylmethyl)-4-(5-methanesulfonyl-2,3-dihydrobenzofuran-7-yl)-4-methylpentan-2-ol;

2-[2-Hydroxy-4-(5-methanesulfonyl-2,3-dihydrobenzofuran-7-yl)-4-methyl-2-trifluoromethylpentyl]-1H-indole-5-carbonitrile;

2-[2-Hydroxy-4-(5-methanesulfonyl-2,3-dihydrobenzofuran-7-yl)-4-methyl-2-trifluoromethylpentyl]-1H-indole-6-carbonitrile;

1,1,1-Trifluoro-4-(5-methanesulfonyl-2,3-dihydrobenzofuran-7-yl)-4-methyl-2-(4-methyl-1H-indol-2-ylmethyl)pentan-2-ol;

2-[4-(5-Fluoro-2-methoxyphenyl)-2-hydroxy-4-methyl-2-trifluoromethylpentyl]-1H-indole-4-carbonitrile;

2-[4-(5-Fluoro-2-hydroxyphenyl)-2-hydroxy-4-methyl-2-trifluoromethylpentyl]-1H-indole-4-carbonitrile;

2-(4-Ethyl-1H-indol-2-ylmethyl)-1,1,1-trifluoro-4-(5-fluoro-2-methoxyphenyl)-4-methylpentan-2-ol;

4-(5-Chloro-2,3-dihydrobenzofuran-7-yl)-1,1,1-trifluoro-2-(2-isopropyl-5H-pyrrolo[3,2-d]pyrimidin-6-ylmethyl)-4-methylpentan-2-ol;

1,1,1-Trifluoro-4-(5-fluoro-2-methoxyphenyl)-2-(2-isopropyl-5H-pyrrolo[3,2-d]pyrimidin-6-ylmethyl)-4-methylpentan-2-ol;

4-(5-Chloro-2,3-dihydrobenzofuran-7-yl)-1,1,1-trifluoro-4-methyl-2-(2-pyrrolidin-1-yl-5H-pyrrolo[3,2-d]pyrimidin-6-ylmethyl)pentan-2-ol;

1,1,1-Trifluoro-4-(5-fluoro-2-methoxyphenyl)-4-methyl-2-(2-pyrrolidin-1-yl-5H-pyrrolo[3,2-d]pyrimidin-6-ylmethyl)pentan-2-ol;

4-Fluoro-2-[4,4,4-trifluoro-3-hydroxy-1,1-dimethyl-3-(2-pyrrolidin-1-yl-5H-pyrrolo[3,2-d]pyrimidin-6-ylmethyl)butyl]phenol;

4-(5-Chloro-2,3-dihydrobenzofuran-7-yl)-1,1,1-trifluoro-4-methyl-2-(2-phenyl-5H-pyrrolo[3,2-d]pyrimidin-6-ylmethyl)pentan-2-ol;

1,1,1-Trifluoro-4-(5-fluoro-2-methylphenyl)-4-methyl-2-(2-phenyl-5H-pyrrolo[3,2-d]pyrimidin-6-ylmethyl)pentan-2-ol;

1,1,1-Trifluoro-4-(5-fluoro-2-methoxyphenyl)-4-methyl-2-(2-phenyl-5H-pyrrolo[3,2-d]pyrimidin-6-ylmethyl)pentan-2-ol;

4-Fluoro-2-[4,4,4-trifluoro-3-hydroxy-1,1-dimethyl-3-(2-phenyl-5H-pyrrolo[3,2-d]pyrimidin-6-ylmethyl)butyl]phenol;

4-(5-Chloro-2,3-dihydrobenzofuran-7-yl)-2-(2-chloro-5H-pyrrolo[3,2-d]pyrimidin-6-ylmethyl)-1,1,1-trifluoro-4-methylpentan-2-ol;

1,1,1-Trifluoro-4-methyl-4-phenyl-2-(2-phenyl-5H-pyrrolo[3,2-d]pyrimidin-6-ylmethyl)pentan-2-ol;

1,1,1-Trifluoro-4-(3-fluorophenyl)-4-methyl-2-(2-phenyl-5H-pyrrolo[3,2-d]pyrimidin-6-ylmethyl)pentan-2-ol;

1,1,1-Trifluoro-4-(2-methoxy-5-methylphenyl)-4-methyl-2-(2-pyrrolidin-1-yl-5H-pyrrolo[3,3-d]pyrimidin-6-ylmethyl)pentan-2-ol;

1,1,1-Trifluoro-4-(2-methoxy-5-methylphenyl)-4-methyl-2-(2-pyrrolidin-1-yl-5H-pyrrolo[3,2-d]pyrimidin-6-ylmethyl)pentan-2-ol;

2-(5-Ethoxy-1H-pyrrolo[2,3-c]pyridin-2-ylmethyl)-1,1,1-trifluoro-4-(5-fluoro-2-methylphenyl)-4-methylpentan-2-ol;

1,1,1-Trifluoro-4-(5-fluoro-2-methoxyphenyl)-4-methyl-2-(5-phenyl-1H-pyrrolo[2,3-c]pyridin-2-ylmethyl)pentan-2-ol;

1,1,1-Trifluoro-4-(5-fluoro-2-methylphenyl)-4-methyl-2-(6-methyl-1H-pyrrolo[3,2-c]pyridin-2-ylmethyl)pentan-2-ol;

1,1,1-Trifluoro-4-(5-fluoro-2-methylphenyl)-4-methyl-2-(4-methyl-1H-pyrrolo[3,2-c]pyridin-2-ylmethyl)pentan-2-ol;

4-(5-Bromo-2-methoxyphenyl)-2-(5-dimethylamino-1H-pyrrolo[2,3-c]pyridin-2-ylmethyl)-1,1,1-trifluoro-4-methylpentan-2-ol;

4-(5-Bromo-2-methoxyphenyl)-1,1,1-trifluoro-2-(5-isopropoxy-1H-pyrrolo[2,3-c]pyridin-2-ylmethyl)-4-methylpentan-2-ol;

1,1,1-Trifluoro-4-(5-fluoro-2-trifluoromethylphenyl)-2-(5-isopropoxy-1H-pyrrolo[2,3-c]pyridin-2-ylmethyl)-4-methylpentan-2-ol;

4-(5-Chloro-2,3-dihydrobenzofuran-7-yl)-1,1,1-trifluoro-4-methyl-2-(6-methyl-1H-pyrrolo[2,3-c]pyridin-2-ylmethyl)pentan-2-ol;

1,1,1-Trifluoro-2-(5-isopropoxy-1H-pyrrolo[2,3-c]pyridin-2-ylmethyl)-4-(2-methoxy-5-pyrimidin-5-ylphenyl)-4-methylpentan-2-ol;

1,1,1-Trifluoro-2-(5-isopropoxy-1H-pyrrolo[2,3-c]pyridin-2-ylmethyl)-4-(4-methoxybiphenyl-3-yl)-4-methylpentan-2-ol;

1,1,1-Trifluoro-2-(5-isopropoxy-1H-pyrrolo[2,3-c]pyridin-2-ylmethyl)-4-(2-methoxy-5-thiophen-3-ylphenyl)-4-methylpentan-2-ol;

2-(5-Dimethylamino-1H-pyrrolo[2,3-c]pyridin-2-ylmethyl)-1,1,1-trifluoro-4-methyl-4-phenylpentan-2-ol;

1,1,1-Trifluoro-4-(2-methoxy-5-pyrimidin-5-ylphenyl)-4-methyl-2-(5-piperidin-1-yl-1H-pyrrolo[2,3-c]pyridin-2-ylmethyl)pentan-2-ol;

1,1,1-Trifluoro-4-(4-methoxybiphenyl-3-yl)-4-methyl-2-(5-piperidin-1-yl-1H-pyrrolo[2,3-c]pyridin-2-ylmethyl)pentan-2-ol;

1,1,1-Trifluoro-4-(2-methoxy-5-pyridin-3-ylphenyl)-4-methyl-2-(5-piperidin-1-yl-1H-pyrrolo[2,3-c]pyridin-2-ylmethyl)pentan-2-ol;

2-(5-Dimethylamino-1H-pyrrolo[2,3-c]pyridin-2-ylmethyl)-1,1,1-trifluoro-4-(2-methoxy-5-pyrimidin-5-ylphenyl)-4-methylpentan-2-ol;

4-Bromo-2-[3-(5-chloro-1H-pyrrolo[2,3-c]pyridin-2-ylmethyl)-4,4,4-trifluoro-3-hydroxy-1,1-dimethylbutyl]phenol;

2-[3-(5-Chloro-1H-pyrrolo[2,3-c]pyridin-2-ylmethyl)-4,4,4-trifluoro-3-hydroxy-1,1-dimethylbutyl]-4-fluorophenol;

2-[2-Hydroxy-4-(4-hydroxybiphenyl-3-yl)-4-methyl-2-trifluoromethylpentyl]-1H-pyrrolo[2,3-c]pyridin-5-ol;

1,1,1-Trifluoro-2-(5-isopropoxy-1H-pyrrolo[2,3-c]pyridin-2-ylmethyl)-4-methyl-4-(5-phenyl-2,3-dihydrobenzofuran-7-yl)pentan-2-ol;

2-[2-Hydroxy-4-(2-methoxy-5-pyrimidin-5-ylphenyl)-4-methyl-2-trifluoromethylpentyl]-1H-pyrrolo[2,3-c]pyridin-5-ol;

Trifluoromethanesulfonic acid 2-[4-(5-fluoro-2-methylphenyl)-2-hydroxy-4-methyl-2-trifluoromethylpentyl]-1H-pyrrolo[2,3-c]pyridin-5-yl ester;

1,1,1-Trifluoro-4-(3-fluorophenyl)-4-methyl-2-(5-piperidin-1-yl-1H-pyrrolo[2,3-c]pyridin-2-ylmethyl)pentan-2-ol;

1,1,1-Trifluoro-4-methyl-4-phenyl-2-(5-piperidin-1-yl-1H-pyrrolo[2,3-c]pyridin-2-ylmethyl)pentan-2-ol;

1,1,1-Trifluoro-4-(3-fluorophenyl)-2-(5-isopropoxy-1H-pyrrolo[2,3-c]pyridin-2-ylmethyl)-4-methylpentan-2-ol;

1,1,1-Trifluoro-2-(5-isopropoxy-1H-pyrrolo[2,3-c]pyridin-2-ylmethyl)-4-methyl-4-phenylpentan-2-ol;

1,1,1-Trifluoro-4-methyl-4-(3-morpholin-4-ylmethylphenyl)-2-(5-morpholin-4-yl-1H-pyrrolo[2,3-c]pyridin-2-ylmethyl)pentan-2-ol;

4-(5-Chloro-2,3-dihydrobenzofuran-7-yl)-1,1,1-trifluoro-2-(5-methoxy-1H-pyrrolo[3,2-b]pyridin-2-ylmethyl)-4-methylpentan-2-ol;

1,1,1-Trifluoro-4-(5-fluoro-2-methylphenyl)-2-(5-methoxy-1H-pyrrolo[3,2-b]pyridin-2-ylmethyl)-4-methylpentan-2-ol;

4-(5-Chloro-2,3-dihydrobenzofuran-7-yl)-2-(5-chloro-1H-pyrrolo[2,3-c]pyridin-2-ylmethyl)-1,1,1-trifluoro-4-methylpentan-2-ol;

1,1,1-Trifluoro-4-(5-fluoro-2-methylphenyl)-2-(4-methoxy-1H-pyrrolo[3,2-c]pyridin-2-ylmethyl)-4-methylpentan-2-ol;

2-[4-(5-Fluoro-2-methylphenyl)-2-hydroxy-4-methyl-2-trifluoromethylpentyl]-1,4-dihydropyrrolo[3,2-b]pyridin-5-one;

2-(5-Chloro-1H-pyrrolo[2,3-c]pyridin-2-ylmethyl)-1,1,1-trifluoro-4-(2-methoxy-5-thiophen-3-ylphenyl)-4-methylpentan-2-ol;

2-(5-Chloro-1H-pyrrolo[2,3-c]pyridin-2-ylmethyl)-1,1,1-trifluoro-4-methyl-4-(5-methylsulfanyl-2,3-dihydrobenzofuran-7-yl)pentan-2-ol;

4-(5-Bromo-2-methoxyphenyl)-2-(5-chloro-1H-pyrrolo[2,3-c]pyridin-2-ylmethyl)-1,1,1-trifluoro-4-methylpentan-2-ol;

1,1,1-Trifluoro-4-(5-fluoro-2-methoxyphenyl)-4-methyl-2-(7H-pyrrolo[2,3-d]pyrimidin-6-ylmethyl)pentan-2-ol;

1,1,1-Trifluoro-4-(2-methoxy-5-naphthalen-1-ylphenyl)-4-methyl-2-(5-morpholin-4-yl-1H-pyrrolo[2,3-c]pyridin-2-ylmethyl)pentan-2-ol;

4-(2'-Chloro-4-methoxybiphenyl-3-yl)-1,1,1-trifluoro-4-methyl-2-(5-morpholin-4-yl-1H-pyrrolo[2,3-c]pyridin-2-ylmethyl)pentan-2-ol;

2-(5-Chloro-1H-pyrrolo[2,3-c]pyridin-2-ylmethyl)-1,1,1-trifluoro-4-(2-methoxy-5-pyrimidin-5-ylphenyl)-4-methylpentan-2-ol;

4'-Methoxy-3'-[4,4,4-trifluoro-3-hydroxy-1,1-dimethyl-3-(5-piperidin-1-yl-1H-pyrrolo[2,3-c]pyridin-2-ylmethyl)butyl]biphenyl-2-carbonitrile;

4-(2'-Chloro-4-methoxybiphenyl-3-yl)-1,1,1-trifluoro-4-methyl-2-(5-piperidin-1-yl-1H-pyrrolo[2,3-c]pyridin-2-ylmethyl)pentan-2-ol;

2-[3-(3-Dimethylaminomethyl-1H-pyrrolo[3,2-c]pyridin-2-ylmethyl)-4,4,4-trifluoro-3-hydroxy-1,1,1-dimethylbutyl]-4-fluorophenol;

1,1,1-Trifluoro4-(5-methanesulfonyl-2,3-dihydrobenzofuran-7-yl)-4-methyl-2-(1H-pyrrolo[3,2-c]pyridin-2-ylmethyl)pentan-2-ol;

2-(3-Chloro-1H-pyrrolo[3,2-c]pyridin-2-ylmethyl)-1,1,1-trifluoro-4-(5-fluoro-2-methoxyphenyl)-4-methylpentan-2-ol;

1,1,1-Trifluoro-4-methyl-4-(5-methylsulfanyl-2,3-dihydrobenzofuran-7-yl)-2-pyrrolo[3,2-b]pyridin-1-ylmethylpentan-2-ol;

1,1,1-Trifluoro-4-(5-methanesulfonyl-2,3-dihydrobenzofuran-7-yl)-4-methyl-2-pyrrolo[3,2-b]pyridin-1-ylmethylpentan-2-ol;

4-(5-Chloro-2,3-dihydrobenzofuran-7-yl)-1,1,1-trifluoro-4-methyl-2-(5-phenyl-1H-pyrrolo[2,3-c]pyridin-2-ylmethyl)pentan-2-ol; and 1,1,1-Trifluoro-4-(5-fluoro-2-methylphenyl)-4-methyl-2-(5-phenyl-1H-pyrrolo[2,3-c]pyridin-2-ylmethyl)pentan-2-ol, or a tautomer, prodrug, solvate, or salt thereof.

The following compounds of the invention of Formula (IB) have been tested and have shown activity as agonists of the glucocorticoid receptor function in one or more of the above assays:

2-Cyclopropyl-4-(5-fluoro-2-methoxyphenyl)-4-methyl-1-(1H-pyrrolo[3,2-c]pyridin-2-yl)pentan-2-ol;

2-Cyclopropyl-4-(5-fluoro-2-methylphenyl)-4-methyl-1-(1H-pyrrolo[2,3-c]pyridin-2-yl)pentan-2-ol;

4-(5-Chloro-2,3-dihydrobenzofuran-7-yl)-2-cyclopropyl-4-methyl-1-(1H-pyrrolo[2,3-c]pyridin-2-yl)pentan-2-ol;

2-Cyclopropyl-4-(5-fluoro-2-methylphenyl)-4-methyl-1-(1H-pyrrolo[3,2-c]pyridin-2-yl)pentan-2-ol;

4-(5-Chloro-2,3-dihydrobenzofuran-7-yl)-2-cyclopropyl-4-methyl-1-(1H-pyrrolo[3,2-c]pyridin-2-yl)pentan-2-ol;

5-(5-Fluoro-2-methoxyphenyl)-2,5-dimethyl-3-(1H-pyrrolo[2,3-c]pyridin-2-ylmethyl)hexan-3-ol;

5-(5-Fluoro-2-methoxyphenyl)-2,2,5-trimethyl-3-(1H-pyrrolo[2,3-c]pyridin-2-ylmethyl)hexan-3-ol;

2-(5-Fluoro-2-methoxyphenyl)-2,5,5-trimethyl-4-(1H-pyrrolo[2,3-c]pyridin-2-ylmethyl)heptan-4-ol;

1,1-Difluoro-4-(5-fluoro-2-methoxyphenyl)-4-methyl-2-(1H-pyrrolo[2,3-c]pyridin-2-ylmethyl)pentan-2-ol;

5-(5-Fluoro-2-methylphenyl)-2,5-dimethyl-3-(1H-pyrrolo[2,3-c]pyridin-2-ylmethyl)hexan-3-ol;

5-(5-Fluoro-2-methylphenyl)-2,2,5-trimethyl-3-(1H-pyrrolo[2,3-c]pyridin-2-ylmethyl)hexan-3-ol;

5-(5-Chloro-2,3-dihydrobenzofuran-7-yl)-2,5-dimethyl-3-(1H-pyrrolo[2,3-c]pyridin-2-ylmethyl)hexan-3-ol;

1,1-Difluoro-4-(5-fluoro-2-methoxyphenyl)-4-methyl-2-(1H-pyrrolo[3,2-c]pyridin-2-ylmethyl)pentan-2-ol;

5-(5-Fluoro-2-methoxyphenyl)-2,5-dimethyl-3-(1H-pyrrolo[3,2-c]pyridin-2-ylmethyl)hexan-3-ol;

5-(5-Fluoro-2-methoxyphenyl)-2,2,5-trimethyl-3-(1H-pyrrolo[3,2-c]pyridin-2-ylmethyl)hexan-3-ol;

2-(1-Fluorocyclopropyl)-4-(5-fluoro-2-methoxyphenyl)-4-methyl-1-(1H-pyrrolo[2,3-c]pyridin-2-yl)pentan-2-ol;

2-[4,4-Difluoro-3-hydroxy-1,1-dimethyl-3-(1H-pyrrolo[3,2-c]pyridin-2-ylmethyl)butyl]-4-fluorophenol;

5-(5-Chloro-2,3-dihydrobenzofuran-7-yl)-2,5-dimethyl-3-(1H-pyrrolo[3,2-c]pyridin-2-ylmethyl)hexan-3-ol;

5-(5-Fluoro-2-methylphenyl)-2,5-dimethyl-3-(1H-pyrrolo[3,2-c]pyridin-2-ylmethyl)hexan-3-ol;

5-(5-Fluoro-2-methylphenyl)-2,2,5-trimethyl-3-(1H-pyrrolo[3,2-c]pyridin-2-ylmethyl)hexan-3-ol;

4-(5-Chloro-2,3-dihydrobenzofuran-7-yl)-1,1-difluoro-4-methyl-2-(1H-pyrrolo[3,2-c]pyridin-2-ylmethyl)pentan-2-ol;

4-(5-Chloro-2,3-dihydrobenzofuran-7-yl)-1,1-difluoro-4-methyl-2-pyrrolo[3,2-b]pyridin-1-ylmethylpentan-2-ol;

5-(5-Chloro-2,3-dihydrobenzofuran-7-yl)-2,2,5-trimethyl-3-(1H-pyrrolo[3,2-c]pyridin-2-ylmethyl)hexan-3-ol;

5-(5-Fluoro-2-methylphenyl)-2,2,5-trimethyl-3-(3-methyl-1H-pyrrolo[2,3-c]pyridin-2-ylmethyl)hexan-3-ol;

5-(5-Chloro-2,3-dihydrobenzofuran-7-yl)-2,5-dimethyl-3-(3-methyl-1H-pyrrolo[2,3-c]pyridin-2-ylmethyl)hexan-3-ol;

5-(5-Chloro-2,3-dihydrobenzofuran-7-yl)-2,5-dimethyl-3-(5-phenyl-1H-pyrrolo[2,3-c]pyridin-2-ylmethyl)hexan-3-ol;

5-(5-Fluoro-2-methylphenyl)-2,2,5-trimethyl-3-(5-phenyl-1H-pyrrolo[2,3-c]pyridin-2-ylmethyl)hexan-3-ol;

5-(5-Fluoro-2-methylphenyl)-2,5-dimethyl-3-(5-phenyl-1H-pyrrolo[2,3-c]pyridin-2-ylmethyl)hexan-3-ol;

4-(5-Chloro-2,3-dihydrobenzofuran-7-yl)-1,1-difluoro-4-methyl-2-(6-methyl-1H-pyrrolo[3,2-c]pyridin-2-ylmethyl)pentan-2-ol; and 2-[2-Difluoromethyl-2-hydroxy-4-(5-methanesulfonyl-2,3-dihydrobenzofuran-7-yl)-4-methylpentyl]-4-methyl-1H-indole-6-carbonitrile, or a tautomer, prodrug, solvate, or salt thereof.

The following compounds of the invention of Formula (IC) have been tested and have shown activity as agonists of the glucocorticoid receptor function in one or more of the above assays:

1-[4-(5-Fluoro-2-methoxyphenyl)-2-hydroxy-4-methyl-2-trifluoromethylpentyl]-1,5,6,7-tetrahydroindol-4-one;

1-[4-(5-Fluoro-2-hydroxyphenyl)-2-hydroxy-4-methyl-2-trifluoromethylpentyl 1,5,6,7-tetrahydroindol-4-one;

1-[4-(2,3-Dihydrobenzofuran-7-yl)-2-hydroxy-4-methyl-2-trifluoromethylpentyl]-1,5,6,7-tetrahydroindol-4-one;

1-[4-(5-Fluoro-2-methylphenyl)-2-hydroxy-4-methyl-2-trifluoromethylpentyl]-1,5,6,7-tetrahydroindol-4-one;

1-[2-Hydroxy-4-methyl-4-(5-pyrimidin-5-yl-2,3-dihydrobenzofuran-7-yl)-2-trifluoromethylpentyl]-1,5,6,7-tetrahydroindol-4-one;

1-[2-Hydroxy-4-(2-methoxy-5-pyrimidin-5-ylphenyl)-4-methyl-2-trifluoromethylpentyl]-1,5,6,7-tetrahydroindol-4-one;

1-[2-Hydroxy-4-(2-hydroxy-5-pyrimidin-5-ylphenyl)-4-methyl-2-trifluoromethylpentyl]-1,5,6,7-tetrahydroindol-4-one;

1-[2-Hydroxy-4-(2-methoxy-5-pyridin-3-ylphenyl)-4-methyl-2-trifluoromethylpentyl]-1,5,6,7-tetrahydroindol-4-one; and 1-[2-Hydroxy-4-(2-hydroxy-5-pyridin-3-ylphenyl)-4-methyl-2-trifluoromethylpentyl]-1,5,6,7-tetrahydroindol-4-one, or a tautomer, prodrug, solvate, or salt thereof.

The following compound of the invention of Formula (ID) have been tested and have shown activity as agonists of the glucocorticoid receptor function in one or more of the above assays:

5,5,5-Trifluoro-2-methyl-2-phenyl-4-quinolin-4-ylmethylpentane-1,4-diol, or a tautomer, prodrug, solvate, or salt thereof.

The invention also provides methods of modulating the glucocorticoid receptor function in a patient comprising administering to the patient a compound according to the invention. If the purpose of modulating the glucocorticoid receptor function in a patient is to treat a disease-state or condition, the administration preferably comprises a therapeutically or pharmaceutically effective amount of a pharmaceutically acceptable compound according to the invention. If the purpose of modulating the glucocorticoid receptor function in a patient is for a diagnostic or other purpose (e.g., to determine the patient's suitability for therapy or sensitivity to various sub-therapeutic doses of the compounds according to the invention), the administration preferably comprises an effective amount of a compound according to the invention, that is, the amount necessary to obtain the desired effect or degree of modulation.

7. Inhibition of Osteocalcin Production from Osteoblast Cell Line MG-63

Human osteosarcoma MG-63 cells (ATCC, Cat. No. CRL-1427) are plated on 96 well plates at 20,000 cells per well the day before use in 200 µL media of 99% D-MEM/F-12 (Gibco-Invitrogen, Cat. No. 11039-021), supplemented with 1% penicillin and streptomycin (Gibco-Invitrogen, Cat. No. 15140-122), 10 µg/mL Vitamin C (Sigma, Cat. No. A-4544), and 1% charcoal filtered Fetal Bovine Serum (HyClone, Cat. No. SH30068.02). The next day, wells are replaced with fresh media. Cells are treated with Vitamin D (Sigma, Cat. No. D1530) to a final concentration of 10 nM, and with the test compounds in concentrations of $10^{-6}$ M to $10^{-9}$ M, in a total volume of 200 µL per well. Samples are done in duplicates. Background control wells do not receive Vitamin D or compounds. Positive control wells receive Vitamin D only, without compounds, and represent maximum (100%) amount of osteocalcin production. Plates are incubated at 37° C. incubator for 48 hours and supernatants are harvested at the end of incubation. Amounts of osteocalcin in the supernatants are determined by the Glype osteocalcin ELISA kit (Zymed, Cat. No. 99-0054) according to manufacture's protocol. Inhibition of osteocalcin by test compounds is expressed in percentage relative to positive controls. $IC_{50}$ values of the test compounds are derived by non-lineal curve fitting.

The following compounds of Formula (IA) inhibit the vitamin D stimulated production of osteocalcin:

2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile;

1,1,1-Trifluoro-4-(5-fluoro-2-methylphenyl)-4-methyl-2-(1H-pyrrolo[2,3-d]pyridazin-2-ylmethyl)pentan-2-ol;

4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol;

4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol;

1,1,1-Trifluoro-4-(5-fluoro-2-methylphenyl)-4-methyl-2-(5-piperidin-1-yl-1H-pyrrolo[2,3-c]pyridin-2-ylmethyl)pentan-2-ol;

2-[2-Hydroxy-4-(5-methanesulfonyl-2,3-dihydrobenzofuran-7-yl)-4-methyl-2-trifluoromethylpentyl]-4-methyl-1H-indole-6-carbonitrile;

2-[4-(5-Bromo-2,3-dihydrobenzofuran-7-yl)-2-hydroxy-4-methyl-2-trifluoromethylpentyl]-1H-indole-5-carboxylic acid amide;

2-[4-(5-Bromo-2,3-dihydrobenzofuran-7-yl)-2-hydroxy-4-methyl-2-trifluoromethylpentyl]-1H-indole-5-carboxylic acid cyanomethylamide;

{2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone;

1,1,1-Trifluoro-4,4-dimethyl-5-phenyl-2-quinolin-4-ylmethylpentan-2-ol;

1,1,1-Trifluoro-4-(5-fluoro-2-methylphenyl)-4-methyl-2-(5-morpholin-4-yl-1H-pyrrolo[2,3-c]pyridin-2-ylmethyl)pentan-2-ol;

1,1,1-Trifluoro-4-(5-methanesulfonyl-2,3-dihydrobenzofuran-7-yl)-4-methyl-2-(5-piperidin-1-yl-1H-pyrrolo[2,3-c]pyridin-2-ylmethyl)pentan-2-ol;

2-[5-(Ethylmethylamino)-1H-pyrrolo[2,3-c]pyridin-2-ylmethyl]-1,1,1-trifluoro-4-(5-fluoro-2-methylphenyl)-4-methylpentan-2-ol;

4-(5-Chloro-2,3-dihydrobenzofuran-7-yl)-2-[5-(ethylmethylamino)-1H-pyrrolo[2,3-c]pyridin-2-ylmethyl]-1,1,1-trifluoro-4-methylpentan-2-ol;

4-(3-Bromophenyl)-1,1,1-trifluoro-4-methyl-2-(5-morpholin-4-yl-1H-pyrrolo[2,3-c]pyridin-2-ylmethyl)pentan-2-ol;

4-(5-Chloro-2,3-dihydrobenzofuran-7-yl)-1,1,1-trifluoro-4-methyl-2-(4-methyl-1H-pyrrolo[3,2-c]pyridin-2-ylmethyl)pentan-2-ol;

1,1,1-Trifluoro-4-methyl-2-(3-methyl-1H-pyrrolo[2,3-c]pyridin-2-ylmethyl)-4-(5-pyrimidin-5-yl-2,3-dihydrobenzofuran-7-yl)pentan-2-ol;

2-[3-(5-Dimethylamino-1H-pyrrolo[2,3-c]pyridin-2-ylmethyl)-4,4,4-trifluoro-3-hydroxy-1,1-dimethylbutyl]-4-fluorophenol;

4-(3-Chlorophenyl)-1,1,1-trifluoro-4-methyl-2-(1H-pyrrolo[3,2-c]pyridin-2-ylmethyl)pentan-2-ol;

1,1,1-Trifluoro-4-(5-fluoro-2,3-dihydrobenzofuran-7-yl)-4-methyl-2-(5-pyridin-3-yl-1H-indol-2-ylmethyl)pentan-2-ol;

1,1,1-Trifluoro-4-(5-fluoro-2-methoxyphenyl)-4-methyl-2-(5-phenyl-1H-pyrrolo[2,3-c]pyridin-2-ylmethyl)pentan-2-ol;

1,1,1-Trifluoro-4-(2-methoxy-5-pyrimidin-5-ylphenyl)-4-methyl-2-(5-piperidin-1-yl-1H-pyrrolo[2,3-c]pyridin-2-ylmethyl)pentan-2-ol;

1,1,1-Trifluoro-4-(2-methoxy-5-pyridin-3-ylphenyl)-4-methyl-2-(5-piperidin-1-yl-1H-pyrrolo[2,3-c]pyridin-2-ylmethyl)pentan-2-ol;

2-[2-Hydroxy-4-(4-hydroxybiphenyl-3-yl)-4-methyl-2-trifluoromethylpentyl]-1H-pyrrolo[2,3-c]pyridin-5-ol;

4-(5-Chloro-2,3-dihydrobenzofuran-7-yl)-1,1,1-trifluoro-4-methyl-2-(5-phenyl-1H-pyrrolo[2,3-c]pyridin-2-ylmethyl)pentan-2-ol; and 1,1,1-Trifluoro-4-(5-fluoro-2-methylphenyl)-4-methyl-2-(5-phenyl-1H-pyrrolo[2,3-c]pyridin-2-ylmethyl)pentan-2-ol, or a tautomer, prodrug, solvate, or salt thereof.

Methods of Therapeutic Use

As pointed out above, the compounds of the invention are useful in modulating the glucocorticoid receptor function. In doing so, these compounds have therapeutic use in treating disease-states and conditions mediated by the glucocorticoid receptor function or that would benefit from modulation of the glucocorticoid receptor function.

As the compounds of the invention modulate the glucocorticoid receptor function, they have very useful anti-inflammatory and antiallergic, immune-suppressive, and anti-proliferative activity and they can be used in patients as drugs, particularly in the form of pharmaceutical compositions as set forth below, for the treatment of disease-states and conditions.

The agonist compounds according to the invention can be used in patients as drugs for the treatment of the following disease-states or indications that are accompanied by inflammatory, allergic, and/or proliferative processes:

(i) Lung diseases: chronic, obstructive lung diseases of any genesis, particularly bronchial asthma and chronic obstructive pulmonary disease (COPD); adult respiratory distress syndrome (ARDS); bronchiectasis; bronchitis of various genesis; all forms of restrictive lung diseases, particularly allergic alveolitis; all forms of lung edema, particularly toxic lung edema; all forms of interstitial lung diseases of any genesis, e.g., radiation pneumonitis; and sarcoidosis and granulomatoses, particularly Boeck disease.

(ii) Rheumatic diseases or autoimmune diseases or joint diseases: all forms of rheumatic diseases, especially rheumatoid arthritis, acute rheumatic fever, and polymyalgia rheumatica; reactive arthritis; rheumatic soft tissue diseases; inflammatory soft tissue diseases of other genesis; arthritic symptoms in degenerative joint diseases (arthroses); traumatic arthritis; collagenoses of any genesis, e.g., systemic lupus erythematosus, scleroderma, polymyositis, dermatomyositis, Sjögren syndrome, Still disease, and Felty syndrome;

(iii) Allergic diseases: all forms of allergic reactions, e.g., angioneurotic edema, hay fever, insect bites, allergic reactions to drugs, blood derivatives, contrast agents, etc., anaphylactic shock (anaphylaxis), urticaria, angioneurotic edema, and contact dermatitis;

(iv) Vasculitis diseases: panarteritis nodosa, polyarteritis nodosa, arteritis temporalis, Wegner granulomatosis, giant cell arthritis, and erythema nodosum;

(v) Dermatological diseases: atopic dermatitis, particularly in children; psoriasis; pityriasis rubra pilaris; erythematous diseases triggered by various noxa, e.g., rays, chemicals, burns, etc.; bullous dermatoses; diseases of the lichenoid complex; pruritus (e.g., of allergic genesis); seborrheic dermatitis; rosacea; pemphigus vulgaris; erythema multiforme exudativum; balanitis; vulvitis; hair loss, such as occurs in alopecia areata; and cutaneous T cell lymphomas;

(vi) Renal diseases: nephrotic syndrome; and all types of nephritis, e.g., glomerulonephritis;

(vii) Hepatic diseases: acute liver cell disintegration; acute hepatitis of various genesis, e.g., viral, toxic, drug-induced; and chronically aggressive and/or chronically intermittent hepatitis;

(viii) Gastrointestinal diseases: inflammatory bowel diseases, e.g., regional enteritis (Crohn disease), colitis ulcerosa; gastritis; peptic esophagitis (refluxoesophagitis); and gastroenteritis of other genesis, e.g., nontropical sprue;

(ix) Proctological diseases: anal eczema; fissures; hemorrhoids; and idiopathic proctitis;

(x) Eye diseases: allergic keratitis, uveitis, or iritis; conjunctivitis; blepharitis; neuritis nervi optici; choroiditis; and sympathetic ophthalmia;

(xi) Diseases of the ear, nose, and throat (ENT) area: allergic rhinitis or hay fever; otitis externa, e.g., caused by contact eczema, infection, etc.; and otitis media;

(xii) Neurological diseases: brain edema, particularly tumor-related brain edema; multiple sclerosis; acute encephalomyelitis; meningitis; acute spinal cord injury; stroke; and various forms of seizures, e.g., nodding spasms;

(xiii) Blood diseases: acquired hemolytic anemia; and idiopathic thrombocytopenia;

(xiv) Tumor diseases: acute lymphatic leukemia; malignant lymphoma; lymphogranulomatoses; lymphosarcoma; extensive metastases, particularly in mammary, bronchial, and prostatic carcinoma;

(xv) Endocrine diseases: endocrine ophthalmopathy; endocrine orbitopathia; thyrotoxic crisis; Thyroiditis de Quervain; Hashimoto thyroiditis; Morbus Basedow; granulomatous thyroiditis; struma lymphomatosa; and Grave disease;

(xvi) Organ and tissue transplantations and graft-versus-host diseases;

(xvii) Severe states of shock, e.g., septic shock, anaphylactic shock, and systemic inflammatory response syndrome (SIRS);

(xviii) Substitution therapy in: congenital primary adrenal insufficiency, e.g., adrenogenital syndrome; acquired primary adrenal insufficiency, e.g., Addison disease, autoimmune adrenalitis, post-infection, tumors, metastases, etc.; congenital secondary adrenal insufficiency, e.g., congenital hypopituitarism; and acquired secondary adrenal insufficiency, e.g., post-infection, tumors, metastases, etc.;

(xix) Pain of inflammatory genesis, e.g., lumbago; and (xx) various other disease-states or conditions including type I diabetes (insulin-dependent diabetes), osteoarthritis, Guillain-Barre syndrome, restenosis following percutaneous transluminal coronary angioplasty, Alzheimer disease, acute and chronic pain, atherosclerosis, reperfusion injury, bone resorption diseases, congestive heart failure, myocardial infarction, thermal injury, multiple organ injury secondary to trauma, acute purulent meningitis, necrotizing enterocolitis and syndromes associated with hemodialysis, leukopheresis, and granulocyte transfusion.

In addition, the compounds according to the invention can be used for the treatment of any other disease-states or conditions not mentioned above which have been treated, are treated, or will be treated with synthetic glucocorticoids (see, e.g., H. J. Hatz, *Glucocorticoide: Immunologische Grundlagen, Pharmakologie und Therapierichtlinien* [Glucocorticoids: Immunological Fundamentals, Pharmacology, and Therapeutic Guidelines], Stuttgart: Verlagsgesellschaft mbH, 1998, which is hereby incorporated by reference in its entirety). Most or all of the indications (i) through (xx) mentioned above are described in detail in H. J. Hatz, *Glucocorticoide: Immunologische Grundlagen. Pharmakologie und Therapierichtlinien*. Furthermore, the compounds of the invention can also be used to treat disorders other than those listed above or mentioned or discussed herein, including in the Background of the Invention.

The antagonist compounds according to the invention, whether full antagonists or partial antagonists, can be used in patients as drugs for the treatment of the following disease-states or indications, without limitation: type II diabetes (non-insulin-dependent diabetes); obesity; cardiovascular diseases; hypertension; arteriosclerosis; neurological diseases, such as psychosis and depression; adrenal and pituitary tumors; glaucoma; and Cushing syndrome based on an ACTH secreting tumor like pituitary adenoma. In particular, the compounds of the invention are useful for treating obesity and all disease-states and indications related to a deregulated fatty acids metabolism such as hypertension, atherosclerosis, and other cardiovascular diseases. Using the compounds of the invention that are GR antagonists, it should be possible to antagonize both the carbohydrate metabolism and fatty acids metabolism. Thus, the antagonist compounds of the invention are useful in treating all disease-states and conditions that involve increased carbohydrate, protein, and lipid metabolism and would include disease-states and conditions leading to catabolism like muscle frailty (as an example of protein metabolism).

Methods of Diagnostic Use

The compounds of the invention may also be used in diagnostic applications and for commercial and other purposes as standards in competitive binding assays. In such uses, the compounds of the invention may be used in the form of the compounds themselves or they may be modified by attaching a radioisotope, luminescence, fluorescent label or the like in order to obtain a radioisotope, luminescence, or fluorescent probe, as would be known by one of skill in the art and as outlined in *Handbook of Fluorescent Probes and Research Chemicals,* 6th Edition, R. P. Haugland (ed.), Eugene: Molecular Probes, 1996; *Fluorescence and Luminescence Probes for Biological Activity*, W. T. Mason (ed.), San Diego: Academic Press, 1993; *Receptor-Ligand Interaction, A Practical Approach*, E. C. Hulme (ed.), Oxford: IRL Press, 1992, each of which is hereby incorporated by reference in their entireties.

General Administration and Pharmaceutical Compositions

When used as pharmaceuticals, the compounds of the invention are typically administered in the form of a pharmaceutical composition. Such compositions can be prepared using procedures well-known in the pharmaceutical art and comprise at least one compound of the invention. The compounds of the invention may also be administered alone or in combination with adjuvants that enhance stability of the compounds of the invention, facilitate administration of pharmaceutical compositions containing them in certain embodiments, provide increased dissolution or dispersion, increased inhibitory activity, provide adjunct therapy, and the like. The compounds according to the invention may be used on their own or in conjunction with other active substances according to the invention, optionally also in conjunction with other pharmacologically active substances. In general, the compounds of this invention are administered in a therapeutically or pharmaceutically effective amount, but may be administered in lower amounts for diagnostic or other purposes.

In particular, the compounds of the invention are useful in combination with glucocorticoids or corticosteroids. As pointed out above, standard therapy for a variety of immune and inflammatory disorders includes administration of corticosteroids, which have the ability to suppress immunologic and inflammatory responses (A. P. Truhan et al., Annals of Allergy, 1989, 62, pp. 375-391; J. D. Baxter, Hospital Practice, 1992, 27, pp. 111-134; R. P. Kimberly, Curr. Opin. Rheumatol., 1992, 4, pp. 325-331; M. H. Weisman, Curr. Opin. Rheumatol., 1995, 7, pp. 183-190; W. Sterry, Arch. Dermatol. Res., 1992, 284 (Suppl.), pp. S27-S29). While therapeutically beneficial, however, the use of corticosteroids is associated with a number of side effects, ranging from mild to possibly life threatening, especially with prolonged and/or high dose steroid usage. Accordingly, methods and compositions that enable the use of a lower effective dosage of corticosteroids (referred to as the "steroid sparing effect") would be highly desirable to avoid unwanted side effects. The compounds of the invention provide such a steroid sparing effect by achieving the desired therapeutic effect while allowing the use of lower doses and less frequent administration of glucocorticoids or corticosteroids.

Administration of the compounds of the invention, in pure form or in an appropriate pharmaceutical composition, can be carried out using any of the accepted modes of administration of pharmaceutical compositions. Thus, administration can be, for example, orally, buccally (e.g., sublingually), nasally, parenterally, topically, transdermally, vaginally, or rectally, in the form of solid, semi-solid, lyophilized powder, or liquid dosage forms, such as, for example, tablets, suppositories, pills, soft elastic and hard gelatin capsules, powders, solutions, suspensions, or aerosols, or the like, preferably in unit dosage forms suitable for simple administration of precise dosages. The pharmaceutical compositions will generally include a conventional pharmaceutical carrier or excipient and a compound of the invention as the/an active agent, and, in addition, may include other medicinal agents, pharmaceutical agents, carriers, adjuvants, diluents, vehicles, or combinations thereof. Such pharmaceutically acceptable excipients, carriers, or additives as well as methods of making pharmaceutical compositions for various modes or administration are well-known to those of skill in the art. The state of the art is evidenced, e.g., by *Remington: The Science and Practice of Pharmacy,* 20th Edition, A. Gennaro (ed.), Lippincott Williams & Wilkins, 2000; *Handbook of Pharmaceutical Additives*, Michael & Irene Ash (eds.), Gower, 1995; *Handbook of Pharmaceutical Excipients*, A. H. Kibbe (ed.), American Pharmaceutical Assn, 2000; H. C. Ansel and N. G. Popovish, *Pharmaceutical Dosage Forms and Drug Delivery Systems,* 5th ed., Lea and Febiger, 1990; each of which is incorporated herein by reference in their entireties to better describe the state of the art.

As one of skill in the art would expect, the forms of the compounds of the invention utilized in a particular pharmaceutical formulation will be selected (e.g., salts) that possess suitable physical characteristics (e.g., water solubility) that is required for the formulation to be efficacious.

Pharmaceutical compositions suitable for buccal (sub-lingual) administration include lozenges comprising a compound of the present invention in a flavored base, usually sucrose, and acacia or tragacanth, and pastilles comprising the compound in an inert base such as gelatin and glycerin or sucrose and acacia.

Pharmaceutical compositions suitable for parenteral administration comprise sterile aqueous preparations of a compound of the present invention. These preparations are preferably administered intravenously, although administration can also be effected by means of subcutaneous, intramuscular, or intradermal injection. Injectable pharmaceutical formulations are commonly based upon injectable sterile saline, phosphate-buffered saline, oleaginous suspensions, or other injectable carriers known in the art and are generally rendered sterile and isotonic with the blood. The injectable pharmaceutical formulations may therefore be provided as a sterile injectable solution or suspension in a nontoxic parenterally acceptable diluent or solvent, including 1,3-butanediol, water, Ringer's solution, isotonic sodium chloride solution, fixed oils such as synthetic mono- or diglycerides, fatty acids such as oleic acid, and the like. Such injectable pharmaceutical formulations are formulated according to the known art using suitable dispersing or setting agents and suspending agents. Injectable compositions will generally contain from 0.1 to 5% w/w of a compound of the invention.

Solid dosage forms for oral administration of the compounds include capsules, tablets, pills, powders, and granules. For such oral administration, a pharmaceutically acceptable composition containing a compound(s) of the invention is formed by the incorporation of any of the normally employed excipients, such as, for example, pharmaceutical grades of mannitol, lactose, starch, pregelatinized starch, magnesium stearate, sodium saccharine, talcum, cellulose ether derivatives, glucose, gelatin, sucrose, citrate, propyl gallate, and the like. Such solid pharmaceutical formulations may include formulations, as are well-known in the art, to provide prolonged or sustained delivery of the drug to the gastrointestinal tract by any number of mechanisms, which include, but are not limited to, pH sensitive release from the dosage form based on the changing pH of the small intestine, slow erosion of a tablet or capsule, retention in the stomach based on the physical properties of the formulation, bioadhesion of the dosage form to the mucosal lining of the intestinal tract, or enzymatic release of the active drug from the dosage form.

Liquid dosage forms for oral administration of the compounds include emulsions, microemulsions, solutions, suspensions, syrups, and elixirs, optionally containing pharmaceutical adjuvants in a carrier, such as, for example, water, saline, aqueous dextrose, glycerol, ethanol and the like. These compositions can also contain additional adjuvants such as wetting, emulsifying, suspending, sweetening, flavoring, and perfuming agents.

Topical dosage forms of the compounds include ointments, pastes, creams, lotions, gels, powders, solutions, sprays, inhalants, eye ointments, eye or ear drops, impregnated dressings and aerosols, and may contain appropriate conventional additives such as preservatives, solvents to assist drug penetration and emollients in ointments and creams. Topical application may be once or more than once per day depending upon the usual medical considerations.

Furthermore, preferred compounds for the present invention can be administered in intranasal form via topical use of suitable intranasal vehicles. The formulations may also contain compatible conventional carriers, such as cream or ointment bases and ethanol or oleyl alcohol for lotions. Such carriers may be present as from about 1% up to about 98% of the formulation, more usually they will form up to about 80% of the formulation.

Transdermal administration is also possible. Pharmaceutical compositions suitable for transdermal administration can be presented as discrete patches adapted to remain in intimate contact with the epidermis of the recipient for a prolonged period of time. To be administered in the form of a transdermal delivery system, the dosage administration will, of course, be continuous rather than intermittent throughout the dosage regimen. Such patches suitably contain a compound of the invention in an optionally buffered, aqueous solution, dissolved and/or dispersed in an adhesive, or dispersed in a polymer. A suitable concentration of the active compound is about 1% to 35%, preferably about 3% to 15%.

For administration by inhalation, the compounds of the invention are conveniently delivered in the form of an aerosol spray from a pump spray device not requiring a propellant gas or from a pressurized pack or a nebulizer with the use of a suitable propellant, e.g., dichlorodifluoromethane, trichlorofluoromethane, dichlorotetrafluoroethane, tetrafluoroethane, heptafluoropropane, carbon dioxide, or other suitable gas. In any case, the aerosol spray dosage unit may be determined by providing a valve to deliver a metered amount so that the resulting metered dose inhaler (MDT) is used to administer the compounds of the invention in a reproducible and controlled way. Such inhaler, nebulizer, or atomizer devices are known in the prior art, for example, in PCT International Publication Nos. WO 97/12687 (particularly FIG. 6 thereof, which is the basis for the commercial RESPIMAT® nebulizer); WO 94/07607; WO 97/12683; and WO 97/20590, to which reference is hereby made and each of which is incorporated herein by reference in their entireties.

Rectal administration can be effected utilizing unit dose suppositories in which the compound is admixed with low-melting water-soluble or insoluble solids such as fats, cocoa butter, glycerinated gelatin, hydrogenated vegetable oils, mixtures of polyethylene glycols of various molecular weights, or fatty acid esters of polyethylene glycols, or the like. The active compound is usually a minor component, often from about 0.05 to 10% by weight, with the remainder being the base component.

In all of the above pharmaceutical compositions, the compounds of the invention are formulated with an acceptable carrier or excipient. The carriers or excipients used must, of course, be acceptable in the sense of being compatible with the other ingredients of the composition and must not be deleterious to the patient. The carrier or excipient can be a solid or a liquid, or both, and is preferably formulated with the compound of the invention as a unit-dose composition, for example, a tablet, which can contain from 0.05% to 95% by weight of the active compound. Such carriers or excipients include inert fillers or diluents, binders, lubricants, disintegrating agents, solution retardants, resorption accelerators, absorption agents, and coloring agents. Suitable binders include starch, gelatin, natural sugars such as glucose or β-lactose, corn sweeteners, natural and synthetic gums such as acacia, tragacanth or sodium alginate, carboxymethylcellulose, polyethylene glycol, waxes, and the like. Lubricants include sodium oleate, sodium stearate, magnesium stearate, sodium benzoate, sodium acetate, sodium chloride, and the like. Disintegrators include starch, methyl cellulose, agar, bentonite, xanthan gum, and the like.

Generally, a therapeutically effective daily dose is from about 0.001 mg to about 15 mg/kg of body weight per day of a compound of the invention; preferably, from about 0.1 mg to about 10 mg/kg of body weight per day; and most preferably, from about 0.1 mg to about 1.5 mg/kg of body weight per day. For example, for administration to a 70 kg person, the dosage range would be from about 0.07 mg to about 1050 mg per day of a compound of the invention, preferably from about 7.0 mg to about 700 mg per day, and most preferably from about 7.0 mg to about 105 mg per day. Some degree of routine dose optimization may be required to determine an optimal dosing level and pattern.

Pharmaceutically acceptable carriers and excipients encompass all the foregoing additives and the like.

Examples of Pharmaceutical Formulations

| A. TABLETS | |
|---|---|
| Component | Amount per tablet (mg) |
| active substance | 100 |
| lactose | 140 |
| corn starch | 240 |
| polyvinylpyrrolidone | 15 |
| magnesium stearate | 5 |
| TOTAL | 500 |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

B. TABLETS

| Component | Amount per tablet (mg) |
|---|---|
| active substance | 80 |
| lactose | 55 |
| corn starch | 190 |
| polyvinylpyrrolidone | 15 |
| magnesium stearate | 2 |
| microcrystalline cellulose | 35 |
| sodium-carboxymethyl starch | 23 |
| TOTAL | 400 |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

C. COATED TABLETS

| Component | Amount per tablet (mg) |
|---|---|
| active substance | 5 |
| lactose | 30 |
| corn starch | 41.5 |
| polyvinylpyrrolidone | 3 |
| magnesium stearate | 0.5 |
| TOTAL | 90 |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

D. CAPSULES

| Component | Amount per capsule (mg) |
|---|---|
| active substance | 50 |
| corn starch | 268.5 |
| magnesium stearate | 1.5 |
| TOTAL | 320 |

The substance and corn starch are mixed and moistened with water. The moist mass is screened and dried. The dry granules are screened and mixed with magnesium stearate. The finished mixture is packed into size 1 hard gelatine capsules.

E. AMPOULE SOLUTION

| Component | Amount per ampoule |
|---|---|
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

F. SUPPOSITORIES

| Component | Amount per suppository (mg) |
|---|---|
| active substance | 50 |
| solid fat | 1650 |
| TOTAL | 1700 |

The hard fat is melted. At 40° C., the ground active substance is homogeneously dispersed therein. The mixture is cooled to 38° C. and poured into slightly chilled suppository molds.

G. METERING AEROSOL

| Component | Amount |
|---|---|
| active substance | 0.005 |
| sorbitan trioleate | 0.11 |
| monofluorotrichloromethane and difluorodichloromethane (2:3) | to 100 |

The suspension is transferred into a conventional aerosol container with a metering valve. Preferably, 50 µL of suspension are delivered per spray. The active substance may also be metered in higher doses if desired (e.g., 0.02% by weight).

H. POWDER FOR INHALATION

| Component | Amount |
|---|---|
| active substance | 1.0 mg |
| lactose monohydrate | to 25 mg |

I. POWDER FOR INHALATION

| Component | Amount |
|---|---|
| active substance | 2.0 mg |
| lactose monohydrate | to 25 mg |

| J. POWDER FOR INHALATION | |
|---|---|
| Component | Amount |
| active substance | 1.0 mg |
| lactose monohydrate | to 5 mg |

| K. POWDER FOR INHALATION | |
|---|---|
| Component | Amount |
| active substance | 2.0 mg |
| lactose monohydrate | to 5 mg |

In Examples H, I, J, and K, the powder for inhalation is produced in the usual way by mixing the individual ingredients together.

| IA | |
|---|---|
| A | B |
| 4-Cyclohexyl-1,1,1-trifluoro-4-methyl-2-quinolin-4-ylmethylpentan-2-ol | 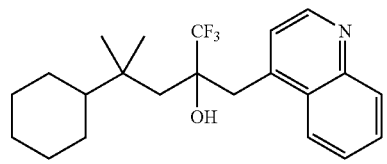 |
| 4-Pyrimidin-5-yl-2-[4,4,4-trifluoro-3-hydroxy-1,1-dimethyl-3-(1H-pyrrolo[2,3-c]pyridin-2-ylmethyl)butyl]phenol | 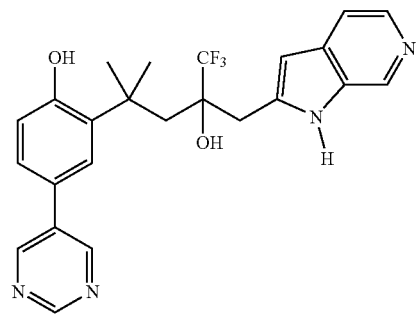 |
| 4-Pyrimidin-5-yl-2-[4,4,4-trifluoro-3-hydroxy-1,1-dimethyl-3-(1H-pyrrolo[3,2-c]pyridin-2-ylmethyl)butyl]phenol | 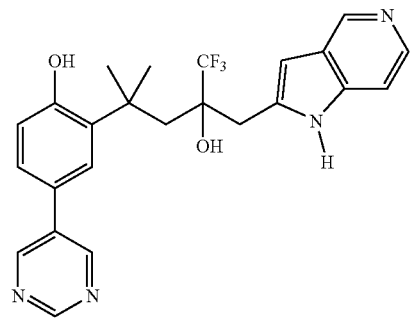 |
| 1,1,1-Trifluoro-4-(5-fluoro-2-methoxyphenyl)-4-methyl-2-(3-methyl-1H-pyrrolo[3,2-c]pyridin-2-ylmethyl)pentan-2-ol | 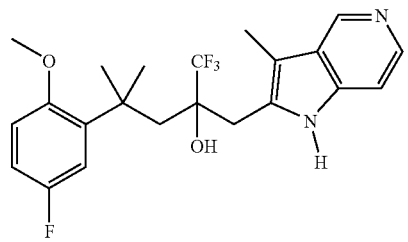 |

-continued

IA

| A | B |
|---|---|
| 1,1,1-Trifluoro-4-(5-fluoro-2,3-dihydrobenzofuran-7-yl)-4-methyl-2-(1H pyrrolo[3,2-c]pyridin-2-ylmethyl)pentan-2-ol | 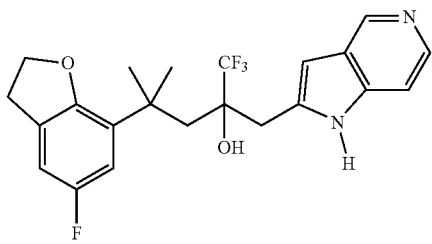 |
| 1,1,1-Trifluoro-4-(5-fluoro-2-methylphenyl)-4-methyl-2-(3-methyl-1H-pyrrolo[2,3-c]pyridin-2-ylmethyl)pentan-2-ol | 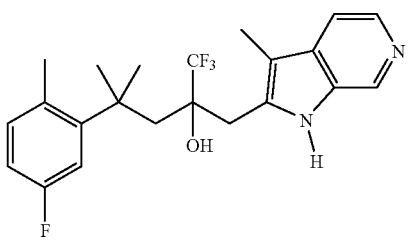 |
| 2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol | 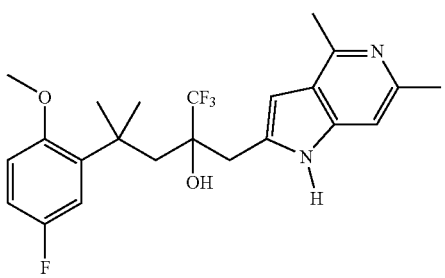 |
| 2-(5,7-Dimethyl-1H-pyrrolo[2,3-c]pyridin-2-ylmethyl)-1,1,1-trifluoro-4-(5-fluoro-2-methoxyphenyl)-4-methylpentan-2-ol | 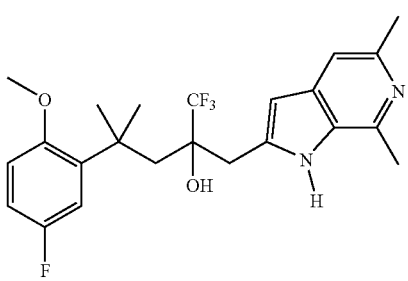 |
| 2-[4-(5-Fluoro-2-methoxyphenyl)-2-hydroxy-4-methyl-2-trifluoromethylpentyl]-1H-pyrrolo[3,2-b]pyridine-5-carbonitrile | 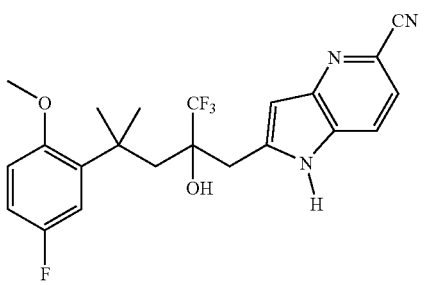 |

-continued

| | IA | |
|---|---|---|
| A | B | |

1,1,1-Trifluoro-4-(5-fluoro-2-methoxyphenyl)-4-methyl-2-(6-methyl-1H-pyrrolo[3,2-c]pyridin-2-ylmethyl)pentan-2-ol

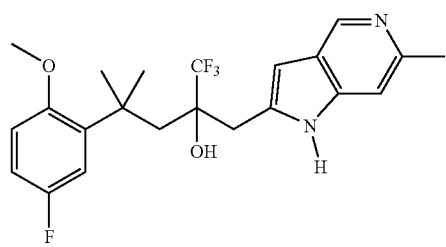 [SMILES: COc1ccc(F)cc1C(C)(C)CC(O)(Cc1cc2cnc(C)cc2[nH]1)C(F)(F)F]

1,1,1-Trifluoro-4-(5-fluoro-2-methoxyphenyl)-4-methyl-2-(4-methyl-1H-pyrrolo[3,2-c]pyridin-2-ylmethyl)pentan-2-ol

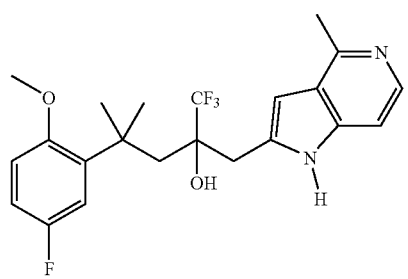 [SMILES: COc1ccc(F)cc1C(C)(C)CC(O)(Cc1cc2c(C)nccc2[nH]1)C(F)(F)F]

2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile

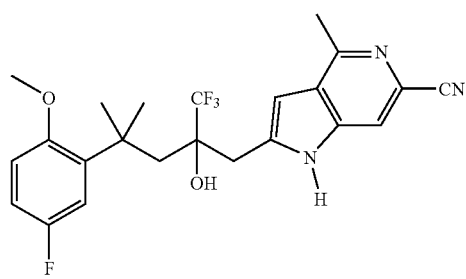 [SMILES: COc1ccc(F)cc1C(C)(C)CC(O)(Cc1cc2c(C)nc(C#N)cc2[nH]1)C(F)(F)F]

2-[4-(5-Fluoro-2-methoxyphenyl)-2-hydroxy-4-methyl-2-trifluoromethylpentyl]-1H-pyrrolo[2,3-c]pyridine-5-carbonitrile

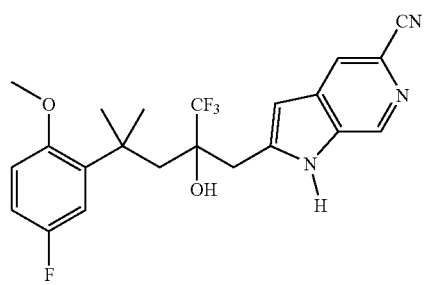 [SMILES: COc1ccc(F)cc1C(C)(C)CC(O)(Cc1cc2cc(C#N)ncc2[nH]1)C(F)(F)F]

2-[4-(5-Fluoro-2-methoxyphenyl)-2-hydroxy-4-methyl-2-trifluoromethylpentyl]-1H-pyrrolo[3,2-c]pyridine-4-carbonitrile

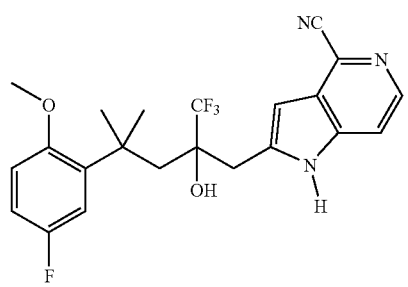

-continued

IA

| A | B |
|---|---|
| 1,1,1-Trifluoro-4-(5-fluoro-2-methoxyphenyl)-4-methyl-2-(5H-pyrrolo[3,2-d]pyrimidin-6-ylmethyl)pentan-2-ol | 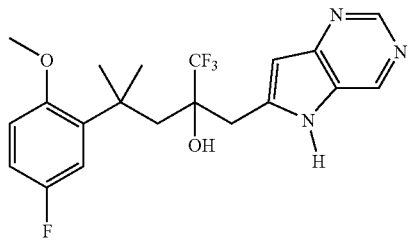 |
| 1,1,1-Trifluoro-4-(5-fluoro-2-methoxyphenyl)-4-methyl-2-thieno[2,3-d]pyridazin-2-ylmethylpentan-2-ol | 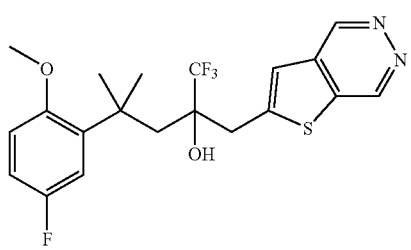 |
| 1,1,1-Trifluoro-4-(5-fluoro-2-methoxyphenyl)-4-methyl-2-(5H-pyrrolo[3,2-c]pyridazin-6-ylmethyl)pentan-2-ol | 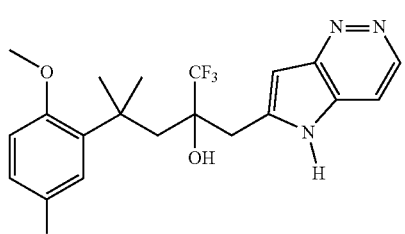 |
| 1,1,1-Trifluoro-4-(5-fluoro-2-methoxyphenyl)-4-methyl-2-(2-methyl-5H-pyrrolo[3,2-d]pyrimidin-6-ylmethyl)pentan-2-ol | 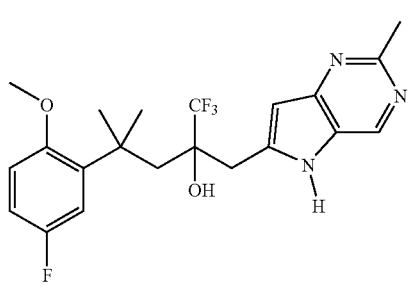 |
| 1,1,1-Trifluoro-4-(5-fluoro-2-methylphenyl)-4-methyl-2-(1H-pyrrolo[2,3-d]pyridazin-2-ylmethyl)pentan-2-ol | 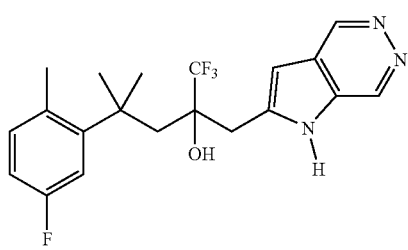 |
| 2-(4,6-Dimethyl-1H-pyrrolo[3,2-c]pyridin-2-ylmethyl)-1,1,1-trifluoro-4-(5-fluoro-2-methylphenyl)-4-methylpentan-2-ol | 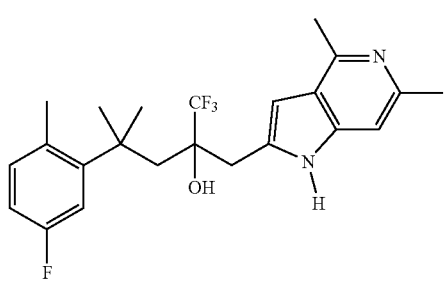 |

-continued

IA

| A | B |
|---|---|
| 4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol | 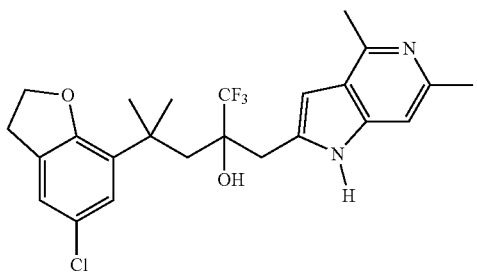 |
| 2-[4-(5-Fluoro-2-methylphenyl)-2-hydroxy-4-methyl-2-trifluoromethylpentyl]-1H-pyrrolo[3,2-b]pyridine-5-carbonitrile | 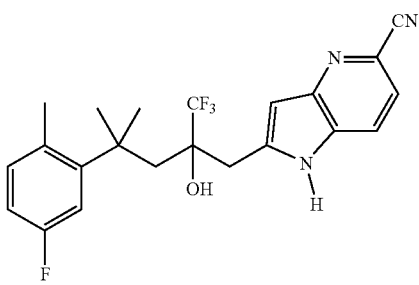 |
| 4-(5-Chloro-2,3-dihydrobenzofuran-7-yl)-1,1,1-trifluoro-4-methyl-2-(3-methyl-1H-pyrrolo[2,3-c]pyridin-2-ylmethyl)pentan-2-ol | 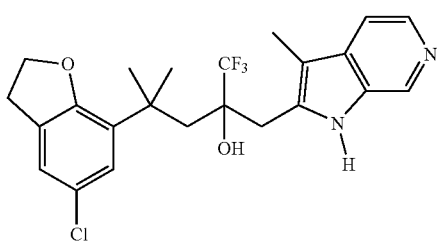 |
| 1,1,1-Trifluoro-4-(5-fluoro-2-methylphenyl)-4-methyl-2-(5H-pyrrolo[3,2-c]pyridazin-6-ylmethyl)pentan-2-ol | 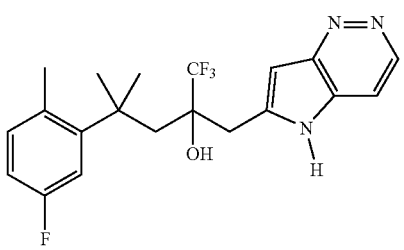 |
| 4-(5-Chloro-2,3-dihydrobenzofuran-7-yl)-1,1,1-trifluoro-4-methyl-2-(5H-pyrrolo[3,2-c]pyridazin-6-ylmethyl)pentan-2-ol | 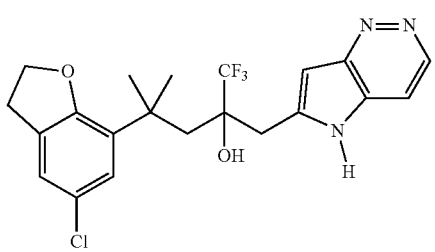 |
| 4-(5-Chloro-2,3-dihydrobenzofuran-7-yl)-1,1,1-trifluoro-4-methyl-2-(1H-pyrrolo[2,3-d]pyridazin-2-ylmethyl)pentan-2-ol | 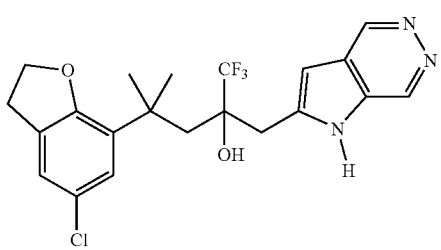 |

-continued

IA

| A | B |
|---|---|
| 1,1,1-Trifluoro-4-(5-fluoro-2-methoxyphenyl)-2-(7-fluoro-1H-pyrrolo[2,3-c]pyridin-2-ylmethyl)-4-methylpentan-2-ol | 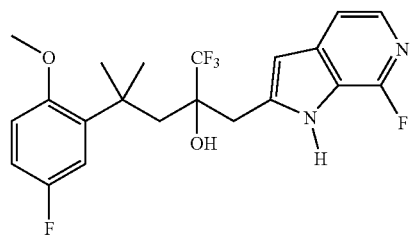 |
| 1,1,1-Trifluoro-4-(5-fluoro-2-methoxyphenyl)-4-methyl-2-(4-methyl-1H-pyrrolo[2,3-c]pyridin-2-ylmethyl)pentan-2-ol | 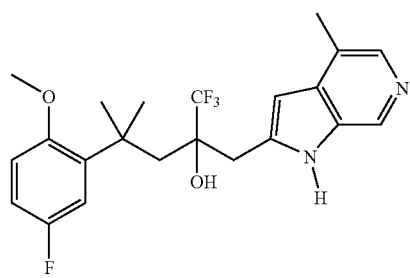 |
| 2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol | 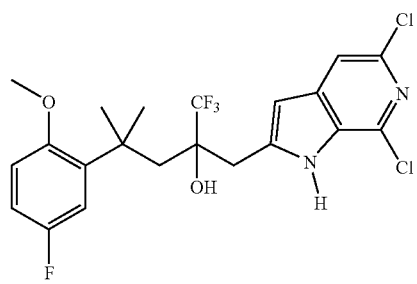 |
| 1,1,1-Trifluoro-4-(5-fluoro-2-methoxyphenyl)-4-methyl-2-(5-trifluoromethyl-1H-pyrrolo[2,3-c]pyridin-2-ylmethyl)pentan-2-ol | 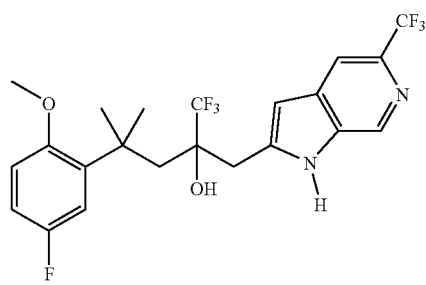 |
| 1,1,1-Trifluoro-4-(5-fluoro-2-methoxyphenyl)-2-(5-methoxy-1H-pyrrolo[2,3-c]pyridin-2-ylmethyl)-4-methylpentan-2-ol | 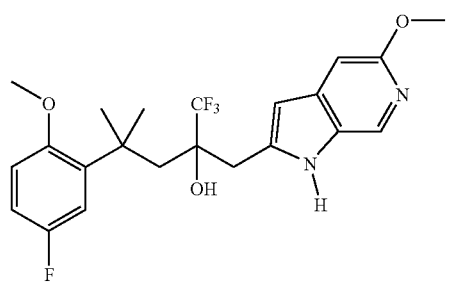 |

-continued

IA

| A | B |
|---|---|
| 1,1,1-Trifluoro-4-(5-fluoro-2-methylphenyl)-4-methyl-2-(4-methyl-1H-pyrrolo[2,3-c]pyridin-2-ylmethyl)pentan-2-ol | 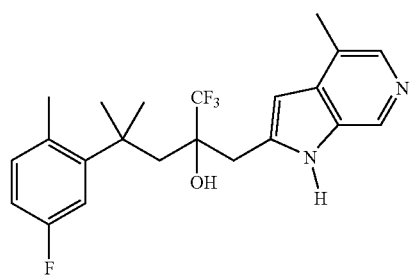 |
| 1,1,1-Trifluoro-4-(5-fluoro-2-methylphenyl)-2-(5-isopropoxy-1H-pyrrolo[2,3-c]pyridin-2-ylmethyl)-4-methylpentan-2-ol | 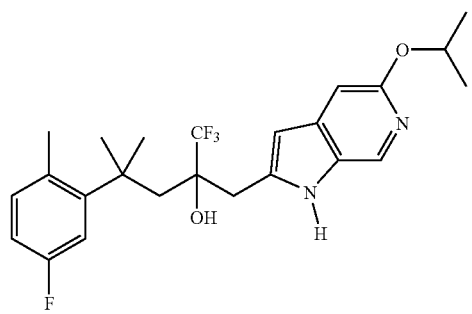 |
| 1,1,1-Trifluoro-4-(5-fluoro-2-methylphenyl)-2-(5-methoxy-1H-pyrrolo[2,3-c]pyridin-2-ylmethyl)-4-methylpentan-2-ol | 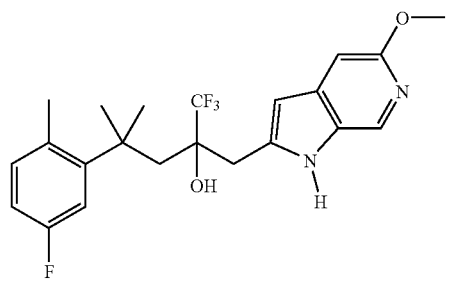 |
| 4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol | 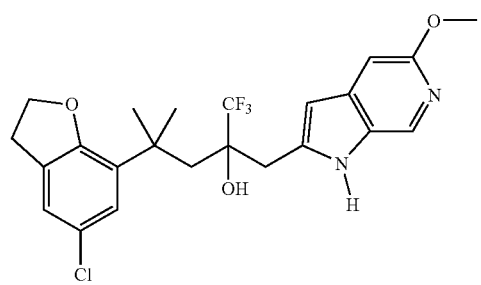 |
| 1,1,1-Trifluoro-4-(5-fluoro-2-methylphenyl)-2-(7-fluoro-1H-pyrrolo[2,3-c]pyridin-2-ylmethyl)-4-methylpentan-2-ol | 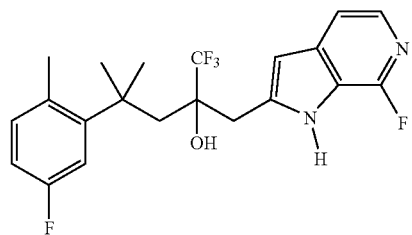 |

-continued

IA

| A | B |
|---|---|
| 4-(5-Chloro-2,3-dihydrobenzofuran-7-yl)-1,1,1-trifluoro-4-methyl-2-(5-trifluoromethyl-1H-pyrrolo[2,3-c]pyridin-2-ylmethyl)pentan-2-ol | 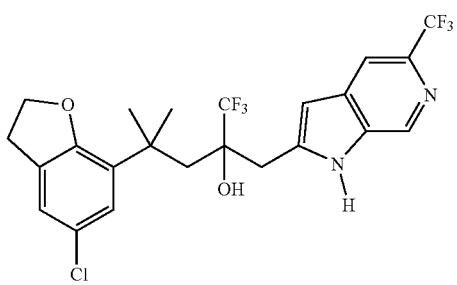 |
| 1,1,1-Trifluoro-4-(5-fluoro-2-methylphenyl)-4-methyl-2-(5-trifluoromethyl-1H-pyrrolo[2,3-c]pyridin-2-ylmethyl)pentan-2-ol | 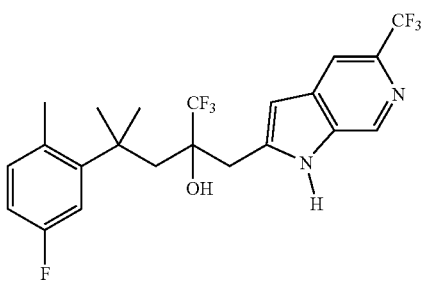 |
| 4-(5-Chloro-2,3-dihydrobenzofuran-7-yl)-1,1,1-trifluoro-2-(5-isopropoxy-1H-pyrrolo[2,3-c]pyridin-2-ylmethyl)-4-methylpentan-2-ol | 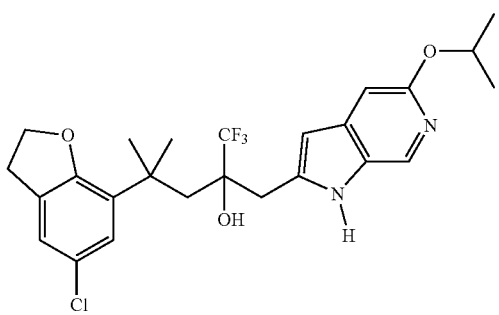 |
| 4-(5-Chloro-2,3-dihydrobenzofuran-7-yl)-1,1,1-trifluoro-2-(7-fluoro-1H-pyrrolo[2,3-c]pyridin-2-ylmethyl)-4-methylpentan-2-ol | 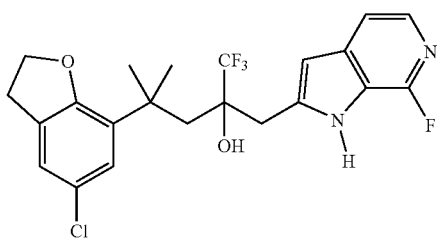 |
| 4-(5-Chloro-2,3-dihydrobenzofuran-7-yl)-2-(5-dimethylamino-1H-pyrrolo[2,3-c]pyridin-2-ylmethyl)-1,1,1-trifluoro-4-methylpentan-2-ol | 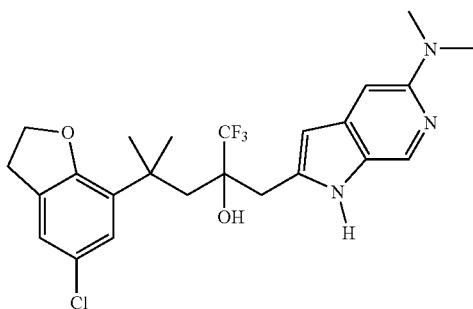 |

| A | B |
|---|---|
| IA | |

| A | B |
|---|---|
| 4-(5-Chloro-2,3-dihydrobenzofuran-7-yl)-1,1,1-trifluoro-4-methyl-2-(5-piperidin-1-yl-1H-pyrrolo[2,3-c]pyridin-2-ylmethyl)pentan-2-ol | 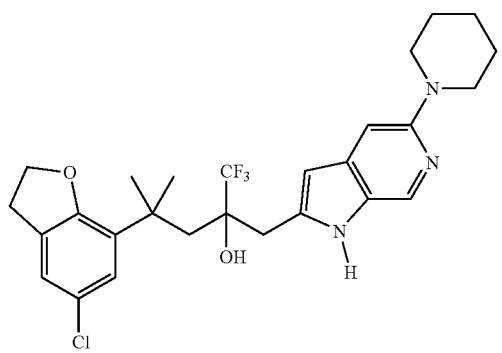 |
| 4-(5-Chloro-2,3-dihydrobenzofuran-7-yl)-1,1,1-trifluoro-4-methyl-2-(5-morpholin-4-yl-1H-pyrrolo[2,3-c]pyridin-2-ylmethyl)pentan-2-ol | 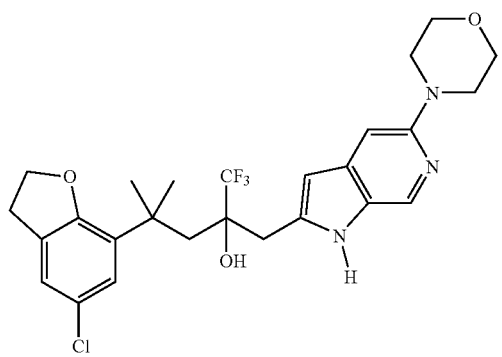 |
| 1,1,1-Trifluoro-4-(5-fluoro-2-methylphenyl)-4-methyl-2-(5-piperidin-1-yl-1H-pyrrolo[2,3-c]pyridin-2-ylmethyl)pentan-2-ol | 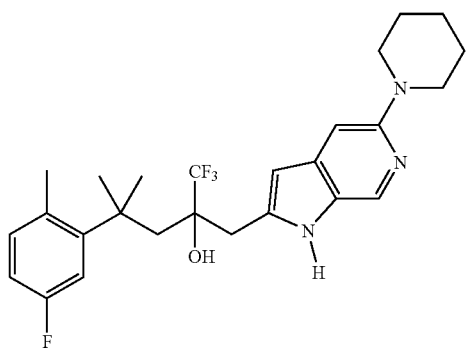 |
| 4-(5-Chloro-2,3-dihydrobenzofuran-7-yl)-2-(5-ethoxy-1H-pyrrolo[2,3-c]pyridin-2-ylmethyl)-1,1,1-trifluoro-4-methylpentan-2-ol | 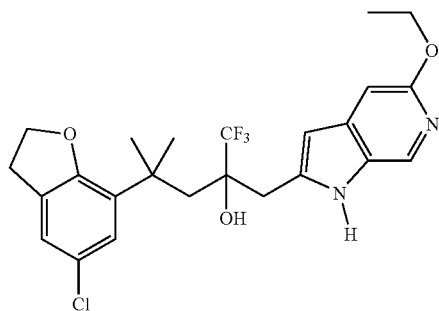 |

-continued

| IA | |
|---|---|
| A | B |

2-(5-Benzyloxy-1H-pyrrolo[2,3-c]pyridin-2-ylmethyl)-1,1,1-trifluoro-4-(5-fluoro-2-methylphenyl)-4-methylpentan-2-ol

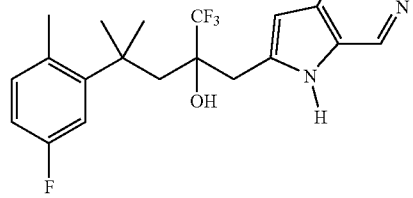

2-(5-Benzyloxy-1H-pyrrolo[2,3-c]pyridin-2-ylmethyl)-4-(5-chloro-2,3-dihydrobenzofuran-7-yl)-1,1,1-trifluoro-4-methylpentan-2-ol

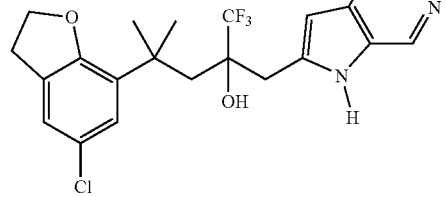

1,1,1-Trifluoro-4-(5-fluoro-2-methoxyphenyl)-2-(5-chloro-1H-pyrrolo[2,3-c]pyridin-2-ylmethyl)-4-methylpentan-2-ol

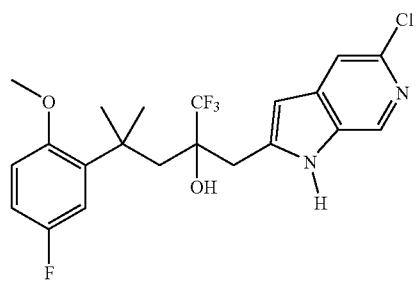 [SMILES: COc1ccc(F)cc1C(C)(C)CC(O)(Cc1cc2cc(Cl)ncc2[nH]1)C(F)(F)F]

1,1,1-Trifluoro-4-(5-fluoro-2-methoxyphenyl)-4-methyl-2-[5-(methylamino)-1H-pyrrolo[2,3-c]pyridin-2-ylmethyl]pentan-2-ol

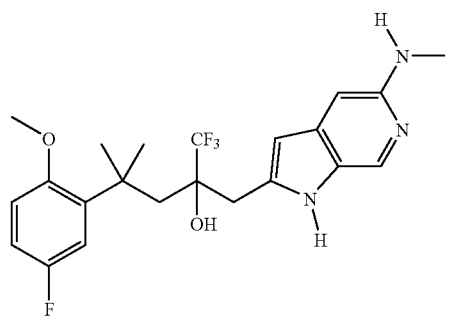 [SMILES: CNc1cc2cc(CC(O)(CC(C)(C)c3cc(F)ccc3OC)C(F)(F)F)[nH]c2cn1]

-continued

IA

| A | B |
|---|---|
| 1,1,1-Trifluoro-4-(5-fluoro-2-methoxyphenyl)-4-methyl-2-(5-amino-1H-pyrrolo[2,3-c]pyridin-2-ylmethyl)pentan-2-ol | 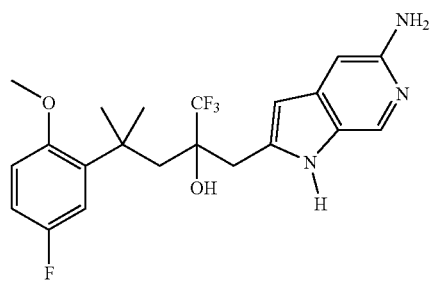 |
| 1,1,1-Trifluoro-4-(5-fluoro-2-methylphenyl)-4-methyl-2-(6-amino-1H-pyrrolo[2,3-c]pyridin-2-ylmethyl)pentan-2-ol | 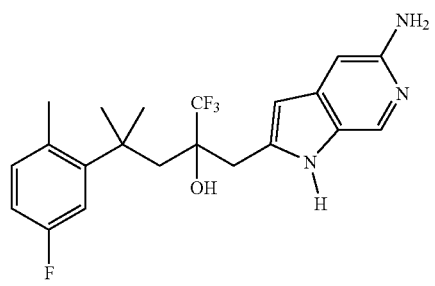 |
| 4-(5-Chloro-2,3-dihydrobenzofuran-7-yl)-1,1,1-trifluoro-2-(5-amino-1H-pyrrolo[2,3-c]pyridin-2-ylmethyl)-4-methylpentan-2-ol | 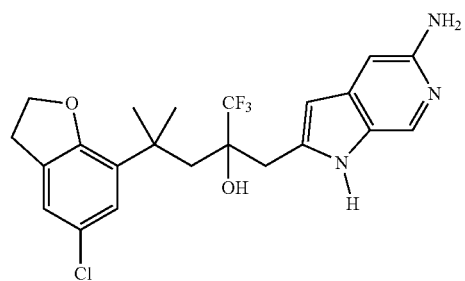 |
| 4-(5-Chloro-2,3-dihydrobenzofuran-7-yl)-1,1,1-trifluoro-4-methyl-2-(5-methylamino-1H-pyrrolo[2,3-c]pyridin-2-ylmethyl)pentan-2-ol | 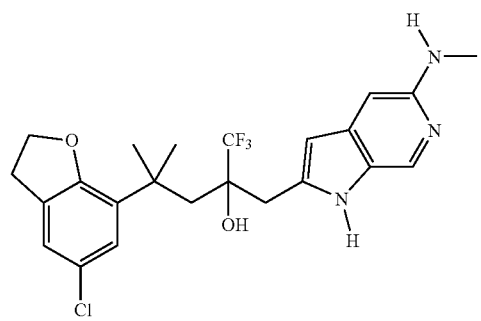 |
| 7-[4-(5-Fluoro-2-methoxyphenyl)-2-hydroxy-4-methyl-2-trifluoromethylpentyl]-1H-pyrrolo[2,3-b]pyridin-7-ium chloride | 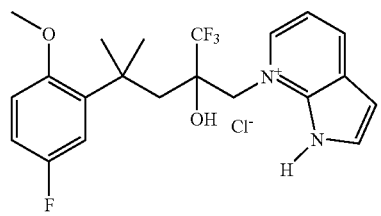 |

-continued

| | IA | |
|---|---|---|
| A | B | |
| 6-[4-(5-Fluoro-2-methoxyphenyl)-2-hydroxy-4-methyl-2-trifluoromethylpentyl]-2-methyl-1H-pyrrolo[2,3-c]pyridin-6-ium chloride | 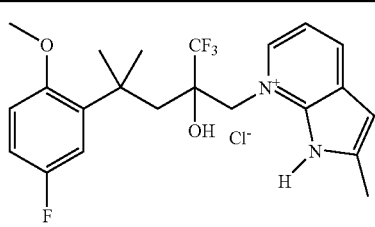 | |
| 4-(5-Bromo-2,3-dihydrobenzofuran-7-yl)-1,1,1-trifluoro-4-methyl-2-(1H-pyrrolo[2,3-c]pyridin-2-ylmethyl)pentan-2-ol | 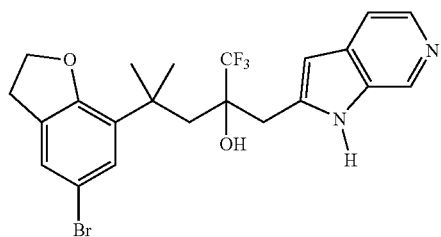 | |
| 1,1,1-Trifluoro-4-methyl-4-(5-methyl-2,3-dihydrobenzofuran-7-yl)-2-(1H-pyrrolo[2,3-c]pyridin-2-ylmethyl)pentan-2-ol | 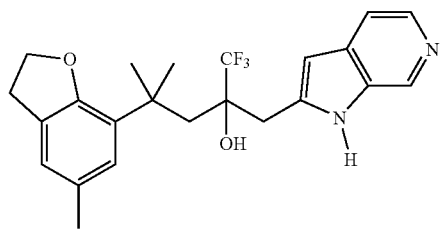 | |
| 4-(5-Chloro-2,3-dihydrobenzofuran-7-yl)-1,1,1-trifluoro-4-methyl-2-(1H-pyrrolo[2,3-c]pyridin-2-ylmethyl)pentan-2-ol | 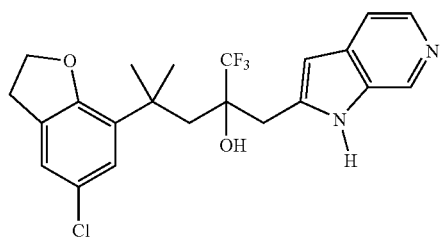 | |
| 1,1,1-Trifluoro-4-(5-fluoro-2-methoxyphenyl)-4-methyl-2-pyrrolo[2,3-b]pyridin-1-ylmethylpentan-2-ol | 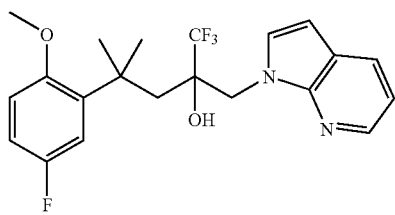 | |
| 1,1,1-Trifluoro-4-(5-fluoro-2-methoxyphenyl)-4-methyl-2-(6-oxy-1H-pyrrolo[2,3-c]pyridin-2-ylmethyl)pentan-2-ol | 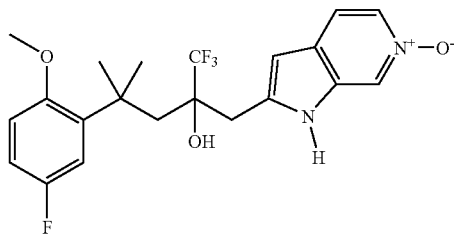 | |

-continued

IA

| A | B |
|---|---|
| 1,1,1-Trifluoro-4-(5-fluoro-2-methoxyphenyl)-4-methyl-2-pyrrolo[2,3-c]pyridin-1-ylmethylpentan-2-ol | 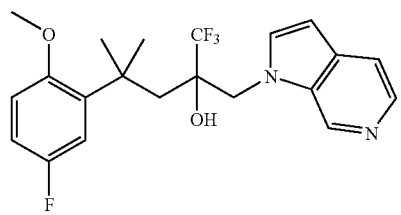 |
| 2-Benzo[b]thiophen-2-ylmethyl-1,1,1-trifluoro-4-(5-fluoro-2-methoxyphenyl)-4-methylpentan-2-ol | 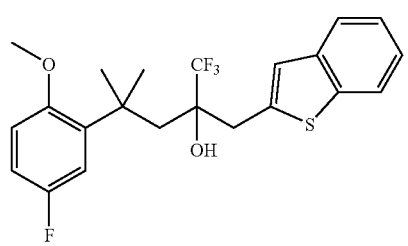 |
| 1,1,1-Trifluoro-4-(5-fluoro-2-methoxyphenyl)-4-methyl-2-thieno[2,3-c]pyridin-2-ylmethylpentan-2-ol | 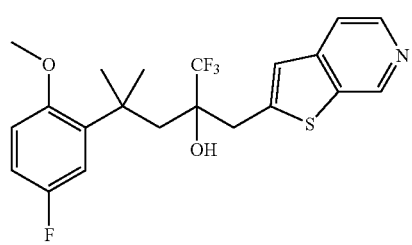 |
| 1,1,1-Trifluoro-4-(5-fluoro-2-methoxyphenyl)-2-indazol-1-ylmethyl-4-methylpentan-2-ol | 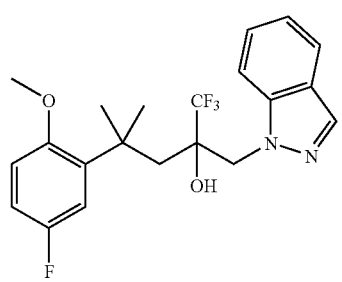 |
| 1,1,1-Trifluoro-4-(5-fluoro-2-methoxyphenyl)-4-methyl-2-[4-((Z)propenyl)-3-vinylpyrazol-1-ylmethyl]pentan-2-ol | 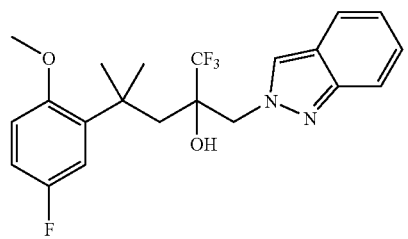 |
| 1,1,1-Trifluoro-4-(5-fluoro-2-methoxyphenyl)-4-methyl-2-pyrazolo[1,5-a]pyridin-2-ylmethylpentan-2-ol | 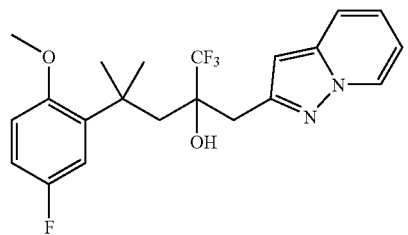 |

-continued

IA

| A | B |
|---|---|
| 4-(5-Chloro-2,3-dihydrobenzofuran-7-yl)-2,4-dimethyl-1-thieno[2,3-c]pyridin-2-ylpentan-2-ol | 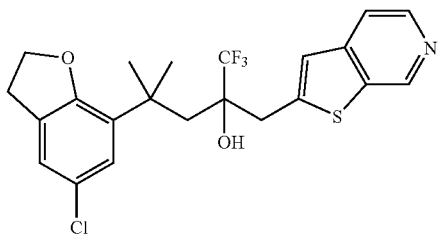 |
| 4-(5-Fluoro-2-methylphenyl)-2,4-dimethyl-1-thieno[2,3-c]pyridin-2-ylpentan-2-ol | 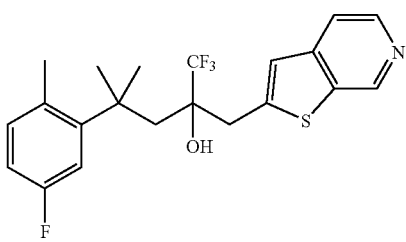 |
| 1,1,1-Trifluoro-4-(5-fluoro-2-methoxyphenyl)-2-furo[2,3-c]pyridin-2-ylmethyl-4-methylpentan-2-ol | 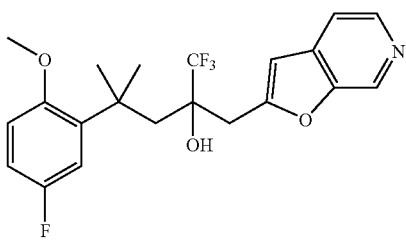 |
| 4-(5-Chloro-2,3-dihydrobenzofuran-7-yl)-1-furo[2,3-c]pyridin-2-yl-2,4-dimethylpentan-2-ol | 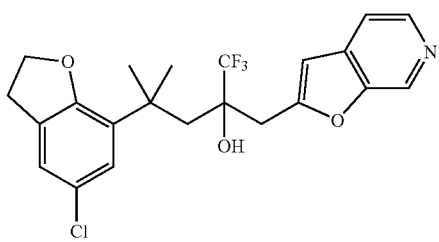 |
| 4-(5-Fluoro-2-methylphenyl)-1-furo[2,3-c]pyridin-2-yl-2,4-dimethylpentan-2-ol | 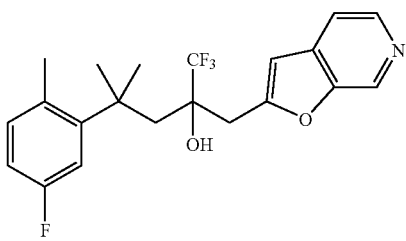 |
| 1,1,1-Trifluoro-4-(5-fluoro-2-methylphenyl)-4-methyl-2-(1H-pyrrolo[3,2-c]pyridin-2-ylmethyl)pentan-2-ol | 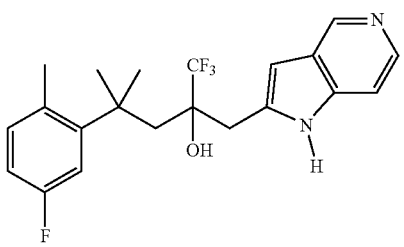 |

-continued

IA

| A | B |
|---|---|
| 1,1,1-Trifluoro-4-methyl-4-(5-methyl-2,3-dihydrobenzofuran-7-yl)-2-(1H-pyrrolo[3,2-c]pyridin-2-ylmethyl)pentan-2-ol | 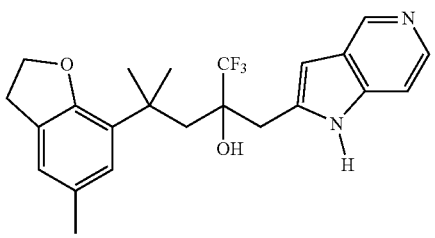 |
| 4-(5-Chloro-2,3-dihydrobenzofuran-7-yl)-1,1,1-trifluoro-4-methyl-2-(1H-pyrrolo[3,2-c]pyridin-2-ylmethyl)pentan-2-ol | 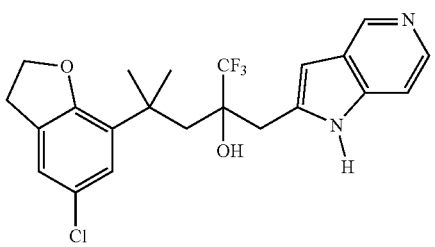 |
| 4-(5-Bromo-2,3-dihydrobenzofuran-7-yl)-1,1,1-trifluoro-4-methyl-2-(1H-pyrrolo[3,2-c]pyridin-2-ylmethyl)pentan-2-ol | 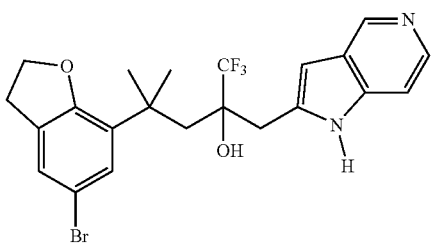 |
| 2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol | 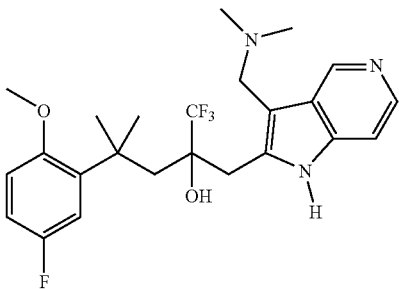 |
| 1,1,1-Trifluoro-4-(5-fluoro-2-methoxyphenyl)-4-methyl-2-pyrrolo[3,2-c]pyridin-1-ylmethylpentan-2-ol | 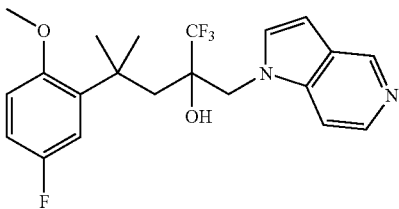 |
| 1,1,1-Trifluoro-4-(5-fluoro-2-methoxyphenyl)-4-methyl-2-pyrrolo[3,2-b]pyridin-1-ylmethylpentan-2-ol | 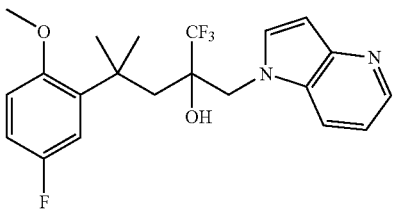 |

-continued

| | IA |
|---|---|
| A | B |

1,1,1-Trifluoro-4-(5-fluoro-2-methoxyphenyl)-2-furo[3,2-c]pyridin-2-ylmethyl-4-methylpentan-2-ol

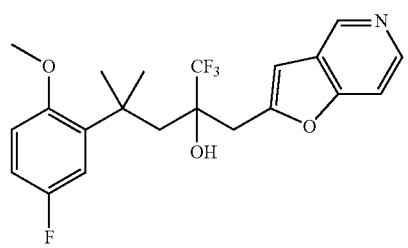 [SMILES: COc1ccc(F)cc1C(C)(C)CC(O)(Cc1cc2cnccc2o1)C(F)(F)F]

4-(5-Chloro-2,3-dihydrobenzofuran-7-yl)-1,1,1-trifluoro-4-methyl-2-pyrrolo[3,2-b]pyridin-1-ylmethylpentan-2-ol

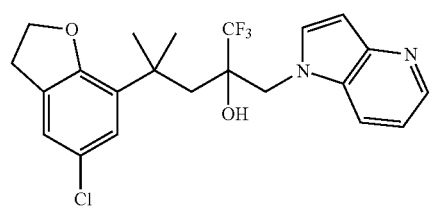 [SMILES: CC(C)(CC(O)(Cn1ccc2ncccc21)C(F)(F)F)c1cc(Cl)cc2c1OCC2]

1,1,1-Trifluoro-4-(5-fluoro-2-methoxyphenyl)-4-methyl-2-thieno[3,2-c]pyridin-2-ylmethylpentan-2-ol

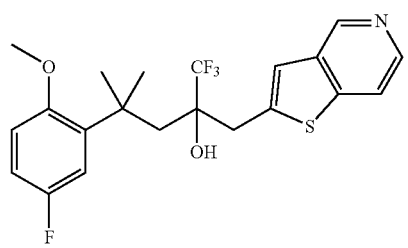 [SMILES: COc1ccc(F)cc1C(C)(C)CC(O)(Cc1cc2cnccc2s1)C(F)(F)F]

4-(5-Chloro-2,3-dihydrobenzofuran-7-yl)-1,1,1-trifluoro-4-methyl-2-thieno[3,2-c]pyridin-2-ylmethylpentan-2-ol

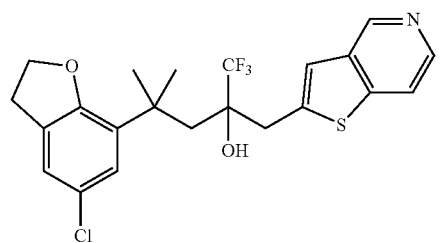 [SMILES: CC(C)(CC(O)(Cc1cc2cnccc2s1)C(F)(F)F)c1cc(Cl)cc2c1OCC2]

1,1,1-Trifluoro-4-(5-fluoro-2-methylphenyl)-4-methyl-2-pyrrolo[3,2-b]pyridin-1-ylmethylpentan-2-ol

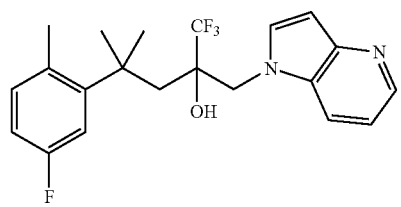 [SMILES: Cc1ccc(F)cc1C(C)(C)CC(O)(Cn1ccc2ncccc21)C(F)(F)F]

1,1,1-Trifluoro-4-(5-fluoro-2-methylphenyl)-4-methyl-2-thieno[3,2-c]pyridin-2-ylmethylpentan-2-ol

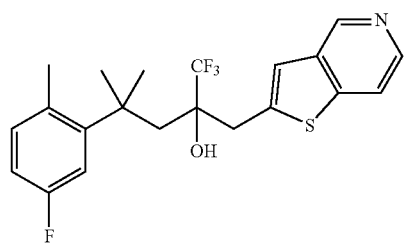 [SMILES: Cc1ccc(F)cc1C(C)(C)CC(O)(Cc1cc2cnccc2s1)C(F)(F)F]

-continued

IA

| A | B |
|---|---|
| 4-Fluoro-2-(4,4,4-trifluoro-3-hydroxy-1,1-dimethyl-3-thieno[3,2-c]pyridin-2-ylmethylbutyl)phenol | 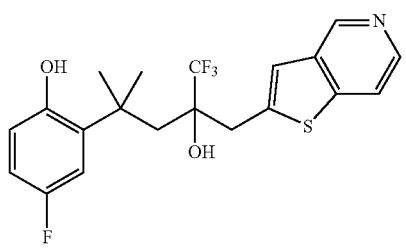 |
| 4-Fluoro-2-(4,4,4-trifluoro-3-furo[3,2-c]pyridin-2-ylmethyl-3-hydroxy-1,1-dimethylbutyl)phenol | 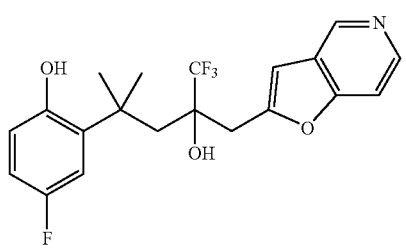 |
| 4-Fluoro-2-(4,4,4-trifluoro-3-hydroxy-1,1-dimethyl-3-pyrrolo[3,2-b]pyridin-1-ylmethylbutyl)phenol | 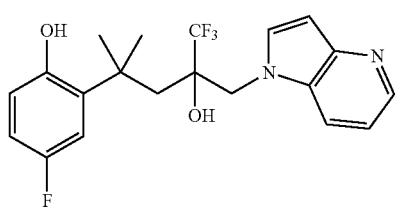 |
| 2-[4-(5-Fluoro-2-hydroxyphenyl)-2-hydroxy-4-methyl-2-trifluoromethylpentyl]-1H-indole-6-carboxylic acid | 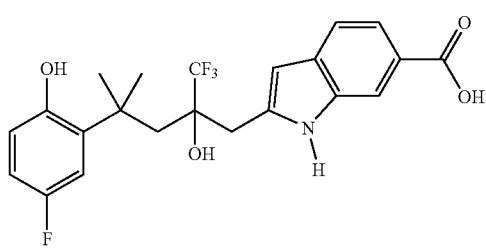 |
| 2-[4-(5-Fluoro-2-hydroxyphenyl)-2-hydroxy-4-methyl-2-trifluoromethylpentyl]-1H-indole-6-carboxylic acid dimethylamide | 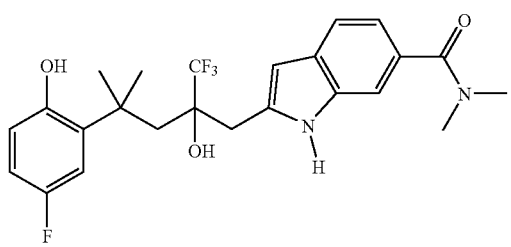 |
| {2-[4-(5-Fluoro-2-hydroxyphenyl)-2-hydroxy-4-methyl-2-trifluoromethylpentyl]-1H-indol-6-yl}morpholin-4-ylmethanone | 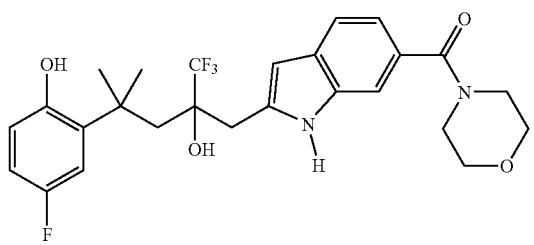 |

-continued

| | IA | |
|---|---|---|
| A | B | |
| 2-[4-(5-Fluoro-2-methoxyphenyl)-2-hydroxy-4-methyl-2-trifluoromethylpentyl]-1H-indole-6-carboxylic acid dimethylamide | 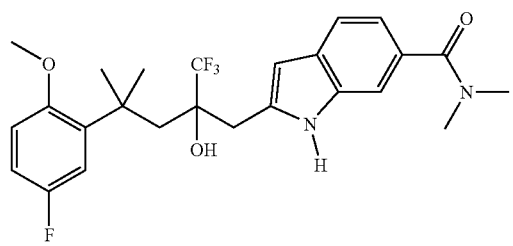 | |
| {2-[4-(5-Fluoro-2-methoxyphenyl)-2-hydroxy-4-methyl-2-trifluoromethylpentyl]-1H-indol-6-yl}morpholin-4-ylmethanone | 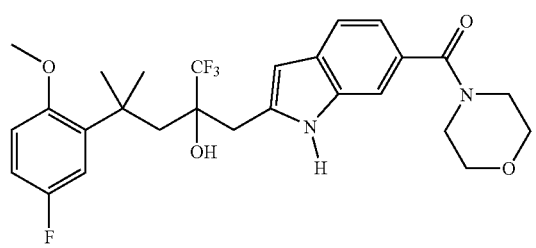 | |
| 2-[4-(5-Fluoro-2-hydroxyphenyl)-2-hydroxy-4-methyl-2-trifluoromethylpentyl]-1H-indole-6-carboxylic acid amide | 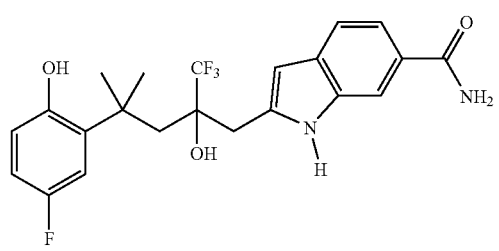 | |
| 2-[4-(5-Fluoro-2-methoxyphenyl)-2-hydroxy-4-methyl-2-trifluoromethylpentyl]-1H-indole-6-carboxylic acid amide | 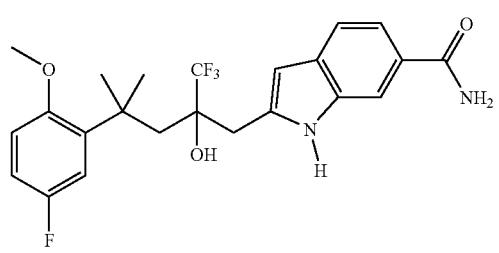 | |
| 4-Fluoro-2-[4,4,4-trifluoro-3-hydroxy-1,1-dimethyl-3-(5-nitro-1H-indol-2-ylmethyl)butyl]phenol | 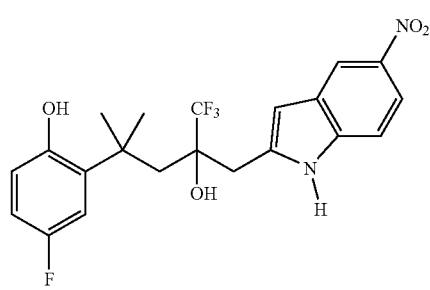 | |
| 2-[4-(5-Fluoro-2-methoxyphenyl)-2-hydroxy-4-methyl-2-trifluoromethylpentyl]-1H-indole-6-carbonitrile | 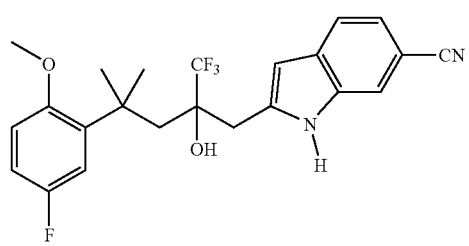 | |

-continued

| IA | |
|---|---|
| A | B |
| 2-[4-(5-Fluoro-2-hydroxyphenyl)-2-hydroxy-4-methyl-2-trifluoromethylpentyl]-1H-indole-6-carbonitrile | 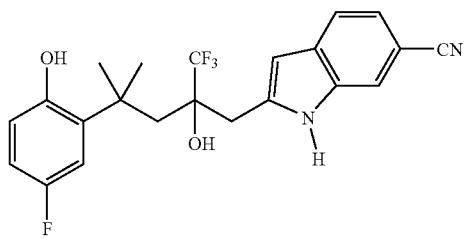 |
| N-{2-[4-(5-Fluoro-2-methoxyphenyl)-2-hydroxy-4-methyl-2-trifluoromethylpentyl]-1H-indol-5-yl}acetamide | 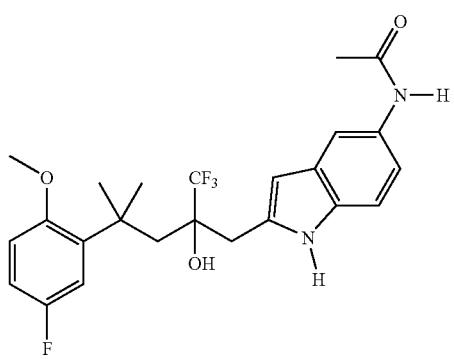 |

| IA | |
|---|---|
| A | B |
| 1,1,1-Trifluoro-4-(4-fluoro-2-methoxyphenyl)-2-(7-fluoro-4-methyl-1H-indol-2-ylmethyl)-4-methylpentan-2-ol | 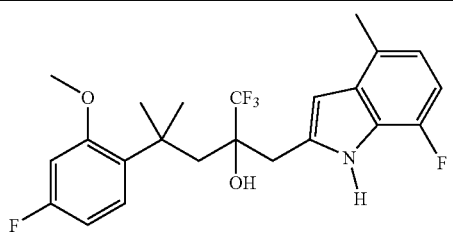 |
| 5-Fluoro-2-[4,4,4-trifluoro-3-(7-fluoro-4-methyl-1H-indol-2-ylmethyl)-3-hydroxy-1,1-dimethylbutyl]phenol | 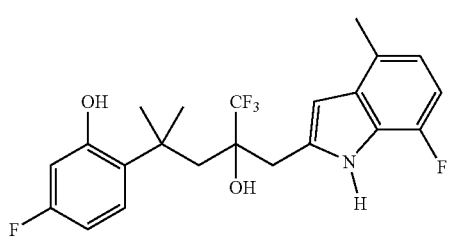 |
| 2-[4-(3-[1,3]Dioxolan-2-ylphenyl)-2-hydroxy-4-methyl-2-trifluoromethylpentyl]-1H-indole-5-carbonitrile | 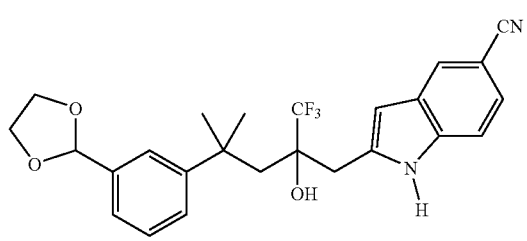 |

-continued

| | IA |
|---|---|
| A | B |

2-[4-(5-Fluoro-2-methoxyphenyl)-2-hydroxy-4-methyl-2-trifluoromethylpentyl]-1H-indole-5-carboxylic acid-2-trimethylsilanylethyl ester

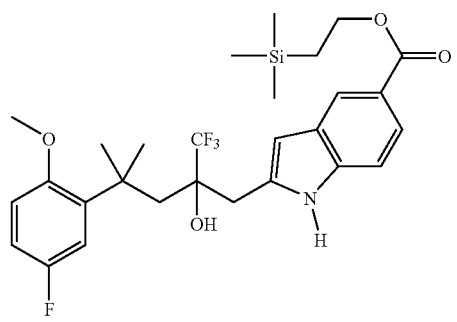 [SMILES: COc1ccc(F)cc1C(C)(C)CC(O)(Cc1cc2cc(C(=O)OCC[Si](C)(C)C)ccc2[nH]1)C(F)(F)F]

2[4-(5-Fluoro-2-methoxyphenyl)-2-hydroxy-4-methyl-2-trifluoromethylpentyl]-1H-indole-5-carboxylic acid

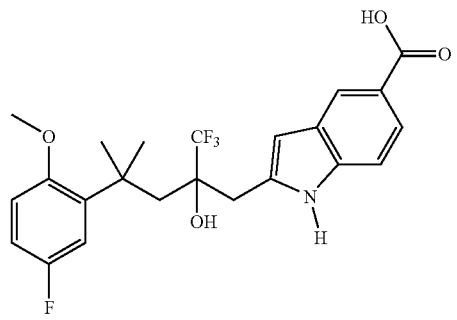 [SMILES: COc1ccc(F)cc1C(C)(C)CC(O)(Cc1cc2cc(C(=O)O)ccc2[nH]1)C(F)(F)F]

2-[4-(4-Fluoro-2-hydroxyphenyl)-2-hydroxy-4-methyl-2-trifluoromethylpentyl]-4-methyl-1H-indole-6-carbonitrile

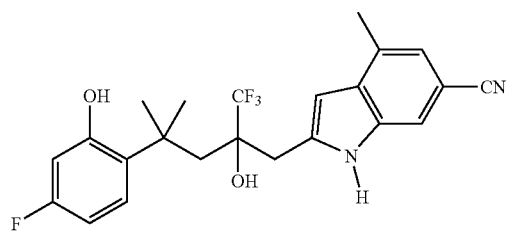 [SMILES: Cc1cc(C#N)cc2[nH]c(CC(O)(CC(C)(C)c3ccc(F)cc3O)C(F)(F)F)cc12]

{2-[4-(5-Fluoro-2-methoxyphenyl)-2-hydroxy-4-methyl-2-trifluoromethylpentyl]-1H-indol-5-yl}piperidin-1-ylmethanone

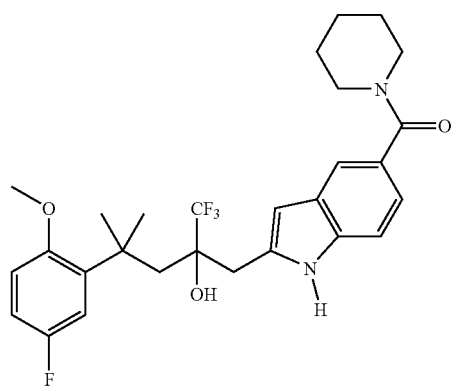 [SMILES: COc1ccc(F)cc1C(C)(C)CC(O)(Cc1cc2cc(C(=O)N3CCCCC3)ccc2[nH]1)C(F)(F)F]

| A | B |
|---|---|
| 2-[4-(5-Fluoro-2-methoxyphenyl)-2-hydroxy-4-methyl-2-trifluoromethylpentyl]-1H-indole-5-carboxylic acid methylamide | 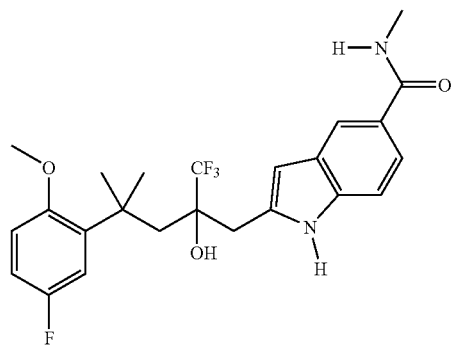 |
| {2-[4-(5-Fluoro-2-methoxyphenyl)-2-hydroxy-4-methyl-2-trifluoromethylpentyl]-1H-indol-5-yl}pyrrolidin-1-ylmethanone | 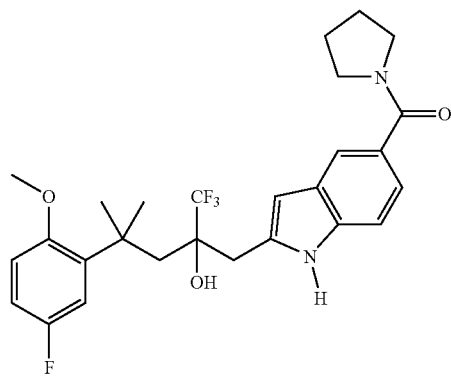 |
| 1-{2-[4-(5-Fluoro-2-methoxyphenyl)-2-hydroxy-4-methyl-2-trifluoromethylpentyl]-1H-indole-5-carbonyl}piperidin-4-one | 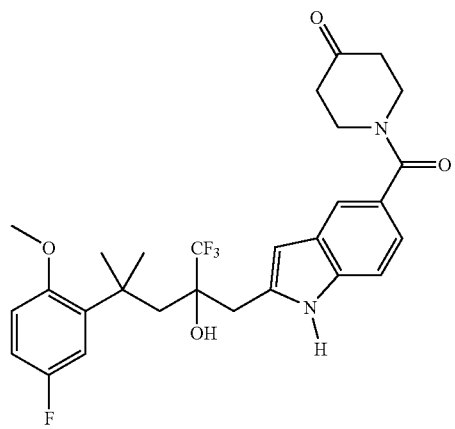 |
| 2-[4-(5-Fluoro-2-methoxyphenyl)-2-hydroxy-4-methyl-2-trifluoromethylpentyl]-1H-indole-5-carboxylic acid (2-hydroxyethyl)amide | 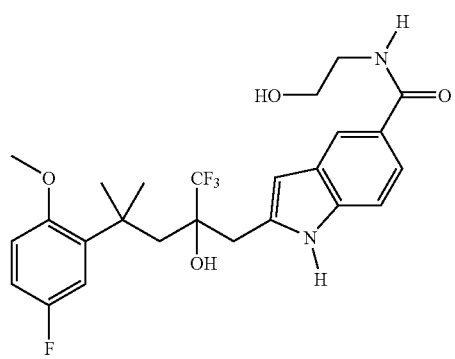 |

| A | B |
|---|---|
| {2-[4-(5-Fluoro-2-methoxyphenyl)-2-hydroxy-4-methyl-2-trifluoromethylpentyl]-1H-indol-5-yl}(4-hydroxypiperidin-1-yl)methanone | 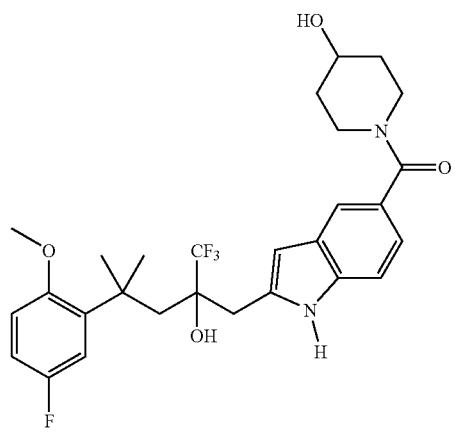 |
| {2-[4-(5-Fluoro-2-methoxyphenyl)-2-hydroxy-4-methyl-2-trifluoromethylpentyl]-1H-indol-5-yl}(3-hydroxypyrrolidin-1-yl)methanone | 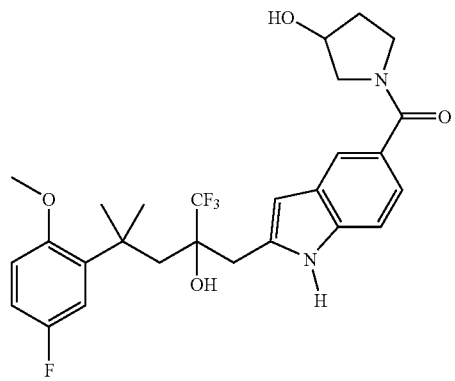 |
| 2-[4-(5-Fluoro-2-methoxyphenyl)-2-hydroxy-4-methyl-2-trifluoromethylpentyl]-1H-indole-5-carboxylic acid cyanomethylamide | 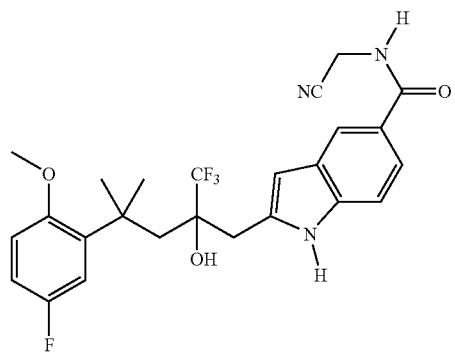 |
| 2-[4-(5-Fluoro-2-methoxyphenyl)-2-hydroxy-4-methyl-2-trifluoromethylpentyl]-1H-indole-5-carboxylic acid (2-dimethylaminoethyl)amide | 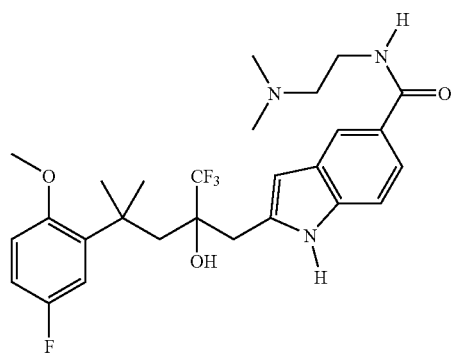 |

-continued

| IA | |
|---|---|
| A | B |
| {2-[4-(5-Fluoro-2-methoxyphenyl)-2-hydroxy-4-methyl-2-trifluoromethylpentyl]-1H-indol-5-yl}(4-methylpiperazin-1-yl)methanone | 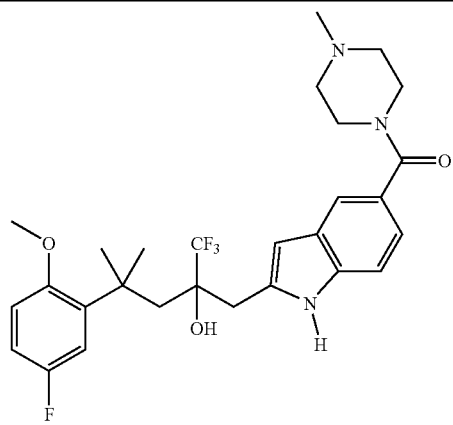 |
| ({2-[4-(5-Fluoro-2-methoxyphenyl)-2-hydroxy-4-methyl-2-trifluoromethylpentyl]-1H-indole-5-carbonyl}amino)acetic acid methyl ester | 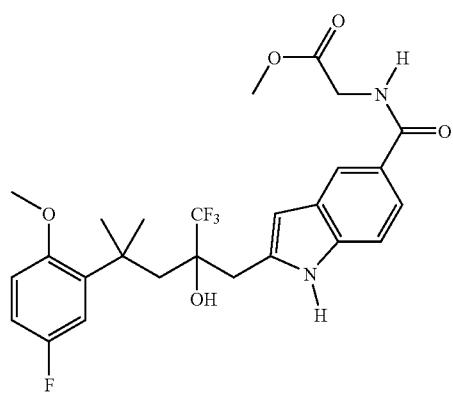 |
| 2-[4-(5-Fluoro-2-methoxyphenyl)-2-hydroxy-4-methyl-2-trifluoromethylpentyl]-1H-indole-5-carboxylic acid carbamoylmethylamide | 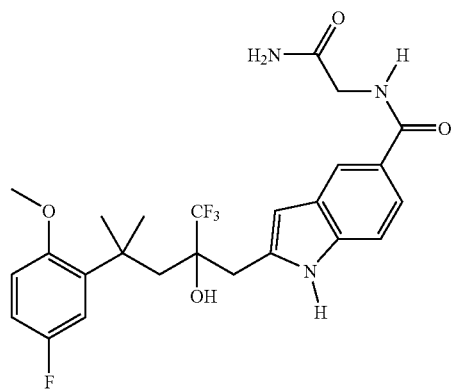 |
| 4-({2-[4-(5-Fluoro-2-methoxyphenyl)-2-hydroxy-4-methyl-2-trifluoromethylpentyl]-1H-indole-5-carbonyl}amino)butyric acid methyl ester | 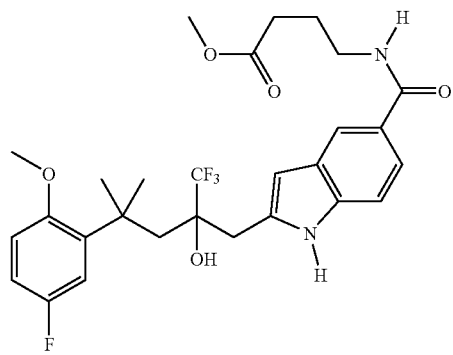 |

-continued

| IA | |
|---|---|
| A | B |
| ({2-[4-(5-Fluoro-2-methoxyphenyl)-2-hydroxy-4-methyl-2-trifluoromethylpentyl]-1H-indole-5-carbonyl}amino)acetic acid | 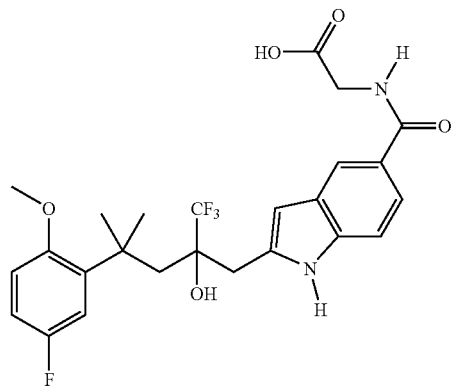 |
| 4-({2-[4-(5-Fluoro-2-methoxyphenyl)-2-hydroxy-4-methyl-2-trifluoromethylpentyl]-1H-indole-5-carbonyl}amino)butyric acid | 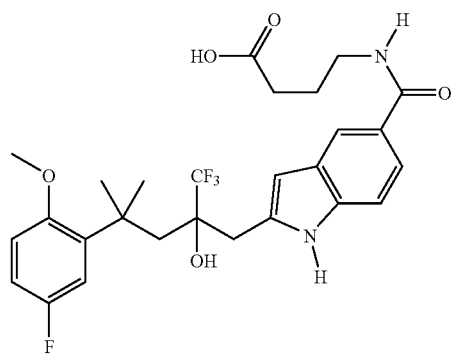 |
| 2[4-(3-Dimethylaminomethylphenyl)-2-hydroxy-4-methyl-2-trifluoromethylpentyl]-1H-indole-5-carbonitrile | 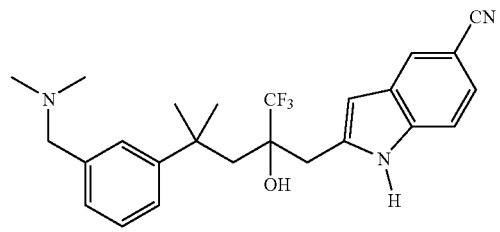 |
| 4-Fluoro-2-[4,4,4-trifluoro-3-hydroxy-1,1-dimethyl-3-(5-trifluoromethyl-1H-indol-2-ylmethyl)butyl]phenol | 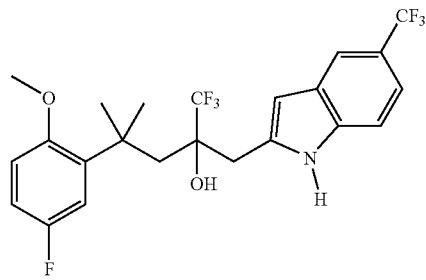 |
| 2-[4-(5-Bromo-2,3-dihydrobenzofuran-7-yl)-2-hydroxy-4-methyl-2-trifluoromethylpentyl]-4-methyl-1H-indole-6-carbonitrile | 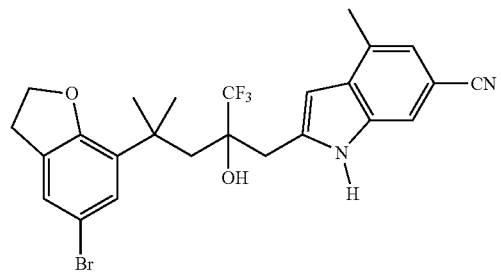 |

-continued

IA

| A | B |
|---|---|
| 2-[2-Hydroxy-4-(5-methanesulfonyl-2,3-dihydrobenzofuran-7-yl)-4-methyl-2-trifluoromethylpentyl]-4-methyl-1H-indole-6-carbonitrile | 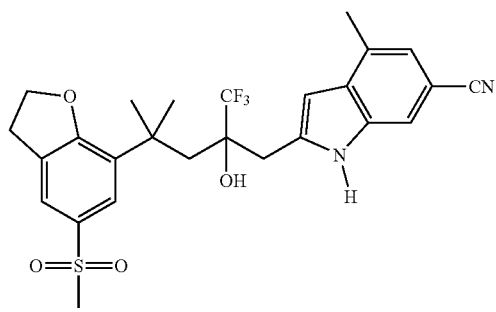 |
| 2-[4-(5-Bromo-2,3-dihydrobenzofuran-7-yl)-2-hydroxy-4-methyl-2-trifluoromethylpentyl]-1H-indole-5-carboxylic acid | 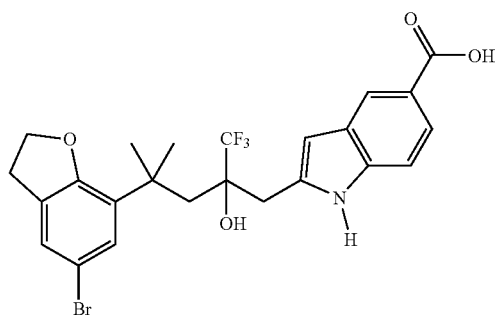 |
| 2-[4-(5-Bromo-2,3-dihydrobenzofuran-7-yl)-2-hydroxy-4-methyl-2-trifluoromethylpentyl]-1H-indole-5-carboxylic acid amide | 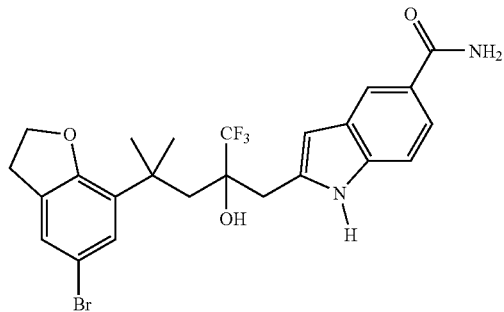 |
| 2-[4-(5-Bromo-2,3-dihydrobenzofuran-7-yl)-2-hydroxy-4-methyl-2-trifluoromethylpentyl]-1H-indole-5-carboxylic acid dimethylamide | 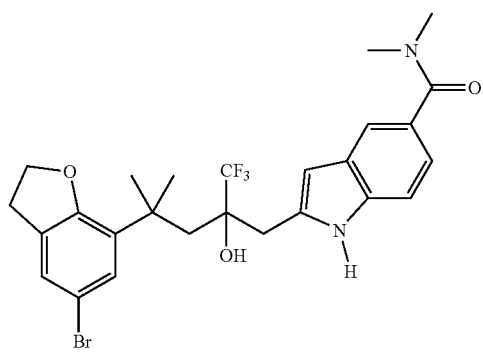 |

-continued

IA

| A | B |
|---|---|
| 2-[4-(5-Bromo-2,3-dihydrobenzofuran-7-yl)-2-hydroxy-4-methyl-2-trifluoromethylpentyl]-1H-indole-5-carboxylic acid cyanomethylamide | 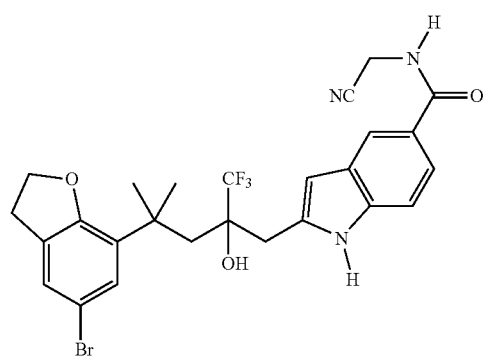 |
| {2-[4-(5-Bromo-2,3-dihydrobenzofuran-7-yl)-2-hydroxy-4-methyl-2-trifluoromethylpentyl]-1H-indol-5-yl}pyrrolidin-1-ylmethanone | 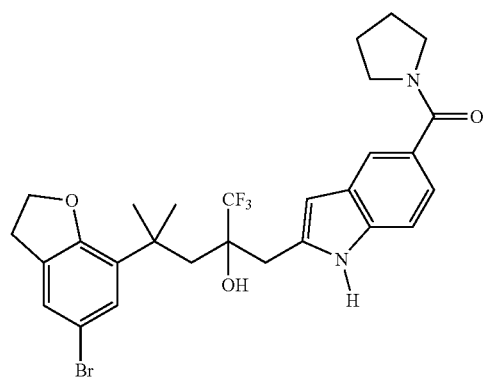 |
| {2-[4-(5-Bromo-2,3-dihydrobenzofuran-7-yl)-2-hydroxy-4-methyl-2-trifluoromethylpentyl]-1H-indol-5-yl}morpholin-4-ylmethanone | 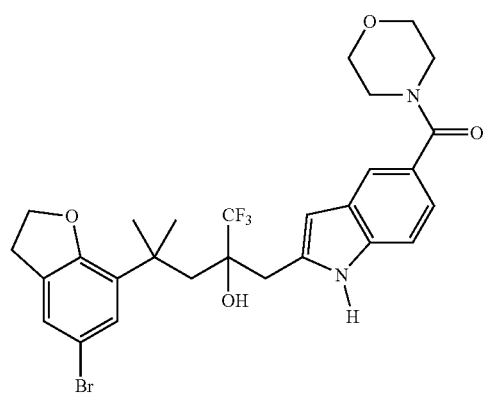 |
| 2-[4-(5-Fluoro-2-methoxyphenyl)-2-hydroxy-4-methyl-2-trifluoromethylpentyl]-1H-indole-5-carboxylic acid amide | 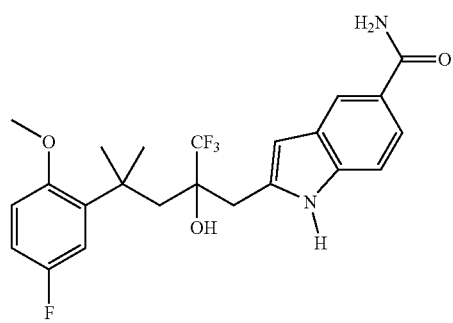 |

-continued

IA

| A | B |
|---|---|
| {2-[4-(5-Fluoro-2-methoxyphenyl)-2-hydroxy-4-methyl-2-trifluoromethylpentyl]-1H-indol-5-yl}morpholin-4-ylmethanone | 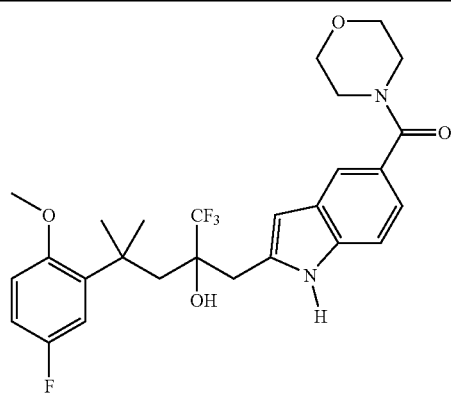 |
| 2-(4-Benzo[1,3]dioxol-4-yl-2-hydroxy-4-methyl-2-trifluoromethylpentyl)-4-methyl-1H-indole-6-carbonitrile | 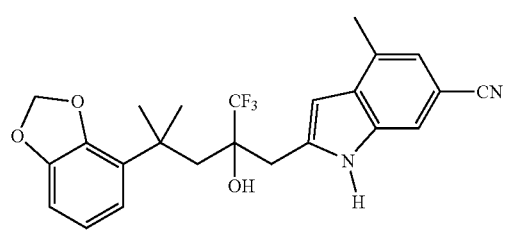 |
| 1,1,1-Trifluoro-4-methyl-4-phenyl-2-quinolin-4-ylmethylhexan-2-ol | 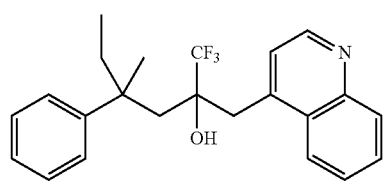 |
| 2-[2-Hydroxy-4-methyl-4-(5-methylsulfanyl-2,3-dihydrobenzofuran-7-yl)-2-trifluoromethylpentyl]-1H-indole-3-carbonitrile | 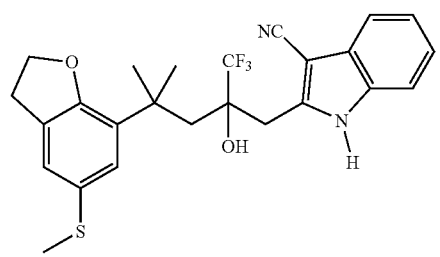 |
| 7-(4,4,4-Trifluoro-3-hydroxy-1,1-dimethyl-3-quinolin-4-ylmethylbutyl)-2,3-dihydrobenzofuran-5-carbonitrile | 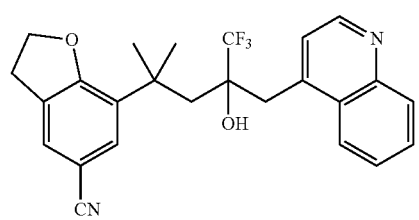 |
| 2-[2-Hydroxy-4-(5-methanesulfonyl-2,3-dihydrobenzofuran-7-yl)-4-methyl-2-trifluoromethylpentyl]-1H-indole-3-carbonitrile | 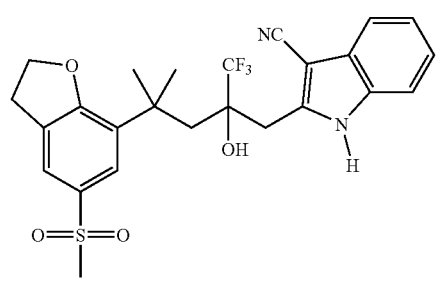 |

-continued

IA

| A | B |
|---|---|
| 2-[2-Hydroxy-4-(2-hydroxy-5-methylphenyl)-4-methyl-2-trifluoromethylpentyl]-4-methyl-1H-indole-6-carbonitrile | 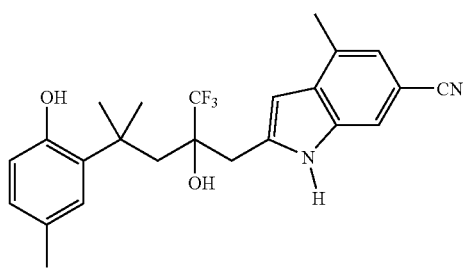 |
| 1,1,1-Trifluoro-4-(5-fluoro-2,3-dihydrobenzofuran-7-yl)-4-methyl-2-(5-methylsulfanyl-1H-indol-2-ylmethyl)pentan-2-ol | 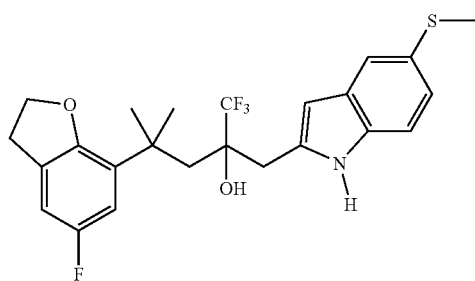 |
| 2-[2-Hydroxy-4-(2-methoxy-5-methylsulfanylphenyl)-4-methyl-2-trifluoromethylpentyl]-1H-indole-3-carbonitrile | 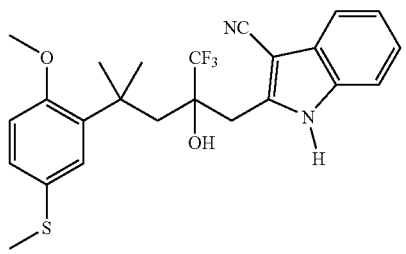 |
| 2-[2-Hydroxy-4-(5-methanesulfonyl-2-methoxyphenyl)-4-methyl-2-trifluoromethylpentyl]-1H-indole-3-carbonitrile | 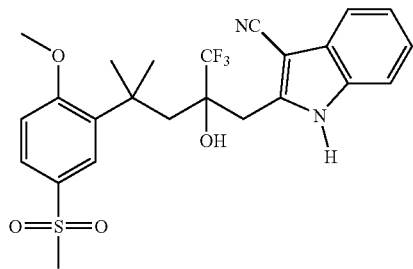 |
| 2-[4-(5-Fluoro-2,3-dihydrobenzofuran-7-yl)-2-hydroxy-4-methyl-2-trifluoromethylpentyl]-1H-indole-5-sulfonic acid dimethylamide | 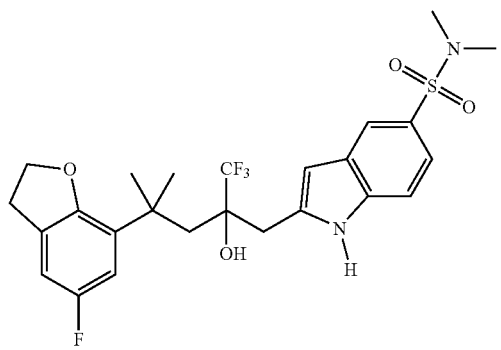 |

| IA | |
|---|---|
| A | B |
| 1,1,1-Trifluoro-4-(5-fluoro-2,3-dihydrobenzofuran-7-yl)-4-methyl-2-(5-phenyl-1H-indol-2-ylmethyl)pentan-2-ol | 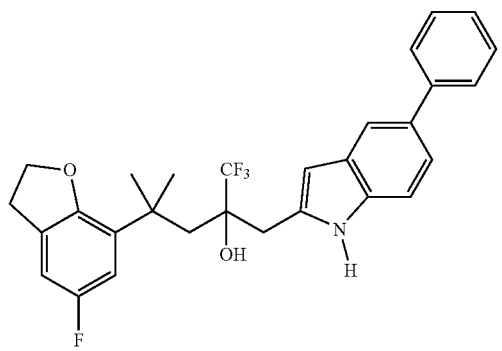 |
| 2-[4-(5-tert-Butyl-2-hydroxyphenyl)-2-hydroxy-4-methyl-2-trifluoromethylpentyl]-1H-indole-3-carbonitrile | 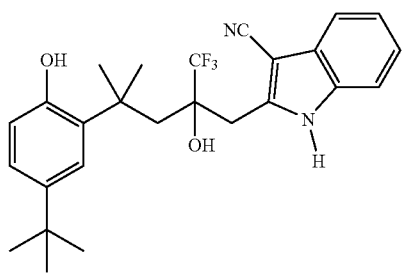 |
| 2-[2-Hydroxy-4-(2-hydroxy-5-isopropylphenyl)-4-methyl-2-trifluoromethylpentyl]-1H-indole-3-carbonitrile | 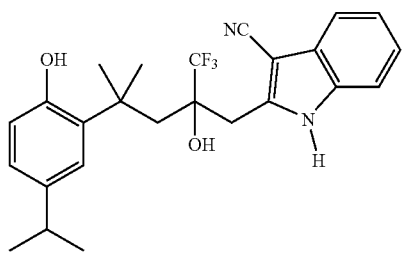 |
| 2-[2-Hydroxy-4-(2-hydroxy-3,5-dimethylphenyl)-4-methyl-2-trifluoromethylpentyl]-1H-indole-3-carbonitrile | 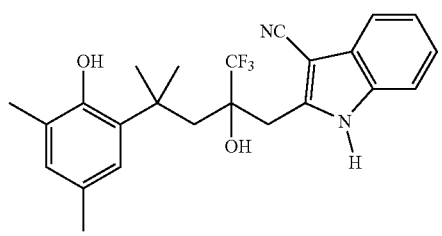 |
| 2-[2-Hydroxy-4-(5-hydroxy-2,4-dimethylphenyl)-4-methyl-2-trifluoromethylpentyl]-1H-indole-3-carbonitrile | 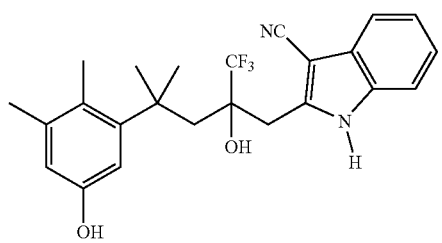 |

-continued

| IA | |
|---|---|
| A | B |
| 2-[4-(5-tert-Butyl-2-methoxyphenyl)-2-hydroxy-4-methyl-2-trifluoromethylpentyl]-1H-indole-3-carbonitrile | 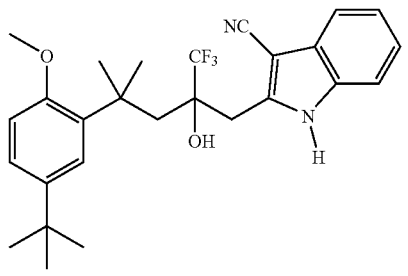 |
| 2-[4-(5-tert-Butyl-2-methoxyphenyl)-2-hydroxy-4-methyl-2-trifluoromethylpentyl]-1-methyl-1H-indole-3-carbonitrile | 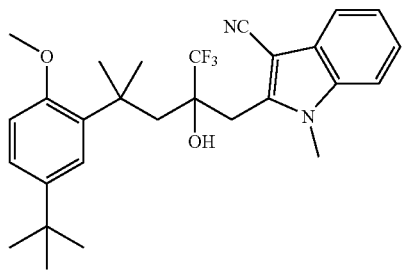 |
| 2-[2-Hydroxy-4-(5-isopropyl-2-methoxyphenyl)-4-methyl-2-trifluoromethylpentyl]-1H-indole-3-carbonitrile | 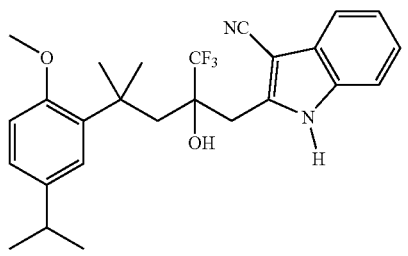 |
| 2-[2-Hydroxy-4-(5-isopropyl-2-methoxyphenyl)-4-methyl-2-trifluoromethylpentyl]-1-methyl-1H-indole-3-carbonitrile | 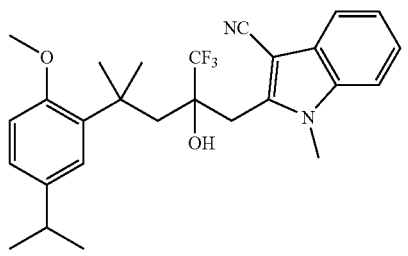 |
| 2-[2-Hydroxy-4-(2-hydroxy-5-methanesulfonylphenyl)-4-methyl-2-trifluoromethylpentyl]-1H-indole-3-carbonitrile | 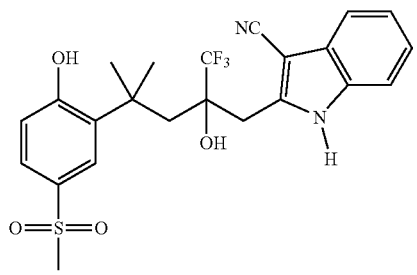 |

-continued

IA

| A | B |
|---|---|
| 2-[2-Hydroxy-4-(2-methoxy-5-methylphenyl)-4-methyl-2-trifluoromethylpentyl]-4-methyl-1H-indole-6-carbonitrile | 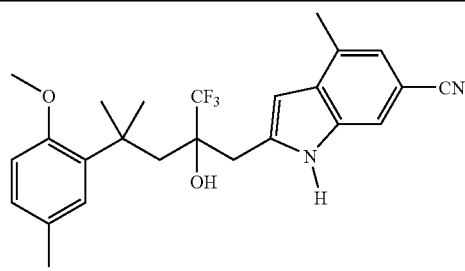 |
| 1,1,1-Trifluoro-4-methyl-2-quinolin-4-ylmethyl-4-o-tolylpentan-2-ol | 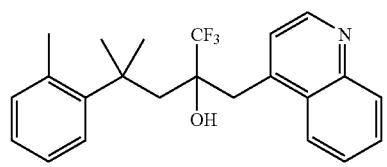 |
| 1,1,1-Trifluoro-4-methyl-2-quinolin-4-ylmethyl-4-m-tolylpentan-2-ol | 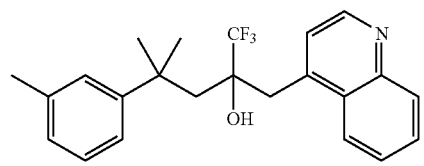 |
| 1,1,1-Trifluoro-4-(2-fluorophenyl)-2-(1H-indol-2-ylmethyl)-4-methylpentan-2-ol | 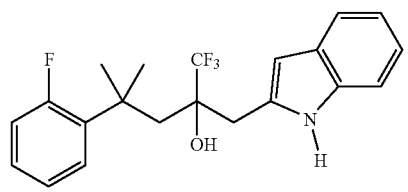 |
| 1,1,1-Trifluoro-4-(2-fluorophenyl)-4-methyl-2-quinolin-4-ylmethylpentan-2-ol | 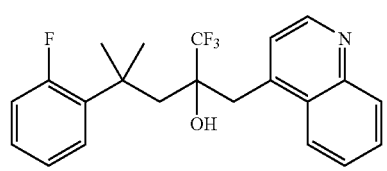 |
| 1,1,1-Trifluoro-4-(3-fluorophenyl)-2-(1H-indol-2-ylmethyl)-4-methylpentan-2-ol | 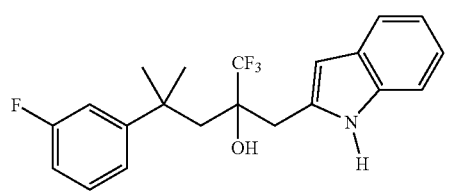 |
| 1,1,1-Trifluoro-4-(3-fluorophenyl)-4-methyl-2-quinolin-4-ylmethylpentan-2-ol | 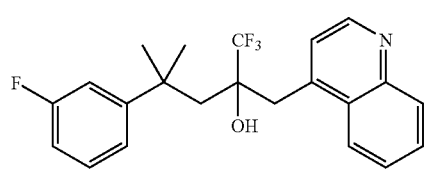 |
| 1,1,1-Trifluoro-4-(4-fluorophenyl)-2-(1H-indol-2-ylmethyl)-4-methylpentan-2-ol | 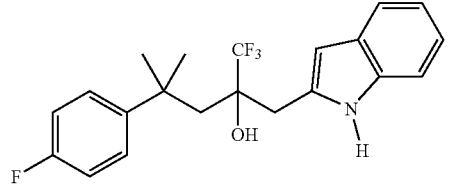 |

-continued

| | IA |
|---|---|
| A | B |

1,1,1-Trifluoro-4-(4-fluorophenyl)-4-methyl-2-quinolin-4-ylmethylpentan-2-ol
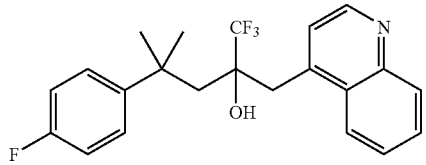 [SMILES: CC(C)(CC(O)(Cc1ccnc2ccccc12)C(F)(F)F)c1ccc(F)cc1]

3-(4,4,4-Trifluoro-3-hydroxy-1,1-dimethyl-3-quinolin-4-ylmethylbutyl)phenol
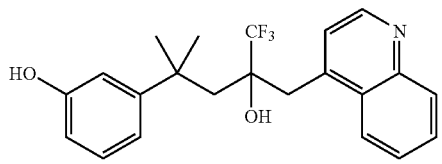 [SMILES: CC(C)(CC(O)(Cc1ccnc2ccccc12)C(F)(F)F)c1cccc(O)c1]

1,1,1-Trifluoro-4-methyl-2-quinolin-4-ylmethyl-4-(2-trifluoromethylphenyl)pentan-2-ol
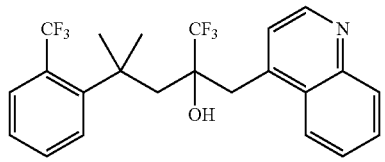 [SMILES: CC(C)(CC(O)(Cc1ccnc2ccccc12)C(F)(F)F)c1ccccc1C(F)(F)F]

1,1,1-Trifluoro-2-(1H-indol-2-ylmethyl)-4-methyl-4-(4-trifluoromethylphenyl)pentan-2-ol
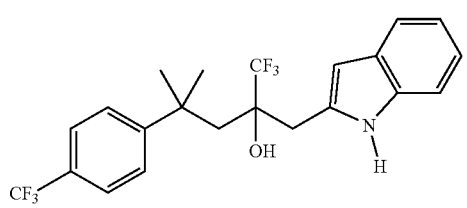 [SMILES: CC(C)(CC(O)(Cc1cc2ccccc2[nH]1)C(F)(F)F)c1ccc(C(F)(F)F)cc1]

1,1,1-Trifluoro-4-methyl-2-quinolin-4-ylmethyl-4-(4-trifluoromethylphenyl)pentan-2-ol
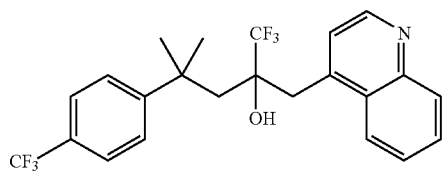 [SMILES: CC(C)(CC(O)(Cc1ccnc2ccccc12)C(F)(F)F)c1ccc(C(F)(F)F)cc1]

4-(3-Chlorophenyl)-1,1,1-trifluoro-2-(1H-indol-2-ylmethyl)-4-methylpentan-2-ol
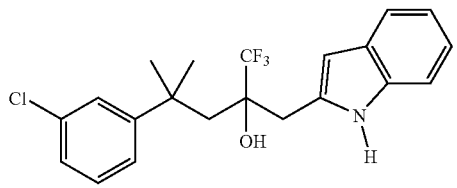 [SMILES: CC(C)(CC(O)(Cc1cc2ccccc2[nH]1)C(F)(F)F)c1cccc(Cl)c1]

4-(3-Chlorophenyl)-1,1,1-trifluoro-4-methyl-2-quinolin-4-ylmethylpentan-2-ol
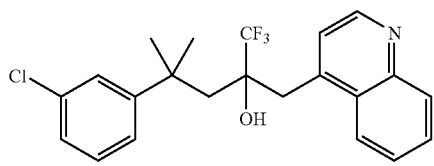 [SMILES: CC(C)(CC(O)(Cc1ccnc2ccccc12)C(F)(F)F)c1cccc(Cl)c1]

4-(4-Dimethylaminophenyl)-1,1,1-trifluoro-2-(1H-indol-2-ylmethyl)-4-methylpentan-2-ol
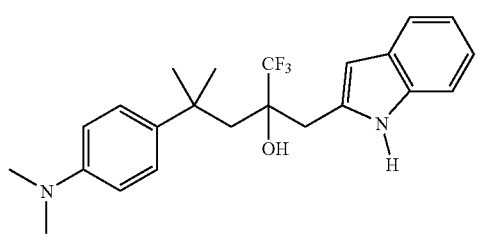 [SMILES: CN(C)c1ccc(C(C)(C)CC(O)(Cc2cc3ccccc3[nH]2)C(F)(F)F)cc1]

| A | B |
|---|---|
| 4-Biphenyl-3-yl-1,1,1-trifluoro-4-methyl-2-quinolin-4-ylmethylpentan-2-ol | 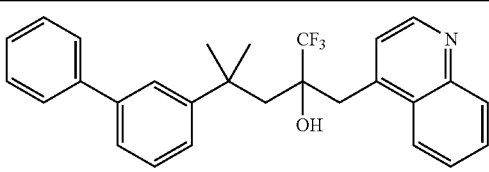 |
| 4-(3-Bromophenyl)-1,1,1-trifluoro-2-(1H-indol-2-ylmethyl)-4-methylpentan-2-ol | 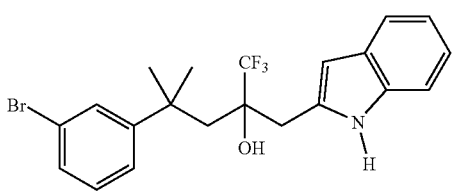 |
| 4-(2-Difluoromethoxy-5-fluorophenyl)-1,1,1-trifluoro-2-(1H-indol-2-ylmethyl)-4-methylpentan-2-ol | 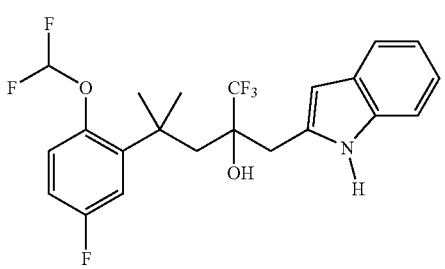 |
| 4-Biphenyl-3-yl-1,1,1-trifluoro-2-(1H-indol-2-ylmethyl)-4-methylpentan-2-ol | 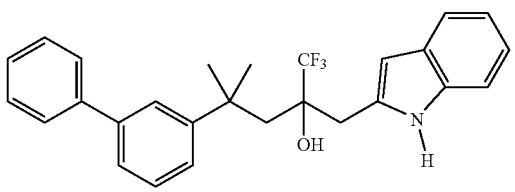 |
| 4-(4-Dimethylaminophenyl)-1,1,1-trifluoro-4-methyl-2-quinolin-4-ylmethylpentan-2-ol | 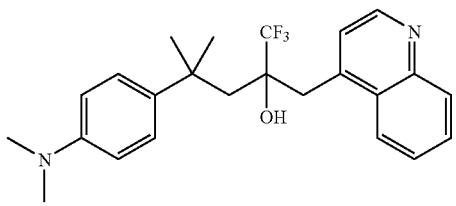 |
| 2-[4-(5-Fluoro-2-methylphenyl)-2-hydroxy-4-methyl-2-trifluoromethylpentyl]-1,6-dihydropyrrolo[2,3-c]pyridin-5-one | 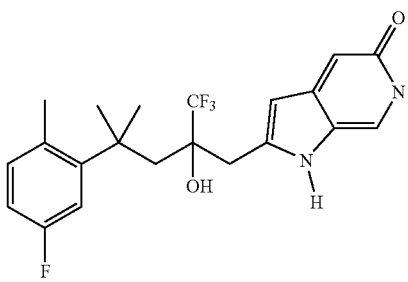 |

| A | B |
|---|---|
| 2-[4-(5-Fluoro-2-methylphenyl)-2-hydroxy-4-methyl-2-trifluoromethylpentyl]-6-methyl-1,6-dihydropyrrolo[2,3-c]pyridin-5-one | 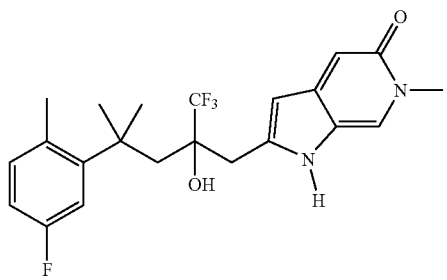 |
| 2-[4-(5-Fluoro-2-methylphenyl)-2-hydroxy-4-methyl-2-trifluoromethylpentyl]-4-methyl-1,4-dihydropyrrolo[3,2-b]pyridin-5-one | 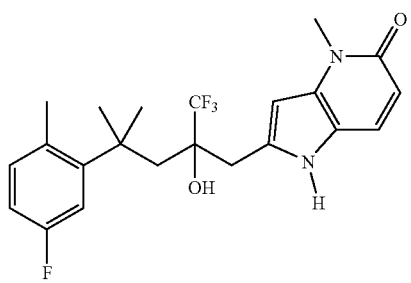 |
| 1,1,1-Trifluoro-4-(5-fluoro-2-methylphenyl)-2-(6-methoxy-1H-pyrrolo[3,2-c]pyridin-2-ylmethyl)-4-methylpentan-2-ol | 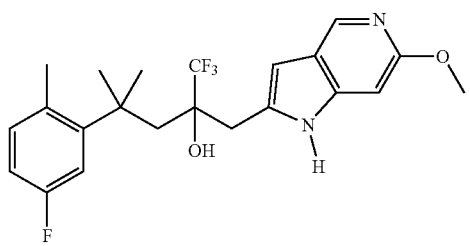 |
| 2-[4-(5-Fluoro-2-methylphenyl)-2-hydroxy-4-methyl-2-trifluoromethylpentyl]-5-methyl-1,5-dihydropyrrolo[3,2-c]pyridin-6-one | 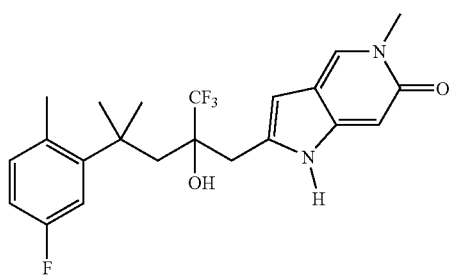 |
| 2-[4-(5-Fluoro-2-methylphenyl)-2-hydroxy-4-methyl-2-trifluoromethylpentyl]-1,3a-dihydropyrrolo[3,2-c]pyridin-6-one | 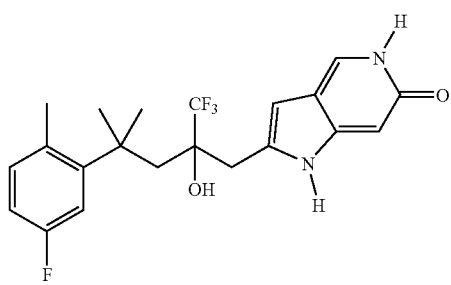 |

|   | IA |
|---|---|
| A | B |
| 2-[4-(5-Fluoro-2-methylphenyl)-2-hydroxy-4-methyl-2-trifluoromethylpentyl]-1,7-dihydropyrrolo[3,2-c]pyridine-4,6-dione | 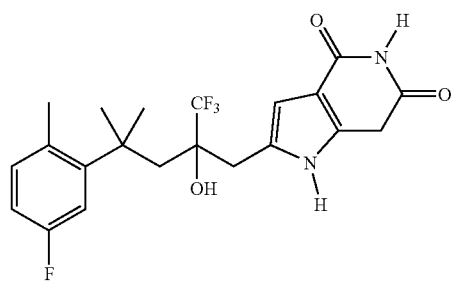 |
| 6-[4-(5-Fluoro-2-methylphenyl)-2-hydroxy-4-methyl-2-trifluoromethylpentyl]-3-methyl-1,7-dihydropyrrolo[2,3-d]pyrimidine-2,4-dione | 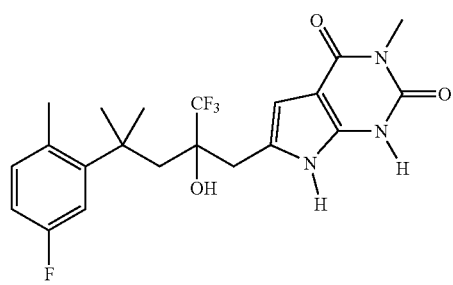 |
| 2-[4-(5-Chloro-2,3-dihydrobenzofuran-7-yl)-2-hydroxy-4-methyl-2-trifluoromethylpentyl]-1,6-dihydropyrrolo[2,3-c]pyridin-5-one | 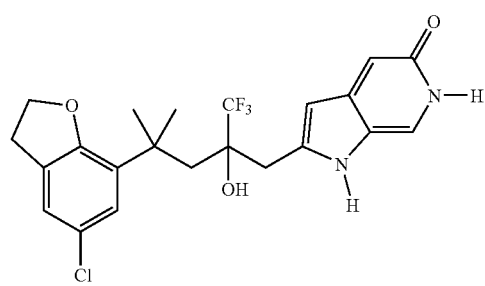 |
| 2-[4-(5-Chloro-2,3-dihydrobenzofuran-7-yl)-2-hydroxy-4-methyl-2-trifluoromethylpentyl]-6-methyl-1,6-dihydropyrrolo[2,3-c]pyridin-5-one | 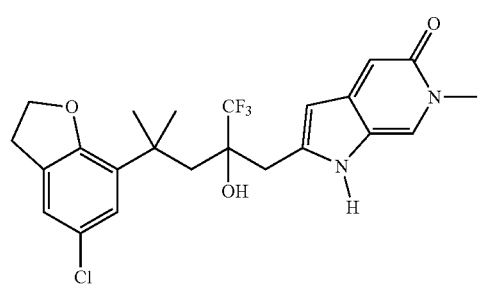 |
| 2-[4-(5-Chloro-2,3-dihydrobenzofuran-7-yl)-2-hydroxy-4-methyl-2-trifluoromethylpentyl]-1,4-dihydropyrrolo[3,2-b]pyridin-5-one | 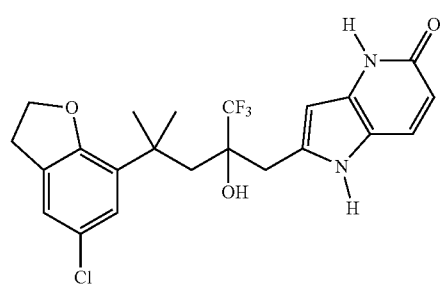 |

-continued

IA

| A | B |
|---|---|
| 2-[4-(5-Chloro-2,3-dihydrobenzofuran-7-yl)-2-hydroxy-4-methyl-2-trifluoromethylpentyl]-4-methyl-1,4-dihydropyrrolo[3,2-b]pyridin-5-one | 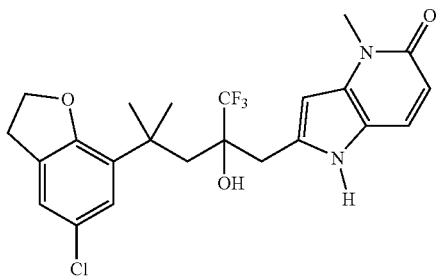 |
| 2-[4-(5-Chloro-2,3-dihydrobenzofuran-7-yl)-2-hydroxy-4-methyl-2-trifluoromethylpentyl]-1,5-dihydropyrrolo[3,2-c]pyridin-6-one | 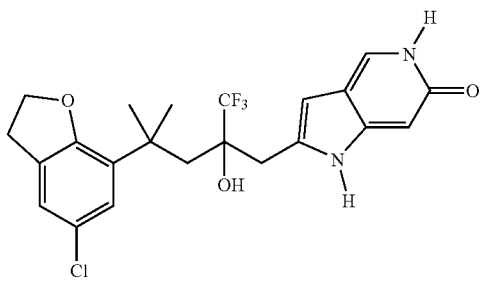 |
| 2-[4-(5-Chloro-2,3-dihydrobenzofuran-7-yl)-2-hydroxy-4-methyl-2-trifluoromethylpentyl]-5-methyl-1,5-dihydropyrrolo[3,2-c]pyridin-6-one | 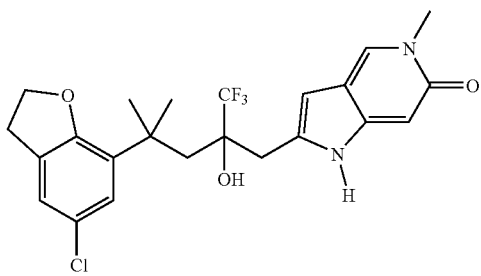 |
| 4-(5-Chloro-2,3-dihydrobenzofuran-7-yl)-1,1,1-trifluoro-2-(6-methoxy-5,6-dihydro-1H-pyrrolo[3,2-c]pyridin-2-ylmethyl)-4-methylpentan-2-ol | 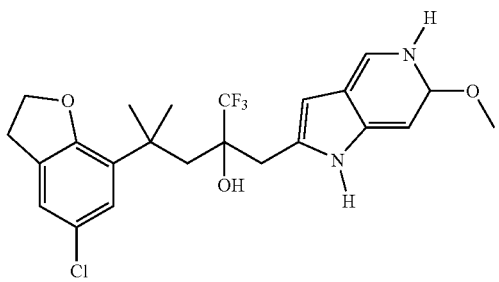 |
| 2-[4-(5-Chloro-2,3-dihydrobenzofuran-7-yl)-2-hydroxy-4-methyl-2-trifluoromethylpentyl]-1,7-dihydropyrrolo[3,2-c]pyridine-4,6-dione | 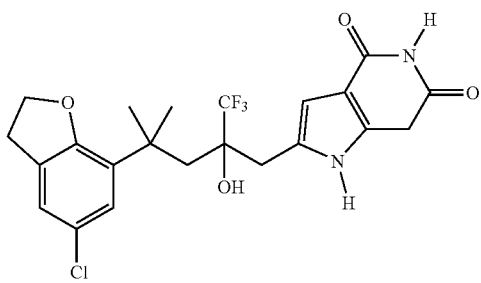 |

| | IA | |
|---|---|---|
| A | | B |
| 6-[4-(5-Chloro-2,3-dihydrobenzofuran-7-yl)-2-hydroxy-4-methyl-2-trifluoromethylpentyl]-3-methyl-1,7-dihydropyrrolo[2,3-d]pyrimidine-2,4-dione | | 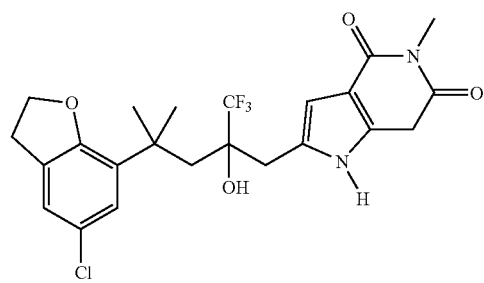 |
| 2-[4-(3-Dimethylaminomethylphenyl)-2-hydroxy-4-methyl-2-trifluoromethylpentyl]-1H-indole-5-carbonitrile | | 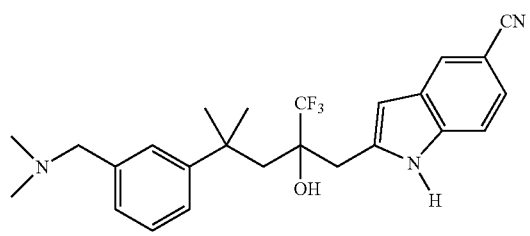 |
| 1,1,1-Trifluoro-2-(1H-indol-2-ylmethyl)-4-methyl-4-(3-morpholin-4-ylmethylphenyl)pentan-2-ol | | 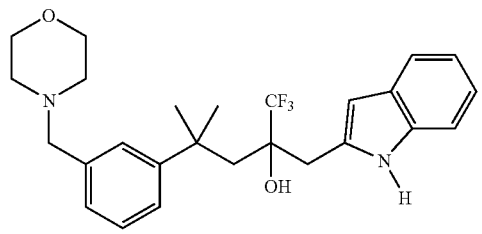 |
| 1,1,1-Trifluoro-4-methyl-4-(3-morpholin-4-ylmethylphenyl)-2-(1H-pyrrolo[2,3-d]pyridazin-2-ylmethyl)pentan-2-ol | | 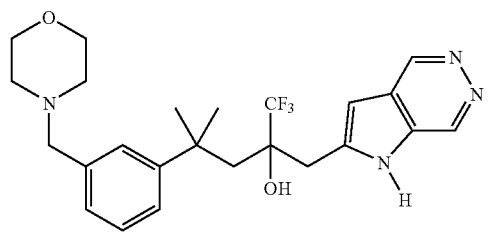 |
| 1,1,1-Trifluoro-4-(5-fluoro-2-ethylphenyl)-4-methyl-2-(5-morpholin-4-ylmethyl-1H-indol-2-ylmethyl)pentan-2-ol | | 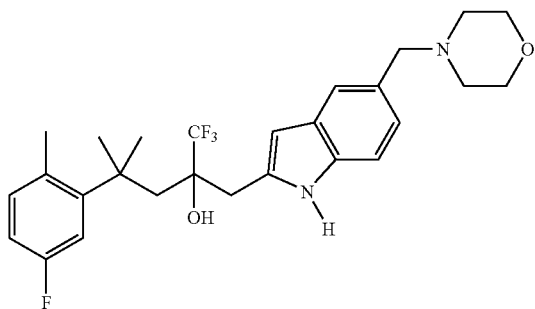 |

IA

| A | B |
|---|---|
| 1,1,1-Trifluoro-4-(5-fluoro-2-methylphenyl)-4-methyl-2-(5-morpholin-4-ylmethyl-1H-pyrrolo[2,3-c]pyridin-2-ylmethyl)pentan-2-ol | 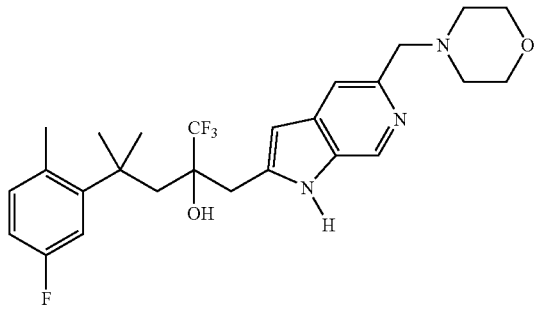 |
| {2-[4-(5-Fluoro-2-methylphenyl)-2-hydroxy-4-methyl-2-trifluoromethylpentyl]-1H-indol-5-yl}phenylmethanone | 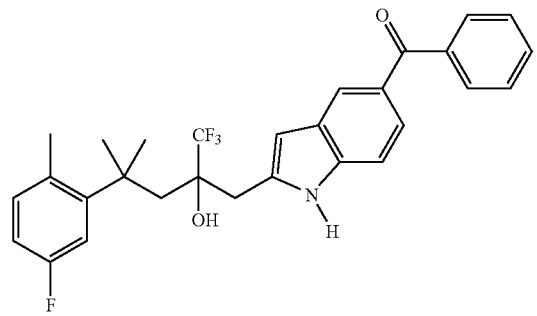 |
| {2-[4-(5-Fluoro-2-methylphenyl)-2-hydroxy-4-methyl-2-trifluoromethylpentyl]-1H-pyrrolo[2,3-c]pyridin-5-yl}phenylmethanone | 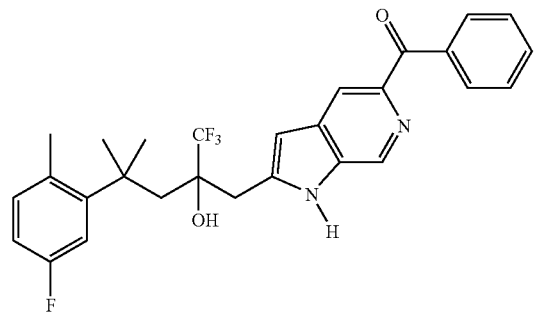 |
| {2-[4-(5-Fluoro-2-methylphenyl)-2-hydroxy-4-methyl-2-trifluoromethylpentyl]-1H-indol-5-yl}furan-2-ylmethanone | 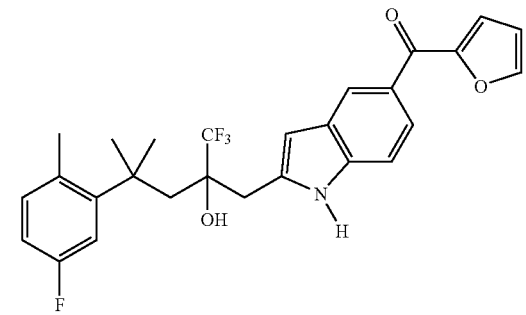 |

-continued

IA

| A | B |
|---|---|
| {2-[4-(5-Fluoro-2-methylphenyl)-2-hydroxy-4-methyl-2-trifluoromethylpentyl]-1H-pyrrolo[2,3-c]pyridin-5-yl}furan-2-ylmethanone | 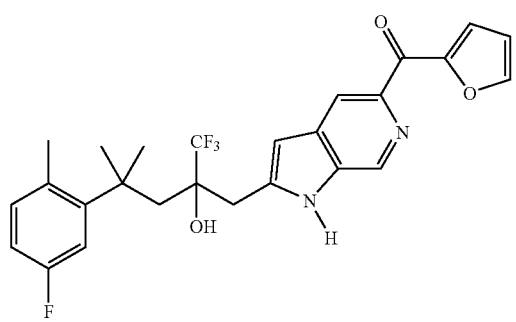 |
| 1,1,1-Trifluoro-2-(1H-indol-2-ylmethyl)-4-methyl-4-pyridin-2-ylpentan-2-ol | 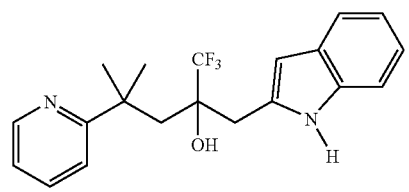 |
| 1,1,1-Trifluoro-4-methyl-4-pyridin-4-yl-2-quinolin-4-ylmethylpentan-2-ol | 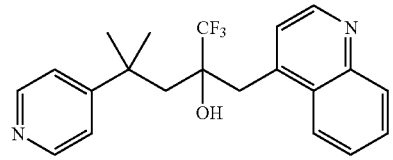 |
| 2-(2,6-Dimethylpyridin-4-ylmethyl)-1,1,1-trifluoro-4-(5-fluoro-2-methoxyphenyl)-4-methylpentan-2-ol | 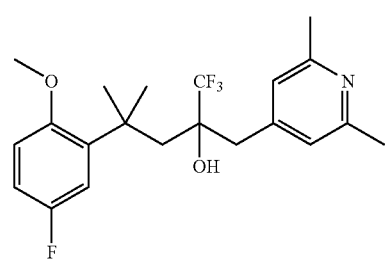 |
| 2-[3-(2,6-Dimethylpyridin-4-ylmethyl)-4,4,4-trifluoro-3-hydroxy-1,1-dimethylbutyl]-4-fluorophenol | 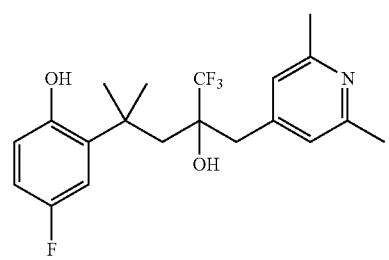 |
| 1,1,1-Trifluoro-4,4-dimethyl-5-phenyl-2-quinolin-4-ylmethylpentan-2-ol | 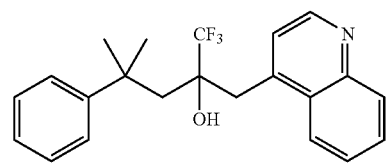 |

-continued

IA

| A | B |
|---|---|
| 1,1,1-Trifluoro-4-(5-fluoro-2-methoxyphenyl)-4-methyl-2-pyridin-4-ylmethylpentan-2-ol | 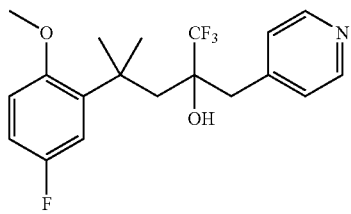 |
| 4-Fluoro-2-[4,4,4-trifluoro-3-(2-fluoropyridin-4-ylmethyl)-3-hydroxy-1,1-dimethylbutyl]phenol | 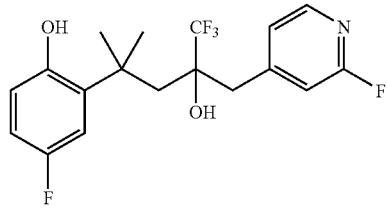 |
| 2-[3-(2-Bromopyridin-4-ylmethyl)-4,4,4-trifluoro-3-hydroxy-1,1-dimethylbutyl]-4-fluorophenol | 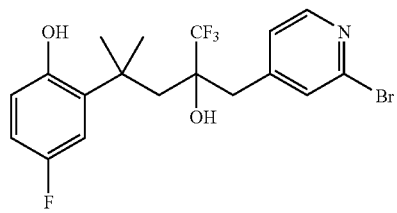 |
| 2-(6,8-Dimethylquinolin-4-ylmethyl)-1,1,1-trifluoro-4-(5-fluoro-2-methoxyphenyl)-4-methylpentan-2-ol | 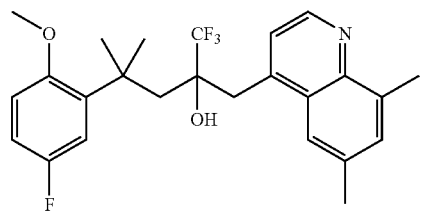 |
| 4-[4-(5-Fluoro-2-methoxyphenyl)-2-hydroxy-4-methyl-2-trifluoromethylpentyl]pyridine-2-carbonitrile | 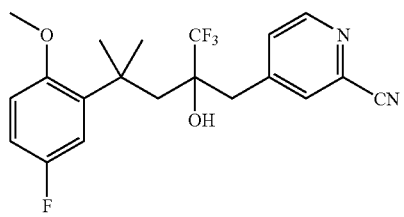 |
| 2,6-Dichloro-4-[4-(5-fluoro-2-methoxyphenyl)-2-hydroxy-4-methyl-2-trifluoromethylpentyl]nicotinonitrile | 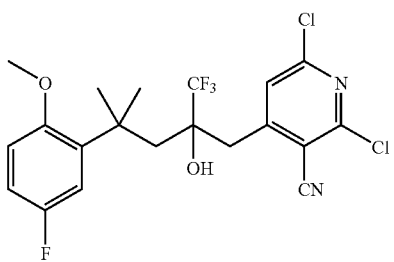 |

-continued

IA

| A | B |
|---|---|
| 4-[4-(5-Fluoro-2-methoxyphenyl)-2-hydroxy-4-methyl-2-trifluoromethylpentyl]quinolin-2-ol | 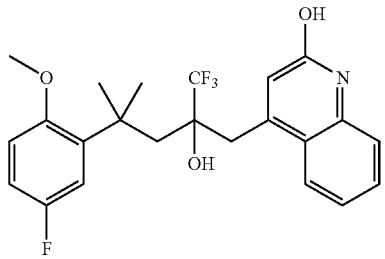 |
| 2,6-Dichloro-4-[4-(5-fluoro-2-hydroxyphenyl)-2-hydroxy-4-methyl-2-trifluoromethylpentyl]nicotinonitrile | 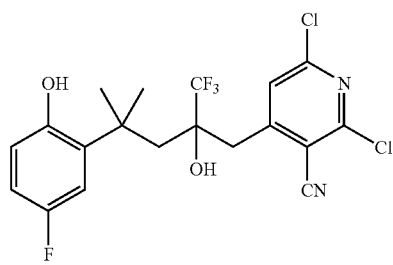 |
| 2-(2-Chloro-8-methylquinolin-4-ylmethyl)-1,1,1-trifluoro-4-(5-fluoro-2-methoxyphenyl)-4-methylpentan-2-ol | 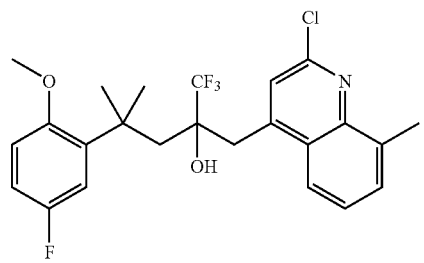 |
| 2-(2,6-Dichloroquinolin-4-ylmethyl)-1,1,1-trifluoro-4-(5-fluoro-2-methoxyphenyl)-4-methylpentan-2-ol | 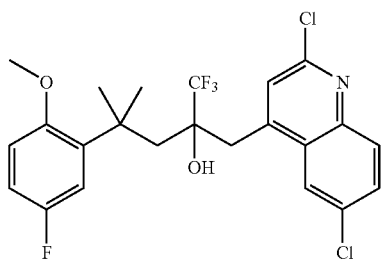 |
| 2-[3-(2-Chloro-8-methylquinolin-4-ylmethyl)-4,4,4-trifluoro-3-hydroxy-1,1-dimethylbutyl]-4-fluorophenol | 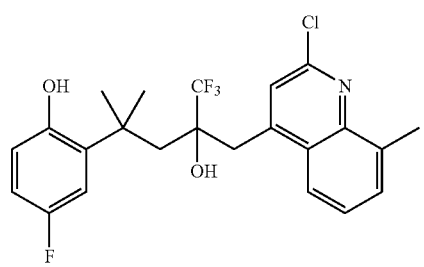 |

-continued

IA

| A | B |
|---|---|
| 2-[3-(2,6-Dichloroquinolin-4-ylmethyl)-4,4,4-trifluoro-3-hydroxy-1,1-dimethylbutyl]-4-fluorophenol | 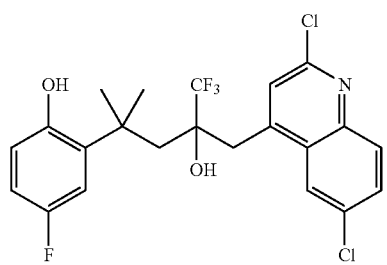 |
| 4-(2,3-Dihydrobenzofuran-7-yl)-2-(2,6-dimethylpyridin-4-ylmethyl)-1,1,1-trifluoro-4-methylpentan-2-ol | 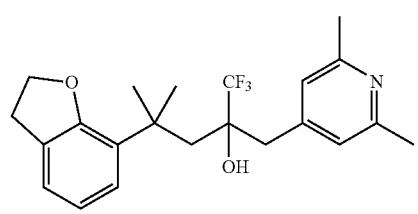 |
| 2-(2,6-Dimethylpyridin-4-ylmethyl)-1,1,1-trifluoro-4-(3-fluorophenyl)-4-methylpentan-2-ol | 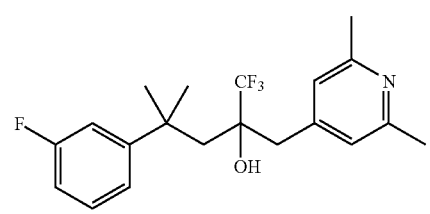 |
| 2-(2,6-Dimethylpyridin-4-ylmethyl)-1,1,1-trifluoro-4-(4-fluorophenyl)-4-methylpentan-2-ol | 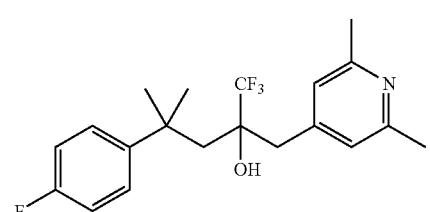 |
| 1,1,1-Trifluoro-4-(5-fluoro-2-methylphenyl)-4-methyl-2-quinolin-4-ylmethylpentan-2-ol | 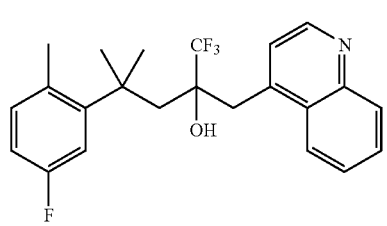 |
| 2-(2,6-Dimethylpyridin-4-ylmethyl)-1,1,1-trifluoro-4-(5-fluoro-2-methylphenyl)-4-methylpentan-2-ol | 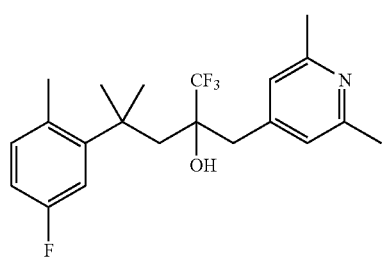 |

IA

| A | B |
|---|---|
| 2-(2,6-Dimethylpyridin-4-ylmethyl)-1,1,1-trifluoro-4-methyl-4-m-tolylpentan-2-ol | 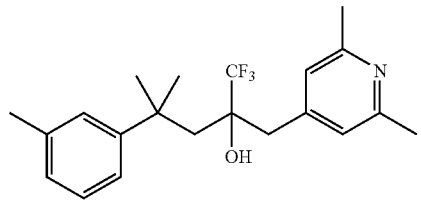 |
| 1,1,1-Trifluoro-4-(5-fluoro-2-methoxyphenyl)-4-methyl-2-(2-methylquinolin-4-ylmethyl)pentan-2-ol | 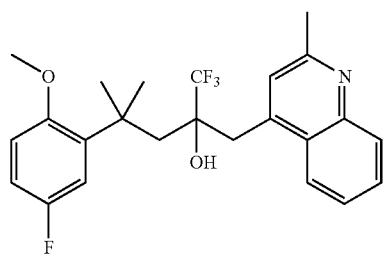 |
| 4-Fluoro-2-(4,4,4-trifluoro-3-hydroxy-1,1-dimethyl-3-quinolin-4-ylmethylbutyl)phenol | 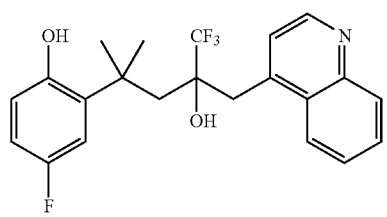 |
| 4-Fluoro-2-[4,4,4-trifluoro-3-hydroxy-1,1-dimethyl-3-(2-methylquinolin-4-ylmethyl)butyl]phenol | 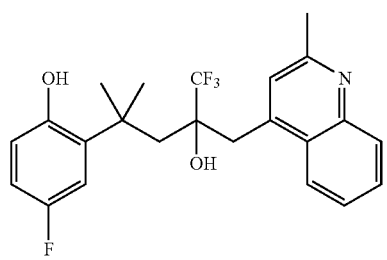 |
| 2-(2,6-Dimethylpyridin-4-ylmethyl)-1,1,1-trifluoro-4-(4-fluoro-2-methoxyphenyl)-4-methylpentan-2-ol | 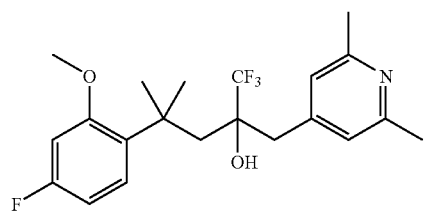 |
| 1,1,1-Trifluoro-4-(5-fluoro-2-methoxyphenyl)-4-methyl-2-(7-methylquinolin-4-ylmethyl)pentan-2-ol | 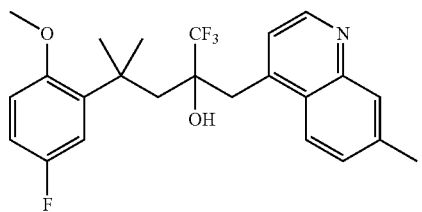 |

-continued

IA

| A | B |
|---|---|
| 2-[3-(2,6-Dimethylpyridin-4-ylmethyl)-4,4,4-trifluoro-3-hydroxy-1,1-dimethylbutyl]-5-fluorophenol | 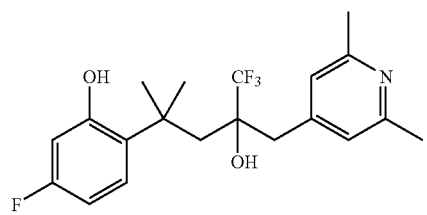 |
| 2-(5,7-Dimethylquinolin-4-ylmethyl)-1,1,1-trifluoro-4-(5-fluoro-2-methoxyphenyl)-4-methylpentan-2-ol | 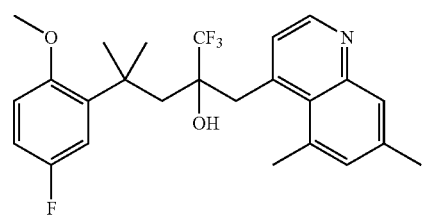 |
| 1,1,1-Trifluoro-4-(4-fluorophenyl)-4-methyl-2-(2-methylquinolin-4-ylmethyl)pentan-2-ol | 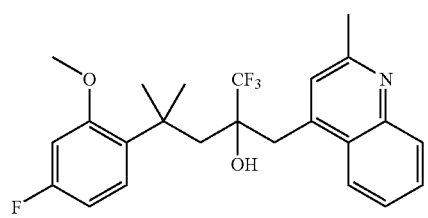 |
| 1,1,1-Trifluoro-4-(3-fluorophenyl)-4-methyl-2-(3-methyl-1H-indol-2-ylmethyl)pentan-2-ol | 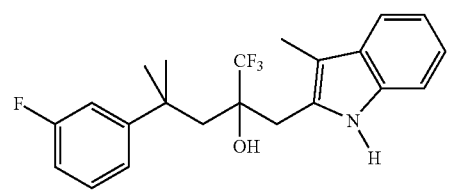 |
| 1,1,1-Trifluoro-2-(1H-indol-2-ylmethyl)-4-methyl-4-(2-trifluoromethylphenyl)pentan-2-ol | 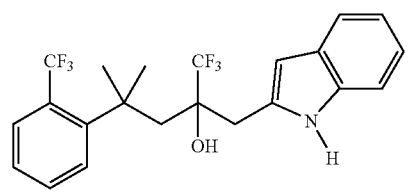 |
| 1,1,1-Trifluoro-4-(5-fluoro-2-methoxyphenyl)-2-(7-fluoro-4-methylquinolin-8-yl)-4-methylpentan-2-ol | 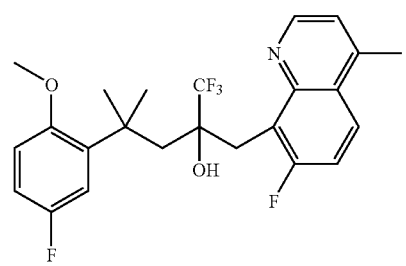 |
| 4-(2,6-Dimethylphenyl)-1,1,1-trifluoro-2-(1H-indol-2-ylmethyl)-4-methylpentan-2-ol | 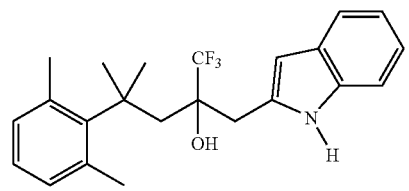 |

-continued

IA

| A | B |
|---|---|
| 2-(3-Bromo-1H-indol-2-ylmethyl)-1,1,1-trifluoro-4-(3-fluorophenyl)-4-methylpentan-2-ol | 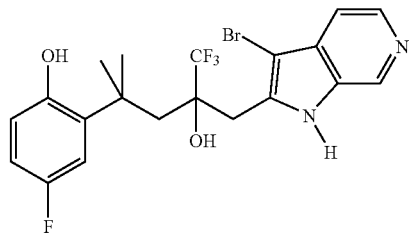 |
| 4-(3,4-Dimethylphenyl)-1,1,1-trifluoro-2-(1H-indol-2-ylmethyl)-4-.methylpentan-2-ol | 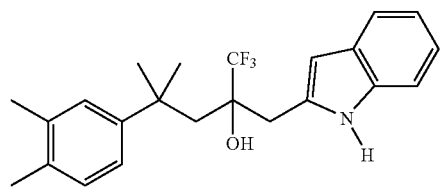 |
| 1,1,1-Trifluoro-4-(3-fluoro-4-methylphenyl)-2-(1H-indol-2-ylmethyl)-4-methylpentan-2-ol | 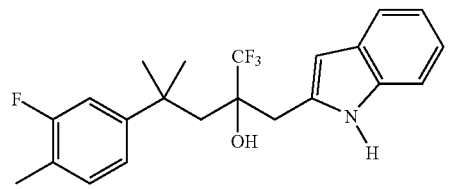 |
| 1,1,1-Trifluoro-4-(4-fluoro-3-methylphenyl)-2-(1H-indol-2-ylmethyl)-4-methylpentan-2-ol | 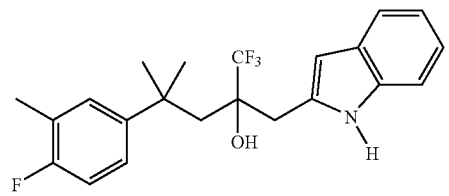 |
| 1,1,1-Trifluoro-4-(3-fluoro-4-methylphenyl)-4-methyl-2-quinolin-4-ylmethylpentan-2-ol | 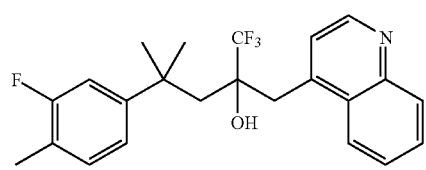 |
| 1,1,1-Trifluoro-4-(4-fluoro-2-methylphenyl)-4-methyl-2-quinolin-4-ylmethylpentan-2-ol | 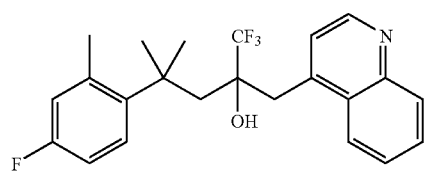 |
| 4-(3,4-Dimethylphenyl)-1,1,1-trifluoro-4-methyl-2-quinolin-4-ylmethylpentan-2-ol | 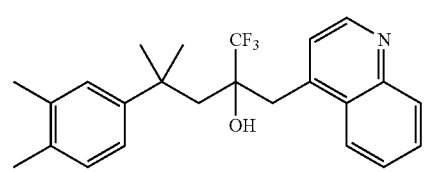 |

-continued

| IA | |
|---|---|
| A | B |
| 4-(2,5-Dimethylphenyl)-1,1,1-trifluoro-2-(1H-indol-2-ylmethyl)-4-methylpentan-2-ol | 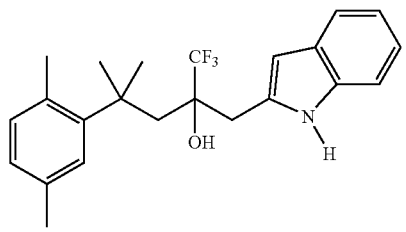 |
| 1,1,1-Trifluoro-2-(1H-indol-2-ylmethyl)-4-(2-methoxy-5-methylphenyl)-4-methylpentan-2-ol | 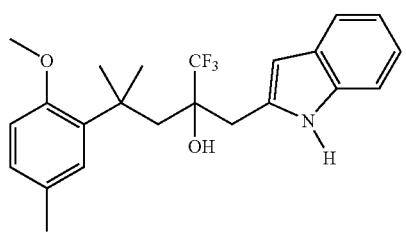 |
| 4-Methyl-2-[4,4,4-trifluoro-3-hydroxy-3-(1H-indol-2-ylmethyl)-1,1-dimethylbutyl]phenol | 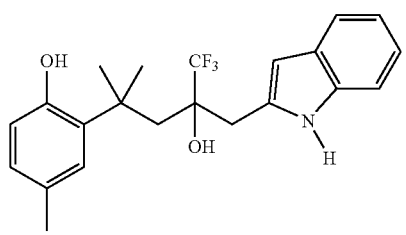 |
| 4-(2,5-Dimethylphenyl)-1,1,1-trifluoro-4-methyl-2-quinolin-4-ylmethylpentan-2-ol | 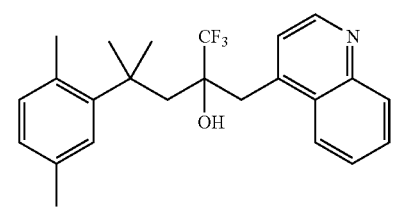 |
| 1,1,1-Trifluoro-4-(2-methoxy-5-methylphenyl)-4-methyl-2-quinolin-4-ylmethylpentan-2-ol | 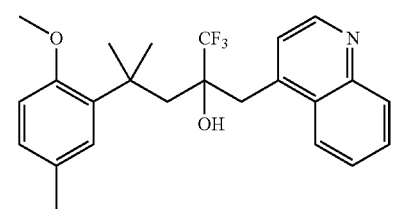 |
| 4-(2,5-Dimethoxyphenyl)-1,1,1-trifluoro-4-methyl-2-(1H-pyrrolo[2,3-c]pyridin-2-ylmethyl)pentan-2-ol | 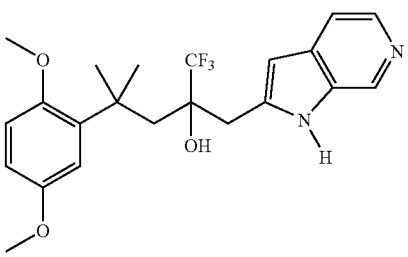 |

-continued

IA

| A | B |
|---|---|
| 1,1,1-Trifluoro-4-(5-fluoro-2-methoxyphenyl)-4-methyl-2-(7H-pyrrolo[2,3-d]pyrimidin-6-ylmethyl)pentan-2-ol | 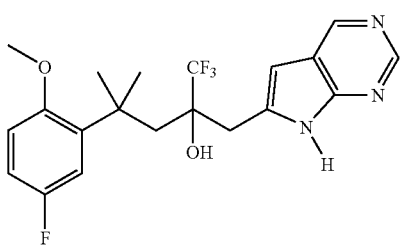 |
| 1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol | 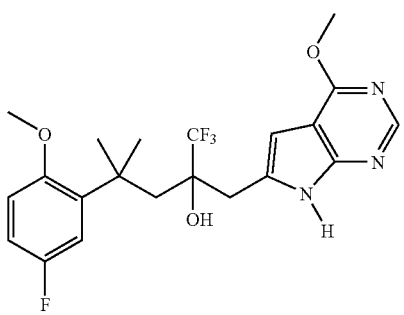 |
| 2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol | 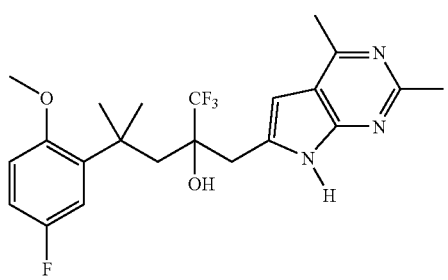 |
| 2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol | 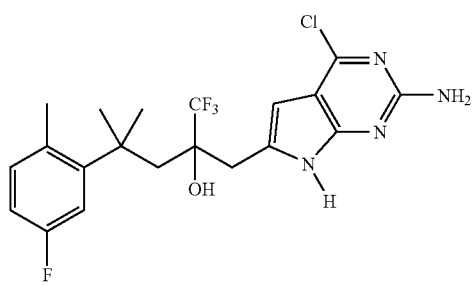 |
| 2-(2,4-Dimethyl-7H-pyrrolo[2,3-d]pyrimidin-6-ylmethyl)-1,1,1-trifluoro-4-(5-fluoro-2-methylphenyl)-4-methylpentan-2-ol | 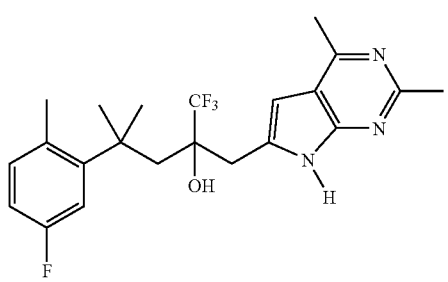 |

-continued

IA

| A | B |
|---|---|
| 2-(5-Chloro-1H-pyrrolo[2,3-c]pyridin-2-ylmethyl)-1,1,1-trifluoro-4-(5-fluoro-2-methylphenyl)-4-methylpentan-2-ol | 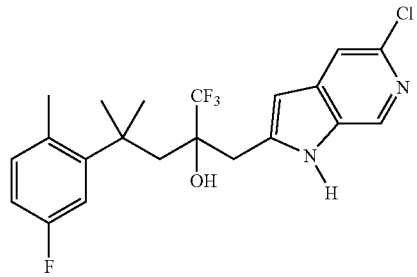 |
| 4-(5-Bromo-2-methoxyphenyl)-1,1,1-trifluoro-4-methyl-2-(5-piperidin-1-yl-1H-pyrrolo[2,3-c]pyridin-2-ylmethyl)pentan-2-ol | 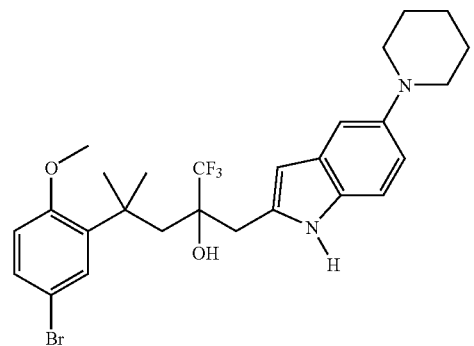 |
| 1,1,1-Trifluoro-4-(5-fluoro-2-methoxyphenyl)-4-methyl-2-(5-morpholin-4-yl-1H-pyrrolo[2,3-c]pyridin-2-ylmethyl)pentan-2-ol | 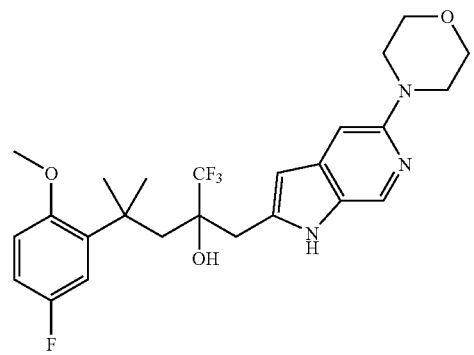 |
| 4-(5-Bromo-2-methoxyphenyl)-1,1,1-trifluoro-4-methyl-2-(5-morpholin-4-yl-1H-pyrrolo[2,3-c]pyridin-2-ylmethyl)pentan-2-ol | 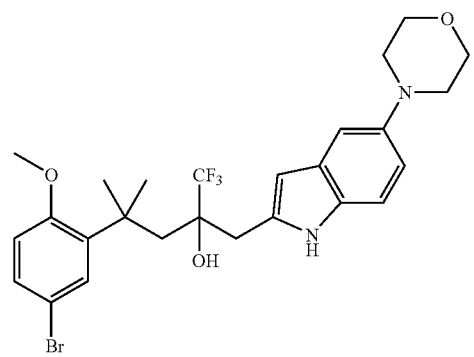 |

| A | B |
|---|---|
| 1,1,1-Trifluoro-4-(5-fluoro-2-methylphenyl)-4-methyl-2-(5-morpholin-4-yl-1H-pyrrolo[2,3-c]pyridin-2-ylmethyl)pentan-2-ol | 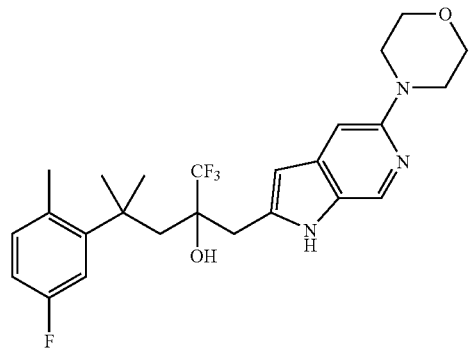 |
| 2-(5-Dimethylamino-1H-pyrrolo[2,3-c]pyridin-2-ylmethyl)-1,1,1-trifluoro-4-(5-methanesulfonyl-2,3-dihydrobenzofuran-7-yl)-4-methylpentan-2-ol | 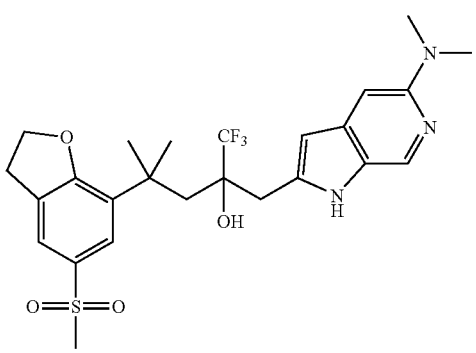 |
| 1,1,1-Trifluoro-4-(5-methanesulfonyl-2,3-dihydrobenzofuran-7-yl)-4-methyl-2-(5-piperidin-1-yl-1H-pyrrolo[2,3-c]pyridin-2-ylmethyl)pentan-2-ol | 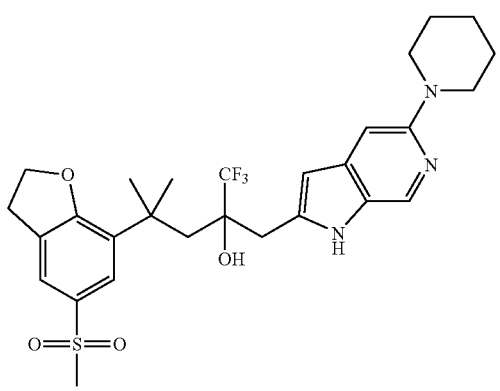 |
| 2-(5-Dimethylamino-1H-pyrrolo[2,3-c]pyridin-2-ylmethyl)-1,1,1-trifluoro-4-(5-fluoro-2-methylphenyl)-4-methylpentan-2-ol | 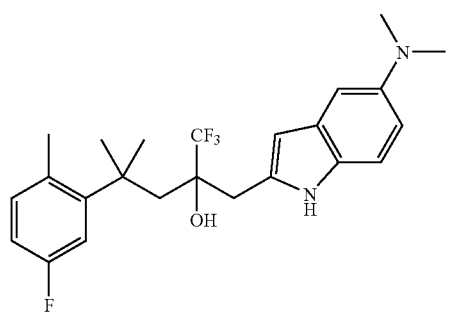 |

-continued

| IA | |
|---|---|
| A | B |

2-[5-(Ethylmethylamino)-1H-pyrrolo[2,3-c]pyridin-2-ylmethyl]-1,1,1-trifluoro-4-(5-fluoro-2-methylphenyl)-4-methylpentan-2-ol

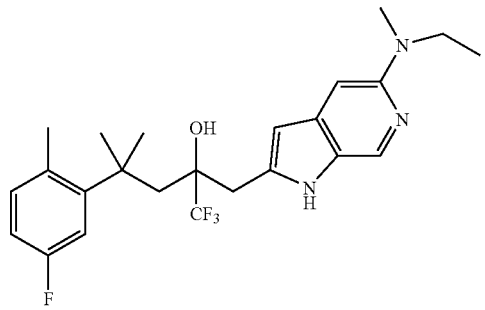 [SMILES: CCN(C)c1cc2cc(CC(O)(CC(C)(C)c3cc(F)ccc3C)C(F)(F)F)[nH]c2cn1]

4-(5-Chloro-2,3-dihydrobenzofuran-7-yl)-2-[5-(ethylmethylamino)-1H-pyrrolo[2,3-c]pyridin-2-ylmethyl]-1,1,1-trifluoro-4-methylpentan-2-ol

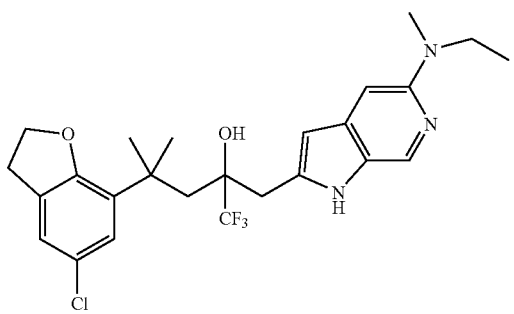 [SMILES: CCN(C)c1cc2cc(CC(O)(CC(C)(C)c3cc(Cl)cc4c3OCC4)C(F)(F)F)[nH]c2cn1]

2-[5-(Ethylmethylamino)-1H-pyrrolo[2,3-c]pyridin-2-ylmethyl]-1,1,1-trifluoro-4-(5-fluoro-2-methoxyphenyl)-4-methylpentan-2-ol

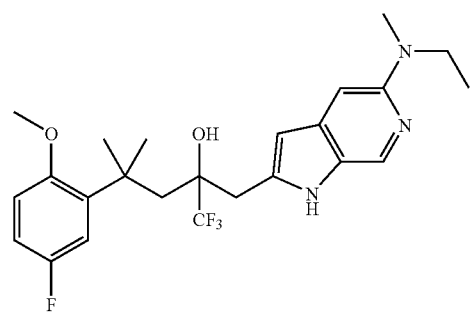 [SMILES: CCN(C)c1cc2cc(CC(O)(CC(C)(C)c3cc(F)ccc3OC)C(F)(F)F)[nH]c2cn1]

1,1,1-Trifluoro-4-methyl-2-(5-morpholin-4-yl-1H-pyrrolo[2,3-c]pyridin-2-ylmethyl)-4-phenylpentan-2-ol

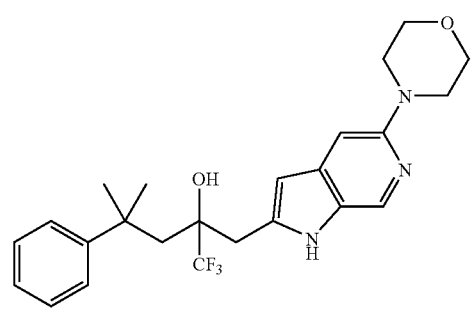 [SMILES: CC(C)(CC(O)(Cc1cc2cc(N3CCOCC3)ncc2[nH]1)C(F)(F)F)c1ccccc1]

1,1,1-Trifluoro-4-(3-fluorophenyl)-4-methyl-2-(5-morpholin-4-yl-1H-pyrrolo[2,3-c]pyridin-2-ylmethyl)pentan-2-ol

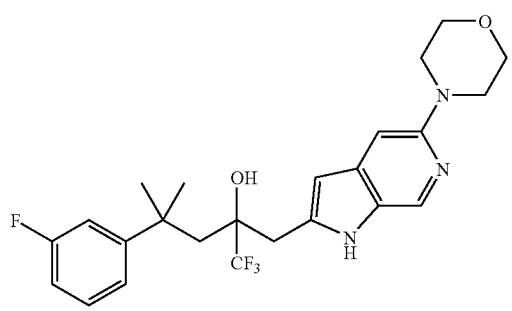 [SMILES: CC(C)(CC(O)(Cc1cc2cc(N3CCOCC3)ncc2[nH]1)C(F)(F)F)c1cccc(F)c1]

-continued

IA

| A | B |
|---|---|
| 1,1,1-Trifluoro-4-(5-fluoro-2-methylphenyl)-4-methyl-2-(5-pyrrolidin-1-yl-1H-pyrrolo[2,3-c]pyridin-2-ylmethyl)pentan-2-ol | 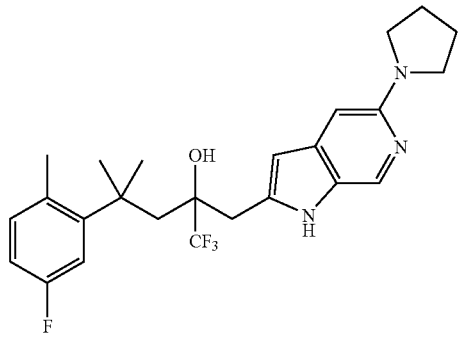 |
| 1,1,1-Trifluoro-4-methyl-4-phenyl-2-(5-pyrrolidin-1-yl-1H-pyrrolo[2,3-c]pyridin-2-ylmethyl)pentan-2-ol | 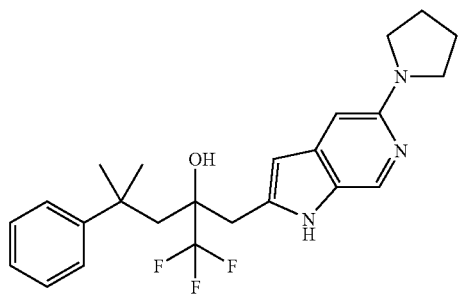 |
| 4'-Methoxy-3'-[4,4,4-trifluoro-3-hydroxy-1,1-dimethyl-3-(5-morpholin-4-yl-1H-pyrrolo[2,3-c]pyridin-2-ylmethyl)butyl]biphenyl-2-carbonitrile | 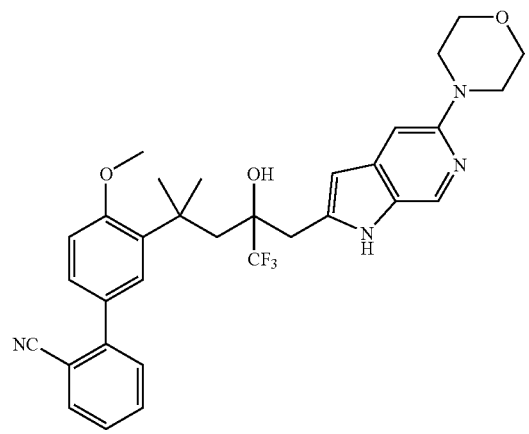 |
| 2-(5-Diethylamino-1H-pyrrolo[2,3-c]pyridin-2-ylmethyl)-1,1,1-trifluoro-4-(5-fluoro-2-methylphenyl)-4-methylpentan-2-ol | 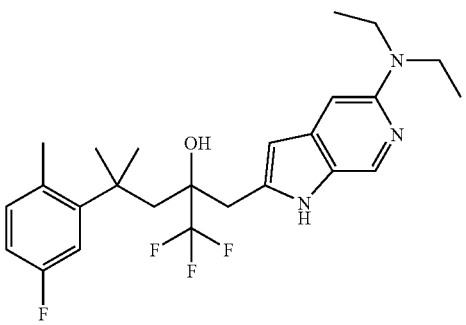 |

-continued

| IA | |
|---|---|
| A | B |
| 1,1,1-Trifluoro-4-(5-fluoro-2-methylphenyl)-2-[5-(isopropylmethylamino)-1H-pyrrolo[2,3-c]pyridin-2-ylmethyl]-4-methylpentan-2-ol | 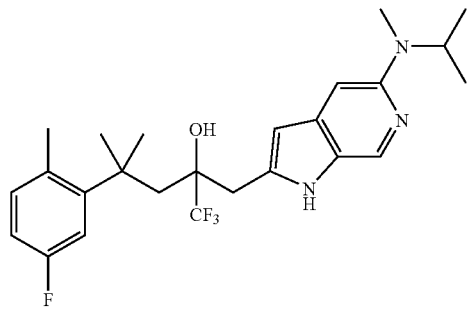 |
| 1,1,1-Trifluoro-2-[5-(isopropylmethylamino)-1H-pyrrolo[2,3-c]pyridin-2-ylmethyl]-4-methyl-4-phenylpentan-2-ol | 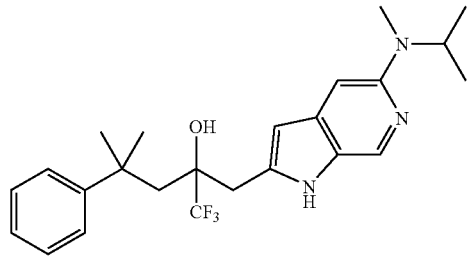 |
| 2-(5-Diethylamino-1H-pyrrolo[2,3-c]pyridin-2-ylmethyl)-1,1,1-trifluoro-4-methyl-4-phenylpentan-2-ol | 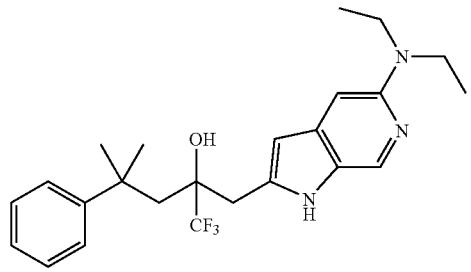 |
| 4-(3-Bromophenyl)-1,1,1-trifluoro-4-methyl-2-(5-morpholin-4-yl-1H-pyrrolo[2,3-c]pyridin-2-ylmethyl)pentan-2-ol | 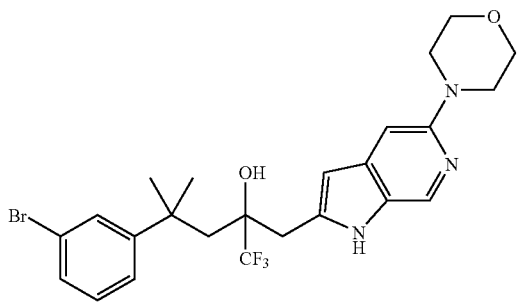 |
| 1,1,1-Trifluoro-4-(4-fluorophenyl)-4-methyl-2-(5-morpholin-4-yl-1H-pyrrolo[2,3-c]pyridin-2-ylmethyl)pentan-2-ol | 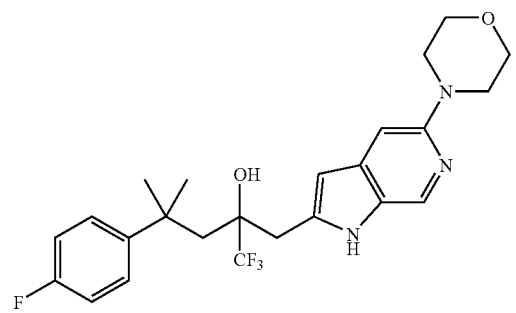 |

-continued

IA

| A | B |
|---|---|
| 1,1,1-Trifluoro-4-(4-fluorophenyl)-4-methyl-2-(5-pyrrolidin-1-yl-1H-pyrrolo[2,3-c]pyridin-2-ylmethyl)pentan-2-ol | 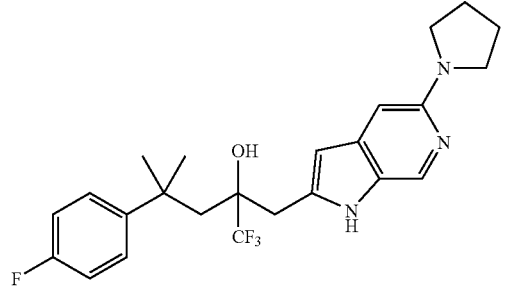 |
| 1,1,1-Trifluoro-4-methyl-2-(5-morpholin-4-yl-1H-pyrrolo[2,3-c]pyridin-2-ylmethyl)-4-(3-pyrimidin-5-ylphenyl)pentan-2-ol | 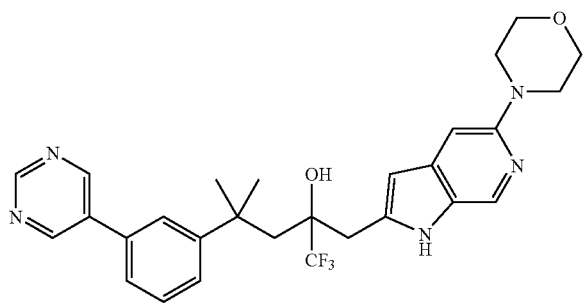 |
| 2-[5-(2,6-Dimethylmorpholin-4-yl)-1H-pyrrolo[2,3-c]pyridin-2-ylmethyl]-1,1,1-trifluoro-4-(5-fluoro-2-methylphenyl)-4-methylpentan-2-ol | 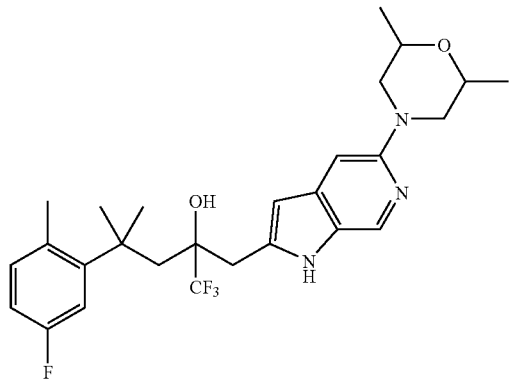 |
| 2-[5-(Ethylmethylamino)-1H-pyrrolo[2,3-c]pyridin-2-ylmethyl]-1,1,1-trifluoro-4-methyl-4-phenylpentan-2-ol | 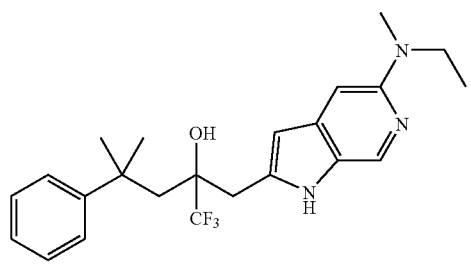 |
| 2-[5-(Ethylmethylamino)-1H-pyrrolo[2,3-c]pyridin-2-ylmethyl]-1,1,1-trifluoro-4-(3-fluorophenyl)-4-methylpentan-2-ol | 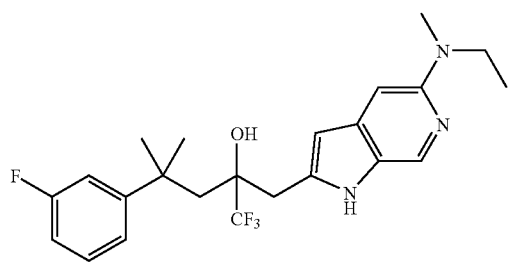 |

-continued

IA

| A | B |
|---|---|
| 1,1,1-Trifluoro-4-(3-fluorophenyl)-4-methyl-2-(5-pyrrolidin-1-yl-1H-pyrrolo[2,3-c]pyridin-2-ylmethyl)pentan-2-ol | 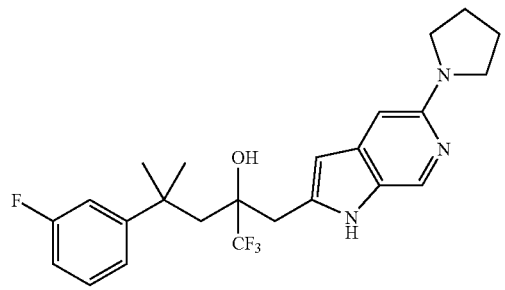 |
| 2-(5-Diethylamino-1H-pyrrolo[2,3-c]pyridin-2-ylmethyl)-1,1,1-trifluoro-4-(3-fluorophenyl)-4-methylpentan-2-ol | 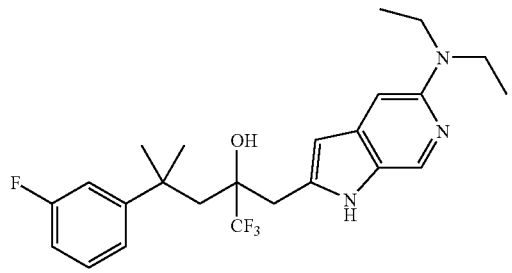 |
| 1,1,1-Trifluoro-4-(3-fluorophenyl)-2-[5-(isopropylmethylamino)-1H-pyrrolo[2,3-c]pyridin-2-ylmethyl]-4-methylpentan-2-ol | 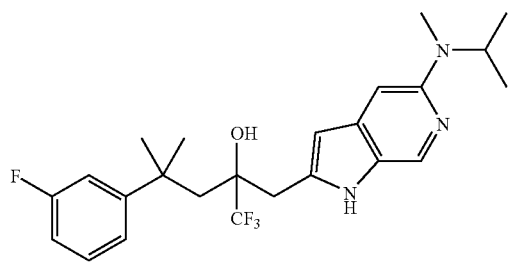 |
| 3'-{3-[5-(Ethylmethylamino)-1H-pyrrolo[2,3-c]pyridin-2-ylmethyl]-4,4,4-trifluoro-3-hydroxy-1,1-dimethylbutyl}-4'-methoxybiphenyl-2-carbonitrile | 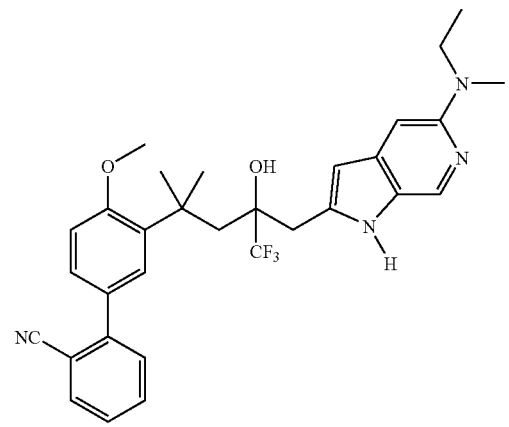 |

-continued

IA

| A | B |
|---|---|
| 2-[5-(Ethylmethylamino)-1H-pyrrolo[2,3-c]pyridin-2-ylmethyl]-1,1,1-trifluoro-4-(2-methoxy-5-pyrimidin-5-ylphenyl)-4-methylpentan-2-ol | 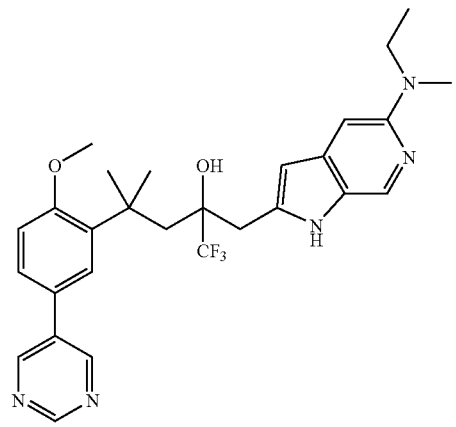 |
| 3'-{3-[5-(Ethylmethylamino)-1H-pyrrolo[2,3-c]pyridin-2-ylmethyl]-4,4,4-trifluoro-3-hydroxy-1,1-dimethylbutyl}-4'-hydroxybiphenyl-2-carbonitrile | 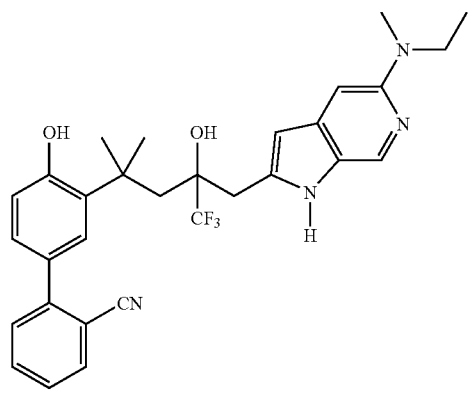 |
| 4'-Hydroxy-3'-[4,4,4-trifluoro-3-hydroxy-1,1-dimethyl-3-(5-morpholin-4-yl-1H-pyrrolo[2,3-c]pyridin-2-ylmethyl)butyl]biphenyl-2-carbonitrile | 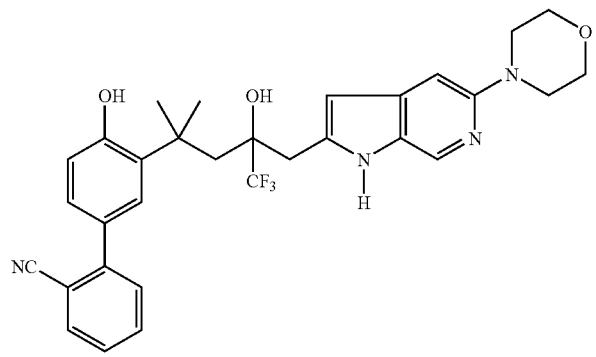 |
| 1,1,1-Trifluoro-4-(5-fluoro-2-methylphenyl)-4-methyl-2-(5-morpholin-4-ylmethyl-1H-pyrrolo[3,2-b]pyridin-2-ylmethyl)pentan-2-ol | 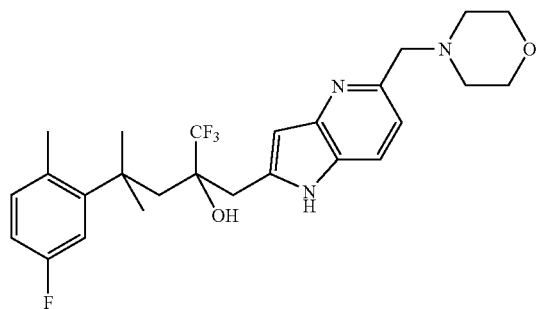 |

IA

| A | B |
|---|---|
| 2-{5-[(Ethylmethylamino)methyl]-1H-pyrrolo[3,2-b]pyridin-2-ylmethyl}-1,1,1-trifluoro-4-(5-fluoro-2-methylphenyl)-4-methylpentan-2-ol | 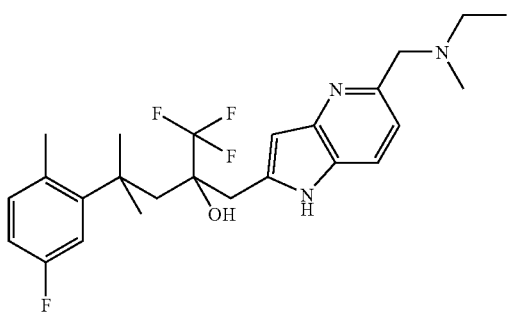 |
| 2-(5-Dimethylaminomethyl-1H-pyrrolo[3,2-b]pyridin-2-ylmethyl)-1,1,1-trifluoro-4-(5-fluoro-2-methylphenyl)-4-methylpentan-2-ol | 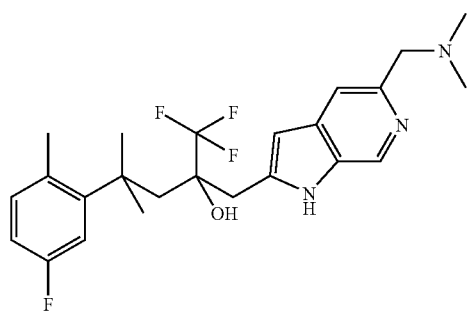 |

IA

| A | B |
|---|---|
| 1,1,1-Trifluoro-4-(5-fluoro-2-methylphenyl)-4-methyl-2-[5-(4-methylpiperazin-1-ylmethyl)-1H-pyrrolo[3,2-b]pyridin-2-ylmethyl]pentan-2-ol | 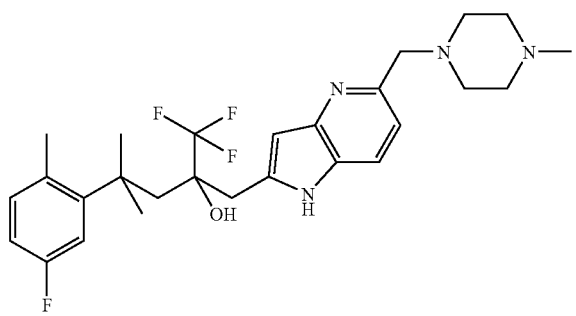 |
| 1,1,1-Trifluoro-4-(5-fluoro-2-methylphenyl)-4-methyl-2-(5-pyrrolidin-1-ylmethyl-1H-pyrrolo[3,2-b]pyridin-2-ylmethyl)pentan-2-ol | 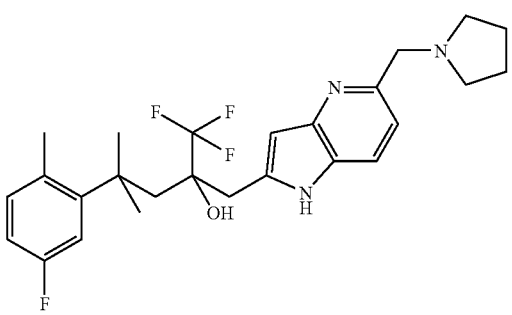 |

-continued

IA

| A | B |
|---|---|
| 2-(5-Diethylaminomethyl-1H-pyrrolo[3,2-b]pyridin-2-ylmethyl)-1,1,1-trifluoro-4-(5-fluoro-2-methylphenyl)-4-methylpentan-2-ol | 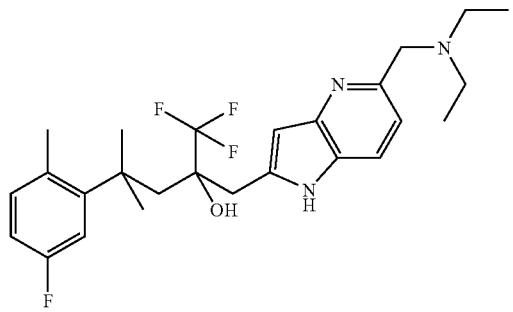 |
| 4-(5-Chloro-2,3-dihydrobenzofuran-7-yl)-2-(5-diethylaminomethyl-1H-pyrrolo[3,2-b]pyridin-2-ylmethyl)-1,1,1-trifluoro-4-methylpentan-2-ol | 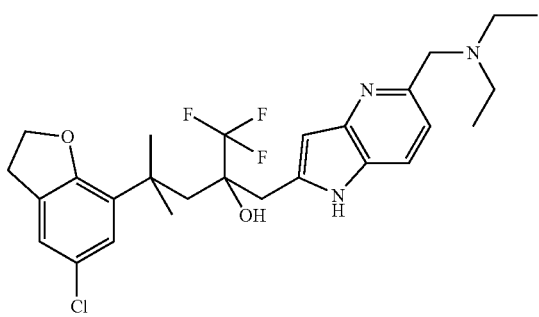 |
| 4-(5-Chloro-2,3-dihydrobenzofuran-7-yl)-2-(5-dimethylaminomethyl-1H-pyrrolo[3,2-b]pyridin-2-ylmethyl)-1,1,1-trifluoro-4-methylpentan-2-ol | 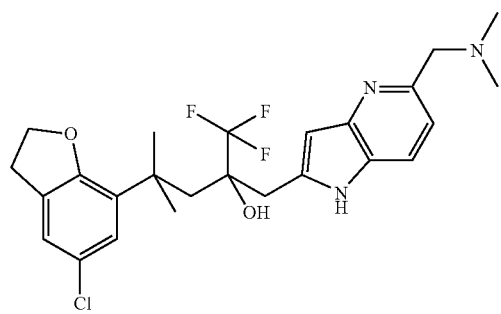 |
| 4-(5-Chloro-2,3-dihydrobenzofuran-7-yl)-2-{5-[(ethylmethylamino)methyl]-1H-pyrrolo[3,2-b]pyridin-2-ylmethyl}-1,1,1-trifluoro-4-methylpentan-2-ol | 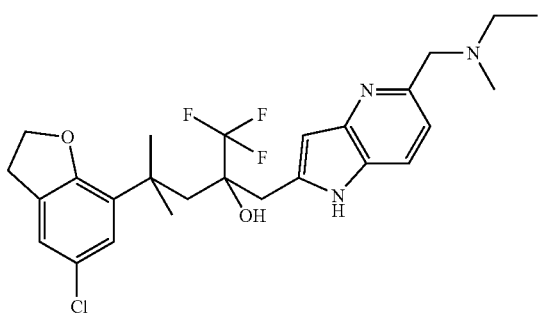 |
| 4-(5-Chloro-2,3-dihydrobenzofuran-7-yl)-1,1,1-trifluoro-4-methyl-2-(5-piperidin-1-ylmethyl-1H-pyrrolo[3,2-b]pyridin-2-ylmethyl)pentan-2-ol | 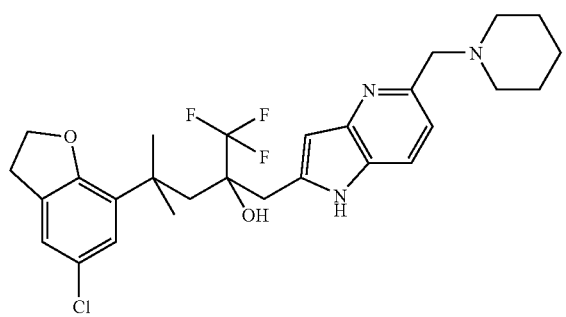 |

-continued

IA

| A | B |
|---|---|
| 4-(5-Chloro-2,3-dihydrobenzofuran-7-yl)-1,1,1-trifluoro-4-methyl-2-(5-morpholin-4-ylmethyl-1H-pyrrolo[3,2-b]pyridin-2-ylmethyl)pentan-2-ol | 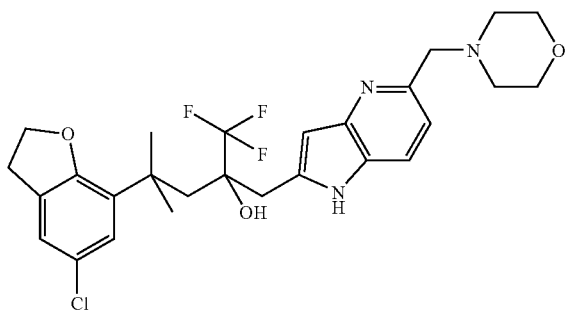 |
| 4-(5-Chloro-2,3-dihydrobenzofuran-7-yl)-1,1,1-trifluoro-4-methyl-2-[5-(4-methylpiperazin-1-ylmethyl)-1H-pyrrolo[3,2-b]pyridin-2-ylmethyl]pentan-2-ol | 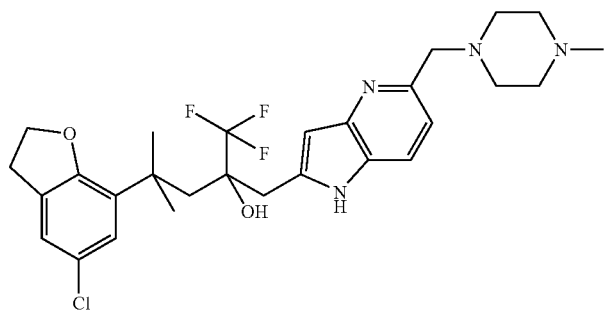 |
| 4-(5-Chloro-2,3-dihydrobenzofuran-7-yl)-1,1,1-trifluoro-4-methyl-2-(5-pyrrolidin-1-ylmethyl-1H-pyrrolo[3,2-b]pyridin-2-ylmethyl)pentan-2-ol | 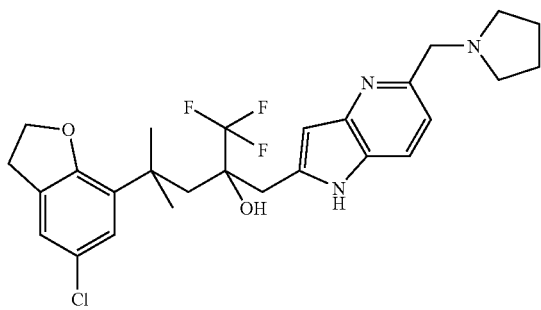 |
| 4-Chloro-2-[4,4,4-trifluoro-3-hydroxy-1,1-dimethyl-3-(5-morpholin-4-ylmethyl-1H-pyrrolo[3,2-b]pyridin-2-ylmethyl)butyl]phenol | 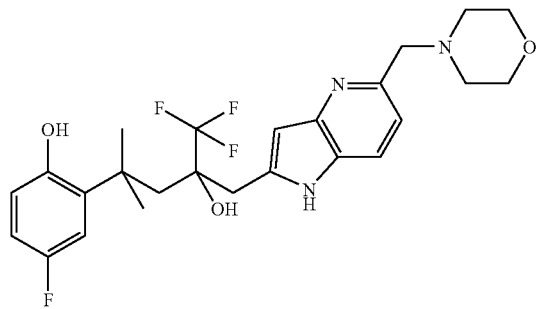 |

-continued

| IA | |
|---|---|
| A | B |

4-Fluoro-2-[4,4,4-trifluoro-3-hydroxy-1,1-dimethyl-3-(5-piperidin-1-ylmethyl-1H-pyrrolo[3,2-b]pyridin-2-ylmethyl)butyl]phenol

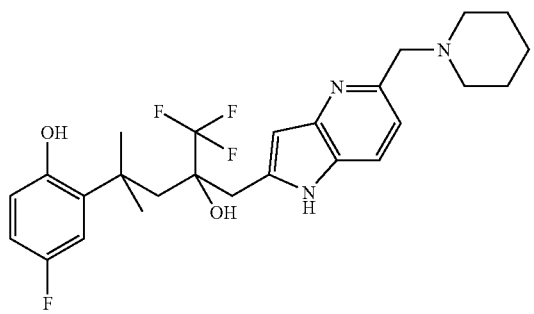 [SMILES: CC(C)(CC(O)(Cc1cc2nc(CN3CCCCC3)ccc2[nH]1)C(F)(F)F)c1cc(F)ccc1O]

4-Fluoro-2-{4,4,4-trifluoro-3-hydroxy-1,1-dimethyl-3-[5-(4-methylpiperazin-1-ylmethyl)-1H-pyrrolo[3,2-b]pyridin-2-ylmethyl]butyl}phenol

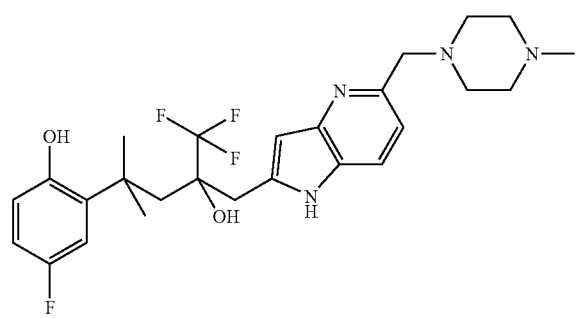 [SMILES: CN1CCN(Cc2ccc3[nH]c(CC(O)(CC(C)(C)c4cc(F)ccc4O)C(F)(F)F)cc3n2)CC1]

2-(3-{5-[(Ethylmethylamino)methyl]-1H-pyrrolo[3,2-b]pyridin-2-ylmethyl}-4,4,4-trifluoro-3-hydroxy-1,1-dimethylbutyl)-4-fluorophenol

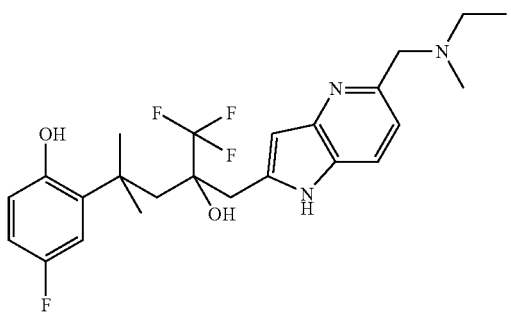 [SMILES: CCN(C)Cc1ccc2[nH]c(CC(O)(CC(C)(C)c3cc(F)ccc3O)C(F)(F)F)cc2n1]

4-Fluoro-2-[4,4,4-trifluoro-3-hydroxy-1,1-dimethyl-3-(5-pyrrolidin-1-ylmethyl-1H-pyrrolo[3,2-b]pyridin-2-ylmethyl)butyl]phenol

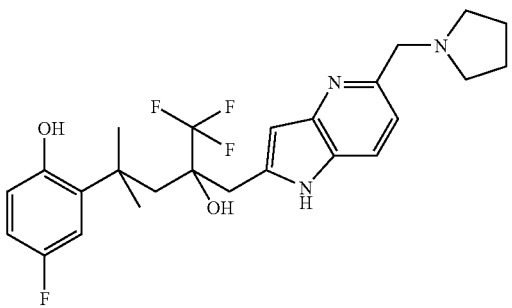 [SMILES: CC(C)(CC(O)(Cc1cc2nc(CN3CCCC3)ccc2[nH]1)C(F)(F)F)c1cc(F)ccc1O]

2-[3-(5-Dimethylaminomethyl-1H-pyrrolo[3,2-b]pyridin-2-ylmethyl)-4,4,4-trifluoro-3-hydroxy-1,1-dimethylbutyl]-4-fluorophenol

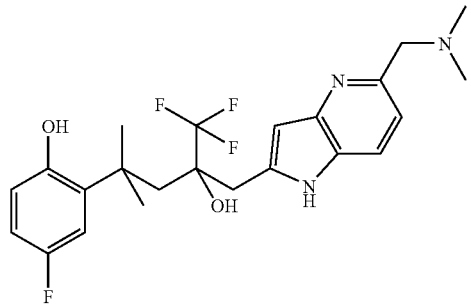 [SMILES: CN(C)Cc1ccc2[nH]c(CC(O)(CC(C)(C)c3cc(F)ccc3O)C(F)(F)F)cc2n1]

-continued

IA

| A | B |
|---|---|
| 2-[3-(5-Diethylaminomethyl-1H-pyrrolo[3,2-b]pyridin-2-ylmethyl)-4,4,4-trifluoro-3-hydroxy-1,1-dimethylbutyl]-4-fluorophenol | 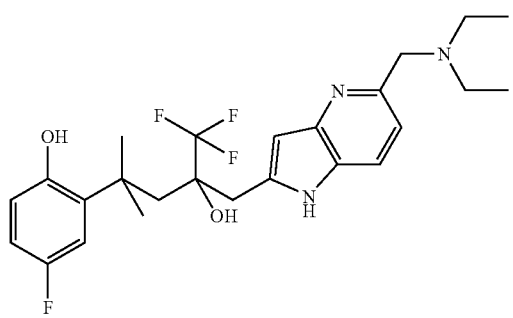 |
| 3-[4,4,4-Trifluoro-3-hydroxy-1,1-dimethyl-3-(5-piperidin-1-ylmethyl-1H-pyrrolo[3,2-b]pyridin-2-ylmethyl)butyl]biphenyl-4-ol | 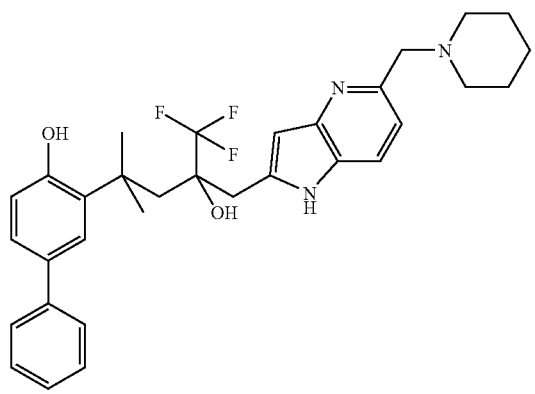 |
| 3-{4,4,4-Trifluoro-3-hydroxy-1,1-dimethyl-3-[5-(4-methylpiperazin-1-ylmethyl)-1H-pyrrolo[3,2-b]pyridin-2-ylmethyl]butyl}biphenyl-4-ol | 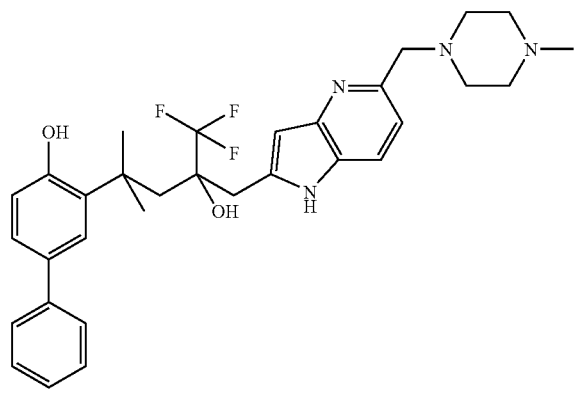 |
| 3-[4,4,4-Trifluoro-3-hydroxy-1,1-dimethyl-3-(5-pyrrolidin-1-ylmethyl-1H-pyrrolo[3,2-b]pyridin-2-ylmethyl)butyl]biphenyl-4-ol | 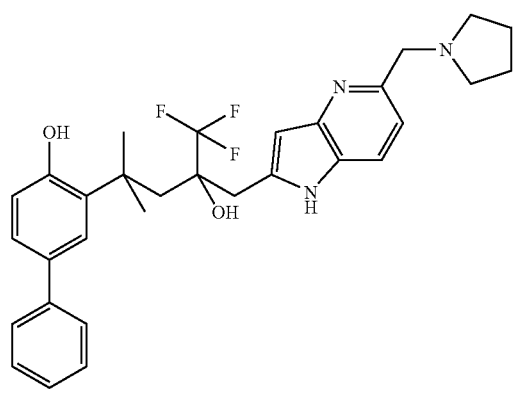 |

| A | B |
|---|---|
| 3-[3-(5-Diethylaminomethyl-1H-pyrrolo[3,2-b]pyridin-2-ylmethyl)-4,4,4-trifluoro-3-hydroxy-1,1-dimethylbutyl]biphenyl-4-ol | 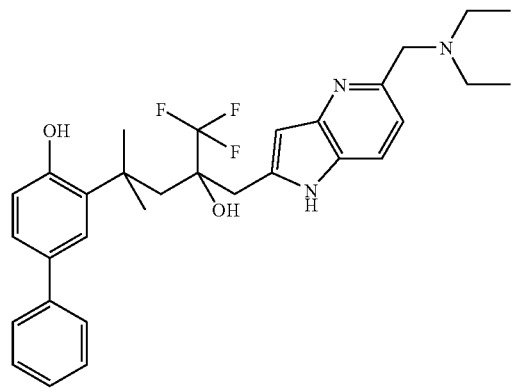 |
| 3-[4,4,4-Trifluoro-3-hydroxy-1,1-dimethyl-3-(5-morpholin-4-ylmethyl-1H-pyrrolo[3,2-b]pyridin-2-ylmethyl)butyl]biphenyl-4-ol | 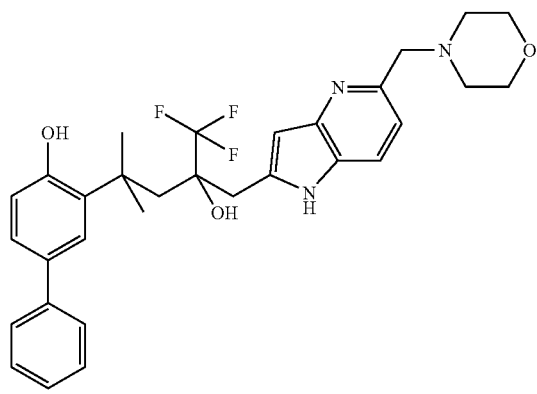 |
| 3-(3-{5-[(Ethylmethylamino)methyl]-1H-pyrrolo[3,2-b]pyridin-2-ylmethyl}-4,4,4-trifluoro-3-hydroxy-1,1-dimethylbutyl)biphenyl-4-ol | 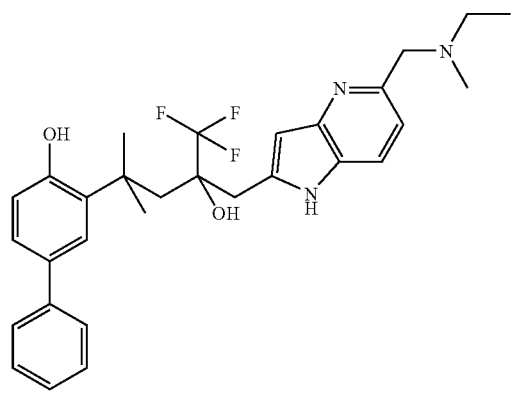 |
| 3-[3-(5-Dimethylaminomethyl-1H-pyrrolo[3,2-b]pyridin-2-ylmethyl)-4,4,4-trifluoro-3-hydroxy-1,1-dimethylbutyl]biphenyl-4-ol | 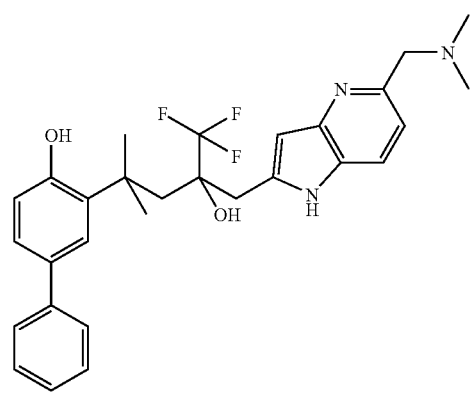 |

-continued

IA

| A | B |
|---|---|
| 4-Pyridin-3-yl-2-[4,4,4-trifluoro-3-hydroxy-1,1-dimethyl-3-(5-piperidin-1-ylmethyl-1H-pyrrolo[3,2-b]pyridin-2-ylmethyl)butyl]phenol | 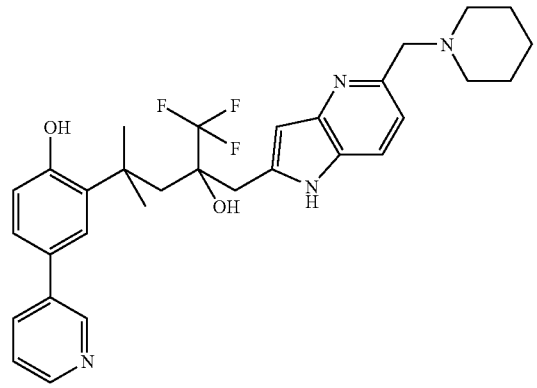 |
| 4-Pyridin-3-yl-2-{4,4,4-trifluoro-3-hydroxy-1,1-dimethyl-3-[5-(4-methylpiperazin-1-ylmethyl)-1H-pyrrolo[3,2-b]pyridin-2-ylmethyl]butyl}phenol | 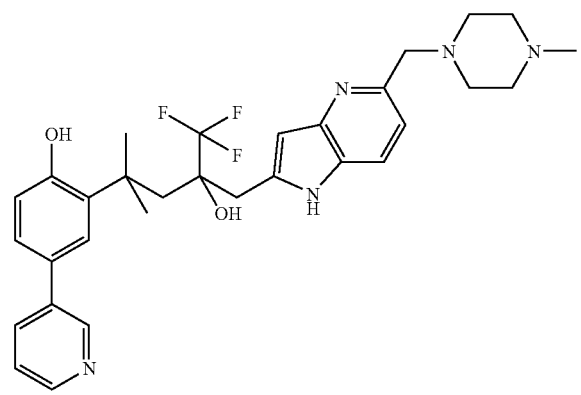 |
| 4-Pyridin-3-yl-2-[4,4,4-trifluoro-3-hydroxy-1,1-dimethyl-3-(5-pyrrolidin-1-ylmethyl-1H-pyrrolo[3,2-b]pyridin-2-ylmethyl)butyl]phenol | 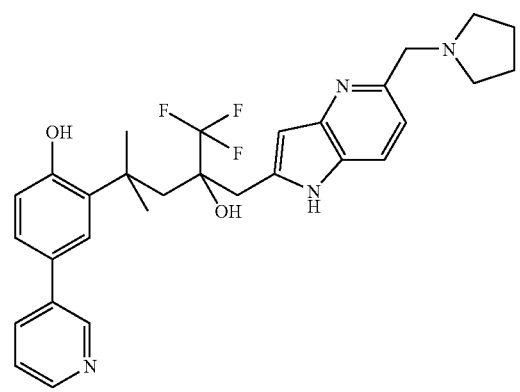 |
| 2-[3-(5-Diethylaminomethyl-1H-pyrrolo[3,2-b]pyridin-2-ylmethyl)-4,4,4-trifluoro-3-hydroxy-1,1-dimethylbutyl]-4-pyridin-3-ylphenol | 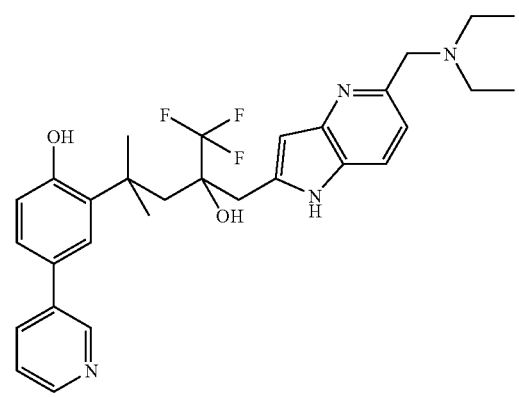 |

-continued

| IA | |
|---|---|
| A | B |

4-Pyridin-3-yl-2-[4,4,4-trifluoro-3-hydroxy-1,1-dimethyl-3-(5-morpholin-4-ylmethyl-1H-pyrrolo[3,2-b]pyridin-2-ylmethyl)butyl]phenol

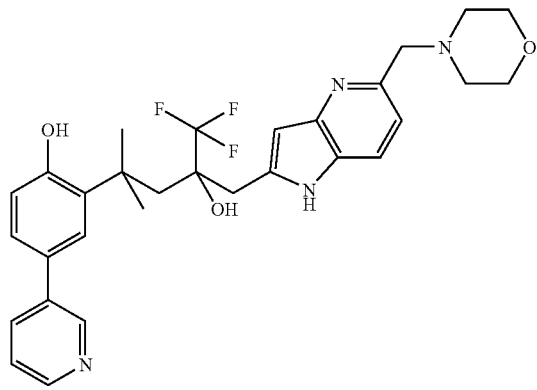 [SMILES: CC(C)(CC(O)(Cc1cc2nc(CN3CCOCC3)ccc2[nH]1)C(F)(F)F)c1cc(-c2cccnc2)ccc1O]

2-(3-{5-[(Ethylmethylamino)methyl]-1H-pyrrolo[3,2-b]pyridin-2-ylmethyl}-4,4,4-trifluoro-3-hydroxy-1,1-dimethylbutyl)-4-pyridin-3-ylphenol

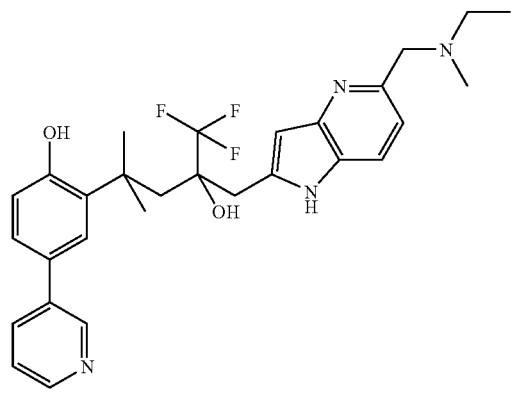

2-[3-(5-Dimethylaminomethyl-1H-pyrrolo[3,2-b]pyridin-2-ylmethyl)-4,4,4-trifluoro-3-hydroxy-1,1-dimethylbutyl]-4-pyridin-3-ylphenol

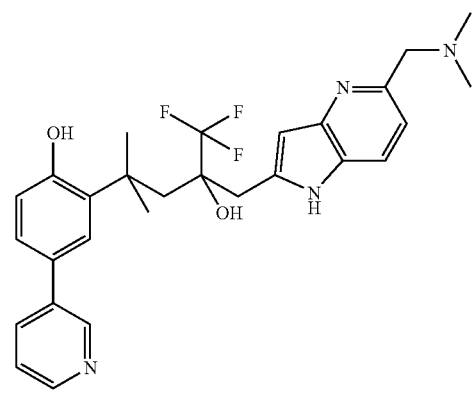

4-Pyrimidin-5-yl-2-[4,4,4-trifluoro-3-hydroxy-1,1-dimethyl-3-(5-piperidin-1-ylmethyl-1H-pyrrolo[3,2-b]pyridin-2-ylmethyl)butyl]phenol

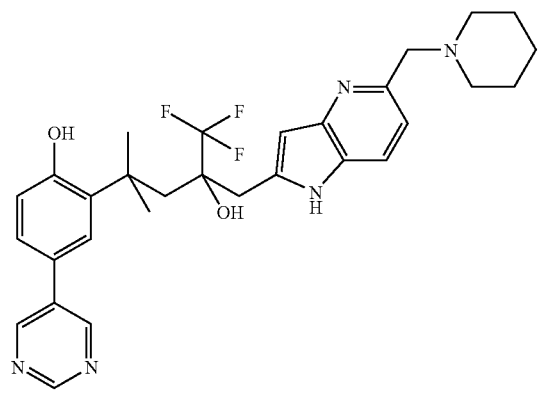 [SMILES: CC(C)(CC(O)(Cc1cc2nc(CN3CCCCC3)ccc2[nH]1)C(F)(F)F)c1cc(-c2cncnc2)ccc1O]

| A | B |
|---|---|
| 4-Pyrimidin-5-yl-2-{4,4,4-trifluoro-3-hydroxy-1,1-dimethyl-3-[5-(4-methylpiperazin-1-ylmethyl)-1H-pyrrolo[3,2-b]pyridin-2-ylmethyl]butyl}phenol | 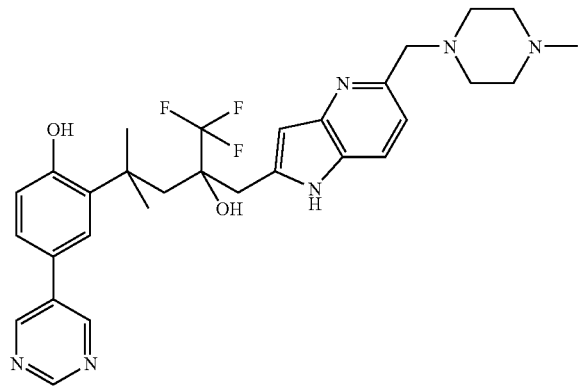 |
| 4-Pyrimidin-5-yl-2-[4,4,4-trifluoro-3-hydroxy-1,1-dimethyl-3-(5-pyrrolidin-1-ylmethyl-1H-pyrrolo[3,2-b]pyridin-2-ylmethyl)butyl]phenol | 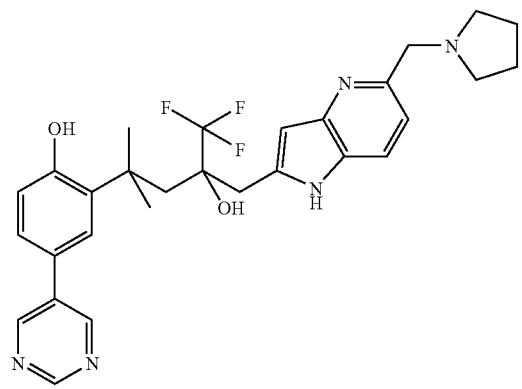 |
| 2-[3-(5-Diethylaminomethyl-1H-pyrrolo[3,2-b]pyridin-2-ylmethyl)-4,4,4-trifluoro-3-hydroxy-1,1-dimethylbutyl]-4-pyrimidin-5-ylphenol | 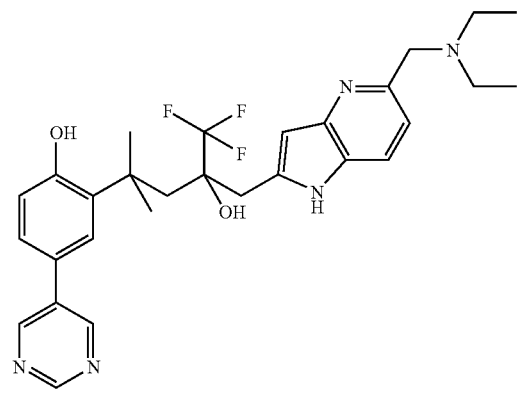 |
| 4-Pyrimidin-5-yl-2-[4,4,4-trifluoro-3-hydroxy-1,1-dimethyl-3-(5-morpholin-4-ylmethyl-1H-pyrrolo[3,2-b]pyridin-2-ylmethyl)butyl]phenol | 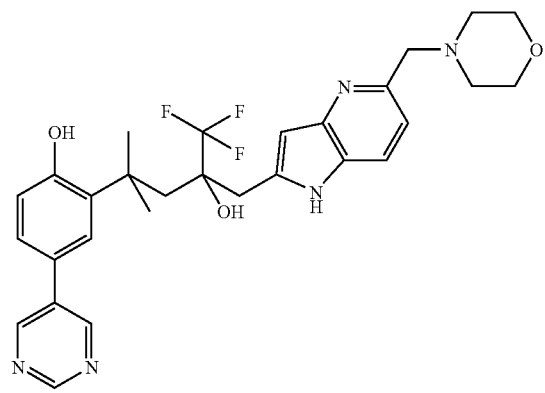 |

| IA | |
|---|---|
| A | B |
2-(3-{5-[(Ethylmethylamino)methyl]-1H-pyrrolo[3,2-b]pyridin-2-ylmethyl}-4,4,4-trifluoro-3-hydroxy-1,1-dimethylbutyl)-4-pyrimidin-5-ylphenol
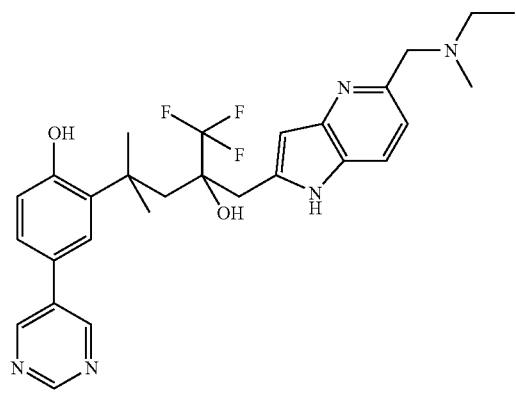 [SMILES: CCN(C)Cc1ccc2[nH]c(CC(O)(CC(C)(C)c3cc(-c4cncnc4)ccc3O)C(F)(F)F)cc2n1]
2-[3-(5-Dimethylaminomethyl-1H-pyrrolo[3,2-b]pyridin-2-ylmethyl)-4,4,4-trifluoro-3-hydroxy-1,1-dimethylbutyl]-4-pyrimidin-5-ylphenol
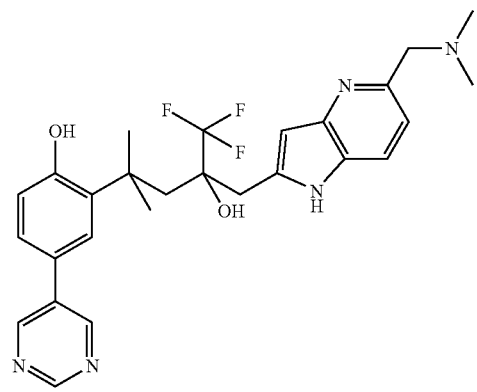 [SMILES: CN(C)Cc1ccc2[nH]c(CC(O)(CC(C)(C)c3cc(-c4cncnc4)ccc3O)C(F)(F)F)cc2n1]
3-[4,4,4-Trifluoro-3-hydroxy-1,1-dimethyl-3-(5-piperidin-1-ylmethyl-1H-pyrrolo[2,3-c]pyridin-2-ylmethyl)butyl]biphenyl-4-ol
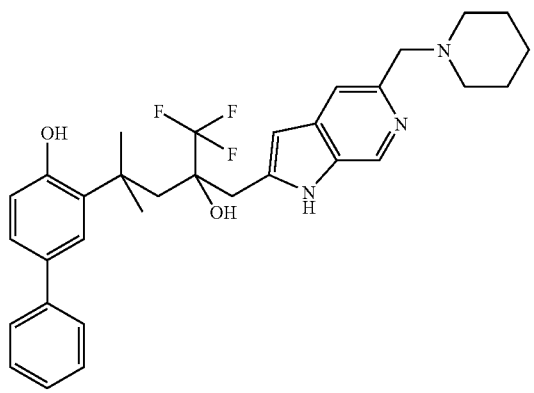

-continued

| IA | |
|---|---|
| A | B |
| 3-{4,4,4-Trifluoro-3-hydroxy-1,1-dimethyl-3-[5-(4-methylpiperazin-1-ylmethyl)-1H-pyrrolo[2,3-c]pyridin-2-ylmethyl]butyl}biphenyl-4-ol | 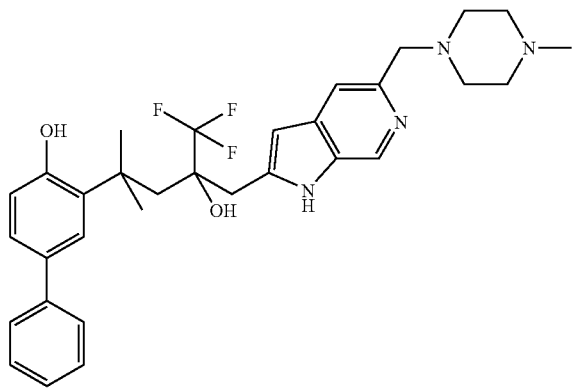 |
| 3-[4,4,4-Trifluoro-3-hydroxy-1,1-dimethyl-3-(5-pyrrolidin-1-ylmethyl-1H-pyrrolo[2,3-c]pyridin-2-ylmethyl)butyl]biphenyl-4-ol | 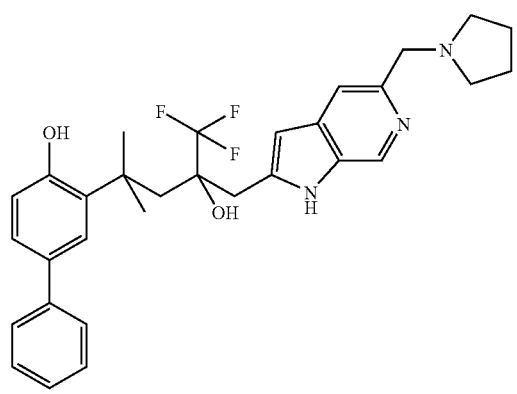 |
| 3-[3-(5-Diethylaminomethyl-1H-pyrrolo[2,3-c]pyridin-2-ylmethyl)-4,4,4-trifluoro-3-hydroxy-1,1-dimethylbutyl]biphenyl-4-ol | 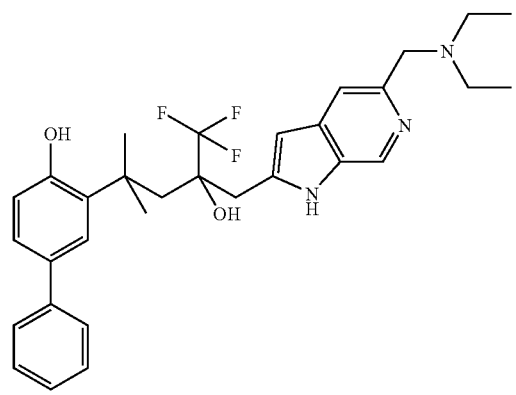 |
| 3-[4,4,4-Trifluoro-3-hydroxy-1,1-dimethyl-3-(5-morpholin-4-ylmethyl-1H-pyrrolo[2,3-c]pyridin-2-ylmethyl)butyl]biphenyl-4-ol | 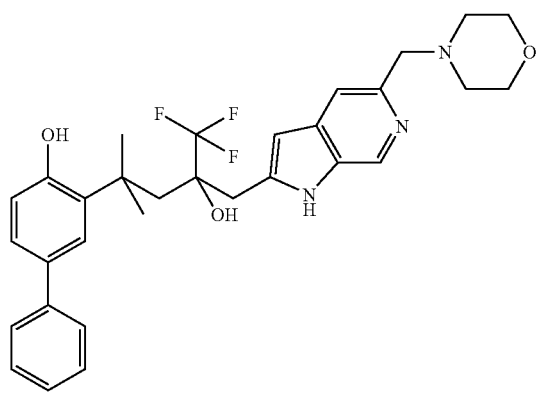 |

-continued

| IA | |
|---|---|
| A | B |

3-(3-{5-[(Ethylmethylamino)methyl]-1H-pyrrolo[2,3-c]pyridin-2-ylmethyl}-4,4,4-trifluoro-3-hydroxy-1,1-dimethylbutyl)biphenyl-4-ol

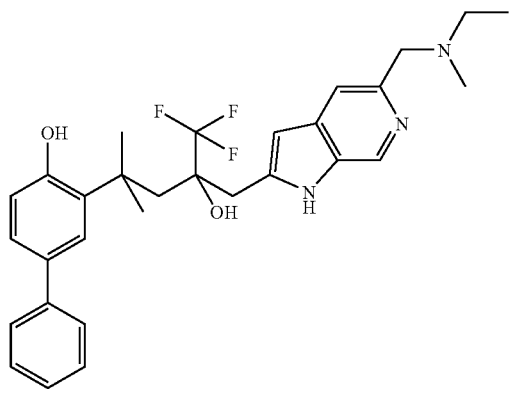 [SMILES: CCN(C)Cc1cc2cc(CC(O)(CC(C)(C)c3cc(-c4ccccc4)ccc3O)C(F)(F)F)[nH]c2cn1]

3-[3-(5-Dimethylaminomethyl-1H-pyrrolo[2,3-c]pyridin-2-ylmethyl)-4,4,4-trifluoro-3-hydroxy-1,1-dimethylbutyl]biphenyl-4-ol

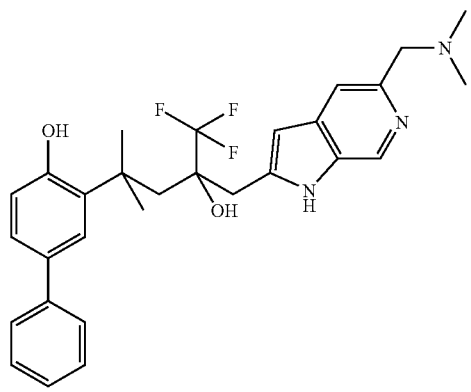

4-Pyridin-3-yl-2-[4,4,4-trifluoro-3-hydroxy-1,1-dimethyl-3-(5-piperidin-1-ylmethyl-1H-pyrrolo[2,3-c]pyridin-2-ylmethyl)butyl]phenol

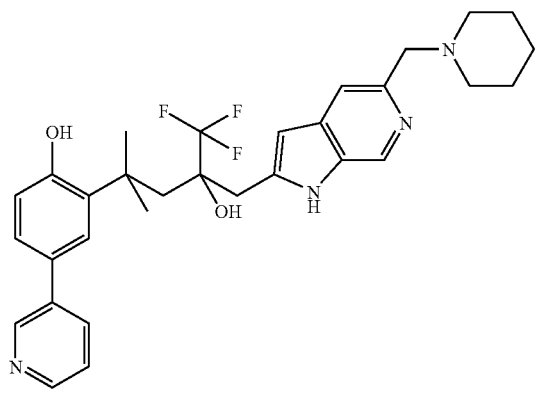 [SMILES: CC(C)(CC(O)(Cc1cc2cc(CN3CCCCC3)ncc2[nH]1)C(F)(F)F)c1cc(-c2cccnc2)ccc1O]

4-Pyridin-3-yl-2-{4,4,4-trifluoro-3-hydroxy-1,1-dimethyl-3-[5-(4-methylpiperazin-1-ylmethyl)-1H-pyrrolo[2,3-c]pyridin-2-ylmethyl]butyl}phenol

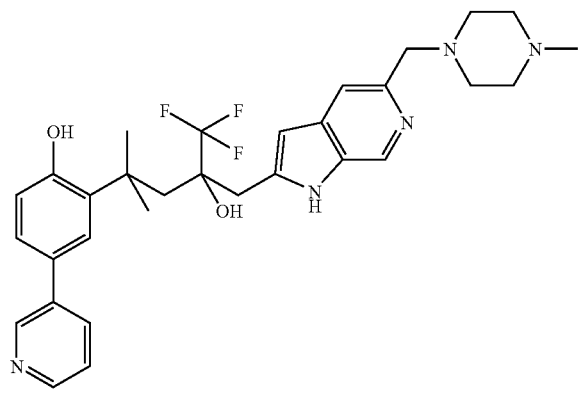

-continued

| IA | |
|---|---|
| A | B |

4-Pyridin-3-yl-2-[4,4,4-trifluoro-3-hydroxy-1,1-dimethyl-3-(5-pyrrolidin-1-ylmethyl-1H-pyrrolo[2,3-c]pyridin-2-ylmethyl)butyl]phenol

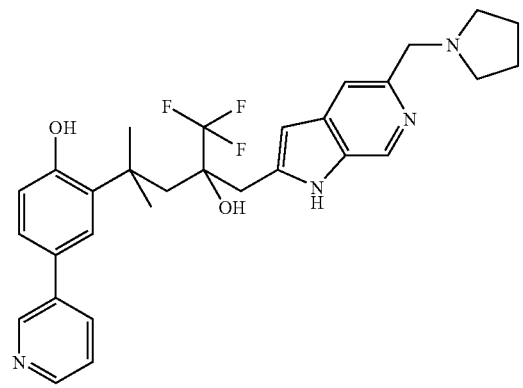 [SMILES: CC(C)(CC(O)(Cc1cc2cc(CN3CCCC3)ncc2[nH]1)C(F)(F)F)c1cc(-c2cccnc2)ccc1O]

2-[3-(5-Diethylaminomethyl-1H-pyrrolo[2,3-c]pyridin-2-ylmethyl)-4,4,4-trifluoro-3-hydroxy-1,1-dimethylbutyl]-4-pyridin-3-ylphenol

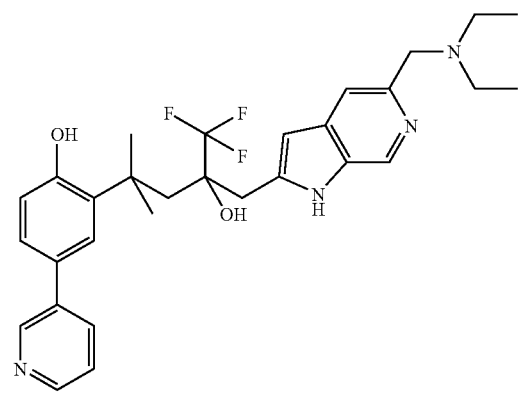

4-Pyridin-3-yl-2-[4,4,4-trifluoro-3-hydroxy-1,1-dimethyl-3-(5-morpholin-4-ylmethyl-1H-pyrrolo[2,3-c]pyridin-2-ylmethyl)butyl]phenol

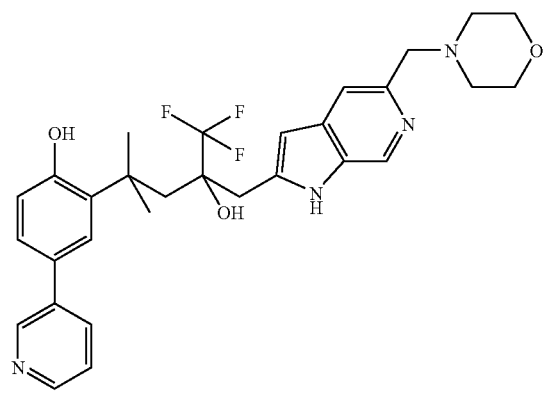 [SMILES: CC(C)(CC(O)(Cc1cc2cc(CN3CCOCC3)ncc2[nH]1)C(F)(F)F)c1cc(-c2cccnc2)ccc1O]

2-(3-{5-[(Ethylmethylamino)methyl]-1H-pyrrolo[2,3-c]pyridin-2-ylmethyl}-4,4,4-trifluoro-3-hydroxy-1,1-dimethylbutyl)-4-pyridin-3-ylphenol

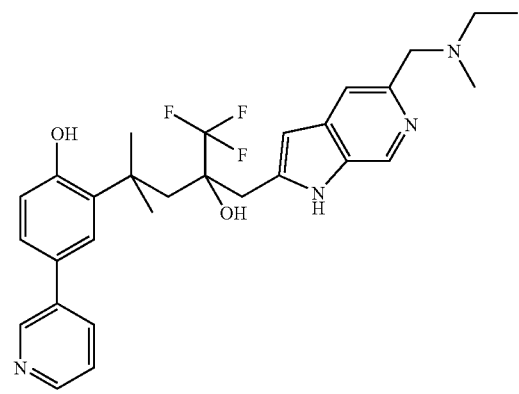 [SMILES: CCN(C)Cc1cc2cc(CC(O)(CC(C)(C)c3cc(-c4cccnc4)ccc3O)C(F)(F)F)[nH]c2cn1]

-continued
| IA | |
|---|---|
| A | B |
2-[3-(5-Dimethylaminomethyl-1H-pyrrolo[2,3-c]pyridin-2-ylmethyl)-4,4,4-trifluoro-3-hydroxy-1,1-dimethylbutyl]-4-pyridin-3-ylphenol
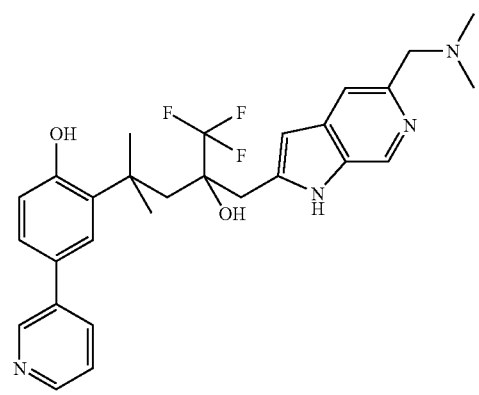 [SMILES: CN(C)Cc1cc2cc(CC(O)(CC(C)(C)c3cc(-c4cccnc4)ccc3O)C(F)(F)F)[nH]c2cn1]
4-Pyrimidin-5-yl-2-[4,4,4-trifluoro-3-hydroxy-1,1-dimethyl-3-(5-piperidin-1-ylmethyl-1H-pyrrolo[2,3-c]pyridin-2-ylmethyl)butyl]phenol
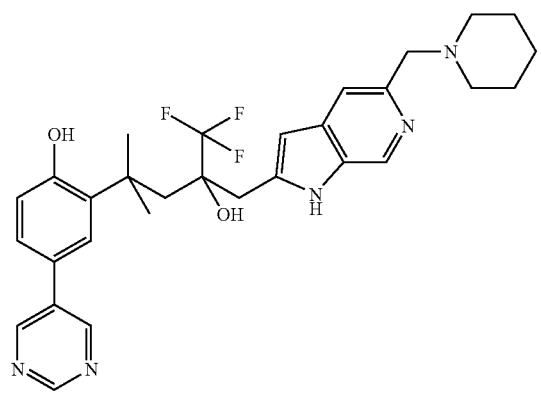
4-Pyrimidin-5-yl-2-{4,4,4-trifluoro-3-hydroxy-1,1-dimethyl-3-[5-(4-methylpiperazin-1-ylmethyl)-1H-pyrrolo[2,3-c]pyridin-2-ylmethyl]butyl}phenol
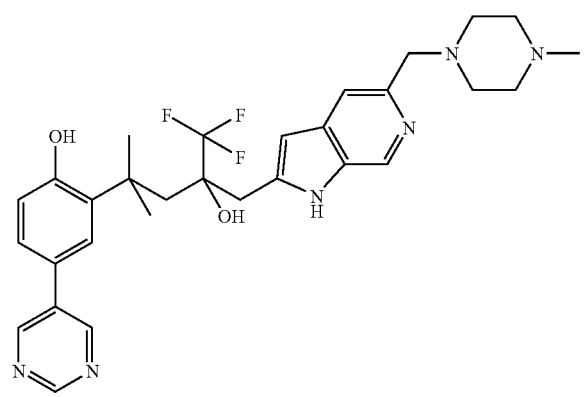 [SMILES: CN1CCN(Cc2cc3cc(CC(O)(CC(C)(C)c4cc(-c5cncnc5)ccc4O)C(F)(F)F)[nH]c3cn2)CC1]

-continued

| IA | |
|---|---|
| A | B |

4-Pyrimidin-5-yl-2-[4,4,4-trifluoro-3-hydroxy-1,1-dimethyl-3-(5-pyrrolidin-1-ylmethyl-1H-pyrrolo[2,3-c]pyridin-2-ylmethyl)butyl]phenol

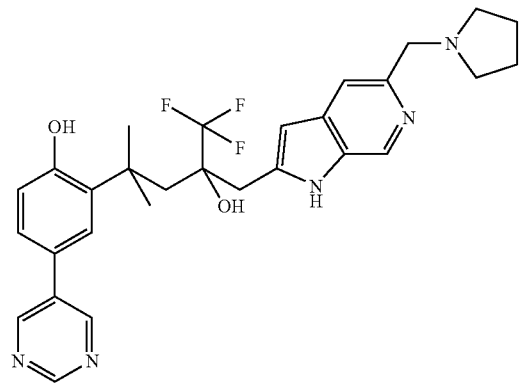

2-[3-(5-Diethylaminomethyl-1H-pyrrolo[2,3-c]pyridin-2-ylmethyl)-4,4,4-trifluoro-3-hydroxy-1,1-dimethylbutyl]-4-pyrimidin-5-ylphenol

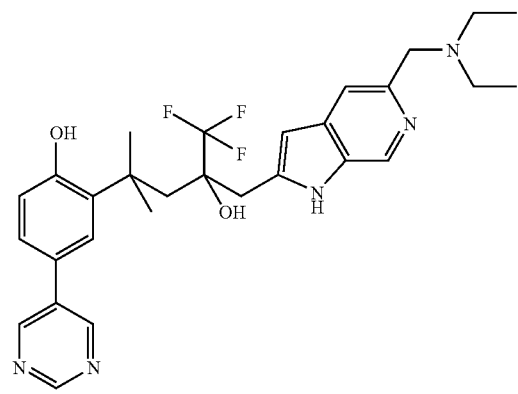

4-Pyrimidin-5-yl-2-[4,4,4-trifluoro-3-hydroxy-1,1-dimethyl-3-(5-morpholin-4-ylmethyl-1H-pyrrolo[2,3-c]pyridin-2-ylmethyl)butyl]phenol

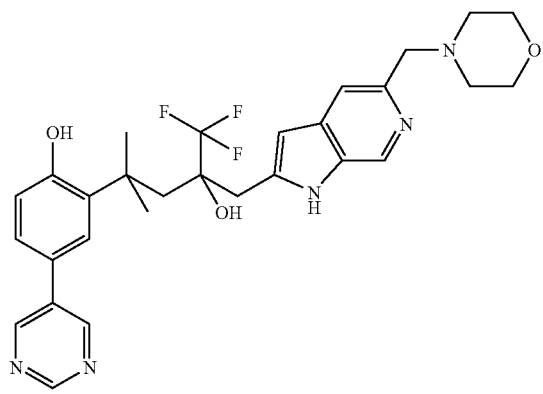

2-(3-{5-[(Ethylmethylamino)methyl]-1H-pyrrolo[2,3-c]pyridin-2-ylmethyl}-4,4,4-trifluoro-3-hydroxy-1,1-dimethylbutyl)-4-pyrimidin-5-ylphenol

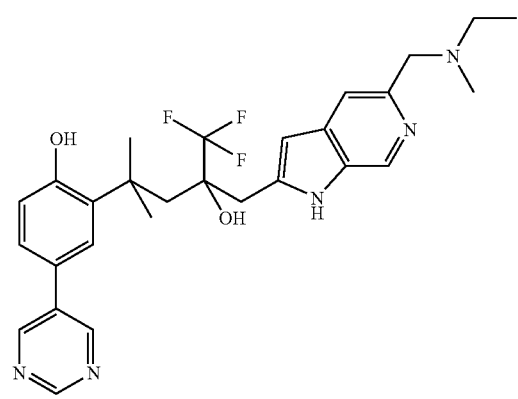 [SMILES: CCN(C)Cc1cc2cc(CC(O)(CC(C)(C)c3cc(-c4cncnc4)ccc3O)C(F)(F)F)[nH]c2cn1]

IA

| A | B |
|---|---|
| 2-[3-(5-Dimethylaminomethyl-1H-pyrrolo[2,3-c]pyridin-2-ylmethyl)-4,4,4-trifluoro-3-hydroxy-1,1-dimethylbutyl]-4-pyrimidin-5-ylphenol | 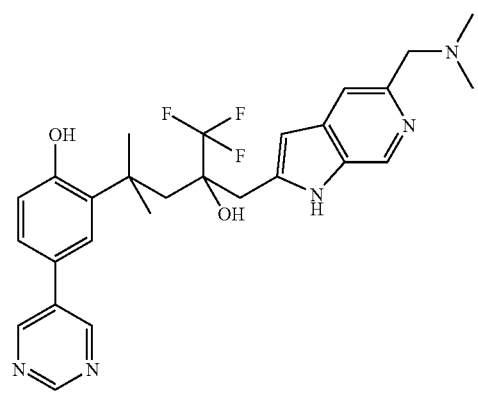 |
| 4-Bromo-2-[4,4,4-trifluoro-3-hydroxy-1,1-dimethyl-3-(5-morpholin-4-ylmethyl-1H-indol-2-ylmethyl)butyl]phenol | 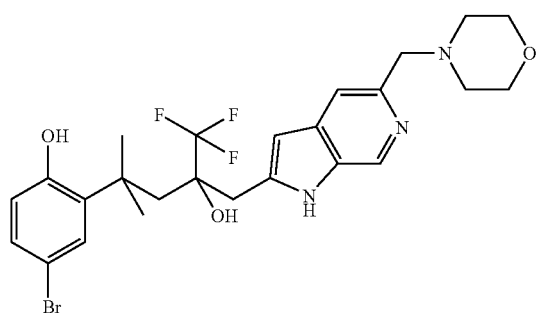 |
| 4-Bromo-2-[4,4,4-trifluoro-3-hydroxy-1,1-dimethyl-3-(5-piperidin-1-ylmethyl-1H-indol-2-ylmethyl)butyl]phenol | 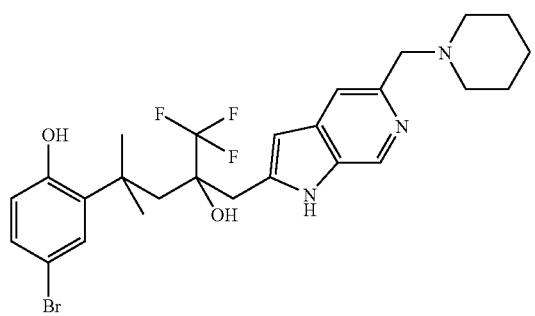 |
| 4-Bromo-2-{4,4,4-trifluoro-3-hydroxy-1,1-dimethyl-3-[5-(4-methylpiperazin-1-ylmethyl)-1H-indol-2-ylmethyl]butyl}phenol | 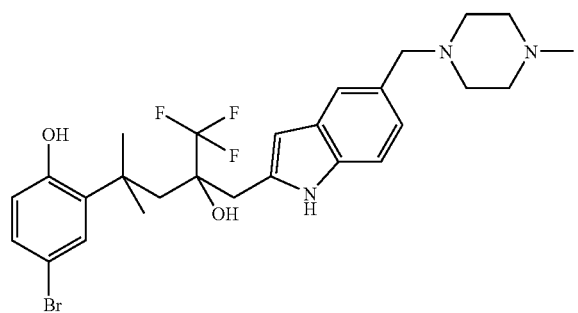 |

IA
| A | B |
|---|---|
| 4-Bromo-2-(3-{5-[(ethylmethylamino)methyl]-1H-indol-2-ylmethyl}-4,4,4-trifluoro-3-hydroxy-1,1-dimethylbutyl)phenol | 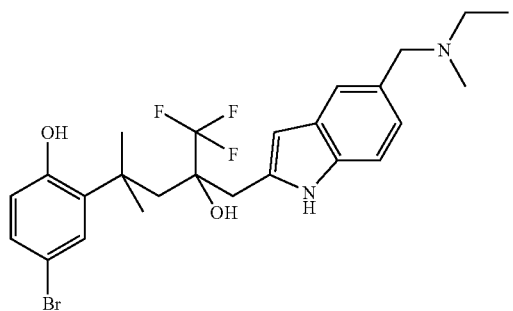 |
| 4-Bromo-2-[4,4,4-trifluoro-3-hydroxy-1,1-dimethyl-3-(5-pyrrolidin-1-ylmethyl-1H-indol-2-ylmethyl)butyl]phenol | 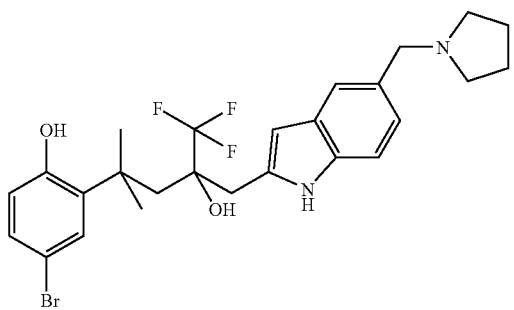 |
| 4-Bromo-2-[3-(5-dimethylaminomethyl-1H-indol-2-ylmethyl)-4,4,4-trifluoro-3-hydroxy-1,1-dimethylbutyl]phenol | 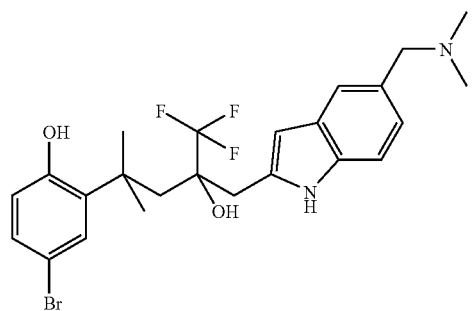 |
| 4-Bromo-2-[3-(5-diethylaminomethyl-1H-indol-2-ylmethyl)-4,4,4-trifluoro-3-hydroxy-1,1-dimethylbutyl]phenol | 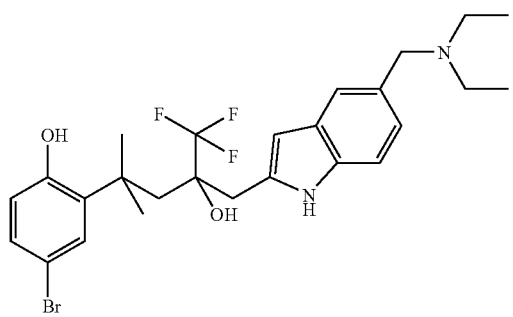 |

-continued

IA

| A | B |
|---|---|
| 3-[4,4,4-Trifluoro-3-hydroxy-1,1-dimethyl-3-(5-morpholin-4-ylmethyl-1H-indol-2-ylmethyl)butyl]biphenyl-4-ol | 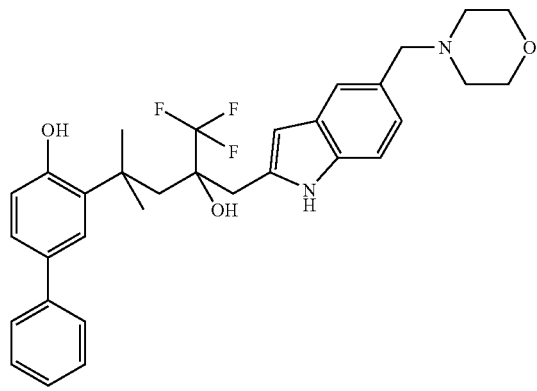 |
| 3-[4,4,4-Trifluoro-3-hydroxy-1,1-dimethyl-3-(5-piperidin-1-ylmethyl-1H-indol-2-ylmethyl)butyl]biphenyl-4-ol | 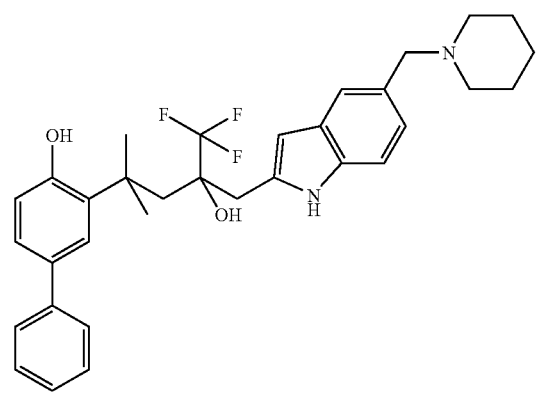 |
| 3-{4,4,4-Trifluoro-3-hydroxy-1,1-dimethyl-3-[5-(4-methylpiperazin-1-ylmethyl)-1H-indol-2-ylmethyl]butyl}biphenyl-4-ol | 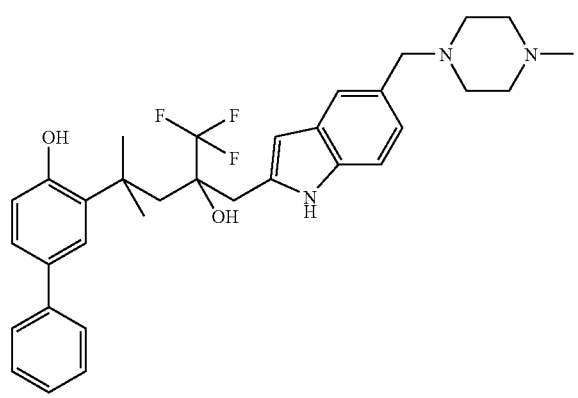 |
| 3-(3-{5-[(Ethylmethylamino)methyl]-1H-indol-2-ylmethyl}-4,4,4-trifluoro-3-hydroxy-1,1-dimethylbutyl)biphenyl-4-ol | 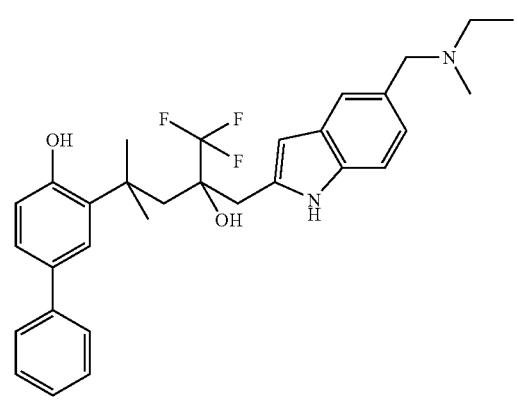 |

IA
| A | B |
|---|---|
| 3-[4,4,4-Trifluoro-3-hydroxy-1,1-dimethyl-3-(5-pyrrolidin-1-ylmethyl-1H-indol-2-ylmethyl)butyl]biphenyl-4-ol | 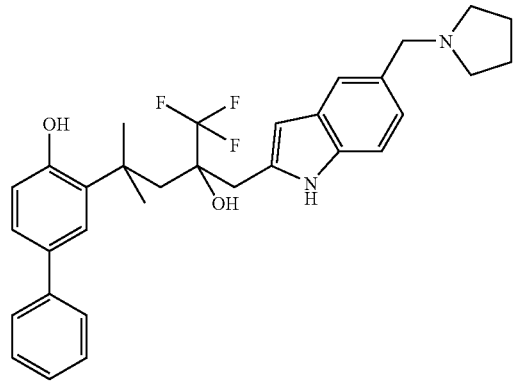 |
| 3-[3-(5-Dimethylaminomethyl-1H-indol-2-ylmethyl)-4,4,4-trifluoro-3-hydroxy-1,1-dimethylbutyl]biphenyl-4-ol | 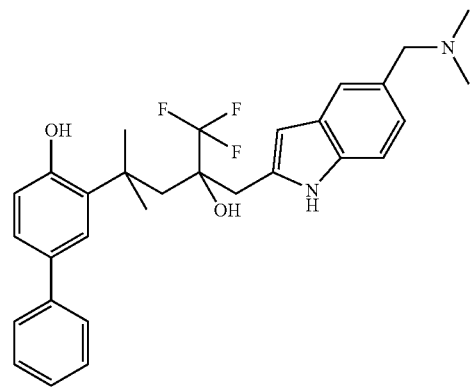 |
| 3-[3-(5-Diethylaminomethyl-1H-indol-2-ylmethyl)-4,4,4-trifluoro-3-hydroxy-1,1-dimethylbutyl]biphenyl-4-ol | 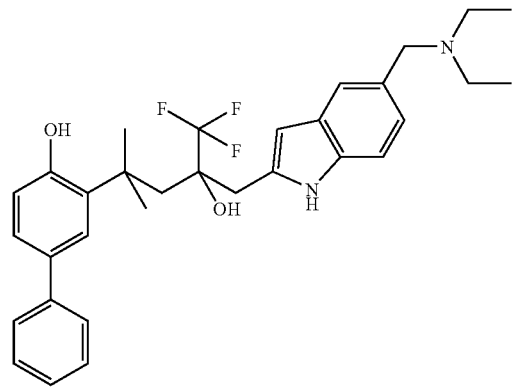 |
| 4-Pyridin-3-yl-2-[4,4,4-trifluoro-3-hydroxy-1,1-dimethyl-3-(5-morpholin-4-ylmethyl-1H-indol-2-ylmethyl)butyl]phenol | 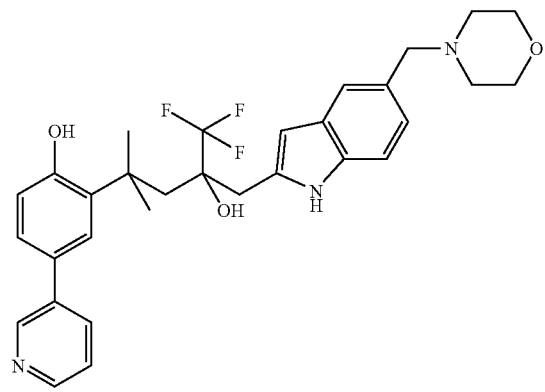 |

|   | IA |
|---|---|
| A | B |
4-Pyridin-3-yl-2-[4,4,4-trifluoro-3-hydroxy-1,1-dimethyl-3-(5-piperidin-1-ylmethyl-1H-indol-2-ylmethyl)butyl]phenol
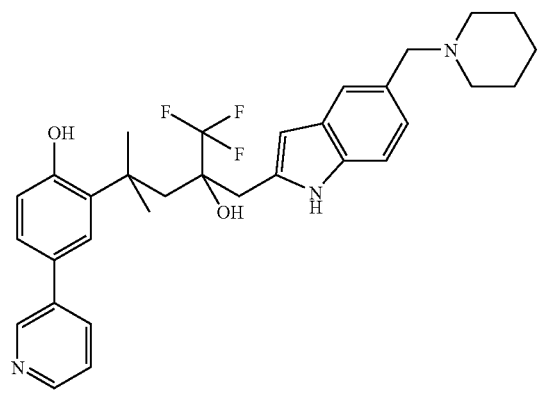
4-Pyridin-3-yl-2-{4,4,4-trifluoro-3-hydroxy-1,1-dimethyl-3-[5-(4-methylpiperazin-1-ylmethyl)-1H-indol-2-ylmethyl]butyl}phenol
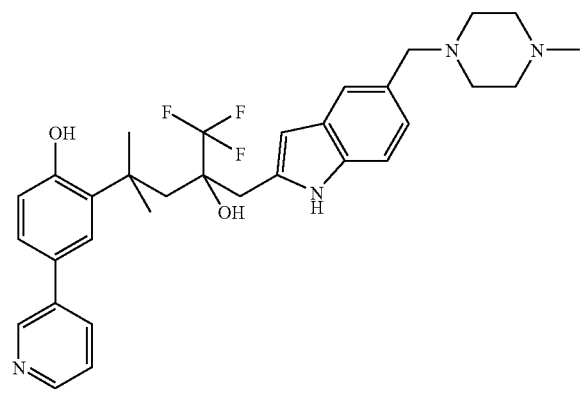 [SMILES: CN1CCN(Cc2ccc3[nH]c(CC(O)(CC(C)(C)c4cc(-c5cccnc5)ccc4O)C(F)(F)F)cc3c2)CC1]
2-(3-{5-[(Ethylmethylamino)methyl]-1H-indol-2-ylmethyl}-4,4,4-trifluoro-3-hydroxy-1,1-dimethylbutyl)-4-pyridin-3-ylphenol
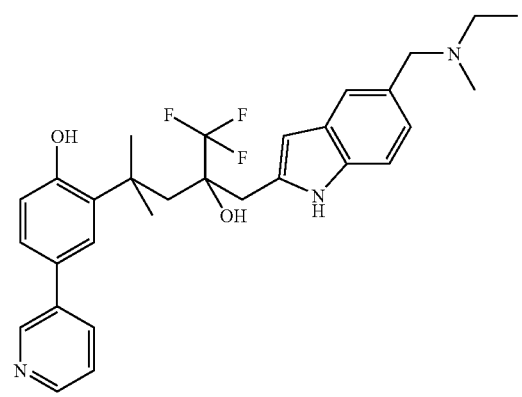 [SMILES: CCN(C)Cc1ccc2[nH]c(CC(O)(CC(C)(C)c3cc(-c4cccnc4)ccc3O)C(F)(F)F)cc2c1]

-continued
| IA | |
|---|---|
| A | B |
| 4-Pyridin-3-yl-2-[4,4,4-trifluoro-3-hydroxy-1,1-dimethyl-3-(5-pyrrolidin-1-ylmethyl-1H-indol-2-ylmethyl)butyl]phenol | 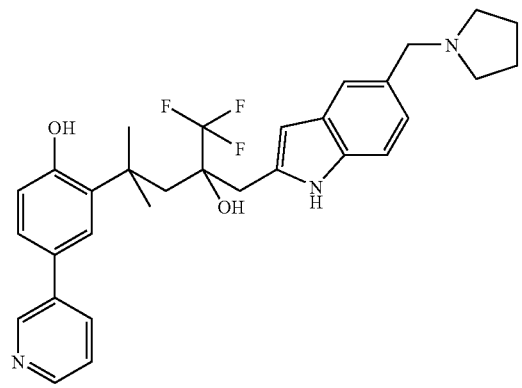 |
| IA | |
|---|---|
| A | B |
| 2-[3-(5-Dimethylaminomethyl-1H-indol-2-ylmethyl)-4,4,4-trifluoro-3-hydroxy-1,1-dimethylbutyl]-4-pyridin-3-ylphenol | 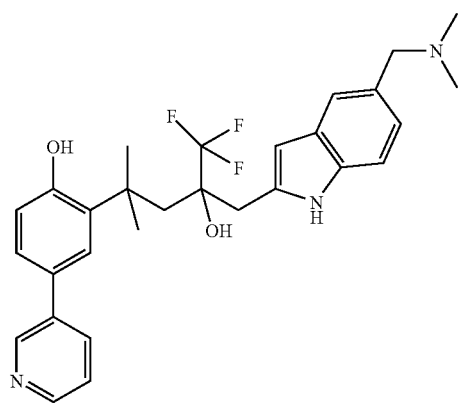 |
| 2-[3-(5-Diethylaminomethyl-1H-indol-2-ylmethyl)-4,4,4-trifluoro-3-hydroxy-1,1-dimethylbutyl]-4-pyridin-3-ylphenol | 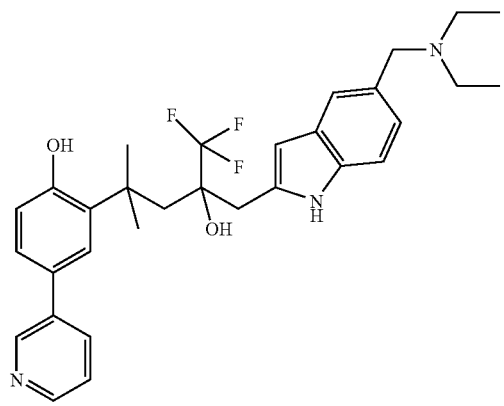 |

-continued
IA
| A | B |
|---|---|
| 4-Pyrimidin-5-yl-2-[4,4,4-trifluoro-3-hydroxy-1,1-dimethyl-3-(5-morpholin-4-ylmethyl-1H-indol-2-ylmethyl)butyl]phenol | 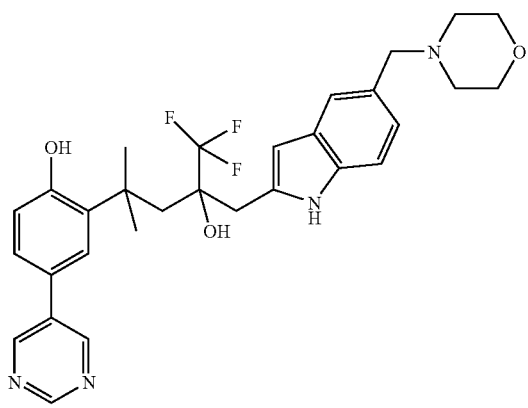 |
| 4-Pyrimidin-5-yl-2-[4,4,4-trifluoro-3-hydroxy-1,1-dimethyl-3-(5-piperidin-1-ylmethyl-1H-indol-2-ylmethyl)butyl]phenol | 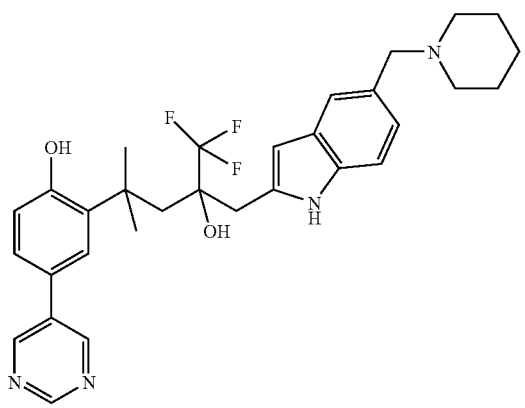 |
| 4-Pyrimidin-5-yl-2-{4,4,4-trifluoro-3-hydroxy-1,1-dimethyl-3-[5-(4-methylpiperazin-1-ylmethyl)-1H-indol-2-ylmethyl]butyl}phenol | 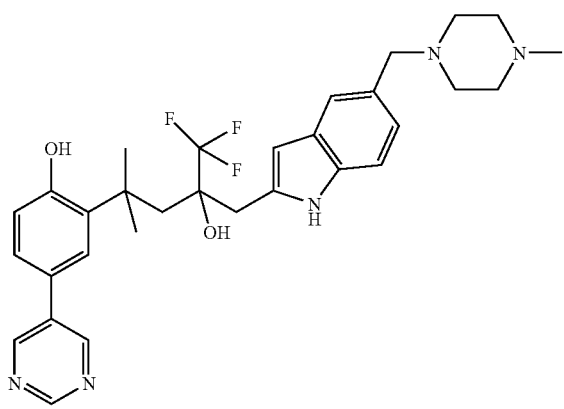 |

| IA | |
|---|---|
| A | B |
2-(3-{5-[(Ethylmethylamino)methyl]-1H-indol-2-ylmethyl}-4,4,4-trifluoro-3-hydroxy-1,1-dimethylbutyl)-4-pyrimidin-5-ylphenol
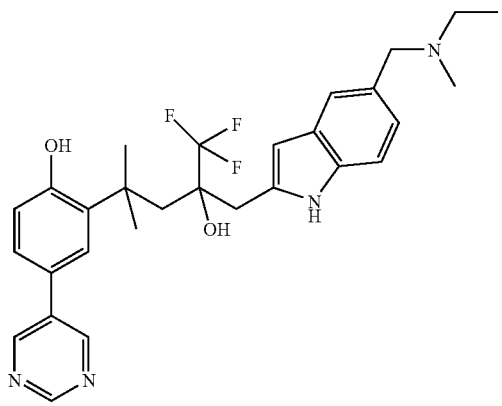 [SMILES: CCN(C)Cc1ccc2[nH]c(CC(O)(CC(C)(C)c3cc(-c4cncnc4)ccc3O)C(F)(F)F)cc2c1]
4-Pyrimidin-5-yl-2-[4,4,4-trifluoro-3-hydroxy-1,1-dimethyl-3-(5-pyrrolidin-1-ylmethyl-1H-indol-2-ylmethyl)butyl]phenol
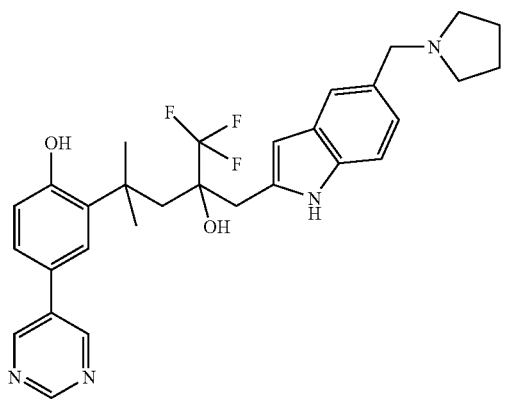 [SMILES: CC(C)(CC(O)(Cc1cc2cc(CN3CCCC3)ccc2[nH]1)C(F)(F)F)c1cc(-c2cncnc2)ccc1O]
2-[3-(5-Dimethylaminomethyl-1H-indol-2-ylmethyl)-4,4,4-trifluoro-3-hydroxy-1,1-dimethylbutyl]-4-pyrimidin-5-ylphenol
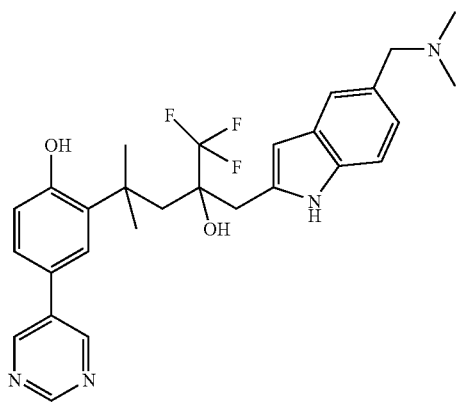 [SMILES: CN(C)Cc1ccc2[nH]c(CC(O)(CC(C)(C)c3cc(-c4cncnc4)ccc3O)C(F)(F)F)cc2c1]

| A | B |
|---|---|
| 2-[3-(5-Diethylaminomethyl-1H-indol-2-ylmethyl)-4,4,4-trifluoro-3-hydroxy-1,1-dimethylbutyl]-4-pyrimidin-5-ylphenol | 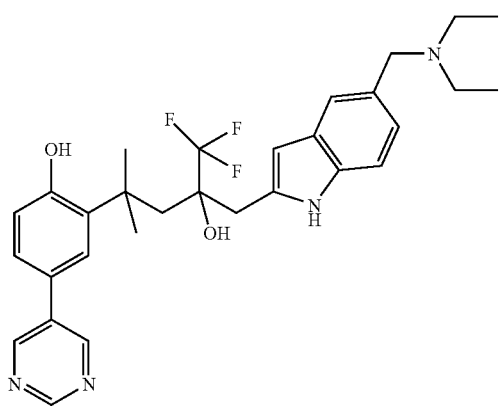 |
| 4-(5-Chloro-2,3-dihydrobenzofuran-7-yl)-1,1,1-trifluoro-4-methyl-2-(4-methyl-1H-pyrrolo[3,2-c]pyridin-2-ylmethyl)pentan-2-ol | 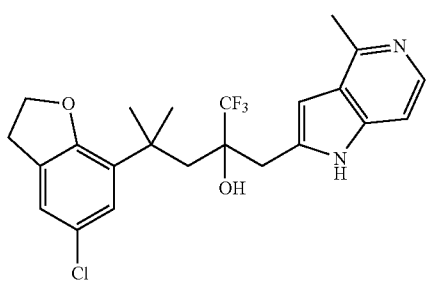 |
| 1,1,1-Trifluoro-4-(5-fluoro-2-methylphenyl)-4-methyl-2-(5-methyl-1H-pyrrolo[2,3-c]pyridin-2-ylmethyl)pentan-2-ol | 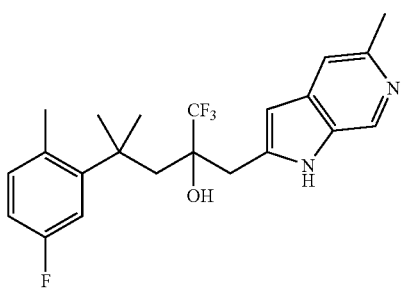 |
| 4-(5-Chloro-2,3-dihydrobenzofuran-7-yl)-1,1,1-trifluoro-4-methyl-2-(5-methyl-1H-pyrrolo[2,3-c]pyridin-2-ylmethyl)pentan-2-ol | 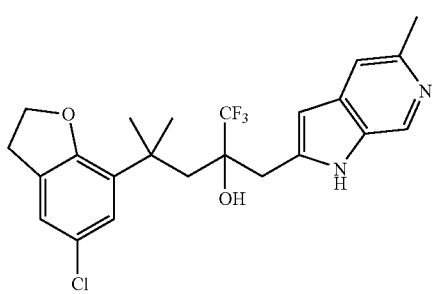 |

| A | B |
|---|---|
| 2-[2-Hydroxy-4-(5-methanesulfonyl-2,3-dihydrobenzofuran-7-yl)-4-methyl-2-trifluoromethylpentyl]-4-methyl-1H-pyrrolo[3,2-c]pyridine-6-carbonitrile | 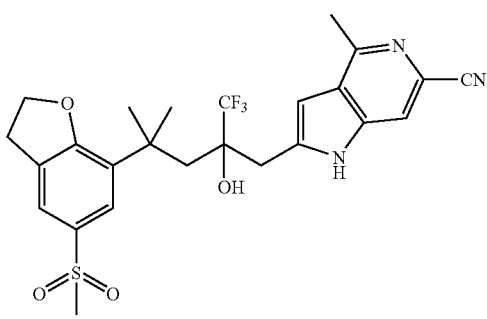 |
| 2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile | 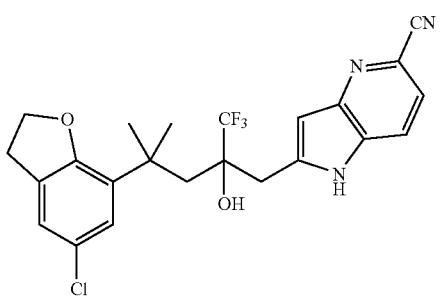 |
| 1,1,1-Trifluoro-4-(5-fluoro-2-methylphenyl)-4-methyl-2-(5H-pyrrolo[3,2-d]pyrimidin-6-ylmethyl)pentan-2-ol | 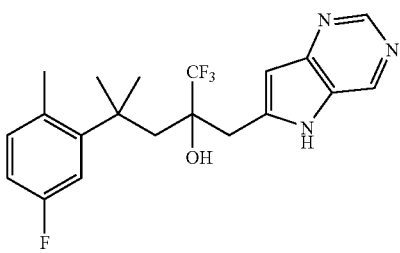 |
| 2-[4-(5-Chloro-2,3-dihydrobenzofuran-7-yl)-2-hydroxy-4-methyl-2-trifluoromethylpentyl]-1H-pyrrolo[2,3-c]pyridine-5-carbonitrile | 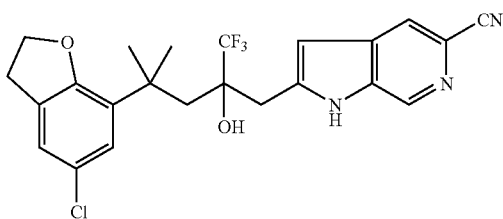 |
| 2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid methyl ester | 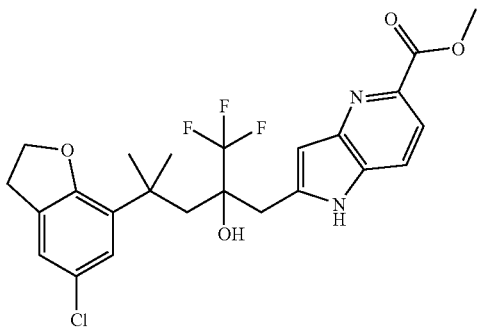 |

IA

| A | B |
|---|---|
| 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}ethanone | 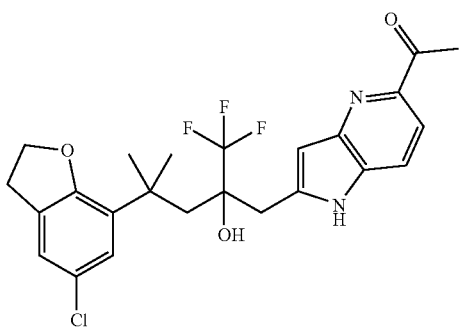 |
| 4-(5-Chloro-2,3-dihydrobenzofuran-7-yl)-1,1,1-trifluoro-4-methyl-2-(6H-pyrrolo[2,3-g]quinoxalin-7-ylmethyl)pentan-2-ol | 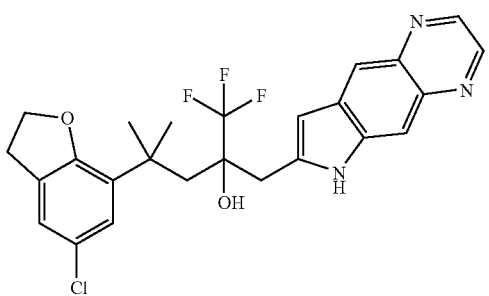 |
| 2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid amide | 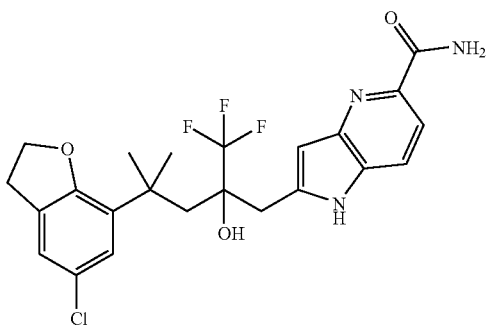 |
| 2-[4-(5-Chloro-2,3-dihydrobenzofuran-7-yl)-2-hydroxy-4-methyl-2-trifluoromethylpentyl]-1H-pyrrolo[3,2-b]pyridine-5-carboxylic acid | 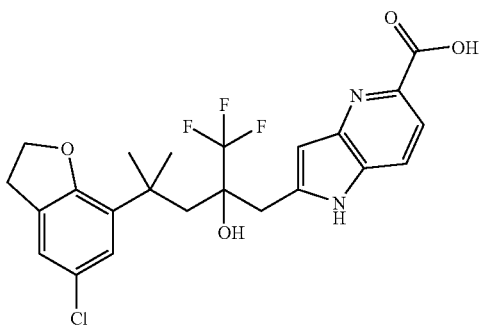 |

-continued

| IA | |
|---|---|
| A | B |
| {2-[4-(5-Chloro-2,3-dihydrobenzofuran-7-yl)-2-hydroxy-4-methyl-2-trifluoromethylpentyl]-1H-pyrrolo[3,2-b]pyridin-5-yl}morpholin-4-ylmethanone | 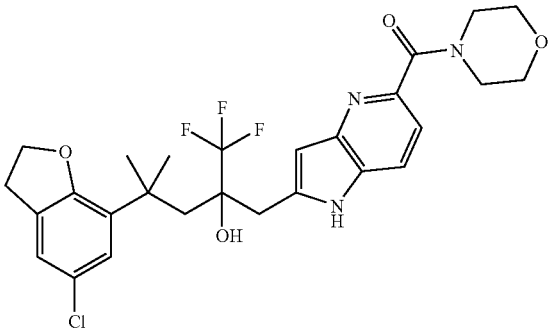 |
| 4-(5-Chloro-2,3-dihydrobenzofuran-7-yl)-1,1,1-trifluoro-2-(5-hydroxymethyl-1H-pyrrolo[3,2-b]pyridin-2-ylmethyl)-4-methylpentan-2-ol | 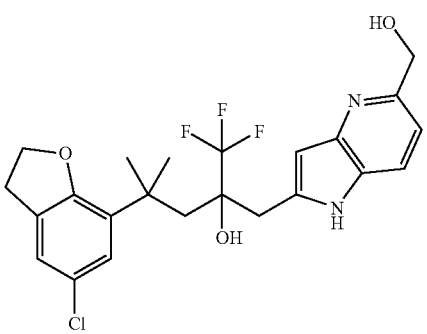 |
| 2-(5-Aminomethyl-1H-pyrrolo[3,2-b]pyridin-2-ylmethyl)-4-(5-chloro-2,3-dihydrobenzofuran-7-yl)-1,1,1-trifluoro-4-methylpentan-2-ol | 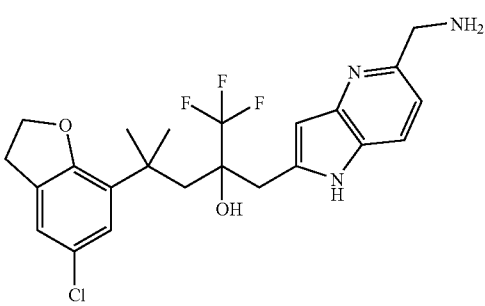 |
| 1,1,1-Trifluoro-4-(5-fluoro-2-methylphenyl)-4-methyl-2-(5H-pyrrolo[3,2-c]pyridazin-6-ylmethyl)pentan-2-ol | 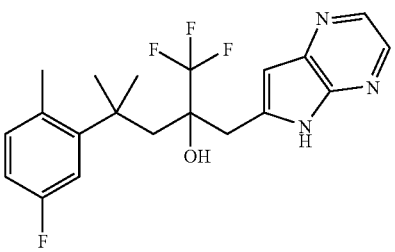 |
| 4-Fluoro-2-[4,4,4-trifluoro-3-hydroxy-1,1-dimethyl-3-(5H-pyrrolo[3,2-c]pyridazin-6-ylmethyl)butyl]phenol | 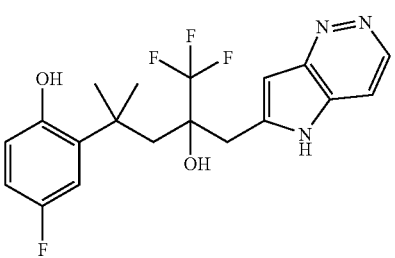 |

-continued

IA

| A | B |
|---|---|
| 4-Fluoro-2-[4,4,4-trifluoro-3-hydroxy-1,1-dimethyl-3-(5H-pyrrolo[3,2-d]pyrimidin-6-ylmethyl)butyl]phenol | 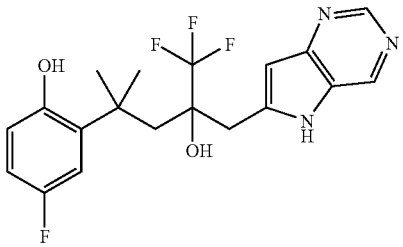 |
| 2-(6-Chloro-1H-pyrrolo[3,2-b]pyridin-2-ylmethyl)-1,1,1-trifluoro-4-(5-fluoro-2-methylphenyl)-4-methylpentan-2-ol | 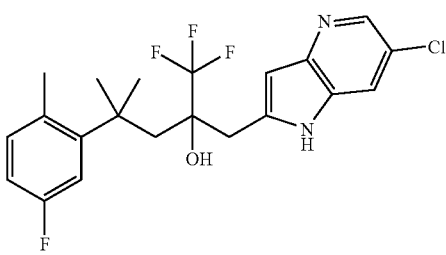 |
| 4-(5-Chloro-2,3-dihydrobenzofuran-7-yl)-2-(6-chloro-1H-pyrrolo[3,2-b]pyridin-2-ylmethyl)-1,1,1-trifluoro-4-methylpentan-2-ol | 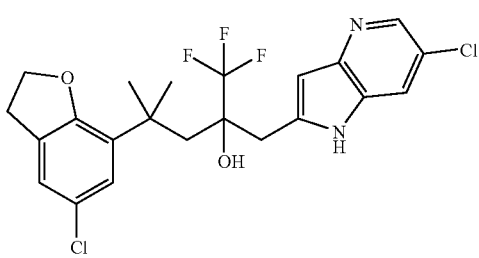 |
| 1,1,1-Trifluoro-4-(4-fluoro-2-methoxyphenyl)-4-methyl-2-(3-methyl-1H-pyrrolo[2,3-c]pyridin-2-ylmethyl)pentan-2-ol | 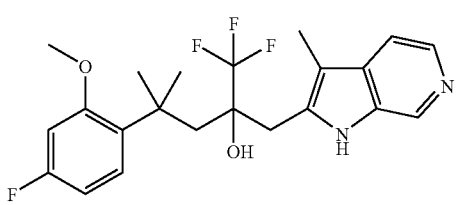 |
| 1,1,1-Trifluoro-4-(3-fluorophenyl)-4-methyl-2-(3-methyl-1H-pyrrolo[2,3-c]pyridin-2-ylmethyl)pentan-2-ol | 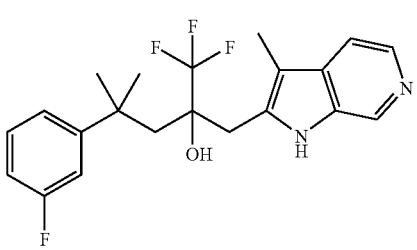 |
| 5-Fluoro-2-[4,4,4-trifluoro-3-hydroxy-1,1-dimethyl-3-(3-methyl-1H-pyrrolo[2,3-c]pyridin-2-ylmethyl)butyl]phenol | 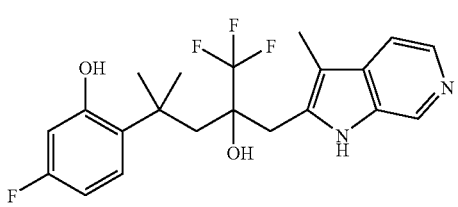 |

-continued

IA

| A | B |
|---|---|
| 4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol | 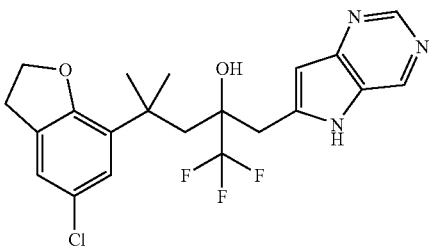 |
| 4-(5-Chloro-2,3-dihydrobenzofuran-7-yl)-1,1,1-trifluoro-4-methyl-2-(3-phenyl-7H-pyrrolo[2,3-c]pyridazin-6-ylmethyl)pentan-2-ol | 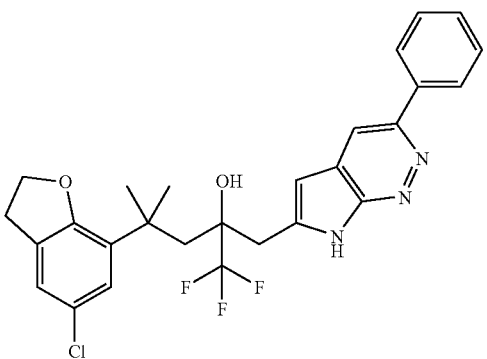 |
| 1,1,1-Trifluoro-4-(5-fluoro-2-methylphenyl)-4-methyl-2-(3-phenyl-7H-pyrrolo[2,3-c]pyridazin-6-ylmethyl)pentan-2-ol | 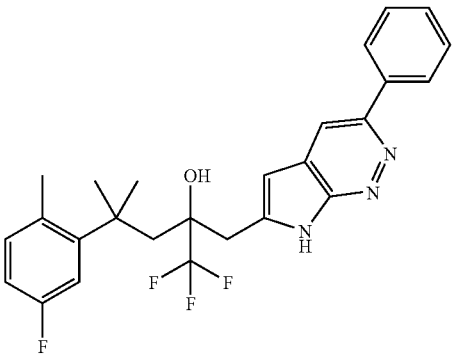 |
| 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2,2-dimethylpropan-1-one | 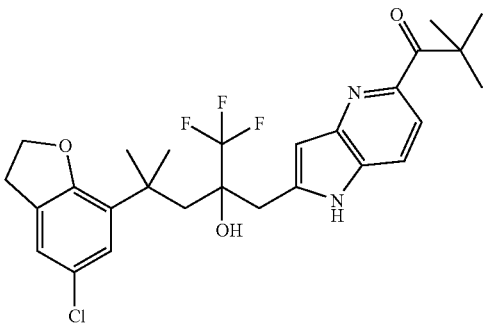 |

-continued

IA

| A | B |
|---|---|
| 2-[5-(1-tert-Butyl-1-hydroxy-2,2-dimethylpropyl)-1H-pyrrolo[3,2-b]pyridin-2-ylmethyl]-4-(5-chloro-2,3-dihydrobenzofuran-7-yl)-1,1,1-trifluoro-4-methylpentan-2-ol | 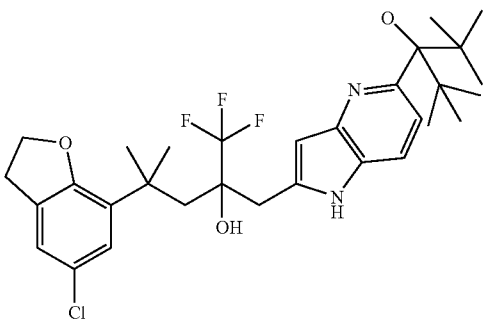 |
| 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}propan-1-one | 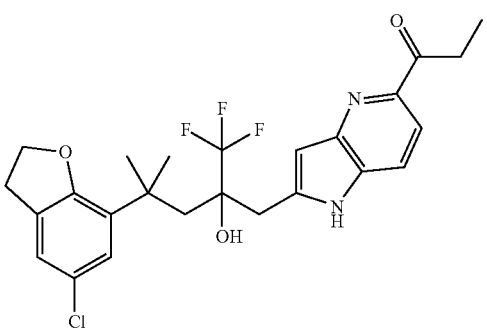 |
| 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2-methylpropan-1-one | 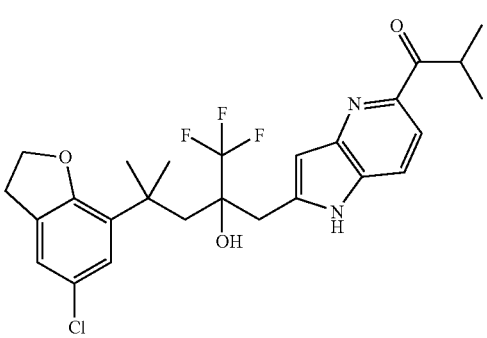 |
| 1,1,1-Trifluoro-4-(4-fluoro-2-methoxyphenyl)-4-methyl-2-(4-methyl-1H-pyrrolo[3,2-c]pyridin-2-ylmethyl)pentan-2-ol | 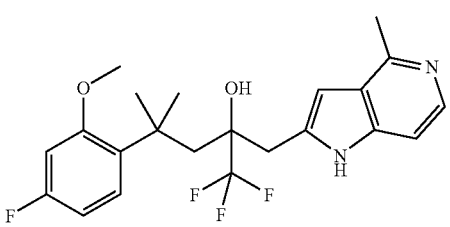 |
| 1,1,1-Trifluoro-4-(2-methoxy-5-thiophen-3-ylphenyl)-4-methyl-2-(4-methyl-1H-pyrrolo[3,2-c]pyridin-2-ylmethyl)pentan-2-ol | 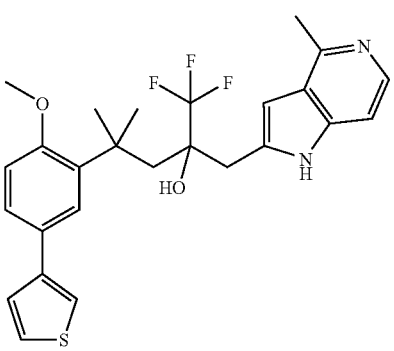 |

| A | B |
|---|---|
| 1,1,1-Trifluoro-4-(4-methoxybiphenyl-3-yl)-4-methyl-2-(4-methyl-1H-pyrrolo[3,2-c]pyridin-2-ylmethyl)pentan-2-ol | 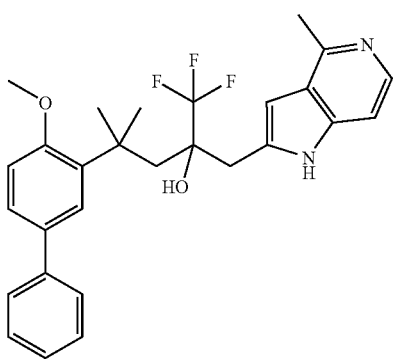 |
| 5-Fluoro-2-[4,4,4-trifluoro-3-hydroxy-1,1-dimethyl-3-(4-methyl-1H-pyrrolo[3,2-c]pyridin-2-ylmethyl)butyl]phenol | 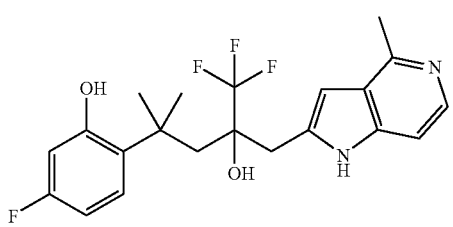 |
| 4-Thiophen-3-yl-2-{4,4,4-trifluoro-3-hydroxy-1,1-dimethyl-3-(4-methyl-1H-pyrrolo[3,2-c]pyridin-2-ylmethyl)butyl]phenol | 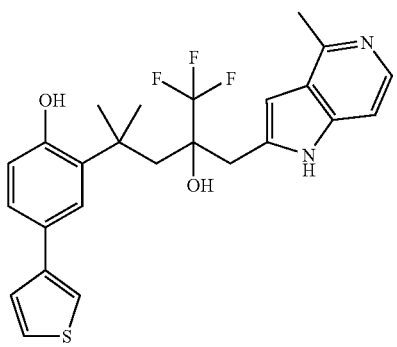 |
| 3-[4,4,4-Trifluoro-3-hydroxy-1,1-dimethyl-3-(4-methyl-1H-pyrrolo[3,2-c]pyridin-2-ylmethyl)butyl]biphenyl-4-ol | 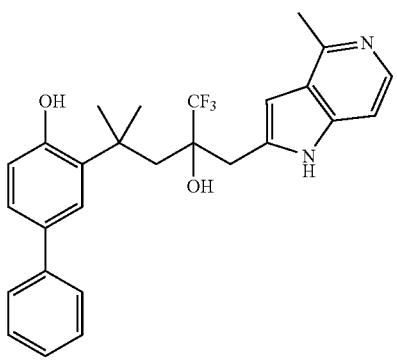 |

IA

| A | B |
|---|---|
| 1,1,1-Trifluoro-4-methyl-2-(3-methyl-1H-pyrrolo[2,3-c]pyridin-2-ylmethyl)-4-(5-pyrimidin-5-yl-2,3-dihydrobenzofuran-7-yl)pentan-2-ol | 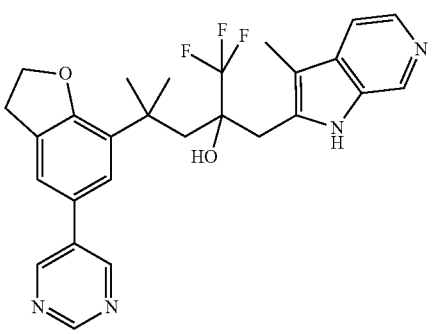 |
| 1,1,1-Trifluoro-4-(2-methoxy-5-pyridin-3-ylphenyl)-4-methyl-2-(3-methyl-1H-pyrrolo[2,3-c]pyridin-2-ylmethyl)pentan-2-ol | 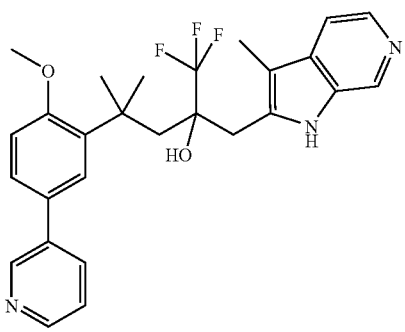 |
| 4-Pyridin-3-yl-2-[4,4,4-trifluoro-3-hydroxy-1,1-dimethyl-3-(3-methyl-1H-pyrrolo[2,3-c]pyridin-2-ylmethyl)butyl]phenol | 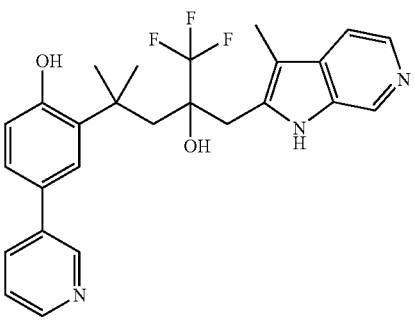 |
| 1,1,1-Trifluoro-4-(5-fluoro-2,3-dihydrobenzofuran-7-yl)-4-methyl-2-(5H-pyrrolo[3,2-d]pyrimidin-6-ylmethyl)pentan-2-ol | 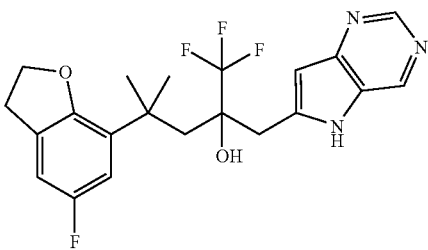 |

| A | B |
|---|---|
| 1,1,1-Trifluoro-4-(2-methoxy-5-pyridin-3-ylphenyl)-4-methyl-2-(5-phenoxy-1H-pyrrolo[2,3-c]pyridin-2-ylmethyl)pentan-2-ol | 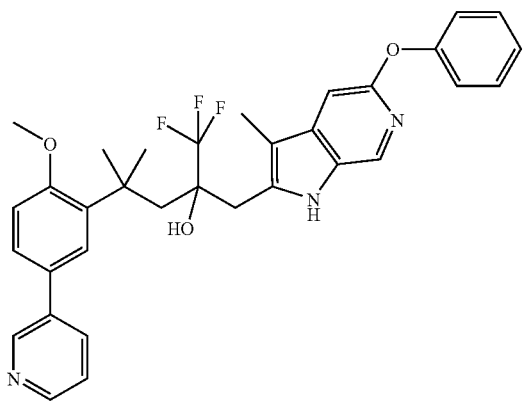 |
| 1,1,1-Trifluoro-4-methyl-4-phenyl-2-(3-phenyl-7H-pyrrolo[2,3-c]pyridazin-6-ylmethyl)pentan-2-ol | 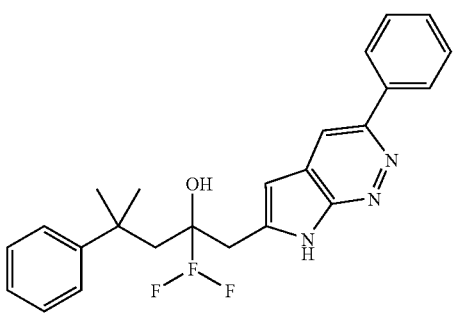 |
| 1,1,1-Trifluoro-4-(3-fluorophenyl)-4-methyl-2-(3-phenyl-7H-pyrrolo[2,3-c]pyridazin-6-ylmethyl)pentan-2-ol | 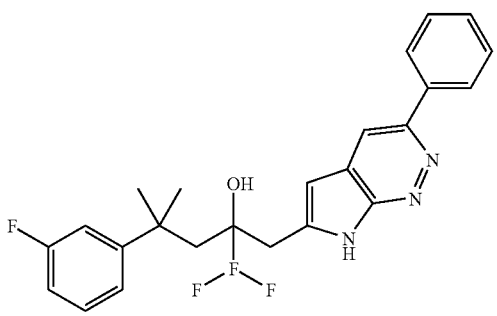 |
| 4-Pyridin-3-yl-2-[4,4,4-trifluoro-3-hydroxy-1,1-dimethyl-3-(5-phenoxy-1H-pyrrolo[2,3-c]pyridin-2-ylmethyl)butyl]phenol | 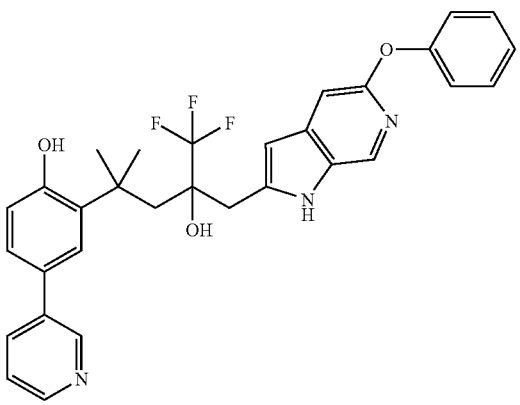 |

| A | B |
|---|---|
| 1,1,1-Trifluoro-4-methyl-2-(4-methyl-1H-pyrrolo[3,2-c]pyridin-2-ylmethyl)-4-(5-pyrimidin-5-yl-2,3-dihydrobenzofuran-7-yl)pentan-2-ol | 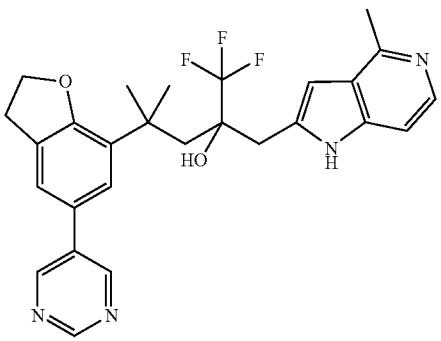 |
| 4-Pyridin-3-yl-2-[4,4,4-trifluoro-3-hydroxy-1,1-dimethyl-3-(4-methyl-1H-pyrrolo[3,2-c]pyridin-2-ylmethyl)butyl]phenol | 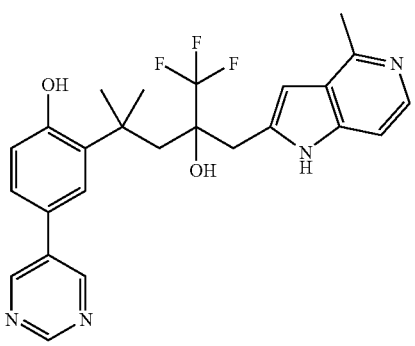 |
| 5-Fluoro-2-[4,4,4-trifluoro-3-hydroxy-1,1-dimethyl-3-(5H-pyrrolo[3,2-d]pyrimidin-6-ylmethyl)butyl]phenol | 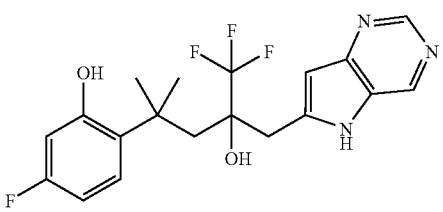 |
| 1,1,1-Trifluoro-4-methyl-4-(3-morpholin-4-ylmethylphenyl)-2-(5-phenyl-1H-pyrrolo[2,3-c]pyridin-2-ylmethyl)pentan-2-ol | 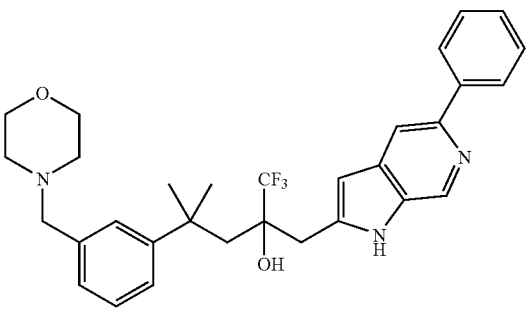 |

-continued
IA
| A | B |
|---|---|
| 1,1,1-Trifluoro-4-(3-fluorophenyl)-2-[5-(4-fluorophenyl)-1H-pyrrolo[2,3-c]pyridin-2-ylmethyl]-4-methylpentan-2-ol | 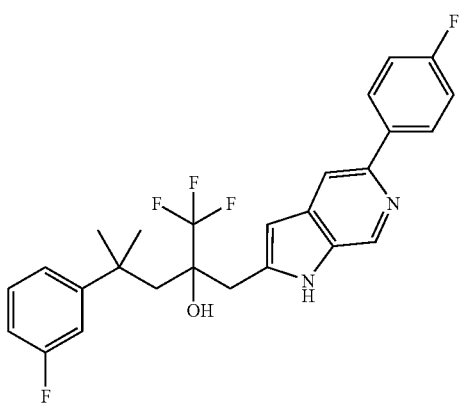 |
| 1,1,1-Trifluoro-4-methyl-2-(5-phenyl-1H-pyrrolo[2,3-c]pyridin-2-ylmethyl)-4-(5-pyridin-3-yl-2,3-dihydrobenzofuran-7-yl)pentan-2-ol | 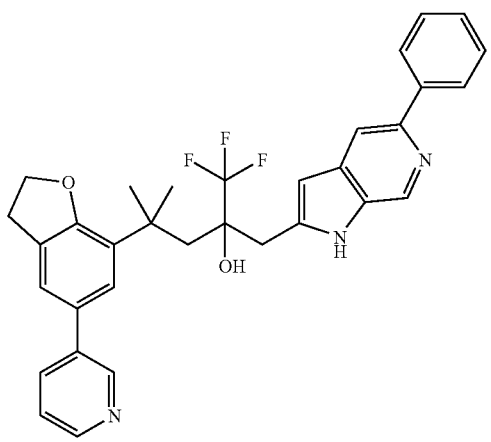 |
| 1,1,1-Trifluoro-4-methyl-2-(5-phenyl-1H-pyrrolo[2,3-c]pyridin-2-ylmethyl)-4-(5-pyrimidin-5-yl-2,3-dihydrobenzofuran-7-yl)pentan-2-ol | 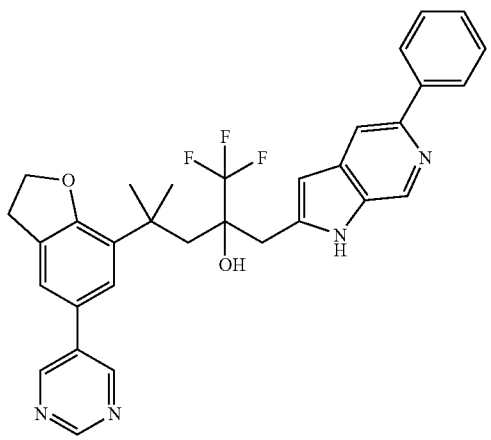 |

-continued

| IA | |
|---|---|
| A | B |

1,1,1-Trifluoro-4-(5-fluoro-2-methylphenyl)-4-methyl-2-(5-piperidin-1-yl-1H-pyrrolo[3,2-b]pyridin-2-ylmethyl)pentan-2-ol

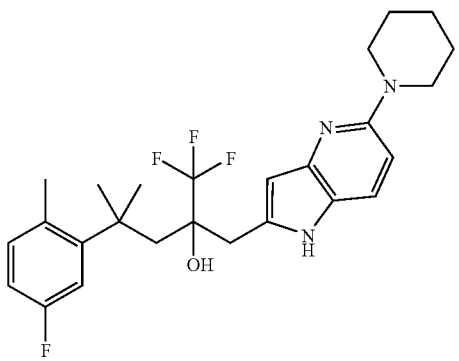 [SMILES: Cc1ccc(F)cc1C(C)(C)CC(O)(Cc1cc2nc(N3CCCCC3)ccc2[nH]1)C(F)(F)F]

1,1,1-Trifluoro-4-(5-fluoro-2-methylphenyl)-4-methyl-2-(5-morpholin-4-yl-1H-pyrrolo[3,2-b]pyridin-2-ylmethyl)pentan-2-ol

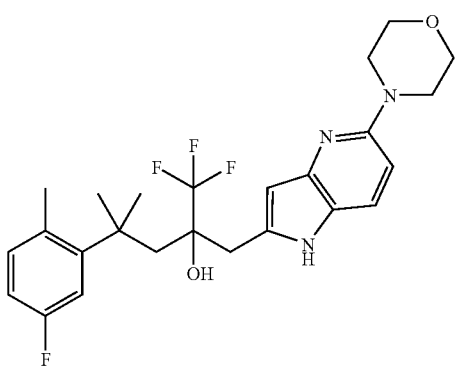 [SMILES: Cc1ccc(F)cc1C(C)(C)CC(O)(Cc1cc2nc(N3CCOCC3)ccc2[nH]1)C(F)(F)F]

2-(5-Dimethylamino-1H-pyrrolo[3,2-b]pyridin-2-ylmethyl)-1,1,1-trifluoro-4-(5-fluoro-2-methylphenyl)-4-methylpentan-2-ol

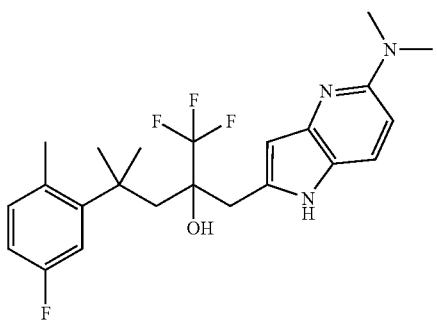 [SMILES: Cc1ccc(F)cc1C(C)(C)CC(O)(Cc1cc2nc(N(C)C)ccc2[nH]1)C(F)(F)F]

1,1,1-Trifluoro-4-(5-fluoro-2-methylphenyl)-4-methyl-2-(5-phenyl-1H-pyrrolo[3,2-b]pyridin-2-ylmethyl)pentan-2-ol

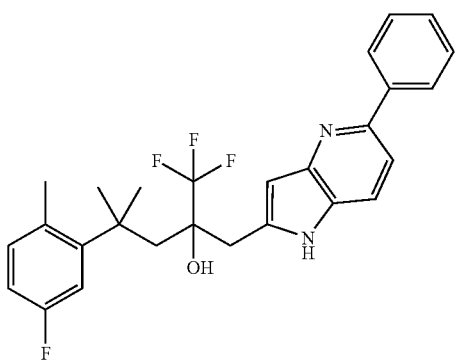 [SMILES: Cc1ccc(F)cc1C(C)(C)CC(O)(Cc1cc2nc(-c3ccccc3)ccc2[nH]1)C(F)(F)F]

-continued

IA

| A | B |
|---|---|
| 1,1,1-Trifluoro-4-(5-fluoro-2-methylphenyl)-2-(5-isopropoxy-1H-pyrrolo[3,2-b]pyridin-2-ylmethyl)-4-methylpentan-2-ol | 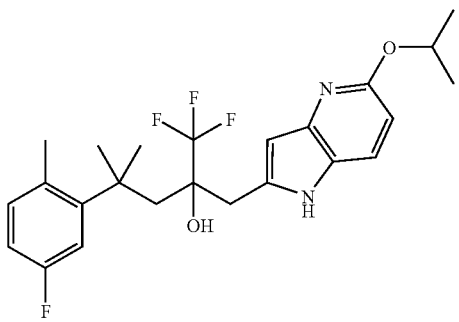 |
| 1,1,1-Trifluoro-4-(5-fluoro-2-methylphenyl)-4-methyl-2-(5-pyridin-2-yl-1H-pyrrolo[2,3-c]pyridin-2-ylmethyl)pentan-2-ol | 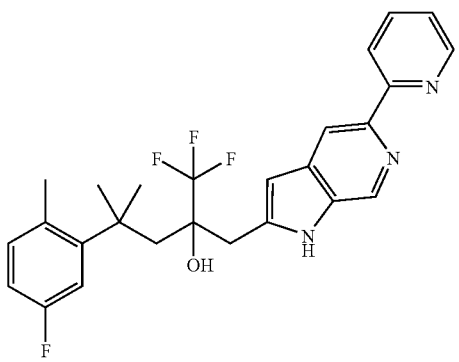 |
| 1,1,1-Trifluoro-4-(5-fluoro-2-methylphenyl)-4-methyl-2-(5-pyridin-3-yl-1H-pyrrolo[2,3-c]pyridin-2-ylmethyl)pentan-2-ol | 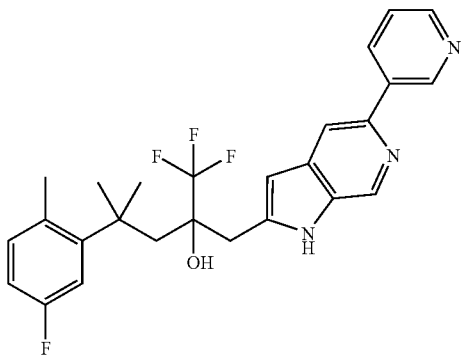 |
| 1,1,1-Trifluoro-4-(5-fluoro-2-methylphenyl)-4-methyl-2-(5-pyridin-4-yl-1H-pyrrolo[2,3-c]pyridin-2-ylmethyl)pentan-2-ol | 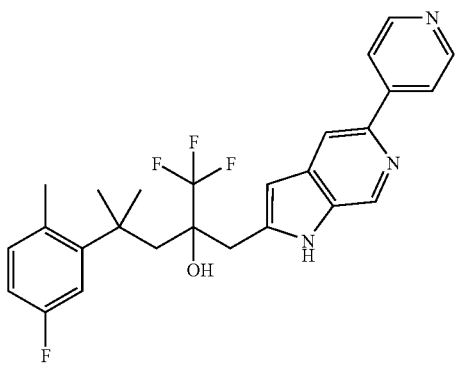 |

| A | B |
|---|---|
| 1-{2-[4-(5-Fluoro-2-methoxyphenyl)-2-hydroxy-4-methyl-2-trifluoromethylpentyl]-1H-pyrrolo[3,2-b]pyridin-5-yl}-2-methylpropan-1-one | 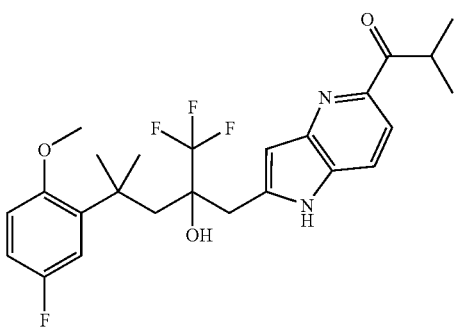 |
| 1-{2-[4-(5-Fluoro-2-hydroxyphenyl)-2-hydroxy-4-methyl-2-trifluoromethylpentyl]-1H-pyrrolo[3,2-bP]pyridin-5-yl}-2-methylpropan-1-one | 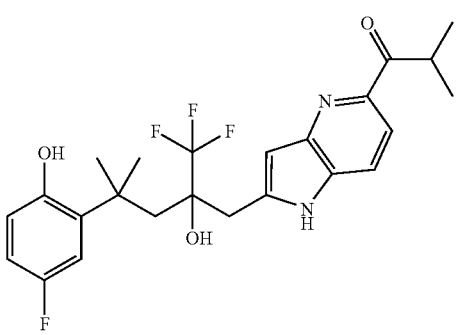 |
| 1-{2-[4-(5-Chloro-2,3-dihydrobenzofuran-7-yl)-2-hydroxy-4-methyl-2-trifluoromethylpentyl]-1H-pyrrolo[3,2-b]pyridin-5-yl}-2-hydroxyethanone | 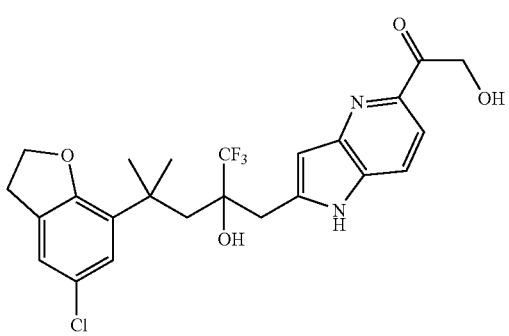 |
| 5-(5-Fluoro-2-methoxyphenyl)-5-methyl-1-(1H-pyrrolo[2,3-c]pyridin-2-yl)-3-trifluoromethylhexan-3-ol | 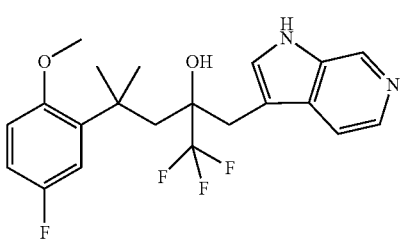 |
| 2-(5-Dimethylamino-1H-pyrrolo[2,3-c]pyridin-2-ylmethyl)-1,1,1-trifluoro-4-(5-fluoro-2-methoxyphenyl)-4-methylpentan-2-ol | 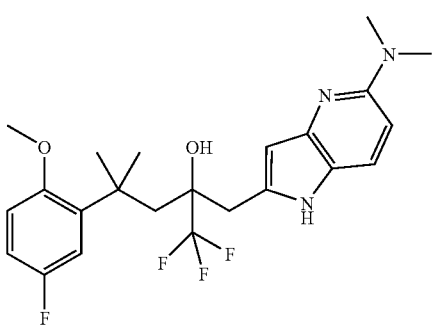 |

-continued

| IA | |
|---|---|
| A | B |

2-(5-Dimethylamino-1H-pyrrolo[2,3-c]pyridin-2-ylmethyl)-1,1,1-trifluoro-4-(4-fluoro-2-methoxyphenyl)-4-methylpentan-2-ol

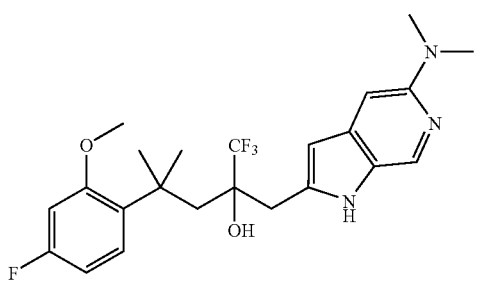 [SMILES: COc1cc(F)ccc1C(C)(C)CC(O)(Cc1cc2cc(N(C)C)ncc2[nH]1)C(F)(F)F]

1,1,1-Trifluoro-4-(3-fluorophenyl)-4-methyl-2-(4-methyl-1H-pyrrolo[2,3-c]pyridin-2-ylmethyl)pentan-2-ol

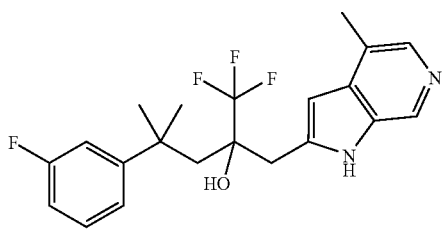 [SMILES: Cc1cncc2[nH]c(CC(O)(CC(C)(C)c3cccc(F)c3)C(F)(F)F)cc12]

1,1,1-Trifluoro-4-(4-fluoro-2-methoxyphenyl)-4-methyl-2-(4-methyl-1H-pyrrolo[2,3-c]pyridin-2-ylmethyl)pentan-2-ol

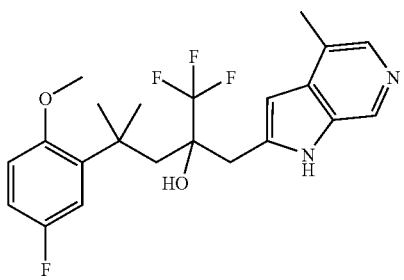 [SMILES: COc1ccc(F)cc1C(C)(C)CC(O)(Cc1cc2c(C)cncc2[nH]1)C(F)(F)F]

2-[3-(5-Dimethylamino-1H-pyrrolo[2,3-c]pyridin-2-ylmethyl)-4,4,4-trifluoro-3-hydroxy-1,1-dimethylbutyl]-4-fluorophenol

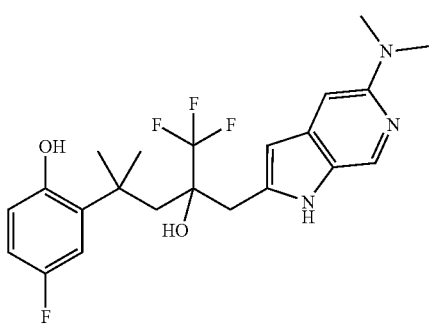 [SMILES: CN(C)c1cc2cc(CC(O)(CC(C)(C)c3cc(F)ccc3O)C(F)(F)F)[nH]c2cn1]

2-[3-(5-Dimethylamino-1H-pyrrolo[2,3-c]pyridin-2-ylmethyl)-4,4,4-trifluoro-3-hydroxy-1,1-dimethylbutyl]-5-fluorophenol

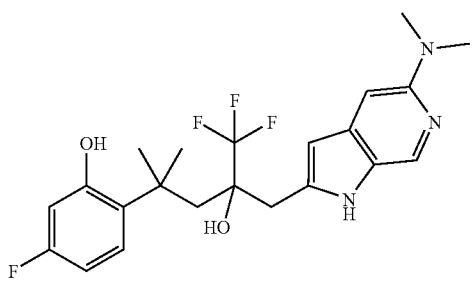 [SMILES: CN(C)c1cc2cc(CC(O)(CC(C)(C)c3ccc(F)cc3O)C(F)(F)F)[nH]c2cn1]

-continued

| A | B |
|---|---|
| 5-Fluoro-2-[4,4,4-trifluoro-3-hydroxy-1,1-dimethyl-3-(4-methyl-1H-pyrrolo[2,3-c]pyridin-2-ylmethyl)butyl]phenol | 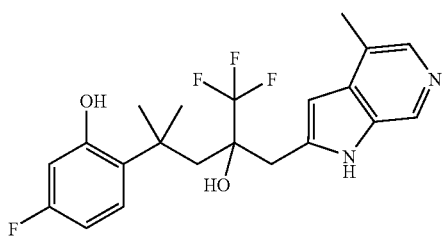 |
| 4-(5-Bromo-2-methoxyphenyl)-1,1,1-trifluoro-4-methyl-2-(1H-pyrrolo[2,3-c]pyridin-2-ylmethyl)pentan-2-ol | 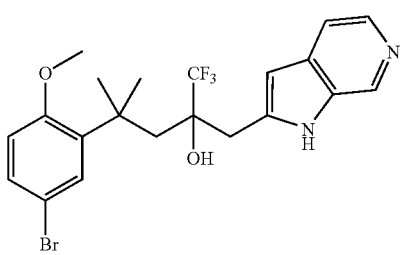 |
| 4-Bromo-2-[4,4,4-trifluoro-3-hydroxy-1,1-dimethyl-3-(1H-pyrrolo[2,3-c]pyridin-2-ylmethyl)butyl]phenol | 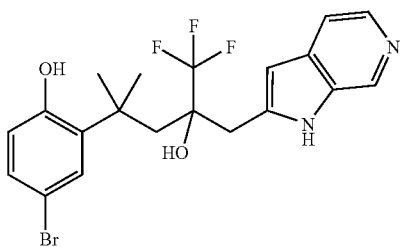 |
| 1,1,1-Trifluoro-4-(2-methoxy-5-pyrimidin-5-ylphenyl)-4-methyl-2-(1H-pyrrolo[2,3-c]pyridin-2-ylmethyl)pentan-2-ol | 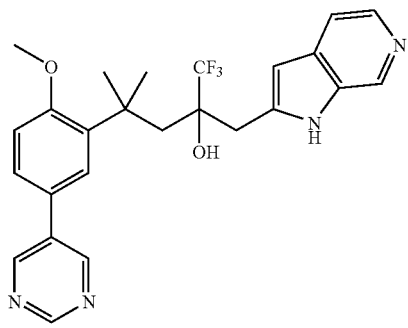 |
| 4-(3-[1,3]Dioxan-2-ylphenyl)-1,1,1-trifluoro-4-methyl-2-(1H-pyrrolo[2,3-c]pyridin-2-ylmethyl)pentan-2-ol | 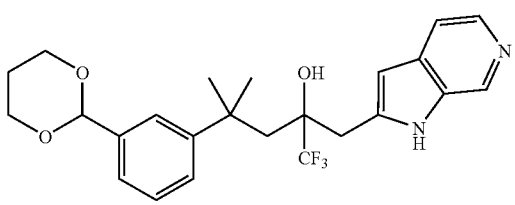 |

-continued

IA

| A | B |
|---|---|
| 1,1,1-Trifluoro-4-(4-methoxybiphenyl-3-yl)-4-methyl-2-(1H-pyrrolo[2,3-c]pyridin-2-ylmethyl)pentan-2-ol | 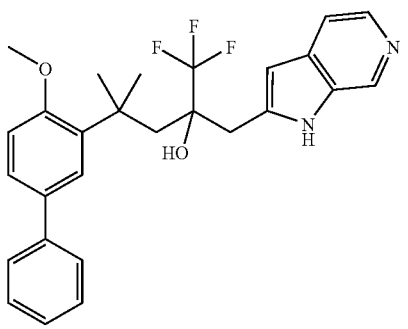 |
| 1,1,1-Trifluoro-4-(2-methoxy-5-pyridin-3-ylphenyl)-4-methyl-2-(1H-pyrrolo[2,3-c]pyridin-2-ylmethyl)pentan-2-ol | 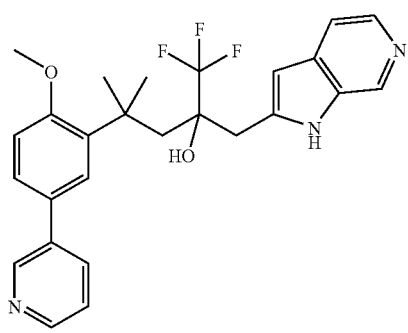 |
| 1,1,1-Trifluoro-4-(2-methoxy-5-thiophen-3-ylphenyl)-4-methyl-2-(1H-pyrrolo[2,3-c]pyridin-2-ylmethyl)pentan-2-ol | 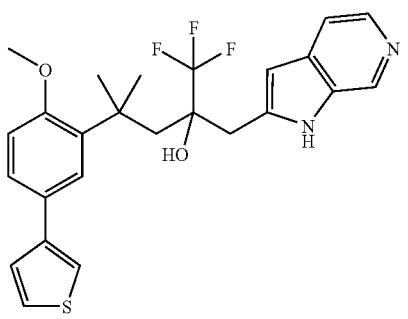 |
| 1,1,1-Trifluoro-4-methyl-4-(3-morpholin-4-ylmethylphenyl)-2-(1H-pyrrolo[2,3-c]pyridin-2-ylmethyl)pentan-2-ol | 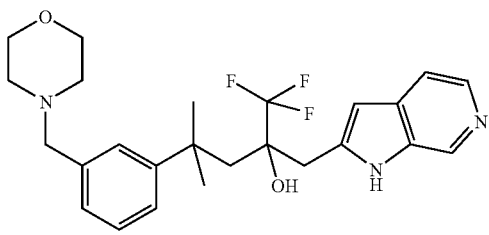 |
| 3-[4,4,4-Trifluoro-3-hydroxy-1,1-dimethyl-3-(1H-pyrrolo[2,3-c]pyridin-2-ylmethyl)butyl]biphenyl-4-ol | 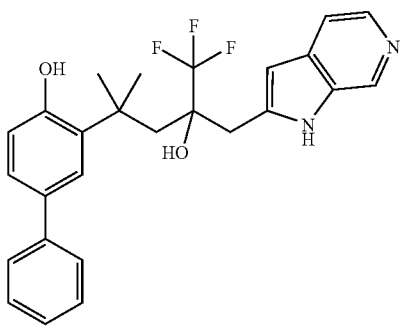 |

-continued

IA

| A | B |
|---|---|
| 4-Thiophen-3-yl-2-[4,4,4-trifluoro-3-hydroxy-1,1-dimethyl-3-(1H-pyrrolo[2,3-c]pyridin-2-ylmethyl)butyl]phenol | 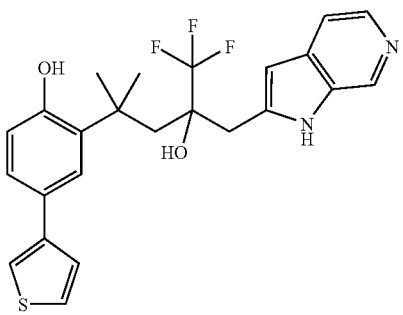 |
| 4-Thiophen-3-yl-2-[4,4,4-trifluoro-3-hydroxy-1,1-dimethyl-3-(1H-pyrrolo[2,3-c]pyridin-2-ylmethyl)butyl]phenol | 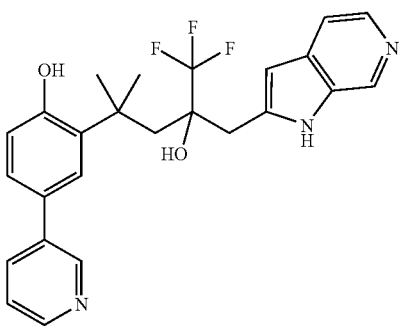 |
| 4-Thiophen-3-yl-2-[4,4,4-trifluoro-3-hydroxy-1,1-dimethyl-3-(1H-pyrrolo[2,3-c]pyridin-2-ylmethyl)butyl]phenol | 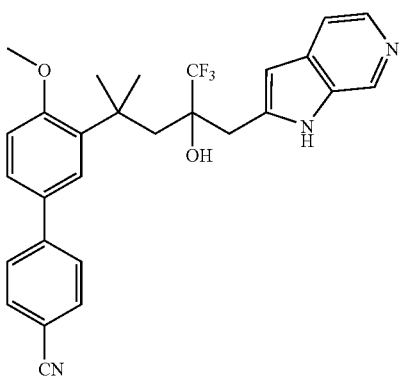 |
| '-Methoxy-3'-[4,4,4-trifluoro-3-hydroxy-1,1-dimethyl-3-(4-methyl-1H-pyrrolo[2,3-c]pyridin-2-ylmethyl)butyl]biphenyl-2-carbonitrile | 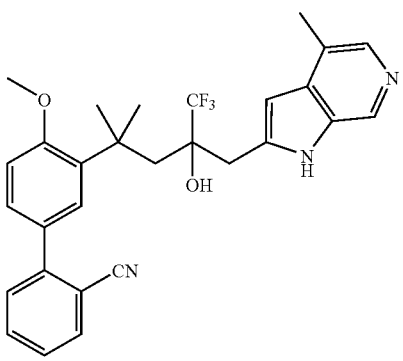 |

-continued

IA

| A | B |
|---|---|
| 4'-Methoxy-3'-[4,4,4-trifluoro-3-hydroxy-1,1-dimethyl-3-(1H-pyrrolo[2,3-c]pyridin-2-ylmethyl)butyl]biphenyl-3-carbonitrile | 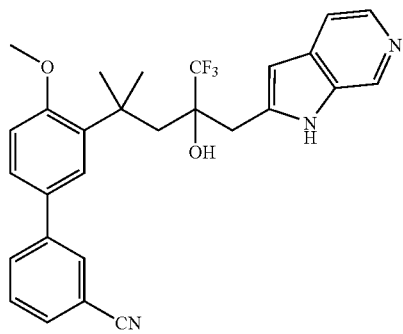 |
| 1,1,1-Trifluoro-4-(2-methoxy-5-pyridin-3-ylphenyl)-4-methyl-2-(4-methyl-1H-pyrrolo[2,3-c]pyridin-2-ylmethyl)pentan-2-ol | 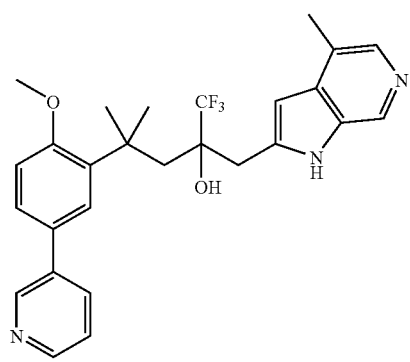 |
| 4-(3-Chlorophenyl)-1,1,1-trifluoro-4-methyl-2-(1H-pyrrolo[3,2-c]pyridin-2-ylmethyl)pentan-2-ol | 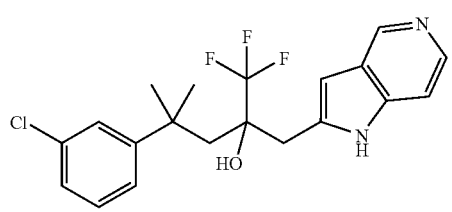 |
| 1,1,1-Trifluoro-4-(2-methoxy-5-pyrimidin-5-ylphenyl)-4-methyl-2-(1H-pyrrolo[3,2-c]pyridin-2-ylmethyl)pentan-2-ol | 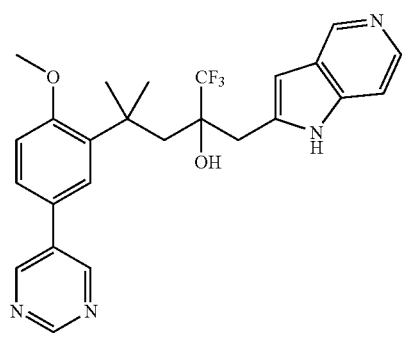 |

| IA | |
|---|---|
| A | B |
| 4-Pyridin-3-yl-2-[4,4,4-trifluoro-3-hydroxy-1,1-dimethyl-3-(1H-pyrrolo[3,2-c]pyridin-2-ylmethyl)butyl]phenol | 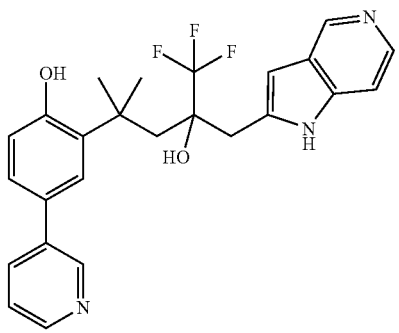 |
| 1,1,1-Trifluoro-4-methyl-4-(3-morpholin-4-ylmethylphenyl)-2-(1H-pyrrolo]3,2-c]pyridin-2-ylmethyl)pentan-2-ol | 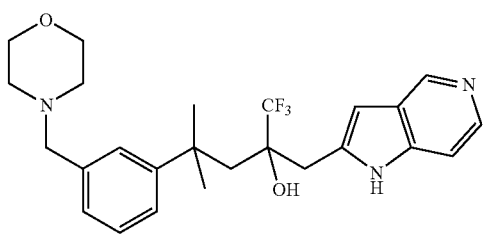 |
| 1,1,1-Trifluoro-4-methyl-2-(4-methyl-1H-pyrrolo]2,3-c]pyridin-2-ylmethyl)-4-(3-morpholin-4-ylmethylphenyl)pentan-2-ol | 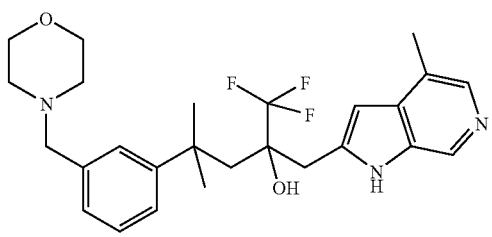 |
| 1,1,1-Trifluoro-4-(2-methoxy-5-pyridin-3-ylphenyl)-4-methyl-2-(1H-pyrrolo[3,2-c]pyridin-2-ylmethyl)pentan-2-ol | 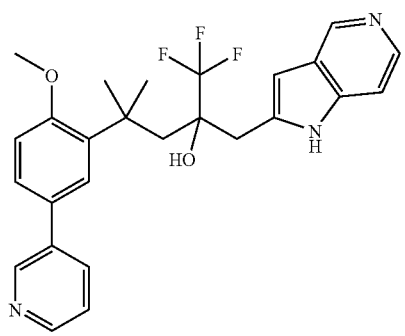 |
| 1,1,1-Trifluoro-4-methyl-4-(3-pyridin-3-ylphenyl)-2-(1H-pyrrolo[3,2-c]pyridin-2-ylmethyl)pentan-2-ol | 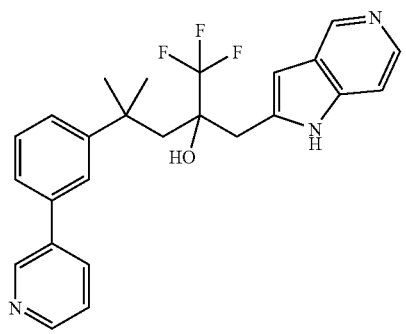 |

-continued
| IA | |
|---|---|
| A | B |
1,1,1-Trifluoro-4-methyl-4-(3-pyrimidin-5-ylphenyl)-2-(1H-pyrrolo[3,2-c]pyridin-2-ylmethyl)pentan-2-ol
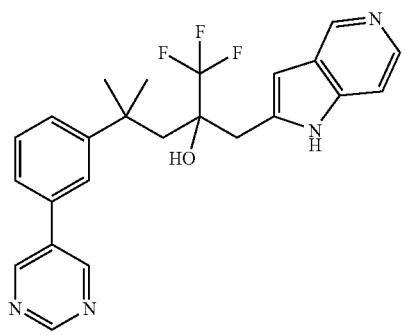 [SMILES: CC(C)(CC(O)(Cc1cc2cnccc2[nH]1)C(F)(F)F)c1cccc(-c2cncnc2)c1]
1,1,1-Trifluoro-4-methyl-4-(3-pyridin-3-ylphenyl)-2-(1H-pyrrolo[2,3-c]pyridin-2-ylmethyl)pentan-2-ol
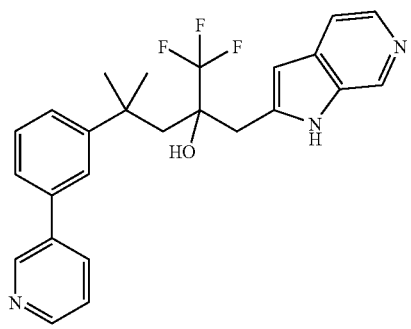 [SMILES: CC(C)(CC(O)(Cc1cc2ccncc2[nH]1)C(F)(F)F)c1cccc(-c2cccnc2)c1]
1,1,1-Trifluoro-4-methyl-4-(3-pyrimidin-5-ylphenyl)-2-(1H-pyrrolo[2,3-c]pyridin-2-ylmethyl)pentan-2-ol
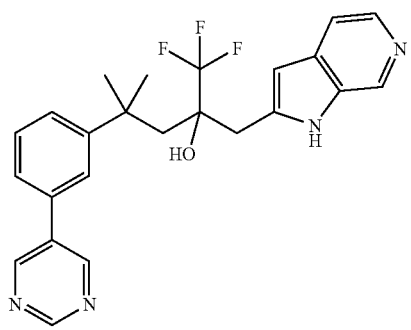 [SMILES: CC(C)(CC(O)(Cc1cc2ccncc2[nH]1)C(F)(F)F)c1cccc(-c2cncnc2)c1]
4-Biphenyl-3-yl-1,1,1-trifluoro-4-methyl-2-(1H-pyrrolo[2,3-c]pyridin-2-ylmethyl)pentan-2-ol
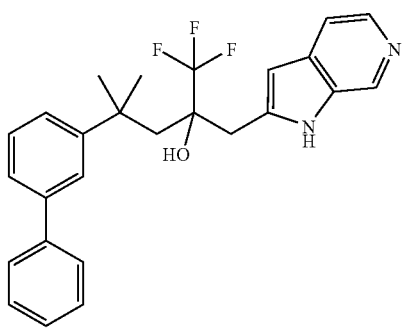 [SMILES: CC(C)(CC(O)(Cc1cc2ccncc2[nH]1)C(F)(F)F)c1cccc(-c2ccccc2)c1]

| A | B |
|---|---|
| 4-Biphenyl-3-yl-1,1,1-trifluoro-4-methyl-2-(1H-pyrrolo[3,2-c]pyridin-2-ylmethyl)pentan-2-ol | 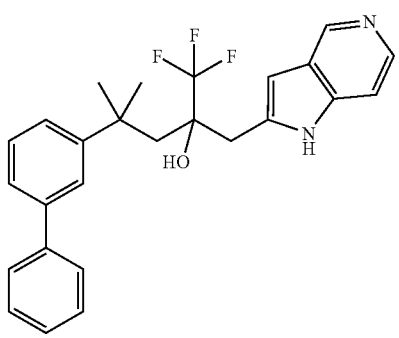 |
| 1,1,1-Trifluoro-4-methyl-4-(3-morpholin-4-ylphenyl)-2-(1H-pyrrolo[2,3-c]pyridin-2-ylmethyl)pentan-2-ol | 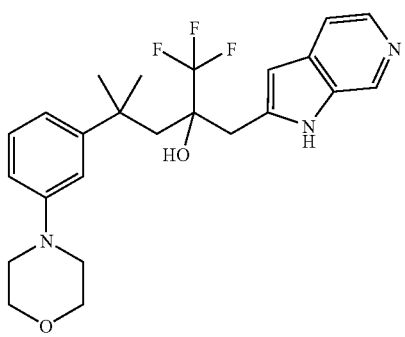 |
| 1,1,1-Trifluoro-4-methyl-4-(3-morpholin-4-ylphenyl)-2-(1H-pyrrolo[3,2-c]pyridin-2-ylmethyl)pentan-2-ol | 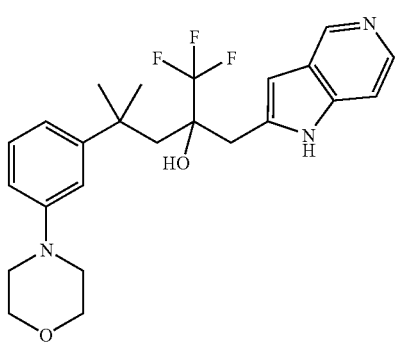 |
| 4-(3-Chlorophenyl)-1,1,1-trifluoro-4-methyl-2-(1H-pyrrolo[2,3-c]pyridin-2-ylmethyl)pentan-2-ol | 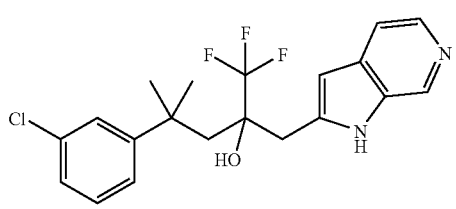 |
| 4-(3-Chlorophenyl)-1,1,1-trifluoro-4-methyl-2-(4-methyl-1H-pyrrolo[2,3-c]pyridin-2-ylmethyl)pentan-2-ol | 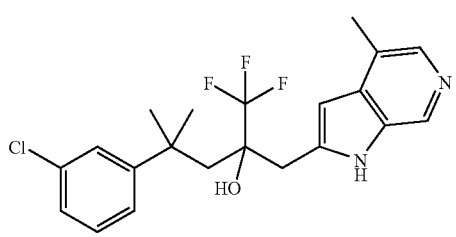 |

-continued

IA

| A | B |
|---|---|
| 1,1,1-Trifluoro-4-methyl-4-(3-piperidin-1-ylphenyl)-2-(1H-pyrrolo[2,3-c]pyridin-2-ylmethyl)pentan-2-ol | 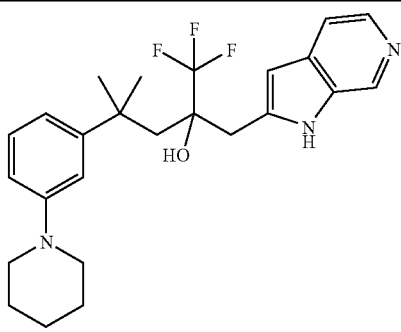 |
| 1,1,1-Trifluoro-4-methyl-4-(3-piperidin-1-ylphenyl)-2-(1H-pyrrolo[3,2-c]pyridin-2-ylmethyl)pentan-2-ol | 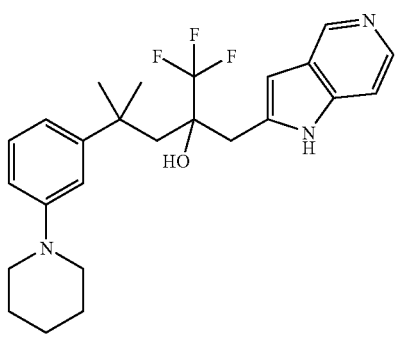 |
| 4-(5-Chloro-2,3-dihydrobenzofuran-7-yl)-1,1,1-trifluoro-4-methyl-2-(5-pyridin-2-yl-1H-indol-2-ylmethyl)pentan-2-ol | 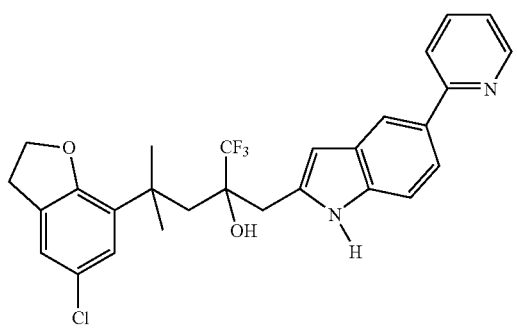 |
| 2-(5-Bromo-1H-indol-2-ylmethyl)-4-(5-chloro-2,3-dihydrobenzofuran-7-yl)-1,1,1-trifluoro-4-methylpentan-2-ol | 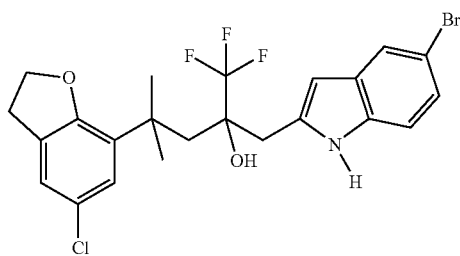 |
| 1,1,1-Trifluoro-4-(5-fluoro-2,3-dihydrobenzofuran-7-yl)-2-(5-methanesulfinyl-1H-indol-2-ylmethyl)-4-methylpentan-2-ol | 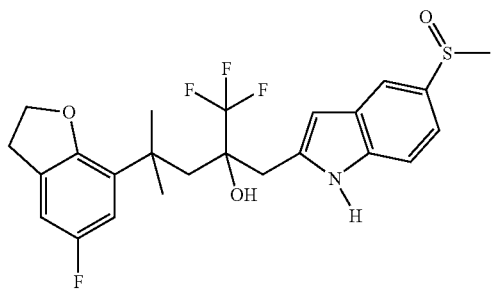 |

-continued

IA

| A | B |
|---|---|
| 7-[3-(5-Bromo-1H-indol-2-ylmethyl)-4,4,4-trifluoro-3-hydroxy-1,1-dimethylbutyl]-2,3-dihydrobenzofuran-5-sulfonic acid amide | 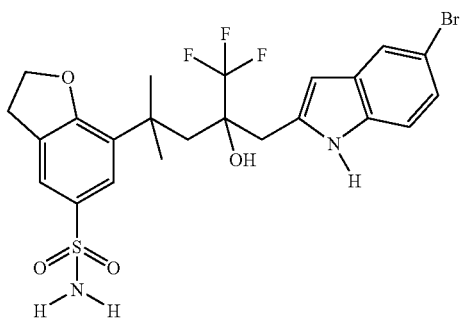 |
| 7-[3-(5-Bromo-1H-indol-2-ylmethyl)-4,4,4-trifluoro-3-hydroxy-1,1-dimethylbutyl]-2,3-dihydrobenzofuran-5-sulfonic acid dimethylamide | 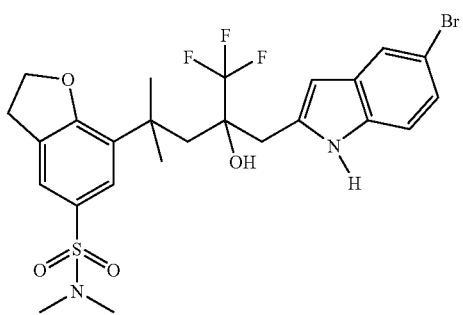 |
| 2-(1-Benzenesulfonyl-5-pyridin-3-yl-1H-indol-2-ylmethyl)-1,1,1-trifluoro-4-(5-fluoro-2,3-dihydrobenzofuran-7-yl)-4-methylpentan-2-ol | 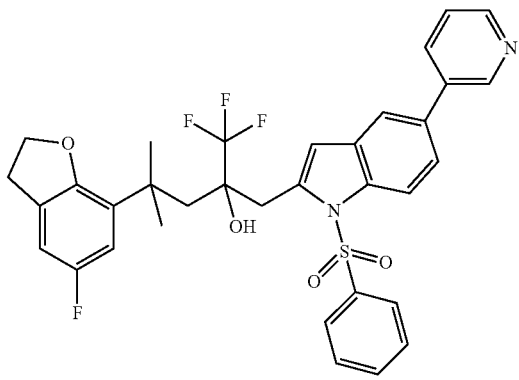 |
| 3-{2-[4-(5-Fluoro-2,3-dihydrobenzofuran-7-yl)-2-hydroxy-4-methyl-2-trifluoromethylpentyl]-1H-indol-5-yl}benzonitrile | 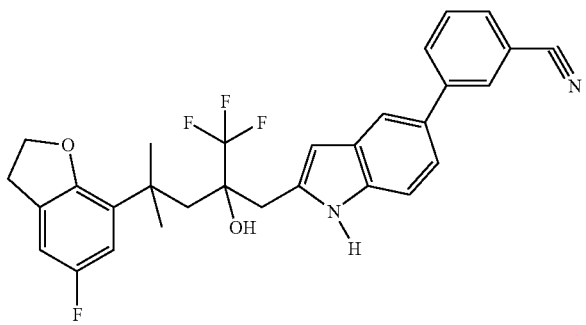 |

-continued

IA

| A | B |
|---|---|
| 1,1,1-Trifluoro-4-(5-fluoro-2,3-dihydrobenzofuran-7-yl)-4-methyl-2-(5-pyridin-4-yl-1H-indol-2-ylmethyl)pentan-2-ol | 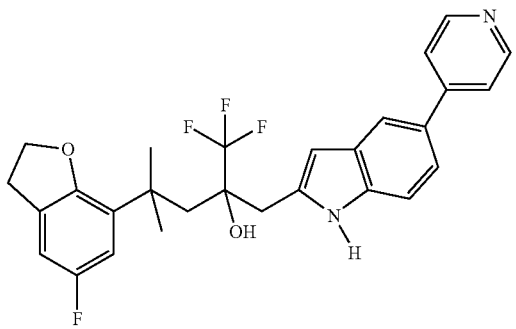 |
| 1,1,1-Trifluoro-4-(5-fluoro-2,3-dihydrobenzofuran-7-yl)-4-methyl-2-(5-pyridin-3-yl-1H-indol-2-ylmethyl)pentan-2-ol | 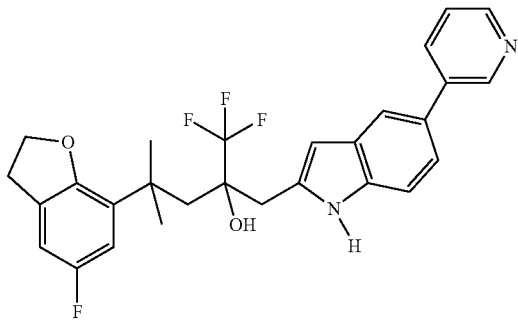 |
| 1,1,1-Trifluoro-4-(5-fluoro-2,3-dihydrobenzofuran-7-yl)-4-methyl-2-(5-pyrimidin-5-yl-1H-indol-2-ylmethyl)pentan-2-ol | 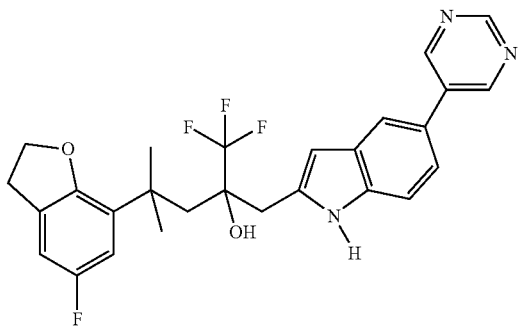 |
| 2-{2-[4-(5-Fluoro-2,3-dihydrobenzofuran-7-yl)-2-hydroxy-4-methyl-2-trifluoromethylpentyl]-1H-indol-5-yl}benzamide | 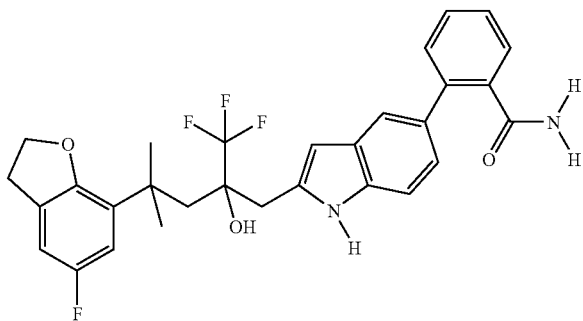 |

| A | B |
|---|---|
| IA | |
| 2-[5-(4-Dimethylaminophenyl)-1H-indol-2-ylmethyl]-1,1,1-trifluoro-4-(5-fluoro-2,3-dihydrobenzofuran-7-yl)-4-methylpentan-2-ol | 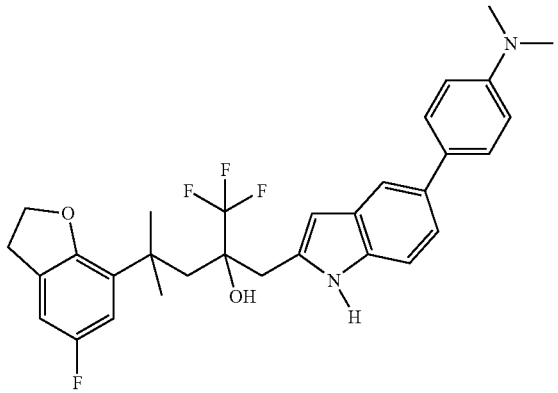 |
| 1,1,1-Trifluoro-2-(7-fluoro-4-methyl-1H-indol-2-ylmethyl)-4-(5-methanesulfonyl-2,3-dihydrobenzofuran-7-yl)-4-methylpentan-2-ol | 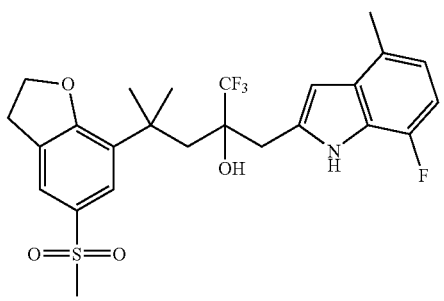 |
| 2-[2-Hydroxy-4-(5-methanesulfonyl-2,3-dihydrobenzofuran-7-yl)-4-methyl-2-trifluoromethylpentyl]-1H-indole-5-carbonitrile | 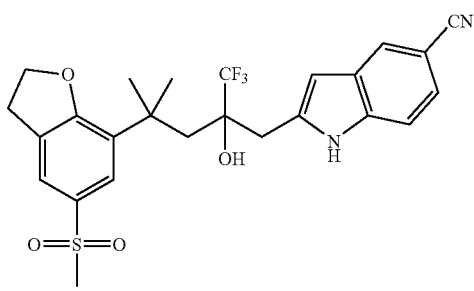 |
| 2-[2-Hydroxy-4-(5-methanesulfonyl-2,3-dihydrobenzofuran-7-yl)-4-methyl-2-trifluoromethylpentyl]-1H-indole-6-carbonitrile | 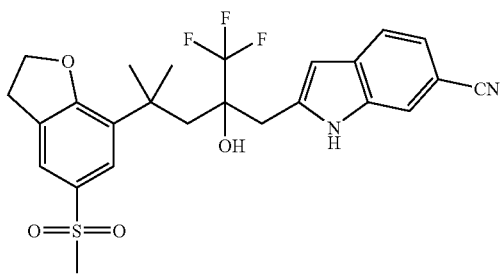 |
| 1,1,1-Trifluoro-2-(7-fluoro-1H-indol-2-ylmethyl)-4-(5-methanesulfonyl-2,3-dihydrobenzofuran-7-yl)-4-methylpentan-2-ol | 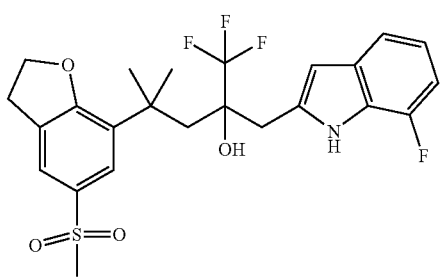 |

-continued

IA

| A | B |
|---|---|
| 1,1,1-Trifluoro-4-(5-methanesulfonyl-2,3-dihydrobenzofuran-7-yl)-4-methyl-2-(4-methyl-1H-indol-2-ylmethyl)pentan-2-ol | 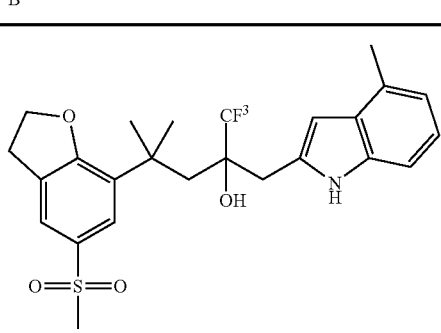 |
| 4-Methanesulfonyl-2-[4,4,4-trifluoro-3-hydroxy-1,1-dimethyl-3-(5-trifluoromethyl-1H-indol-2-ylmethyl)butyl]phenol | 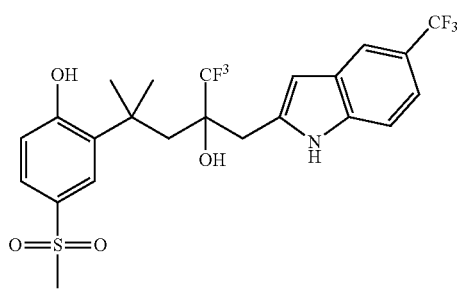 |
| 1,1,1-Trifluoro-2-(7-fluoro-5-methyl-1H-indol-2-ylmethyl)-4-(5-methanesulfonyl-2,3-dihydrobenzofuran-7-yl)-4-methylpentan-2-ol | 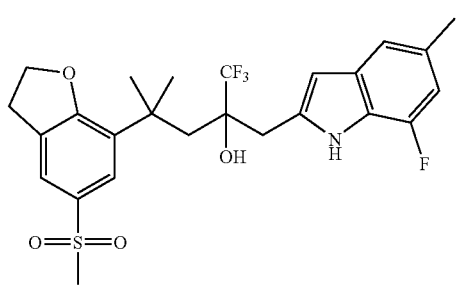 |
| 7-Fluoro-2-[2-hydroxy-4-(5-methanesulfonyl-2,3-dihydrobenzofuran-7-yl)-4-methyl-2-trifluoromethylpentyl]-1H-indole-5-carbonitrile | 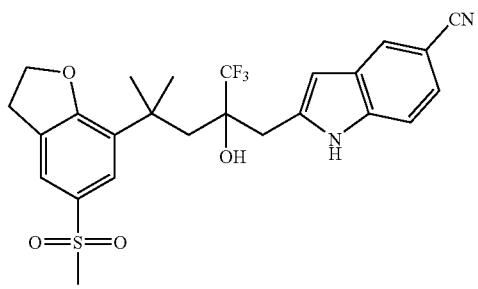 |
| 2-[4-(5-Fluoro-2-methoxyphenyl)-2-hydroxy-4-methyl-2-trifluoromethylpentyl]-1H-indole-4-carboxylic acid methyl ester | 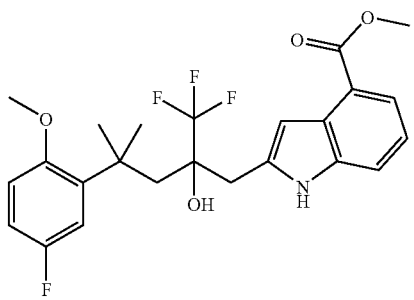 |

-continued

IA

| A | B |
|---|---|
| 2-[4-(5-Fluoro-2-hydroxyphenyl)-2-hydroxy-4-methyl-2-trifluoromethylpentyl]-1H-indole-4-carboxylic acid methyl ester | 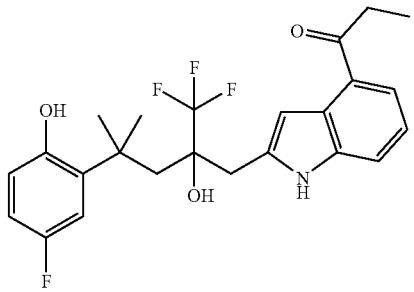 |
| 2-[4-(5-Fluoro-2-methoxyphenyl)-2-hydroxy-4-methyl-2-trifluoromethylpentyl]-1H-indole-4-carboxylic acid | 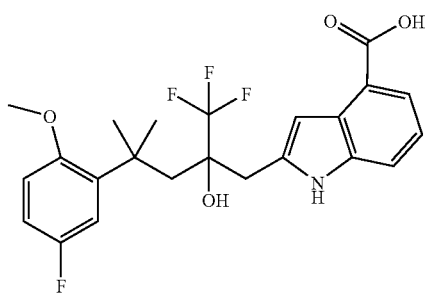 |
| 2-[4-(5-Fluoro-2-methoxyphenyl)-2-hydroxy-4-methyl-2-trifluoromethylpentyl]-1H-indole-4-carboxylic acid amide | 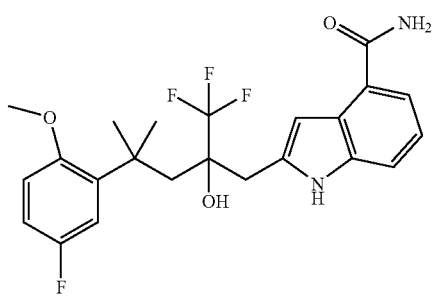 |
| 2-[4-(5-Fluoro-2-hydroxyphenyl)-2-hydroxy-4-methyl-2-trifluoromethylpentyl]-1H-indole-4-carboxylic acid amide | 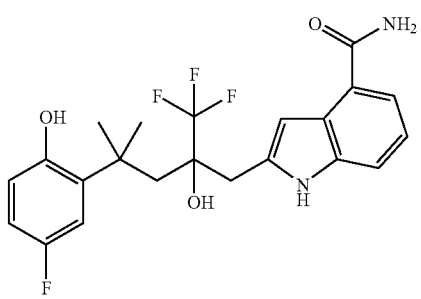 |
| 2-[4-(5-Fluoro-2-methoxyphenyl)-2-hydroxy-4-methyl-2-trifluoromethylpentyl]-1H-indole-4-carbonitrile | 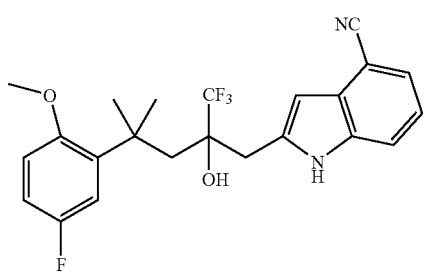 |

-continued

IA

| A | B |
|---|---|
| 2-[4-(5-Fluoro-2-hydroxyphenyl)-2-hydroxy-4-methyl-2-trifluoromethylpentyl]-1H-indole-4-carbonitrile | 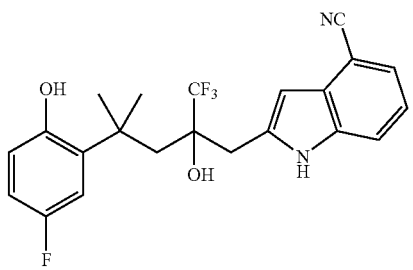 |
| 2-(4-Ethyl-1H-indol-2-ylmethyl)-1,1,1-trifluoro-4-(5-fluoro-2-methoxyphenyl)-4-methylpentan-2-ol | 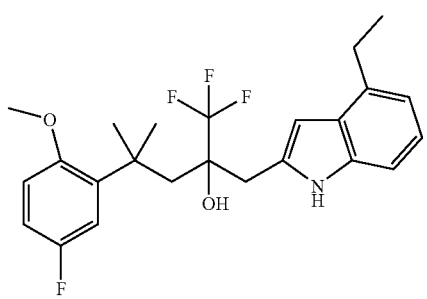 |
| 2-[3-(4-Ethyl-1H-indol-2-ylmethyl)-4,4,4-trifluoro-3-hydroxy-1,1-dimethylbutyl]-4-fluorophenol | 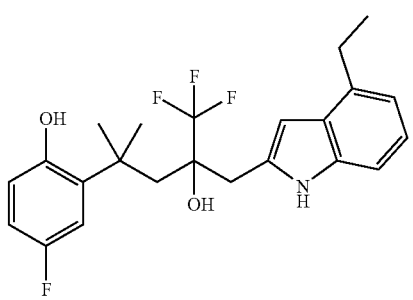 |
| 4-(5-Chloro-2,3-dihydrobenzofuran-7-yl)-1,1,1-trifluoro-2-(2-isopropyl-5H-pyrrolo[3,2-]pyrimidin-6-ylmethyl)-4-methylpentan-2-ol | 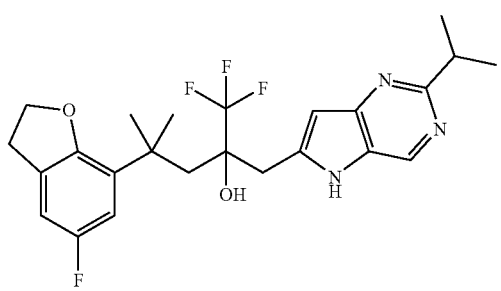 |
| 1,1,1-Trifluoro-4-(5-fluoro-2-methylphenyl)-2-(2-isopropyl-5H-pyrrolo[3,2-d]pyrimidin-6-ylmethyl)-4-methylpentan-2-ol | 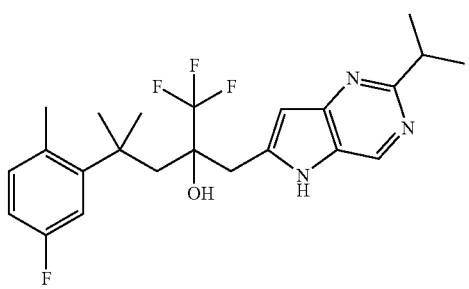 |

-continued

IA

| A | B |
|---|---|
| 1,1,1-Trifluoro-4-(5-fluoro-2-methoxyphenyl)-2-(2-isopropyl-5H-pyrrolo[3,2-d]pyrimidin-6-ylmethyl)-4-methylpentan-2-ol | 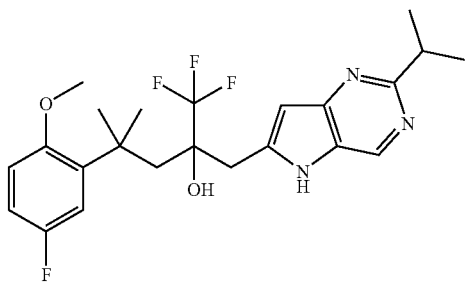 |
| 4-Fluoro-2-[4,4,4-trifluoro-3-hydroxy-3-(2-isopropyl-5H-pyrrolo[3,2-d]pyrimidin-6-ylmethyl)-1,1-dimethylbutyl]phenol | 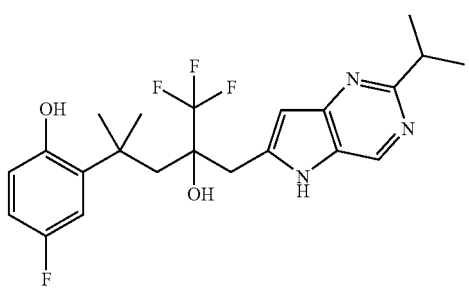 |
| 4-(5-Chloro-2,3-dihydrobenzofuran-7-yl)-1,1,1-trifluoro-4-methyl-2-(2-pyrrolidin-1-yl-5H-pyrrolo[3,2-d]pyrimidin-6-ylmethyl)pentan-2-ol | 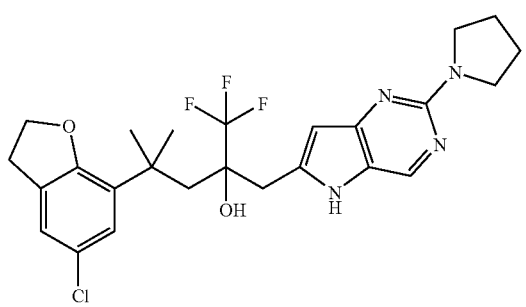 |
| 1,1,1-Trifluoro-4-(5-fluoro-2-methylphenyl)-4-methyl-2-(2-pyrrolidin-1-yl-5H-pyrrolo[3,2-d]pyrimidin-6-ylmethyl)pentan-2-ol | 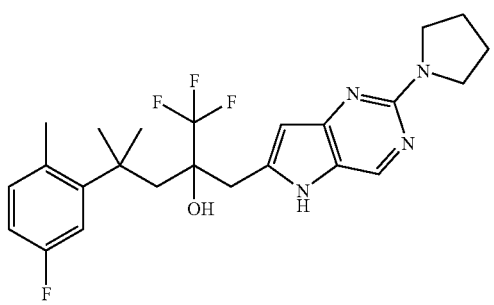 |
| 1,1,1-Trifluoro-4-(5-fluoro-2-methoxyphenyl)-4-methyl-2-(2-pyrrolidin-1-yl-5H-pyrrolo[3,2-d]pyrimidin-6-ylmethyl)pentan-2-ol | 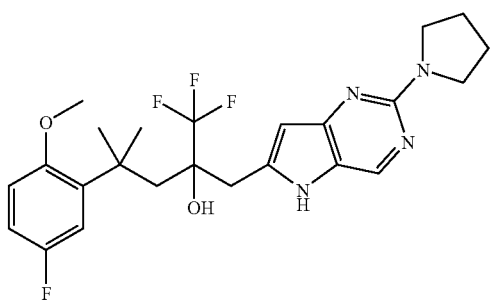 |

-continued

IA

| A | B |
|---|---|
| 4-Fluoro-2-[4,4,4-trifluoro-3-hydroxy-1,1-dimethyl-3-(2-pyrrolidin-1-yl-5H-pyrrolo[3,2-d]pyrimidin-6-ylmethyl)butyl]phenol | 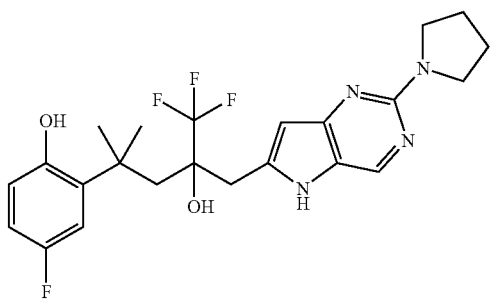 |
| 4-(5-Chloro-2,3-dihydrobenzofuran-7-yl)-1,1,1-trifluoro-4-methyl-2-(2-phenyl-5H-pyrrolo[3,2-d]pyrimidin-6-ylmethyl)pentan-2-ol | 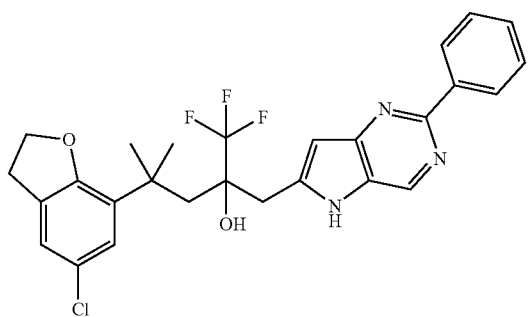 |
| 1,1,1-Trifluoro-4-(5-fluoro-2-methylphenyl)-4-methyl-2-(2-phenyl-5H-pyrrolo[3,2-d]pyrimidin-6-ylmethyl)pentan-2-ol | 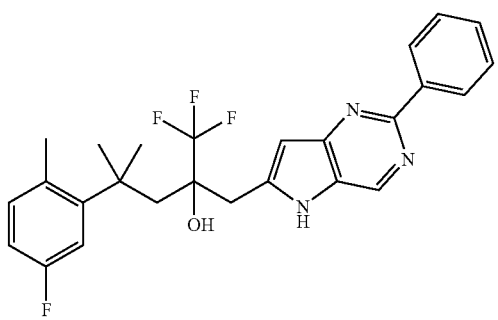 |
| 1,1,1-Trifluoro-4-(5-fluoro-2-methoxyphenyl)-4-methyl-2-(2-phenyl-5H-pyrrolo[3,2-d]pyrimidin-6-ylmethyl)pentan-2-ol | 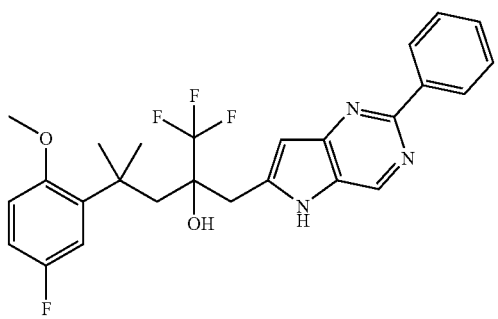 |

-continued

IA

| A | B |
|---|---|
| 4-Fluoro-2-[4,4,4-trifluoro-3-hydroxy-1,1-dimethyl-3-(2-phenyl-5H-pyrrolo[3,2-d]pyrimidin-6-ylmethyl)butyl]phenol | 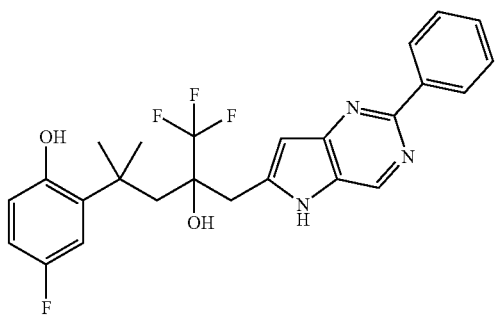 |
| 4-(5-Chloro-2,3-dihydrobenzofuran-7-yl)-2-(2-chloro-5H-pyrrolo[3,2-d]pyrimidin-6-ylmethyl)-1,1,1-trifluoro-4-methylpentan-2-ol | 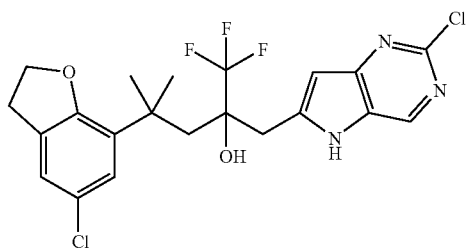 |
| 1,1,1-Trifluoro-4-methyl-4-phenyl-2-(2-phenyl-5H-pyrrolo[3,2-d]pyrimidin-6-ylmethyl)pentan-2-ol | 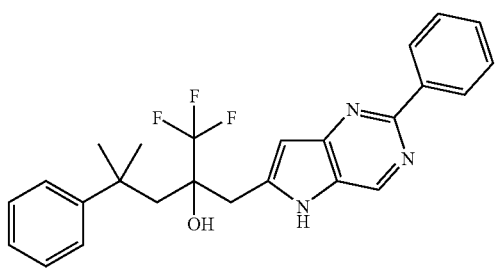 |
| 1,1,1-Trifluoro-4-(3-fluorophenyl)-4-methyl-2-(2-phenyl-5H-pyrrolo[3,2-d]pyrimidin-6-ylmethyl)pentan-2-ol | 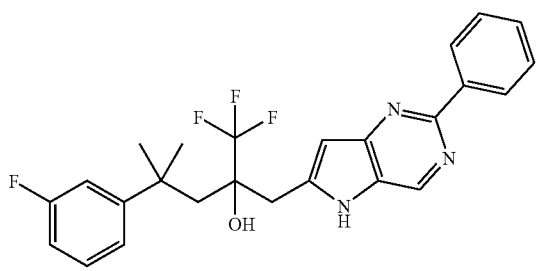 |
| 4-[4,4,4-Trifluoro-3-hydroxy-1,1-dimethyl-3-(2-phenyl-5H-pyrrolo[3,2-d]pyrimidin-6-ylmethyl)butyl]benzonitrile | 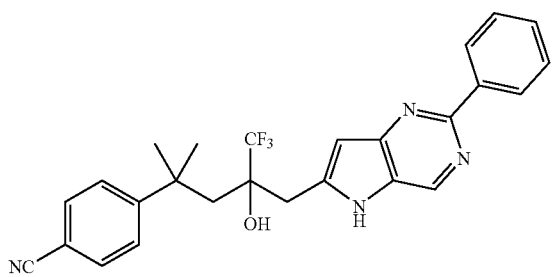 |

-continued

| IA | |
|---|---|
| A | B |

1,1,1-Trifluoro-4-(2-methoxy-5-methylphenyl)-4-methyl-2-(2-pyrrolidin-1-yl-5H-pyrrolo[3,2-d]pyrimidin-6-ylmethyl)pentan-2-ol

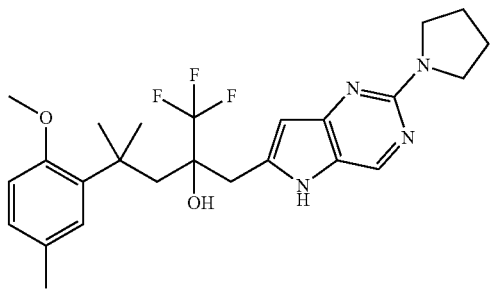 [SMILES: COc1ccc(C)cc1C(C)(C)CC(O)(Cc1cc2nc(N3CCCC3)ncc2[nH]1)C(F)(F)F]

1,1,1-Trifluoro-4-(2-methoxy-5-methylphenyl)-4-methyl-2-(2-pyrrolidin-1-yl-5H-pyrrolo[3,2-d]pyrimidin-6-ylmethyl)pentan-2-ol

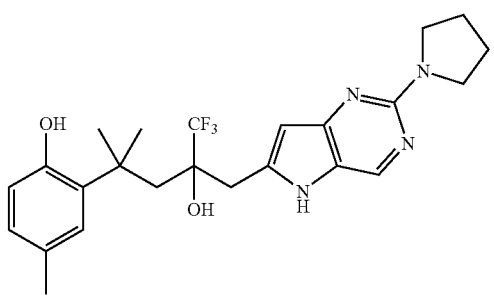 [SMILES: Cc1ccc(O)c(C(C)(C)CC(O)(Cc2cc3nc(N4CCCC4)ncc3[nH]2)C(F)(F)F)c1]

1,1,1-Trifluoro-4-(4-fluoro-2-methoxyphenyl)-4-methyl-2-(2-pyrrolidin-1-yl-5H-pyrrolo[3,2-d]pyrimidin-6-ylmethyl)pentan-2-ol

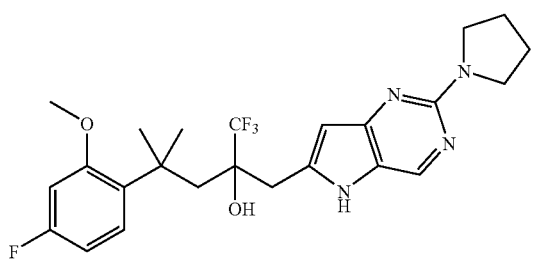 [SMILES: COc1cc(F)ccc1C(C)(C)CC(O)(Cc1cc2nc(N3CCCC3)ncc2[nH]1)C(F)(F)F]

5-Fluoro-2-[4,4,4-trifluoro-3-hydroxy-1,1-dimethyl-3-(2-pyrrolidin-1-yl-5H-pyrrolo[3,2-d]pyrimidin-6-ylmethyl)butyl]phenol

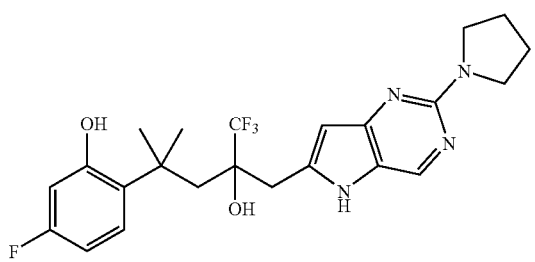 [SMILES: CC(C)(CC(O)(Cc1cc2nc(N3CCCC3)ncc2[nH]1)C(F)(F)F)c1ccc(F)cc1O]

2-(5-Ethoxy-1H-pyrrolo[2,3-c]pyridin-2-ylmethyl)-1,1,1-trifluoro-4-(5-fluoro-2-methylphenyl)-4-methylpentan-2-ol

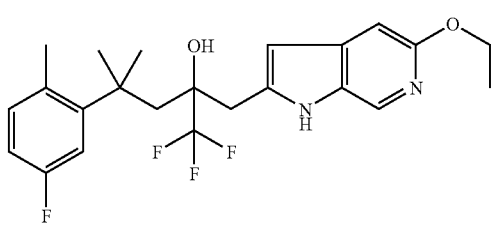 [SMILES: CCOc1cc2cc(CC(O)(CC(C)(C)c3cc(F)ccc3C)C(F)(F)F)[nH]c2cn1]

-continued

IA

| A | B |
|---|---|
| 1,1,1-Trifluoro-4-(5-fluoro-2-methoxyphenyl)-4-methyl-2-(5-phenyl-1H-pyrrolo[2,3-c]pyridin-2-ylmethyl)pentan-2-ol | 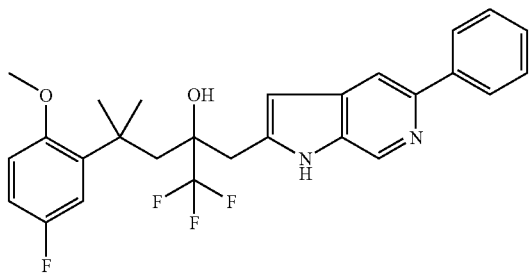 |
| 1,1,1-Trifluoro-4-(5-fluoro-2-methylphenyl)-4-methyl-2-(6-methyl-1H-pyrrolo[3,2-c]pyridin-2-ylmethyl)pentan-2-ol | 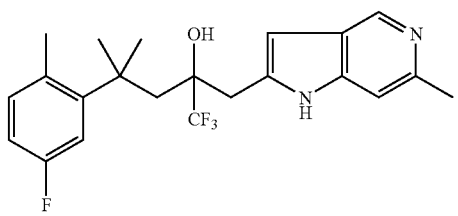 |
| 1,1,1-Trifluoro-4-(5-fluoro-2-methylphenyl)-4-methyl-2-(4-methyl-1H-pyrrolo[3,2-c]pyridin-2-ylmethyl)pentan-2-ol | 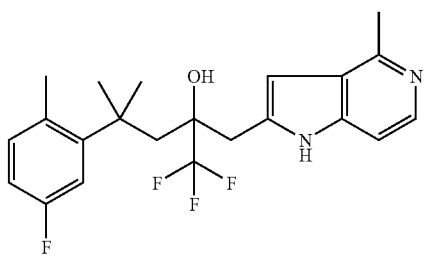 |
| 4-(5-Bromo-2-methoxyphenyl)-2-(5-dimethylamino-1H-pyrrolo[2,3-c]pyridin-2-ylmethyl)-1,1,1-trifluoro-4-methylpentan-2-ol | 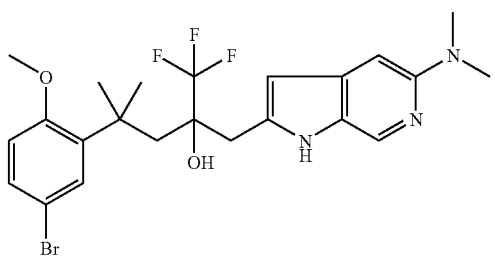 |
| 4-(5-Bromo-2-methoxyphenyl)-1,1,1-trifluoro-2-(5-isopropoxy-1H-pyrrolo[2,3-c]pyridin-2-ylmethyl)-4-methylpentan-2-ol | 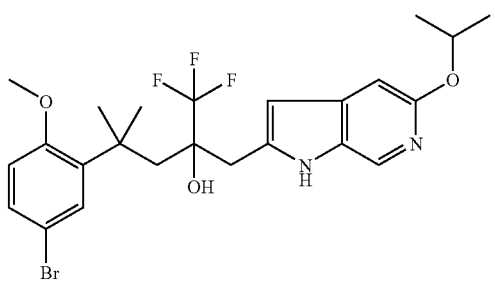 |

-continued

IA

| A | B |
|---|---|
| 1,1,1-Trifluoro-4-(5-fluoro-2-trifluoromethylphenyl)-2-(5-isopropoxy-1H-pyrrolo[2,3-c]pyridin-2-ylmethyl)-4-methylpentan-2-ol | 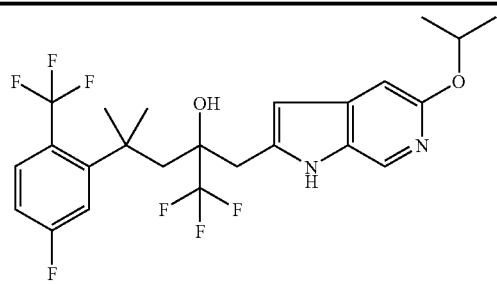 |
| 4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol | 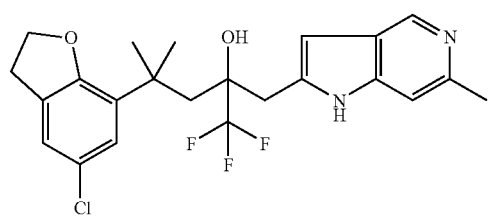 |
| 1,1,1-Trifluoro-2-(5-isopropoxy-1H-pyrrolo[2,3-c]pyridin-2-ylmethyl)-4-(2-methoxy-5-pyrimidin-5-ylphenyl)-4-methylpentan-2-ol | 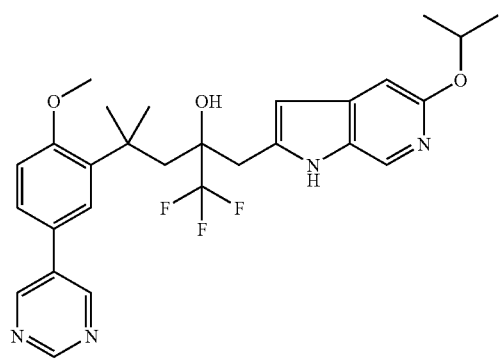 |
| 1,1,1-Trifluoro-2-(5-isopropoxy-1H-pyrrolo[2,3-c]pyridin-2-ylmethyl)-4-(4-methoxybiphenyl-3-yl)-4-methylpentan-2-ol | 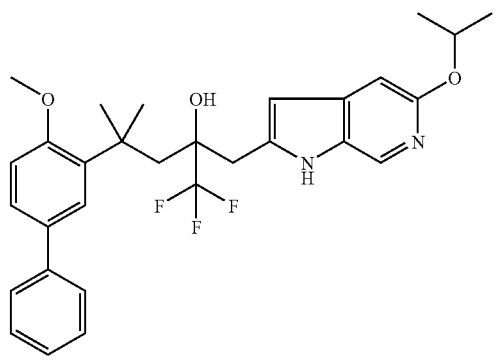 |
| 1,1,1-Trifluoro-2-(5-isopropoxy-1H-pyrrolo[2,3-c]pyridin-2-ylmethyl)-4-(2-methoxy-5-thiophen-3-ylphenyl)-4-methylpentan-2-ol | 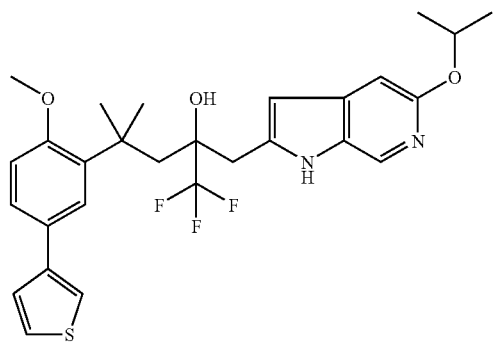 |

IA

| A | B |
|---|---|
| 2-(5-Dimethylamino-1H-pyrrolo[2,3-c]pyridin-2-ylmethyl)-1,1,1-trifluoro-4-methyl-4-phenylpentan-2-ol | 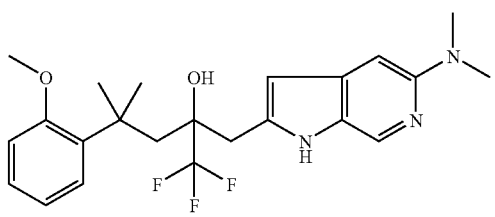 |
| 1,1,1-Trifluoro-4-(2-methoxy-5-pyrimidin-5-ylphenyl)-4-methyl-2-(5-piperidin-1-yl-1H-pyrrolo[2,3-c]pyridin-2-ylmethyl)pentan-2-ol | 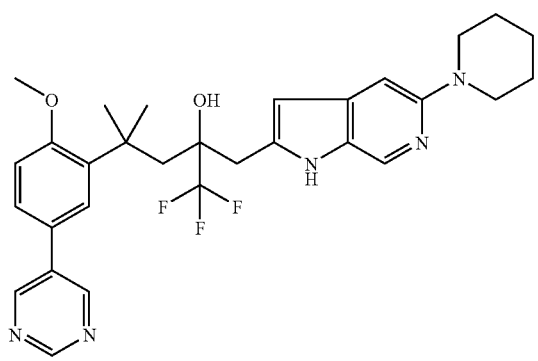 |
| 1,1,1-Trifluoro-4-(4-methoxybiphenyl-3-yl)-4-methyl-2-(5-piperidin-1-yl-1H-pyrrolo[2,3-c]pyridin-2-ylmethyl)pentan2-ol | 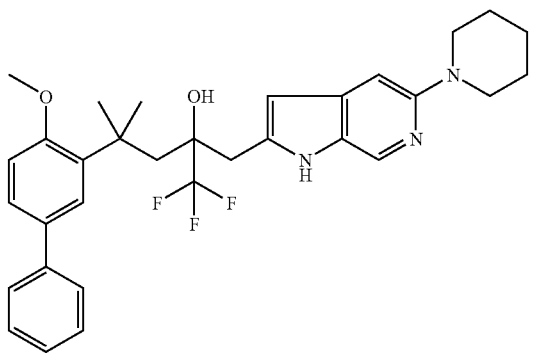 |
| 1,1,1-Trifluoro-4-(2-methoxy-5-pyridin-3-ylphenyl)-4-methyl-2-(5-piperidin-1-yl-1H-pyrrolo[2,3-c]pyridin-2-ylmethyl)pentan-2-ol | 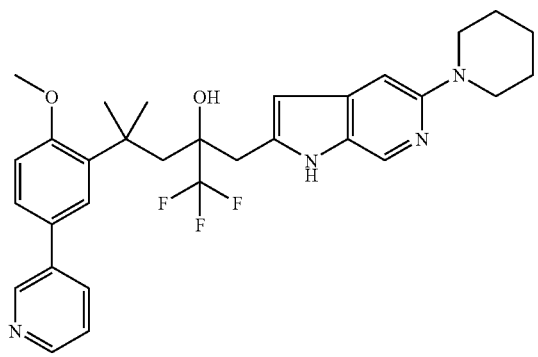 |

-continued

| A | B |
|---|---|
| 2-(5-Dimethylamino-1H-pyrrolo[2,3-c]pyridin-2-ylmethyl)-1,1,1-trifluoro-4-(2-methoxy-5-pyrimidin-5-ylphenyl)-4-methylpentan-2-ol | 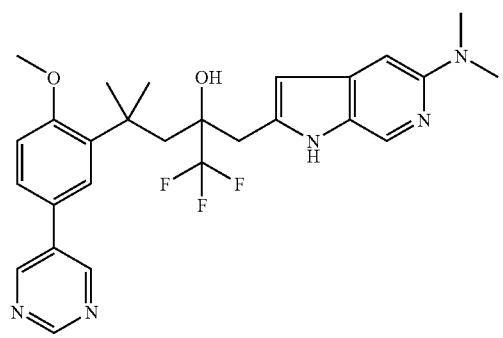 |
| 4-Bromo-2-[3-(5-chloro-1H-pyrrolo[2,3-c]pyridin-2-ylmethyl)-4,4,4-trifluoro-3-hydroxy-1,1-dimethylbutyl]phenol | 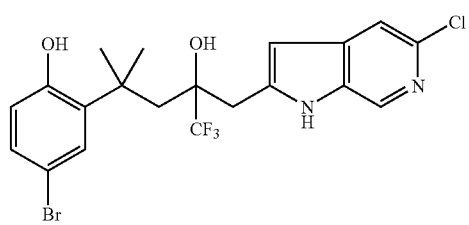 |
| 2-[3-(5-Chloro-1H-pyrrolo[2,3-c]pyridin-2-ylmethyl)-4,4,4-trifluoro-3-hydroxy-1,1-dimethylbutyl]-4-fluorophenol | 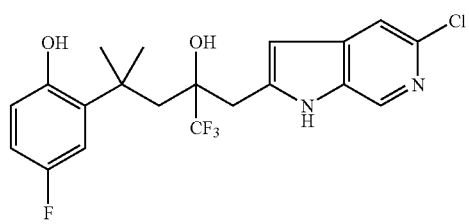 |
| 2-[2-Hydroxy-4-(4-hydroxybiphenyl-3-yl)-4-methyl-2-trifluoromethylpentyl]-1H-pyrrolo[2,3-c]pyridin-5-ol | 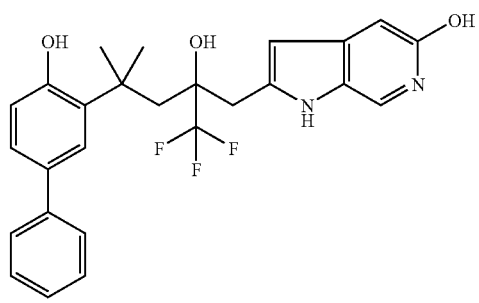 |
| 1,1,1-Trifluoro-2-(5-isopropoxy-1H-pyrrolo[2,3-c]pyridin-2-ylmethyl)-4-methyl-4-(5-phenyl-2,3-dihydrobenzofuran-7-yl)pentan-2-ol | 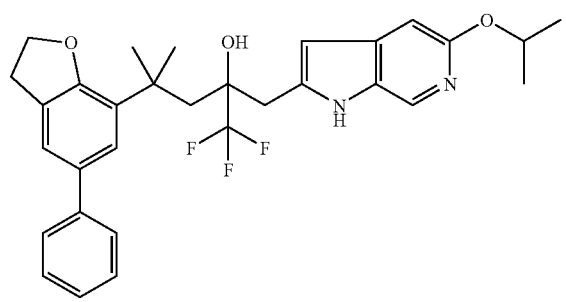 |

TABLE IA (continued)

| A | B |
|---|---|
| 2-[2-Hydroxy-4-(2-methoxy-5-pyrimidin-5-ylphenyl)-4-methyl-2-trifluoromethylpentyl]-1H-pyrrolo[2,3-c]pyridin-5-ol | 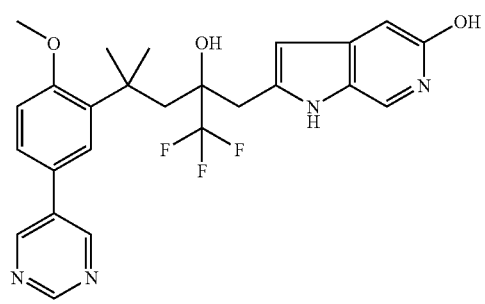 |
| Trifluoromethanesulfonic acid 2-[4-(5-fluoro-2-methylphenyl)-2-hydroxy-4-methyl-2-trifluoromethylpentyl]-1H-pyrrolo[2,3-c]pyridin-5-yl ester | 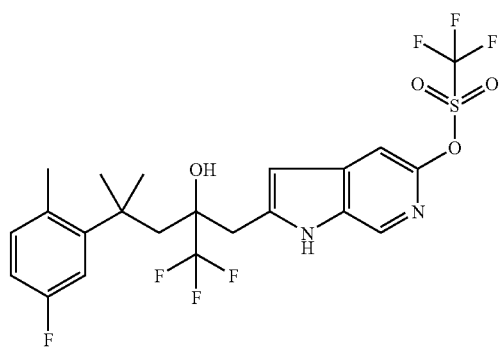 |
| 2-[5-(2,6-Dimethylmorpholin-4-yl)-1H-pyrrolo[2,3-c]pyridin-2-ylmethyl]-1,1,1-trifluoro-4-methyl-4-phenylpentan-2-ol | 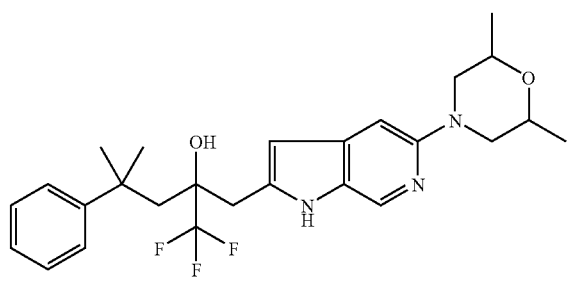 |
| 1,1,1-Trifluoro-4-(3-fluorophenyl-4-methyl-2-(5-piperidin-1-yl-1H-pyrrolo[2,3-c]pyridin-2-ylmethyl)pentan-2-ol | 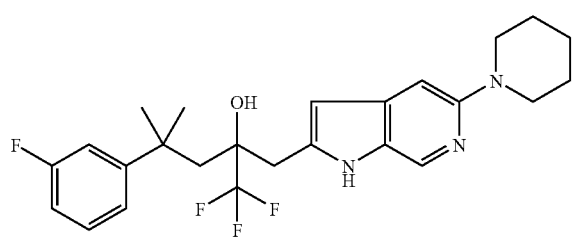 |
| 1,1,1-Trifluoro-4-methyl-4-phenyl-2-(5-piperidin-1-yl-1H-pyrrolo[2,3-c]pyridin-2-ylmethyl)pentan-2-ol | 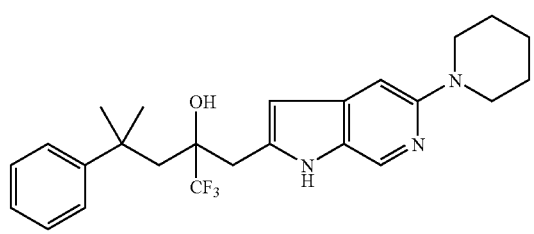 |

-continued

IA

| A | B |
|---|---|
| 1,1,1-Trifluoro-4-(3-fluorophenyl)-2-(5-isopropoxy-1H-pyrrolo[2,3-c]pyridin-2-ylmethyl)-4-methylpentan-2-ol | 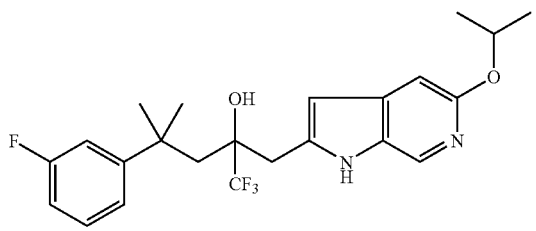 |
| 1,1,1-Trifluoro-2-(5-isopropoxy-1H-pyrrolo[2,3-c]pyridin-2-ylmethyl)-4-methyl-4-phenylpentan-2-ol | 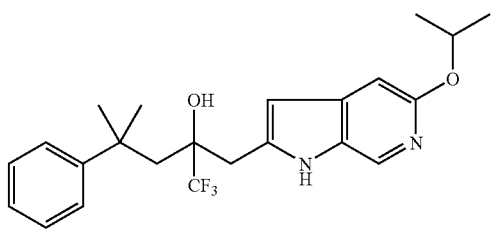 |
| 1,1,1-Trifluoro-4-methyl-4-(3-morpholin-4-ylmethylphenyl)-2-(5-piperidin-1-yl-1H-pyrrolo[2,3-c]pyridin-2-ylmethyl)pentan-2-ol | 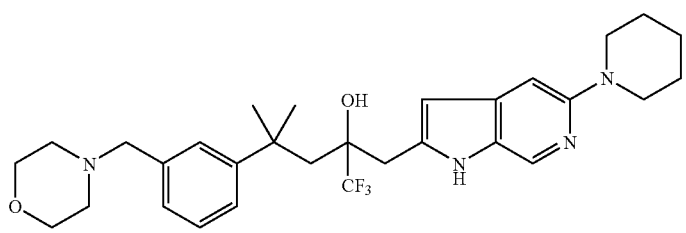 |
| 1,1,1-Trifluoro-4-methyl-4-(3-morpholin-4-ylmethylphenyl)-2-(5-morpholin-4-yl-1H-pyrrolo[2,3-c]pyridin-2-ylmethyl)pentan-2-ol | 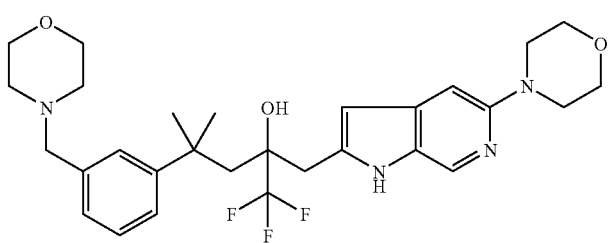 |
| 2-(5-Diethylamino-1H-pyrrolo[2,3-c]pyridin-2-ylmethyl)-1,1,1-trifluoro-4-(2-methoxy-5-pyrimidin-5-ylphenyl)-4-methylpentan-2-ol | 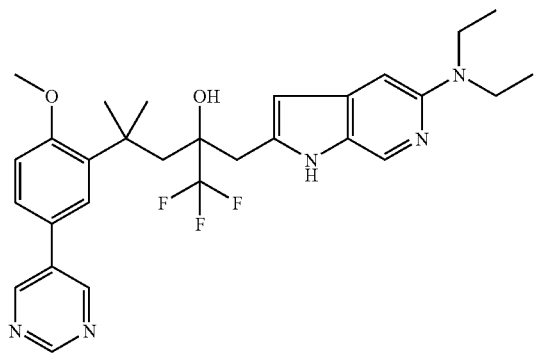 |
| 4-(5-Chloro-2,3-dihydrobenzofuran-7-yl)-1,1,1-trifluoro-2-(5-methoxy-1H-pyrrolo[3,2-b]pyridin-2-ylmethyl)-4-methylpentan-2-ol | 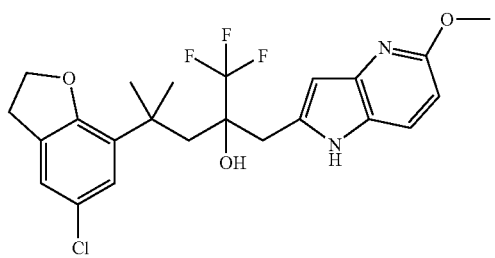 |

-continued

| IA | |
|---|---|
| A | B |
| 1,1,1-Trifluoro-4-(5-fluoro-2-methylphenyl)-2-(5-methoxy-1H-pyrrolo[3,2-b]pyridin-2-ylmethyl)-4-methylpentan-2-ol | 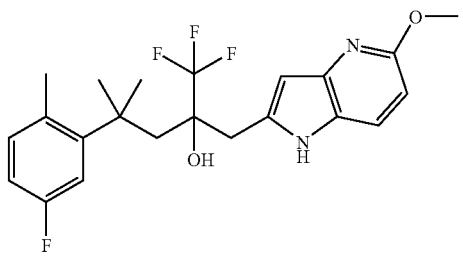 |
| 4-(5-Chloro-2,3-dihydrobenzofuran-7-yl)-2-(5-chloro-1H-pyrrolo[2,3-c]pyridin-2-ylmethyl)-1,1,1-trifluoro-4-methylpentan-2-ol | 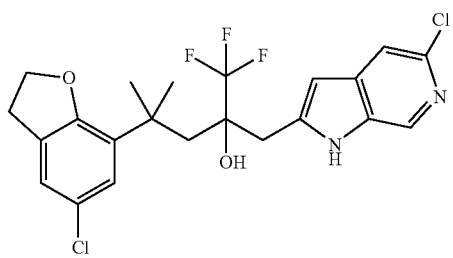 |

| IA | |
|---|---|
| A | B |
| 1,1,1-Trifluoro-4-(5-fluoro-2-methylphenyl)-2-(4-methoxy-1H-pyrrolo[3,2-c]pyridin-2-ylmethyl)-4-methylpentan-2-ol | 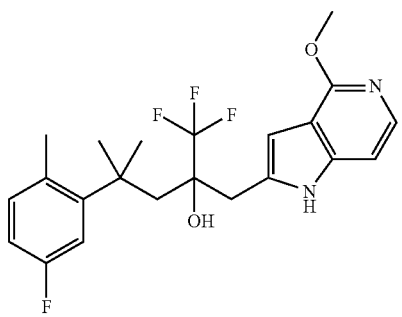 |
| 2-[4-(5-Fluoro-2-methylphenyl)-2-hydroxy-4-methyl-2-trifluoromethylpentyl]-1,5-dihydropyrrolo[3,2-c]pyridin-4-one | 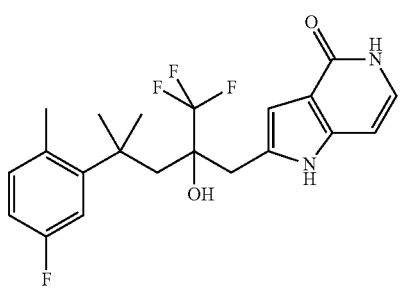 |

-continued

IA

| A | B |
|---|---|
| 2-[4-(5-Fluoro-2-methylphenyl)-2-hydroxy-4-methyl-2-trifluoromethylpentyl]-1,4-dihydropyrrolo[3,2-b]pyridin-5-one | 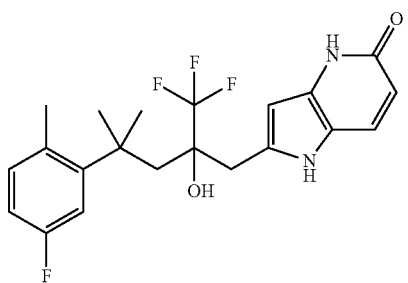 |
| 2-(5,7-Dimethoxy-1H-pyrrolo[2,3-c]pyridin-2-ylmethyl)-1,1,1-trifluoro-4-(5-fluoro-2-methylphenyl)-4-methylpentan-2-ol | 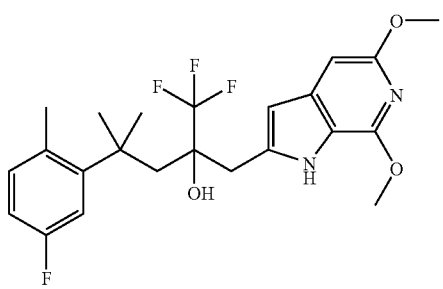 |
| 2-[4-(5-Fluoro-2-methylphenyl)-2-hydroxy-4-methyl-2-trifluoromethylpentyl]-5-hydroxy-1,6-dihydropyrrolo[2,3-c]pyridin-7-one | 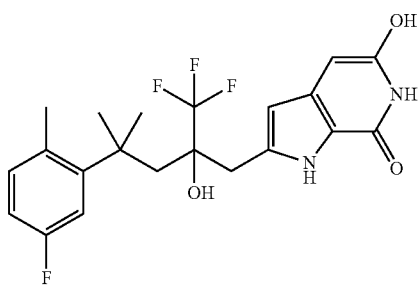 |
| 2-(5-Chloro-1H-pyrrolo[2,3-c]pyridin-2-ylmethyl)-1,1,1-trifluoro-4-(5-methanesulfonyl-2,3-dihydrobenzofuran-7-yl)-4-methylpentan-2-ol | 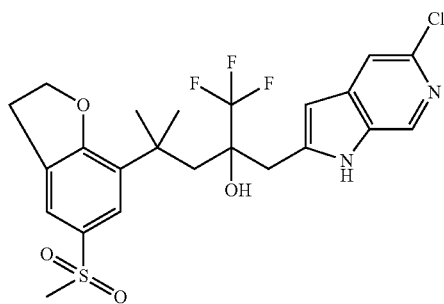 |
| 2-(5-Chloro-1H-pyrrolo[2,3-c]pyridin-2-ylmethyl)-1,1,1-trifluoro-4-(2-methoxy-5-thiophen-3-ylphenyl)-4-methylpentan-2-ol | 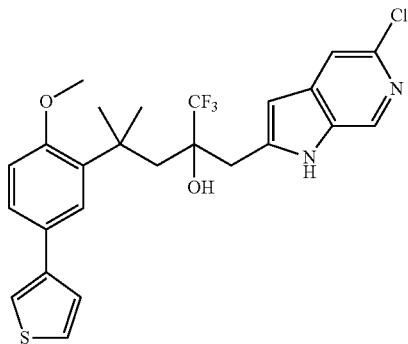 |

-continued

IA

| A | B |
|---|---|
| 2-[2-Hydroxy-4-(5-methanesulfonyl-2,3-dihydrobenzofuran-7-yl)-4-methyl-2-trifluoromethylpentyl]-1H-pyrrolo[3,2-b]pyridine-5-carbonitrile | 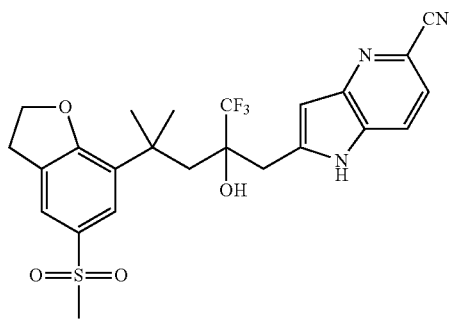 |
| 2-(5-Chloro-1H-pyrrolo[2,3-c]pyridin-2-ylmethyl)-1,1,1-trifluoro-4-methyl-4-(5-methylsulfanyl-2,3-dihydrobenzofuran-7-yl)pentan-2-ol | 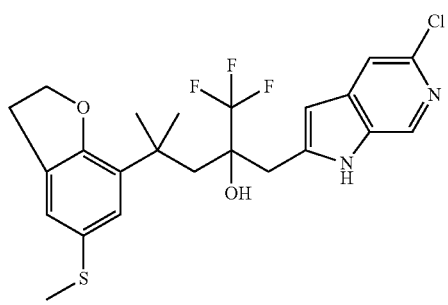 |
| 4-(5-Bromo-2-methoxyphenyl)-2-(5-chloro-1H-pyrrolo[2,3-c]pyridin-2-ylmethyl)-1,1,1-trifluoro-4-methylpentan-2-ol | 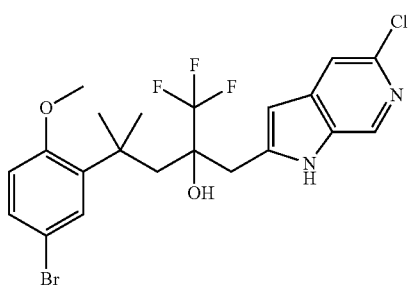 |
| 1,1,1-Trifluoro-4-(5-fluoro-2-methoxyphenyl)-4-methyl-2-(7H-pyrrolo[2,3-d]pyrimidin-6-ylmethyl)pentan-2-ol | 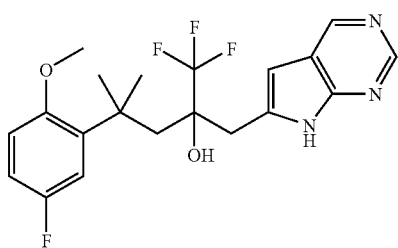 |

| A | B |
|---|---|
| 1,1,1-Trifluoro-4-(2-methoxy-5-naphthalen-1-ylphenyl)-4-methyl-2-(5-morpholin-4-yl-1H-pyrrolo[2,3-c]pyridin-2-ylmethyl)pentan-2-ol | 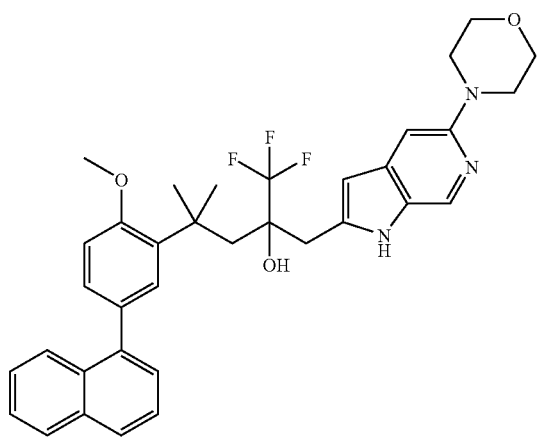 |
| 4-(2'-Chloro-4-methoxybiphenyl-3-yl)-1,1,1-trifluoro-4-methyl-2-(5-morpholin-4-yl-1H-pyrrolo[2,3-c]pyridin-2-ylmethyl)pentan-2-ol | 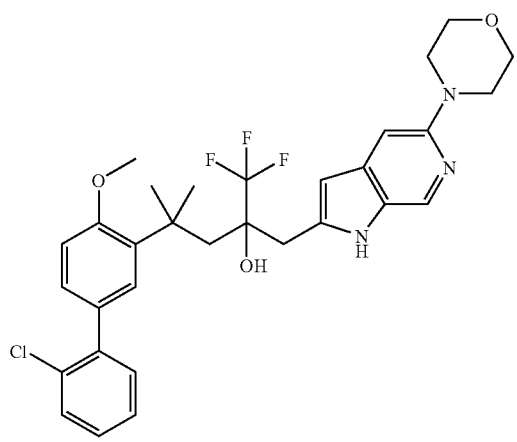 |
| 2-(5-Chloro-1H-pyrrolo[2,3-c]pyridin-2-ylmethyl)-1,1,1-trifluoro-4-(2-methoxy-5-pyrimidin-5-ylphenyl)-4-methylpentan-2-ol | 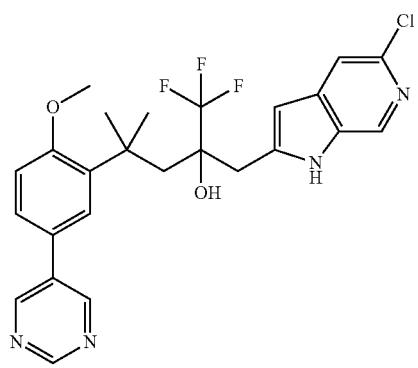 |

-continued

IA

| A | B |
|---|---|
| 4'-Methoxy-3'-[4,4,4-trifluoro-3-hydroxy-1,1-dimethyl-3-(5-piperidin-1-yl-1H-pyrrolo[2,3-c]pyridin-2-ylmethyl)butyl]biphenyl-2-carbonitrile | 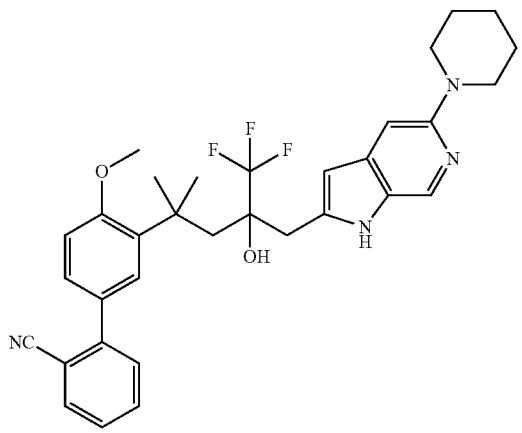 |
| 4-(2'-Chloro-4-methoxybiphenyl-3-yl)-1,1,1-trifluoro-4-methyl-2-(5-piperidin-1-yl-1H-pyrrolo[2,3-c]pyridin-2-ylmethyl)pentan-2-ol | 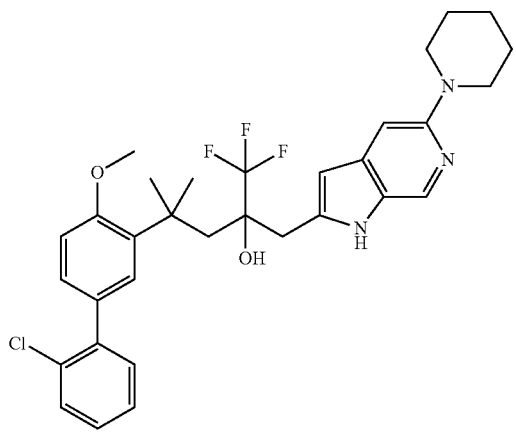 |
| 1,1,1-Trifluoro-4-methyl-2-(5-morpholin-4-yl-1H-pyrrolo[2,3-c]pyridin-2-ylmethyl)-4-(3-pyridin-3-ylphenyl)pentan-2-ol | 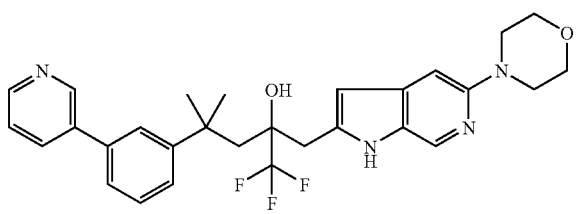 |
| 1,1,1-Trifluoro-4-methyl-4-(3-morpholin-4-ylphenyl)-2-(5-morpholin-4-yl-1H-pyrrolo[2,3-c]pyridin-2-ylmethyl)pentan-2-ol | 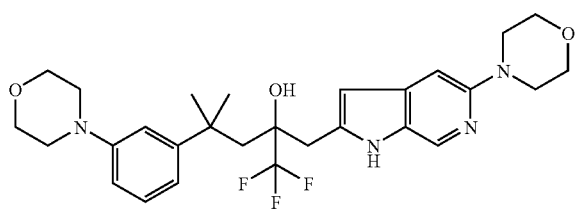 |
| 1,1,1-Trifluoro-4-methyl-4-(3-morpholin-4-ylphenyl)-2-(5-piperidin-1-yl-1H-pyrrolo[2,3-c]pyridin-2-ylmethyl)pentan-2-ol | 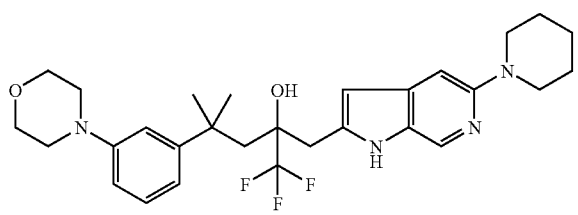 |

-continued

IA

| A | B |
|---|---|
| 1,1,1-Trifluoro-4-(2-methoxy-5-piperidin-1-ylphenyl)-4-methyl-2-(5-morpholin-4-yl-1H-pyrrolo[2,3-c]pyridin-2-ylmethyl)pentan-2-ol | 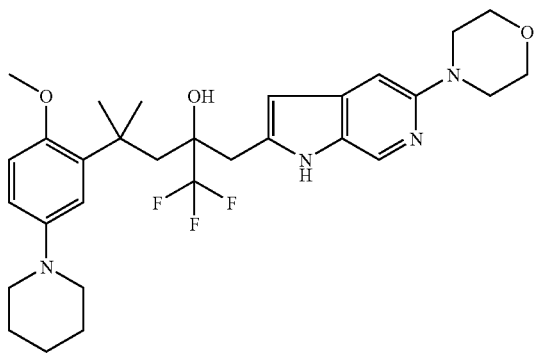 |
| 1,1,1-Trifluoro-4-methyl-2-(5-piperidin-1-yl-1H-pyrrolo[2,3-c]pyridin-2-ylmethyl)-4-(3-pyridin-3-ylphenyl)pentan-2-ol | 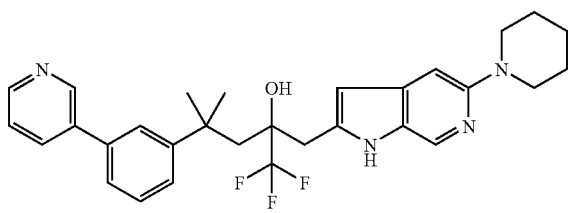 |
| 1,1,1-Trifluoro-4-methyl-2-(5-piperidin-1-yl-1H-pyrrolo[2,3-c]pyridin-2-ylmethyl)-4-(3-pyrimidin-5-ylphenyl)pentan-2-ol | 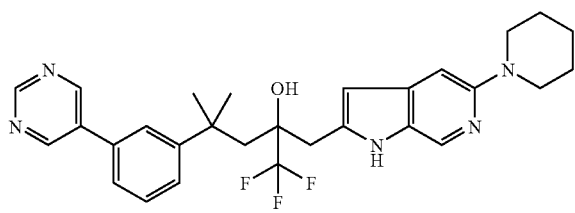 |
| 1,1,1-Trifluoro-4-methyl-4-(3-pyridin-3-ylphenyl)-2-(5-pyrrolidin-1-yl-1H-pyrrolo[2,3-c]pyridin-2-ylmethyl)pentan-2-ol | 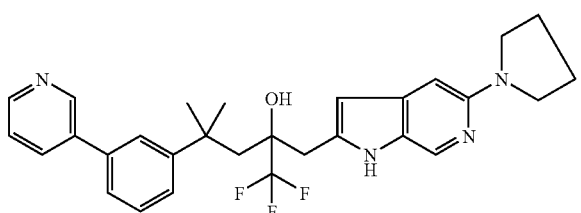 |
| 1,1,1-Trifluoro-4-methyl-4-(3-pyrimidm-5-ylphenyl)-2-(5-pyrrolidin-1-yl-1H-pyrrolo[2,3-c]pyridin-2-ylmethyl)pentan-2-ol | 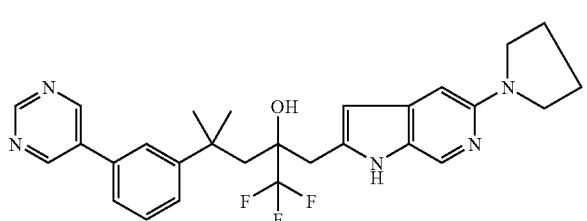 |
| 1,1,1-Trifluoro-4-(5-fluoro-2-methylphenyl)-4-methyl-2-(5-methylamino-1H-pyrrolo[2,3-c]pyridin-2-ylmethyl)pentan-2-ol | 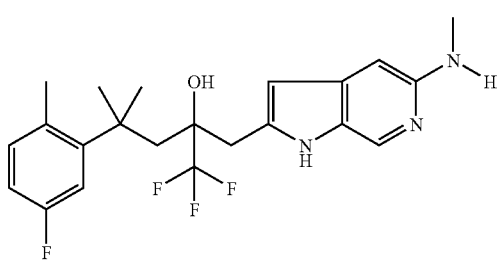 |

| A | B |
|---|---|
| 1,1,1-Trifluoro-4-(4-fluorophenyl)-4-methyl-2-(5-piperidin-1-yl-1H-pyrrolo[2,3-c]pyridin-2-ylmethyl)pentan-2-ol | 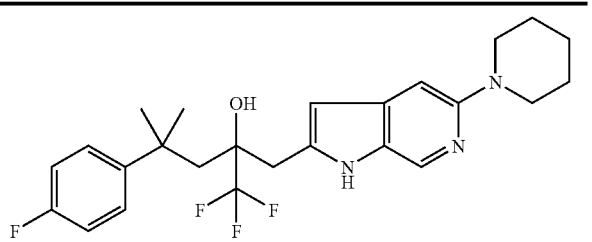 |
| 3'-[4,4,4-Trifluoro-3-hydroxy-1,1-dimethyl-3-(5-piperidin-1-yl-1H-pyrrolo[2,3-c]pyridin-2-ylmethyl)butyl]biphenyl-2-carbonitrile | 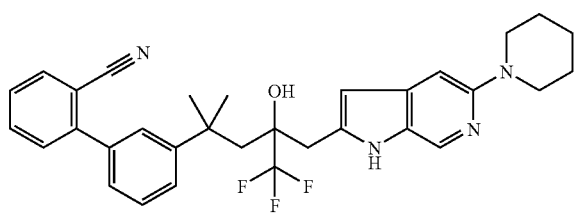 |
| 3'-[4,4,4-Trifluoro-3-hydroxy-1,1-dimethyl-3-(5-morpholin-4-yl-1H-pyrrolo[2,3-c]pyridin-2-ylmethyl)butyl]biphenyl-2-carbonitrile | 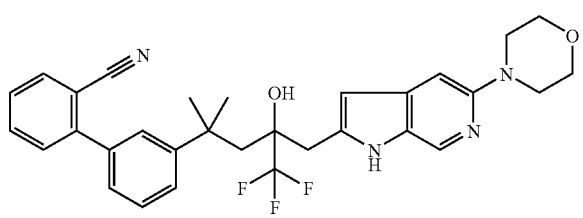 |
| 4-Piperidin-1-yl-2-[4,4,4-trifluoro-3-hydroxy-1,1-dimethyl-3-(5-morpholin-4-yl-1H-pyrrolo[2,3-c]pyridin-2-ylmethyl)butyl]phenol | 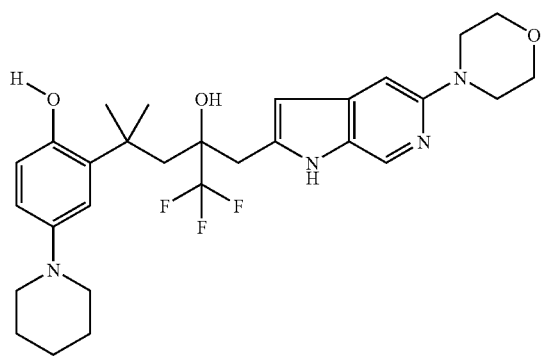 |
| 4-Morpholin-4-yl-2-[4,4,4-trifluoro-3-hydroxy-1,1-dimethyl-3-(5-morpholin-4-yl-1H-pyrrolo[2,3-c]pyridin-2-ylmethyl)butyl]phenol | 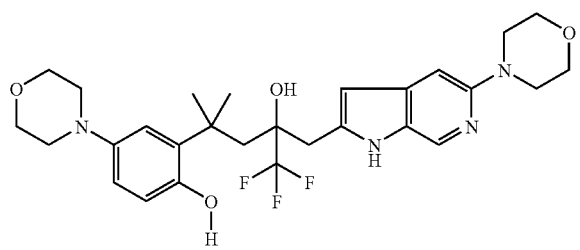 |
| 1,1,1-Trifluoro-4-(2-methoxy-5-morpholin-4-ylphenyl)-4-methyl-2-(5-morpholin-4-yl-1H-pyrrolo[2,3-c]pyridin-2-ylmethyl)pentan-2-ol | 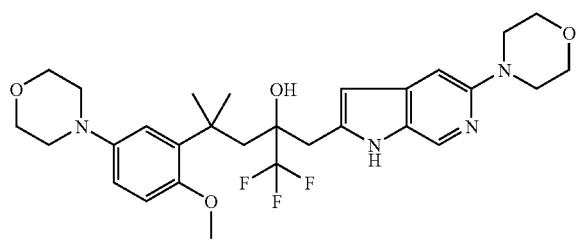 |

-continued

IA

| A | B |
|---|---|
| 4-Piperidin-1-yl-2-[4,4,4-trifluoro-3-hydroxy-1,1-dimethyl-3-(5-piperidin-1-yl-1H-pyrrolo[2,3-c]pyridin-2-ylmethyl)butyl]phenol | 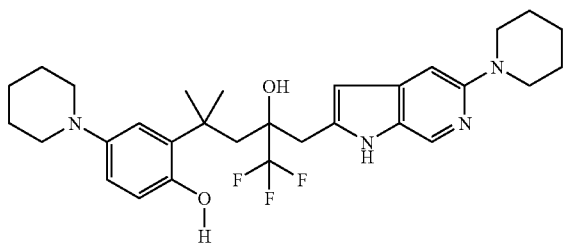 |
| 1,1,1-Trifluoro-4-(2-methoxy-5-piperidin-1-ylphenyl)-4-methyl-2-(5-piperidin-1-yl-1H-pyrrolo[2,3-c]pyridin-2-ylmethyl)pentan-2-ol | 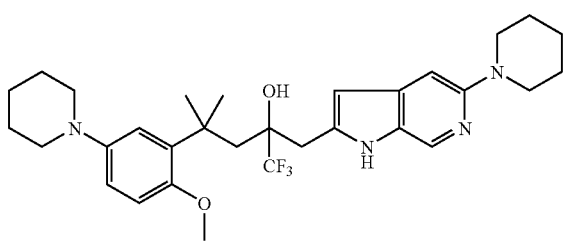 |
| 2-[3-(3-Dimethylaminomethyl-1H-pyrrolo[3,2-c]pyridin-2-ylmethyl)-4,4,4-trifluoro-3-hydroxy-1,1-dimethylbutyl]-4-fluorophenol | 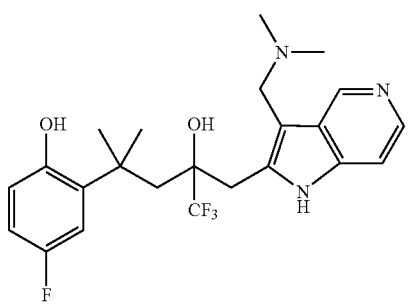 |
| 1,1,1-Trifluoro-4-(5-methanesulfonyl-2,3-dihydrobenzofuran-7-yl)-4-methyl-2-(1H-pyrrolo[3,2-c]pyridin-2-ylmethyl)pentan-2-ol | 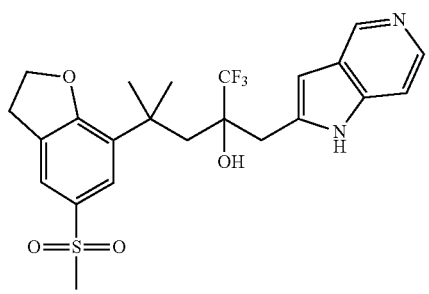 |
| 2-(3-Chloro-1H-pyrrolo[3,2-c]pyridin-2-ylmethyl)-1,1,1-trifluoro-4-(5-fluoro-2-methoxyphenyl)-4-methylpentan-2-ol | 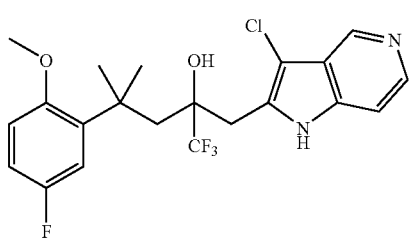 |
| 1,1,1-Trifluoro-4-methyl-4-(5-methylsulfanyl-2,3-dihydrobenzofuran-7-yl)-2-pyrrolo[3,2-b]pyridin-1-ylmethylpentan-2-ol | 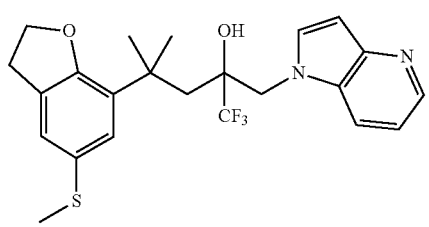 |

-continued

IA

| A | B |
|---|---|
| 1,1,1-Trifluoro-4-(5-methanesulfonyl-2,3-dihydrobenzofuran-7-yl)-4-methyl-2-pyrrolo[3,2-b]pyridin-1-ylmethylpentan-2-ol | 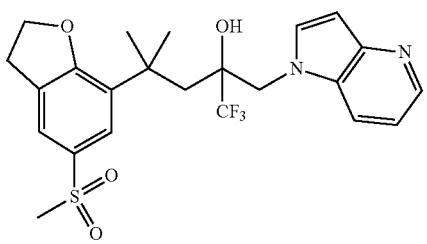 |
| 4-(5-Chloro-2,3-dihydrobenzofuran-7-yl)-1,1,1-trifluoro-4-methyl-2-(5-phenyl-1H-pyrrolo[2,3-c]pyridin-2-ylmethyl)pentan-2-ol | 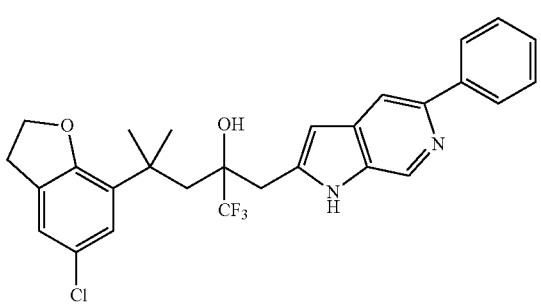 |
| 1,1,1-Trifluoro-4-(5-fluoro-2-methylphenyl)-4-methyl-2-(5-phenyl-1H-pyrrolo[2,3-c]pyridin-2-ylmethyl)pentan-2-ol | 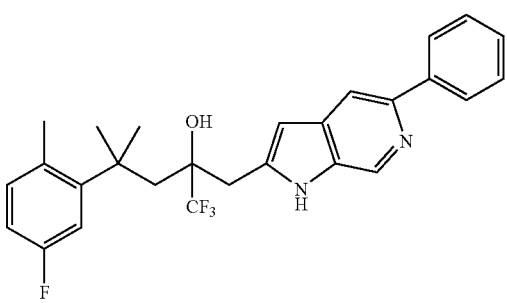 |
| 1,1,1-Trifluoro-4-methyl-4-(5-pyrimidin-5-yl-2,3-dihydrobenzofuran-7-yl)-2-pyrrolo[3,2-b]pyridin-1-ylmethylpentan-2-ol | 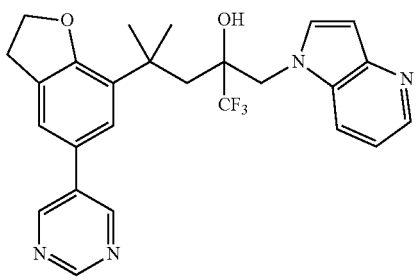 |
| 1,1,1-Trifluoro-4-(2-methoxy-5-pyrimidin-5-ylphenyl)-4-methyl-2-pyrrolo[3,2-b]pyridin-1-ylmethylpentan-2-ol | 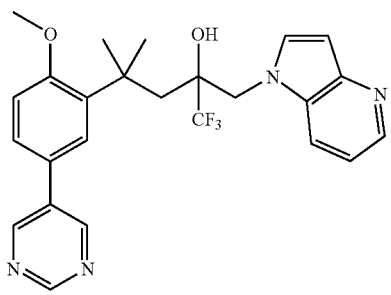 |

IA

| A | B |
|---|---|
| 1,1,1-Trifluoro-4-(2-methoxy-5-pyridin-3-ylphenyl)-4-methyl-2-pyrrolo[3,2-b]pyridin-1-ylmethylpentan-2-ol | 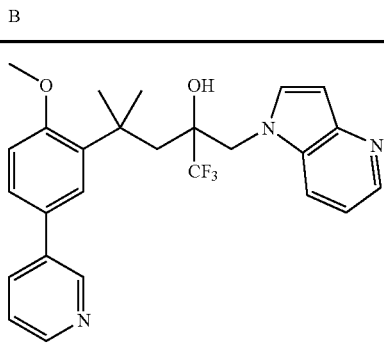 |
| 4-Pyridin-3-yl-2-(4,4,4-trifluoro-3-hydroxy-1,1-dimethyl-3-pyrrolo[3,2-b]pyridin-1-ylmethylbutyl)phenol | 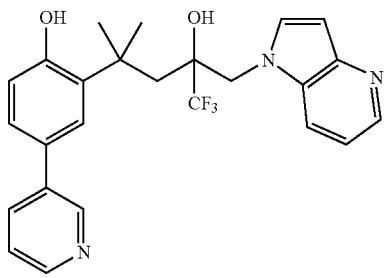 |
| 1,1,1-Trifluoro-4-methyl-4-(5-pyridin-3-yl-2,3-dihydrobenzofuran-7-yl)-2-pyrrolo[3,2-b]pyridin-1-ylmethylpentan-2-ol | 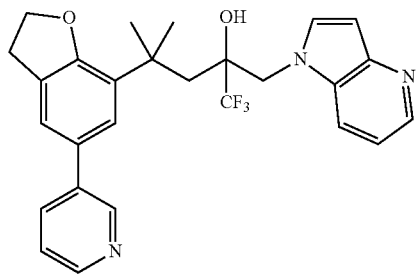 |
| 3'-Chloro-3-(4,4,4-trifluoro-3-hydroxy-1,1-dimethyl-3-pyrrolo[3,2-b]pyridin-1-ylmethylbutyl)biphenyl-4-ol | 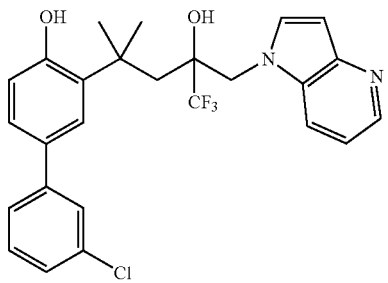 |
| 4'-Hydroxy-3'-(4,4,4-trifluoro-3-hydroxy-1,1-dimethyl-3-pyrrolo[3,2-b]pyridin-1-ylmethylbutyl)biphenyl-3-carbonitrile | 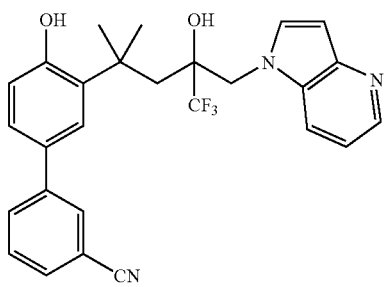 | or a tautomer, prodrug, solvate, or salt thereof.

| IB | |
|---|---|
| A | B |
| 2-Cyclopropyl-4-(5-fluoro-2-methoxyphenyl)-4-methyl-1-(1H-pyrrolo[3,2-c]pyridin-2-yl)pentan-2-ol | 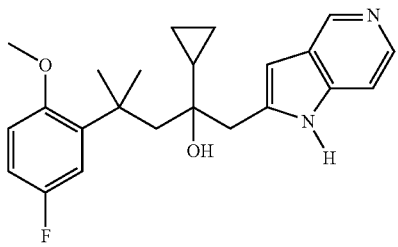 |
| 4-(5-Fluoro-2-methoxyphenyl)-2-hydroxy-4-methyl-2-(1H-pyrrolo[2,3-c]pyridin-2-ylmethyl)pentanoic acid | 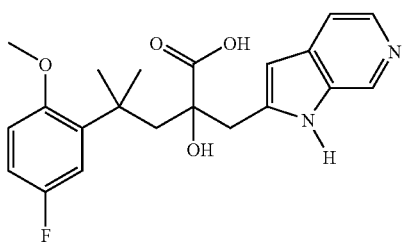 |
| 4-(5-Fluoro-2-methoxyphenyl)-2-hydroxy-4-methyl-2-(1H-pyrrolo[2,3-c]pyridin-2-ylmethyl)pentanoic acid methyl ester | 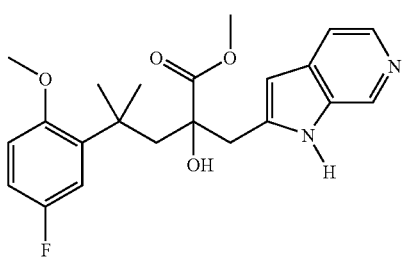 |
| 2-Cyclopropyl-4-(5-fluoro-2-methylphenyl)-4-methyl-1-(1H-pyrrolo[2,3-c]pyridin-2-yl)pentan-2-ol | 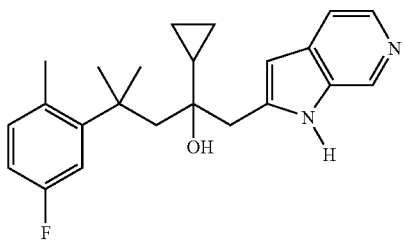 |
| 4-(5-Chloro-2,3-dihydrobenzofuran-7-yl)-2-cyclopropyl-4-methyl-1-(1H-pyrrolo[2,3-c]pyridin-2-yl)pentan-2-ol | 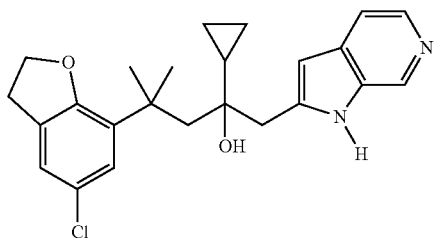 |
| 2-Cyclopropyl-4-(5-fluoro-2-methylphenyl)-4-methyl-1-(1H-pyrrolo[3,2-c]pyridin-2-yl)pentan-2-ol | 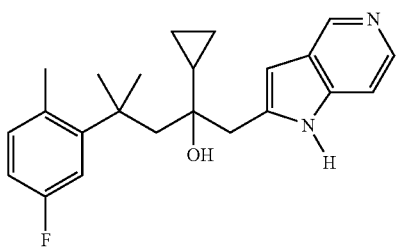 |

-continued

| IB | |
|---|---|
| A | B |
| 4-(5-Chloro-2,3-dihydrobenzofuran-7-yl)-2-cyclopropyl-4-methyl-1-(1H-pyrrolo[3,2-c]pyridin-2-yl)pentan-2-ol | 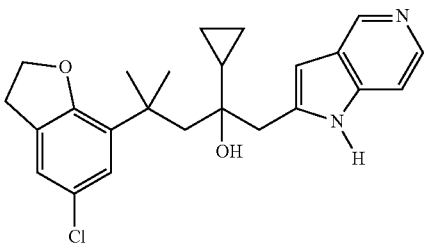 |
| 4-(5-Fluoro-2-methoxyphenyl)-2,4-dimethyl-1-(1H-pyrrolo[2,3-c]pyridin-2-yl)pentan-2-ol | 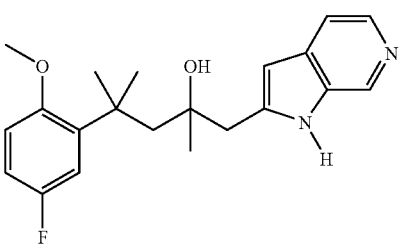 |
| 5-(5-Fluoro-2-methoxyphenyl)-2,5-dimethyl-3-(1H-pyrrolo[2,3-c]pyridin-2-ylmethyl)hexan-3-ol | 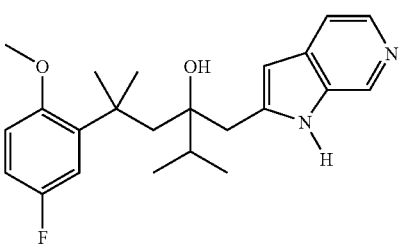 |
| 5-(5-Fluoro-2-methoxyphenyl)-2,2,5-trimethyl-3-(1H-pyrrolo[2,3-c]pyridin-2-ylmethyl)hexan-3-ol | 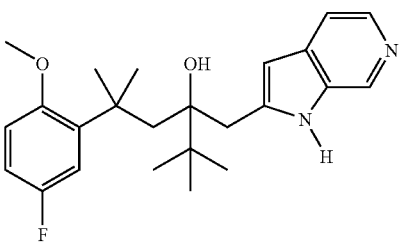 |
| 2-Cyclohexyl-4-(5-fluoro-2-methoxyphenyl)-4-methyl-1-(1H-pyrrolo[2,3-c]pyridin-2-yl)pentan-2-ol | 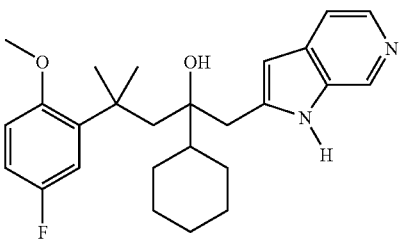 |
| 2-Cyclopentyl-4-(5-fluoro-2-methoxyphenyl)-4-methyl-1-(1H-pyrrolo[2,3-c]pyridin-2-yl)pentan-2-ol | 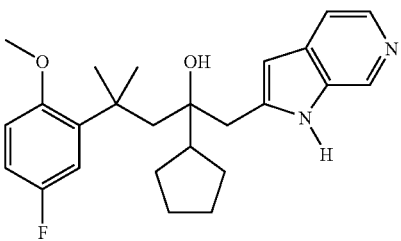 |

-continued

| IB | |
|---|---|
| A | B |
| 5-(5-Fluoro-2-methoxyphenyl)-5-methyl-3-(1H-pyrrolo[2,3-c]pyridin-2-ylmethyl)hexan-3-ol | 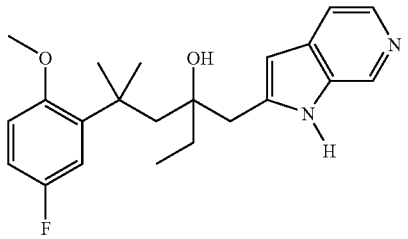 |
| 2-(5-Fluoro-2-methoxyphenyl)-2,6-dimethyl-4-(1H-pyrrolo[2,3-c]pyridin-2-ylmethyl)heptan-4-ol | 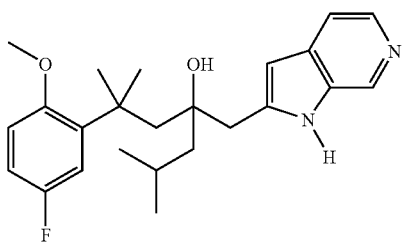 |
| 2-(5-Fluoro-2-methoxyphenyl)-2,5,5-trimethyl-4-(1H-pyrrolo[2,3-c]pyridin-2-ylmethyl)heptan-4-ol | 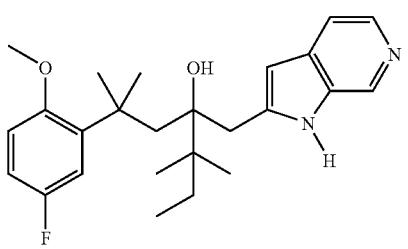 |
| 1,1-Difluoro-4-(5-fluoro-2-methoxyphenyl)-4-methyl-2-(1H-pyrrolo[2,3-c]pyridin-2-ylmethyl)pentan-2-ol | 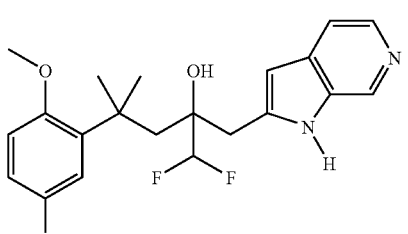 |
| 1-Cyclohexyl-4-(5-fluoro-2-methoxyphenyl)-4-methyl-2-(1H-pyrrolo[2,3-c]pyridin-2-ylmethyl)pentan-2-ol | 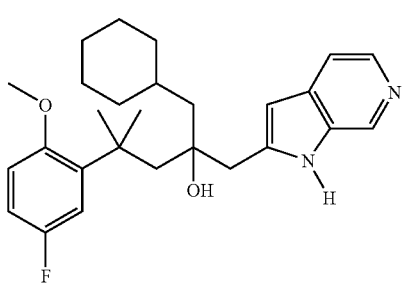 |
| 5-(5-Fluoro-2-methylphenyl)-2,5-dimethyl-3-(1H-pyrrolo[2,3-c]pyridin-2-ylmethyl)hexan-3-ol | 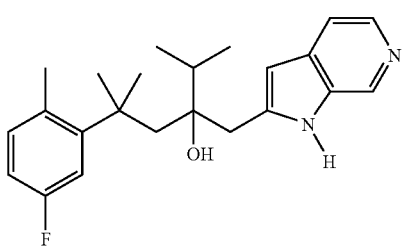 |

| IB | |
|---|---|
| A | B |
| 5-(5-Fluoro-2-methylphenyl)-2,2,5-trimethyl-3-(1H-pyrrolo[2,3-c]pyridin-2-ylmethyl)hexan-3-ol | 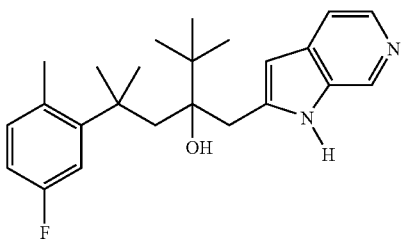 |
| 5-(5-Chloro-2,3-dihydrobenzofuran-7-yl)-2,5-dimethyl-3-(1H-pyrrolo[2,3-c]pyridin-2-ylmethyl)hexan-3-ol | 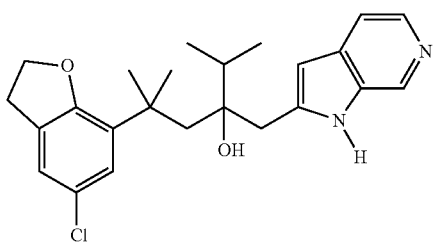 |
| 2-Cyclobutyl-4-(5-fluoro-2-methoxyphenyl)-4-methyl-1-(1H-pyrrolo[2,3-c]pyridin-2-yl)pentan-2-ol | 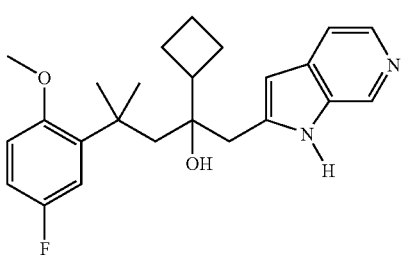 |
| 2-(5-Fluoro-2-methoxyphenyl)-2,6,6-trimethyl-4-(1H-pyrrolo[2,3-c]pyridin-2-ylmethyl)heptan-4-ol | 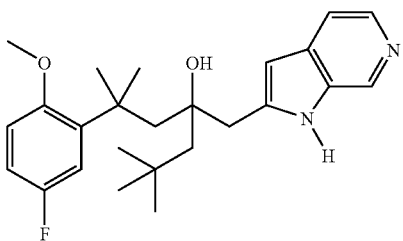 |
| 5-(5-Fluoro-2-methoxyphenyl)-5-methyl-3-(1H-pyrrolo[2,3-c]pyridin-2-ylmethyl)hex-1-en-3-ol | 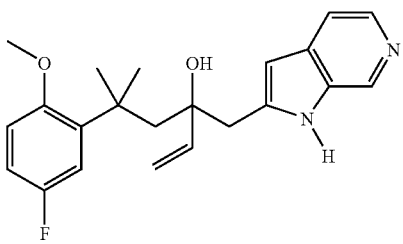 |
| 5-(5-Fluoro-2-methoxyphenyl)-5-methyl-3-(1H-pyrrolo[2,3-c]pyridin-2-ylmethyl)hex-1-yn-3-ol | 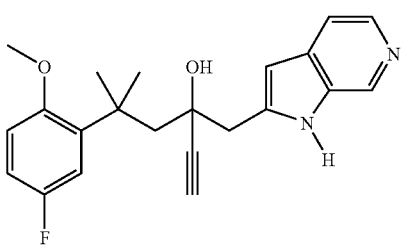 |

-continued

| IB | |
|---|---|
| A | B |

1-Fluoro-4-(5-fluoro-2-methoxyphenyl)-4-methyl-2-(1H-pyrrolo[2,3-c]pyridin-2-ylmethyl)pentan-2-ol

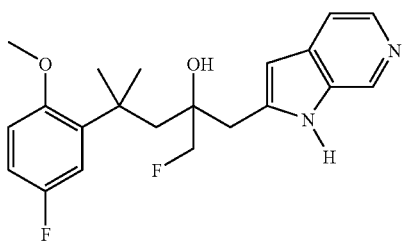 [SMILES: COc1ccc(F)cc1C(C)(C)CC(O)(CF)Cc1cc2ccncc2[nH]1]

2,2-Difluoro-5-(5-fluoro-2-methoxyphenyl)-5-methyl-3-(1H-pyrrolo[2,3-c]pyridin-2-ylmethyl)hexan-3-ol

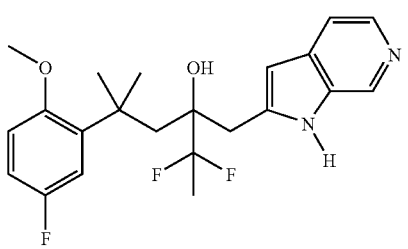 [SMILES: COc1ccc(F)cc1C(C)(C)CC(O)(Cc1cc2ccncc2[nH]1)C(C)(F)F]

2-Fluoro-5-(5-fluoro-2-methoxyphenyl)-2,5-dimethyl-3-(1H-pyrrolo[2,3-c]pyridin-2-ylmethyl)hexan-3-ol

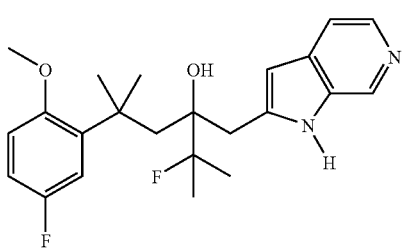

2-Fluoro-5-(5-fluoro-2-methoxyphenyl)-5-methyl-3-(1H-pyrrolo[2,3-c]pyridin-2-ylmethyl)hexan-3-ol

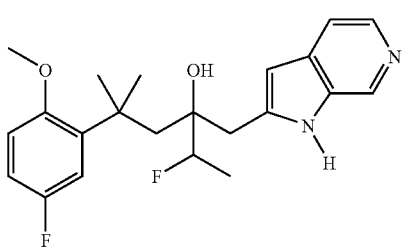

5-(5-Fluoro-2-methoxyphenyl)-2,5-dimethyl-3-(1H-pyrrolo[2,3-c]pyridin-2-ylmethyl)hex-1-en-3-ol

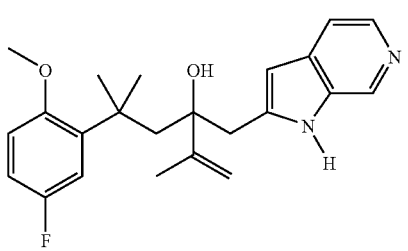 [SMILES: C=C(C)C(O)(Cc1cc2ccncc2[nH]1)CC(C)(C)c1cc(F)ccc1OC]

1,1,1-Trifluoro-5-(5-fluoro-2-methoxyphenyl)-5-methyl-3-(1H-pyrrolo[2,3-c]pyridin-2-ylmethyl)hexan-3-ol

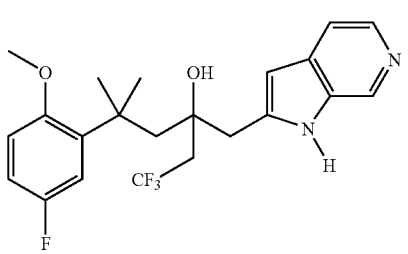 [SMILES: COc1ccc(F)cc1C(C)(C)CC(O)(Cc1cc2ccncc2[nH]1)CC(F)(F)F]

IB

| A | B |
|---|---|
| 4-(5-Fluoro-2-methoxyphenyl)-4-methyl-2-phenyl-1-(1H-pyrrolo[2,3-c]pyridin-2-yl)pentan-2-ol | 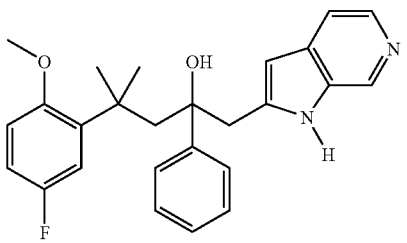 |
| 5-(5-Chloro-2,3-dihydrobenzofuran-7-yl)-2,2,5-trimethyl-3-(1H-pyrrolo[2,3-c]pyridin-2-ylmethyl)hexan-3-ol | 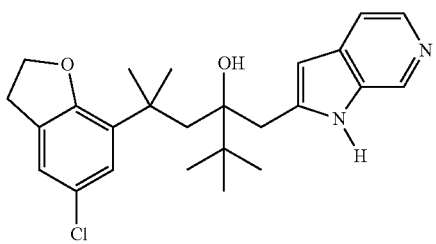 |
| 5-(5-Fluoro-2-methylphenyl)-2,2,5-trimethyl-3-thieno[2,3-c]pyridin-2-ylmethylhexan-3-ol | 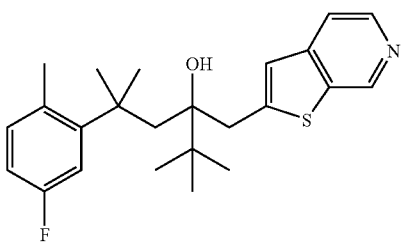 |
| 1,1-Difluoro-4-(5-fluoro-2-methoxyphenyl)-4-methyl-2-(1H-pyrrolo[3,2-c]pyridin-2-ylmethyl)pentan-2-ol | 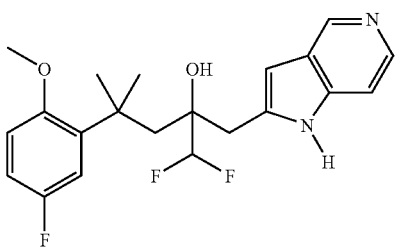 |
| 5-(5-Fluoro-2-methoxyphenyl)-2,5-dimethyl-3-(1H-pyrrolo[3,2-c]pyridin-2-ylmethyl)hexan-3-ol | 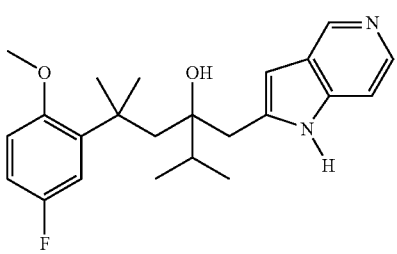 |
| 5-(5-Fluoro-2-methoxyphenyl)-2,2,5-trimethyl-3-(1H-pyrrolo[3,2-c]pyridin-2-ylmethyl)hexan-3-ol | 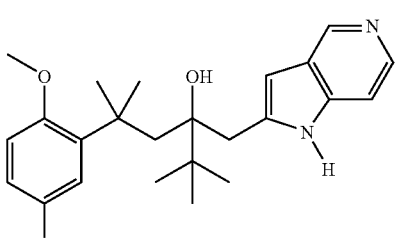 |

|   | IB |
|---|---|
| A | B |

2-(1-Fluorocyclopropyl)-4-(5-fluoro-2-methoxyphenyl)-4-methyl-1-(1H-pyrrolo[2,3-c]pyridin-2-yl)pentan-2-ol

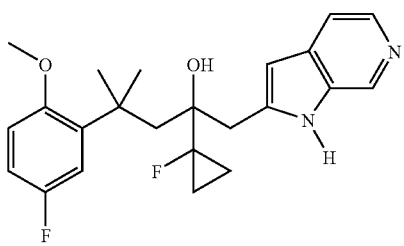 [SMILES: COc1ccc(F)cc1C(C)(C)CC(O)(Cc1cc2ccncc2[nH]1)C1(F)CC1]

2-(1-Fluorocyclopropyl)-4-(4-fluorophenyl)-4-methyl-1-quinolin-4-ylpentan-2-ol

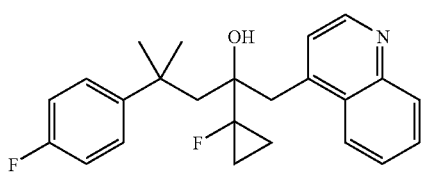 [SMILES: CC(C)(CC(O)(Cc1ccnc2ccccc12)C1(F)CC1)c1ccc(F)cc1]

2-[4,4-Difluoro-3-hydroxy-1,1-dimethyl-3-(1H-pyrrolo[3,2-c]pyridin-2-ylmethyl)butyl]-4-fluorophenol

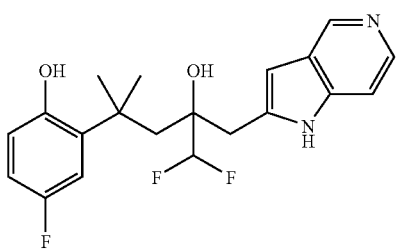 [SMILES: CC(C)(CC(O)(Cc1cc2cnccc2[nH]1)C(F)F)c1cc(F)ccc1O]

5-(5-Chloro-2,3-dihydrobenzofuran-7-yl)-2,5-dimethyl-3-(1H-pyrrolo[3,2-c]pyridin-2-ylmethyl)hexan-3-ol

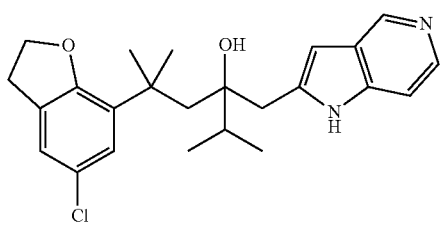 [SMILES: CC(C)C(O)(Cc1cc2cnccc2[nH]1)CC(C)(C)c1cc(Cl)cc2c1OCC2]

5-(5-Fluoro-2-methylphenyl)-2,5-dimethyl-3-(1H-pyrrolo[3,2-c]pyridin-2-ylmethyl)hexan-3-ol

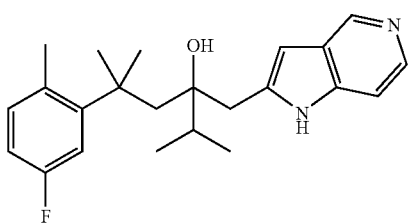 [SMILES: Cc1ccc(F)cc1C(C)(C)CC(O)(Cc1cc2cnccc2[nH]1)C(C)C]

5-(5-Fluoro-2-methylphenyl)-2,2,5-trimethyl-3-(1H-pyrrolo[3,2-c]pyridin-2-ylmethyl)hexan-3-ol

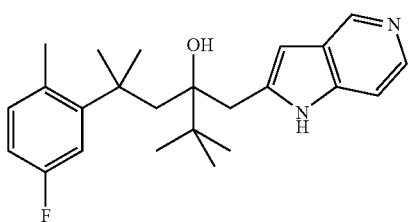 [SMILES: Cc1ccc(F)cc1C(C)(C)CC(O)(Cc1cc2cnccc2[nH]1)C(C)(C)C]

-continued

IB

| A | B |
|---|---|
| 4-(5-Chloro-2,3-dihydrobenzofuran-7-yl)-1,1-difluoro-4-methyl-2-(1H-pyrrolo[3,2-c]pyridin-2-ylmethyl)pentan-2-ol | 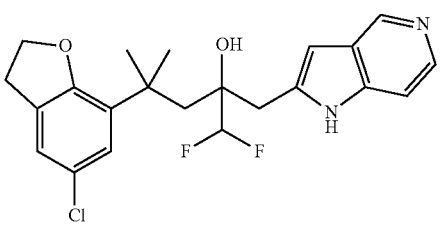 |
| 4-(5-Chloro-2,3-dihydrobenzofuran-7-yl)-1,1-difluoro-4-methyl-2-pyrrolo[3,2-b]pyridin-1-ylmethylpentan-2-ol | 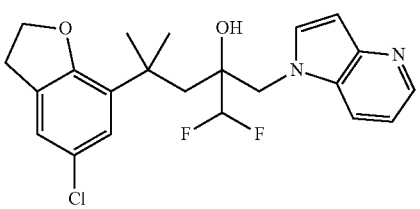 |
| 5-(5-Chloro-2,3-dihydrobenzofuran-7-yl)-2,2,5-trimethyl-3-(1H-pyrrolo[3,2-c]pyridin-2-ylmethyl)hexan-3-ol | 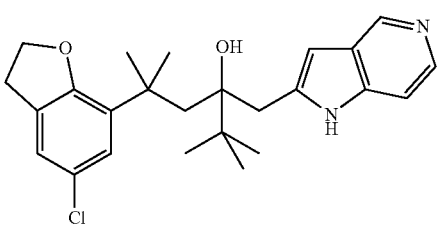 |
| 5-(5-Fluoro-2-methylphenyl)-2,2,5-trimethyl-3-(3-methyl-1H-pyrrolo[2,3-c]pyridin-2-ylmethyl)hexan-3-ol | 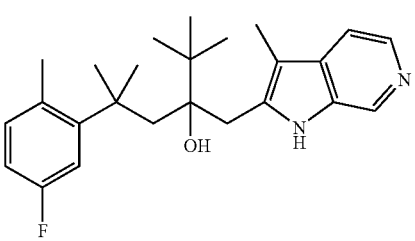 |
| 5-(5-Chloro-2,3-dihydrobenzofuran-7-yl)-2,5-dimethyl-3-(3-methyl-1H-pyrrolo[2,3-c]pyridin-2-ylmethyl)hexan-3-ol | 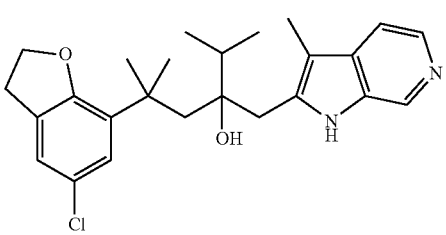 |
| 5-(5-Chloro-2,3-dihydrobenzofuran-7-yl)-2,5-dimethyl-3-(5-phenyl-1H-pyrrolo[2,3-c]pyridin-2-ylmethyl)hexan-3-ol | 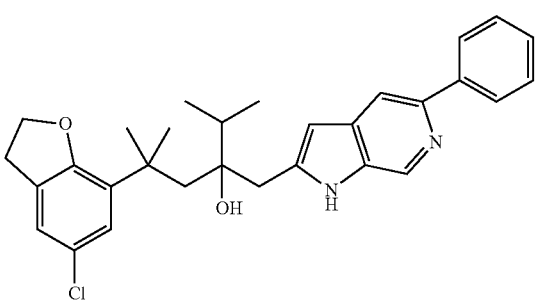 |

-continued

| IB | |
|---|---|
| A | B |
| 5-(5-Fluoro-2-methylphenyl)-2,2,5-trimethyl-3-(5-phenyl-1H-pyrrolo[2,3-c]pyridin-2-ylmethyl)hexan-3-ol | 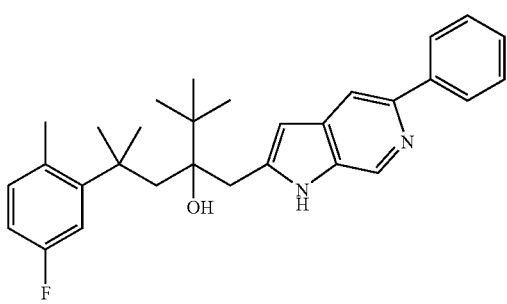 |
| 5-(5-Fluoro-2-methylphenyl)-2,5-dimethyl-3-(5-phenyl-1H-pyrrolo[2,3-c]pyridin-2-ylmethyl)hexan-3-ol | 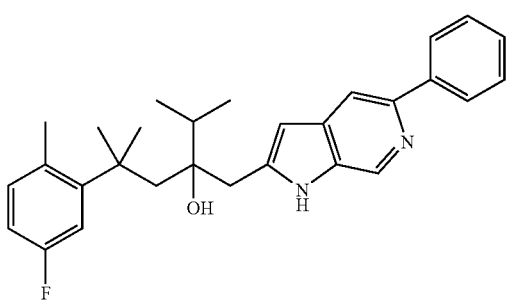 |
| 5-(5-Fluoro-2-methylphenyl)-5-methyl-3-(5-phenyl-1H-pyrrolo[2,3-c]pyridin-2-ylmethyl)hexan-3-ol | 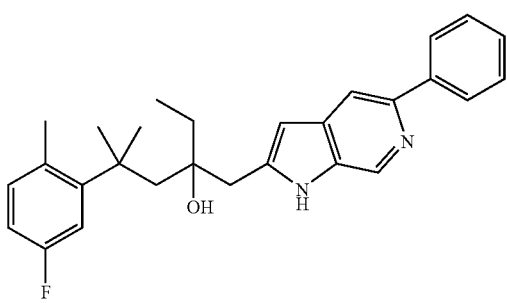 |
| 4-(5-Fluoro-2-methylphenyl)-2,4-dimethyl-1-(5-phenyl-1H-pyrrolo[2,3-c]pyridin-2-yl)pentan-2-ol | 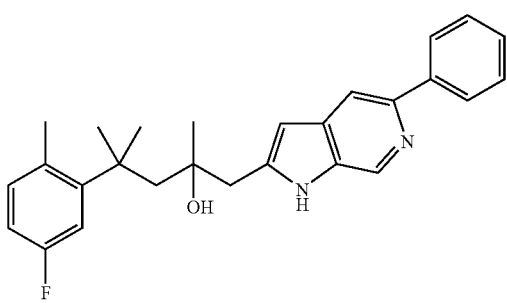 |
| 4-(5-Chloro-2,3-dihydrobenzofuran-7-yl)-1,1-difluoro-4-methyl-2-(6-methyl-1H-pyrrolo[3,2-c]pyridin-2-ylmethyl)pentan-2-ol | 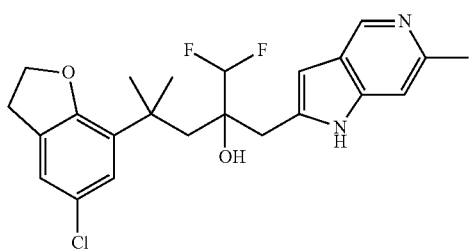 |

-continued

| IB | |
|---|---|
| A | B |
| 5-(5-Fluoro-2-methylphenyl)-2,5-dimethyl-3-(5-pyridin-3-yl-1H-pyrrolo[2,3-c]pyridin-2-ylmethyl)hexan-3-ol | 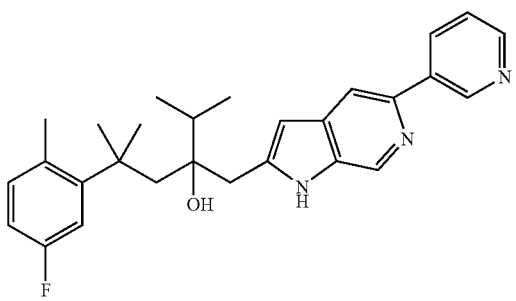 |
| 5-(5-Chloro-2,3-dihydrobenzofuran-7-yl)-5-methyl-3-(5-phenyl-1H-pyrrolo[2,3-c]pyridin-2-ylmethyl)hexan-3-ol | 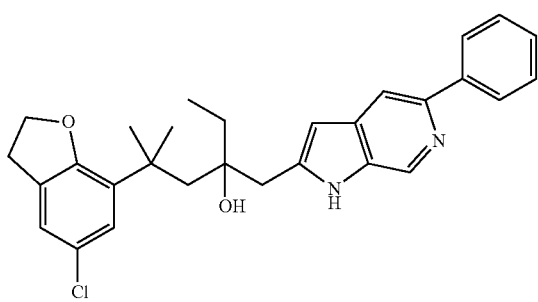 |
| 4-(5-Chloro-2,3-dihydrobenzofuran-7-yl)-2,4-dimethyl-1-(5-phenyl-1H-pyrrolo[2,3-c]pyridin-2-yl)pentan-2-ol | 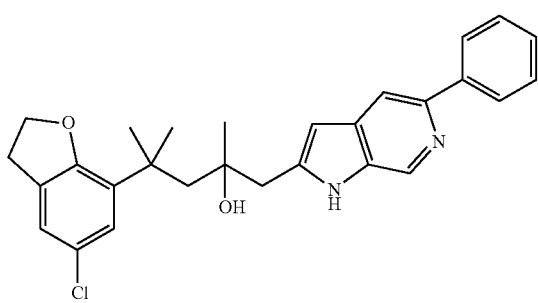 |
| 1,1-Difluoro-4-(5-methanesulfonyl-2,3-dihydrobenzofuran-7-yl)-4-methyl-2-(1H-pyrrolo[2,3-c]pyridin-2-ylmethyl)pentan-2-ol | 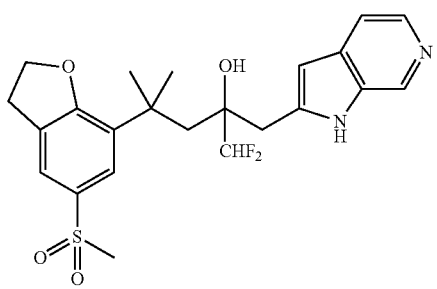 |
| 5-(5-Chloro-2,3-dihydrobenzofuran-7-yl)-2,5-dimethyl-3-(5-pyridin-3-yl-1H-pyrrolo[2,3-c]pyridin-2-ylmethyl)hexan-3-ol | 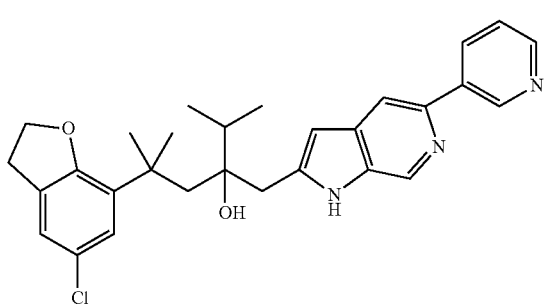 |

| | IB |
|---|---|
| A | B |
| 2-(5-Bromo-1H-indol-2-ylmethyl)-1,1-difluoro-4-(5-methanesulfonyl-2,3-dihydrobenzofuran-7-yl)-4-methylpentan-2-ol | 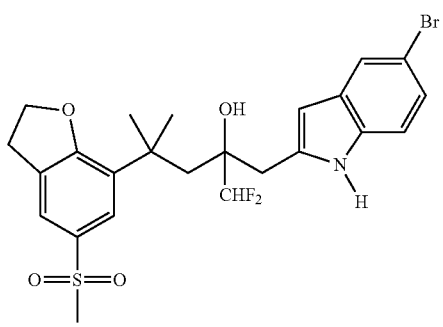 |
| 2-[2-Difluoromethyl-2-hydroxy-4-(5-methanesulfonyl-2,3-dihydrobenzofuran-7-yl)-4-methylpentyl]-4-methyl-1H-indole-6-carbonitrile | 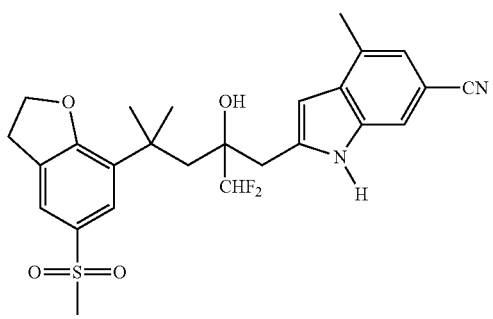 | or a tautomer, prodrug, solvate, or salt thereof.

| | IC |
|---|---|
| A | B |
| 1-[4-(5-Fluoro-2-methoxyphenyl)-2-hydroxy-4-methyl-2-trifluoromethylpentyl]-1,5,6,7-tetrahydroindol-4-one | 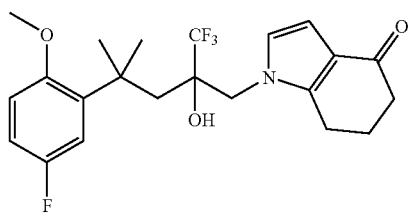 |
| 1-[4-(5-Fluoro-2-hydroxyphenyl)-2-hydroxy-4-methyl-2-trifluoromethylpentyl-1,5,6,7-tetrahydroindol-4-one | 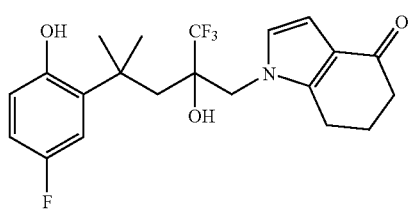 |
| 1-[4-(2,3-Dihydrobenzofuran-7-yl)-2-hydroxy-4-methyl-2-trifluoromethylpentyl]-1,5,6,7-tetrahydroindol-4-one | 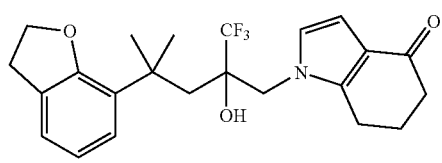 |

-continued

| | IC | |
|---|---|---|
| A | B | |
| 1-[4-(5-Fluoro-2-methylphenyl)-2-hydroxy-4-methyl-2-trifluoromethylpentyl]-1,5,6,7-tetrahydroindol-4-one | 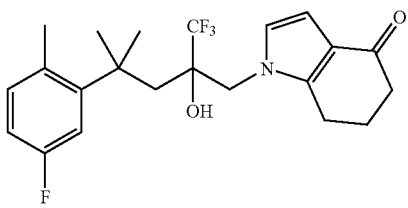 | |
| 1,1,1-Trifluoro-4-(5-fluoro-2-methoxyphenyl)-4-methyl-2-(4,5,6,7-tetrahydroindazol-2-ylmethyl)pentan-2-ol | 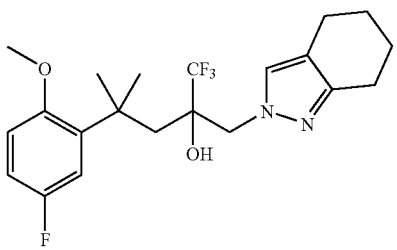 | |
| 1-[2-Hydroxy-4-(5-methanesulfonyl-2,3-dihydrobenzofuran-7-yl)-4-methyl-2-trifluoromethylpentyl]-1,5,6,7-tetrahydroindol-4-one | 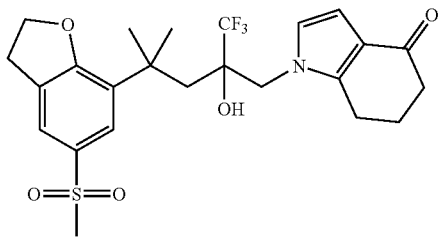 | |
| 1-[4-(5-Fluoro-2-methylphenyl)-2-hydroxy-4-methyl-2-trifluoromethylpentyl]-1,5,6,7-tetrahydrobenzoimidazol-4-one | 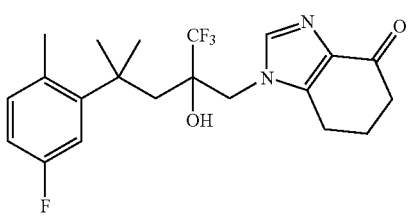 | |
| 1-[2-Hydroxy-4-(5-methanesulfonyl-2,3-dihydrobenzofuran-7-yl)-4-methyl-2-trifluoromethylpentyl]-1,5,6,7-tetrahydrobenzoimidazol-4-one | 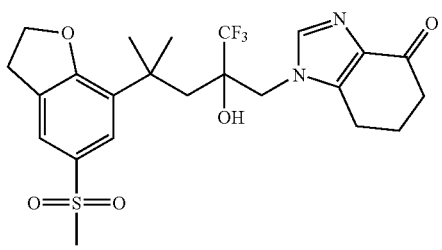 | |
| 1-[2-Hydroxy-4-methyl-4-(5-pyrimidin-5-yl-2,3-dihydrobenzofuran-7-yl)-2-trifluoromethylpentyl]-1,5,6,7-tetrahydroindol-4-one | 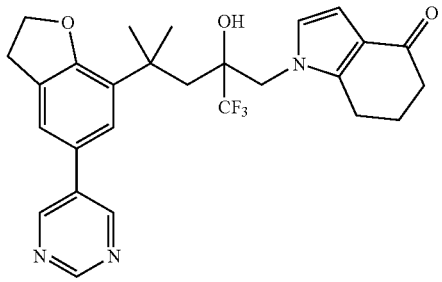 | |

-continued

| | IC |
|---|---|
| A | B |

| | |
|---|---|
| 1-[2-Hydroxy-4-(2-methoxy-5-pyrimidin-5-ylphenyl)-4-methyl-2-trifluoromethylpentyl]-1,5,6,7-tetrahydroindol-4-one | 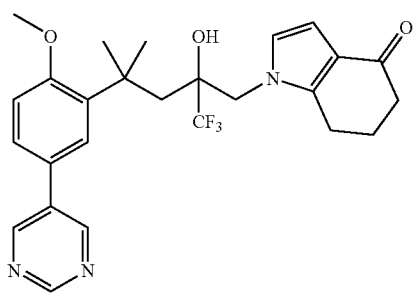 |
| 1-[2-Hydroxy-4-(2-hydroxy-5-pyrimidin-5-ylphenyl)-4-methyl-2-trifluoromethylpentyl]-1,5,6,7-tetrahydroindol-4-one | 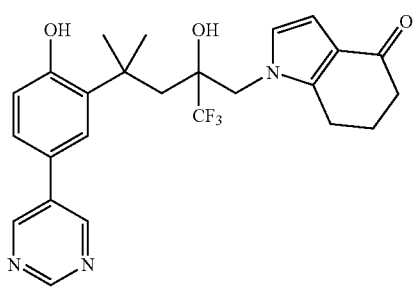 |
| 1-[2-Hydroxy-4-(2-methoxy-5-pyridin-3-ylphenyl)-4-methyl-2-trifluoromethylpentyl]-1,5,6,7-tetrahydroindol-4-one | 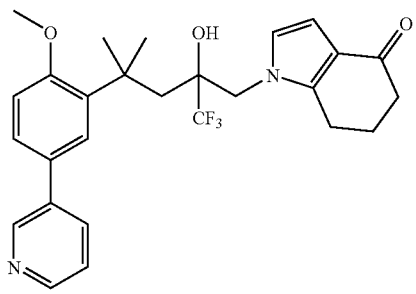 |
| 1-[2-Hydroxy-4-(2-hydroxy-5-pyridin-3-ylphenyl)-4-methyl-2-trifluoromethylpentyl]-1,5,6,7-tetrahydroindol-4-one | 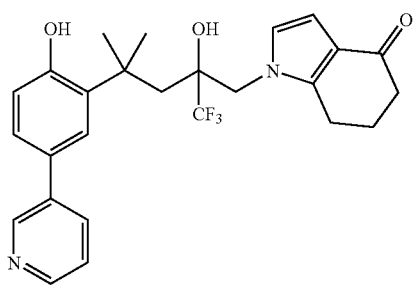 |
| 1-[2-Hydroxy-4-methyl-4-(5-pyridin-3-yl-2,3-dihydrobenzofuran-7-yl)-2-trifluoromethylpentyl]-1,5,6,7-tetrahydroindol-4-one | 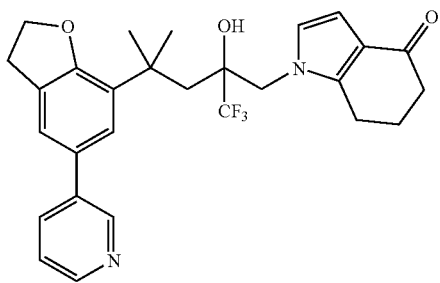 |

-continued

| | IC | |
|---|---|---|
| A | B | |

| | | |
|---|---|---|
| 5-{4-Hydroxy-3-[4,4,4-trifluoro-3-hydroxy-1,1-dimethyl-3-(4-oxo-4,5,6,7-tetrahydroindol-1-ylmethyl)butyl]phenyl}nicotinonitrile | 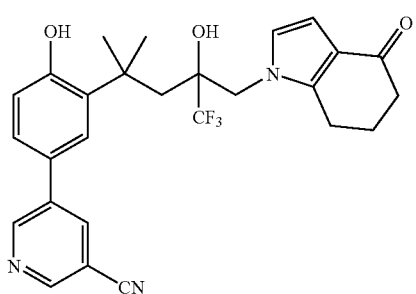 | |
| 1-[2-Hydroxy-4-(2-methoxy-5-pyrimidin-2-ylphenyl)-4-methyl-2-trifluoromethylpentyl]-1,5,6,7-tetrahydroindol-4-one | 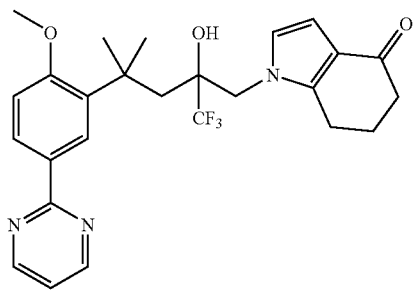 | |
| 1-[2-Hydroxy-4-(2-methoxy-5-pyrazin-2-ylphenyl)-4-methyl-2-trifluoromethylpentyl]-1,5,6,7-tetrahydroindol-4-one | 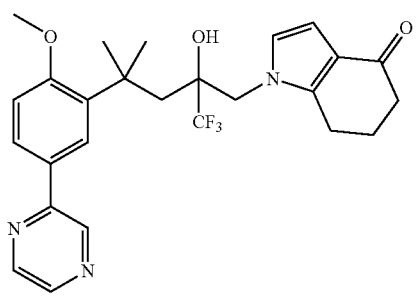 | |
| 1-{4-[5-(5-Chloropyridin-3-yl)-2-hydroxyphenyl]-2-hydroxy-4-methyl-2-trifluoromethylpentyl}-1,5,6,7-tetrahydroindol-4-one | 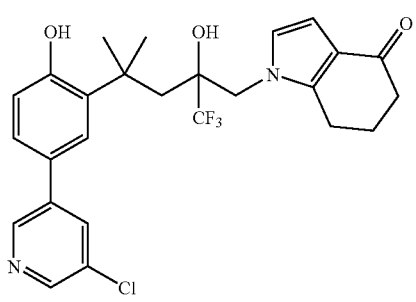 | |
| 1-[2-Hydroxy-4-methyl-4-(5-pyridin-4-yl-2,3-dihydrobenzofuran-7-yl)-2-trifluoromethylpentyl]-1,5,6,7-tetrahydroindol-4-one | 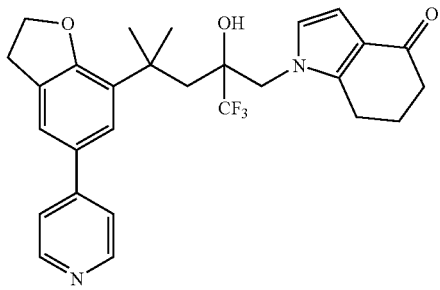 | |

IC

| A | B |
|---|---|
| 1-[2-Hydroxy-4-methyl-4-(5-pyridin-2-yl-2,3-dihydrobenzofuran-7-yl)-2-trifluoromethylpentyl]-1,5,6,7-tetrahydroindol-4-one | 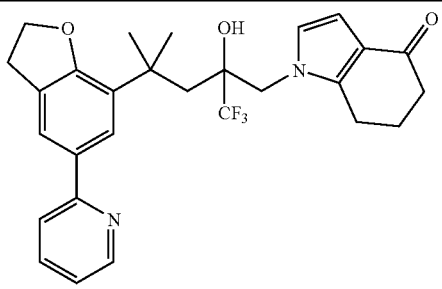 | or a tautomer, prodrug, solvate, or salt thereof.

ID

| A | B |
|---|---|
| 1,1,1-Trifluoro-5-methoxy-4-methyl-4-phenyl-2-quinolin-4-ylmethylpentan-2-ol | 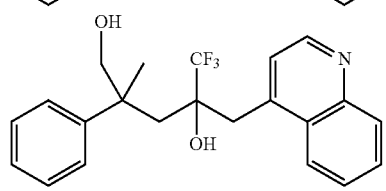 |
| 5,5,5-Trifluoro-2-methyl-2-phenyl-4-quinolin-4-ylmethylpentane-1,4-diol | 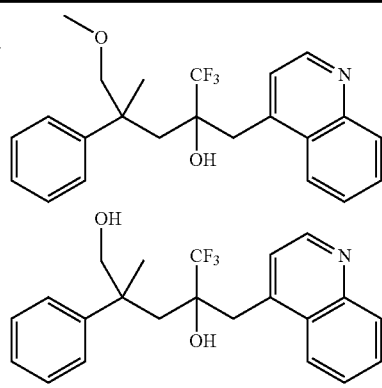 | or a tautomer, prodrug, solvate, or salt thereof.

We claim:

1. A compound selected from one of the following compounds:

| Compound Name | Compound Structure |
|---|---|
| 1,1,1-Trifluoro-4-(5-fluoro-2-methoxyphenyl)-4-methyl-2-(3-methyl-1H-pyrrolo[3,2-c]pyridin-2-ylmethyl)pentan-2-ol | 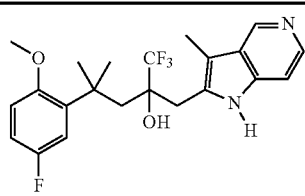 |
| 2-(4,6-Dimethyl-1H-pyrrolo[3,2-c]pyridin-2-ylmethyl)-1,1,1-trifluoro-4-(5-fluoro-2-methoxyphenyl)-4-methylpentan-2-ol | 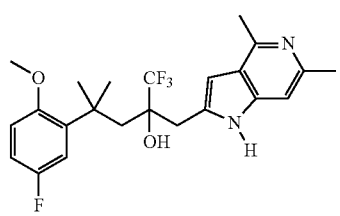 [SMILES: COc1ccc(F)cc1C(C)(C)CC(O)(Cc1cc2c(C)nc(C)cc2[nH]1)C(F)(F)F] |
| 2-(5,7-Dimethyl-1H-pyrrolo[2,3-c]pyridin-2-ylmethyl)-1,1,1-trifluoro-4-(5-fluoro-2-methoxyphenyl)-4-methylpentan-2-ol | 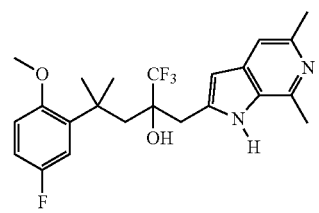 [SMILES: COc1ccc(F)cc1C(C)(C)CC(O)(Cc1cc2cc(C)nc(C)c2[nH]1)C(F)(F)F] |
| 2-[4-(5-Fluoro-2-methoxyphenyl)-2-hydroxy-4-methyl-2-trifluoromethylpentyl]-1H-pyrrolo[3,2-b]pyridine-5-carbonitrile | 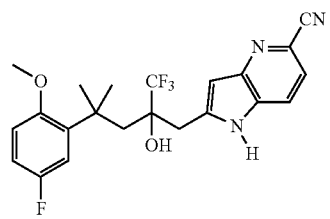 [SMILES: COc1ccc(F)cc1C(C)(C)CC(O)(Cc1cc2nc(C#N)ccc2[nH]1)C(F)(F)F] |

| Compound Name | Compound Structure |
|---|---|
| 1,1,1-Trifluoro-4-(5-fluoro-2-methoxyphenyl)-4-methyl-2-(6-methyl-1H-pyrrolo[3,2-c]pyridin-2-ylmethyl)pentan-2-ol | 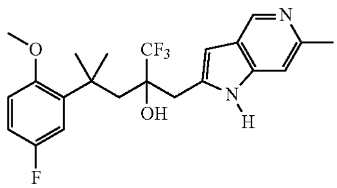 [SMILES: COc1ccc(F)cc1C(C)(C)CC(O)(Cc1cc2cnc(C)cc2[nH]1)C(F)(F)F] |
| 1,1,1-Trifluoro-4-(5-fluoro-2-methoxyphenyl)-4-methyl-2-(4-methyl-1H-pyrrolo[3,2-c]pyridin-2-ylmethyl)pentan-2-ol | 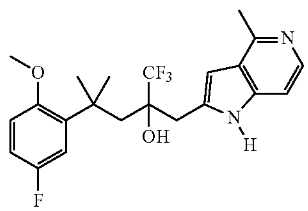 [SMILES: COc1ccc(F)cc1C(C)(C)CC(O)(Cc1cc2c(C)nccc2[nH]1)C(F)(F)F] |
| 2-[4-(5-Fluoro-2-methoxyphenyl)-2-hydroxy-4-methyl-2-trifluoromethylpentyl]-4-methyl-1H-pyrrolo[3,2-c]pyridine-6-carbonitrile | 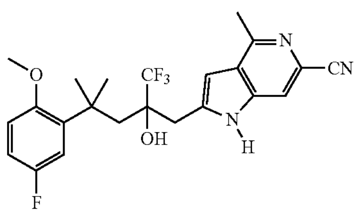 [SMILES: COc1ccc(F)cc1C(C)(C)CC(O)(Cc1cc2c(C)nc(C#N)cc2[nH]1)C(F)(F)F] |
| 2-[4-(5-Fluoro-2-methoxyphenyl)-2-hydroxy-4-methyl-2-trifluoromethylpentyl]-1H-pyrrolo[2,3-c]pyridine-5-carbonitrile | 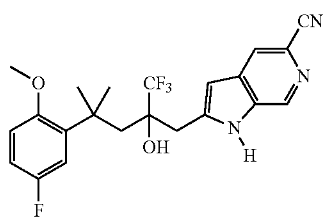 [SMILES: COc1ccc(F)cc1C(C)(C)CC(O)(Cc1cc2cc(C#N)ncc2[nH]1)C(F)(F)F] |
| 2-[4-(5-Fluoro-2-methoxyphenyl)-2-hydroxy-4-methyl-2-trifluoromethylpentyl]-1H-pyrrolo[3,2-c]pyridine-4-carbonitrile | 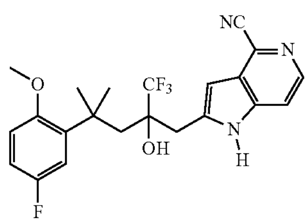 [SMILES: COc1ccc(F)cc1C(C)(C)CC(O)(Cc1cc2c(C#N)nccc2[nH]1)C(F)(F)F] |
| 1,1,1-Trifluoro-4-(5-fluoro-2-methoxyphenyl)-4-methyl-2-(5H-pyrrolo[3,2-d]pyrimidin-6-ylmethyl)pentan-2-ol | 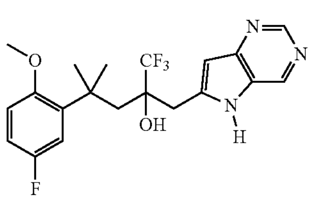 [SMILES: COc1ccc(F)cc1C(C)(C)CC(O)(Cc1cc2ncncc2[nH]1)C(F)(F)F] |
| 1,1,1-Trifluoro-4-(5-fluoro-2-methoxyphenyl)-4-methyl-2-(5H-pyrrolo[3,2-c]pyridazin-6-ylmethyl)pentan-2-ol | 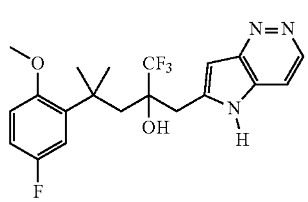 [SMILES: COc1ccc(F)cc1C(C)(C)CC(O)(Cc1cc2nnccc2[nH]1)C(F)(F)F] |
| 1,1,1-Trifluoro-4-(5-fluoro-2-methoxyphenyl)-4-methyl-2-(2-methyl-5H-pyrrolo[3,2-d]pyrimidin-6-ylmethyl)pentan-2-ol | |
| 1,1,1-Trifluoro-4-(5-fluoro-2-methoxyphenyl)-4-methyl-2-(1H-pyrrolo[2,3-d]pyridazin-2-ylmethyl)pentan-2-ol | |
| 2-(4,6-Dimethyl-1H-pyrrolo[3,2-c]pyridin-2-ylmethyl)-1,1,1-trifluoro-4-(5-fluoro-2-methylphenyl)-4-methylpentan-2-ol | |
| 4-(5-Chloro-2,3-dihydrobenzofuran-7-yl)-2-(4,6-dimethyl-1H-pyrrolo[3,2-c]pyridin-2-ylmethyl)-1,1,1-trifluoro-4-methylpentan-2-ol | |
| 4-(5-Chloro-2,3-dihydrobenzofuran-7-yl)-1,1,1-trifluoro-4-methyl-2-(6-methyl-1H-pyrrolo[3,2-c]pyridin-2-ylmethyl)pentan-2-ol | |
| 1,1,1-Trifluoro-4-(5-fluoro-2-methylphenyl)-4-methyl-2-(6-methyl-1H-pyrrolo[3,2-c]pyridin-2-ylmethyl)pentan-2-ol | |
| 2-[4-(5-Fluoro-2-methylphenyl)-2-hydroxy-4-methyl-2-trifluoromethylpentyl]-1H-pyrrolo[3,2-b]pyridine-5-carbonitrile | |

| Compound Name | Compound Structure |
|---|---|
| 2-[4-(5-Chloro-2,3-dihydrobenzofuran-7-yl)-2-hydroxy-4-methyl-2-trifluoromethylpentyl]-1H-pyrrolo[3,2-b]pyridine-5-carbonitrile | 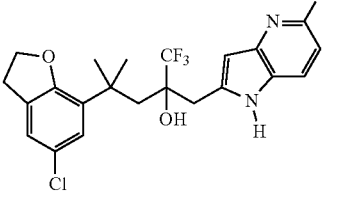 |
| 1,1,1-Trifluoro-4-(5-fluoro-2-methylphenyl)-4-methyl-2-(5H-pyrrolo[3,2-d]pyrimidin-6-ylmethyl)pentan-2-ol | 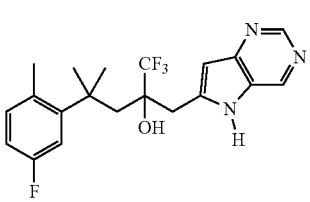 [SMILES: Cc1ccc(F)cc1C(C)(C)CC(O)(Cc1cc2ncncc2[nH]1)C(F)(F)F] |
| 4-(5-Chloro-2,3-dihydrobenzofuran-7-yl)-1,1,1-trifluoro-4-methyl-2-(5H-pyrrolo[3,2-d]pyrimidin-6-ylmethyl)pentan-2-ol | 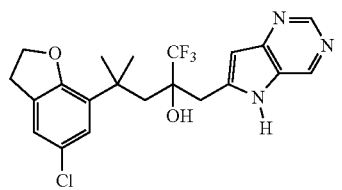 [SMILES: CC(C)(CC(O)(Cc1cc2ncncc2[nH]1)C(F)(F)F)c1cc(Cl)cc2c1OCC2] |
| 1,1,1-Trifluoro-4-(5-fluoro-2-methylphenyl)-4-methyl-2-(5H-pyrrolo[3,2-c]pyridazin-6-ylmethyl)pentan-2-ol | 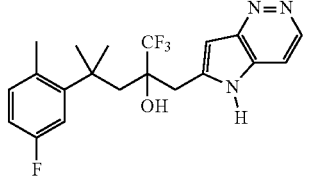 [SMILES: Cc1ccc(F)cc1C(C)(C)CC(O)(Cc1cc2nnccc2[nH]1)C(F)(F)F] |
| 4-(5-Chloro-2,3-dihydrobenzofuran-7-yl)-1,1,1-trifluoro-4-methyl-2-(5H-pyrrolo[3,2-c]pyridazin-6-ylmethyl)pentan-2-ol | 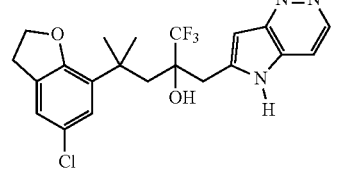 |
| 4-(5-Chloro-2,3-dihydrobenzofuran-7-yl)-1,1,1-trifluoro-4-methyl-2-(1H-pyrrolo[2,3-d]pyridazin-2-ylmethyl)pentan-2-ol | 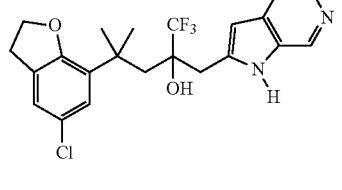 |
| 2-(5,7-Dichloro-1H-pyrrolo[2,3-c]pyridin-2-ylmethyl)-1,1,1-trifluoro-4-(5-fluoro-2-methoxyphenyl)-4-methylpentan-2-ol | 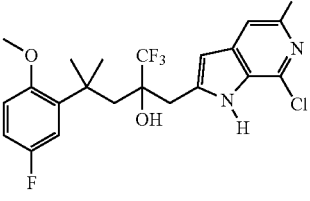 |

| Compound Name | Compound Structure |
|---|---|
| 1,1,1-Trifluoro-4-(5-fluoro-2-methoxyphenyl)-2-(5-methoxy-1H-pyrrolo[2,3-c]pyridin-2-ylmethyl)-4-methylpentan-2-ol | 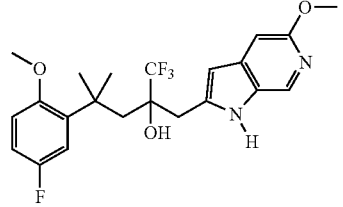 [SMILES: COc1cc2cc(CC(O)(CC(C)(C)c3cc(F)ccc3OC)C(F)(F)F)[nH]c2cn1] |
| 1,1,1-Trifluoro-4-(5-fluoro-2-methylphenyl)-2-(5-isopropoxy-1H-pyrrolo[2,3-c]pyridin-2-ylmethyl)-4-methylpentan-2-ol | 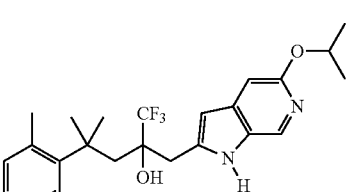 |
| 1,1,1-Trifluoro-4-(5-fluoro-2-methylphenyl)-2-(5-methoxy-1H-pyrrolo[2,3-c]pyridin-2-ylmethyl)-4-methylpentan-2-ol | 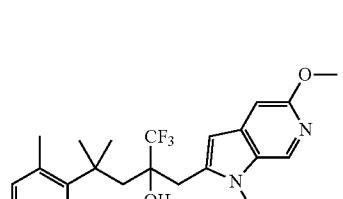 |
| 4-(5-Chloro-2,3-dihydrobenzofuran-7-yl)-1,1,1-trifluoro-2-(5-methoxy-1H-pyrrolo[2,3-c]pyridin-2-ylmethyl)-4-methylpentan-2-ol | 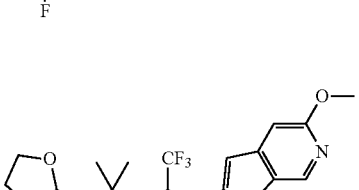 |
| 4-(5-Chloro-2,3-dihydrobenzofuran-7-yl)-1,1,1-trifluoro-2-(5-isopropoxy-1H-pyrrolo[2,3-c]pyridin-2-ylmethyl)-4-methylpentan-2-ol | 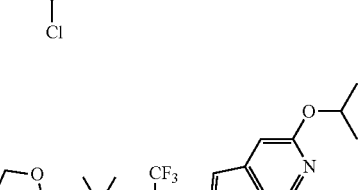 |
| 4-(5-Chloro-2,3-dihydrobenzofuran-7-yl)-2-(5-dimethylamino-1H-pyrrolo[2,3-c]pyridin-2-ylmethyl)-1,1,1-trifluoro-4-methylpentan-2-ol | 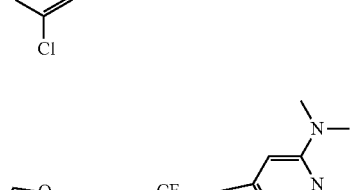 |

| Compound Name | Compound Structure | | Compound Name | Compound Structure |
|---|---|---|---|---|
| 4-(5-Chloro-2,3-dihydrobenzofuran-7-yl)-1,1,1-trifluoro-4-methyl-2-(5-piperidin-1-yl-1H-pyrrolo[2,3-c]pyridin-2-ylmethyl)pentan-2-ol | | | 2-(5-Ethoxy-1H-pyrrolo[2,3-c]pyridin-2-ylmethyl)-1,1,1-trifluoro-4-(5-fluoro-2-methylphenyl)-4-methylpentan-2-ol | |
| 4-(5-Chloro-2,3-dihydrobenzofuran-7-yl)-1,1,1-trifluoro-4-methyl-2-(5-morpholin-4-yl-1H-pyrrolo[2,3-c]pyridin-2-ylmethyl)pentan-2-ol | | | 2-(5-Benzyloxy-1H-pyrrolo[2,3-c]pyridin-2-ylmethyl)-1,1,1-trifluoro-4-(5-fluoro-2-methylphenyl)-4-methylpentan-2-ol | |
| 1,1,1-Trifluoro-4-(5-fluoro-2-methylphenyl)-4-methyl-2-(5-morpholin-4-yl-1H-pyrrolo[2,3-c]pyridin-2-ylmethyl)pentan-2-ol | | | 2-(5-Benzyloxy-1H-pyrrolo[2,3-c]pyridin-2-ylmethyl)-4-(5-chloro-2,3-dihydrobenzofuran-7-yl)-1,1,1-trifluoro-4-methylpentan-2-ol | |
| 1,1,1-Trifluoro-4-(5-fluoro-2-methylphenyl)-4-methyl-2-(5-piperidin-1-yl-1H-pyrrolo[2,3-c]pyridin-2-ylmethyl)pentan-2-ol | | | 1,1,1-Trifluoro-4-(5-fluoro-2-methoxyphenyl)-2-(5-chloro-1H-pyrrolo[2,3-c]pyridin-2-ylmethyl)-4-methylpentan-2-ol | |
| 2-(5-Dimethylamino-1H-pyrrolo[2,3-c]pyridin-2-ylmethyl)-1,1,1-trifluoro-4-(5-fluoro-2-methylphenyl)-4-methylpentan-2-ol | | | 1,1,1-Trifluoro-4-(5-fluoro-2-methoxyphenyl)-4-methyl-2-[5-(methylamino)-1H-pyrrolo[2,3-c]pyridin-2-ylmethyl]pentan-2-ol | |
| 4-(5-Chloro-2,3-dihydrobenzofuran-7-yl)-2-(5-ethoxy-1H-pyrrolo[2,3-c]pyridin-2-ylmethyl)-1,1,1-trifluoro-4-methylpentan-2-ol | | | 1,1,1-Trifluoro-4-(5-fluoro-2-methoxyphenyl)-4-methyl-2-(5-amino-1H-pyrrolo[2,3-c]pyridin-2-ylmethyl)pentan-2-ol | |

| Compound Name | Compound Structure |
|---|---|
| 1,1,1-Trifluoro-4-(5-fluoro-2-methylphenyl)-4-methyl-2-(6-amino-1H-pyrrolo[2,3-c]pyridin-2-ylmethyl)pentan-2-ol | 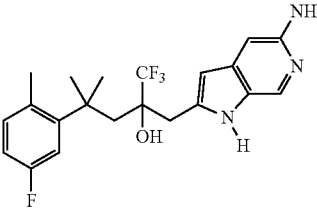 |
| 1,1,1-Trifluoro-4-(5-fluoro-2-methylphenyl)-2-(5-[methylamino]-1H-pyrrolo[2,3-c]pyridin-2-ylmethyl)-4-methylpentan-2-ol | 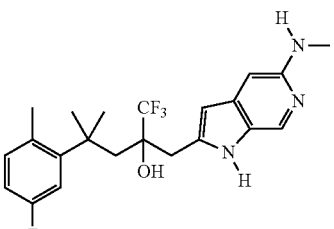 |
| 4-(5-Chloro-2,3-dihydrobenzofuran-7-yl)-1,1,1-trifluoro-2-(5-amino-1H-pyrrolo[2,3-c]pyridin-2-ylmethyl)-4-methylpentan-2-ol | 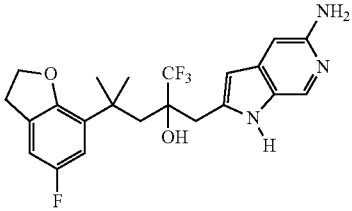 [SMILES: CC(C)(CC(O)(Cc1cc2cc(N)ncc2[nH]1)C(F)(F)F)c1cc(F)cc2c1OCC2] |
| 4-(5-Chloro-2,3-dihydrobenzofuran-7-yl)-1,1,1-trifluoro-4-methyl-2-(5-methylamino-1H-pyrrolo[2,3-c]pyridin-2-ylmethyl)pentan-2-ol | 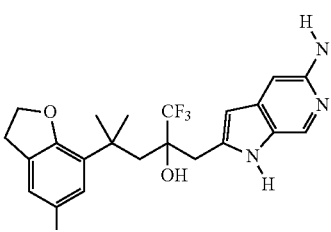 |
| 1,1,1-Trifluoro-4-(5-fluoro-2-methoxyphenyl)-4-methyl-2-pyrrolo[2,3-b]pyridin-1-ylmethylpentan-2-ol | 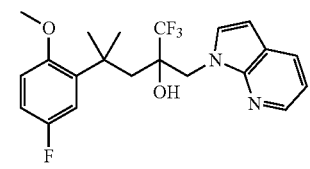 [SMILES: COc1ccc(F)cc1C(C)(C)CC(O)(Cn1ccc2cccnc21)C(F)(F)F] |
| 1,1,1-Trifluoro-4-(5-fluoro-2-methoxyphenyl)-4-methyl-2-pyrrolo[2,3-c]pyridin-1-ylmethylpentan-2-ol | 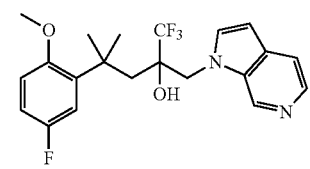 [SMILES: COc1ccc(F)cc1C(C)(C)CC(O)(Cn1ccc2ccncc21)C(F)(F)F] |
| 2-(3-Dimethylaminomethyl-1H-pyrrolo[3,2-c]pyridin-2-ylmethyl)-1,1,1-trifluoro-4-(5-fluoro-2-methoxyphenyl)-4-methylpentan-2-ol | 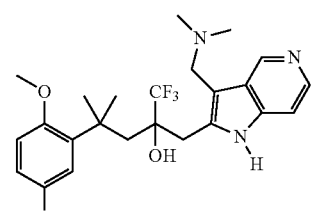 |

| Compound Name | Compound Structure |
|---|---|
| 1,1,1-Trifluoro-4-(5-fluoro-2-methoxyphenyl)-4-methyl-2-pyrrolo[3,2-c]pyridin-1-ylmethylpentan-2-ol | 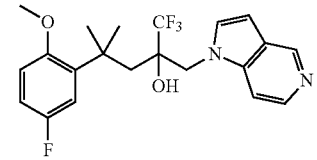 [SMILES: COc1ccc(F)cc1C(C)(C)CC(O)(Cn1ccc2cnccc21)C(F)(F)F] |
| 1,1,1-Trifluoro-4-(5-fluoro-2-methoxyphenyl)-4-methyl-2-pyrrolo[3,2-b]pyridin-1-ylmethylpentan-2-ol | 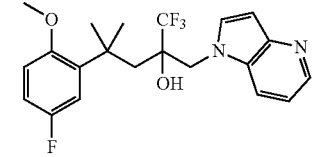 [SMILES: COc1ccc(F)cc1C(C)(C)CC(O)(Cn1ccc2ncccc21)C(F)(F)F] |
| 4-(5-Chloro-2,3-dihydrobenzofuran-7-yl)-1,1,1-trifluoro-4-methyl-2-pyrrolo[3,2-b]pyridin-1-ylmethylpentan-2-ol | 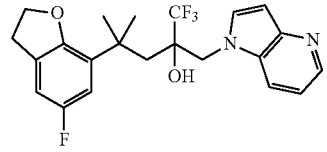 [SMILES: CC(C)(CC(O)(Cn1ccc2ncccc21)C(F)(F)F)c1cc(F)cc2c1OCC2] |
| 1,1,1-Trifluoro-4-(5-fluoro-2-methylphenyl)-4-methyl-2-pyrrolo[3,2-b]pyridin-1-ylmethylpentan-2-ol | 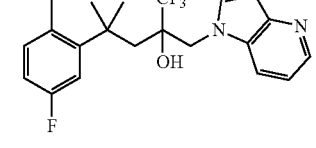 |
| 4-Fluoro-2-(4,4,4-trifluoro-3-hydroxy-1,1-dimethyl-3-pyrrolo[3,2-b]pyridin-1-ylmethylbutyl)phenol | 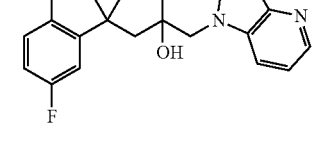 |
| 2-[4-(5-Fluoro-2-methylphenyl)-2-hydroxy-4-methyl-2-trifluoromethylpentyl]-1,6-dihydropyrrolo[2,3-c]pyridin-5-one | 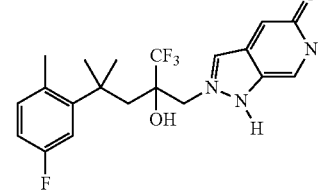 |
| 2-[4-(5-Fluoro-2-methylphenyl)-2-hydroxy-4-methyl-2-trifluoromethylpentyl]-6-methyl-1,6-dihydropyrrolo[2,3-c]pyridin-5-one | 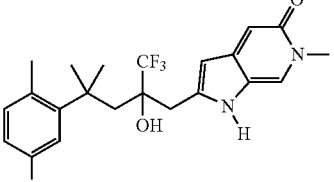 |
| 2-[4-(5-Fluoro-2-methylphenyl)-2-hydroxy-4-methyl-2-trifluoromethylpentyl]-1,4-dihydropyrrolo[3,2-b]pyridin-5-one | 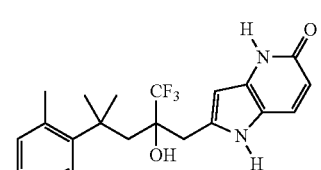 |

| Compound Name | Compound Structure |
|---|---|
| 2-[4-(5-Fluoro-2-methylphenyl)-2-hydroxy-4-methyl-2-trifluoromethylpentyl]-4-methyl-1,4-dihydropyrrolo[3,2-b]pyridin-5-one | 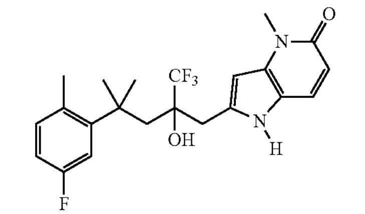 [SMILES: Cc1ccc(F)cc1C(C)(C)CC(O)(Cc1cc2c(ccc(=O)n2C)[nH]1)C(F)(F)F] |
| 1,1,1-Trifluoro-4-(5-fluoro-2-methylphenyl)-2-(5-methoxy-1H-pyrrolo[3,2-b]pyridin-2-ylmethyl)-4-methylpentan-2-ol | 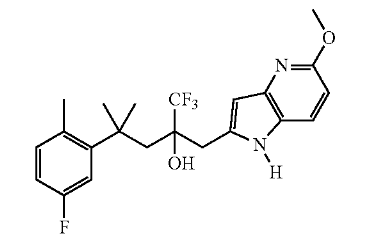 [SMILES: COc1ccc2[nH]c(CC(O)(CC(C)(C)c3cc(F)ccc3C)C(F)(F)F)cc2n1] |
| 1,1,1-Trifluoro-4-(5-fluoro-2-methylphenyl)-2-(6-methoxy-1H-pyrrolo[3,2-c]pyridin-2-ylmethyl)-4-methylpentan-2-ol | 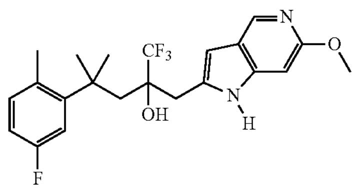 [SMILES: COc1cc2[nH]c(CC(O)(CC(C)(C)c3cc(F)ccc3C)C(F)(F)F)cc2cn1] |
| 2-[4-(5-Fluoro-2-methylphenyl)-2-hydroxy-4-methyl-2-trifluoromethylpentyl]-5-methyl-1,5-dihydropyrrolo[3,2-c]pyridin-6-one | 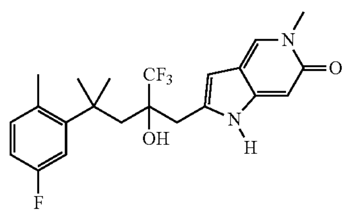 [SMILES: Cc1ccc(F)cc1C(C)(C)CC(O)(Cc1cc2cn(C)c(=O)cc2[nH]1)C(F)(F)F] |
| 2-[4-(5-Fluoro-2-methylphenyl)-2-hydroxy-4-methyl-2-trifluoromethylpentyl]-1,3a-dihydropyrrolo[3,2-c]pyridin-6-one | 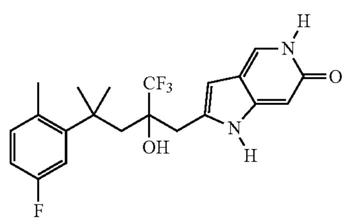 [SMILES: Cc1ccc(F)cc1C(C)(C)CC(O)(Cc1cc2c[nH]c(=O)cc2[nH]1)C(F)(F)F] |
| 2-[4-(5-Fluoro-2-methylphenyl)-2-hydroxy-4-methyl-2-trifluoromethylpentyl]-1,7-dihydropyrrolo[3,2-c]pyridine-4,6-dione | 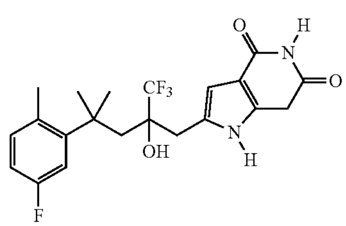 [SMILES: Cc1ccc(F)cc1C(C)(C)CC(O)(Cc1cc2c([nH]1)CC(=O)NC2=O)C(F)(F)F] |
| 6-[4-(5-Fluoro-2-methylphenyl)-2-hydroxy-4-methyl-2-trifluoromethylpentyl]-3-methyl-1,7-dihydropyrrolo[2,3-d]pyrimidine-2,4-dione | 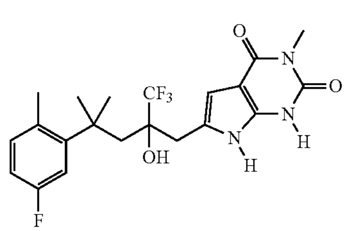 [SMILES: Cc1ccc(F)cc1C(C)(C)CC(O)(Cc1cc2c(=O)n(C)c(=O)[nH]c2[nH]1)C(F)(F)F] |
| 2-[4-(5-Chloro-2,3-dihydrobenzofuran-7-yl)-2-hydroxy-4-methyl-2-trifluoromethylpentyl]-1,6-dihydropyrrolo[2,3-c]pyridin-5-one | |
| 2-[4-(5-Chloro-2,3-dihydrobenzofuran-7-yl)-2-hydroxy-4-methyl-2-trifluoromethylpentyl]-6-methyl-1,6-dihydropyrrolo[2,3-c]pyridin-5-one | |
| 2-[4-(5-Chloro-2,3-dihydrobenzofuran-7-yl)-2-hydroxy-4-methyl-2-trifluoromethylpentyl]-1,4-dihydropyrrolo[3,2-b]pyridin-5-one | |
| 2-[4-(5-Chloro-2,3-dihydrobenzofuran-7-yl)-2-hydroxy-4-methyl-2-trifluoromethylpentyl]-4-methyl-1,4-dihydropyrrolo[3,2-b]pyridin-5-one | |
| 2-[4-(5-Chloro-2,3-dihydrobenzofuran-7-yl)-2-hydroxy-4-methyl-2-trifluoromethylpentyl]-1,5-dihydropyrrolo[3,2-c]pyridin-6-one | |
| 2-[4-(5-Chloro-2,3-dihydrobenzofuran-7-yl)-2-hydroxy-4-methyl-2-trifluoromethylpentyl]-5-methyl-1,5-dihydropyrrolo[3,2-c]pyridin-6-one | |
| 2-[4-(5-Chloro-2,3-dihydrobenzofuran-7-yl)-2-hydroxy-4-methyl-2-trifluoromethylpentyl]-1,7-dihydropyrrolo[3,2-c]pyridine-4,6-dione | |

| Compound Name | Compound Structure |
|---|---|
| 6-[4-(5-Chloro-2,3-dihydrobenzofuran-7-yl)-2-hydroxy-4-methyl-2-trifluoromethylpentyl]-3-methyl-1,7-dihydropyrrolo[2,3-d]pyrimidine-2,4-dione | 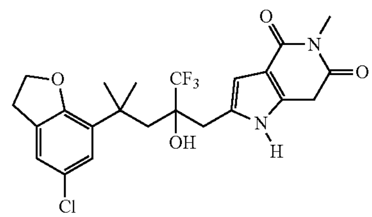 [SMILES: CN1C(=O)Cc2[nH]c(CC(O)(CC(C)(C)c3cc(Cl)cc4c3OCC4)C(F)(F)F)cc2C1=O] |
| 1,1,1-Trifluoro-4-(5-fluoro-2-methylphenyl)-4-methyl-2-(5-morpholin-4-ylmethyl-1H-pyrrolo[2,3-c]pyridin-2-ylmethyl)pentan-2-ol | 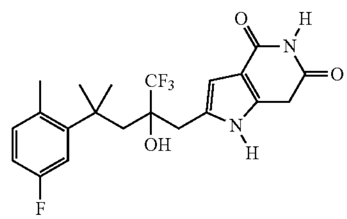 [SMILES: Cc1ccc(F)cc1C(C)(C)CC(O)(Cc1cc2c([nH]1)CC(=O)NC2=O)C(F)(F)F] |
| {2-[4-(5-Fluoro-2-methylphenyl)-2-hydroxy-4-methyl-2-trifluoromethylpentyl]-1H-pyrrolo[2,3-c]pyridin-5-yl}phenylmethanone | 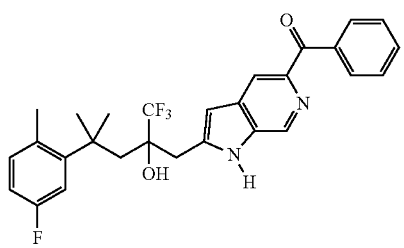 [SMILES: Cc1ccc(F)cc1C(C)(C)CC(O)(Cc1cc2cc(C(=O)c3ccccc3)ncc2[nH]1)C(F)(F)F] |
| {2-[4-(5-Fluoro-2-methylphenyl)-2-hydroxy-4-methyl-2-trifluoromethylpentyl]-1H-pyrrolo[2,3-c]pyridin-5-yl}furan-2-ylmethanone | 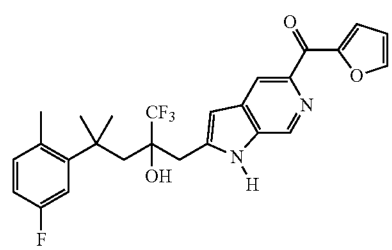 [SMILES: Cc1ccc(F)cc1C(C)(C)CC(O)(Cc1cc2cc(C(=O)c3ccco3)ncc2[nH]1)C(F)(F)F] |
| 2-(3-Bromo-1H-indol-2-ylmethyl)-1,1,1-trifluoro-4-(3-fluorophenyl)-4-methylpentan-2-ol | 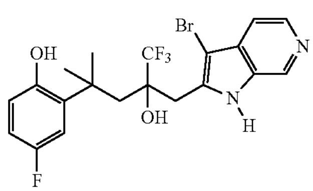 [SMILES: CC(C)(CC(O)(Cc1[nH]c2cnccc2c1Br)C(F)(F)F)c1cc(F)ccc1O] |
| 1,1,1-Trifluoro-4-(5-fluoro-2-methoxyphenyl)-4-methyl-2-(7H-pyrrolo[2,3-d]pyrimidin-6-ylmethyl)pentan-2-ol | 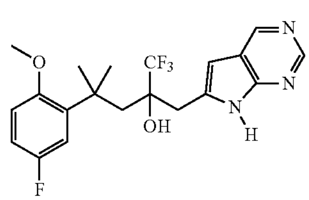 [SMILES: COc1ccc(F)cc1C(C)(C)CC(O)(Cc1cc2cncnc2[nH]1)C(F)(F)F] |
| 1,1,1-Trifluoro-4-(5-fluoro-2-methoxyphenyl)-2-(4-methoxy-7H-pyrrolo[2,3-d]pyrimidin-6-ylmethyl)-4-methylpentan-2-ol | |
| 2-(2,4-Dimethyl-7H-pyrrolo[2,3-d]pyrimidin-6-ylmethyl)-1,1,1-trifluoro-4-(5-fluoro-2-methoxyphenyl)-4-methylpentan-2-ol | |
| 2-(2-Amino-4-chloro-7H-pyrrolo[2,3-d]pyrimidin-6-ylmethyl)-1,1,1-trifluoro-4-(5-fluoro-2-methoxyphenyl)-4-methylpentan-2-ol | |
| 2-(2,4-Dimethyl-7H-pyrrolo[2,3-d]pyrimidin-6-ylmethyl)-1,1,1-trifluoro-4-(5-fluoro-2-methylphenyl)-4-methylpentan-2-ol | |
| 2-(5-Chloro-1H-pyrrolo[2,3-c]pyridin-2-ylmethyl)-1,1,1-trifluoro-4-(5-fluoro-2-methylphenyl)-4-methylpentan-2-ol | | or a tautomer, ester, amide, or salt thereof.

2. A pharmaceutical composition comprising an effective amount of a compound according to claim 1, or a tautomer, ester, amide, or salt thereof, and a pharmaceutically acceptable excipient or carrier.

3. A kit for the in vitro diagnostic determination of the glucocorticoid receptor function in a sample, comprising:
   (a) a diagnostically effective amount of a compound according to claim 1, or a tautomer, ester, amide, or salt thereof; and
   (b) instructions for use of the diagnostic kit.

* * * * *